United States Patent
Chen et al.

(10) Patent No.: US 10,968,215 B2
(45) Date of Patent: Apr. 6, 2021

(54) PYRIDO FIVE-ELEMENT AROMATIC RING COMPOUND, PREPARATION METHOD THEREFOR AND USE THEREOF

(71) Applicants: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

(72) Inventors: Xuxing Chen, Shanghai (CN); Meiyu Geng, Shanghai (CN); Lei Jiang, Shanghai (CN); Yi Chen, Shanghai (CN); Jianhua Cao, Shanghai (CN); Qingyun Jiang, Shanghai (CN); Qianqian Shen, Shanghai (CN); Jian Ding, Shanghai (CN); Yucai Yao, Shanghai (CN); Zhao Zhao, Shanghai (CN); Yuanfang Xiong, Shanghai (CN)

(73) Assignees: SHANGHAI HAIHE PHARMACEUTICAL CO., LTD., Shanghai (CN); SHANGHAI INSTITUTE OF MATERIA MEDICA, CHINESE ACADEMY OF SCIENCES, Shanghai (CN)

( * ) Notice: Subject to any disclaimer, the term of this patent is extended or adjusted under 35 U.S.C. 154(b) by 0 days.

(21) Appl. No.: 16/331,090

(22) PCT Filed: Sep. 6, 2017

(86) PCT No.: PCT/CN2017/100747
§ 371 (c)(1),
(2) Date: Mar. 6, 2019

(87) PCT Pub. No.: WO2018/045971
PCT Pub. Date: Mar. 15, 2018

(65) Prior Publication Data
US 2019/0211010 A1    Jul. 11, 2019

(30) Foreign Application Priority Data
Sep. 7, 2016  (CN) .................. 201610807947.2

(51) Int. Cl.
C07D 471/04    (2006.01)
A61K 31/5377   (2006.01)
A61K 31/444    (2006.01)
A61P 35/00     (2006.01)
A61K 31/4545   (2006.01)
A61K 31/496    (2006.01)
A61P 37/06     (2006.01)
C07D 519/00    (2006.01)

(52) U.S. Cl.
CPC .......... *C07D 471/04* (2013.01); *A61K 31/444* (2013.01); *A61K 31/4545* (2013.01); *A61K 31/496* (2013.01); *A61K 31/5377* (2013.01); *A61P 35/00* (2018.01); *A61P 37/06* (2018.01); *C07D 519/00* (2013.01)

(58) Field of Classification Search
CPC ........................... C07D 471/04; A61K 31/444
USPC ......................................................... 546/112
See application file for complete search history.

(56) References Cited

U.S. PATENT DOCUMENTS

2005/0049276 A1* 3/2005 Kaufman ............. C07D 471/04
                                                          514/303

FOREIGN PATENT DOCUMENTS

CN   103987842 A    8/2014
WO   2016/102493 A1 6/2016

OTHER PUBLICATIONS

Xiaobao yang et al. Structure-Activity Relationship Studies for Enhancer of Zeste Homologue 2 (EZH2) and enhancer of Zeste Homomlogue 1(EZH1) inhibitors. (Year: 2016).*
International Search Report corresponding to PCT/CN2017/100747 dated Dec. 12, 2017; 2 pages.

* cited by examiner

*Primary Examiner* — Rita J Desai
(74) *Attorney, Agent, or Firm* — Mintz Levin Cohn Ferris Glovsky and Popeo PC

(57) ABSTRACT

The present invention provides a pyrido five-element aromatic ring compound, and a preparation method therefor and a use thereof. The compound provided in the present invention has an inhibitory effect on wild-type and/or mutant EZH2, and is well positioned to become a novel anti-tumor drug or a drug for the treatment of autoimmune diseases.

9 Claims, No Drawings

PYRIDO FIVE-ELEMENT AROMATIC RING COMPOUND, PREPARATION METHOD THEREFOR AND USE THEREOF

FIELD OF THE INVENTION

The invention belongs to field of medicinal chemistry. In particular, the present invention relates to a pyridino five-membered aromatic ring compound or a pharmaceutically acceptable salt thereof, a preparation process thereof and use thereof. The compound of the present invention can be used for the treatment of *Drosophila* enhancer of Zeste homolog 2 (EZH2)-related diseases such as malignant tumors.

BACKGROUND OF THE INVENTION

Epigenetics means that expression of a gene has undergone heritable changes while the nucleotide sequence of the gene keep unchanged, which play an important role in regulating cell proliferation, differentiation, survival and apoptosis. An important mechanism of epigenetic regulation is histone covalent modification. In eukaryotic cells, DNA surrounds the histones to form nucleosomes, which is the basic structure of chromatin. In each nucleosome, two molecules of H2A, H2B, H3 and H4 form a histone octamer. A variety of covalent modifications occur at the N-terminal amino acid end of each histone, such as methylation, acetylation, phosphorylation, ubiquitination, etc., so as to control gene expression. Enzymes which catalyze the methylation of histones are called histone methyltransferases (HMTs).

The polycomb protein PRC2 is a multiprotein complex that functions to catalyze the methylation of lysine (H3K27) at position 27 of histone H3, thus causing silencing of related genes. The catalytic subunit of PRC2 is EZH1 or EZH2. EZH1 or EZH2 alone has no catalytic function and must be combined with EED and SUZ12 before it can exert methyltransfertion. EZH2 is highly expressed in cells of various tumors (such as breast cancer, colorectal cancer, endometrioma, gastric cancer, liver cancer, kidney cancer, lung cancer, melanoma, ovarian cancer, pancreatic cancer, prostate cancer and bladder cancer), and is closely related to a process of tumor cells, such as proliferation, invasion, drug resistance and migration.

In recent years, EZH2 has been found to have mutated in 8-24% of non-Hodgkin's lymphomas, such as Y641F, Y641N, Y641S, Y641H, A677G and A687V. These mutants have enhanced dimethylation and trimethylation catalytic functions to histone H3 at position 27 of lysine compared with wild-type EZH2. Excessive expression or mutation of EZH2 causes an increase in the level of 27 lysine trimethylation products (H3K27me3) of H3, and high levels of H3K27me3 plays an important role in tumor cell proliferation and survival. Abnormal EZH2 activity leads to the development of tumors. The multiple target genes regulated by EZH2 are tumor suppressor genes, and the silencing of tumor suppressor genes may be an important mechanism. Down-regulation of EZH2 by siRNA or shRNA or indirect inhibition of EZH2 by SAH hydrolase inhibitor 3-deazaneplanocin A (3-DZNep) can significantly reduce the proliferation and invasion of tumor cells in vitro and the growth of tumors in vivo.

EZH2 also plays an important role in the differentiation of T cells. EZH2 reduces the expression of Th1/Th2 cytokines (such as IFN-γ, IL-4, IL-5, etc.), inhibits Th1/Th2-dependent T cell migration, and activates regulatory T cells. In the tumor microenvironment, EZH2 inhibits Th1 chemokines such as CXCL9 and CXCL10, which is an important mechanism for tumor immune escape.

In summary, there is an urgent need in the art to develop effective drugs capable of inhibiting wild-type and/or mutant EZH2.

SUMMARY OF THE INVENTION

An object of the present invention is to provide a pyridino five-membered aromatic ring compound, a preparation process thereof and the use as an EZH2 inhibitor thereof. The compounds of the present invention have a clear structure-activity relationship and have an inhibitory effect on wild-type and/or mutant EZH2, thus being expected to be novel drugs for anti-tumor or autoimmune diseases.

According to a first aspect of the invention, a compound of formula I, or a pharmaceutically acceptable salt, an enantiomer, a diastereomer, a tautomer, a solvate thereof, a polymorph or prodrug thereof is provided,

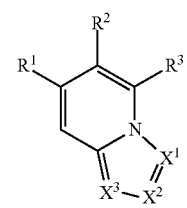

where $X^1$ is $CR^4$ or N;
$X^2$ is $CR^5$ or N;
$X^3$ is $CR^6$ or N; and at most one of $X^1$, $X^2$, $X^3$ is N;
$R^4$ is selected from H, a halogen, substituted or unsubstituted C1-C6 alkyl;
$R^5$ or $R^6$ is selected from H, a halogen, —COOH, —CN, substituted or unsubstituted 5-8 membered aryl, substituted or unsubstituted 5-8 membered heteroaryl, substituted or unsubstituted 5-8 membered aryl fused to substituted or unsubstituted 5-8 membered heterocyclic group, substituted or unsubstituted 5-8 membered heteroaryl fused to substituted or unsubstituted 5-8 membered heterocyclic group, substituted or unsubstituted 5-8 membered aryl fused to substituted or unsubstituted 5-8 membered carbocyclic group, substituted or unsubstituted 5-8 membered heteroaryl fused to substituted or unsubstituted 5-8 membered carbocyclic group, substituted or unsubstituted 4-8 membered saturated or unsaturated carbocyclic group, substituted or unsubstituted 4-8 membered saturated or unsaturated heterocyclic group, substituted or unsubstituted C1-C6 alkylcarbonyl group, —C(O)O— (substituted or unsubstituted C1-C6 alkyl), —C(O)(NR$^a$R$^b$), substituted or unsubstituted —(CH$_2$)$_m$NR$^a$R$^b$, substituted or unsubstituted C1-C6 alkyl, boronic acid group, substituted or unsubstituted C2-C8 alkenyl, substituted or unsubstituted C2-C8 alkynyl; wherein the heteroaryl or heterocyclic group contains 1-3 hetero atoms selected from N, O, S, P; m is an integer from 0 to 5; and said "substituted" means having one or more (e.g., 1, 2, 3, or 4) substituents selected from group A;

Wherein $R^a$, $R^b$ are each independently selected from H, a halogen, substituted or unsubstituted C1-C6 alkyl, substituted or unsubstituted 5-8 membered carbocyclic ring, substituted or unsubstituted 5-8 membered heterocyclic ring or $R^a$ and $R^b$ are bonded to N to form a substituted or unsubstituted 4-8 membered heterocyclic ring; wherein said heterocyclic ring contains 1-3 hetero atoms selected from N, O, S, or P;

$R^1$ is selected from

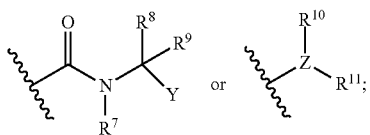

$R^2$ is selected from H, a halogen, substituted or unsubstituted C1-C6 alkyl, substituted or unsubstituted aryl;

$R^3$ is selected from

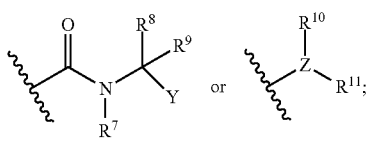

and when $R^1$ is

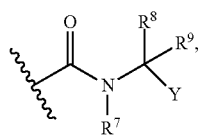

then $R^3$ is

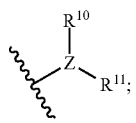

wherein, $R^7$ is selected from H, a substituted or unsubstituted C1-C6 alkyl;

$R^8$ and $R^9$ are each independently selected from H, a substituted or unsubstituted C1-C6 alkyl;

Y is selected from

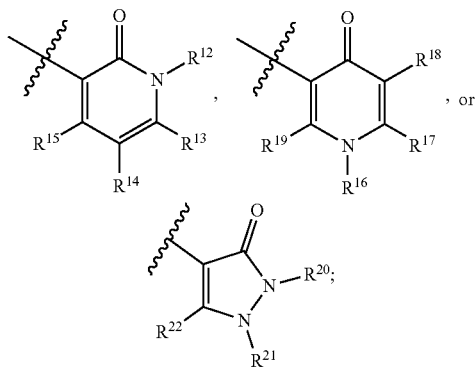

wherein, $R^{12}$ and $R^{13}$ are each independently selected from H, a substituted or unsubstituted C1-C4 alkyl;

$R^{14}$ and $R^{15}$ are each independently selected from H, a halogen, —$NH_2$, —$NO_2$, —$CF_3$, substituted or unsubstituted C1-C4 alkyl, substituted or unsubstituted C1-C4 alkoxy, substituted or unsubstituted $(CH_2)_n NR^c R^d$, or $R^{14}$ and $R^{15}$ are joined to form a 5-6 membered saturated heterocyclic ring, or $R^{14}$ and $R^{15}$ are linked to form a 5-6 membered aromatic ring; n is an integer of 0-4;

$R^{16}$ is H, a substituted or unsubstituted C1-C4 alkyl;

$R^{17}$ and $R^{19}$ are each independently selected from H, a substituted or substituted C1-C4 alkyl, substituted or unsubstituted C1-C4 alkoxy, —$(CH_2)_n NR^c R^d$; n is an integer from 0-4;

$R^{18}$ is selected from H, a halogen, —$NH_2$, —$NO_2$, substituted or substituted C1-C4 alkyl, substituted or unsubstituted C1-C4 alkoxy, substituted or unsubstituted $(CH_2)_n NR^c R^d$; where n is an integer from 0-4;

$R^{20}$ and $R^{21}$ are each independently selected from H, a substituted or substituted C1-C4 alkyl;

$R^{22}$ is selected from H, a substituted or unsubstituted C1-C4 alkyl;

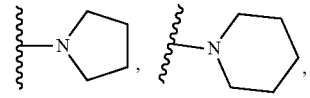

or substituted or unsubstituted C1-C4 alkoxy;

wherein $R^c$, $R^d$ are each independently selected from H, a substituted or unsubstituted C1-C4 alkyl;

Z is selected from N or CH;

$R^{10}$ and $R^{11}$ are each independently selected from: H, —OH, a substituted or unsubstituted C1-C6 alkyl, —$OR^e$, substituted or unsubstituted 4-8 membered heterocyclic group, substituted or unsubstituted 4-8 membered carbocyclic group, substituted or unsubstituted 5-8 membered aryl, —$NR^f R^g$; wherein said heterocyclic ring contains 1-3 hetero atoms selected from N, O, S, or P; and said "substituted" means having one or more (e.g., 1, 2, 3 or 4) substituents selected from group B;

wherein $R^e$ is selected from H, a substituted or unsubstituted C1-C6 alkyl, substituted or unsubstituted C2-C6 alkenyl, substituted or unsubstituted C2-C6 alkynyl, substituted or unsubstituted saturated or unsaturated 4-8 membered carbocyclic ring, substituted or unsubstituted saturated or unsaturated 4-8 membered heterocyclic ring, substituted or unsubstituted 5-8 membered aryl, substituted or unsubstituted 5-8 membered heteroaryl, —$(CH_2)_p$ (substituted or unsubstituted 5-8 membered aryl), —$(CH_2)_p$ (substituted or unsubstituted 5-8 membered heteroaryl); wherein the heterocyclic or heteroaryl group comprises 1-3 heteroatoms selected from N, O, S, or P; p is an integer from 0 to 3; and said "substituted" refers to one or more of the following (e.g., 1, 2, 3 or 4) substituent: halogen, a C1-C4 alkyl, C1-C4 alkoxy, —$NO_2$, —$NR^s R^t$;

wherein $R^f$ and $R^g$ are each independently selected from: H, a substituted or unsubstituted C1-C6 alkyl, wherein the substituent is —OH, C1-C4 alkoxy, or —$NR^s R^t$;

group A substituents are selected from the group consisting of H, =O, —CN, —COOH, —$NR^s R^t$, a halogen, substituted or unsubstituted C1-C6 alkoxycarbonyl, unsubstituted or substituted C1-C6 alkyl, substituted or unsubstituted 4-8 membered heterocyclic group, substituted or unsubstituted C1-C4 alkoxy; wherein the heterocyclic group contains 1-3 hetero atoms selected from N, O, S or P;

group B substituents are selected from the group consisting of H, —OH, a halogen, unsubstituted or substituted C1-C6 alkyl, —NR$^s$R$^t$, —NO$_2$, substituted or unsubstituted C1-C6 alkoxycarbonyl, substituted or unsubstituted C1-C6 alkylsulfonyl, substituted or unsubstituted C1-C6 alkylcarbonyl, substituted or unsubstituted C1-C6 alkoxy, substituted or unsubstituted 4-6 membered heterocyclic ring, unsubstituted or substituted C5-C8 heteroaryl, Boc, benzyl; wherein said heteroaryl comprises 1-3 heteroatoms selected from N, O, S or P;

also, in the group A and group B substituents and R$^a$, R$^b$, the substitution means having one or more (e.g. 1, 2, 3 or 4) substitutions selected from group C: H, a halogen, —OH, —CN, C1-C4 alkyl, C1-C4 alkoxy, —NR$^s$R$^t$, 5-8 membered aryl, 4-8 membered heterocyclic group, Boc, C1-C4 acyl; and said substitution is one or more (e.g., 1, 2, 3 or 4) substituents;

and, in the R$^7$, R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^c$, R$^d$, the "substituted" means having one or more (e.g., 1, 2, 3 or 4) substituents selected from the group D: H, a halogen, C1-C4 alkyl, C1-C4 haloalkyl, nitro, —OH, amino;

R$^s$ and R$^t$ are each independently selected from the group consisting of: H, a C1-C4 alkyl, C1-C4 haloalkyl.

In another preferred embodiment, R$^{10}$ is a substituted or unsubstituted C1-C4 alkoxy, substituted or unsubstituted C1-C4 alkyl.

In another preferred embodiment, R$^{10}$ is selected from methyl or ethyl.

In another preferred embodiment, R$^{11}$ is selected from the group consisting of —OH,

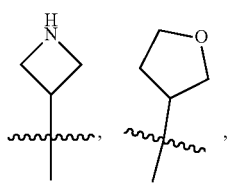

—OR$^e$, —NR$^f$R$^g$,

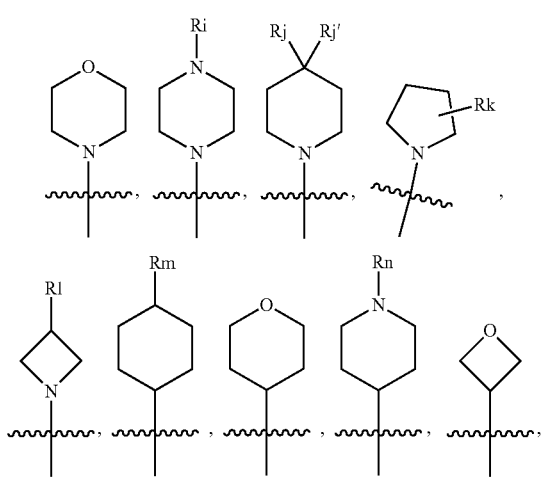

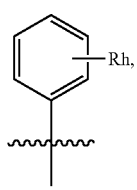

wherein R$^e$ is selected from the group consisting of a substituted or unsubstituted C1-C4 alkyl, allyl, isobutenyl, propargyl, cyclohexane group, cyclohexenyl,

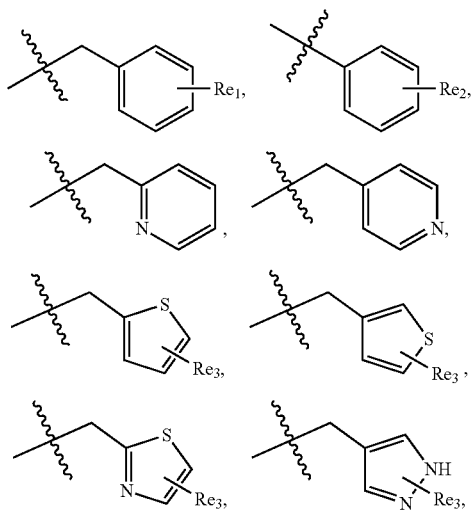

wherein, R$^{e1}$ is selected from the group consisting of H, a halogen, C1-C4 alkoxy, phenyl; and the number of R$^{e1}$ is 1-3; R$^{e2}$ is selected from —NO$_2$, —NH$_2$, —N(CH$_3$)$_2$; R$^{e2}$ is selected from H, a halogen, —NR$^s$R$^t$, substituted or unsubstituted C1-C4 alkyl (preferably methyl);

R$^f$ is H, or a substituted or unsubstituted C1-C4 alkyl;

R$^g$ is a C1-C4 alkoxy or —NR$^s$R$^t$ substituted C1-C4 alkyl, or cyclopentyl;

R$^h$ is selected from H, a halogen;

R$^i$ is selected from H, an unsubstituted or substituted C1-C4 alkyl, substituted or unsubstituted C1-C4 alkylcarbonyl, substituted or unsubstituted C1-C4 alkoxycarbonyl, substituted or unsubstituted C1-C4 alkylsulfonyl, trifluoromethyl C1-C2 alkyl, difluoromethyl C1-C2 alkyl, —NR$^s$R$^t$,

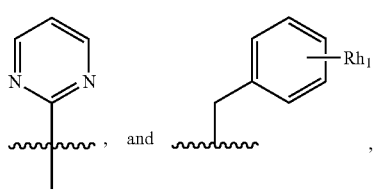

wherein R$^{h1}$ is selected from —OH, —CN, a C1-C4 alkyl;

R$^j$ is selected from the group consisting of: —OH, a halogen, C1-C4 alkoxy, —NR$^s$R$^t$,

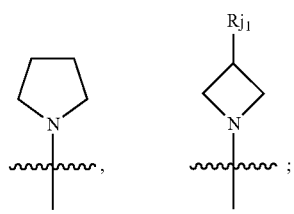

wherein $R^{j1}$ is selected from a C1-C4 alkoxy (preferably dimethylamino, —OH, —NH$_2$, methoxy);

$R^{j'}$ is selected from H or a halogen;

and when $R^j$ is a halogen, then $R^{j'}$ is a halogen;

$R^k$ is selected from the group consisting of H, —OH, a C1-C4 alkoxy, $R^l$ is selected from the group consisting of H, —NR$^s$R$^t$, preferably H or dimethylamino;

$R^m$ is selected from the group consisting of: H, —NR$^s$R$^t$, preferably H or dimethylamino;

$R^n$ is selected from the group consisting of trifluoromethyl C1-C4 alkyl, preferably CF$_3$CH$_2$—.

In another preferred embodiment, $R^5$ or $R^6$ are each independently selected from the group consisting of: H, a substituted or unsubstituted C1-C4 alkyl, —CN, halogen, C1-C4 alkylcarbonyl, $R^{51}$(C1-C4 alkoxy)carbonyl, $R^{52}$C(O)—, —COOH, —C(O)(NR$^a$R$^b$),

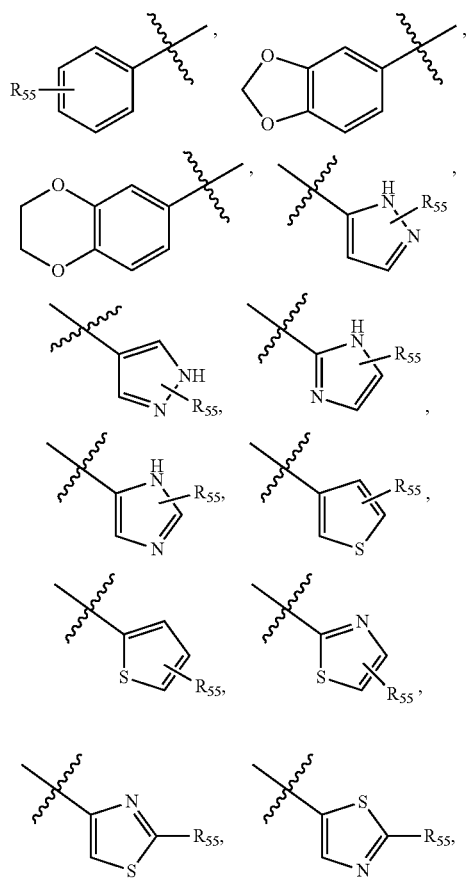

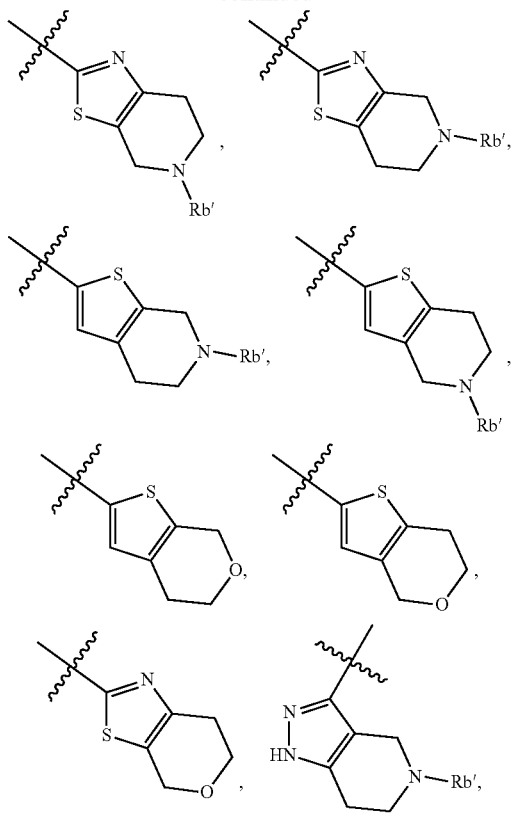

-continued

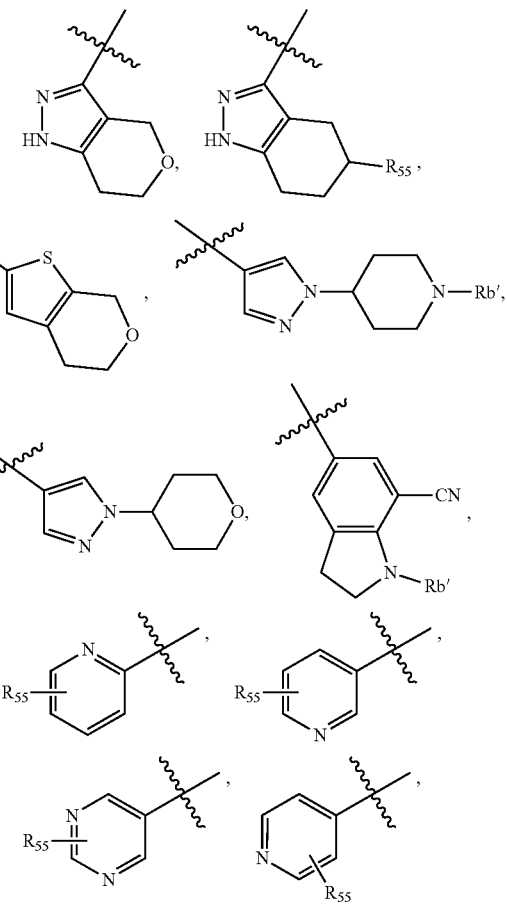

-continued

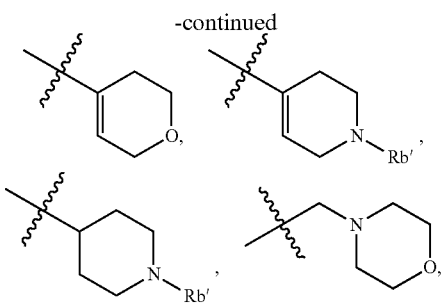

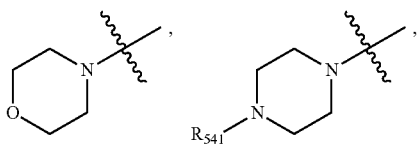

R⁵⁷(C1-C3)alkylalkynyl;
wherein R⁵¹ is selected from the group consisting of dimethylamino,

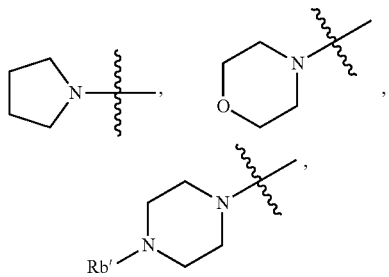

and wherein $R^b$ is selected from the group consisting of H, a C1-C4 alkyl, Boc, C1-C4 acyl;
R⁵² is selected from

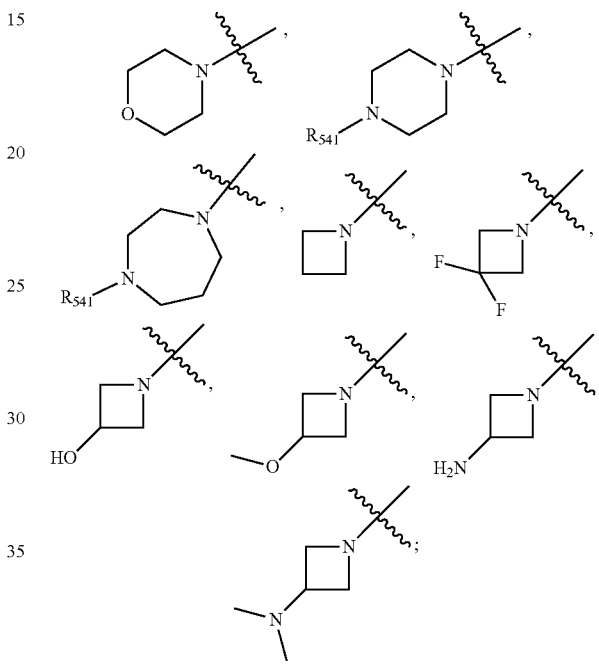

R⁵⁵¹(C1-C6)alkyl OC(O)—, —COOH, —C(O)(NRᵃRᵇ); wherein R⁵⁵¹ is H, —OH, a C1-C4 alkoxy, amino, dimethylamino, methylamino, diethylamino, methylethylamino, ethylamino,

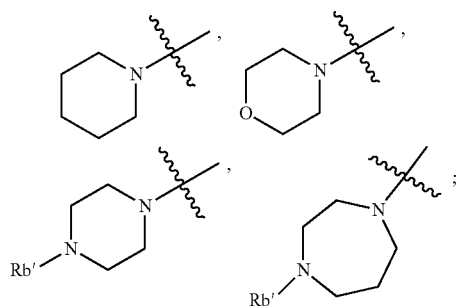

$R^a$ is selected from H, a substituted or unsubstituted C1-C4 alkyl;
$R^b$ is selected from H, a substituted or unsubstituted C1-C4 alkyl,

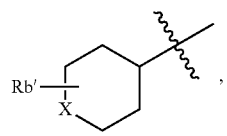

cyclopentyl, $R^{b''}$ (C1-C4)alkyl; wherein X is a hetero atom selected from N, O or S;
R⁵⁵ is 1-3 substituents selected from the group consisting of H, R⁵⁵¹C1-C4 alkyl, halogen, —CN, —NH₂, (R⁵⁵¹C1-C4 alkyl) NH—, (R⁵⁵¹C1-C4 alkyl)O—, dimethylamino, —CH₂(Me)₂, wherein R⁵⁴¹ is selected from H, a C1-C4 alkyl;
R⁵⁷ is selected from a (C1-C4)alkyl,

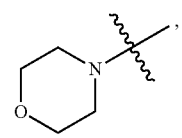

dimethylamino;
$R^{b''}$ is selected from the group consisting of —OH, a C1-C3 alkoxy, dimethylamino,

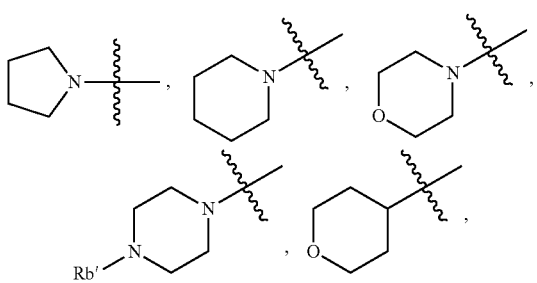

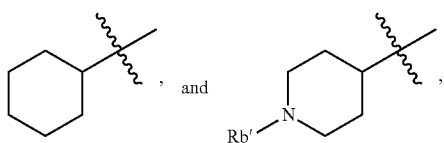, and

In another preferred embodiment, the compound of formula I has the structure of formula Ia:

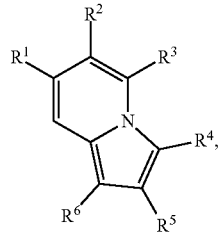

Ia wherein, the $R^1$, $R^2$, $R^3$, $R^4$, $R^5$, and $R^6$ are as described above.

In another preferred embodiment, $R^2$, $R^4$, $R^7$-$R^9$, $R^{12}$-$R^{22}$, $R^a$, $R^b$, $R^c$, $R^d$, $R^e$ are substituted by a substituent selected from the group consisting of halogen, a C1-4 alkyl, trifluoromethyl, amino, nitro, —OH.

In another preferred embodiment, $R^7$ is H.

In another preferred embodiment, $R^8$=$R^9$=H.

In another preferred embodiment, Z is CH.

In another preferred embodiment, $R^2$ is methyl.

In another preferred embodiment, the compound is selected from the group consisting of:

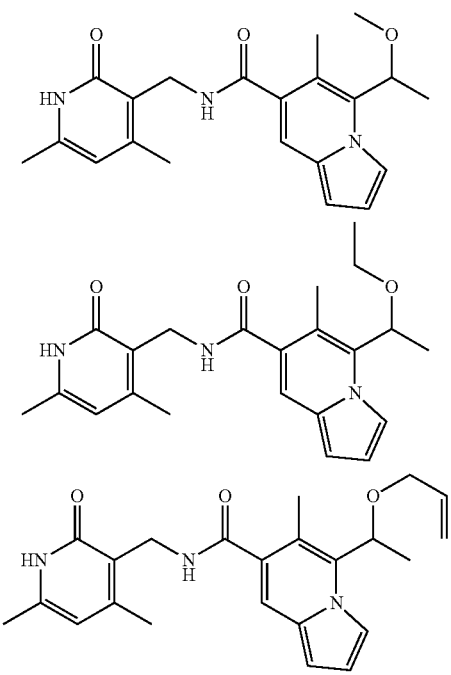

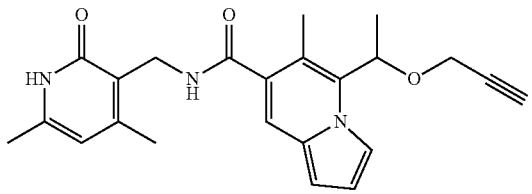

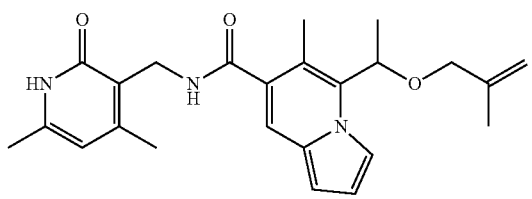

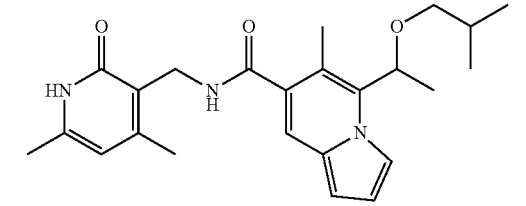

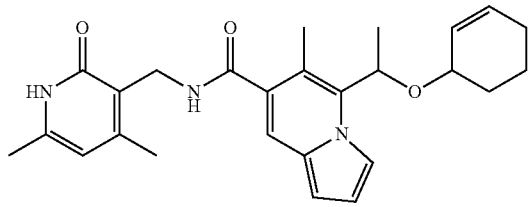

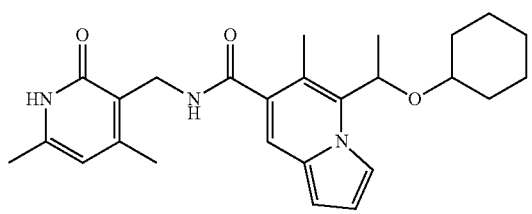

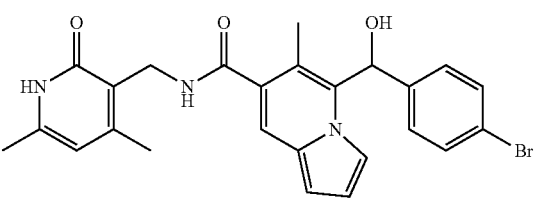

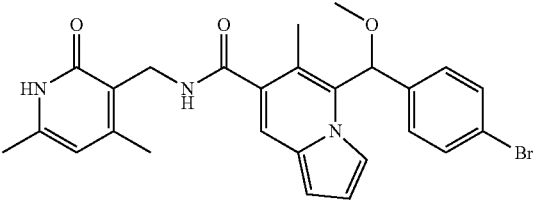

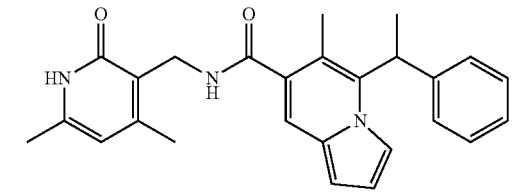

13
-continued
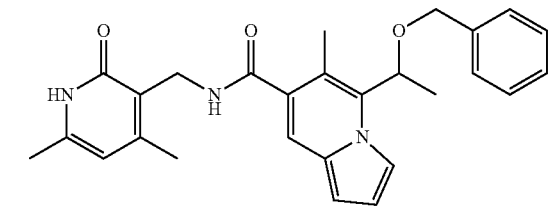
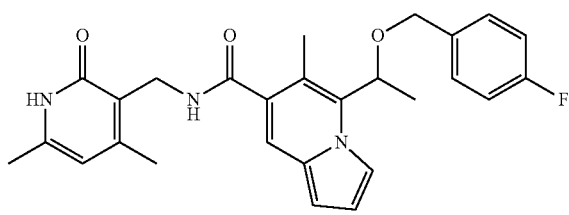
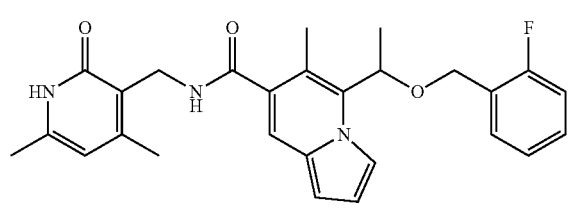
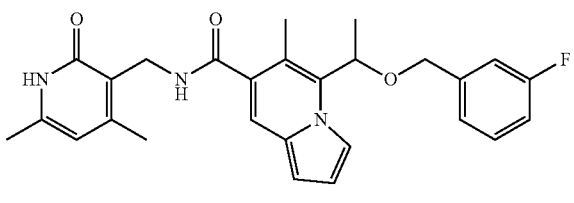
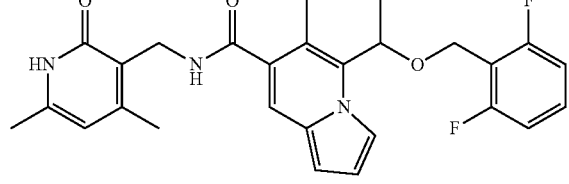
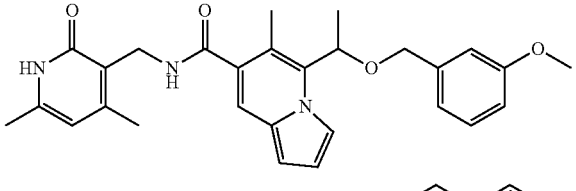
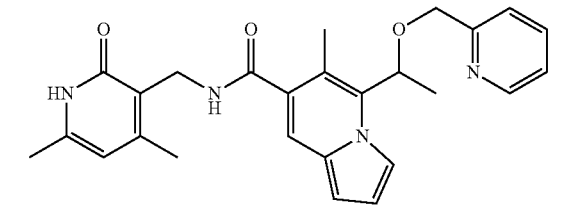
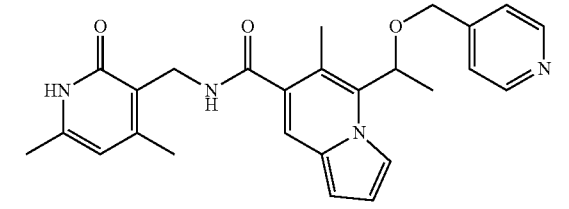
14
-continued
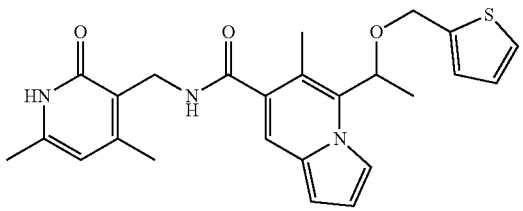
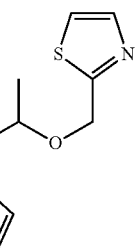
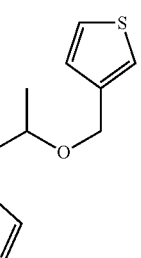
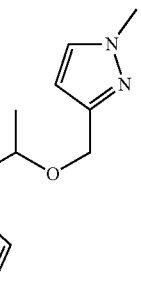
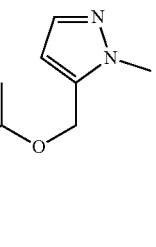
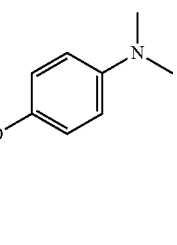

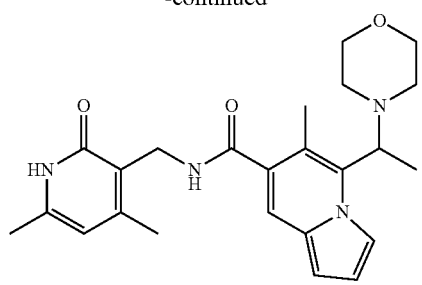
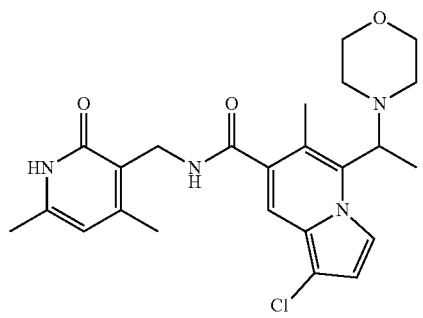
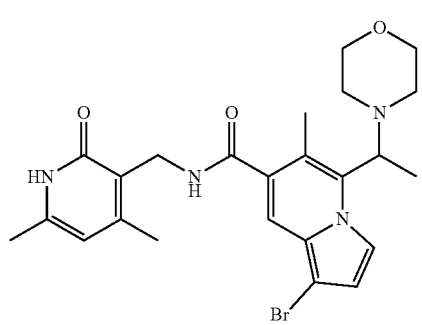
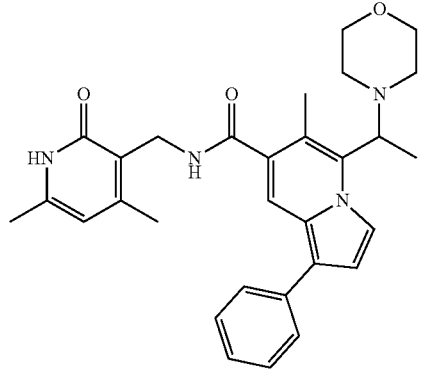
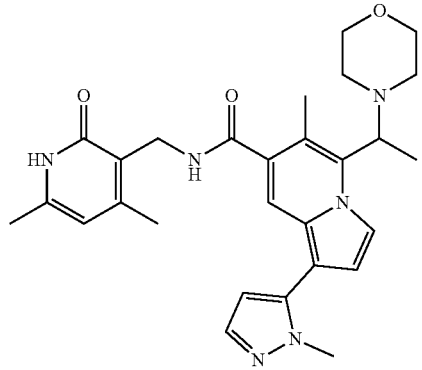
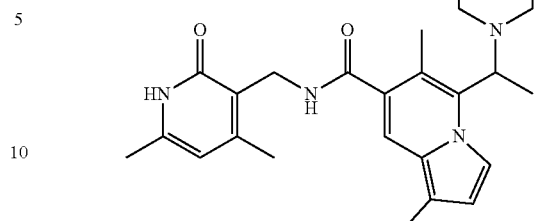
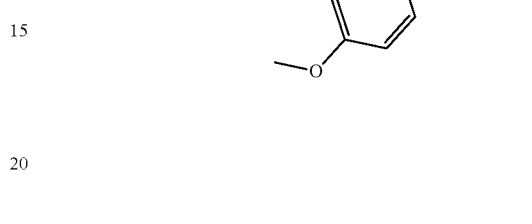
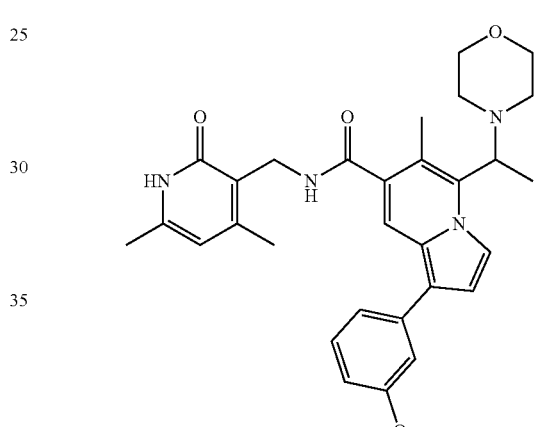
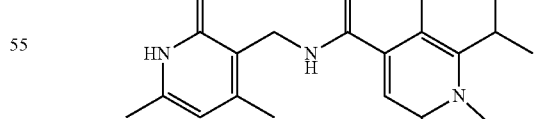
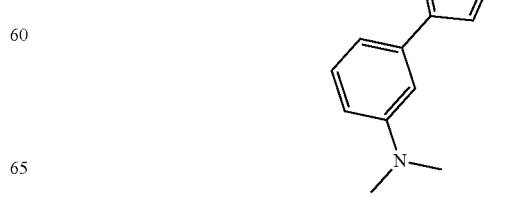

-continued
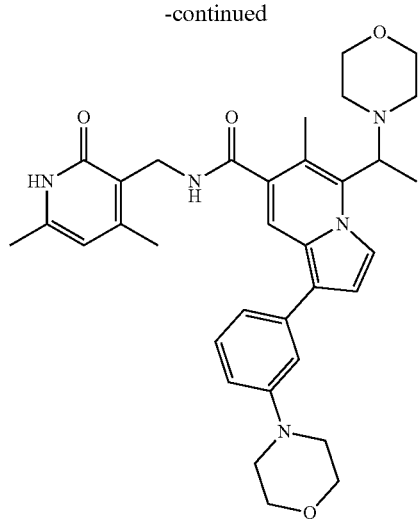
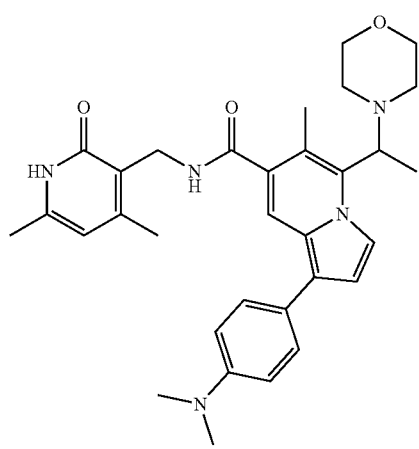
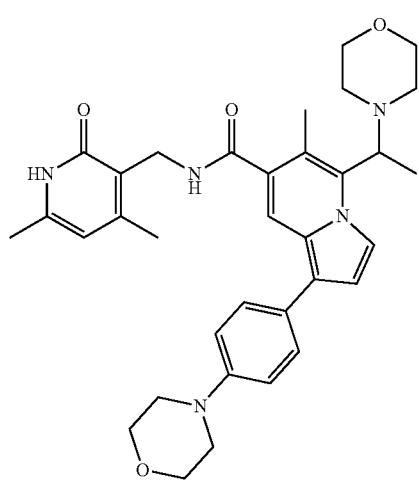
-continued
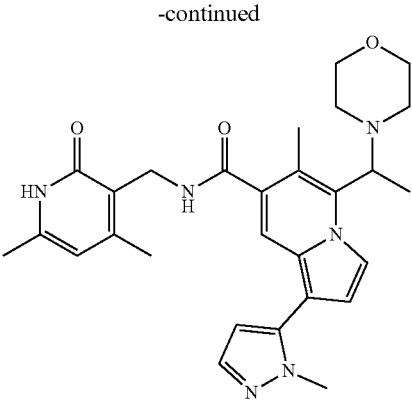
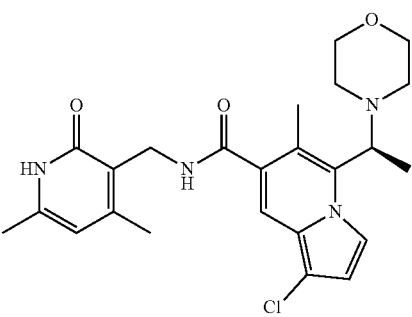
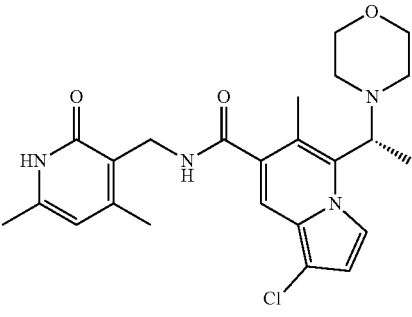
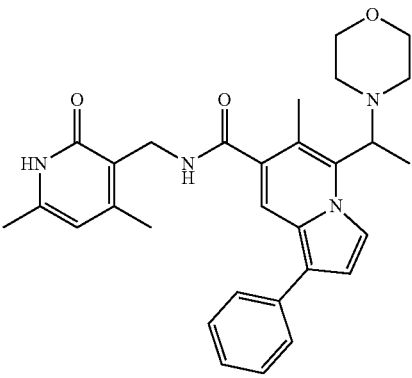

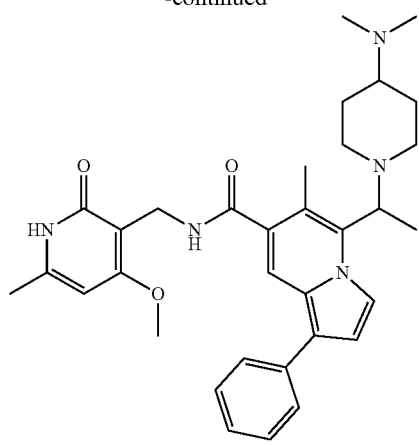
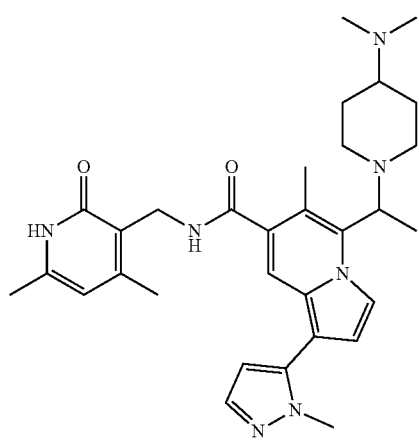
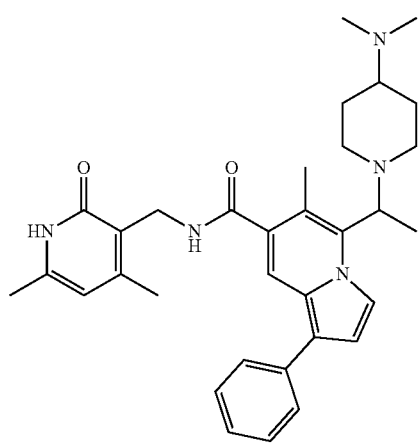
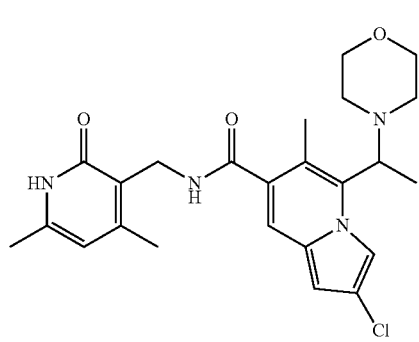
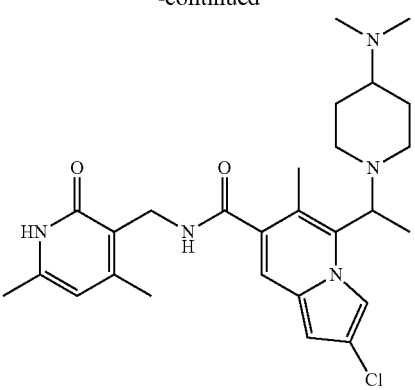
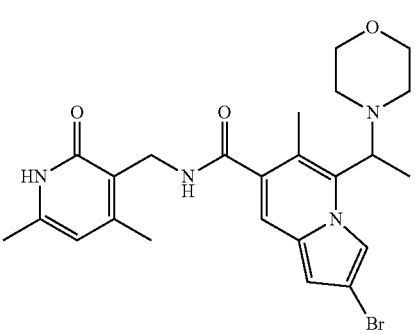
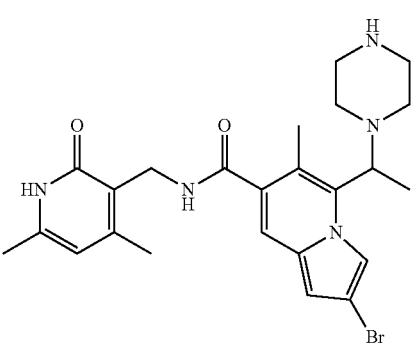
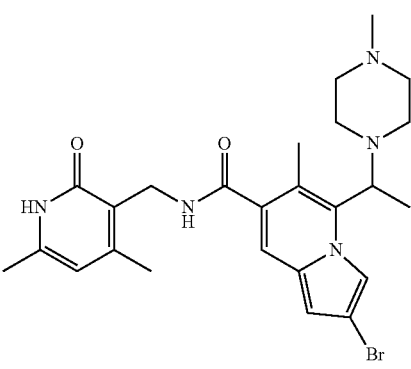

-continued
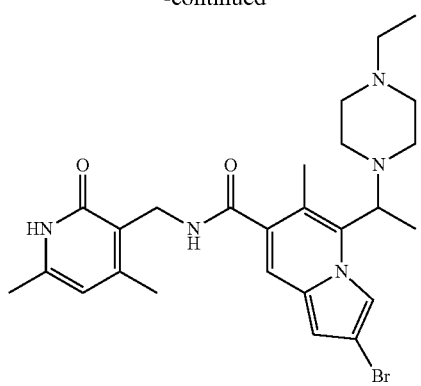
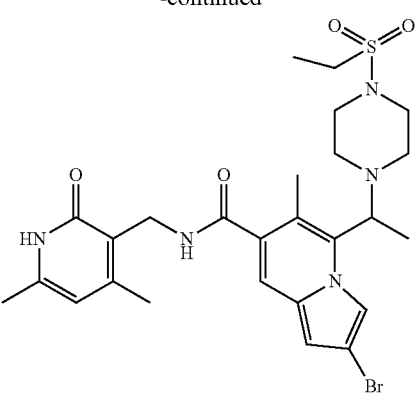
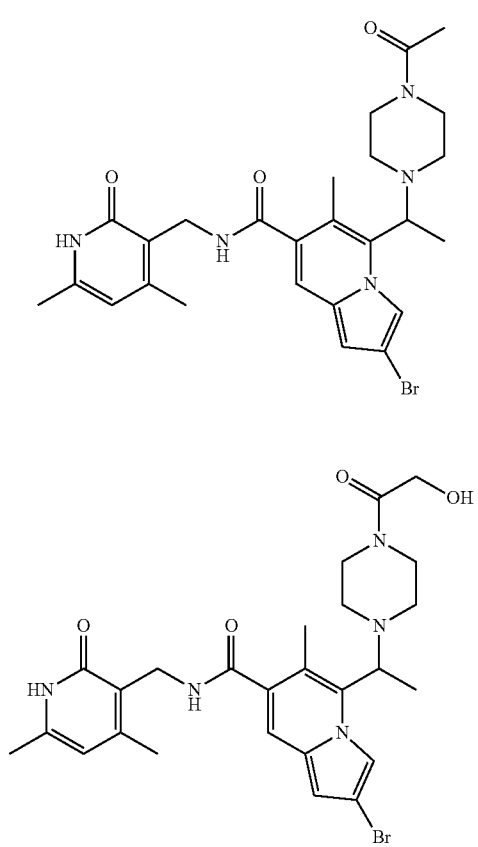
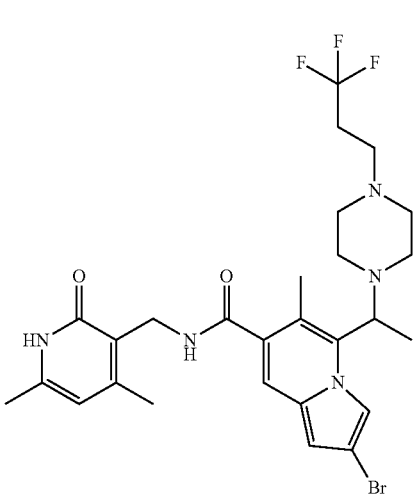
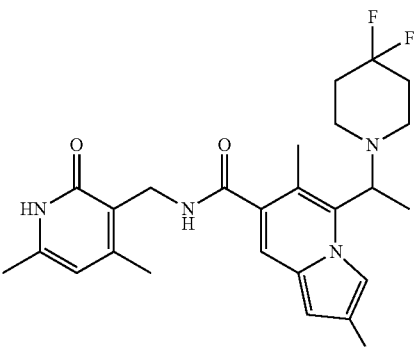
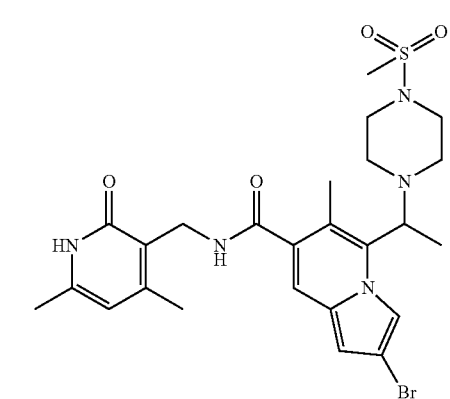
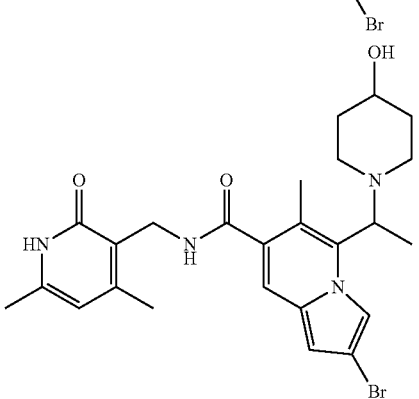

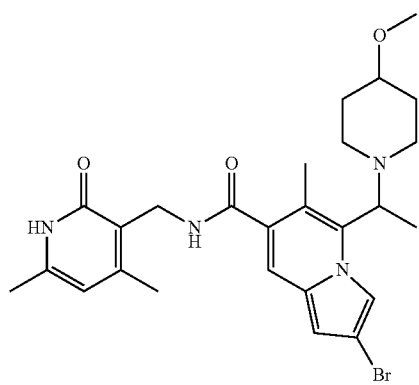
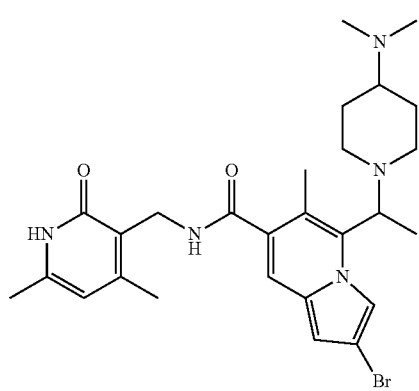
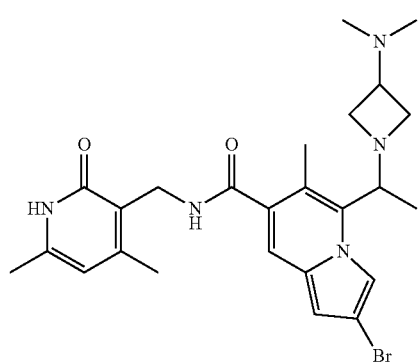
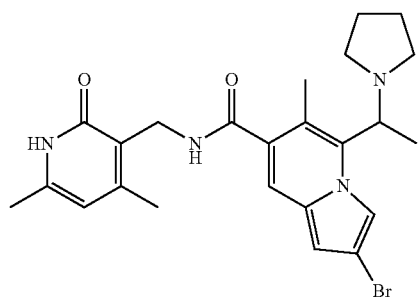
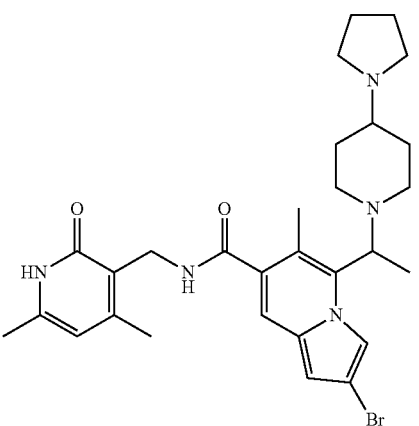
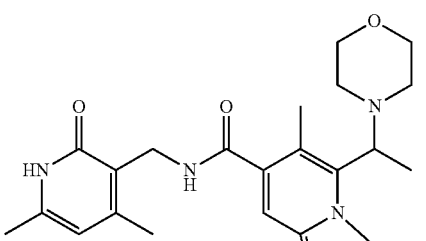
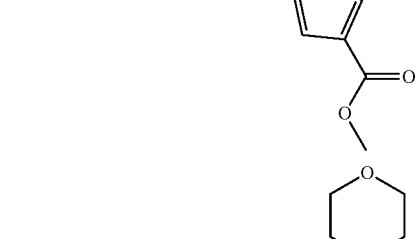
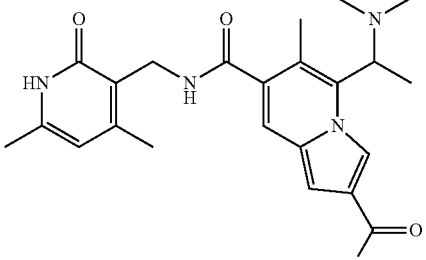
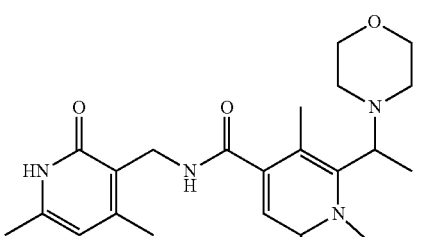
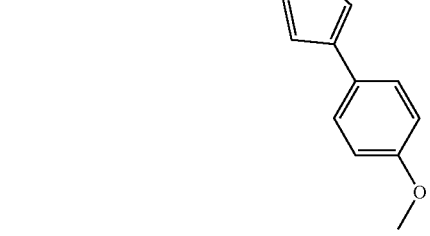

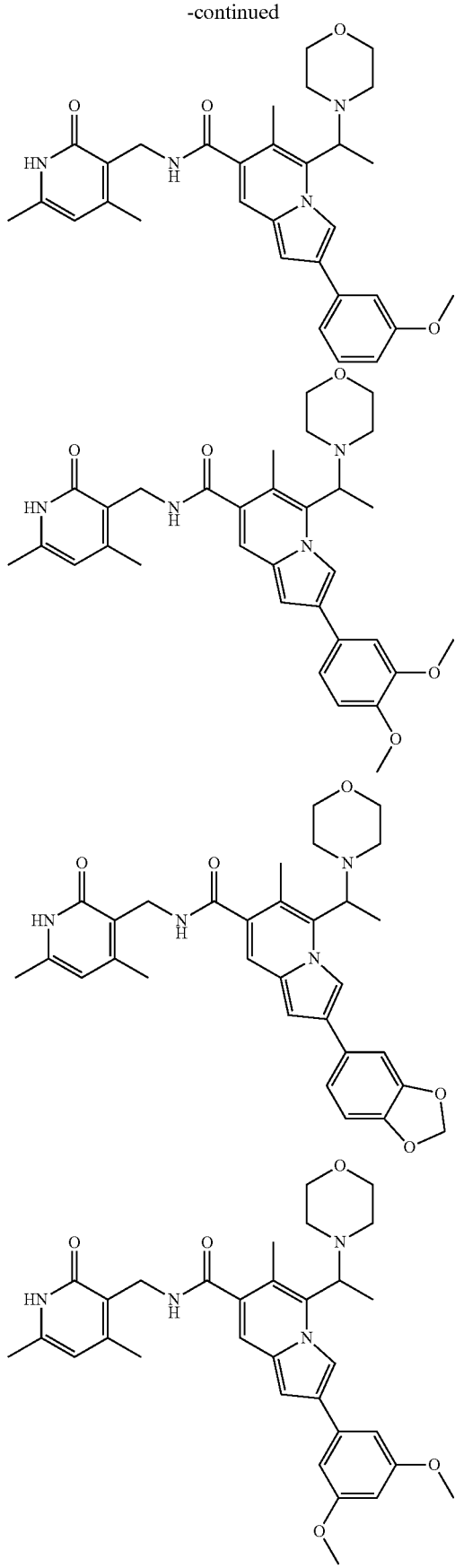
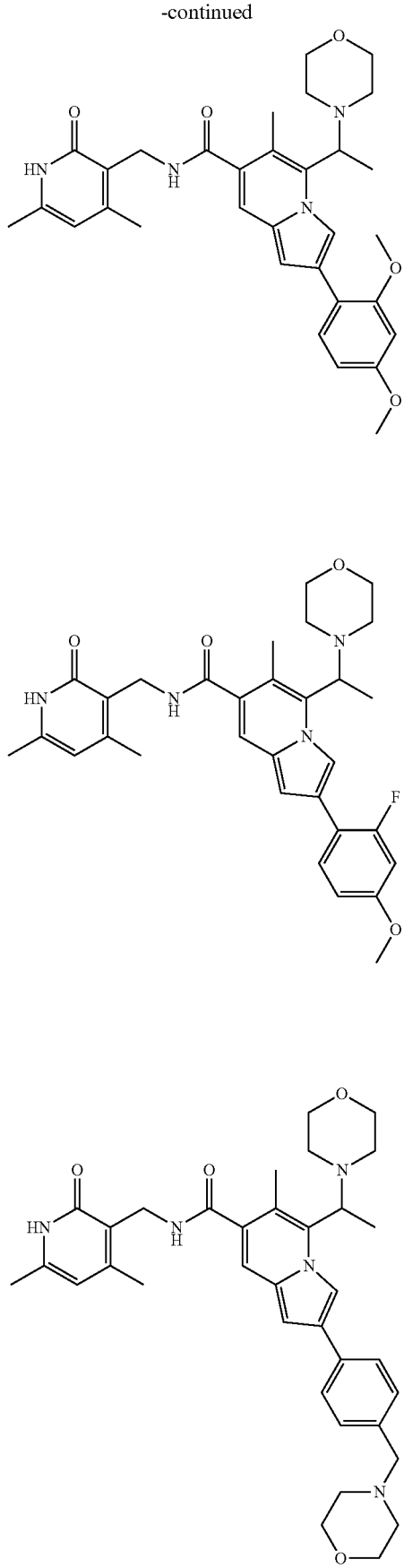

27
-continued
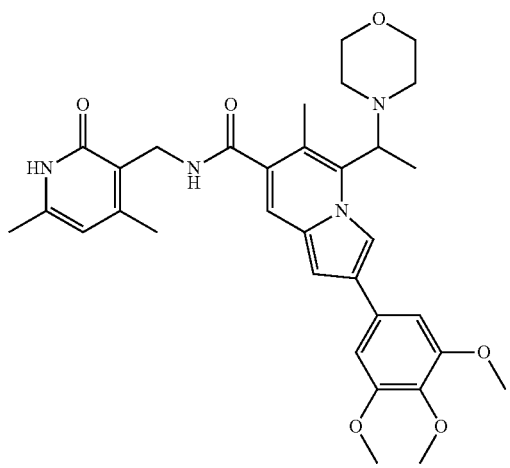
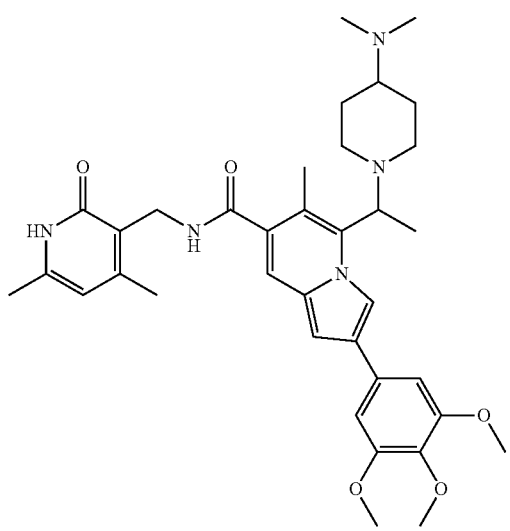
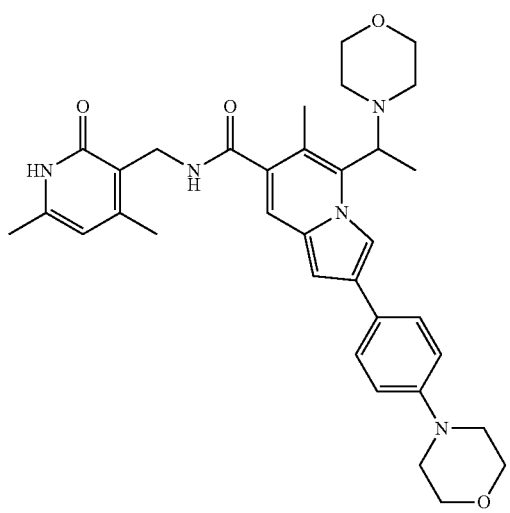
28
-continued
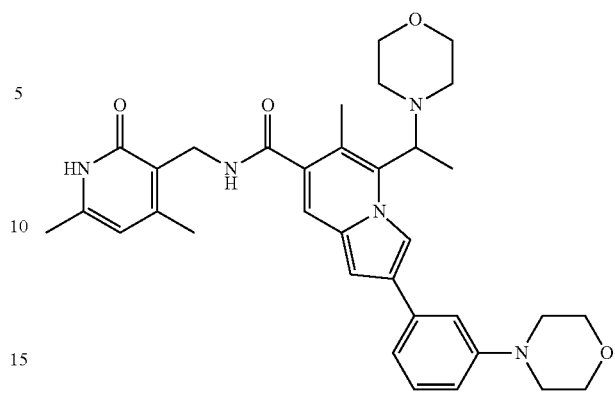
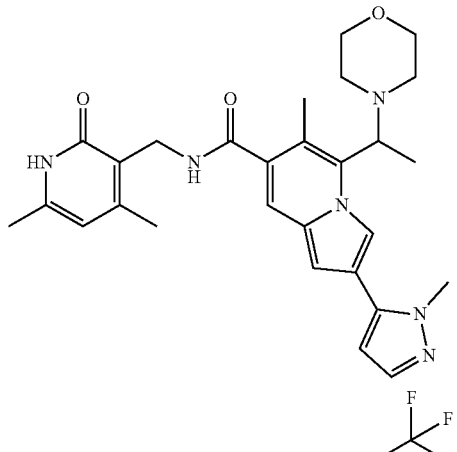
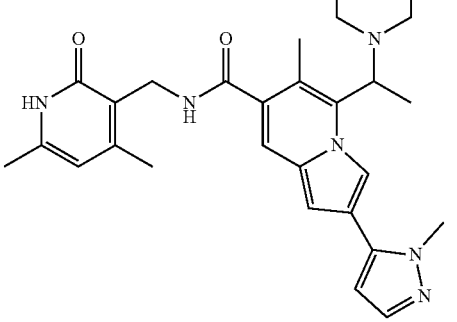
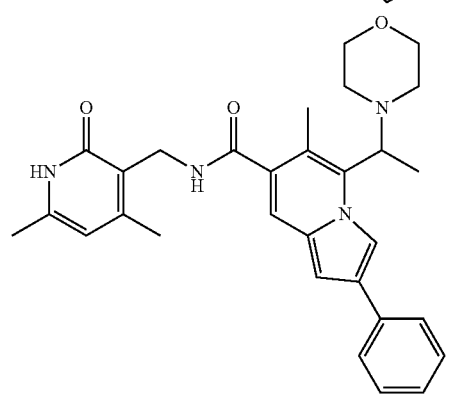

29
-continued
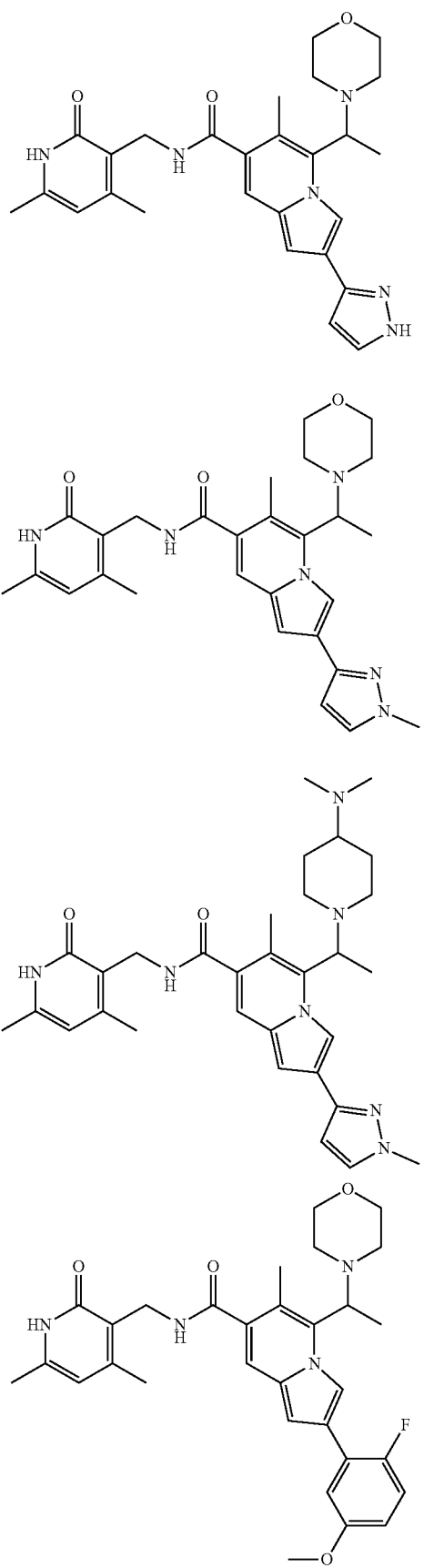
30
-continued
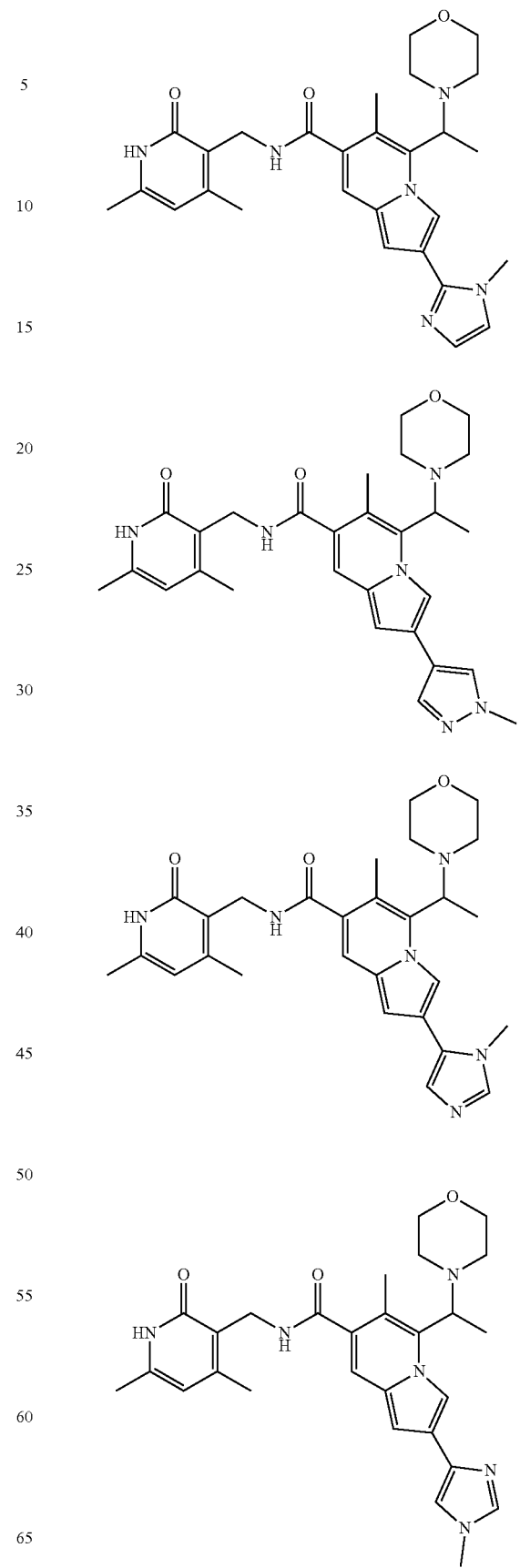

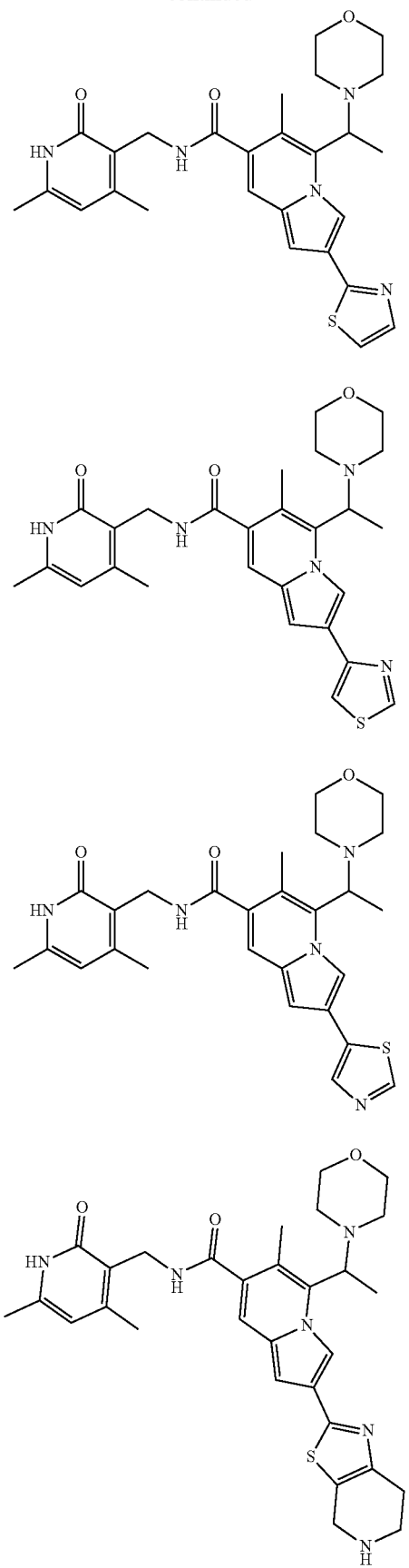
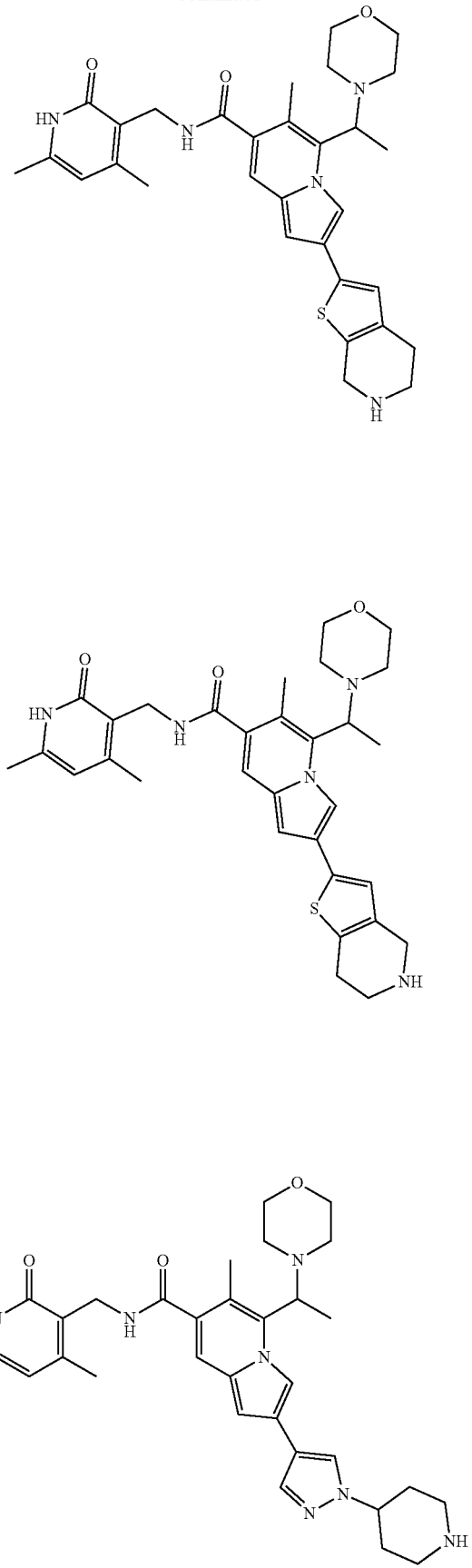

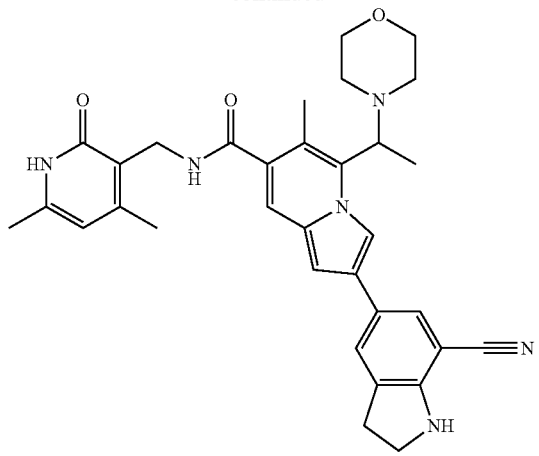
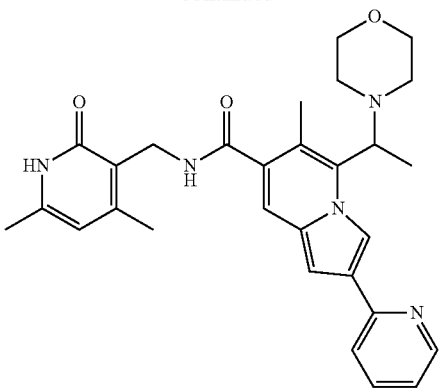
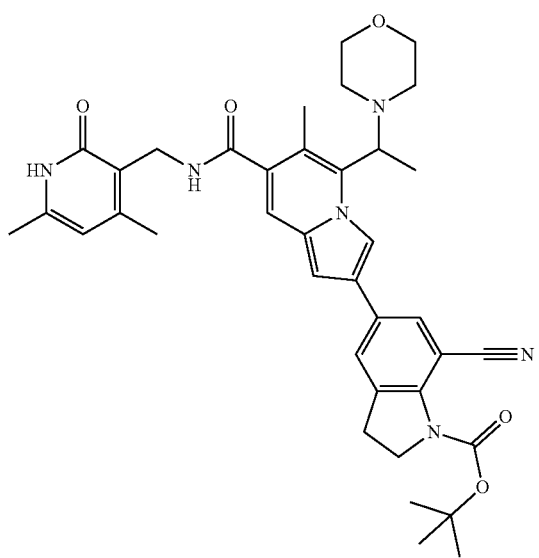
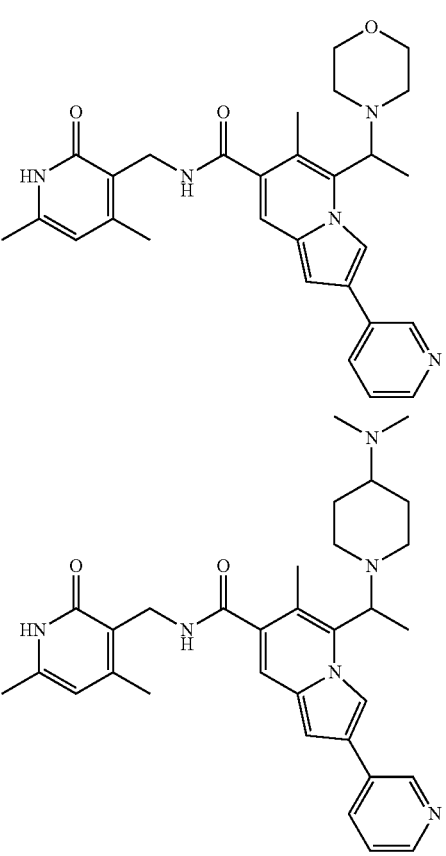
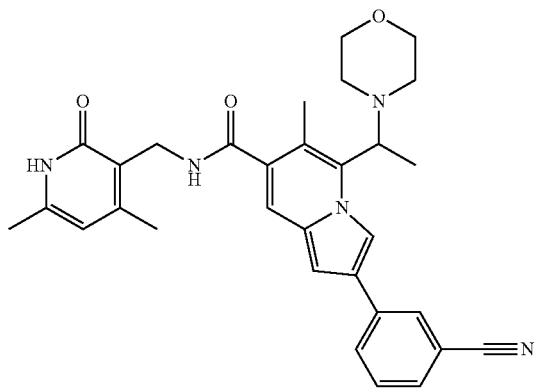

35
-continued
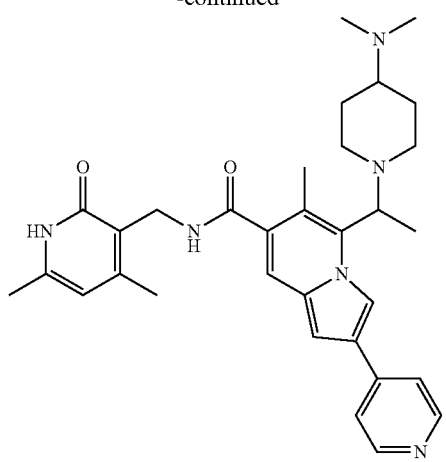
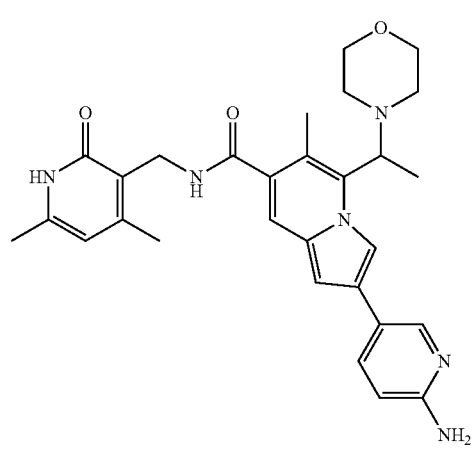
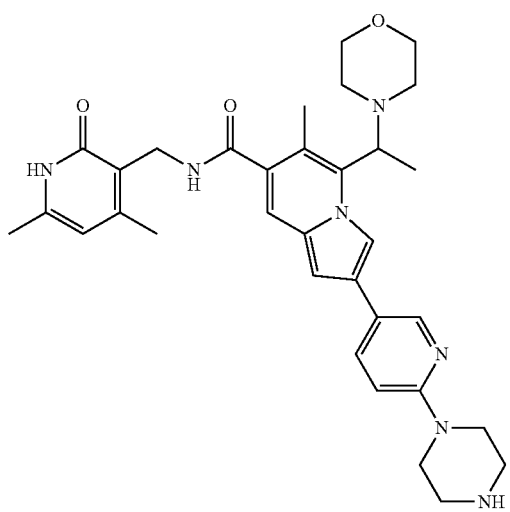
36
-continued
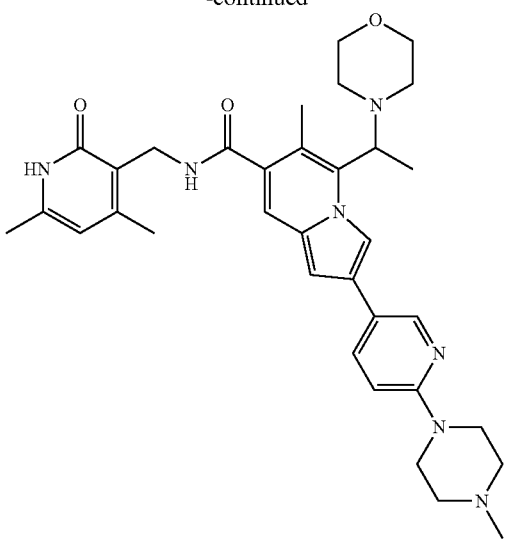
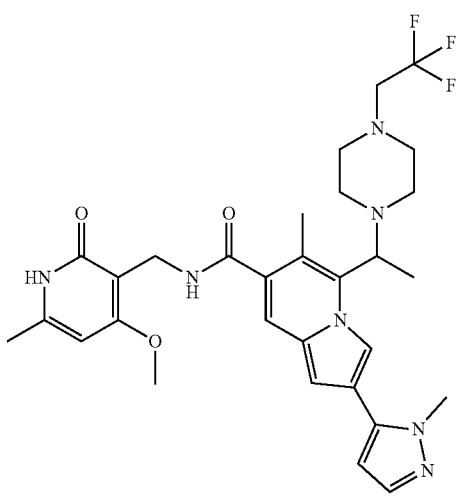
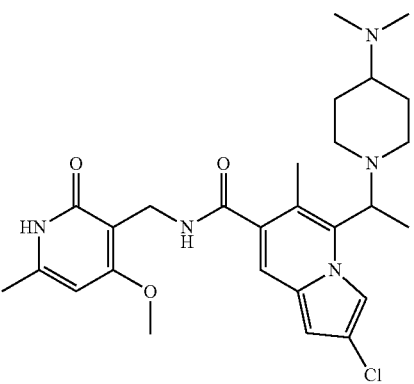

37
-continued
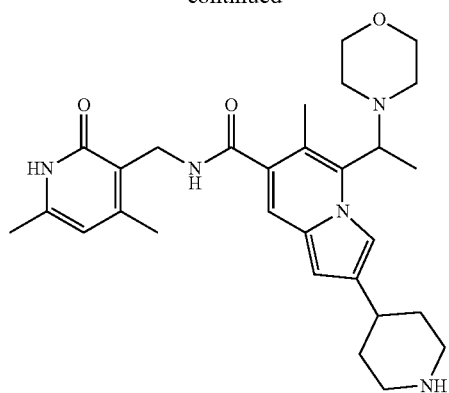
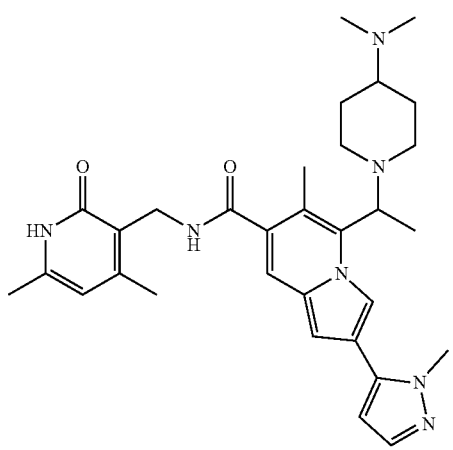
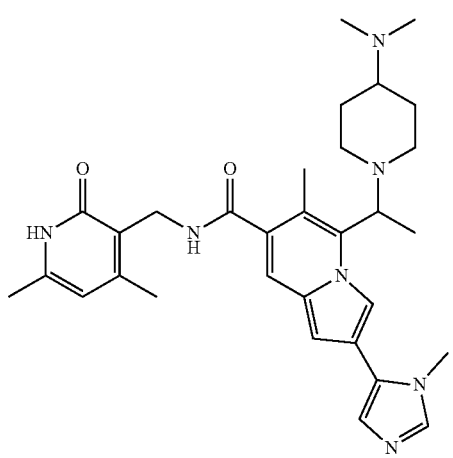
38
-continued
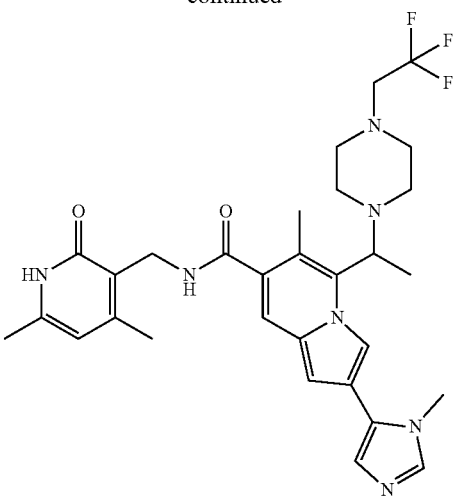
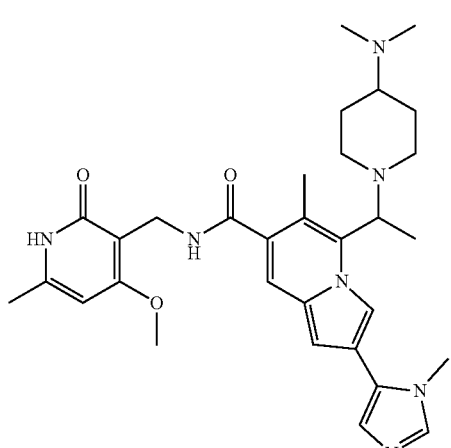
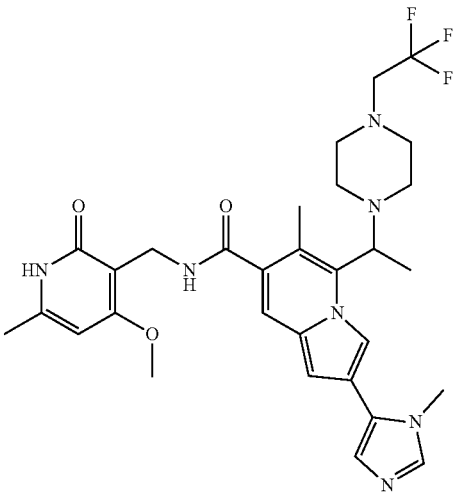

39
-continued
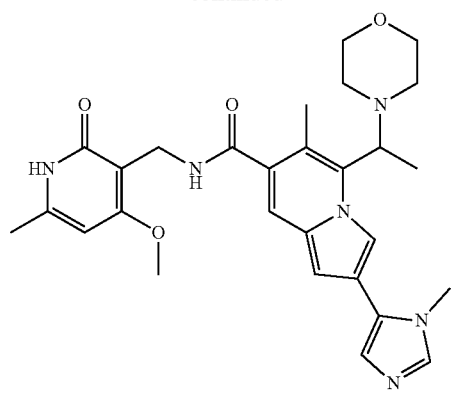
40
-continued
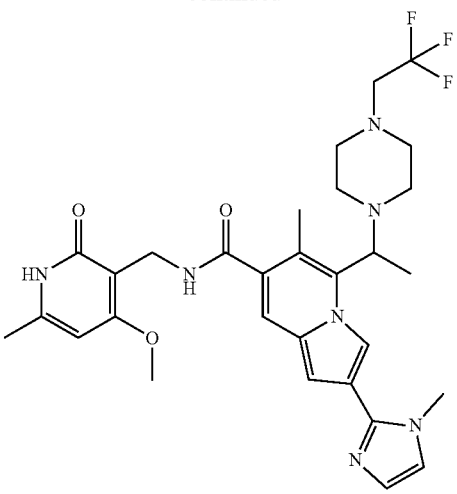
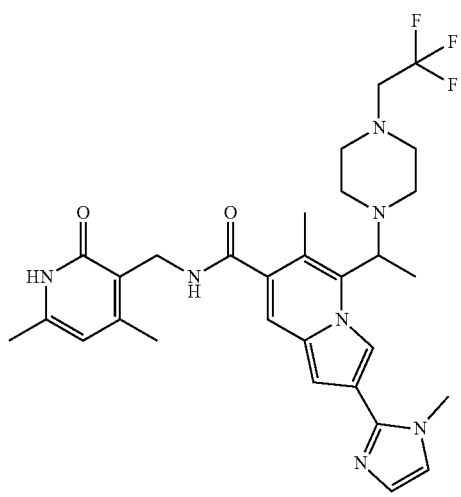
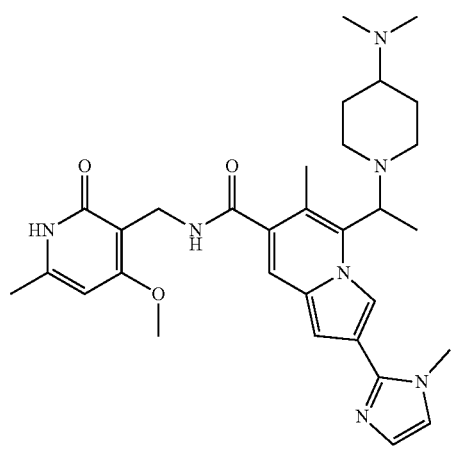
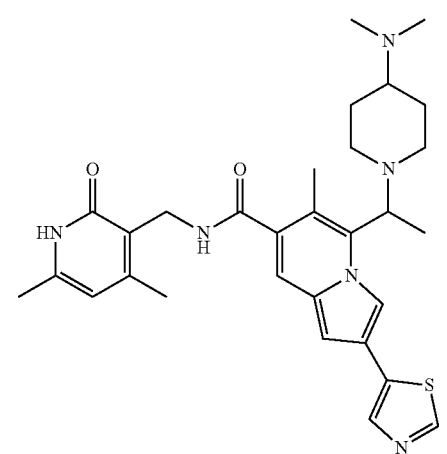

41
-continued
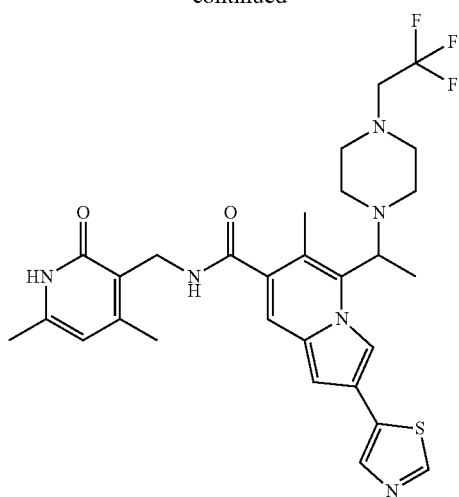
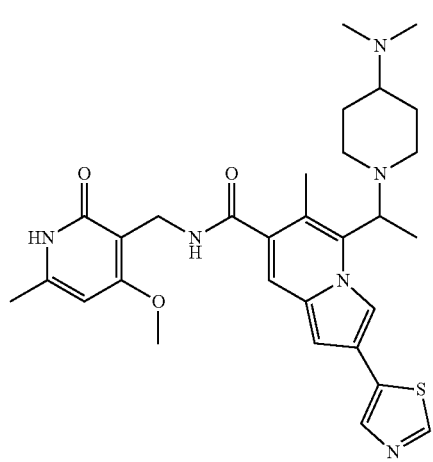
42
-continued
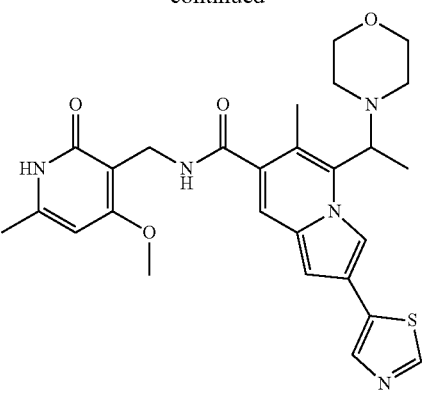
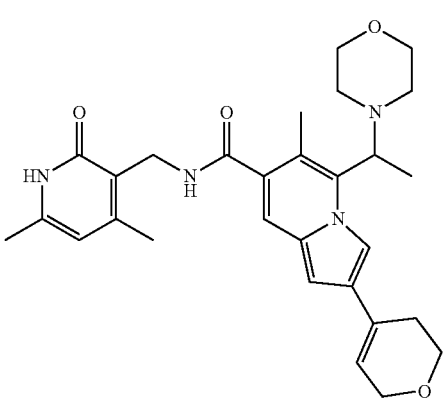
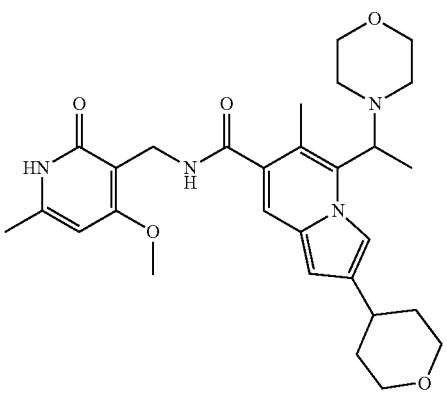
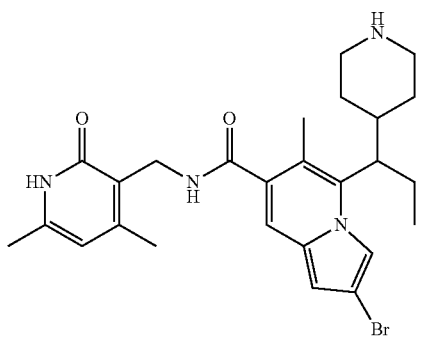

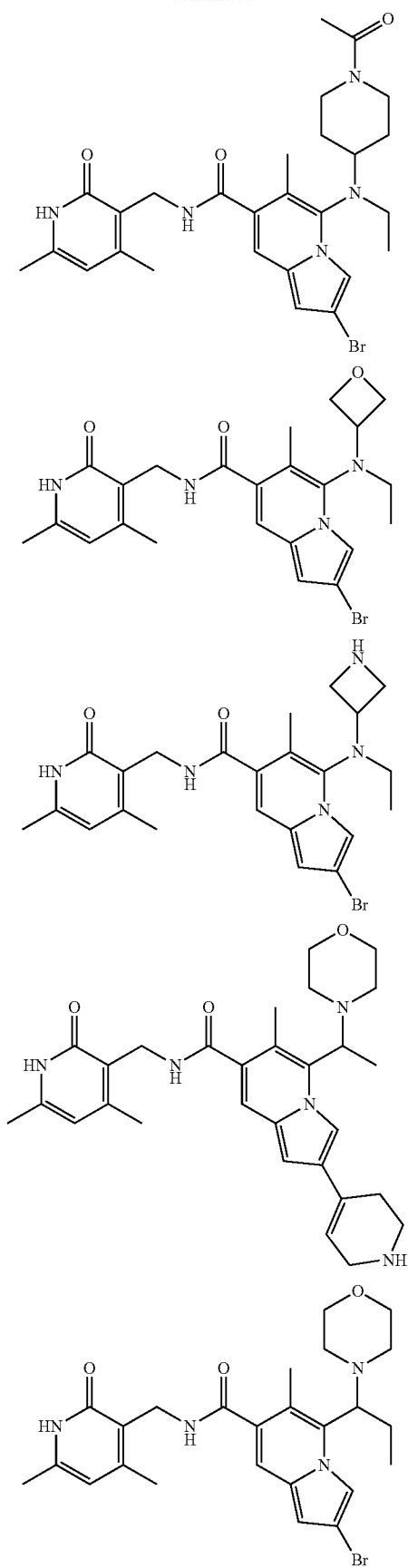
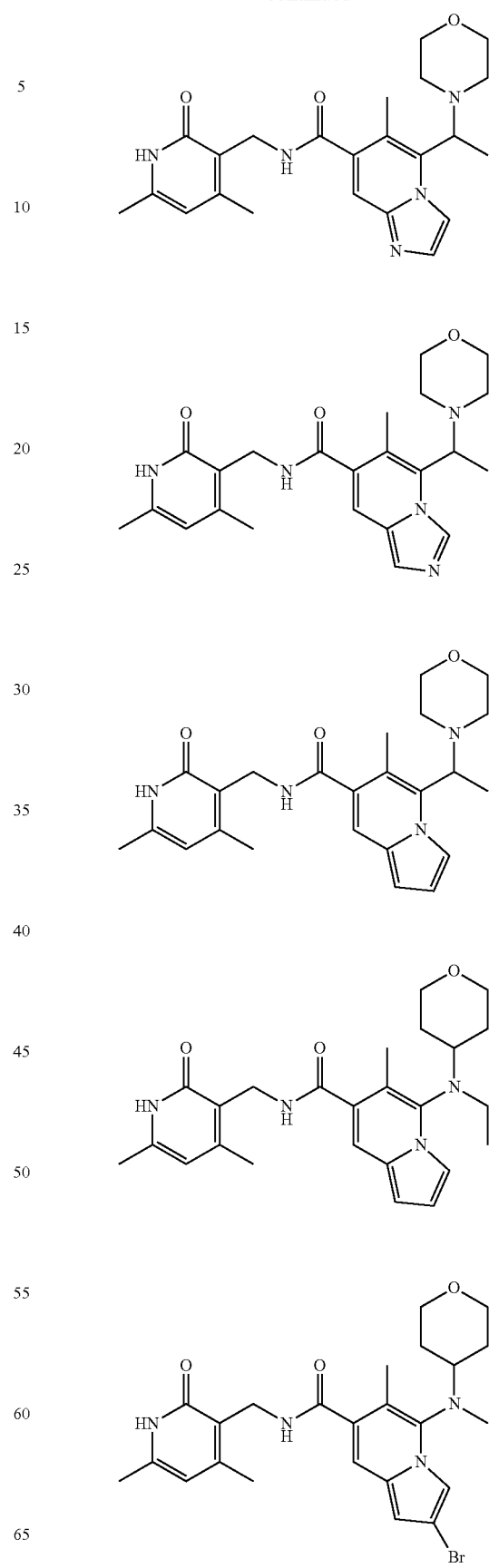

-continued
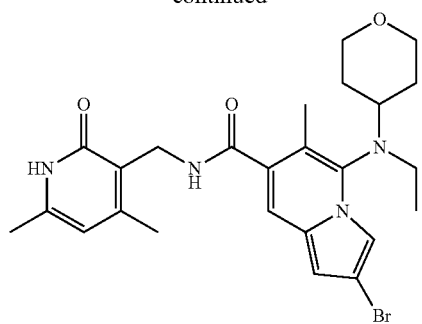
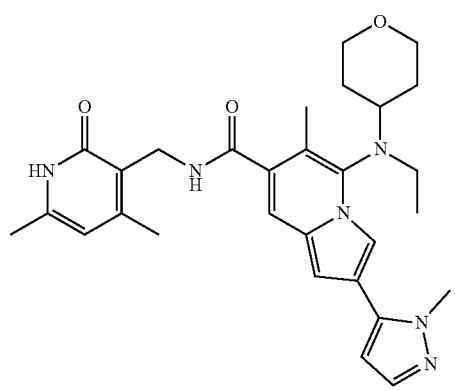
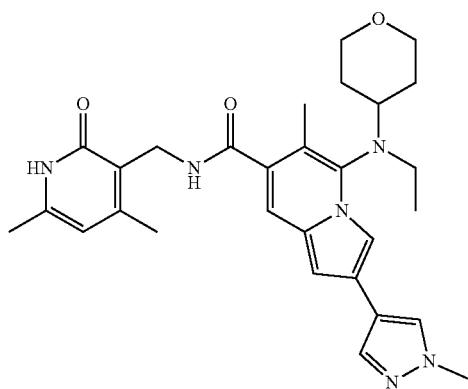
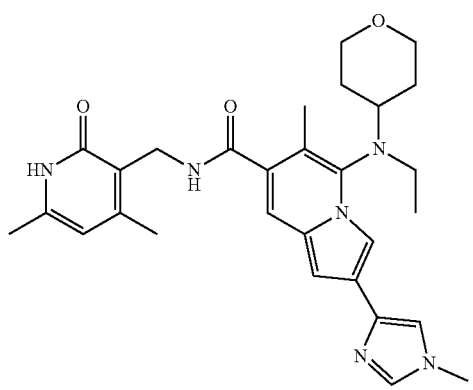
-continued
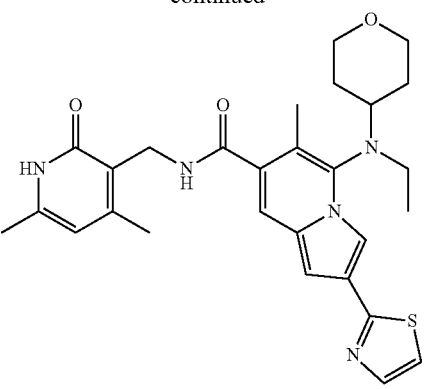
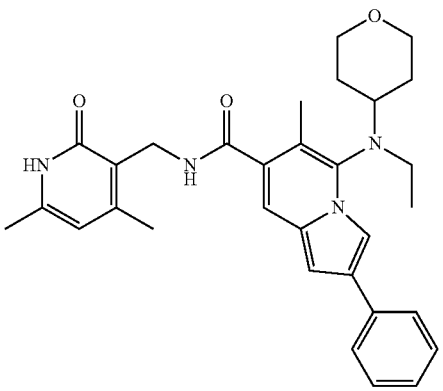
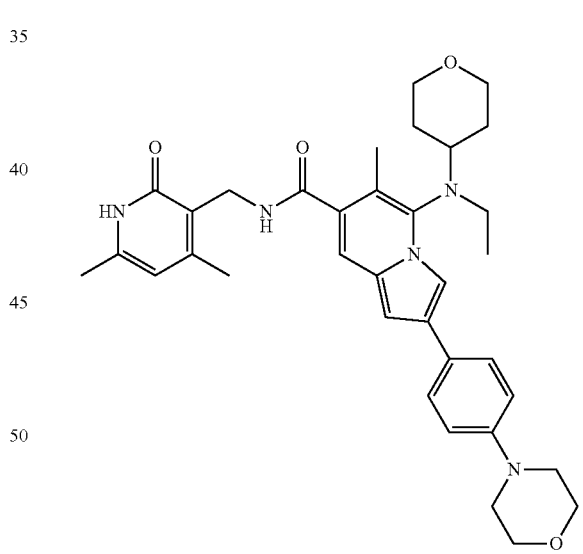
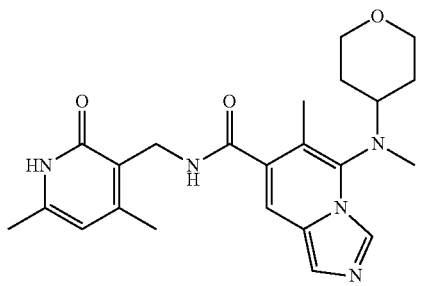

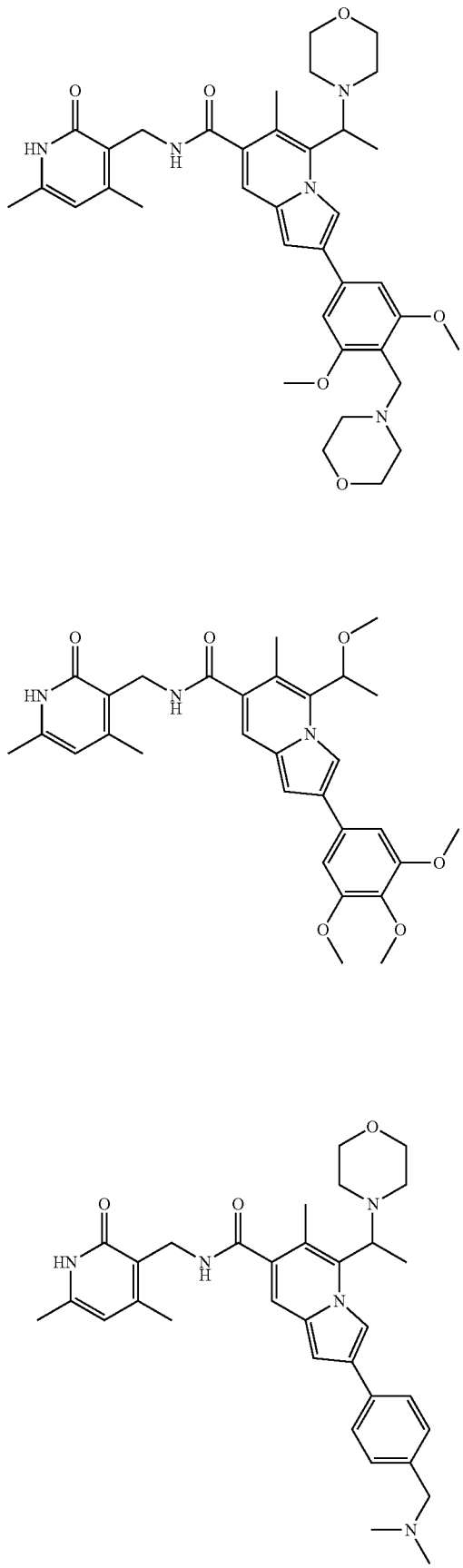
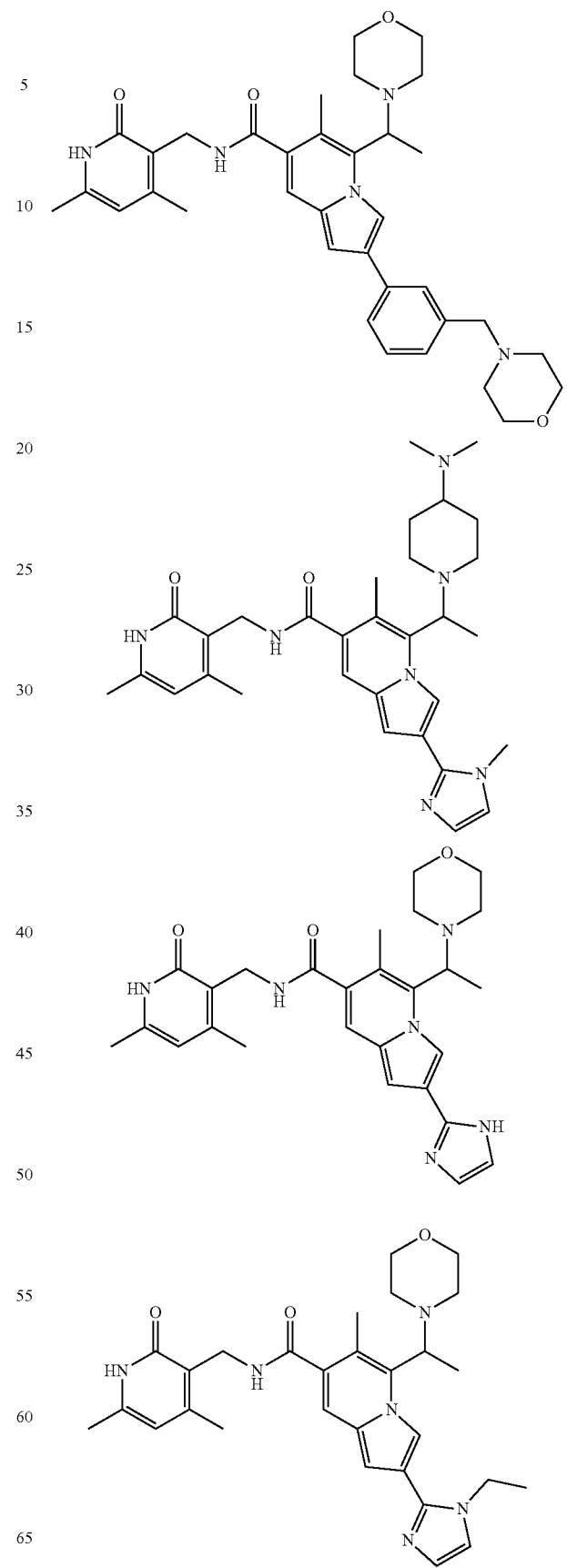

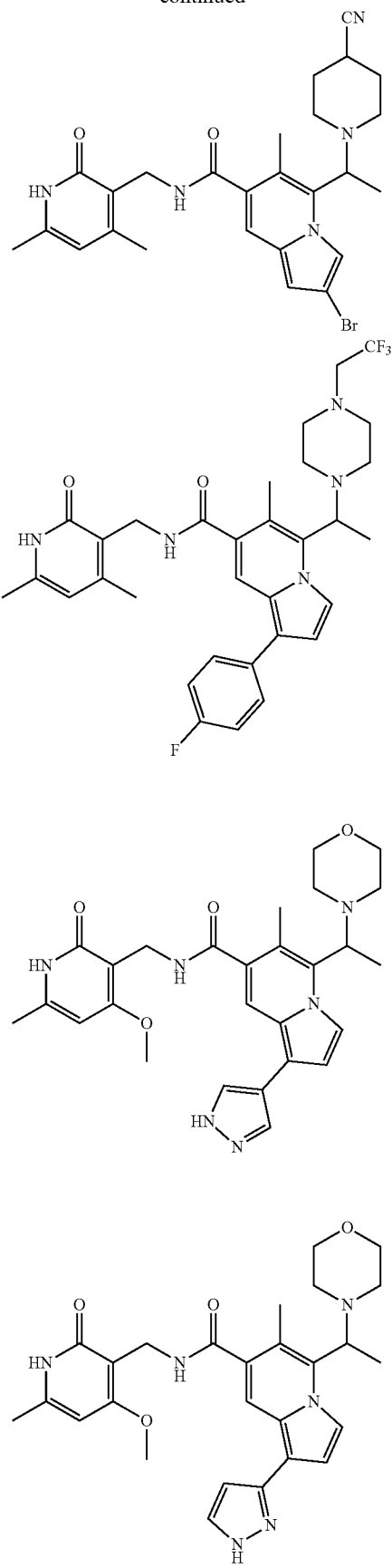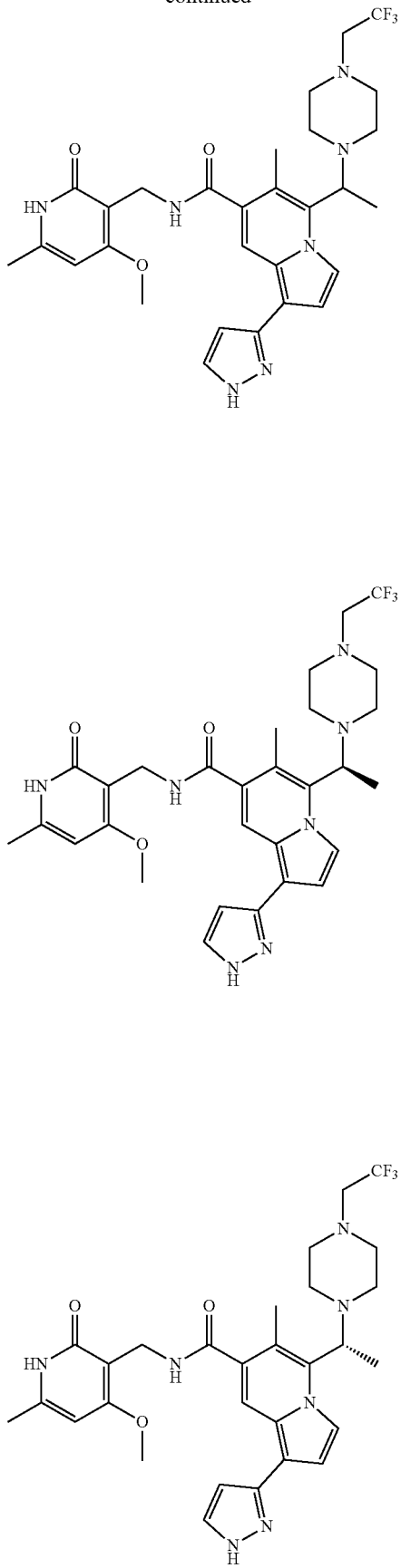

51
-continued
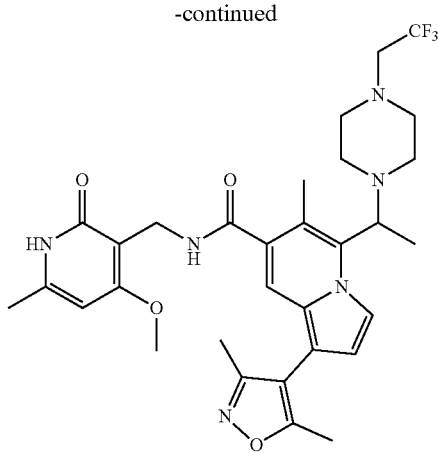
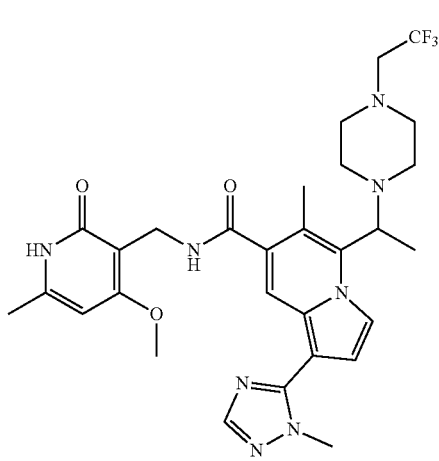
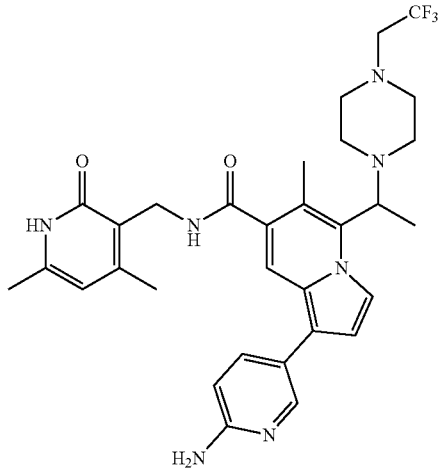
52
-continued
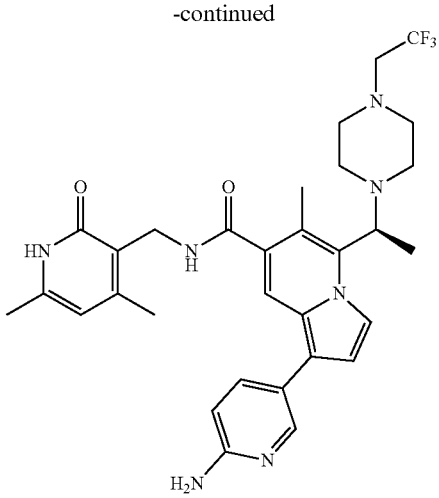
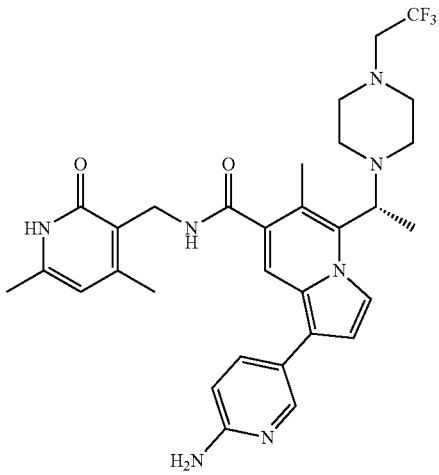
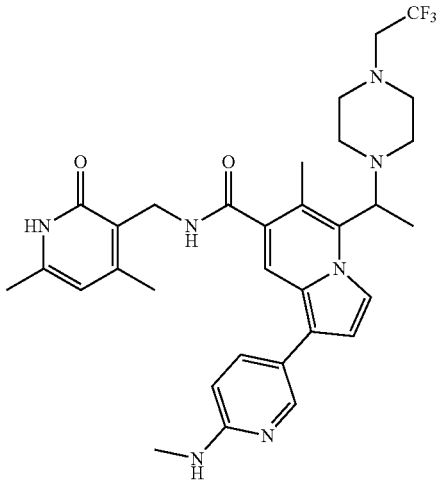

53
-continued
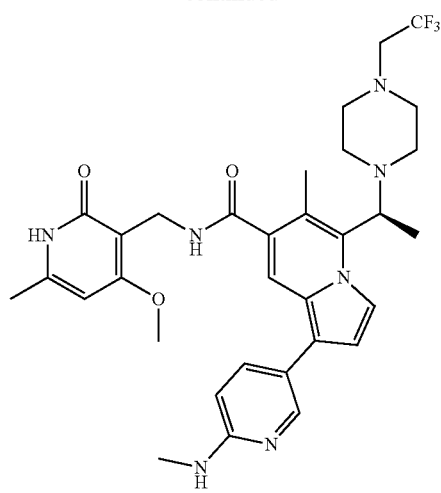
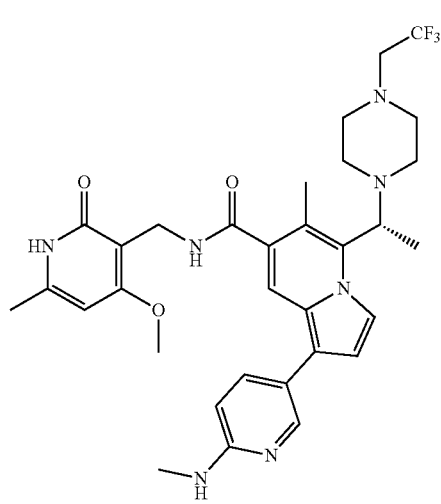
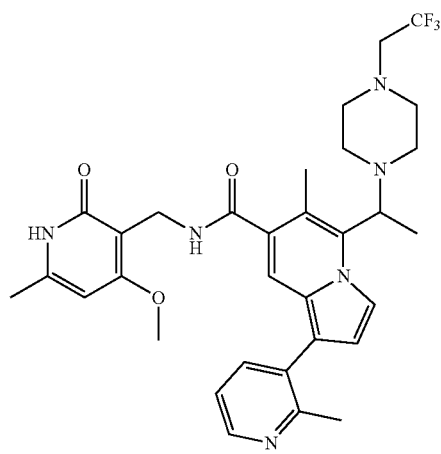
54
-continued
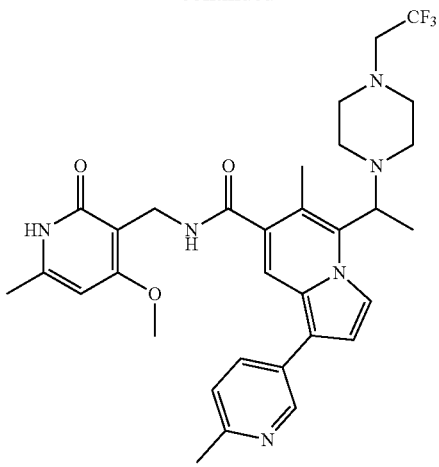
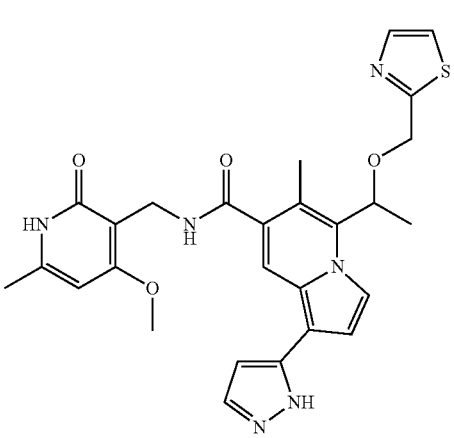
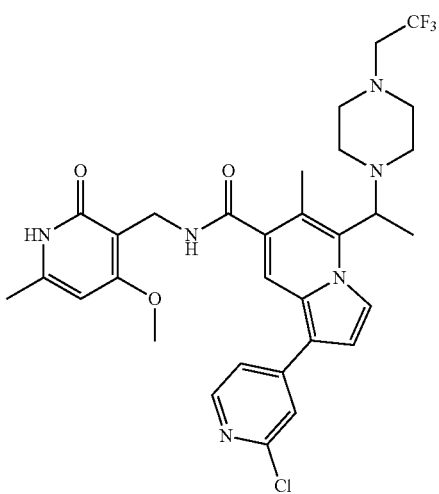

55
-continued
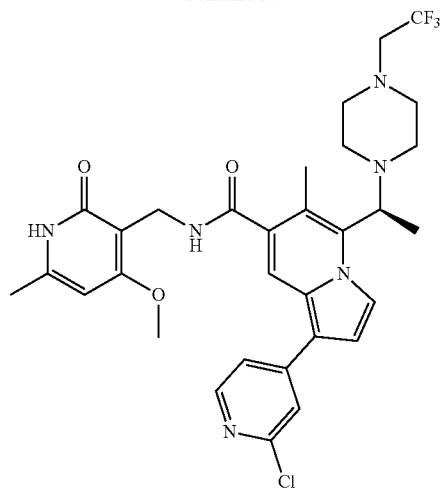
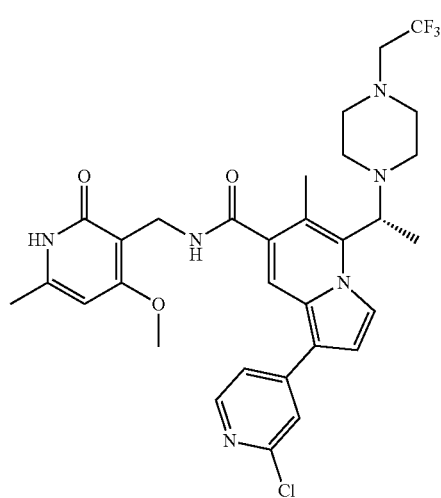
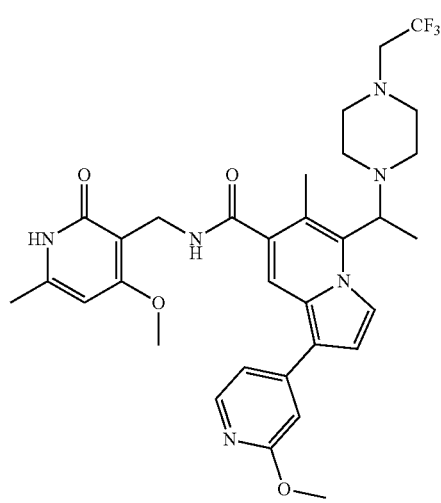
56
-continued
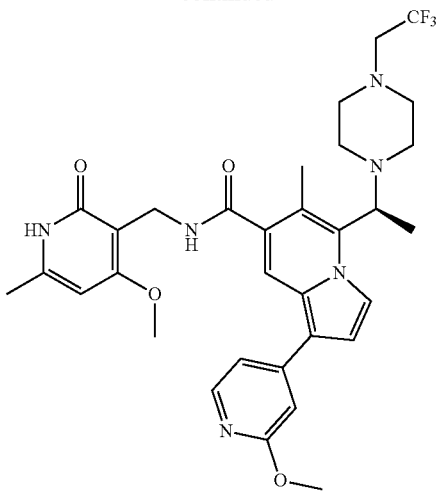
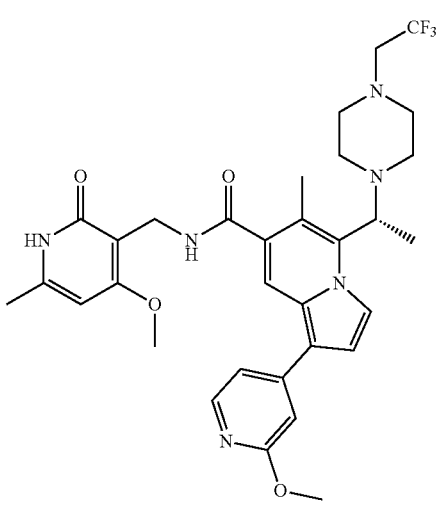
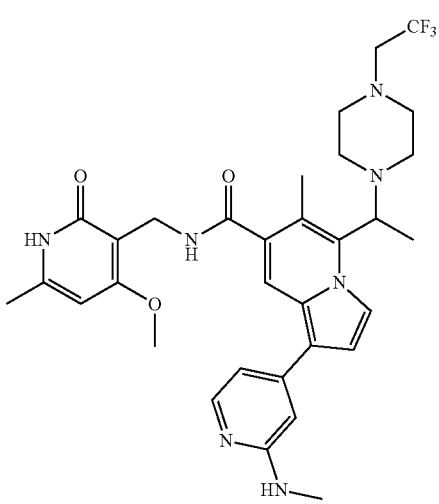

57
-continued
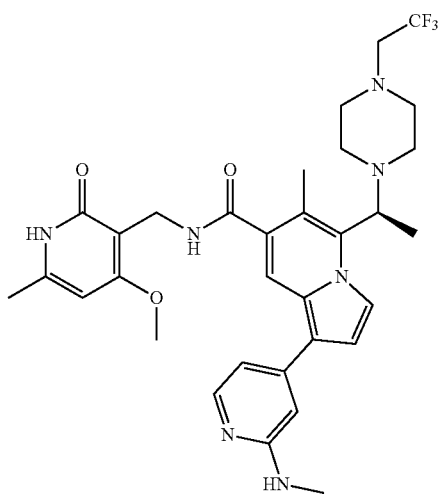
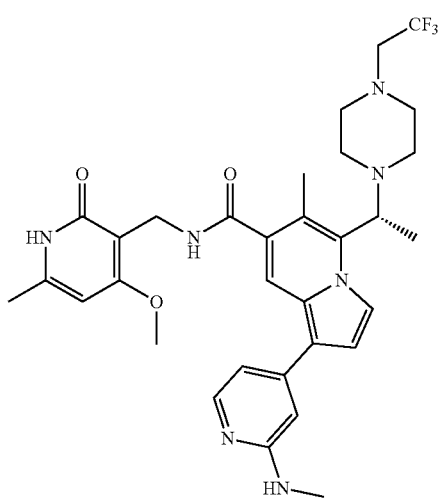
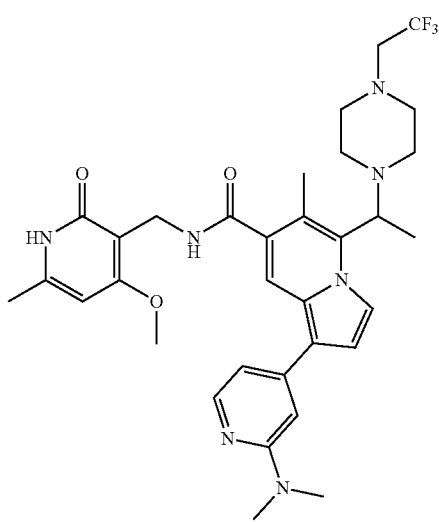
58
-continued
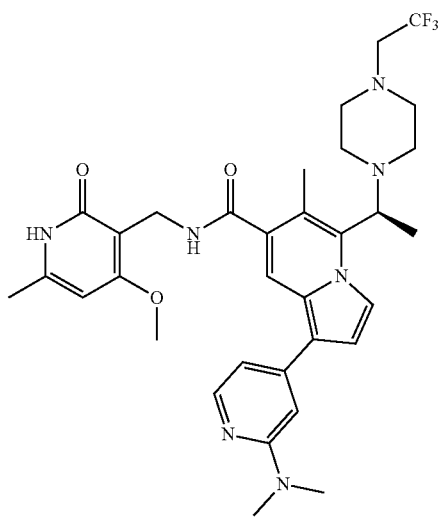
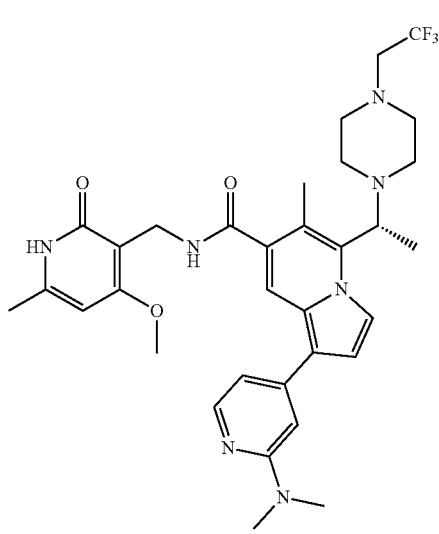

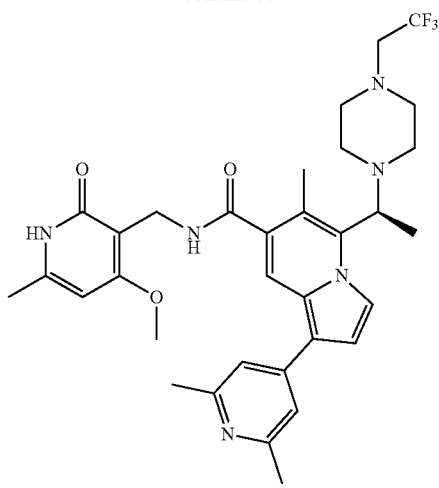
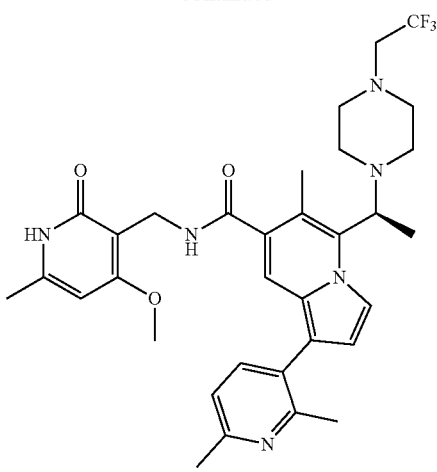
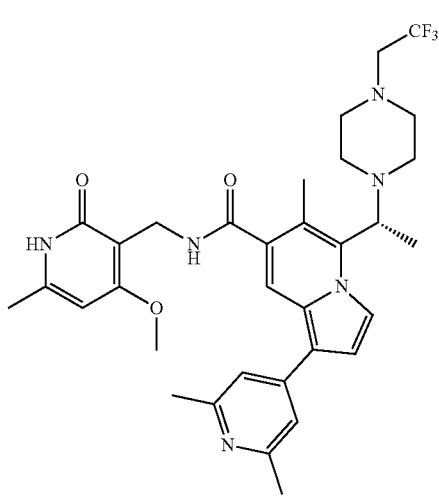
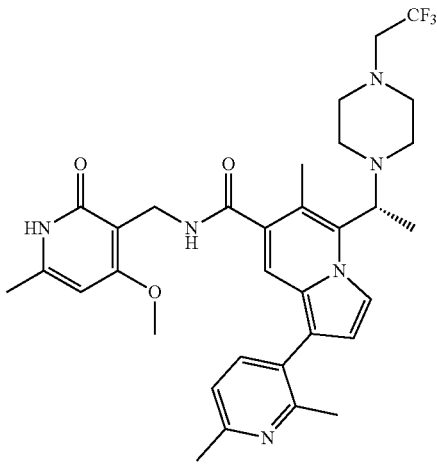
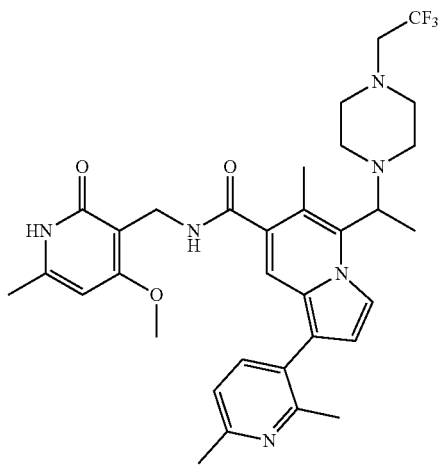

61
-continued
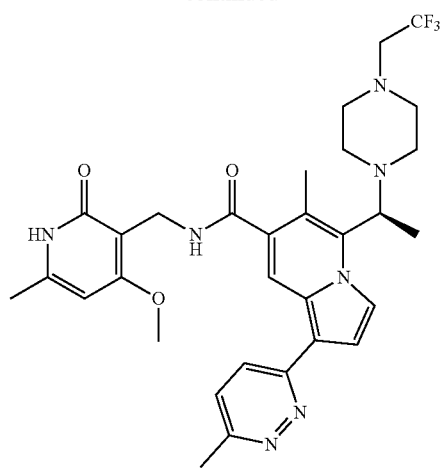
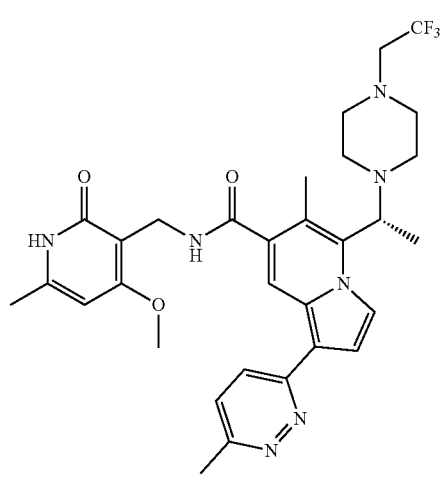
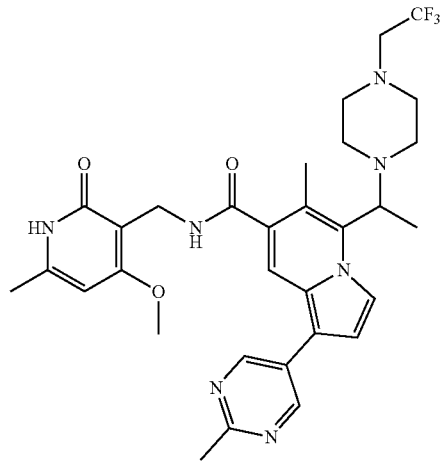
62
-continued
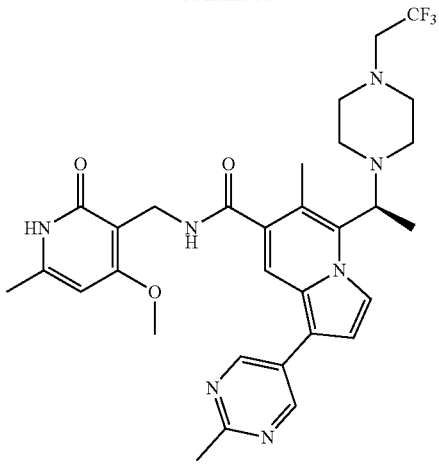
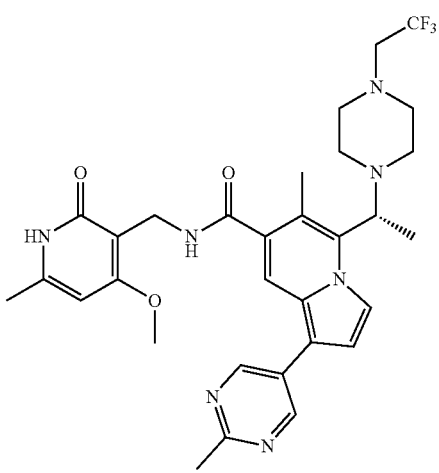
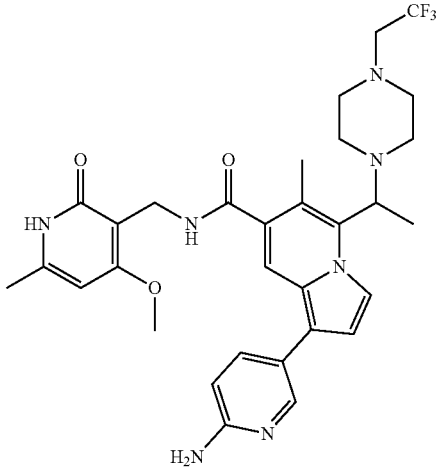

63
-continued
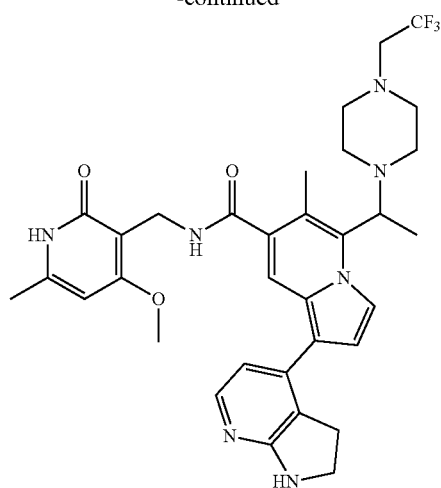
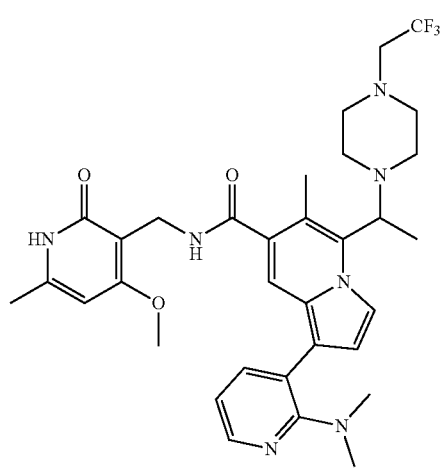
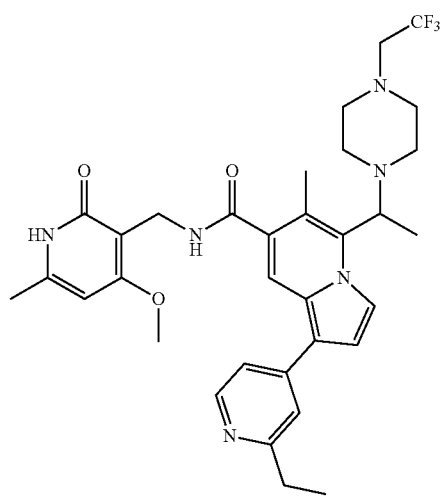
64
-continued
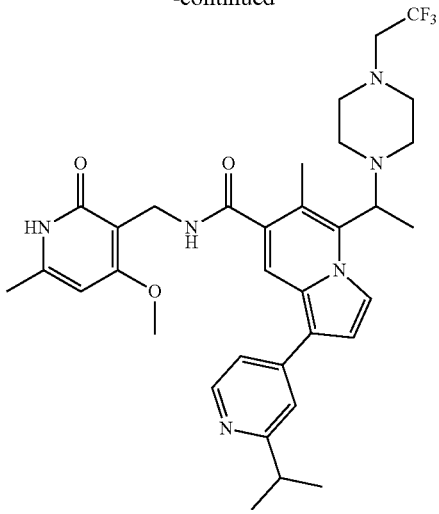
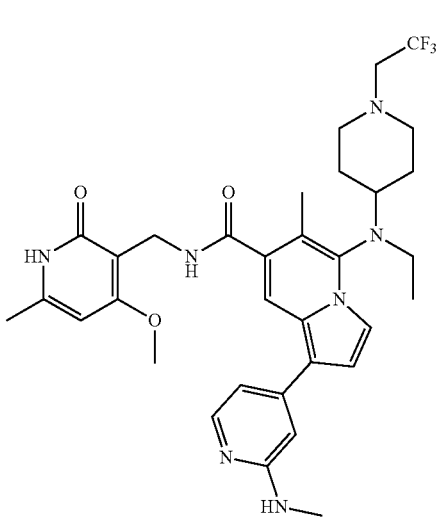
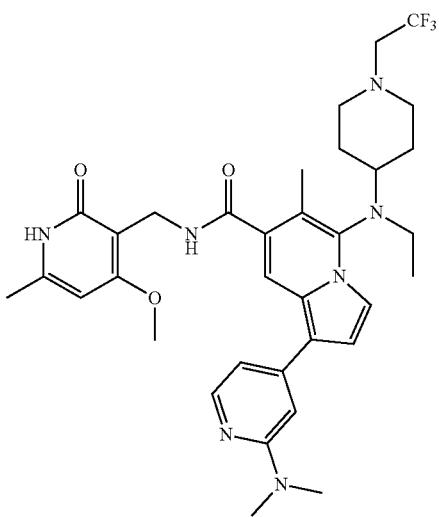

65
-continued
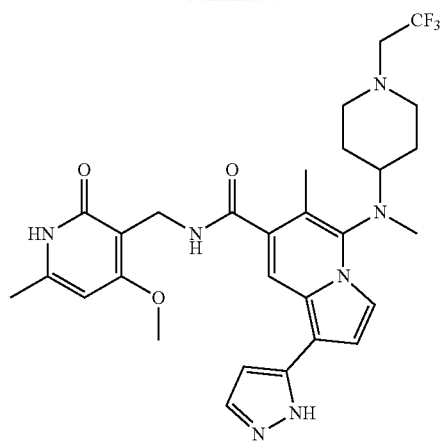
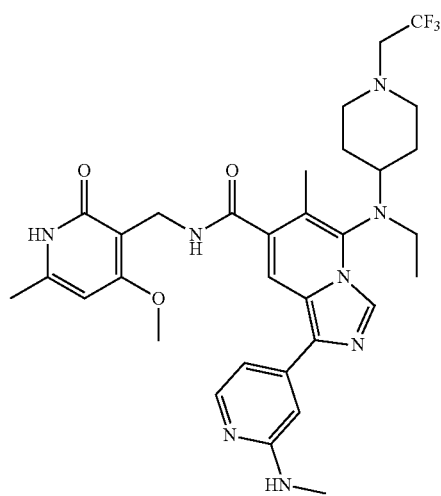
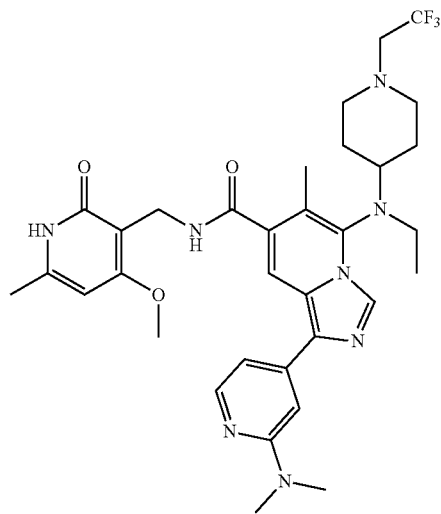
66
-continued
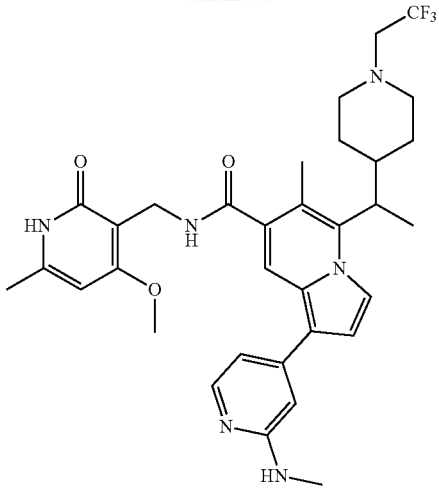
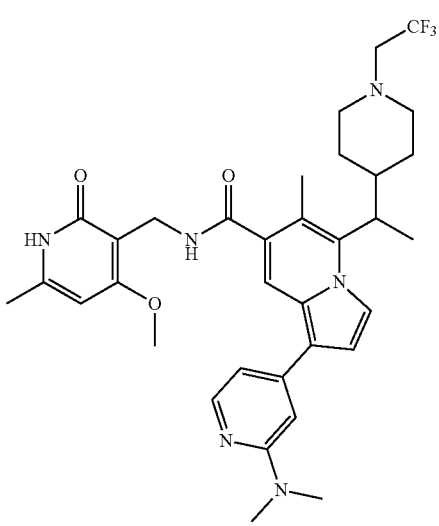

67
-continued
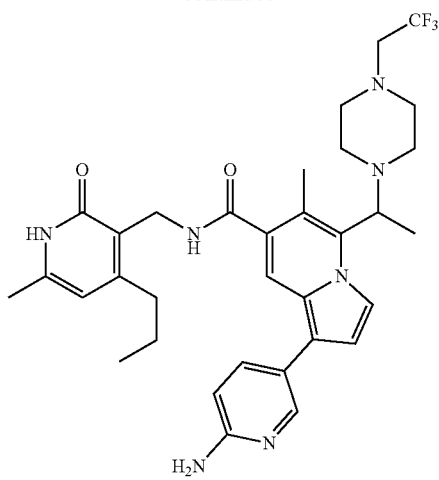
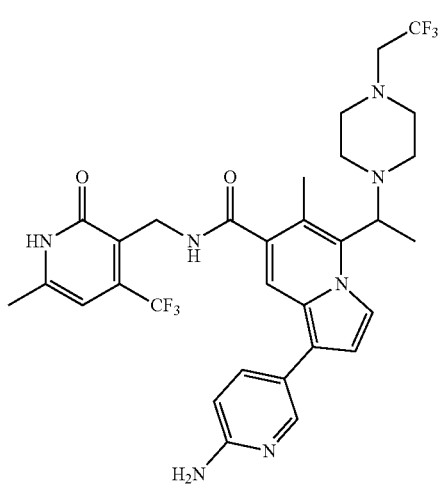
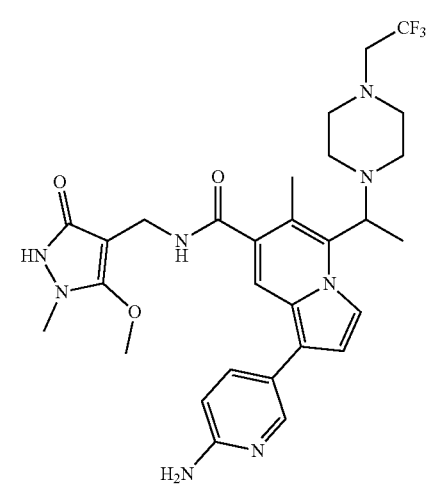
68
-continued
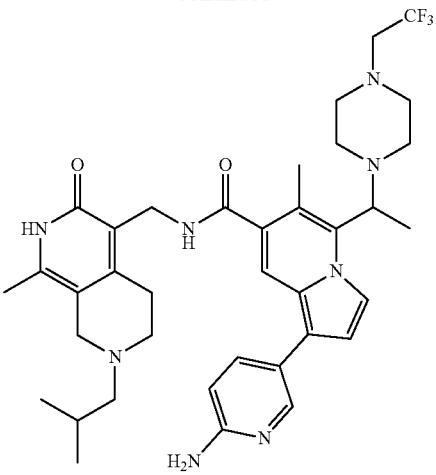
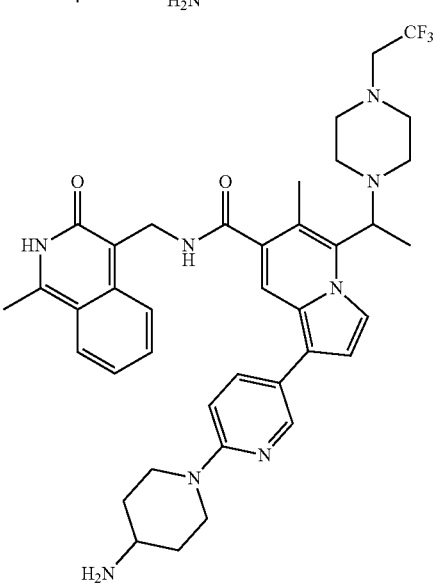
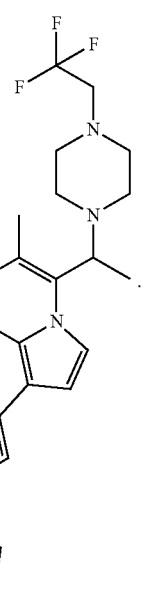
In another preferred embodiment, the compound of formula I is selected from compound 1-151.

According to the second aspect of the present invention, a process for the preparation of compound of formula I as described in the first aspect of the invention is provided, wherein the compound of formula I has the structure shown in formula I-1 and comprises steps:

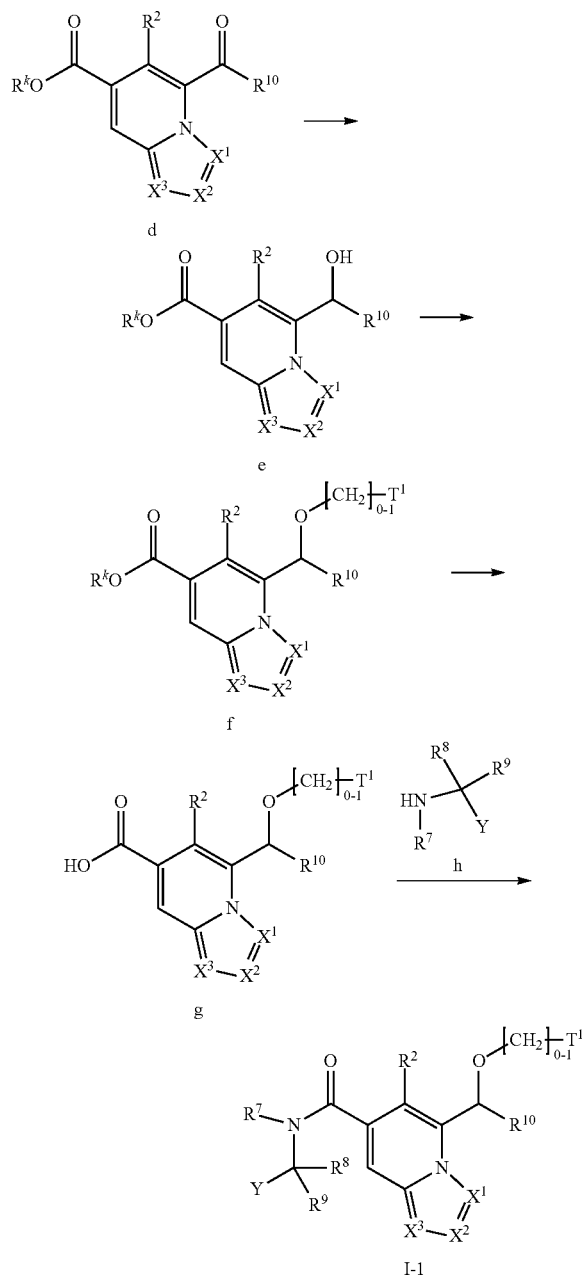

(1) in the presence of a reducing agent, reducing compound d to form compound e, while the reducing agent is selected from the group consisting of sodium borohydride, lithium borohydride, potassium borohydride, or combinations thereof;

(2) in the presence of a base, reacting compound e with a corresponding hydrocarbylation reagent to form compound f, wherein, The base is selected from the group consisting of sodium hydride, potassium t-butoxide, sodium hydroxide, potassium hydroxide, n-butyl lithium, lithium diisopropylamide, lithium hexamethyldisilazide, sodium hexamethyldisilazide, potassium hexamethyldisilazide, potassium carbonate, cesium carbonate, sodium carbonate, or combinations thereof;

The alkylating agent is selected from the group consisting of halogenated hydrocarbons, methanesulfonate, p-toluenesulfonate, trifluoroacetate, triflate, or combinations thereof;

(3) hydrolyzing compound f to form compound g;

(4) condensing compound g with an amine compound to form compound I-1, wherein $R^2$, $R^3$, $R^7$, $R^8$, $R^9$, $R^{10}$, $T^1$, $R^e$, $R^f$, $X^1$, $X^2$, $X^3$ and Y are as defined above, and $R^k$ is a C1-C4 linear or branched alkyl.

In another preferred embodiment, before the step (1), the method further comprises a step (1-1): in an inert solvent, reacting the compound a with b in the presence of a catalyst to form compound d,

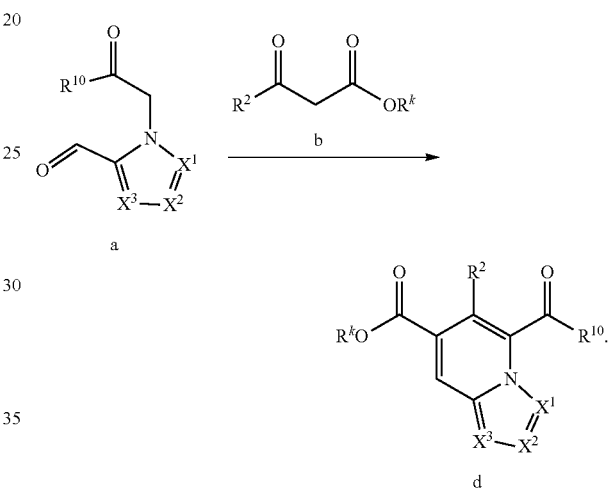

In another preferred embodiment, in the step (1-1), the inert solvent is selected from the group consisting of isopropanol, ethanol, methanol, tetrahydrofuran, chloroform, N,N-dimethylformamide, N,N-dimethylacetamide, dimethyl sulfoxide, or combinations thereof.

In another preferred embodiment, in the step (1-1), the catalyst is selected from the group consisting of alkali such as cesium carbonate, potassium carbonate, sodium carbonate, potassium phosphate, triethylamine, 1,8-diazabicycloundec-7-ene or the like, or ammonium acetate, piperidine acetate salt, or combinations thereof.

In another preferred embodiment, before the step (1), the method further comprises the step (1-1'): in an inert solvent, using compound a and compound c to conduct Michael addition reaction under basic conditions to form compound d.

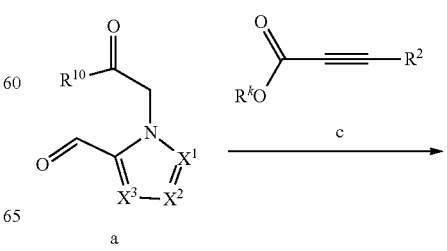

-continued

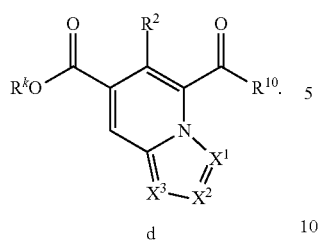

d

In another preferred embodiment, in the step (1-1'), the solvent is selected from the group consisting of N,N-dimethylformamide, N,N-dimethylacetamide, dimethyl sulfoxide, tetrahydrofuran, or combinations thereof.

In another preferred embodiment, in the step (1-1'), the alkali is selected from the group consisting of cesium carbonate, potassium carbonate, sodium carbonate, potassium phosphate, or combinations thereof.

According to the third aspect of the present invention, a process for the preparation of compound of formula I as described in the first aspect of the invention is provided, wherein the compound of formula I has the structure shown in formula I-2 and comprises steps:

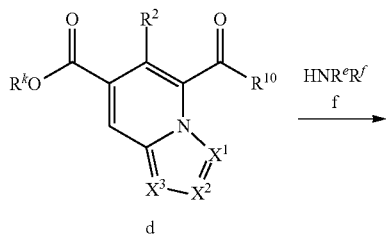

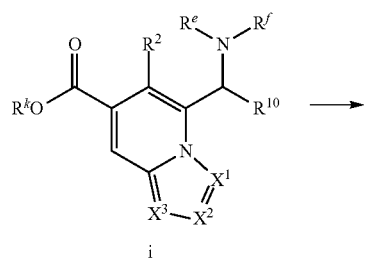

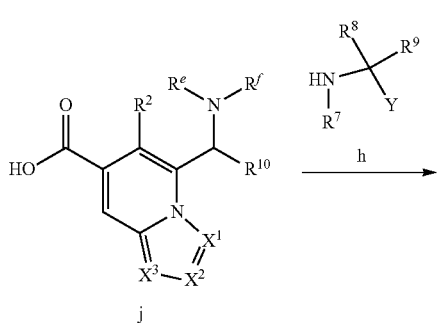

-continued

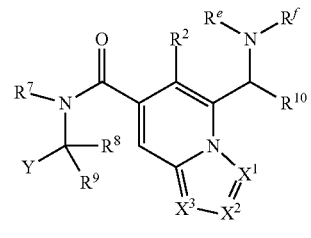

I-2

(i) in an inert solvent, in the presence of reducing agent, reacting compound d with compound f to form compound i;

(ii) hydrolyzing compound i to form compound j;

(iii) condensing compound j with amine compound to form compound I-2;

wherein the $R^2$, $R^3$, $R^7$, $R^8$, $R^9$, $R^{10}$, $R^e$, $R^f$, $R^k$, $X^1$, $X^2$, $X^3$ and Y are as described above.

In another preferred embodiment, in the step (i), the inert solvent is selected from the group consisting of titanium tetraisopropyloxide, tetrahydrofuran, acetic acid, trifluoroacetic acid, or combinations thereof.

In another preferred embodiment, in the step (i), the reducing agent is selected from the group consisting of sodium borohydride, sodium cyanoborohydride, sodium triacetoxyborohydride, or combinations thereof.

According to the fourth aspect of the present invention, a process for the preparation of compound of formula I as described in the first aspect of the invention is provided, wherein the compound of formula I has the structure shown in formula I-3 and comprises steps:

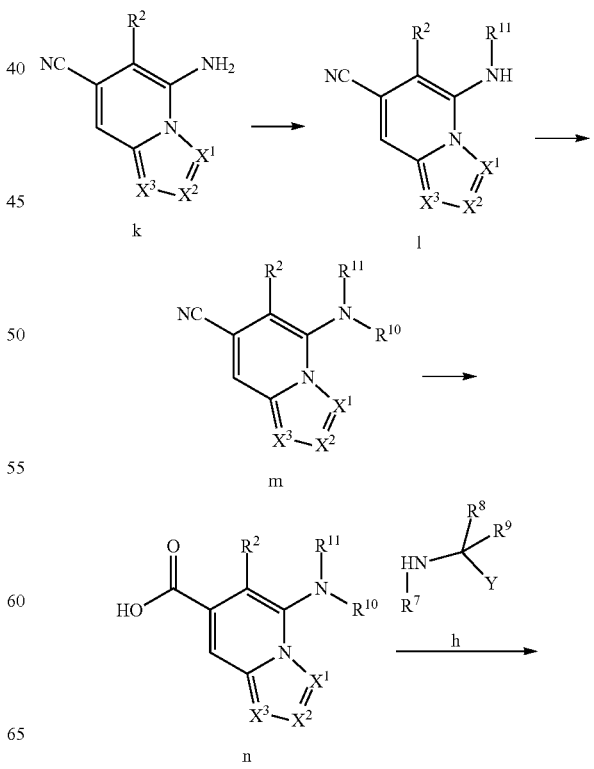

-continued

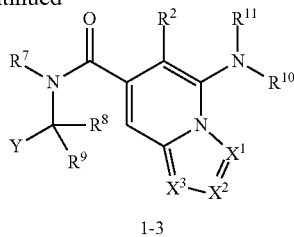

1-3

(a) in an inert solvent, in the presence of reducing agent, reducing compound k to form compound l;
(b) in the presence of alkylating agent, reacting compound l to form compound m, and said alkylating agent is selected from the group consisting of X—$R^{10'}$, $HSO_4$—$R^{10'}$, HO—$R^{10'}$, $R^{10'}$—O—$R^{10'}$, or combinations thereof;
wherein X is halogen; $R^{10'}$ is a substituted or unsubstituted C1-C6 alkyl, substituted or unsubstituted C2-C6 alkenyl, substituted or unsubstituted C2-C6 alkynyl, substituted or unsubstituted saturated or unsaturated 4-8 membered heterocyclic group, substituted or unsubstituted saturated or unsaturated 4-8 membered carbocyclic group, substituted or unsubstituted 5-8 membered aryl, saturated or unsaturated; wherein said heterocyclic ring comprises 1-3 heteroatoms selected from N, O, S, P; and said "substituted" means having one or more (e.g., 1, 2, 3 or 4) substituents selected from group B as set forth in the first aspect of the present invention;
(c) hydrolyzing compound m to form compound n;
(d) condensing compound n with amine compound to form compound I-3;
wherein the $R^2$, $R^3$, $R^7$, $R^8$, $R^9$, $R^{10}$, $R^e$, $R^f$, $R^k$, $X^1$, $X^2$, $X^3$ and Y are as described above.

According to the fifth aspect of the invention, a pharmaceutical composition is provided, comprising:
(1) a compound of the first aspect of the present invention, or a pharmaceutically acceptable salt, enantiomer, diastereomer, tautomer, solvate, polymorph or prodrug thereof; and
(2) pharmaceutically acceptable carriers.

According to a sixth aspect of the invention, use of Formula I compound of the first aspect of the present invention, or a pharmaceutically acceptable salt, enantiomer, diastereomer, tautomer, solvate, polymorph or prodrug thereof is provided, wherein the use is selected from the group consisting of:
(a) preparing a medicament for preventing or treating a disease associated with EZH2 mutation, activity or expression;
(b) non-therapeutic inhibition of the activity of EZH2 and the mutants thereof in vitro; and/or
(c) non-therapeutic inhibition of tumor cell proliferation in vitro.

In another preferred embodiment, the disease associated with EZH2 mutation, activity or expression is selected from the group consisting of tumor or autoimmune disease.

In another preferred embodiment, the disease associated with EZH2 mutation, activity or expression is selected from the group consisting of B cell lymphoma, malignant rhabdomyomas, synovial sarcoma, breast cancer, colorectal cancer, endometrioma, gastric cancer, liver cancer, kidney cancer, lung cancer, melanoma, ovarian cancer, pancreatic cancer, prostate cancer, or bladder cancer.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Through extensive and intensive research, the present inventors have for the first time unexpectedly discovered a pyrido-5-membered aromatic ring compound, a preparation process and use thereof, and the compound of the present invention has an inhibitory effect on wild-type and/or mutant EZH2. The present invention is completed on this basis.

Terms

Unless otherwise defined, all technical and scientific terms used herein have the same meaning as commonly understood by one of ordinary skill in the art to which this invention belongs.

As used herein, when used in reference to a particular recited value, the term "about" means that the value can vary by no more than 1% from the recited value. For example, as used herein, the expression "about 100" includes all the values between 99 and 101 and (eg, 99.1, 99.2, 99.3, 99.4, etc.).

As used herein, the terms "containing" or "including (comprising)" may be opened form, semi-closed form, or closed form. In other words, the terms also include situations such as "essentially consisting of . . . " or "consisting of . . . "

Group Definitions

The definition of standard chemical terms can be found in references (including Carey and Sundberg "ADVANCED ORGANIC CHEMISTRY 4TH ED." Vols. A (2000) and B (2001), Plenum Press, New York). Unless otherwise indicated, conventional methods within the skill of the art, such as mass spectrometry, NMR, IR and UV/VIS spectroscopy and pharmacological methods are employed. Unless specifically defined, the terms relates to analytical chemistry, organic synthetic chemistry, and pharmaceutical and pharmaceutical chemistry used herein are known in the art. Standard techniques can be used in chemical synthesis, chemical analysis, pharmaceutical preparation, formulation and delivery, and treatment of patients. For example, the reaction can be carried out and purified according to the manufacturer's instructions for use of the kit, or by methods well known in the art or as described in the present invention. The above techniques and methods can generally be carried out according to conventional methods well known in the art, as described in the various summaries and more specific references cited and discussed in this specification. In the present specification, the group and its substituents can be selected by those skilled in the art to provide stable structural moieties and compounds.

When a substituent is described by a conventional chemical formula written from left to right, the substituent also includes the chemically equivalent substituent obtained when the structural formula is written from right to left. For example, —$CH_2O$— is equivalent to —$OCH_2$—.

The section headings used herein are for the purpose of organizing articles only and are not to be construed as limiting the subject matter. All documents or parts of the literature cited in this application, including but not limited to patents, patent applications, articles, books, operating manuals and papers, are hereby incorporated by reference in their entirety.

Certain chemical groups defined herein are preceded by a simplified symbol to indicate the total number of carbon atoms present in the group. For example, C1-C6 alkyl refers to an alkyl as defined below having a total of from 1 to 6 carbon atoms. The total number of carbon atoms in the simplified symbol does not include carbon that may be present in the substituents of the group.

In addition to the foregoing, when used in the specification and claims of the present application, unless otherwise specifically indicated, the following terms have the meanings indicated below.

In the present application, the term "halogen" means fluoro, chloro, bromo or iodo.

"Hydroxy" means —OH group.

"Hydroxyalkyl" means alkyl groups as defined below which is substituted by hydroxy group (—OH).

"Carbonyl" means —C(=O)— group.

"Nitro" means —NO$_2$.

"Cyano" means —CN.

"Amino" means —NH$_2$.

"Substituted amino" means amino groups substituted by one or two alkyl, alkylcarbonyl, arylalkyl, heteroarylalkyl as defined below, for example, monoalkylamino, dialkylamino, alkylamido, arylalkylamino, heteroarylalkylamino.

"Carboxyl" means —COOH.

In the present application, as a group or part of another group (for example, used in a group such as a halogen-substituted alkyl group), the term "alkyl" means a fully saturated straight or branched hydrocarbon chain group which consists only of carbon atoms and hydrogen atoms, and has, for example, 1 to 12 (preferably 1 to 8, more preferably 1 to 6) carbon atoms, and is bonded to the rest of a molecule by a single bond, for example, including but not limited to, methyl, ethyl, n-propyl, isopropyl, n-butyl, isobutyl, sec-butyl, tert-butyl, n-pentyl, 2-methylbutyl, 2,2-dimethylpropyl, n-hexyl, heptyl, 2-methylhexyl, 3-methylhexyl, octyl, decyl and decyl. For the present invention, the term "alkyl" refers to alkyl containing from 1 to 6 carbon atoms.

In the present application, as a group or part of another group, the term "alkenyl" means a straight or branched hydrocarbon chain group consisting only of carbon atoms and hydrogen atoms, containing at least one double bond, and having for example 2 to 14 (preferably 2 to 10, more preferably 2 to 6) carbon atoms and being attached to the remaining part of a molecule by a single bond, e.g., but not limited to, vinyl, propenyl, allyl, but-1-enyl, but-2-enyl, pent-1-enyl, pentane-1,4-dienyl, and the like.

In the present application, as a group or part of another group, the term "cycloalkyl" means a stable non-aromatic monocyclic or polycyclic hydrocarbon group consisting of carbon atoms and hydrogen atoms only, which may include fused ring system, bridged ring system or spiro ring system having from 3 to 15 carbon atoms, preferably from 3 to 10 carbon atoms, more preferably from 3 to 8 carbon atoms, and which is saturated or unsaturated and may attach to the rest of a molecule by a single bond via any suitable atoms. Unless otherwise specifically indicated in the specification, carbon atoms in the cyclic hydrocarbon groups may be optionally oxidized. Examples of cycloalkyl groups include, but are not limited to, cyclopropyl, cyclobutyl, cyclopentyl, cyclopentenyl, cyclohexyl, cyclohexenyl, cyclohexadienyl, cycloheptyl, cyclooctyl, 1H-indenyl, 2,3-indanyl, 1,2,3,4-tetrahydro-naphthyl, 5,6,7,8-tetrahydro-naphthyl, 8,9-dihydro-7H-benzocycloheptene-6-yl, 6,7,8,9-tetrahydro-5H-benzocycloheptenyl, 5,6,7,8,9,10-hexahydro-benzocyclooctenyl, fluorenyl, bicyclo [2.2.1] heptyl, 7,7-dimethyl-bicyclo[2.2.1]heptyl, bicyclo[2.2.1]heptenyl, bicyclo[2.2.2] octyl, bicyclo[3.1.1]heptyl, bicyclo[3.2.1]octyl, bicyclo[2.2.2]octenyl, bicyclo[3.2.1]octenyl, adamantyl, octahydro-4,7-methylene-1H-indenyl and octahydro-2,5-methylene-cyclopentadienyl and the like.

In the present application, as a group or part of another group, the term "heterocyclyl" means a stable 3- to 20-membered non-aromatic cyclic group consisted of 2 to 14 carbon atoms and 1 to 6 heteroatoms selected from the group consisting of nitrogen, phosphorus, oxygen and sulfur. Unless otherwise specifically indicated in the specification, heterocyclic group may be monocyclic, bicyclic, tricyclic or ring system with ever more cyclic, which may include fused ring system, bridged ring system or spiro ring system; the nitrogen, carbon or sulfur atom may optionally be oxidized; the nitrogen atom may optionally be quaternized; and the heterocyclic group may be partially or fully saturated. The heterocyclic group may be bonded to the remaining part of a molecule via a carbon atom or a hetero atom through a single bond. In the heterocyclic group containing a fused ring, one or more of the rings may be aryl or heteroaryl as defined hereinafter, provided that the point of attachment to the rest part of a molecule is a non-aromatic ring atom. For the purposes of the present invention, the heterocyclic group is preferably a stable 4 to 11 membered non-aromatic monocyclic, bicyclic, bridged or spiro group containing from 1 to 3 heteroatoms selected from nitrogen, oxygen and sulfur. More preferably, it is a stable 4- to 8-membered non-aromatic monocyclic, bicyclic, bridged or spiro group containing from 1 to 3 heteroatoms selected from nitrogen, oxygen and sulfur. Examples of heterocyclic groups include, but are not limited to, pyrrolidinyl, morpholinyl, piperazinyl, homopiperazinyl, piperidinyl, thiomorpholinyl, 2,7-di-aza-spiro[3.5]nonane-7-yl, 2-oxa-6-aza-spiro[3.3]heptane-6-yl, 2,5-diaza-bicyclo[2.2.1]heptan-2-yl, aza-cyclobutane, pyranyl, tetrahydropyranyl, thiapyranyl, tetrahydrofuranyl, oxazinyl, dioxocyclopentyl, tetrahydroisoquinolinyl, decahydroisoquinolinyl, imidazolinyl, imidazolidinyl, quinazolidinyl, thiazolidinyl, isothiazolidinyl, isoxazolidinyl, dihydroindolyl, octahydroindolyl, octahydroisodolyl, pyrrolidinyl, pyrazolidinyl, phthalimidoyl and the like.

In the present application, as a group or part of another group, the term "aryl" means a conjugated hydrocarbon ring system group having 6 to 18 carbon atoms, preferably having 6 to 10 carbon atoms. For the purposes of the present invention, an aryl may be a monocyclic, bicyclic, tricyclic ring system or a ring system of even more rings, and may also be fused to a cycloalkyl or heterocyclic group as defined above, provided that the aryl group connected to the rest of a molecule by a single bond via atoms on the aromatic ring. Examples of aryl groups include, but are not limited to, phenyl, naphthyl, anthracenyl, phenanthryl, anthryl, 2,3-dihydro-1H-isoindolyl, 2-benzoxazolinone, 2H-1,4-benzoxazine-3(4H)-keto-7-yl, and the like.

In the present application, the term "arylalkyl" refers to an alkyl as defined above substituted by a aryl group as defined above.

In the present application, as a group or part of another group, the term "heteroaryl" means a conjugated hydrocarbon ring system group having 1 to 15 carbon atoms (preferably having 1 to 10 carbon atoms) and 1 to 6 heteroatoms selected from nitrogen, oxygen and sulfur. Unless otherwise indicated in the present invention, a heteroaryl may be a monocyclic, bicyclic, tricyclic ring system or a ring system of even more rings, and may also be fused to a cycloalkyl or heterocyclic group as defined above, provided that the aryl group connected to the rest of the molecule by a single bond via atoms on the aromatic ring. The nitrogen, carbon or sulfur atom in the heteroaryl group can be optionally oxidized; and the nitrogen atom can optionally be quaternized. For the purposes of the present invention, the heterocyclic group is preferably a stable 5 to 12 membered aromatic group containing from 1 to 5 heteroatoms selected from nitrogen, oxygen and sulfur. More preferably, it is a stable 5- to 10-membered aromatic group containing from 1 to 3 heteroatoms selected from nitrogen, oxygen and sulfur, or 5- to 6-membered aromatic group containing from 1 to 3 heteroatoms selected from nitrogen, oxygen and sulfur Examples of heteroaryl groups include, but are not limited to, thienyl, imidazolyl, pyrazolyl, thiazolyl, oxazolyl, oxadiazolyl, isoxazolyl, pyridyl, pyrimidinyl, pyrazinyl, pyridazinyl, benzimidazolyl, benzopyrazolyl, indolyl, furyl, pyrrolyl, triazolyl, tetrazolyl, triazinyl, indolizinyl, isoindolyl, indazolyl, isoindazolyl, purinyl, quinolyl, isoquinolyl, diazonaphthyl, naphthyridinyl, quinoxalinyl, pteridinyl, carbazolyl, carboline, phenanthridinyl, phenanthrolinyl, acridinyl, phenazinyl, isothiazolyl, benzothiazolyl, benzothienyl, oxatriazole, cinnolinyl, quinazolinyl, phenylthio, purrocolinyl, orthophenanthrolenyl, isoxazolyl, phenoxazinyl, phenothiazine, 4,5,6,7-tetrahydrobenzo[b]thienyl, naphthopyridyl, [1,2,4]triazolo[4,3-b]pyridazine, [1,2,4]triazolo[4,3-a]pyrazine, [1,2,4]triazolo[4,3-c]pyrimidine, [1,2,4]triazolo[4,3-a]pyridine, imidazo[1,2-a]pyridine, imidazo[1,2-b]pyridazine, imidazo[1,2-a]pyrazine, etc.

In the present application, the term "heteroarylalkyl" refers to a alkyl as defined above which is substituted by a heteroaryl as defined above.

In the present application, "optional" or "optionally" means that the subsequently described event or condition may or may not occur, and that the description includes both the occurrence or non-occurrence of the event or condition. For example, "optionally substituted aryl" means that the aryl is substituted or unsubstituted, and the description includes both the substituted aryl and the unsubstituted aryl. The "optional" substituents described in the claims and the specification of the present invention are selected from the group consisting of an alkyl, alkenyl, alkynyl, halogen, haloalkyl, haloalkenyl, haloalkynyl, cyano, nitro, optionally substituted aryl, optionally substituted heteroaryl, optionally substituted cycloalkyl, optionally substituted heterocyclic hydrocarbon group.

The terms "part", "structural moiety", "chemical moiety", "group", and "chemical group", as used herein, refer to a particular fragment or functional group in a molecule. A chemical moiety is generally considered to be a chemical entity that is embedded or attached to a molecule.

"Stereoisomer" refers to a compound composed of same atoms, bonded by the same bonds, but having a different three-dimensional structure. The invention will cover various stereoisomers and mixtures thereof.

When the compound of the present invention contains olefinic double bonds, the compounds of the present invention are intended to comprise E- and Z-geometric isomers unless otherwise stated.

"Tautomer" refers to an isomer formed by the transfer of a proton from one atom of a molecule to another atom of the same molecule. All tautomeric forms of the compounds of the invention will also be embraced within the scope of the invention.

The compounds of the invention, or pharmaceutically acceptable salts thereof, may contain one or more chiral carbon atoms and, thus, may give rise to enantiomers, diastereomers, and other stereoisomeric forms. Each chiral carbon atom can be defined as (R)- or (S)-based on stereochemistry. The invention is intended to include all possible isomers, as well as racemic and optically pure forms thereof. Racemates, diastereomers or enantiomers may employed as starting materials or intermediates of the preparation of the compounds of the invention. Optically active isomers can be prepared by chiral synthons or chiral reagents, or resolved using conventional techniques, such as by crystallization and chiral chromatography.

Conventional techniques for the preparation/isolation of individual isomers include chiral synthesis from a suitable optically pure precursor, or resolution of the racemate (or racemic form of a salt or derivative) using, for example, chiral high performance liquid chromatography. For example, see Gerald Gübitz and Martin G. Schmid (Eds.), Chiral Separations, Methods and Protocols, Methods in Molecular Biology, Vol. 243, 2004; A M Stalcup, Chiral Separations, Annu. Rev. Anal. Chem. 3:341-63, 2010; Fumiss et al. (eds.), VOGEL'S ENCYCLOPEDIA OF PRACTICAL ORGANIC CHEMISTRY 5.sup.TH ED., Longman Scientific and Technical Ltd., Essex, 1991, 809-816; Heller, Acc. Chem Res. 1990, 23, 128.

In the present application, the term "pharmaceutically acceptable salt" includes pharmaceutically acceptable acid addition salts and pharmaceutically acceptable base addition salts.

"Pharmaceutically acceptable acid addition salt" means a salt formed with an inorganic or organic acid which retains the bioavailability of the free base without bringing other side effects. Inorganic acid salts include, but are not limited to, hydrochlorides, hydrobromides, sulfates, nitrates, phosphates, and the like; organic acid salts include, but are not limited to, formate, acetate, 2,2-dichloroacetate, trifluoroacetate, propionate, hexanoate, octoate, decanoate, undecylenate, glycolate, gluconate, lactate, sebacate, adipates, glutaric acid salts, malonates, oxalates, maleates, succinates, fumarates, tartrates, citrates, palmitates, stearates, oleates, cinnamate, laurate, malate, glutamate, pyroglutamate, aspartate, benzoate, methanesulfonate, besylate, p-toluenesulfonate, alginate, ascorbate, salicylate, 4-aminosalicylate, naphthalene disulfonate, and the like. These salts can be prepared by methods known in the art.

"Pharmaceutically acceptable base addition salt" means a salt formed with an inorganic or organic base capable of maintaining the bioavailability of the free acid without bringing other side effects. Salts derived from inorganic bases include, but are not limited to, sodium salts, potassium salts, lithium salts, ammonium salts, calcium salts, magnesium salts, iron salts, zinc salts, copper salts, manganese salts, aluminum salts, and the like. Preferred inorganic salts are ammonium, sodium, potassium, calcium and magnesium salts. Salts derived from organic bases include, but are not limited to, the following salts: primary amines, secondary amines and tertiary amines, substituted amines, including naturally substituted amines, cyclic amines, and basic ion exchange resins. For example, ammonia, isopropylamine, trimethylamine, diethylamine, triethylamine, tripropylamine, ethanolamine, diethanolamine, triethanolamine, dimethylethanolamine, 2-dimethylaminoethanol, 2-diethylaminoethanol, bicyclo hexylamine, lysine, arginine, histidine, caffeine, procaine, choline, betaine, ethylenediamine, glucosamine, methylglucosamine, theobromine, purine, piperazine, piperidine, N-ethylpiperidine, polyamine resin, and the like. Preferred organic bases include isopropylamine, diethylamine, ethanolamine, trimethylamine, dicyclohexylamine, choline, and caffeine. These salts can be prepared by methods known in the art.

In the present application, "pharmaceutical composition" refers to a formulation of a compound of the invention and a medium generally accepted in the art for delivery of a biologically active compound to a mammal, such as a human. The medium comprises pharmaceutically acceptable carriers. The purpose of the pharmaceutical composition is to promote the administration of the organism, thus facilitating the absorption of the active ingredients and thereby exerting the biological activity.

The term "pharmaceutically acceptable" as used herein, refers to a substance (such as a carrier or diluent) that does not affect the biological activity or properties of the compound of the invention, and is relatively non-toxic, ie, the substance can be administered to an individual without causing undesirable organisms, or interacts with any of the components contained in the composition in an undesirable manner.

In the present application, "pharmaceutically acceptable excipients" include, but are not limited to, any adjuvants, carriers, excipients, glidants, sweeteners, diluents, preservatives, dyes/colorants, flavoring agents, surfactants, wetting agents, dispersing agents, suspending agents, stabilizers, isotonic agents, solvents or emulsifiers approved by the relevant government authorities for acceptable use in humans or domestic animals.

The "tumor" of the present invention includes, but is not limited to, glioma, sarcoma, melanoma, articular chondrocarcinoma, cholangiocarcinoma, leukemia, gastrointestinal stromal tumor, histiocytic lymphoma, non-small cell lung cancer, small cell lung cancer, pancreatic cancer, lung squamous cell carcinoma, lung adenocarcinoma, breast cancer, prostate cancer, liver cancer, skin cancer, epithelial cell carcinoma, cervical cancer, ovarian cancer, intestinal cancer, nasopharyngeal cancer, brain cancer, bone cancer, esophageal cancer, melanin tumor, kidney cancer, oral cancer and other diseases.

The terms "prevention", "preventing" and "prevented" as used herein include the possibility of reducing the occurrence or progression of a disease or condition by a patient.

The term "treatment" and other similar synonyms as used herein includes the following meanings:

(i) preventing the occurrence of a disease or condition in a mammal, particularly when such a mammal is susceptible to the disease or condition, but has not been diagnosed as having the disease or condition;

(ii) inhibiting a disease or condition, i.e., inhibiting its development;

(iii) alleviating the disease or condition, i.e., degrading the condition of the disease or illness; or (iv) alleviating the symptoms caused by the disease or condition.

The term "effective amount," "therapeutically effective amount," or "pharmaceutically effective amount," as used herein, refers to an amount of at least one agent or compound that, after administration, is sufficient to alleviate one or more symptoms of the disease or condition being treated to some extent. The result can be reduction and/or alleviation of signs, symptoms or causes, or any other desired change in the biological system. For example, an "effective amount" for treatment is an amount of a composition comprising a compound disclosed herein that is required to provide a significant conditional relief effect in clinic. An effective amount suitable for any individual case can be determined using techniques such as dose escalation testing.

The terms "take", "administrate", "apply" and the like, as used herein, refers to a method of delivering compound or composition to a desired site for biological action. These methods include, but are not limited to, oral, duodenal, parenteral injection (including intravenous, subcutaneous, intraperitoneal, intramuscular, intraarterial injection or infusion), topical administration, and rectal administration. The techniques of administration of the compounds and methods described herein are well known to those skilled in the art, for example, those discussed in Goodman and Gilman, The Pharmacological Basis of Therapeutics, current ed.; Pergamon; and Remington's, Pharmaceutical Sciences (current edition), Mack Publishing Co., Easton, Pa. In a preferred embodiment, the compounds and compositions discussed herein are administered orally.

The terms "pharmaceutical combination", "drug combination", "combination", "administering other treatments", "administering other therapeutic agents" and the like, as used herein, mean a pharmaceutical treatment obtained by mixing or combining more than one active ingredient which includes both fixed and unfixed combinations of active ingredients. The term "fixed combination" refers to simultaneous administrating at least one compound described herein and at least one synergistic agent to a patient in the form of a single entity or a single dosage form. The term "unfixed combination" refers to simultaneous administrating, administrating in combination or sequentially administrating in variable interval time at least one of the compounds described herein and at least one synergistic formulation to the patient in the form of separate entities. These can also be applied to cocktail therapy, for example, administrating three or more active ingredients.

It will also be understood by those skilled in the art that in the methods described below, functional groups of an intermediate compound may need to be protected by suitable protecting groups. Such functional groups include hydroxyl, amino, thiol, and carboxyl. Suitable hydroxy protecting groups include trialkylsilyl or diarylalkylsilyl groups (e.g., tert-butyldimethylsilyl, tert-butyldiphenylsilyl or trimethylsilyl), tetrahydropyranyl, benzyl, and the like. Suitable protecting groups for amino, amidine group and guanidyl include t-butoxycarbonyl, benzyloxycarbonyl, and the like. Suitable thiol protecting groups include —C(O)—R" (wherein R" is alkyl, aryl or aralkyl), p-methoxybenzyl, trityl, and the like. Suitable carboxy protecting groups include alkyl, aryl or aralkyl esters.

Protecting groups can be introduced and removed according to standard techniques known to those skilled in the art and as described herein. The use of protecting groups is described in detail in Greene, T. W. and P. G. M. Wuts, Protective Groups in Organi Synthesis, (1999), 4th Ed., Wiley. The protecting group can also be polymeric resins.

The main advantages of the present invention are:

1. Providing a compound of formula I.

2. Providing a composition of novel structure for the prevention and treatment of diseases associated with EZH2 mutations.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacturer's instructions. Unless indicated otherwise, parts and percentage are weight parts and weight percentage.

The experimental materials and reagents used in the following examples are available from commercially available sources unless otherwise specified.

In each of the examples, the $^1$H NMR was recorded by Varian Mercury-300 or Varian Mercury-400 NMR spectrometer, and the $^{13}$C NMR was recorded by Varian Mercury-400 or Varian Mercury-500 or Varian Mercury-600 NMR spectrometer, chemical shifts are expressed as δ (ppm); mass spectrum is recorded by Finnigan/MAT-95 (EI) and Finnigan LCQ/DECA and Micromass Ultra Q-TOF (ESI) mass spectrometer; reverse phase preparative HPLC separation silica gel is 200-300 mesh.

Among them, names of reagents represented by the chemical formula or the alphabet abbreviations are as follows:

iPrOH: isopropanol; EtOH: ethanol; DCM: dichloromethane; TFA: trifluoroacetic acid; MeOH: methanol; NaOH: sodium hydroxide; HCl: hydrogen chloride; TEA: triethylamine; Raney Ni: Raney Nickel; 1,4-dioxane: 1,4-dioxane; NaH: sodium hydride; H$_2$O: water; Pd/C: palladium/carbon; H$_2$: hydrogen; HATU: 2-(7-oxidizedbenzotriazole)-N,N,N',N'-tetramethylurea hexafluorophosphate; DMF: N,N-dimethylformamide; THF: tetrahydrofuran; Boc$_2$O: di-tert-butyl dicarbonate; NBS: N-bromosuccinimide; NCS: N-chlorosuccinimide; NIS: N-iodosuccinimide; MeCN: acetonitrile; DIPEA: N,N-diisopropylethylamine; NaBH$_4$: Sodium borohydride; AcOH: acetic acid; ethyl acetate: ethyl acetate; NaBH$_3$CN: sodium cyanoborohydride; K$_2$CO$_3$: potassium carbonate; Cs$_2$CO$_3$: cesium carbonate; nBuLi: n-butyllithium; LiAlH$_4$: lithium aluminum hydride; Pd(dppf)Cl$_2$: [1,1-bis(diphenylphosphino)ferrocene]palladium dichloride; KOAc: potassium acetate. Fumaronitrile: fumaric acid nitrile; P(nBu)$_3$: tri-n-butylphosphine; LDA: lithium diisopropylamide; LiOH: lithium hydroxide; MeI: methyl iodide; EtI: ethyl iodide; (CH$_2$O)$_n$: paraformaldehyde; HCO$_2$H: formic acid; CH$_3$COCl: acetyl chloride.

Example 1: Preparation of N-((4,6-Dimethyl-2-oxo-1,2-dihydropyridin-3-yl)methyl)-5-(1-methoxyethyl)-6-methylindolizine-7-carboxamide

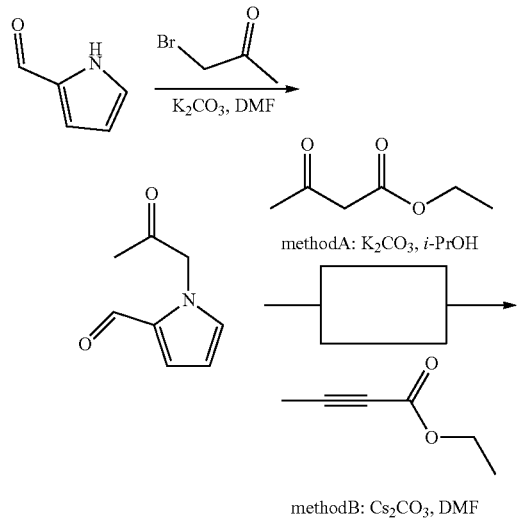

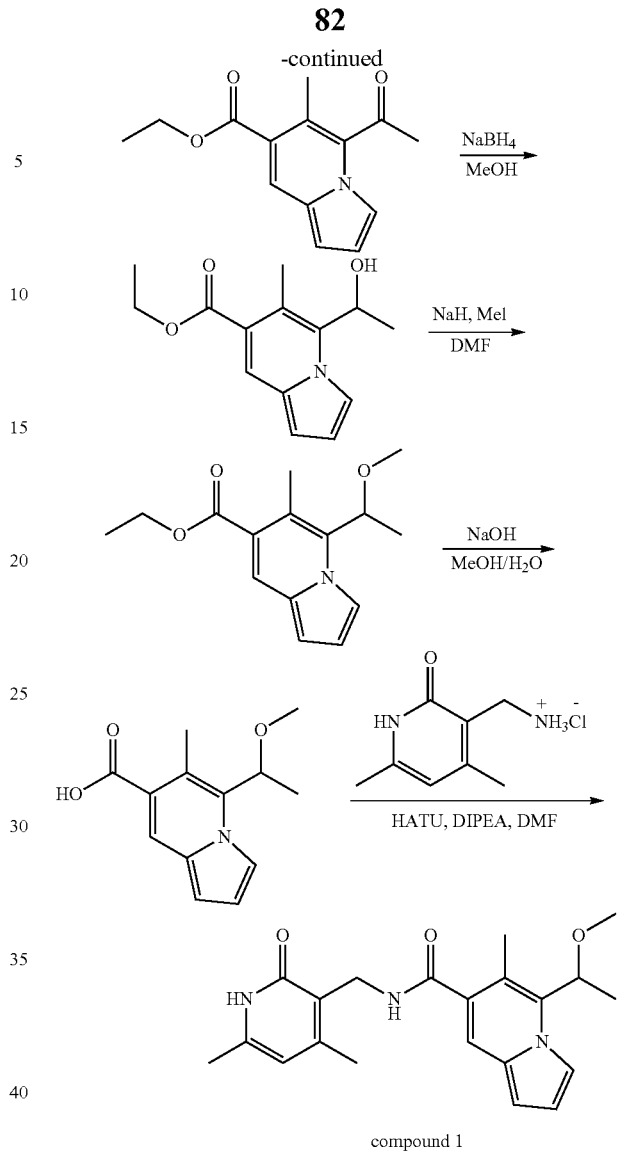

compound 1

Step 1: Preparation of 1-(2-oxopropyl)-1H-pyrrole-2-carbaldehyde: In a dry nitrogen-protected 250 mL single-necked flask, compound 1H-pyrrole-2-carbaldehyde (15 g, 158 mmol) was dissolved in 100 mL of DMF, and potassium carbonate (43.6 g, 316 mmol) and bromoacetone (53.7 g, 395 mmol) were added to the solution, and the mixture was stirred at room temperature overnight. The reaction mixture was extracted with ethyl acetate (200 mL), washed with water (100 mL×2) and saturated brine (100 mL). The organic phase was dried over anhydrous sodium sulfate, filtered and concentrated to provide a crude product. After purified by column chromatography (petroleum ether:EtOAc=4:1), brown solid (7 g, yield: 30%) was obtained.

$^1$H NMR (CDCl$_3$, 400 MHz) δ ppm 9.49 (s, 1H), 7.00 (d, J=8.0 Hz, 1H), 6.87 (brs, 1H), 6.32-6.31 (m, 1H), 5.09 (s, 2H), 2.23 (s, 3H).

Step 2: Preparation of ethyl 5-acetyl-6-methylindolizine-7-carboxylate

Method A: The compound 1-(2-oxopropyl)-1H-pyrrole-2-carbaldehyde (7.0 g, 46.0 mmol) was dissolved in 150 mL of DMF in a dry nitrogen-protected 250 mL single-necked flask. Ethyl acetoacetate (17.9 g, 138 mmol) and potassium carbonate (9.52 g, 69 mmol) were added successively, and the mixture was warmed to reflux for two hours. The mixture was extracted with ethyl acetate (200 mL) and water (100 mL×2). The organic layer was dried over anhydrous sodium sulfate, filtered and concentrated to give a crude product. After purified by column chromatography (petroleum ether:EtOAc=10:1), yellow oil (5.4 g, yield: 48%) was obtained and stood for curing.

Method B: The compound 1-(2-oxopropyl)-1H-pyrrole-2-carbaldehyde (7.0 g, 46.0 mmol) was dissolved in 50 mL of DMF in a dry nitrogen-protected 100 mL single-necked flask. Ethyl 2-butynoate (6.3 g, 56 mmol) and cesium carbonate (22.7 g, 69 mmol) were added successively, and the mixture was warmed to 50° C. and stirred for 4 to 5 hours. The reaction mixture was extracted with ethyl acetate (200 mL) and washed with water (100 mL×2) and brine (100 mL). The organic phase was dried over anhydrous sodium sulfate, filtered and concentrated to provide a crude product. After purified by column chromatography (petroleum ether:EtOAc=10:1), yellow oil (1.4 g, yield: 12.4%) was obtained and stood for curing.

$^1$H NMR (CDCl$_3$, 400 MHz) δ ppm 9.20 (s, 1H), 7.21 (brs, 1H), 6.87 (t, J=4.0 Hz, 1H), 6.74 (d, J=4.0 Hz, 1H), 4.34 (q, J=7.2 Hz, 2H), 2.64 (s, 3H), 2.44 (s, 3H), 1.39 (t, J=7.2 Hz, 3H).

Step 3: Preparation of ethyl 5-(1-hydroxyethyl)-6-methylindolizine-7-carboxylate: compound ethyl 5-acetyl-6-methylindolizine-7-carboxylate (1 g, 4.1 mmol) and 50 mL of methanol were added to a dry nitrogen-protected 100 mL single-necked flask. Sodium borohydride (310.2 mg, 8.2 mmol) was added portionwise after cooled to 0° C. The reaction was stirred at room temperature for 3-4 hours, and then the mixture was extracted with ethyl acetate (200 mL) and washed with water (100 mL×2) and brine (100 mL). The organic phase was dried over anhydrous sodium sulfate, filtered and concentrated to provide a crude product. After purified by column chromatography (petroleum ether:EtOAc=8:1), yellow oil (650 mg, yield: 65%) was obtained.

$^1$H NMR (CDCl$_3$, 400 MHz) δ ppm 8.09 (s, 1H), 8.01 (s, 1H), 6.84 (t, J=3.6 Hz, 1H), 6.67 (d, J=4.0 Hz, 1H), 5.75-5.73 (m, 1H), 4.31 (q, J=7.2 Hz, 2H), 2.47 (s, 3H), 1.68 (d, J=8 Hz, 3H), 1.38 (t, J=6.8 Hz, 3H).

Step 4: Preparation of ethyl 5-(1-methoxyethyl)-6-methylindolizine-7-carboxylate: compound ethyl 5-(1-hydroxyethyl)-6-methylindolizine-7-carboxylate (40 mg, 0.16 mmol) and 15 mL of DMF were added to a dry nitrogen-protected 50 mL single-necked flask. Sodium hydride (16.2 mg, 0.24 mmol) was added portionwise after cooled to 0° C. The reaction was stirred at room temperature for 30 min, iodomethane (34 mg, 0.24 mmol) was added, and the mixture was stirred at room temperature overnight, and then the mixture was extracted with ethyl acetate (100 mL) and washed with water (50 mL×2) and brine (50 mL). The organic phase was dried over anhydrous sodium sulfate, filtered and concentrated to provide a crude product. After purified by column chromatography (petroleum ether:EtOAc=10:1), yellow oil (20 mg, yield: 47.6%) was obtained.

$^1$H NMR (MeOD, 400 MHz) δ ppm 8.40 (s, 2H), 6.82 (t, J=3.2 Hz, 1H), 6.77 (d, J=3.6 Hz, 1H), 5.26 (q, J=7.8 Hz, 1H), 3.85 (s, 3H), 3.19 (s, 3H), 2.48 (s, 3H), 1.59 (d, J=7.8 Hz, 3H).

Step 5: Preparation of 5-(1-methoxyethyl)-6-methylindolizine-7-carboxylic acid: The compound Ethyl 5-(1-methoxyethyl)-6-methylindolizine-7-carboxylate (20 mg, 0.077 mmol) and 5 mL of methanol were added successively in a 25 mL nitrogen-protected one-necked bottle. Sodium hydroxide (12.4 mg, 0.31 mmol) was dissolved in 5 mL water, added to the reaction system, and stirred overnight under room temperature. The mixture was neutralized with diluted hydrochloric acid to pH 5, extracted with dichloromethane (100 mL), washed with water (50 mL×2) and brine (50 mL). The organic phase was dried over anhydrous sodium sulfate, filtered and concentrated to provide pale yellow oil (18 mg, yield: 100%). $^1$H NMR (MeOD, 400 MHz) δ ppm 8.05 (s, 1H), 6.81 (t, J=3.2 Hz, 1H), 6.66 (t, J=3.2 Hz, 1H), 5.27 (q, J=7.8 Hz, 1H), 3.19 (s, 3H), 2.50 (s, 3H), 1.60 (d, J=7.8 Hz, 3H).

Step 6: Preparation of N-((4,6-Dimethyl-2-oxo-1,2-dihydropyridin-3-yl)methyl)-5-(1-methoxyethyl)-6-methylindolizine-7-carboxamide: 5-(1-methoxyethyl)-6-methylindolizine-7-carboxylic acid (18 mg, 0.077 mmol), 3-(aminomethyl)-4,6-lutidine-2(1H)-one hydrochloride (23.5 mg, 0.125 mmol) (the synthesis of which can be found in WO2015023915), HATU (44 mg, 0.116 mmol), DIPEA (29.9 mg, 0.232 mmol) and DMF 20 mL were added sequentially to a 25 mL nitrogen-protected one-necked bottle, stirred at room temperature for 30 min. The mixture was extracted with ethyl acetate (100 mL), washed with water (50 mL×2) and brine (50 mL). The organic phase was dried over anhydrous sodium sulfate, filtered and concentrated to provide a crude product. After purified by column chromatography (dichloromethanol:methanol=20:1), white solid was obtained (20 mg, yield: 71%). $^1$H NMR (CDCl$_3$, 400 MHz) δ ppm 7.97 (s, 1H), 7.38 (s, 1H), 6.84-6.78 (m, 2H), 6.53 (d, J=3.6 Hz, 1H), 6.37 (s, 1H), 5.10 (q, J=7.8 Hz, 1H), 4.54 (brs, 2H), 3.19 (s, 3H), 2.57 (s, 3H), 2.41 (s, 3H), 2.31 (s, 3H), 1.60 (d, J=7.8 Hz, 3H); MS (ESI) m/z 368 [M+H]$^+$.

Example 2: Preparation of N-((4,6-Dimethyl-2-oxo-1,2-dihydropyridin-3-yl)methyl)-5-(1-ethoxyethyl)-6-methylindolizine-7-carboxamide

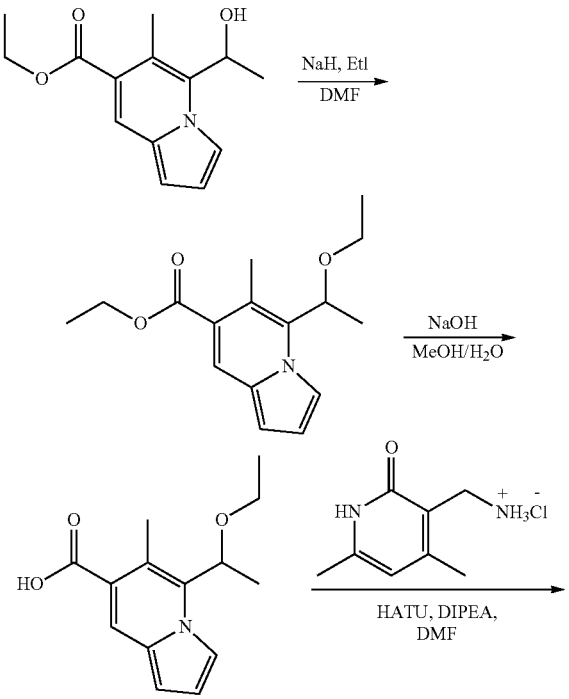

85

-continued

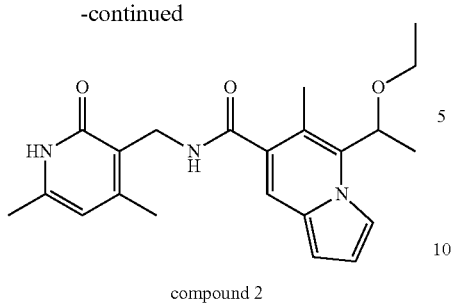

compound 2

Step 1: Preparation of ethyl 5-(1-ethoxyethyl)-6-methylindolizine-7-carboxylate: Ethyl 5-(1-ethoxyethyl)-6-methylindolizine-7-carboxylate was prepared by a method similar to Step 4 of Example 1 except ethyl iodide was used, yield 15%. MS (ESI) m/z 276 [M+H]⁺.

Step 2: Preparation of 5-(1-ethoxyethyl)-6-methylindolizine-7-carboxylic acid: 5-(1-ethoxyethyl)-6-methylindolizine-7-carboxylic acid was prepared by a method similar to Step 5 of Example 1, yield 95%. MS (ESI) m/z 248 [M+H]⁺.

Step 3: Preparation of N-((4,6-Dimethyl-2-oxo-1,2-dihydropyridin-3-yl)methyl)-5-(1-ethoxyethyl)-6-methylindolizine-7-carboxamide: N-((4,6-Dimethyl-2-oxo-1,2-dihydropyridin-3-yl)methyl)-5-(1-ethoxyethyl)-6-methylindolizine-7-carboxamide was prepared by a method similar to Step 6 of Example 1, yield 35%. ¹H NMR (400 MHz, CDCl₃) δ ppm 8.02 (s, 1H), 7.36 (s, 1H), 6.99 (s, 1H), 6.77 (s, 1H), 6.50 (s, 1H), 6.14 (s, 1H), 5.34 (brs, 1H), 5.20 (q, J=7.8 Hz, 1H), 4.51 (brs, 2H), 3.36-3.34 (m, 1H), 3.23-3.21 (m, 1H), 2.48 (s, 3H), 2.22 (s, 6H), 1.26 (d, J=7.6 Hz, 3H), 0.88 (t, J=7.8 Hz, 3H); MS (ESI) m/z 382 [M+H]⁺.

Example 3: Preparation of 5-(1-(Allyloxy)ethyl)-N-((4,6-dimethyl-2-oxo-1,2-dihydropyridin-3-yl)methyl 6-methylindolizine-7-carboxamide

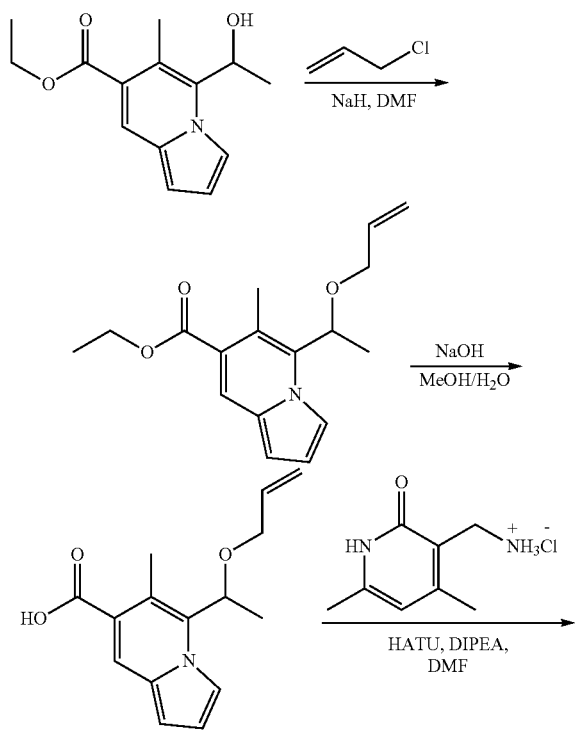

86

-continued

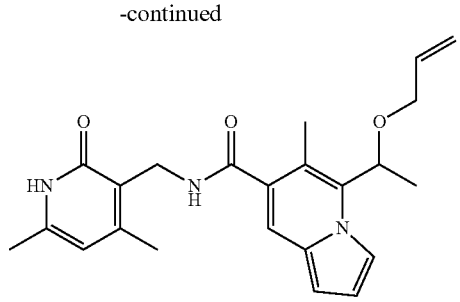

compound 3

Step 1: Step 1: Preparation of ethyl 5-(1-(allyloxy)ethyl)-6-methylindolizine-7-carboxylate: Ethyl 5-(1-(allyloxy)ethyl)-6-methylindolizine-7-carboxylate was prepared by a method similar to Step 4 of Example 1 except that allyl chloride was used, yield 49%. MS (ESI) m/z 288 [M+H]⁺.

Step 2: Preparation of 5-(1-(allyloxy)ethyl)-6-methylindolizine-7-carboxylic acid: 5-(1-(allyloxy)ethyl)-6-methylindolizine-7-carboxylic acid was prepared by a method similar to Step 5 of Example 1, yield 98%. MS (ESI) m/z 260 [M+H]⁺.

Step 3: Preparation of 5-(1-(allyloxy)ethyl)-N-((4,6-dimethyl-2-oxo-1,2-dihydropyridin-3-yl)methyl)-6-methylindolizine-7-carboxamide: 5-(1-(allyloxy)ethyl)-N-((4,6-dimethyl-2-oxo-1,2-dihydropyridin-3-yl)methyl)-6-methylindolizine-7-carboxamide was prepared by a method similar to Step 6 of Example 1, yield 53%. ¹H NMR (400 MHz, CDCl₃) δ ppm 8.01 (s, 1H), 7.37 (s, 1H), 6.91 (s, 1H), 6.78 (s, 1H), 6.26 (s, 1H), 6.14 (s, 1H), 5.91-5.83 (m, 1H), 5.23-5.14 (m, 3H), 4.54-4.52 (m, 2H), 3.86-3.73 (m, 2H), 2.52 (s, 3H), 2.36 (s, 3H), 2.29 (s, 3H), 1.62 (d, J=7.8 Hz, 3H); S (ESI) m/z 394 [M+H]⁺.

Example 4: Preparation of N-((4,6-dimethyl-2-oxo-1,2-dihydropyridin-3-yl)methyl)-6-methyl-5-(1-(prop-2-yn-1-yloxy) ethyl)indolizine-7-carboxamide

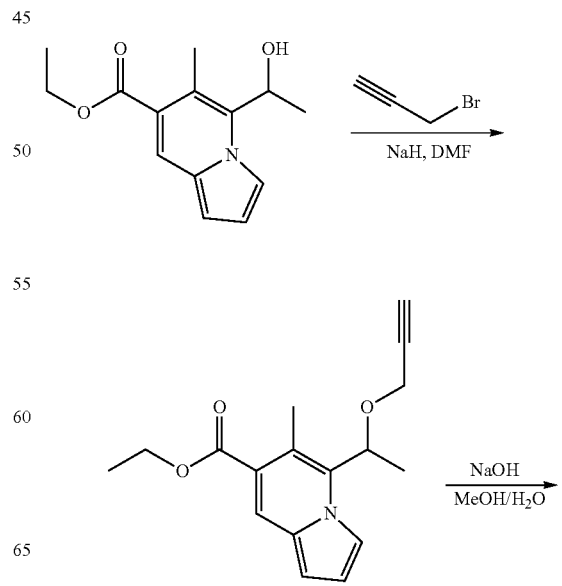

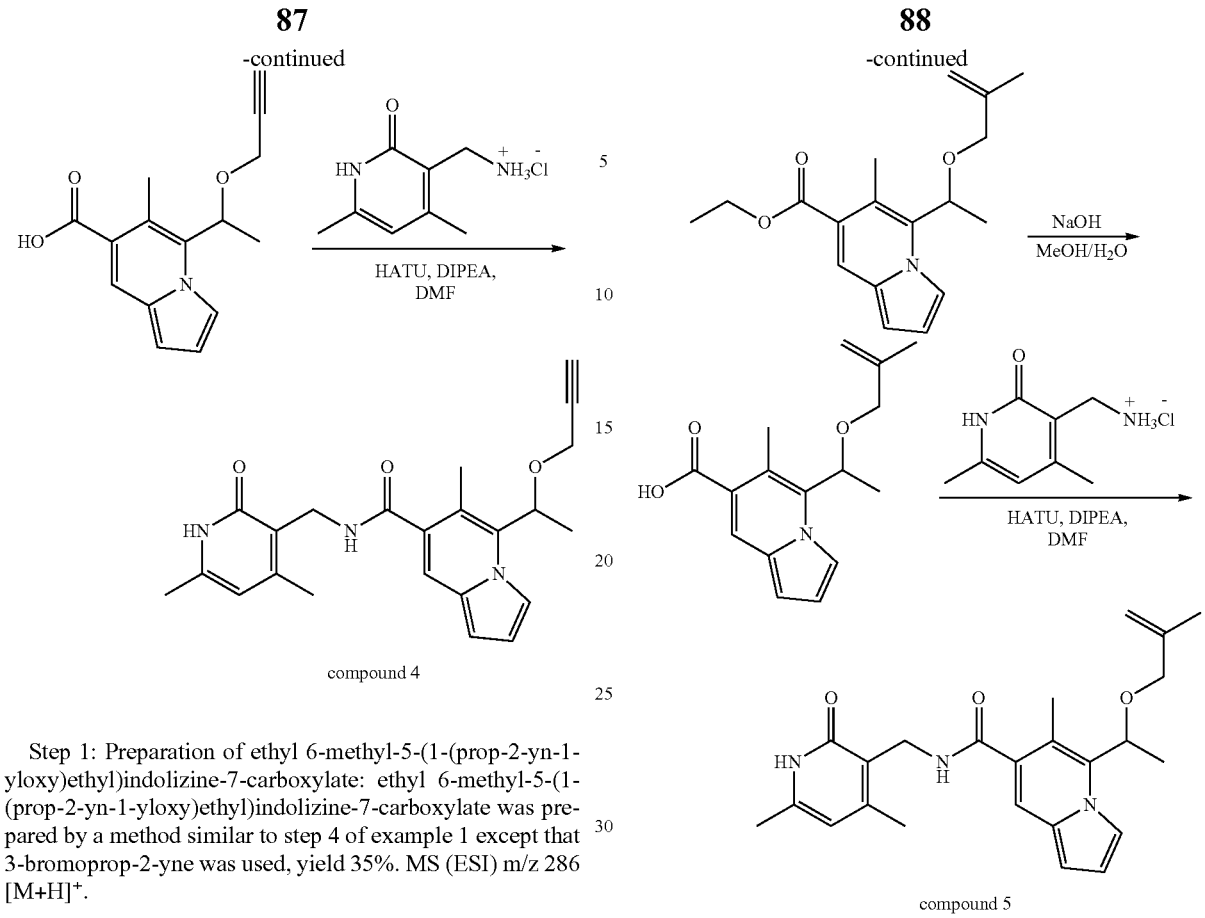

Step 1: Preparation of ethyl 6-methyl-5-(1-(prop-2-yn-1-yloxy)ethyl)indolizine-7-carboxylate: ethyl 6-methyl-5-(1-(prop-2-yn-1-yloxy)ethyl)indolizine-7-carboxylate was prepared by a method similar to step 4 of example 1 except that 3-bromoprop-2-yne was used, yield 35%. MS (ESI) m/z 286 [M+H]+.

Step 2: Preparation of 6-methyl-5-(1-(prop-2-yn-1-yloxy)ethyl)indolizine-7-carboxylic acid: 6-methyl-5-(1-(prop-2-yn-1-yloxy)ethyl)indolizine-7-carboxylic acid was prepared by a method similar to step 5 of example 1, yield 100%. MS (ESI) m/z 258 [M+H]+.

Step 3: Preparation of N-((4,6-Dimethyl-2-oxo-1,2-dihydropyridin-3-yl)methyl)-6-methyl-5-(1-(prop-2-yn-1-yloxy)ethyl)indolizine-7-carboxamide: N-((4,6-Dimethyl-2-oxo-1,2-dihydropyridin-3-yl)methyl)-6-methyl-5-(1-(prop-2-yn-1-yloxy) ethyl)indolizine-7-carboxamide was prepared by a method similar to Step 6 of Example 1, yield 20%. ¹H NMR (DMSO-d₆, 400 MHz) δ ppm 8.19 (s, 1H), 7.83 (s, 1H), 7.36 (s, 1H), 6.77 (d, J=2.8 Hz, 1H), 6.52 (d, J=3.2 Hz, 1H), 5.88 (s, 1H), 5.46-5.44 (m, 1H), 4.28-4.27 (m, 2H), 4.10 (d, J=16.0 Hz, 1H), 3.80 (d, J=16.0 Hz, 1H), 2.26 (s, 3H), 2.21 (s, 3H), 2.12 (s, 3H), 1.56 (d, J=6.8 Hz, 3H); MS (ESI) m/z 392 [M+H]+.

Example 5: Preparation of N-((4,6-Dimethyl-2-oxo-1,2-dihydropyridin-3-yl)methyl)-6-methyl-5-(1-((2-methylallyl)oxy) ethyl)indolizine-7-carboxamide

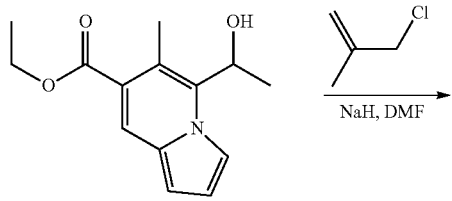

Step 1: Preparation of ethyl 6-methyl-5-(1-((2-methylallyl)oxy)ethyl)indolizine-7-carboxylate: ethyl 6-methyl-5-(1-((2-methylallyl)oxy)ethyl)pyridazin-7-carboxylate was prepared by a method similar to step 4 of Example 1 except that 3-chloro-2-methylprop-1-ene was used, yield 44%. ¹H NMR (CDCl₃, 400 MHz) δ ppm 8.10 (brs, 1H), 8.05 (s, 1H), 6.84 (t, J=2.0 Hz, 1H), 6.69 (t, J=2.0 Hz, 1H), 5.30 (q, J=6.8 Hz, 1H), 4.91 (d, J=3.9 Hz, 2H), 4.34 (q, J=6.4 Hz, 2H), 3.70 (d, J=12.0 Hz, 1H), 3.62 (d, J=12.0 Hz, 1H), 2.47 (s, 3H), 1.71 (s, 3H), 1.65 (d, J=6.8 Hz, 3H), 1.40 (t, J=6.4 Hz, 3H).

Step 2: Preparation of 6-methyl-5-(1-((2-methylallyl)oxy)ethyl)indolizine-7-carboxylic acid: 6-Methyl-5-(1-((2-methylallyl)oxy)ethyl)indolizine-7-carboxylic acid was prepared by a method similar to step 5 of Example 1, yield 94%. ¹H NMR (CDCl₃, 400 MHz) δ ppm 8.26 (s, 1H), 8.16 (s, 1H), 6.86 (brs, 1H), 6.75 (brs, 1H), 5.32 (q, J=6.8 Hz, 1H), 4.91 (d, J=4.4 Hz, 2H), 3.72 (d, J=12.0 Hz, 1H), 3.66 (d, J=12.0 Hz, 1H), 2.52 (s, 3H), 1.71 (s, 3H), 1.65 (d, J=6.8 Hz, 1H).

Step 3: Preparation of N-((4,6-Dimethyl-2-oxo-1,2-dihydropyridin-3-yl)methyl)-6-methyl-5-(1-((2-methallyl)oxy)ethyl)indolizine-7-carboxamide: N-((4,6-Dimethyl-2-oxo-1,2-dihydropyridin-3-yl)methyl)-6-methyl-5-(1-((2-methallyl)oxy)ethyl)indolizine-7-carboxamide was prepared by a method similar to step 6 of Example 1, yield 18%. ¹H NMR (CDCl₃, 400 MHz) 8.02 (s, 1H), 7.35 (s, 1H), 6.93 (s, 1H), 6.76 (s, 1H), 6.48 (brs, 1H), 6.30 (brs, 1H), 5.20 (q, J=6.8 Hz, 1H), 4.90 (q, J=10.8 Hz, 2H), 4.51 (d, J=5.6 Hz, 2H), 3.70 (d, J=12.0 Hz, 1H), 3.65 (d, J=12.0 Hz, 1H), 2.52 (s, 3H), 2.34 (s, 3H), 2.28 (s, 3H), 1.69 (s, 3H), 1.61 (d, J=6.8 Hz, 3H); MS (ESI) m/z 408 [M+H]+.

Example 6: Preparation of N-((4,6-Dimethyl-2-oxo-1,2-dihydropyridin-3-yl)methyl)-5-(1-isobutyloxyethyl)-6-methylindolizine-7-carboxamide

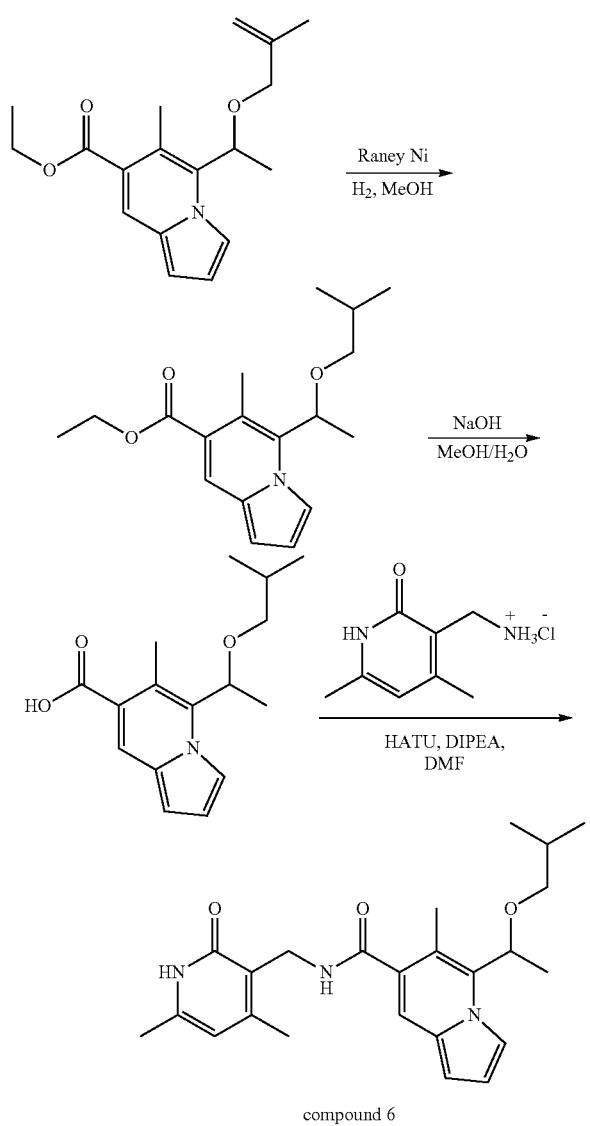

compound 6

Step 1: Preparation of ethyl 5-(1-isobutyloxyethyl)-6-methylindolizine-7-carboxylate: ethyl 6-methyl-5-(1-((2-methylallyl)oxy)ethyl)indolizine-7-carboxylate (60 mg, 0.2 mmol)), Raney Ni (6 mg) and 10 ml of methanol were added sequentially to a 25 mL single-necked flask, exchanged with hydrogen and stirred at room temperature for two hours. The organic phase was concentrated to provide a yellow oily product (50 mg, yield: 86%). MS (ESI) m/z 304 [M+H]$^+$.

Step 2: Preparation of 5-(1-isobutyloxyethyl)-6-methylindolizine-7-carboxylic acid: 5-(1-isobutyloxyethyl)-6-methylindolizine-7-carboxylic acid was prepared by a method similar to step 5 of Example 1, yield 89%. MS (ESI) m/z 276 [M+H]$^+$.

Step 3: Preparation of N-((4,6-dimethyl-2-oxo-1,2-dihydropyridin-3-yl)methyl)-5-(1-isobutyloxyethyl)-6-methylindolizine-7-carboxamide: N-((4,6-dimethyl-2-oxo-1,2-dihydropyridin-3-yl)methyl)-5-(1-isobutyloxyethyl)-6-methylindolizine-7-carboxamide was prepared by a method similar to Step 6 of Example 1, yield 20%. $^1$H NMR (DMSO-d$_6$, 400 MHz) δ ppm 8.17 (s, 1H), 7.91 (s, 1H), 7.34 (s, 1H), 6.76 (brs, 1 H), 6.49 (d, J=2.8 Hz, 1H), 5.88 (s, 1H), 5.20 (q, J=6.8 Hz, 1H), 4.28 (brs, 2H), 3.20-3.16 (m, 1H), 2.85-2.82 (m, 1H), 2.24 (s, 3H), 2.21 (s, 3H), 2.12 (s, 3H), 1.69-1.66 (m, 1H), 1.53 (d, J=6.8 Hz, 3H), 0.82-0.79 (m, 6H); MS (ESI) m/z 410 [M+H]$^+$.

Example 7: Preparation of 5-((cyclohex-2-en-1-yloxy)ethyl)-N-((4,6-dimethyl-2-oxo-1,2-dihydropyridin-3-yl)methyl)-6-methylindolizine-7-carboxamide

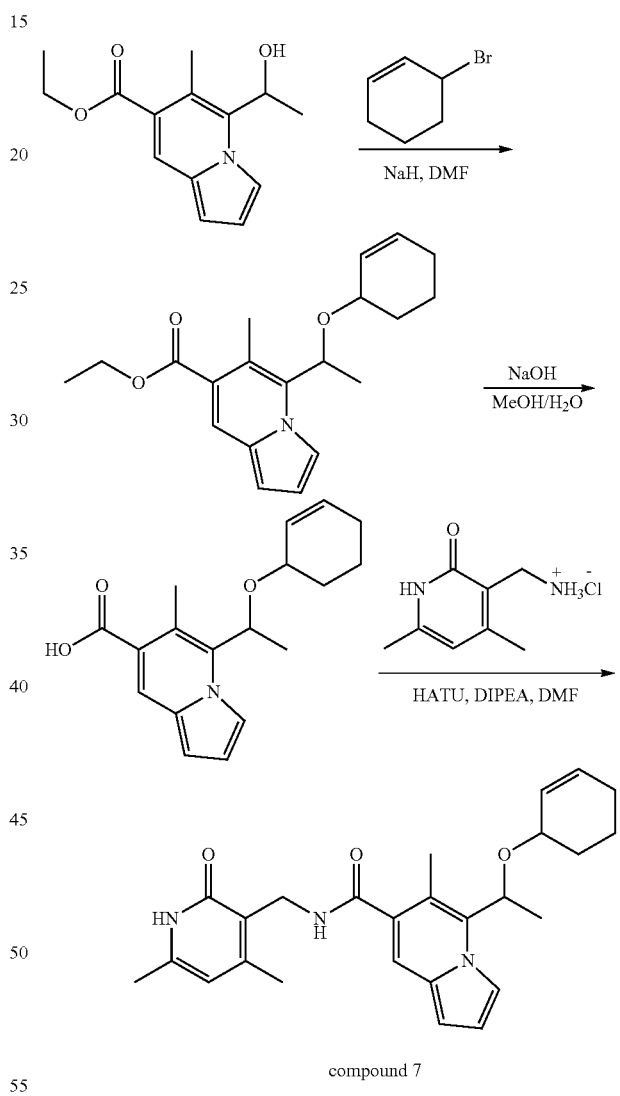

compound 7

Step 1: Preparation of ethyl 5-(1-(cyclohex-2-en-1-yloxy)ethyl)-6-methylindolizine-7-carboxylate: ethyl 5-(1-(cyclohex-2-en-1-yloxy)ethyl)-6-methylindolizine-7-carboxylate was prepared by a method similar to Step 4 of Example 1 except that 3-bromo-2-cyclohex-1-ene was used, yield 38%. MS (ESI) m/z 328 [M+H]$^+$.

Step 2: Preparation of 5-(1-(cyclohex-2-en-1-yloxy)ethyl)-6-methylindolizine-7-carboxylic acid: 5-(1-(cyclohex-2-en-1-yloxy)ethyl)-6-methylindolizine-7-carboxylic acid was prepared by a method similar to step 5 of example 1, yield 66%. MS (ESI) m/z 300 [M+H]$^+$.

Step 3: Preparation of 5-(1-(cyclohex-2-en-1-yloxy)ethyl)-N-((4,6-dimethyl-2-oxo-1,2-dihydropyridine-3-yl)methyl)-6-methylindolizine-7-carboxamide: 5-(1-(cyclohex-2-en-1-yloxy)ethyl)-6-methylindolizine-7-carboxylic acid was prepared by a method similar to step 6 of example 1, yield 19%. $^1$H NMR (DMSO-$d_6$, 400 MHz) δ ppm 8.19 (s, 1H), 7.97 (s, 1H), 7.34 (s, 1H), 6.76 (s, 1H), 6.49 (s, 1H), 5.88 (s, 1H), 5.84-5.69 (m, 1H), 5.42-5.32 (m, 1H), 4.27 (brs, 1H), 3.67 (s, 1H), 2.25 (s, 3H), 2.21 (s, 3H), 2.12 (s, 3H), 1.97-1.93 (m, 1H), 1.86-1.79 (m, 2H), 1.67 (s, 1H), 1.52 (d, J=6.8 Hz, 3H), 1.47-1.46 (m, 1H), 1.36-1.35 (m, 1H); MS (ESI) m/z 434 [M+H]$^+$.

Example 8: Preparation of 5-(1-(cyclohexyloxy)ethyl)-N-((4,6-dimethyl-2-oxo-1,2-dihydropyridin-3-yl)methyl)-6-methylindolizine-7-carboxamide Step 2: Preparation of 5-(1-(cyclohexyloxy)ethyl)-6-methylindolizine-7-carboxylic acid: 5-(1-(cyclohexyloxy)ethyl)-6-methylindolizine-7-carboxylic acid was prepared by a method similar to step 5 of example 1, yield 82%. MS (ESI) m/z 302 [M+H]$^+$.

Step 3: Preparation of 5-(1-(cyclohexyloxy)ethyl)-N-((4,6-dimethyl-2-oxo-1,2-dihydropyridine-3-yl)methyl)-6-methylindolizine-7-carboxamide: 5-(1-(cyclohexyloxy)ethyl)-6-methylindolizine-7-carboxylic acid was prepared by a method similar to step 6 of example 1, yield 5%. $^1$H NMR (DMSO-$d_6$, 400 MHz) δ ppm 8.18 (brs, 1H), 7.98 (s, 1H), 7.32 (s, 1H), 6.75 (s, 1H), 6.48 (d, J=3.0 Hz, 1H), 5.87 (s, 1H), 5.35 (q, J=6.8 Hz, 1H), 4.26 (d, J=4.8 Hz, 2H), 3.23 (s, 1H), 2.23 (s, 3H), 2.20 (s, 3H), 2.11 (s, 3H), 1.99-1.97 (m, 1H), 1.66 (s, 1H), 1.50 (d, J=6.8 Hz, 3H), 1.33-1.12 (m, 5H); MS (ESI) m/z 433 [M+H]$^+$.

Example 9: Preparation of 5-(1-(benzyloxy)ethyl)-N-((4,6-dimethyl-2-oxo-1,2-dihydropyridin-3-yl)methyl)-6-methylindolizine-7-carboxamide

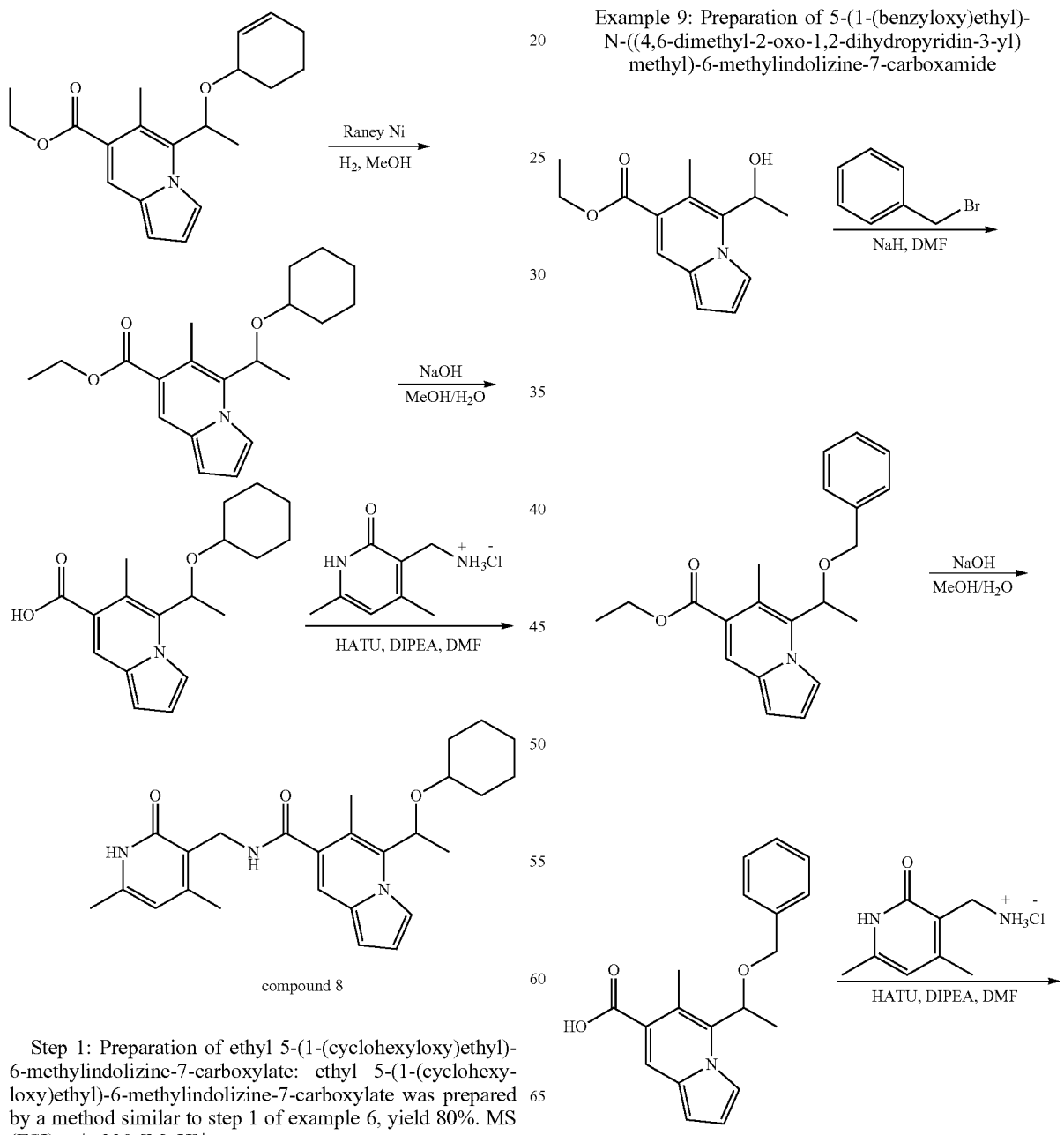

compound 8

Step 1: Preparation of ethyl 5-(1-(cyclohexyloxy)ethyl)-6-methylindolizine-7-carboxylate: ethyl 5-(1-(cyclohexyloxy)ethyl)-6-methylindolizine-7-carboxylate was prepared by a method similar to step 1 of example 6, yield 80%. MS (ESI) m/z 330 [M+H]$^+$.

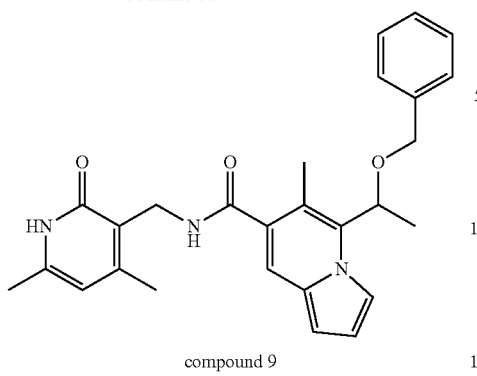

compound 9

Step 1: Preparation of ethyl 5-(1-(benzyloxy)ethyl)-6-methylindolizine-7-carboxylate: ethyl 5-(1-(benzyloxy)ethyl)-6-methylindolizine-7-carboxylate was prepared by a method similar to step 6 of example 1 except benzyl bromide was used, yield 64%. MS (ESI) m/z 338 [M+H]+.

Step 2: Preparation of 5-(1-(benzyloxy)ethyl)-6-methylindolizine-7-carboxylic acid: 5-(1-(benzyloxy)ethyl)-6-methylindolizine-7-carboxylic acid was prepared by a method similar to step 5 of example 1, yield 92%. $^1$H NMR (CDCl$_3$, 400 MHz) δ ppm 8.31 (s, 1H), 8.22 (brs, 1H), 7.34-7.24 (m, 5H), 6.89 (t, J=2.8 Hz, 1H), 6.79 (t, J=2.8 Hz, 1H), 5.37 (q, J=6.8 Hz, 1H), 4.40 (d, J=11.6 Hz, 1H), 4.24 (d, J=11.6 Hz, 1H), 2.47 (s, 3H), 1.67 (d, J=6.8 Hz, 1H).

Step 3: Preparation of 5-(1-(benzyloxy)ethyl)-N-((4,6-dimethyl-2-oxo-1,2-dihydropyridin-3-yl)methyl)-6-methylindolizine-7-carboxamide: 5-(1-(benzyloxy)ethyl)-N-((4,6-dimethyl-2-oxo-1,2-dihydropyridin-3-yl)methyl)-6-methylindolizine-7-carboxamide was prepared by a method similar to step 6 of example 1, yield 10%. $^1$H NMR (DMSO-d$_6$, 400 MHz) δ ppm 11.48 (s, 1H), 8.18 (s, 1H), 7.97 (s, 1H), 7.37-7.24 (m, 5H), 7.11 (s, 1H), 6.98 (s, 1H), 6.78 (s, 1H), 6.52 (s, 1H), 5.32 (q, J=6.8 Hz, 1H), 4.37-4.34 (m, 1H), 4.27-4.22 (m, 3H), 2.19 (d, J=6.8 Hz, 3H), 2.11 (s, 3H), 1.58 (d, J=6.4 Hz, 3H); MS (ESI) m/z 444 [M+H]+.

Example 10: Preparation of N-((4,6-dimethyl-2-oxo-1,2-dihydropyridin-3-yl)methyl)-5-(1-((4-fluorobenzyl))oxy)ethyl)-6-methylindolizine-7-carboxamide

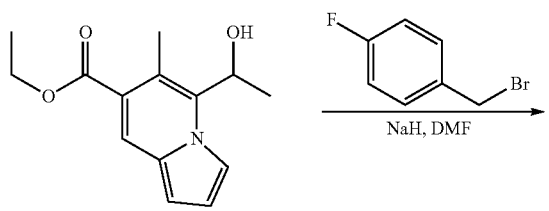

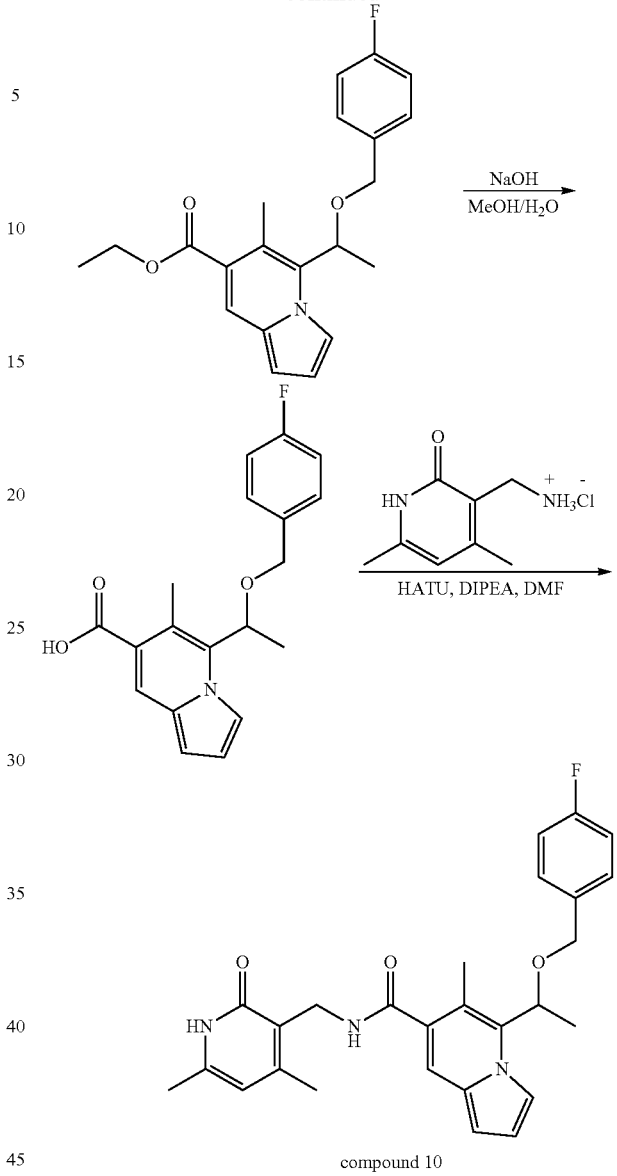

compound 10

N-((4,6-dimethyl-2-oxo-1,2-dihydropyridin-3-yl)methyl)-5-(1-((4-fluorobenzyl))oxy)ethyl)-6-methylindolizine-7-carboxamide was prepared by a method similar to example 9.

Step 1: Preparation of ethyl 5-(1-((4-fluorobenzyl)oxy)ethyl)-6-methylindolizine-7-carboxylate: Yield 63%. MS (ESI) m/z 356 [M+H]+.

Step 1: Preparation of 5-(1-((4-fluorobenzyl)oxy)ethyl)-6-methylindolizine-7-carboxylic acid: Yield 88%. MS (ESI) m/z 328 [M+H]+.

Step 3: Preparation of N-((4,6-dimethyl-2-oxo-1,2-dihydropyridin-3-yl)methyl)-5-(1-((4-fluorobenzyl)oxy)ethyl)-6-methylindolizine-7-carboxamide: Yield 30%. $^1$H NMR (400 MHz, CDCl$_3$) δ ppm 11.5 (s, 1H), 8.02 (s, 1H), 7.41 (s, 1H), 7.24-7.17 (m, 2H), 7.00-6.96 (m, 2H), 6.78 (t, J=2.8 Hz, 1H), 6.51 (t, J=2.8 Hz, 1H), 5.94 (s, 1H), 5.24 (q, J=6.8 Hz, 1H), 4.52 (d, J=4.8 Hz, 2H), 4.30 (d, J=12.0 Hz, 1H), 4.19 (d, J=12.0 Hz, 1H), 2.39 (s, 3H), 2.25 (s, 3H), 2.23 (s, 3H), 1.63 (d, J=6.8 Hz, 3H); MS (ESI) m/z 462 [M+H]+.

Example 11: Preparation of N-((4,6-dimethyl-2-oxo-1,2-dihydropyridin-3-yl)methyl)-5-(1-((2-fluorobenzyl))oxy)ethyl)-6-methylindolizine-7-carboxamide

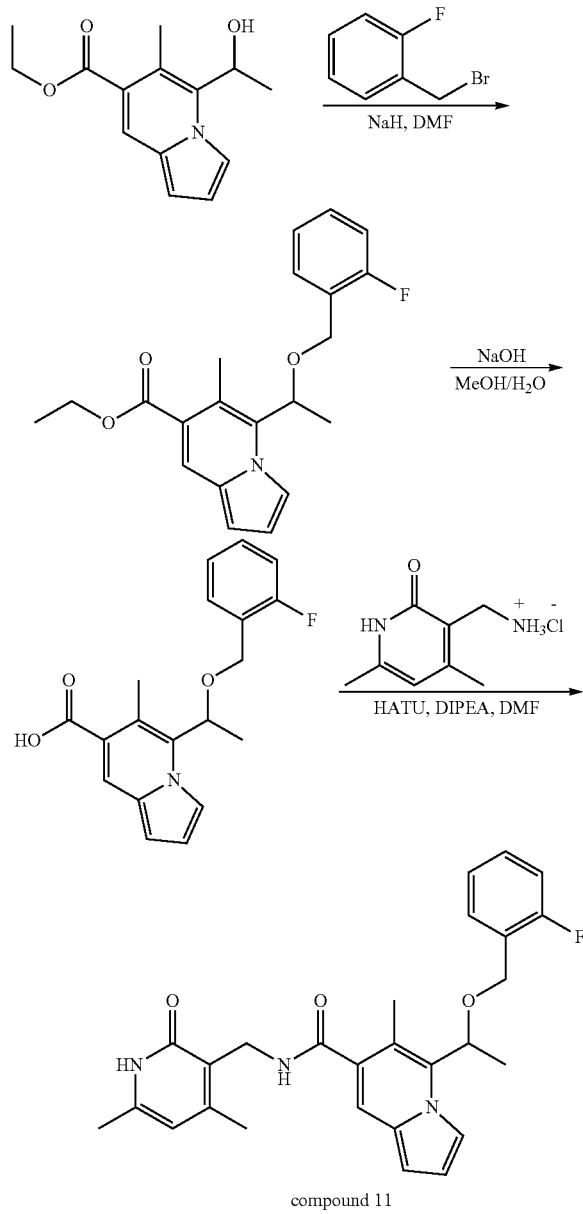

compound 11

N-((4,6-dimethyl-2-oxo-1,2-dihydropyridin-3-yl)methyl)-5-(1-((2-fluorobenzyl)oxy)ethyl)-6-methylindolizine-7-carboxamide was prepared by a method similar to example 9.

Step 1: Preparation of ethyl 5-(1-((2-fluorobenzyl)oxy)ethyl)-6-methylindolizine-7-carboxylate: Yield 63%. MS (ESI) m/z 356 [M+H]$^+$.

Step 2: Preparation of 5-(1-((2-fluorobenzyl)oxy)ethyl)-6-methylindolizine-7-carboxylic acid: Yield 84%. MS (ESI) m/z 328 [M+H]$^+$.

Step 3: Preparation of N-((4,6-dimethyl-2-oxo-1,2-dihydropyridin-3-yl)methyl)-5-(1-((2-fluorobenzyl)oxy)ethyl)-6-methylindolizine-7-carboxamide: Yield 4%. $^1$H NMR (DMSO-d$_6$, 400 MHz) δ ppm 8.19 (brs, 1H), 7.93 (s, 1H), 7.36-7.34 (m, 3H), 7.18-7.16 (m, 2H), 6.76 (t, J=2.8 Hz, 1H), 6.52 (t, J=2.8 Hz, 1H), 5.88 (s, 1H), 5.45 (q, J=6.8 Hz, 1H), 4.46 (d, J=12.0 Hz, 1H), 4.28-4.25 (m, 3H), 2.22 (s, 3H), 2.21 (s, 3H), 2.12 (s, 3H), 1.58 (d, J=6.8 Hz, 3H); MS (ESI) m/z 462 [M+H]$^+$.

Example 12: Preparation of N-((4,6-dimethyl-2-oxo-1,2-dihydropyridin-3-yl)methyl)-5-(1-((3-fluorobenzyl))oxy)ethyl)-6-methylindolizine-7-carboxamide

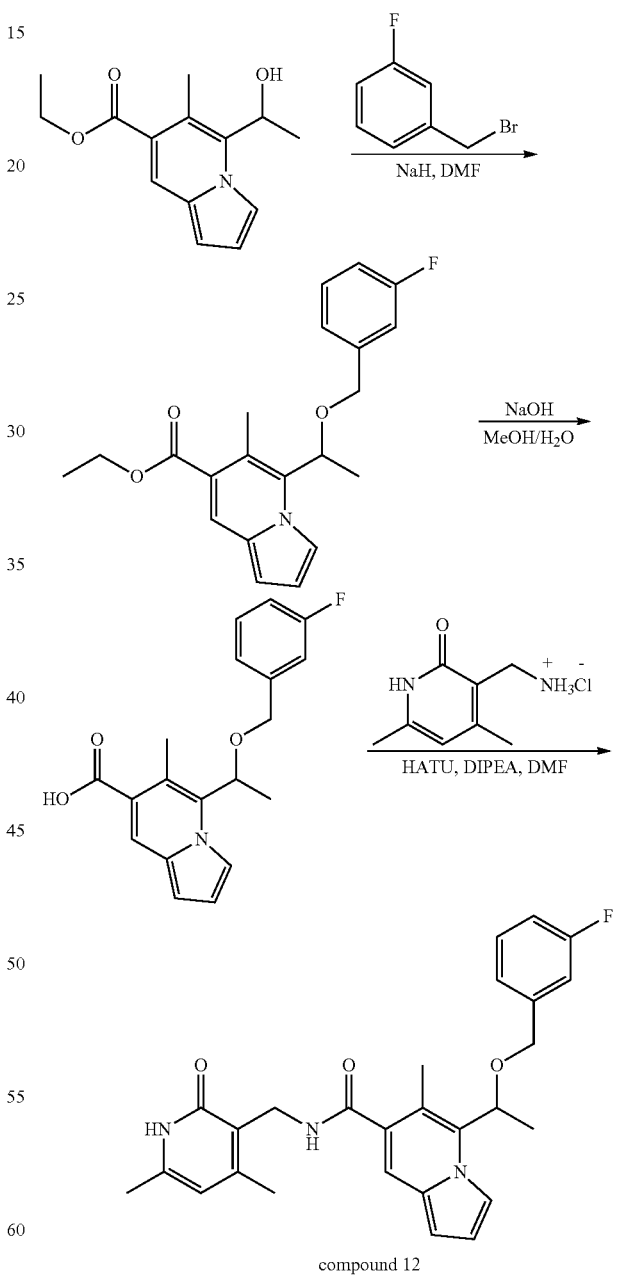

compound 12

N-((4,6-dimethyl-2-oxo-1,2-dihydropyridin-3-yl)methyl)-5-(1-((3-fluorobenzyl))oxy)ethyl)-6-methylindolizine-7-carboxamide was prepared by a method similar to example 9.

Step 1: Preparation of ethyl 5-(1-((3-fluorobenzyl)oxy)ethyl)-6-methylindolizine-7-carboxylate: Yield 66%. MS (ESI) m/z 356 [M+H]⁺.

Step 2: Preparation of 5-(1-((3-fluorobenzyl)oxy)ethyl)-6-methylindolizine-7-carboxylic acid: Yield 87%. MS (ESI) m/z 328 [M+H]⁺.

Step 3: Preparation of N-((4,6-dimethyl-2-oxo-1,2-dihydropyridin-3-yl)methyl)-5-(1-((3-fluorobenzyl)oxy)ethyl)-6-methylindolizine-7-carboxamide: Yield 11%. $^1$H NMR (DMSO-d$_6$, 400 MHz) δ ppm 12.50 (brs, 1H), 7.95 (brs, 1H), 7.40 (s, 1H), 7.36-7.32 (m, 2H), 7.96-6.82 (m, 3H), 6.75 (t, J=2.8 Hz, 1H), 6.47 (t, J=2.8 Hz, 1H), 5.87 (s, 1H), 5.25 (q, J=6.8 Hz, 1H), 4.46 (d, J=4.0 Hz, 2H), 4.26 (d, J=12.0 Hz, 1H), 4.18 (d, J=12.0 Hz, 1H), 2.38 (s, 3H), 2.21 (s, 3H), 2.18 (s, 3H), 1.54 (d, J=6.8 Hz, 3H); MS (ESI) m/z 462 [M+H]⁺.

Example 13: Preparation of 5-(1-((2,6-difluorobenzyl)oxy)ethyl)-N-((4,6-dimethyl-2-oxo-1,2-dihydropyridine)-3-yl)methyl)-6-methylindolizine-7-carboxamide

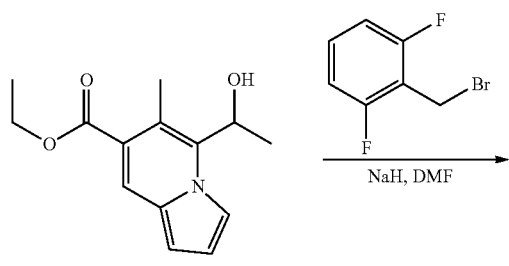

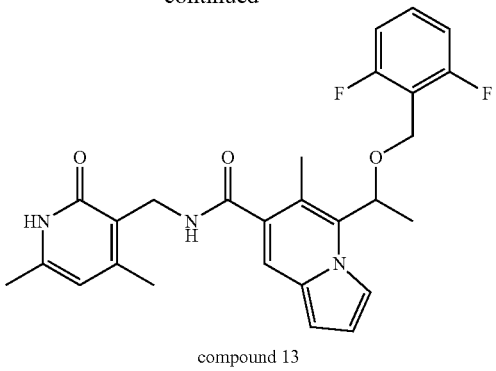

compound 13

5-(1-((2,6-difluorobenzyl)oxy)ethyl)-N-((4,6-dimethyl-2-oxo-1,2-dihydropyridine)-3-yl) methyl)-6-methylindolizine-7-carboxamide was prepared by a method similar to example 9.

Step 1: Preparation of ethyl 5-(1-((2,6-difluorobenzyl)oxy)ethyl)-6-methylindolizine-7-carboxylate: Yield 70%. MS (ESI) m/z 374 [M+H]⁺.

Step 2: Preparation of 5-(1-((3-fluorobenzyl)oxy)ethyl)-6-methylindolizine-7-carboxylic acid: Yield 78%. MS (ESI) m/z 346 [M+H]⁺.

Step 3: Preparation of 5-(1-((2,6-difluorobenzyl)oxy)ethyl)-N-((4,6-dimethyl-2-oxo-1,2-dihydropyridine-3-yl)methyl)-6-methylindolizine-7-carboxamide: Yield 16%. $^1$H NMR (CDCl$_3$, 400 MHz) δ ppm 12.40 (brs, 1H), 7.95 (brs, 1H), 7.38 (s, 1H), 7.30-7.18 (m, 1H), 6.75 (t, J=7.8 Hz 3H), 6.67 (t, J=2.8 Hz, 1H), 6.43 (t, J=2.8 Hz, 1H), 5.91 (s, 1H), 5.25 (q, J=6.8 Hz, 1H), 4.46 (d, J=4.0 Hz, 2H), 4.35 (s, 2H), 2.32 (s, 3H), 2.27 (s, 3H), 2.15 (s, 3H), 1.58 (d, J=6.8 Hz, 3H); MS (ESI) m/z 480 [M+H]⁺.

Example 14: Preparation of N-((4,6-dimethyl-2-oxo-1,2-dihydropyridin-3-yl)methyl)-5-(1-((3-methoxybenzyl)oxy)ethyl)-6-methylindolizine-7-carboxamide

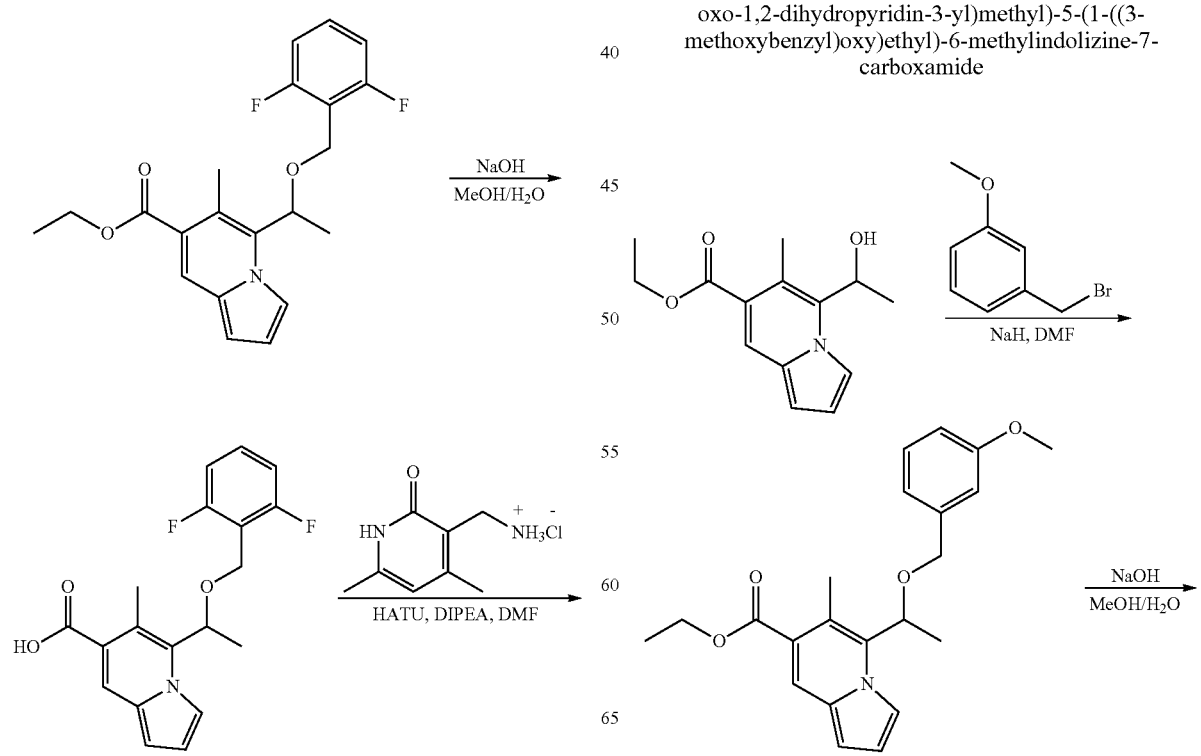

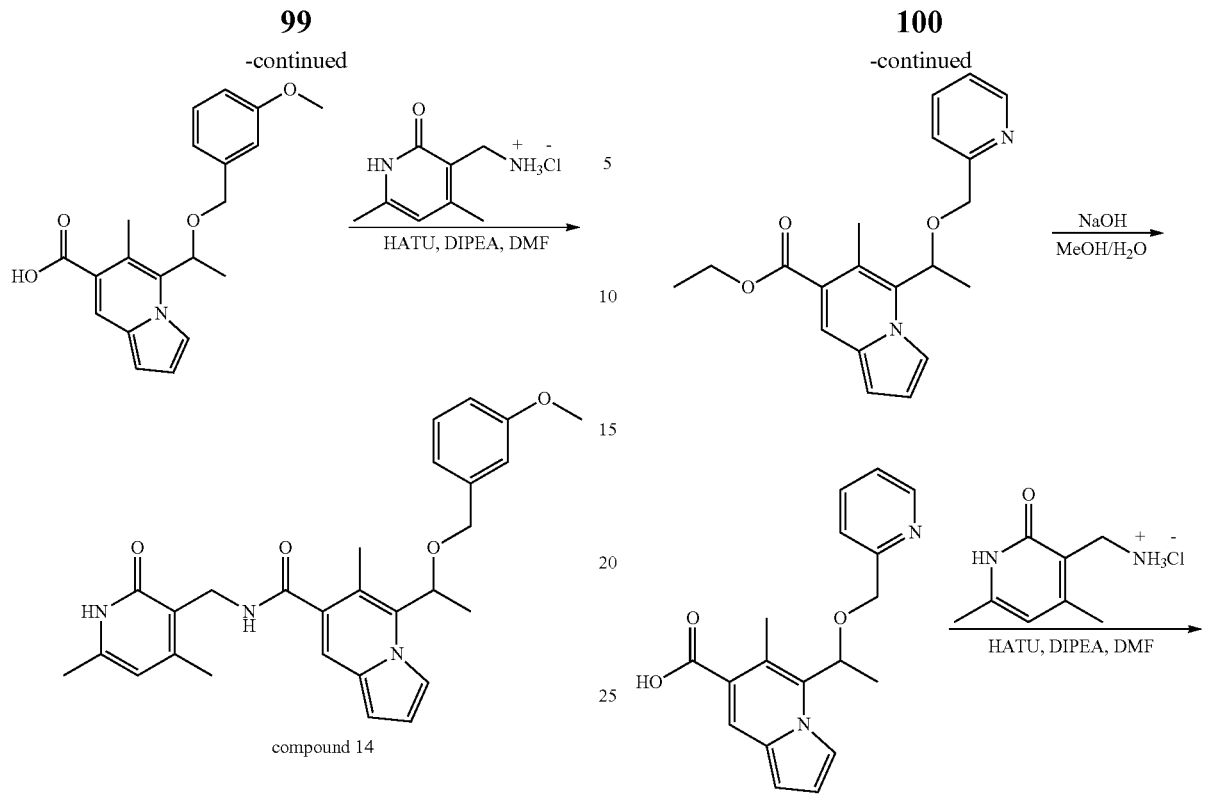

N-((4,6-dimethyl-2-oxo-1,2-dihydropyridin-3-yl)methyl)-5-(1-((3-methoxybenzyl)oxy)ethyl)-6-methylindolizine-7-carboxamide was prepared by a method similar to example 9.

Step 1: Preparation of ethyl 5-(1-((2,6-difluorobenzyl)oxy)ethyl)-6-methylindolizine-7-carboxylate: Yield 65%. MS (ESI) m/z 368 [M+H]⁺.

Step 2: Preparation of 5-(1-((3-fluorobenzyl)oxy)ethyl)-6-methylindolizine-7-carboxylic acid: Yield 69%. MS (ESI) m/z 340 [M+H]⁺.

Step 3: Preparation of 5-(1-((2,6-difluorobenzyl)oxy)ethyl)-N-((4,6-dimethyl-2-oxo-1,2-dihydropyridine-3-yl)methyl)-6-methylindolizine-7-carboxamide: Yield 13%. ¹H NMR (DMSO-d₆, 400 MHz) δ ppm 8.17 (brs, 1H), 7.97 (brs, 1H), 7.37 (s, 1H), 7.26 (brs, 2H), 6.84-6.79 (m, 4H), 6.51 (t, J=2.8 Hz, 1H), 5.88 (s, 1H), 5.32 (q, J=6.8 Hz, 1H), 4.34-4.21 (m, 4H), 3.70 (s, 3H), 2.21 (s, 3H), 2.19 (s, 3H), 2.12 (s, 3H), 1.58 (d, J=6.8 Hz, 3H); MS (ESI) m/z 474 [M+H]⁺.

Example 15: Preparation of N-((4,6-dimethyl-2-oxo-1,2-dihydropyridin-3-yl)methyl)-6-methyl-5-(1-(pyridine-2-ylmethoxy)ethyl)indolizine-7-carboxamide

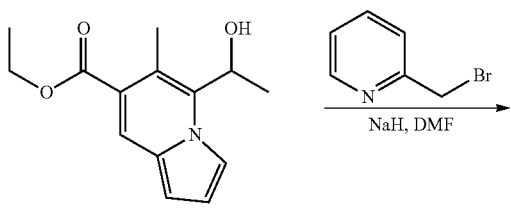

N-((4,6-dimethyl-2-oxo-1,2-dihydropyridin-3-yl)methyl)-6-methyl-5-(1-(pyridin-2-ylmethoxy)ethyl)indolizine-7-carboxamide was prepared by a method similar to example 9.

Step 1: Preparation of ethyl 6-methyl-5-(1-(pyridin-2-ylmethoxy)ethyl)indolizine-7-carboxylate: Yield 30%. MS (ESI) m/z 339 [M+H]⁺.

Step 2: Preparation of 6-methyl-5-(1-(pyridin-2-ylmethoxy)ethyl)indolizine-7-carboxylic acid: yield 90%. MS (ESI) m/z 311 [M+H]⁺.

Step 3: Preparation of N-((4,6-dimethyl-2-oxo-1,2-dihydropyridin-3-yl)methyl)-6-methyl-5-(1-(pyridine-2-ylmethoxy)ethyl)indolizine-7-carboxamide: Yield 20%. ¹H NMR (400 MHz, CDCl₃) δ ppm 8.62 (d, J=4.8 Hz, 1H), 7.91-7.84 (m, 2H), 7.52-7.51 (m, 1H), 7.42-7.39 (m, 1H), 7.32 (s, 1H), 7.09 (s, 1H), 6.76 (d, J=3.2 Hz, 1H), 6.48 (d, J=3.2 Hz, 1H), 6.33 (s, 1H), 5.36 (q, J=6.8 Hz, 1H), 4.70 (d, J=12.0 Hz, 1H), 4.57-4.49 (m, 3H), 2.52 (s, 3H), 2.37 (s, 3H), 2.23 (s, 3H), 1.70 (d, J=6.8 Hz, 3H); MS (ESI) m/z 445 [M+H]⁺.

Example 16: Preparation of N-((4,6-dimethyl-2-oxo-1,2-dihydropyridin-3-yl)methyl)-6-methyl-5-(1-(pyridine-4-ylmethoxy)ethyl)indolizine-7-carboxamide

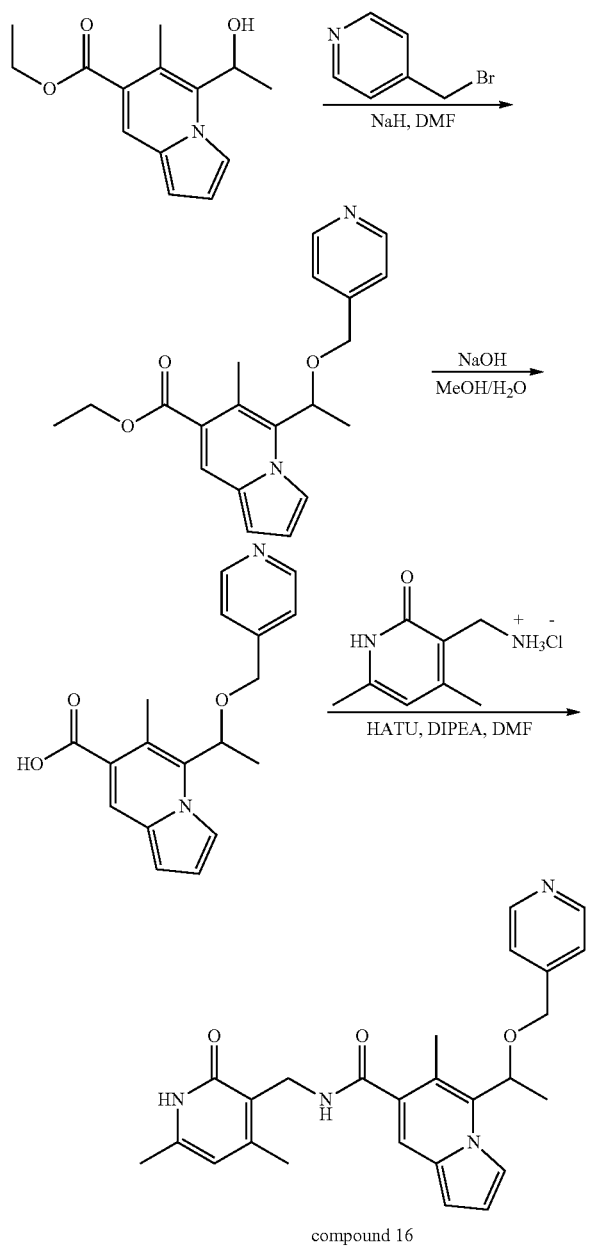

compound 16

N-((4,6-dimethyl-2-oxo-1,2-dihydropyridin-3-yl)methyl)-6-methyl-5-(1-(pyridin-4-ylmethoxy)ethyl)indolizine-7-carboxamide was prepared by a method similar to example 9.

Step 1: Preparation of ethyl 6-methyl-5-(1-(pyridin-4-ylmethoxy)ethyl)indolizine-7-carboxylate: Yield 37%. MS (ESI) m/z 339 [M+H]⁺.

Step 2: Preparation of 6-methyl-5-(1-(pyridin-4-ylmethoxy)ethyl)indolizine-7-carboxylic acid: yield 85%. MS (ESI) m/z 311 [M+H]⁺.

Step 3: Preparation of N-((4,6-dimethyl-2-oxo-1,2-dihydropyridin-3-yl)methyl)-6-methyl-5-(1-(pyridine-4-yl-methoxy)ethyl)indolizine-7-carboxamide: Yield 6%. $^1$H NMR (400 MHz, CDCl$_3$) δ ppm 8.61 (d, J=6.4 Hz, 1H), 7.87 (s, 1H), 7.60-7.59 (m, 2H), 7.35 (s, 1H), 7.05 (s, 1H), 6.79 (t, J=2.8 Hz, 1H), 6.52 (t, J=2.8 Hz, 1H), 6.43 (s, 1H), 5.32 (q, J=6.8 Hz, 1H), 4.66-4.46 (m, 4H), 2.57 (s, 3H), 2.43 (s, 3H), 2.27 (s, 3H), 1.75 (d, J=6.8 Hz, 3H); MS (ESI) m/z 445 [M+H]⁺.

Example 17: Preparation of N-((4,6-dimethyl-2-oxo-1,2-dihydropyridin-3-yl)methyl)-6-methyl-5-(1-(thiophene-2-ylmethoxy)ethyl)indolizine-7-carboxamide

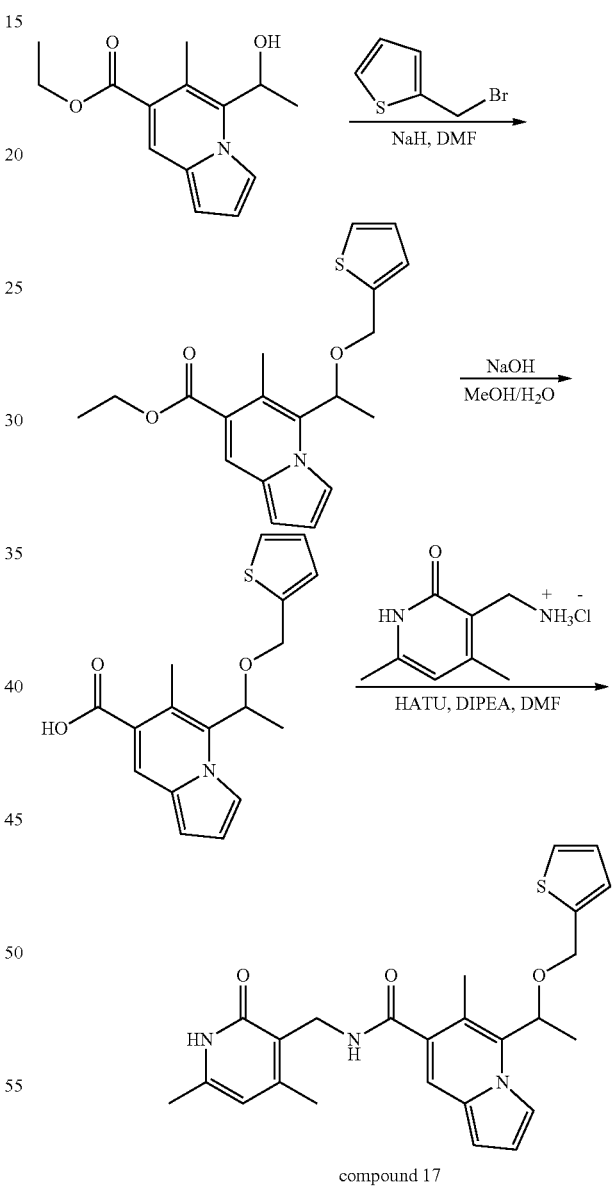

compound 17

N-((4,6-dimethyl-2-oxo-1,2-dihydropyridin-3-yl)methyl)-6-methyl-5-(1-(thiophene-2-yl methoxy)ethyl)indolizine-7-carboxamide was prepared by a method similar to example 9.

Step 1: Preparation of ethyl 6-methyl-5-(1-(thiophene-2-ylmethoxy)ethyl)indolizine-7-carboxylate: Yield 39%. MS (ESI) m/z 344 [M+H]⁺.

Step 2: Preparation of 6-methyl-5-(1-(thiophene-2-yl-methoxy)ethyl)indolizine-7-carboxylic acid: yield 82%. MS (ESI) m/z 316 [M+H]+.

Step 3: Preparation of N-((4,6-dimethyl-2-oxo-1,2-dihydropyridin-3-yl)methyl)-6-methyl-5-(1-(thiophene-2-yl-methoxy)ethyl)indolizine-7-carboxamide: Yield 8%. 1H NMR (400 MHz, CDCl3) δ ppm 7.40 (s, 1H), 7.28 (s, 1H), 6.93 (t, J=3.0 Hz, 1H), 6.87-6.81 (m, 3H), 6.55 (d, J=3.0 Hz, 1H), 6.34 (s, 1H), 5.28 (q, J=6.8 Hz, 1H), 4.55-4.52 (m, 3H), 4.38 (d, J=11.8 Hz, 1H), 2.56 (s, 3H), 2.40 (s, 3H), 2.11 (s, 3H), 1.62 (d, J=6.8 Hz, 3H); MS (ESI) m/z 450 [M+H]+.

Example 18: Preparation of N-((4,6-dimethyl-2-oxo-1,2-dihydropyridin-3-yl)methyl)-6-methyl-5-(1-(thiazole-2-ylmethoxy)ethyl)indolizine-7-carboxamide

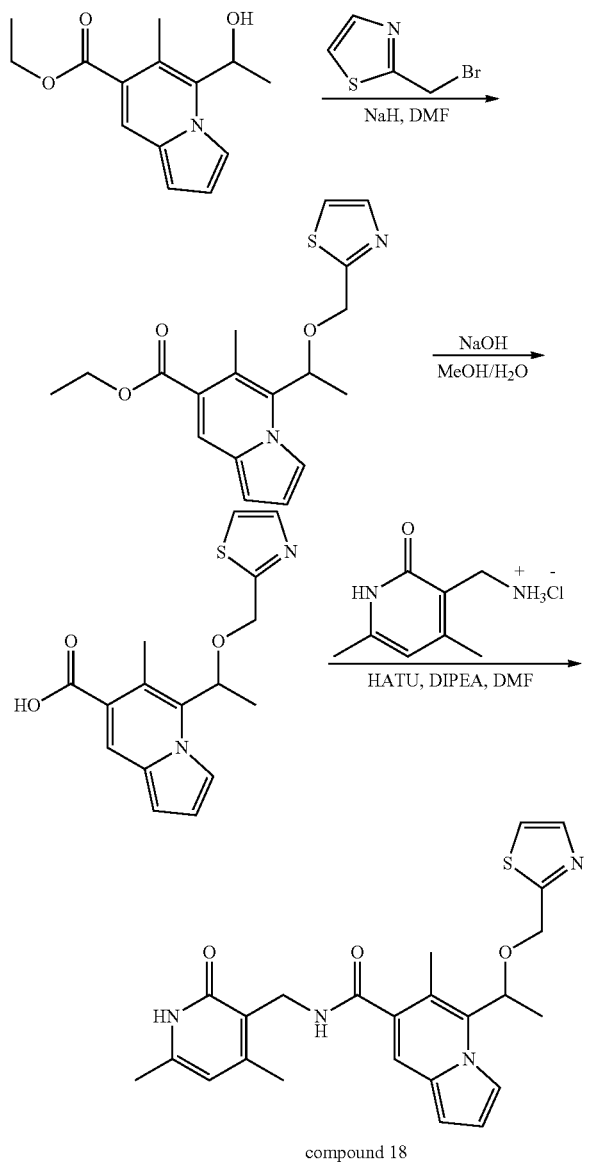

compound 18

N-((4,6-dimethyl-2-oxo-1,2-dihydropyridin-3-yl)methyl)-6-methyl-5-(1-(thiazole-2-ylmethoxy)ethyl)indolizine-7-carboxamide was prepared by a method similar to example 9.

Step 1: Preparation of ethyl 6-methyl-5-(1-(thiazol-2-ylmethoxy)ethyl)indolizine-7-carboxylate: Yield 45%. MS (ESI) m/z 345 [M+H]+.

Step 2: Preparation of 6-methyl-5-(1-(thiazol-2-ylmethoxy)ethyl)indolizine-7-carboxylic acid: yield 89%. MS (ESI) m/z 317 [M+H]+.

Step 3: Preparation of N-((4,6-dimethyl-2-oxo-1,2-dihydropyridin-3-yl)methyl)-6-methyl-5-(1-(thiazol-2-ylmethoxy)ethyl)indolizine-7-carboxamide: Yield 11%. 1H NMR (400 MHz, CDCl3) δ ppm 12.1 (brs, 1H), 7.94 (s, 1H), 7.64 (s, 1H), 7.24-7.21 (m, 2H), 6.71 (t, J=3.0 Hz, 1H), 6.42 (d, J=3.0 Hz, 1H), 5.88 (s, 1H), 5.32 (q, J=6.8 Hz, 1H), 4.56 (s, 1H), 4.45 (d, J=6.4 Hz, 2H), 2.32 (s, 3H), 2.23 (s, 3H), 2.16 (s, 3H), 1.62 (d, J=6.8 Hz, 3H); MS (ESI) m/z 451 [M+H]+.

Example 19: Preparation of N-((4,6-dimethyl-2-oxo-1,2-dihydropyridin-3-yl)methyl)-6-methyl-5-(1-(thiophene-3-ylmethoxy)ethyl)indolizine-7-carboxamide

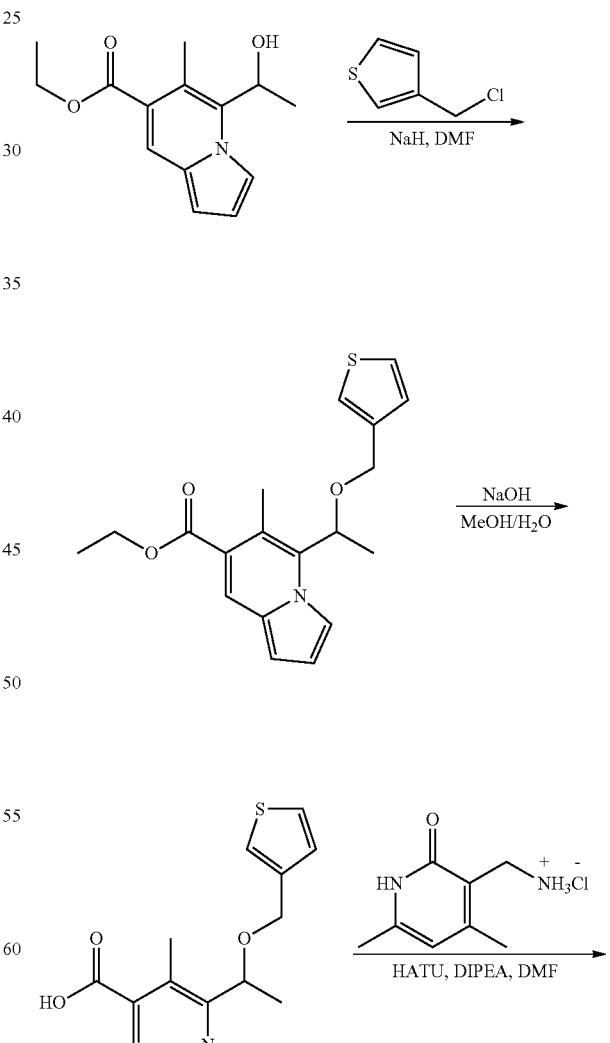

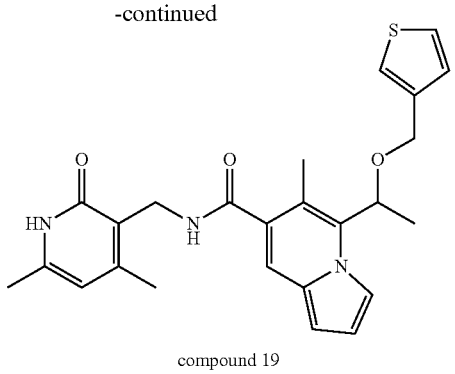

compound 19

N-((4,6-dimethyl-2-oxo-1,2-dihydropyridin-3-yl)methyl)-6-methyl-5-(1-(thiophene-3-yl methoxy)ethyl)indolizine-7-carboxamide was prepared by a method similar to example 9.

Step 1: Preparation of ethyl 6-methyl-5-(1-(thiophene-3-ylmethoxy)ethyl)indolizine-7-carboxylate: Yield 34%. MS (ESI) m/z 344 [M+H]$^+$.

Step 2: Preparation of 6-methyl-5-(1-(thiophene-3-ylmethoxy)ethyl)indolizine-7-carboxylic acid: yield 71%. MS (ESI) m/z 316 [M+H]$^+$.

Step 3: Preparation of N-((4,6-dimethyl-2-oxo-1,2-dihydropyridin-3-yl)methyl)-6-methyl-5-(1-(thiophene-3-ylmethoxy)ethyl)indolizine-7-carboxamide: Yield 13%. $^1$H NMR (400 MHz, CDCl$_3$) δ ppm 12.30 (brs, 1H), 8.06 (s, 1H), 7.41 (s, 1H), 7.29-7.24 (m, 1H), 7.11 (brs, 1H), 6.98 (brs, 1H), 6.79 (d, J=3.0 Hz, 1H), 6.49 (d, J=3.0 Hz, 1H), 5.98 (s, 1H), 5.24 (q, J=6.8 Hz, 1H), 4.53 (d, J=6.4 Hz, 2H), 4.34 (d, J=11.4 Hz, 1H), 4.26 (d, J=11.4 Hz, 1H), 2.34 (s, 3H), 2.26 (s, 3H), 2.24 (s, 3H), 1.61 (d, J=6.8 Hz, 3H); MS (ESI) m/z 450 [M+H]$^+$.

Example 20: Preparation of N-((4,6-dimethyl-2-oxo-1,2-dihydropyridin-3-yl)methyl)-6-methyl-5-(1-methyl-1H-pyrazol-3-yl)methoxy)ethyl)indolizine-7-carboxamide

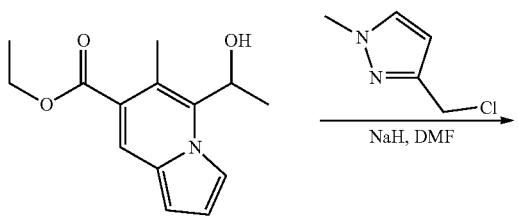

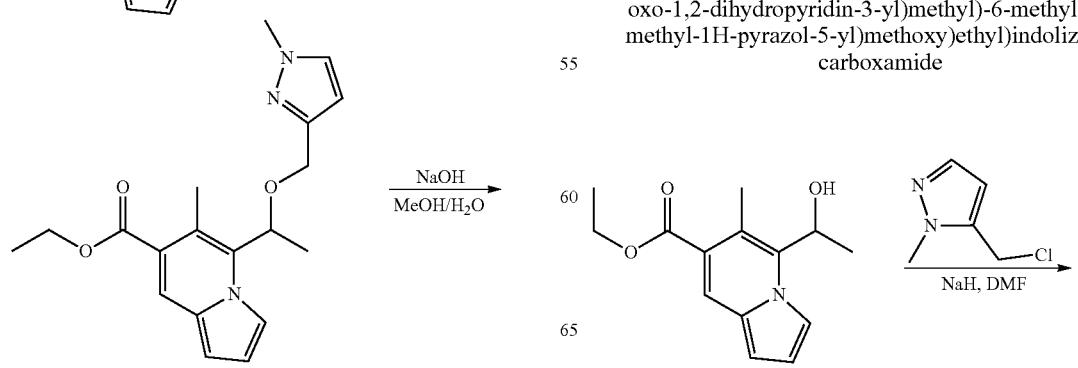

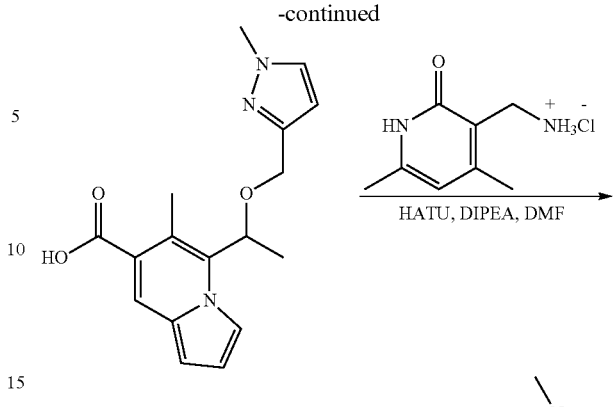

compound 20

N-((4,6-dimethyl-2-oxo-1,2-dihydropyridin-3-yl)methyl)-6-methyl-5-(1-methyl-1H-pyrazol-3-yl)methoxy)ethyl)indolizine-7-carboxamide was prepared by a method similar to example 9.

Step 1: Preparation of ethyl 6-methyl-5-(1-((1-methyl-1H-pyrazol-3-yl)methoxy)ethyl)indolizine-7-carboxylate: Yield 43%. MS (ESI) m/z 342 [M+H]$^+$.

Step 2: Preparation of 6-methyl-5-(1-((1-methyl-1H-pyrazol-3-yl)methoxy)ethyl)indolizine-7-carboxylic acid: yield 82%. MS (ESI) m/z 314 [M+H]$^+$.

Step 3: Preparation of N-((4,6-dimethyl-2-oxo-1,2-dihydropyridin-3-yl)methyl)-6-methyl-5-(1-((1-methyl-1H-pyrazol-3-yl)methoxy)ethyl)indolizine-7-carboxamide: Yield 16%. $^1$H NMR (400 MHz, CDCl$_3$) δ ppm 12.51 (brs, 1H), 8.06 (brs, 1H), 7.39 (s, 1H), 7.29-7.23 (m, 1H), 6.78 (d, J=3.0 Hz, 1H), 6.47 (d, J=3.0 Hz, 1H), 6.07 (brs, 1H), 5.95 (s, 1H), 5.31 (q, J=6.8 Hz, 1H), 4.53 (d, J=6.4 Hz, 2H), 4.32 (t, J=11.4 Hz, 2H), 3.84 (s, 3H), 2.38 (s, 3H), 2.30 (s, 3H), 2.22 (s, 3H), 1.61 (d, J=6.8 Hz, 3H); MS (ESI) m/z 448 [M+H]$^+$.

Example 21: Preparation of N-((4,6-dimethyl-2-oxo-1,2-dihydropyridin-3-yl)methyl)-6-methyl-5-(1-methyl-1H-pyrazol-5-yl)methoxy)ethyl)indolizine-7-carboxamide

Example 22: Preparation of N-((4,6-dimethyl-2-oxo-1,2-dihydropyridin-3-yl)methyl)-5-(1-(4-(dimethylamino))phenyloxy)ethyl)-6-methylindolizine-7-carboxamide

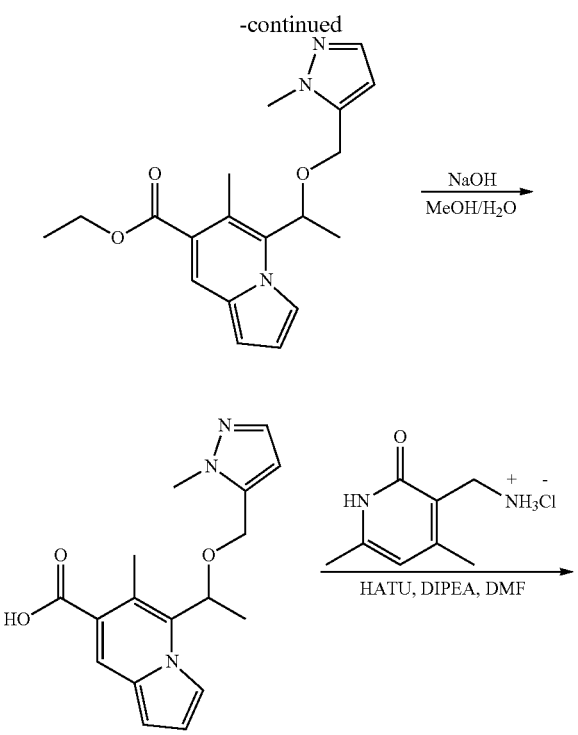

compound 21

N-((4,6-dimethyl-2-oxo-1,2-dihydropyridin-3-yl)methyl)-6-methyl-5-(1-methyl-1H-pyrazol-5-yl)methoxy)ethyl)indolizine-7-carboxamide was prepared by a method similar to example 9.

Step 1: Preparation of ethyl 6-methyl-5-(1-((1-methyl-1H-pyrazol-5-yl)methoxy)ethyl)indolizine-7-carboxylate: Yield 33%. MS (ESI) m/z 342 [M+H]$^+$.

Step 2: Preparation of 6-methyl-5-(1-((1-methyl-1H-pyrazol-5-yl)methoxy)ethyl)indolizine-7-carboxylic acid: yield 81%. MS (ESI) m/z 314 [M+H]$^+$.

Step 3: Preparation of N-((4,6-dimethyl-2-oxo-1,2-dihydropyridin-3-yl)methyl)-6-methyl-5-(1-methyl-1H-pyrazol-5-yl)methoxy)ethyl)indolizine-7-carboxamide: Yield 13%. $^1$H NMR (400 MHz, DMSO-d$_6$) δ ppm 13.08 (brs, 1H), 8.20 (brs, 1H), 7.89 (s, 1H), 7.38 (s, 1H), 7.32 (s, 1H), 6.78 (t, J=3.0 Hz, 1H), 6.52 (d, J=3.0 Hz, 1H), 6.12 (brs, 1H), 5.89 (s, 1H), 5.29 (q, J=6.8 Hz, 1H), 4.41-4.26 (m, 4H), 3.68 (s, 3H), 2.38 (s, 3H), 2.21 (s, 3H), 2.20 (s, 3H), 1.56 (d, J=6.8 Hz, 3H); MS (ESI) m/z 448 [M+H]$^+$.

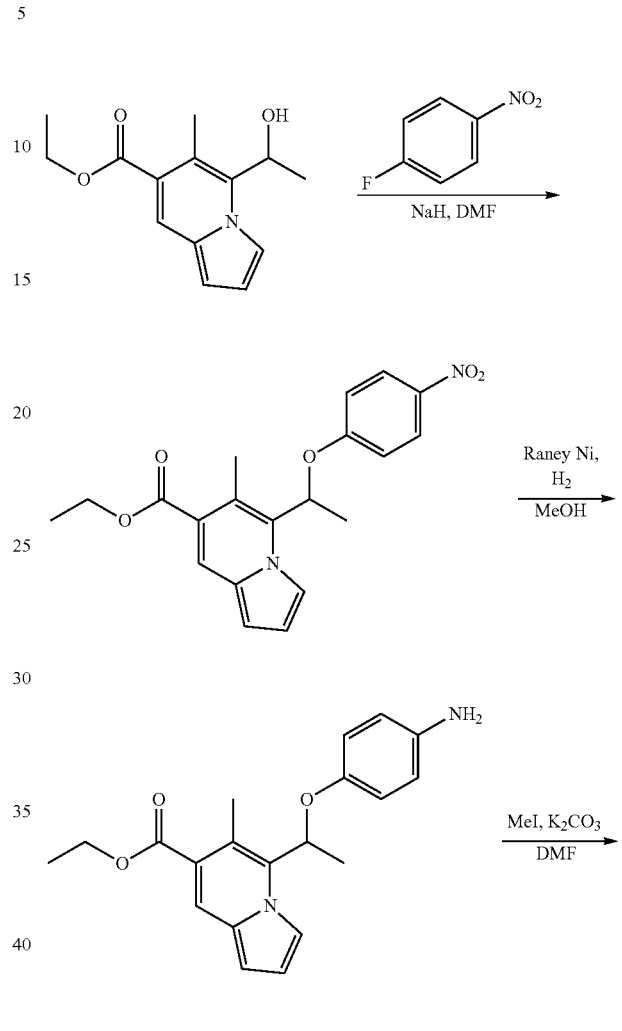

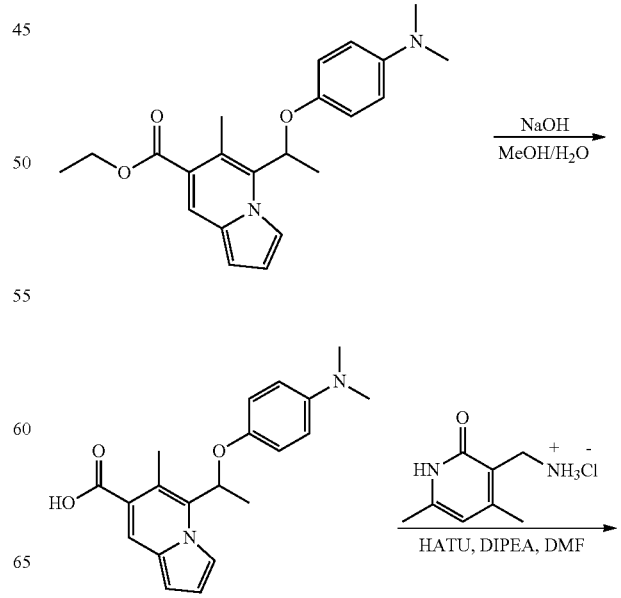

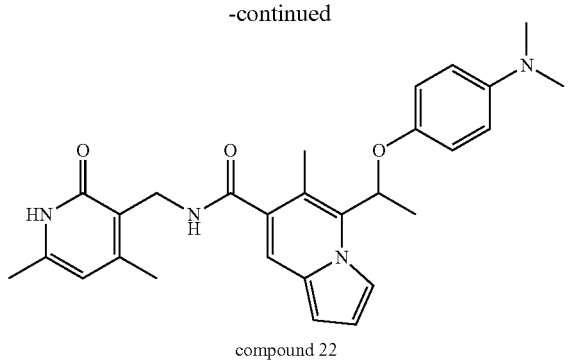

compound 22

Step 1: Preparation of ethyl 6-methyl-5-(1-(4-nitrophenyloxy)ethyl)indolizine-7-carboxylate: ethyl 6-methyl-5-(1-(4-nitrophenyloxy)ethyl)indolizine-7-carboxylate was prepared by a mathed similar to Step 4 of example 1 except that p-nitrofluorobenzene was used, yield 65%. MS (ESI) m/z 369 [M+H]+.

Step 2: Preparation of ethyl 5-(1-(4-aminophenyloxy)ethyl)-6-methylindolizine-7-carboxylate: ethyl 6-methyl-5-(1-((4-aminophenyloxy)ethyl)indolizine-7-carboxylate (125 mg, 0.34 mmol)), Raney Ni (10 mg) and 10 ml of methanol were added sequentially to a 25 mL single-necked flask, exchanged with hydrogen and stirred at room temperature for 4 hours, and filtered. The organic phase was concentrated and purified through column chromatography (petroleum ether:ethyl acetate=4:1) to provide a product as yellow oil (100 mg, yield: 87%). MS (ESI) m/z 339 [M+H]+.

Step 3: Preparation of ethyl 5-(1-(4-dimethylaminophenyloxy)ethyl)-6-methylindolizine-7-carboxylate: ethy 5-(1-(4-aminophenyloxy)ethyl)-6-methylindolizine-7-carboxylate (100 mg, 0.30 mmol) in DMF (1.0 mL) was added with potassium carbonate (104 mg, 0.75 mmol) and methyl iodide (94 mg, 0.66 mmol), stirred at room temperature for 2 h. The mixture was extracted with ethyl acetate (100 mL), washed with water (50 mL×2) and brine (50 mL). The organic phase was dried over anhydrous sodium sulfate, filtered and concentrated to provide a crude product, which was purified through column chromatography (petroleum ether:ethyl acetate=4:1) to provide a product as white solid (40 mg, yield: 36%). MS (ESI) m/z 367 [M+H]+.

Step 4: Preparation of 5-(1-(4-dimethylaminophenyloxy)ethyl)-6-methylindolizine-7-carboxylic acid: 5-(1-(4-dimethylaminophenyloxy)ethyl)-6-methylindolizine-7-carboxylic acid was prepared by a method similar to step 5 of example 1, yield 89%. MS (ESI) m/z 339 [M+H]+.

Step 5: Preparation of N-((4,6-dimethyl-2-oxo-1,2-dihydropyridin-3-yl)methyl)-5-(1-(4-(dimethylamino)benzyloxy)ethyl)-6-methylindolizine-7-carboxamide: N-((4,6-dimethyl-2-oxo-1,2-dihydropyridin-3-yl)methyl)-5-(1-(4-(dimethylamino)benzyloxy)ethyl)-6-methylindolizine-7-carboxamide was prepared by a method similar to Step 6 of Example 1, yield 6%. 1H NMR (400 MHz, DMSO-d6) δ ppm 11.49 (brs, 1H), 8.21 (t, J=3.0 Hz, 1H), 8.03 (s, 1H), 7.34 (s, 1H), 7.29 (brs, 2H), 6.93-6.90 (m, 2H), 6.80 (t, J=3.0 Hz, 1H), 6.51 (d, J=3.0 Hz, 1H), 6.12 (q, J=6.8 Hz, 1H), 5.86 (s, 1H), 4.25 (d, J=6.4 Hz, 2H), 2.95 (s, 6H), 2.34 (s, 3H), 2.26 (s, 3H), 2.22 (s, 3H), 1.73 (d, J=6.8 Hz, 3H); MS (ESI) m/z 473 [M+H]+.

Example 23: Preparation of 5-((4-bromophenyl)(hydroxy)methyl)-N-((4,6-dimethyl-2-oxo-1,2-dihydropyridin-3-yl)methyl)-6-methylindolizine-7-carboxamide

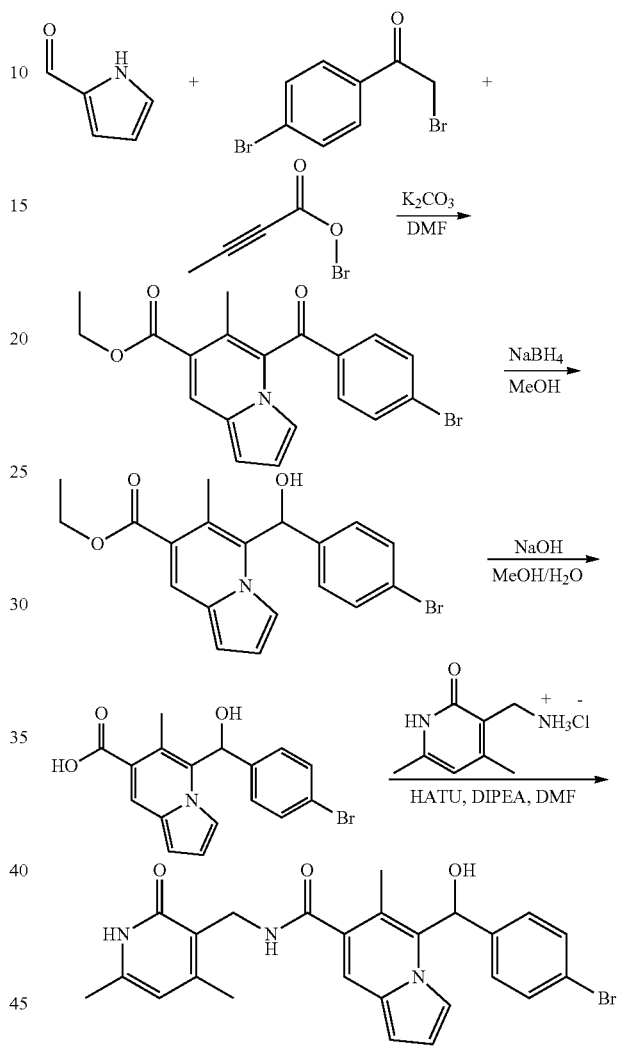

compound 23

Step 1: Preparation of ethyl 5-(4-bromobenzoyl)-6-methylindolizine-7-carboxylate: In a dry nitrogen-protected 100 mL three-necked flask, 1H-pyrrole-2-formaldehyde (2.5 g, 26 mmol), 2,4-dibromoacetophenone (7.23 g, 26 mmol), ethyl 2-butynoate (3.5 g, 31.2 mmol) and potassium carbonate (7.18 g, 52 mmol) and 50 mL DMF were added successively. The mixture was stirred for 5 hours at 90° C., and cooled to room temperature. The mixture was extracted with ethyl acetate (200 mL), washed with water (100 mL×2) and brine (100 mL). The organic phase was dried over anhydrous sodium sulfate, filtered and concentrated to provide a crude product, which was purified through column chromatography (petroleum ether:ethyl acetate=4:1) to provide a product as yellow oil (2.0 g, yield: 20%). 1H NMR (CDCl3, 400 MHz) δ ppm 8.29 (s, 1H), 7.73 (d, J=7.6 Hz, 2H), 7.63 (d, J=7.6 Hz, 2H), 6.99 (s, 1H), 6.77 (s, 2H), 4.36 (q, J=7.2 Hz, 2H), 2.31 (s, 3H), 1.42 (t, J=7.2 Hz, 3H).

Step 2: Preparation of ethyl 5-((4-bromophenyl)(hydroxy)methyl)-6-methylindolizine-7-carboxylate: Ethyl ((4-bromophenyl)(hydroxy)methyl)-6-methylindolizine-7-carboxylate was prepared by a method similar to step 3 of example 1, yield 86%. MS (ESI) m/z 388 [M+H]⁺.

Step 3: Preparation of 5-((4-bromophenyl)(hydroxy)methyl)-6-methylindolizine-7-carboxylic acid: 5-((4-bromophenyl)(hydroxy)methyl)-6-methylindolizine-7-carboxylic acid was prepared by a method similar to Step 5 of Example 1, yield 83%. $^1$H NMR (DMSO-d$_6$, 400 MHz) δ ppm 8.13 (s, 1H), 7.56 (d, J=7.6 Hz, 2H), 7.33 (d, J=7.6 Hz, 2H), 6.70 (s, 1H), 6.61-6.55 (m, 2H), 2.64 (s, 3H).

Step 4: Preparation of 5-((4-Bromophenyl)(hydroxy)methyl)-N-((4,6-dimethyl-2-oxo-1,2-dihydropyridin-3-yl)-6-methylindolizine-7-carboxamide: 5-((4-Bromophenyl)(hydroxy)methyl)-N-((4,6-dimethyl-2-oxo-1,2-dihydropyridin-3-yl)-6-methylindolizine-7-carboxamide was prepared by a method similar to step 6 of example 1, yield 10%. $^1$H NMR (DMSO-d$_6$, 400 MHz) δ ppm 11.50 (brs, 1H), 8.25 (t, J=2.8 Hz, 2H), 7.63 (d, J=7.6 Hz, 2H), 7.38 (s, 1H), 6.54 (t, J=2.8 Hz, 1H), 6.45 (s, 1H), 6.41 (t, J=2.8 Hz, 1H), 5.88 (s, 1H), 4.29 (s, 2H), 2.37 (s, 3H), 2.33 (s, 3H), 2.22 (s, 3H); MS (ESI) m/z 494 [M+H]⁺.

Example 24: Preparation of 5-((4-bromophenyl)(methoxy)methyl)-N-((4,6-dimethyl-2-oxo-1,2-dihydropyridin-3-yl)methyl)-6-methylindolizine-7-carboxamide

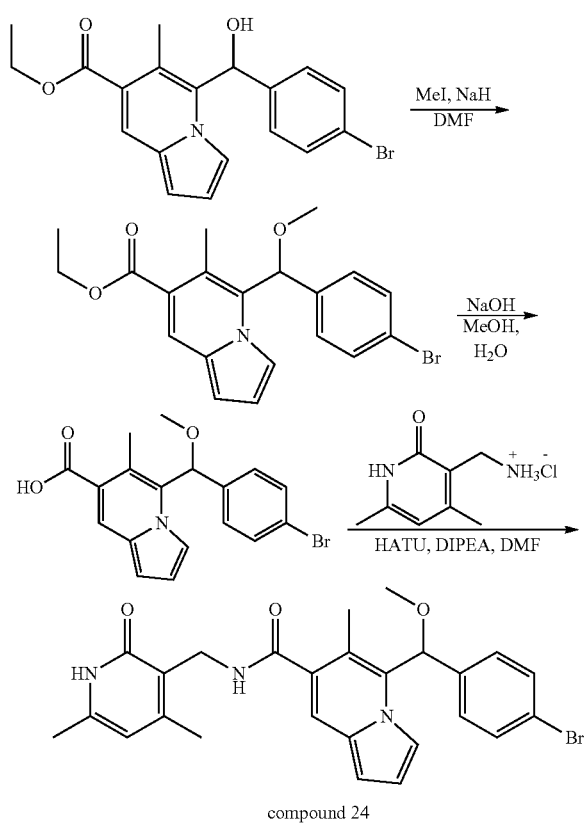

compound 24

Step 1: Preparation of ethyl 5-((4-bromophenyl)(methoxy)methyl)-6-methylindolizine-7-carboxylate: ethyl 5-((4-bromophenyl)(methoxy)methyl)-6-methylindolizine-7-carboxylate was prepared by a method similar to Step 4 of Example 1, yield 80%. MS (ESI) m/z 402 [M+H]⁺.

Step 2: Preparation of 5-((4-bromophenyl)(methoxy)methyl)-6-methylindolizine-7-carboxylic acid: 5-((4-bromophenyl)(methoxy)methyl)-6-methylindolizine-7-carboxylic acid was prepared by a method similar to Step 5 of Example 1, yield 83%. MS (ESI) m/z 374 [M+H]⁺.

Step 3: Preparation of 5-((4-Bromophenyl)(methoxy)methyl)-N-((4,6-dimethyl-2-oxo-1,2-dihydropyridin-3-yl)-6-methylindolizine-7-carboxamide: 5-((4-Bromophenyl)(methoxy)methyl)-N-((4,6-dimethyl-2-oxo-1,2-dihydropyridin-3-yl)-6-methylindolizine-7-carboxamide was prepared by a method similar to step 6 of example 1, yield 14%. $^1$H NMR (400 MHz, CDCl$_3$) δ ppm 7.47 (s, 1H), 7.37-7.31 (m, 3H), 7.18 (d, J=7.6 Hz, 2H), 6.99 (brs, 1H), 6.60 (t, J=2.8 Hz, 1H), 6.48 (t, J=2.8 Hz, 1H), 6.29 (s, 1H), 6.05 (s, 1H), 4.56 (d, J=6.4 Hz, 2H), 3.36 (s, 3H), 2.55 (s, 3H), 2.45 (s, 3H), 2.37 (s, 3H); MS (ESI) m/z 508 [M+H]⁺.

Example 25: Preparation of N-((4,6-dimethyl-2-oxo-1,2-dihydropyridin-3-yl)methyl)-6-methyl-5-(1-phenylethyl)indolizine-7-carboxamide

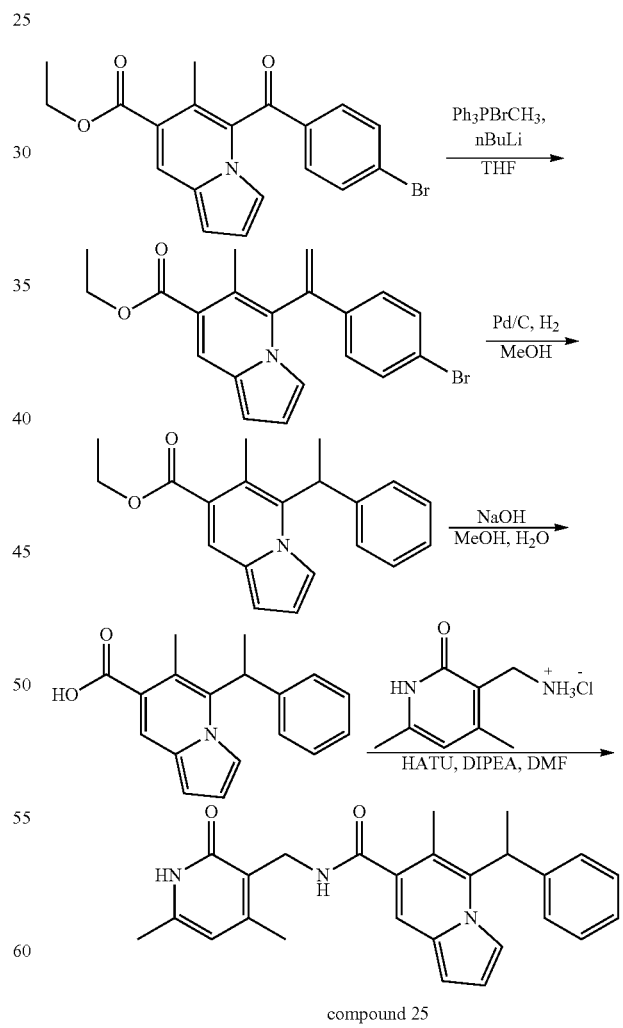

compound 25

Step 1: Preparation of ethyl 5-(1-(4-bromophenyl)vinyl)-6-methylindolizine-7-carboxylate: Triphenyl methylphosphonium bromide (329 mg, 0.856 mmol) and 10 mL of tetrahydrofuran were added into dry nitrogen-protected 100 ml single-necked bottle, cooled to −78° C., and then nBuLi in tetrahydrofuran (0.5 mL, 1.6 M) was slowly added dropwise. After warmed to room temperature and stirred for half an hour, ethyl 5-(4-bromobenzoyl)-6-methylindolizine-7-carboxylate (150 mg, 0.39 mmol) was added, and then warmed to 50° C. and stirred for 3-4 hours, and then 50 mL of water was slowly added dropwise in an ice bath, extracted with ethyl acetate (100 mL). The organic phase was preserved and concentrated to provide a crude product, which was purified through column chromatography (petroleum ether:ethyl acetate=4:1) to provide a product as yellow viscous liquid (85 mg, yield: 57%). MS (ESI) m/z 384 [M+H]⁺.

Step 2: Preparation of ethyl 6-methyl-5-(1-phenylethyl)-6-methylindolizine-7-carboxylate: 5-(1-((4-bromophenyl)ethylene)-6-methylindolizine-7-carboxylate (85 mg, 0.22 mmol)), Pd/C (10 mg) and 10 ml of methanol were added sequentially to a 25 mL single-necked flask, exchanged with hydrogen and stirred at room temperature for 48 hours, and filtered. The organic phase was concentrated to provide a product as yellow oil (65 mg, yield: 97%). MS (ESI) m/z 308 [M+H]⁺.

Step 3: Preparation of 6-methyl-5-(1-phenylethyl)indolizine-7-carboxylic acid: ethyl 6-methyl-5-(1-phenylethyl)indolizine-7-carboxylate was prepared by a method similar to Step 5 of example 1, yield 90%. MS (ESI) m/z 280 [M+H]⁺.

Step 4: Preparation of N-((4,6-dimethyl-2-oxo-1,2-dihydropyridin-3-yl)methyl)-6-methyl-5-(1-phenylethyl)indolizine-7-carboxamide: N-((4,6-dimethyl-2-oxo-1,2-dihydropyridin-3-yl)methyl)-6-methyl-5-(1-phenylethyl)indolizine-7-carboxamide was prepared by a method similar to Step 6 of Example 1, yield 17%. ¹H NMR (400 MHz, CDCl₃) δ ppm 10.78 (brs, 1H), 7.52 (s, 1H), 7.40-7.22 (m, 5H), 6.91 (t, J=2.8 Hz, 1H), 6.55 (t, J=2.8 Hz, 1H), 6.41 (t, J=2.8 Hz, 1H), 5.94 (s, 1H), 5.04 (q, J=6.8 Hz, 1H), 4.54 (d, J=6.4 Hz, 2H), 2.41 (s, 3H), 2.39 (s, 3H), 2.23 (s, 3H), 1.80 (q, J=6.8 Hz, 3H); MS (ESI) m/z 414 [M+H]⁺.

Example 26: Preparation of N-((4,6-dimethyl-2-oxo-1,2-dihydropyridin-3-yl)methyl)-6-methyl-5-(1-morpholinylethyl)indolizine-7-carboxamide

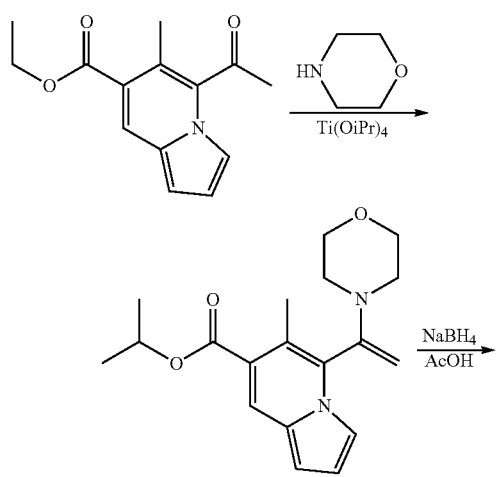

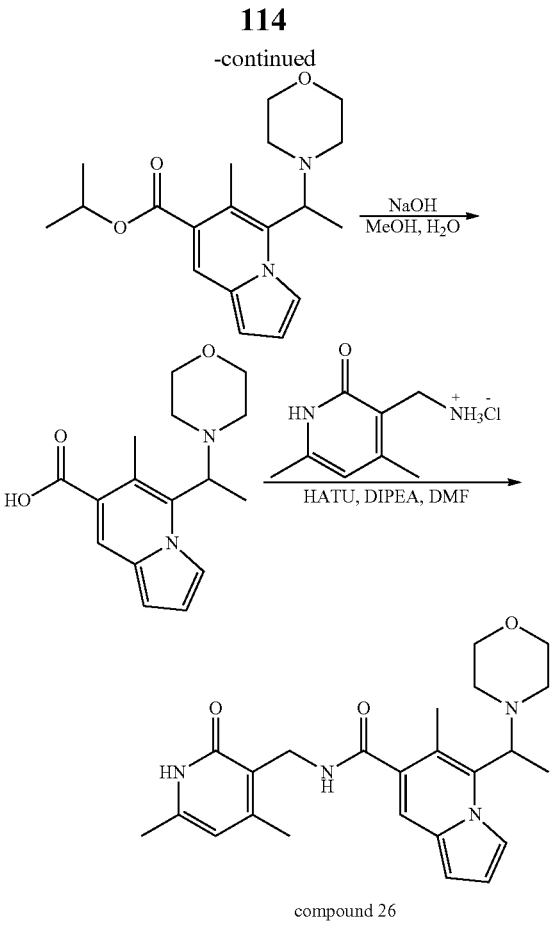

compound 26

Step 1: Preparation of isopropyl 6-methyl-5-(1-morphinolinylvinyl)indolizine-7-carboxylate: Ethyl 5-acetyl-6-methylindolizine-7-carboxylate (200 mg, 0.80 mmol), Morpholine (1.0 mL) and 2.0 mL of tetraisopropyl oxytitanium were added successively to a dried nitrogen-protected 10 mL microwave tube, heated to 60° C. and stirred overnight, 10 mL of water was added into the reaction system, stirred for 10 minutes and concentrated to remove water. The solid was washed with dichloromethane (20 mL×3) and the organic phase was concentrated and used directly in the next step. ¹H NMR (400 MHz, CDCl₃) δ 8.09 (s, 1H), 7.48 (brs, 1H), 6.80 (dd, J=4.0, 2.6 Hz, 1H), 6.66 (dd, J=4.0, 1.4 Hz, 1H), 5.22 (sept, J=6.2 Hz, 1H), 4.49 (s, 1H), 4.24 (s, 1H), 3.72-3.59 (m, 4H), 2.99-2.80 (m, 4H), 2.46 (s, 4H), 2.46 (s, 3H), 1.38 (d, J=6.2 Hz, 6H); MS (ESI) m/z 329 [M+H]⁺.

Step 2: Preparation of isopropyl 6-methyl-5-(1-morphinolinylethyl)indolizine-7-carboxyate: in an ice bath, sodium borohydride (114 mg, 3.0 mmol) was added in portions to a solution of isopropyl 6-methyl-5-(1-morphinolinylvinyl)indolizine-7-carboxylate (50 mg, 0.15 mmol) in acetic acid, and stirred in room temperature for 4 hours. Most of acetic acid was removed under reduced pressure, and the remaining part was extracted with dichloromethane (50 mL×3), washed with water (30 mL×3) and saturated brine (30 mL), filtered to provide a crude product, which was purified through column chromatography (petroleum ether:ethyl acetate=10:1) to provide a product as pale yellow oil (35 mg, yield: 73%). ¹H NMR (400 MHz, CDCl₃) δ 8.50 (s, 1H), 7.95 (s, 1H), 6.80 (s, 1H), 6.65 (s, 1H), 5.21 (dt, J=6.3 Hz, 1H), 4.17-4.06 (m, 1H), 3.68 (brs, 4H), 2.66 (brs, 2H), 2.50 (s, 3H), 2.26 (brs, 2H), 1.49 (d, J=5.7 Hz, 3H), 1.37 (d, J=6.3 Hz, 6H); MS (ESI) m/z 331 [M+H]⁺.

Step 3: Preparation of 6-methyl-5-(1-morpholinylethyl)indolizine-7-carboxylic acid: 6-methyl-5-(1-morpholinylethyl)indolizine-7-carboxylic acid was prepared by a method similar to Step 5 of example 1, yield 63%. MS (ESI) m/z 202 [M−87+H]⁺.

Step 4: Preparation of N-((4,6-dimethyl-2-oxo-1,2-dihydropyridin-3-yl)methyl)-6-methyl-5-(1-morpholinylethyl)indolizine-7-carboxamide:

N-((4,6-dimethyl-2-oxo-1,2-dihydropyridin-3-yl)methyl)-6-methyl-5-(1-morpholinylethyl)indolizine-7-carboxamide was prepared by a method similar to Step 6 of Example 1, yield 68%. ¹H NMR (400 MHz, CDCl₃) δ 11.53 (brs, 1H), 8.44 (brs, 1H), 7.37 (brs, 1H), 7.22 (brs, 1H), 6.77 (brs, 1H), 6.47 (brs, 1H), 5.96 (s, 1H), 4.51 (dd, J=5.9, 3.0 Hz, 2H), 3.70 (brs, 4H), 3.48 (q, J=7.0 Hz, 2H), 2.65 (brs, 2H), 2.40 (s, 3H), 2.35 (s, 3H), 2.26 (brs, 2H), 2.24 (s, 3H), 1.24 (brs, 3H); MS (ESI) m/z 423 [M+H]⁺.

Example 27: Preparation of 1-chloro-N-((4,6-dimethyl-2-oxo-1,2-dihydropyridin-3-yl)methyl)-6-methyl-5-(1-morpholinylethyl)indolizine-7-carboxamide

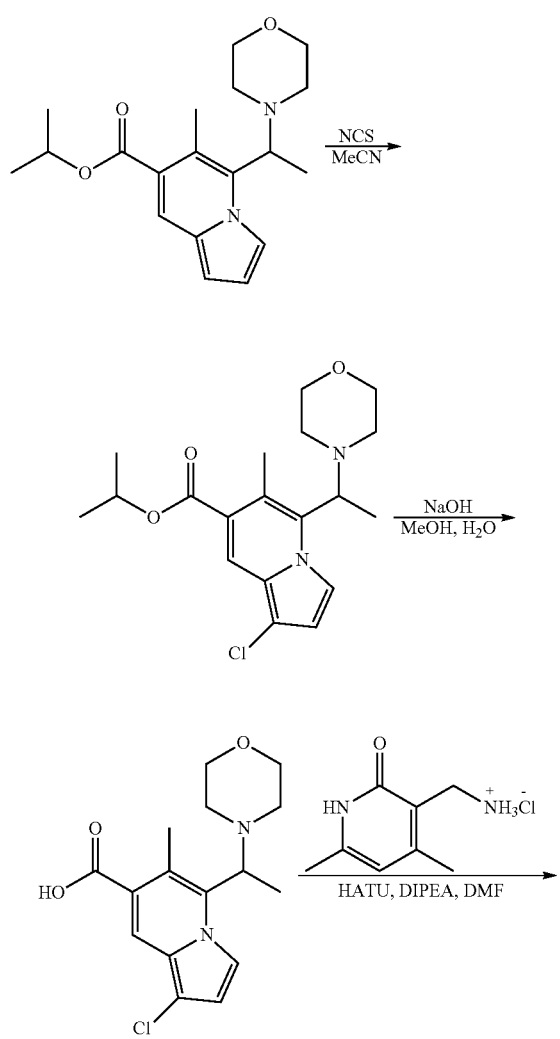

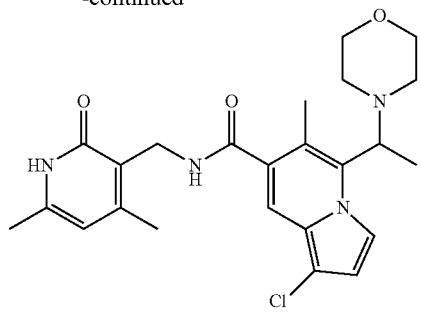

compound 27

Step 1: Preparation 1-chloro-6-methyl-5-(1-morpholinylethyl)indolizine-7-carboxamide: 6-methyl-5-(1-morpholinylethyl)indolizine-7-carboxamide (450 mg, 1.37 mmol)), NCS (183 mg, 1.37 mmol) and 10 ml of acetonitrile were added sequentially to a 100 mL single-necked bottle, and stirred at room temperature for 30 hours, which was purified through column chromatography (petroleum ether: ethyl acetate=10:1) to provide a product as yellow oil (30 mg, yield: 63%).

¹H NMR (500 MHz, CDCl₃) δ 7.84 (s, 1H), 6.67 (d, J=2.9 Hz, 1H), 5.15 (sept, J=6.1 Hz, 1H), 4.03 (q, J=6.5 Hz, 1H), 3.66-3.56 (m, 4H), 2.63-2.52 (m, 2H), 2.41 (s, 3H), 2.23-2.10 (m, 2H), 1.40 (d, J=6.8 Hz, 3H), 1.31 (d, J=6.3 Hz, 6H); MS (ESI) m/z 364 [M+H]⁺.

Step 2: Preparation of 1-chloro-6-methyl-5-(1-morpholinylethyl)indolizine-7-carboxylic acid: 1-chloro-6-methyl-5-(1-morpholinylethyl)indolizine-7-carboxylic acid was prepared by a method similar to Step 5 of example 1, yield 75%. MS (ESI) m/z 323 [M+H]⁺.

Step 3: Preparation of 1-chloro-N-((4,6-dimethyl-2-oxo-1,2-dihydropyridin-3-yl)methyl)-6-methyl-5-(1-morpholinylethyl)indolizine-7-carboxamide: 1-chloro-N-((4,6-dimethyl-2-oxo-1,2-dihydropyridin-3-yl)methyl)-6-methyl-5-(1-morpholinylethyl)indolizine-7-carboxamide was prepared by a method similar to Step 6 of Example 1, yield 68%. ¹H NMR (400 MHz, MeOD) δ 7.33 (s, 1H), 6.49 (s, 1H), 6.13 (s, 1H), 4.44 (s, 2H), 4.26-4.20 (qm, 4H), 3.63 (q, J=6.4 Hz, 1H), 3.21 (s, 3H), 2.86-2.84 (m, 2H), 2.69-2.65 (m, 2H), 2.36 (s, 3H), 2.30 (s, 3H), 1.84 (d, J=6.8 Hz, 3H); MS (ESI) m/z 457 [M+H]⁺.

Example 28: Preparation of (S)-1-Chloro-N-((4,6-dimethyl-2-oxo-1,2-dihydropyridin-3-yl)methyl)-6-methyl-5-(1-morpholinylethyl)pyridazin-7-carboxamide or (R)-1-chloro-N-((4,6-dimethyl-2-oxo-1,2-dihydro)pyridin-3-yl)methyl)-6-methyl-5-(1-morpholinylethyl)pyridazin-7-carboxamide: 1-chloro-N-((4,6-dimethyl)-2-oxo-1,2-dihydropyridin-3-yl)methyl)-6-methyl-5-(1-morpholinylethyl)indolizine-7-carboxamide was resolved through chiral preparative liquid chromatography to provide compound 28 and compound 29.

The separation conditions were: column type: AD-H; column size: 0.46 cm I.D.×15 cm L; injection volume: 5 μL; mobile phase: Hep/EtOH (0.1% DEA)=60/40 (v/v); flow rate: 0.5 ml/min; detection conditions: UV λ=254 nm; column temperature: 25° C.

Compound 28: ¹H NMR (400 MHz, MeOD) δ 7.33 (s, 1H), 6.49 (s, 1H), 6.13 (s, 1H), 4.44 (s, 2H), 4.26-4.20 (qm, 4H), 3.63 (q, J=6.4 Hz, 1H), 3.21 (s, 3H), 2.86-2.84 (m, 2H), 2.69-2.65 (m, 2H), 2.36 (s, 3H), 2.30 (s, 3H), 1.84 (d, J=6.8 Hz, 3H); MS (ESI) m/z 457 [M+H]⁺; $t_R$=3.849 min.

Compound 29: ¹H NMR (400 MHz, MeOD) δ 7.33 (s, 1H), 6.49 (s, 1H), 6.13 (s, 1H), 4.44 (s, 2H), 4.26-4.20 (qm, 4H), 3.63 (q, J=6.4 Hz, 1H), 3.21 (s, 3H), 2.86-2.84 (m, 2H), 2.69-2.65 (m, 2H), 2.36 (s, 3H), 2.30 (s, 3H), 1.84 (d, J=6.8 Hz, 3H); MS (ESI) m/z 457 [M+H]⁺; $t_R$=4.309 min.

Example 29: Preparation of 2-bromo-N-((4,6-dimethyl-2-oxo-1,2-dihydropyridin-3-yl)methyl)-6-methyl-5-(1-morpholinylethyl)indolizine-7-carboxamide

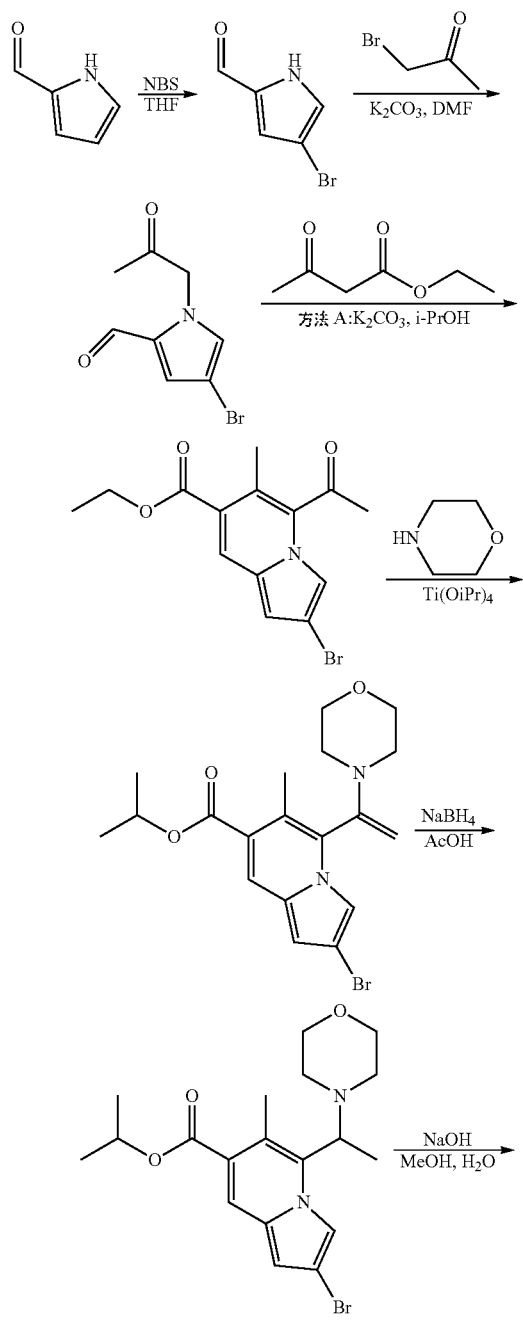

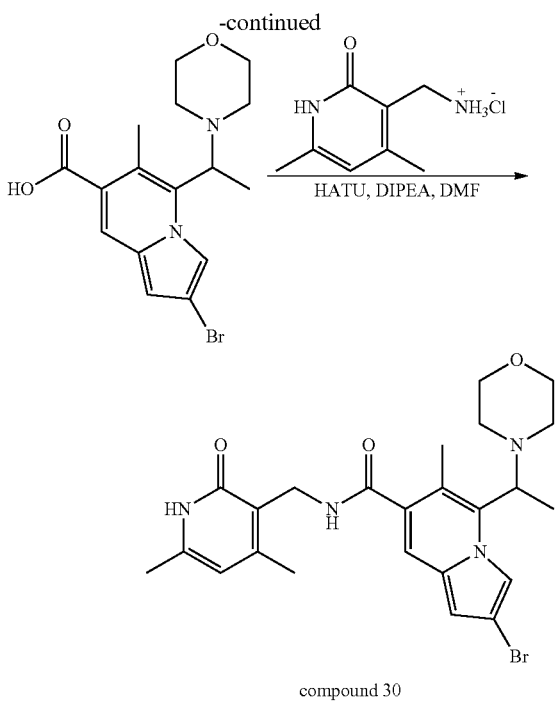

compound 30

Step 1: 4-bromo-1H-pyrrole-2-carbaldehyde was prepared according to Outlaw, et al., Org Lett, 2015, 17, 1822-5. Yield: 80%. ¹H NMR (CDCl₃, 400 MHz) δ 10.3 (brs, 1H), 9.46 (s, 1H), 7.14 (s, 1H), 6.98 (s, 1H); MS (ESI) m/z 174 [M+H]⁺.

Step 2: Preparation of 4-bromo-1-(2-oxopropyl)-1H-pyrrole-2-carbaldehyde: 4-bromo-1-(2-oxopropyl)-1H-pyrrole-2-carbaldehyde was prepared by a method similar to Step 1 of Example 1, yield 75%. MS (ESI) m/z 202 [M–28+H]⁺.

Step 3: Preparation of ethyl 5-acetyl-2-bromo-6-methylindolizine-7-carboxylate: Ethyl 5-acetyl-2-bromo-6-methylindolizine-7-carboxylate was prepared by a method similar to step 2 of example 1, yield 50%. ¹H NMR (400 MHz, CDCl₃) δ 8.09 (s, 1H), 7.24 (d, J=1.3 Hz, 1H), 6.76 (d, J=1.4 Hz, 1H), 4.35 (q, J=7.2 Hz, 2H), 2.64 (s, 3H), 2.44 (s, 3H), 1.40 (t, J=7.1 Hz, 3H); MS (ESI) m/z 324 [M+H]⁺.

Step 4: Preparation of isopropyl 2-bromo-6-methyl-5-(1-morphinolinylethylene)indolizine-7-carboxylate: isopropyl 2-bromo-6-methyl-5-(1-morphinolinylethylene)indolizine-7-carboxylate was prepared by a method similar to Step 1 of example 26, and was directly used in the next step reaction. MS (ESI) m/z 407 [M+H]⁺.

Step 5: Preparation of isopropyl 2-bromo-6-methyl-5-(1-morphinolinylethyl)indolizine-7-carboxylate: isopropyl 2-bromo-6-methyl-5-(1-morphinolinylethyl)indolizine-7-carboxylate was prepared by a method similar to Step 2 of example 1, yield 84%. MS (ESI) m/z 409 [M+H]⁺.

Step 6: Preparation of 2-bromo-6-methyl-5-(1-morphinolinylethyl)indolizine-7-carboxylic acid: 2-bromo-6-methyl-5-(1-morphinolinylethyl)indolizine-7-carboxylic acid was prepared by a method similar to step 5 of example 1, yield 95%. MS (ESI) m/z 367 [M+H]⁺.

Step 7: Preparation of 2-bromo-N-((4,6-dimethyl-2-oxo-1,2-dihydropyridin-3-yl)methyl)-6-methyl-5-(1-morphinolinylethyl)indolizine-7-carboxamide: 2-bromo-N-((4,6-dimethyl-2-oxo-1,2-dihydropyridin-3-yl)methyl)-6-methyl-5-(1-morpholinylethyl)indolizine-7-carboxamide was prepared by a method similar to Step 6 of Example 1, yield 56%. ¹H NMR (400 MHz, CDCl₃) δ 14.37 (brs, 1H), 8.42

(s, 1H), 6.80 (t, J=5.5 Hz, 1H), 6.56 (brs, 1H), 6.51 (brs, 1H), 4.54 (d, J=6.1 Hz, 2H), 4.16 (q, J=6.7 Hz, 1H), 3.76 (brs, 4H), 2.61 (s, 3H), 2.46 (s, 3H), 2.30 (s, 3H), 1.57 (d, J=6.8 Hz, 3H); MS (ESI) m/z 501 [M+H]$^+$.

Example 30: Preparation of 2-bromo-N-((4,6-dimethyl-2-oxo-1,2-dihydropyridin-3-yl)methyl)-5-(1-(4-(dimethylamino)) phenyloxy)ethyl)-6-methylindolizine-7-carboxamide

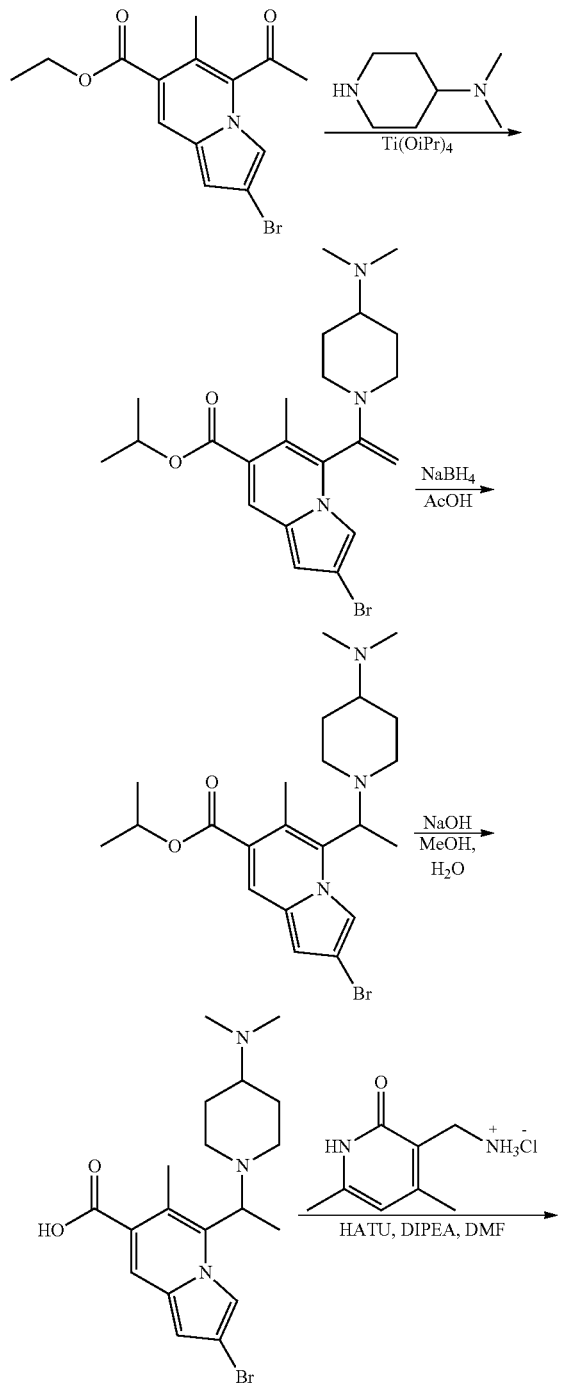

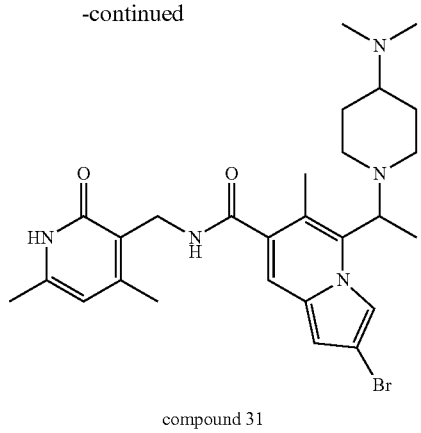

compound 31

Step 1: Preparation of isopropyl 2-bromo-5-(1-(4-(dimethylamino)piperidin-1-yl)vinyl)-6-methylindolizine-7-carboxylate: isopropyl 2-bromo-5-(1-(4-(dimethylamino)piperidin-1-yl)ethylene)-6-methylindolizine-7-carboxylate was prepared by a method similar to Step 1 of example 26. MS (ESI) m/z 448 [M+H]$^+$.

Step 2: Preparation of isopropyl 2-bromo-5-(1-(4-(dimethylamino)piperidin-1-yl)ethyl)-6-methylindolizine-7-carboxylate: isopropyl 2-bromo-5-(1-(4-(dimethylamino)piperidin-1-yl)ethyl)-6-methylindolizine-7-carboxylate was prepared by a method similar to step 2 of example 26, yield 80%. MS (ESI) m/z 450 [M+H]$^+$.

Step 3: Preparation of 2-bromo-5-(1-(4-(dimethylamino)piperidin-1-yl)ethyl)-6-methylindolizine-7-carboxylic acid: 2-bromo-5-(1-(4-(dimethylamino)piperidin-1-yl)ethyl)-6-methylindolizine-7-carboxylic acid was prepared by a method similar to step 5 of example 1, yield 56%. MS (ESI) m/z 408 [M+H]$^+$.

Step 4: Preparation of 2-bromo-N-((4,6-dimethyl-2-oxo-1,2-dihydropyridin-3-yl)methyl)-5-(1-(4-(dimethylamino)) Piperidin-1-yl)ethyl)-6-methylindolizine-7-carboxamide: 2-bromo-N-((4,6-dimethyl-2-oxo-1,2-dihydropyridin-3-yl) methyl)-5-(1-(4-(dimethylamino)) Piperidin-1-yl)ethyl)-6-methylindolizine-7-carboxamide was prepared by a method similar to Step 6 of Example 1, yield 30%. $^1$H NMR (400 MHz, DMSO-d$_6$) δ 11.49 (brs, 1H), 9.37 (brs, 1H), 8.29 (s, 1H), 8.24 (t, J=4.3 Hz, 1H), 7.26 (brs, 1H), 6.61 (brs, 1H), 5.87 (s, 1H), 4.25 (d, J=5.0 Hz, 2H), 4.03 (dd, J=13.8, 7.3 Hz, 1H), 3.47-3.34 (m, 2H), 3.18-3.02 (m, 2H), 2.80-2.69 (m, 6H), 2.19 (s, 3H), 2.11 (s, 3H), 2.04-1.93 (m, 2H), 1.88-1.80 (m, 2H), 1.41 (d, J=6.7 Hz, 3H); MS (ESI) m/z 542 [M+H]$^+$.

Example 31: Preparation of 2-(benzo[d][1,3]dioxol-5-yl)-N-((4,6-dimethyl-2-oxo-1,2-dihydropyridine-3-yl)methyl)-6-methyl-5-(1-morpholinylethyl)indolizin-7-carboxamide

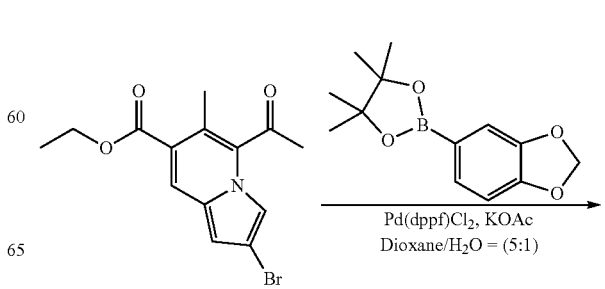

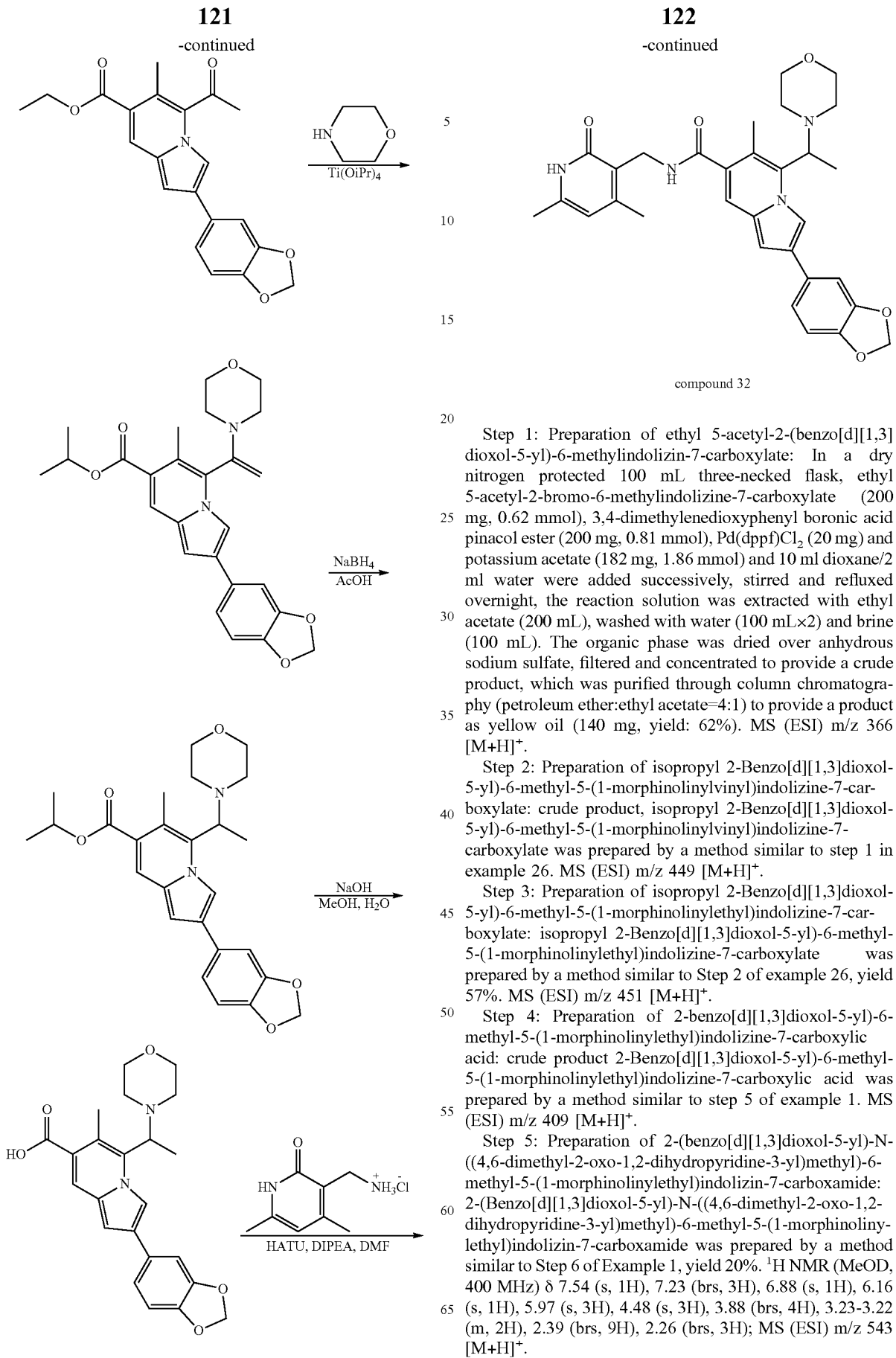

compound 32

Step 1: Preparation of ethyl 5-acetyl-2-(benzo[d][1,3]dioxol-5-yl)-6-methylindolizin-7-carboxylate: In a dry nitrogen protected 100 mL three-necked flask, ethyl 5-acetyl-2-bromo-6-methylindolizine-7-carboxylate (200 mg, 0.62 mmol), 3,4-dimethylenedioxyphenyl boronic acid pinacol ester (200 mg, 0.81 mmol), Pd(dppf)Cl$_2$ (20 mg) and potassium acetate (182 mg, 1.86 mmol) and 10 ml dioxane/2 ml water were added successively, stirred and refluxed overnight, the reaction solution was extracted with ethyl acetate (200 mL), washed with water (100 mL×2) and brine (100 mL). The organic phase was dried over anhydrous sodium sulfate, filtered and concentrated to provide a crude product, which was purified through column chromatography (petroleum ether:ethyl acetate=4:1) to provide a product as yellow oil (140 mg, yield: 62%). MS (ESI) m/z 366 [M+H]$^+$.

Step 2: Preparation of isopropyl 2-Benzo[d][1,3]dioxol-5-yl)-6-methyl-5-(1-morphinolinylvinyl)indolizine-7-carboxylate: crude product, isopropyl 2-Benzo[d][1,3]dioxol-5-yl)-6-methyl-5-(1-morphinolinylvinyl)indolizine-7-carboxylate was prepared by a method similar to step 1 in example 26. MS (ESI) m/z 449 [M+H]$^+$.

Step 3: Preparation of isopropyl 2-Benzo[d][1,3]dioxol-5-yl)-6-methyl-5-(1-morphinolinylethyl)indolizine-7-carboxylate: isopropyl 2-Benzo[d][1,3]dioxol-5-yl)-6-methyl-5-(1-morphinolinylethyl)indolizine-7-carboxylate was prepared by a method similar to Step 2 of example 26, yield 57%. MS (ESI) m/z 451 [M+H]$^+$.

Step 4: Preparation of 2-benzo[d][1,3]dioxol-5-yl)-6-methyl-5-(1-morphinolinylethyl)indolizine-7-carboxylic acid: crude product 2-Benzo[d][1,3]dioxol-5-yl)-6-methyl-5-(1-morphinolinylethyl)indolizine-7-carboxylic acid was prepared by a method similar to step 5 of example 1. MS (ESI) m/z 409 [M+H]$^+$.

Step 5: Preparation of 2-(benzo[d][1,3]dioxol-5-yl)-N-((4,6-dimethyl-2-oxo-1,2-dihydropyridine-3-yl)methyl)-6-methyl-5-(1-morphinolinylethyl)indolizin-7-carboxamide: 2-(Benzo[d][1,3]dioxol-5-yl)-N-((4,6-dimethyl-2-oxo-1,2-dihydropyridine-3-yl)methyl)-6-methyl-5-(1-morphinolinylethyl)indolizin-7-carboxamide was prepared by a method similar to Step 6 of Example 1, yield 20%. $^1$H NMR (MeOD, 400 MHz) δ 7.54 (s, 1H), 7.23 (brs, 3H), 6.88 (s, 1H), 6.16 (s, 1H), 5.97 (s, 3H), 4.48 (s, 3H), 3.88 (brs, 4H), 3.23-3.22 (m, 2H), 2.39 (brs, 9H), 2.26 (brs, 3H); MS (ESI) m/z 543 [M+H]$^+$.

Example 32: Preparation of N-((4,6-dimethyl-2-oxo-1,2-dihydropyridin-3-yl)methyl)-6-methyl-5-(1-morphinolinylethyl)-2-(4-morphinolinylphenyl)indolizine-7-carboxamide

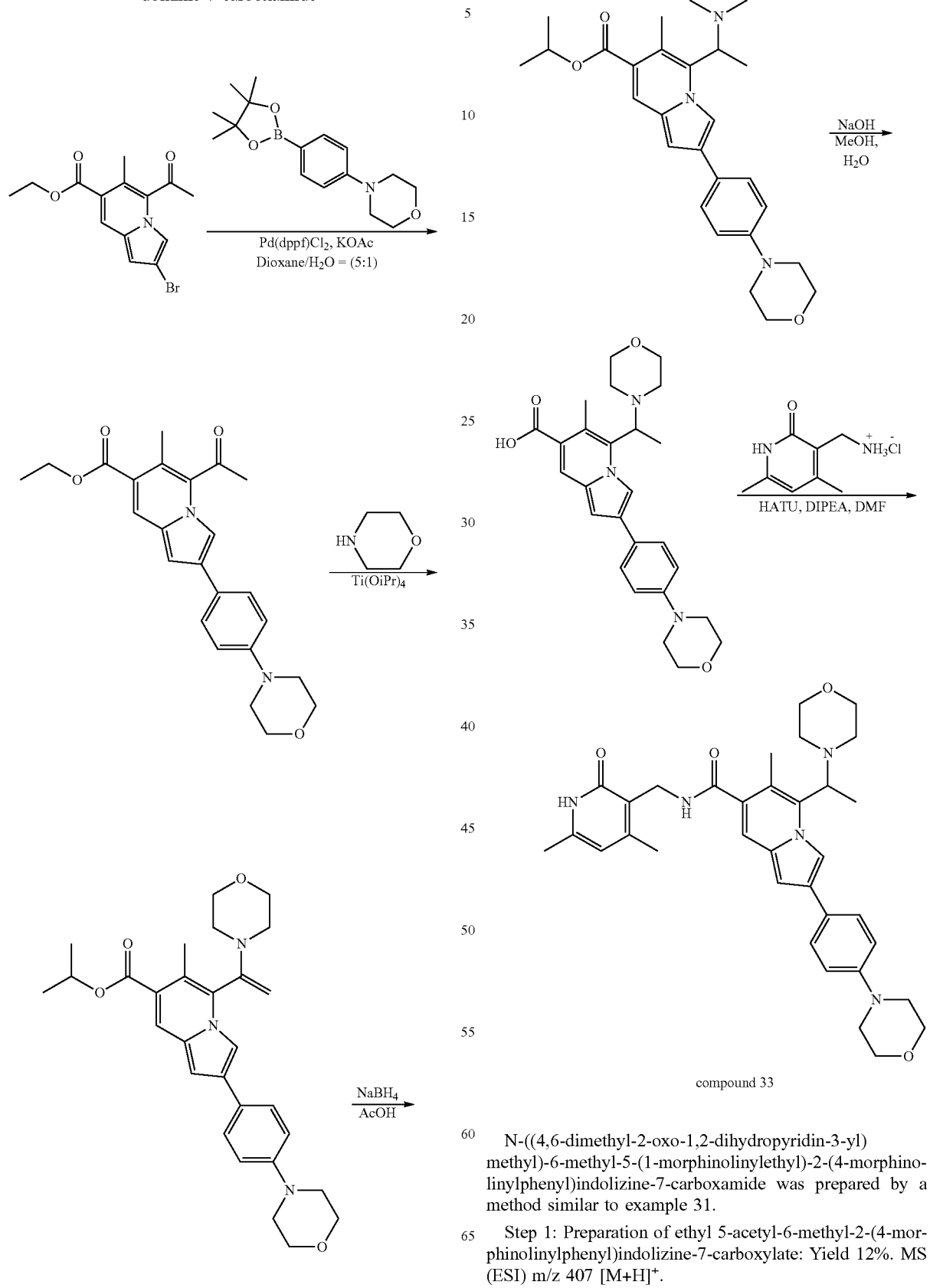

compound 33

N-((4,6-dimethyl-2-oxo-1,2-dihydropyridin-3-yl)methyl)-6-methyl-5-(1-morphinolinylethyl)-2-(4-morphinolinylphenyl)indolizine-7-carboxamide was prepared by a method similar to example 31.

Step 1: Preparation of ethyl 5-acetyl-6-methyl-2-(4-morphinolinylphenyl)indolizine-7-carboxylate: Yield 12%. MS (ESI) m/z 407 [M+H]$^+$.

Step 2: Preparation of isopropyl 6-methyl-2-(4-morpholinylphenyl)-5-(1-morpholinylvinyl)indolizine-7-carboxylate: MS (ESI) m/z 490 [M+H]⁺.

Step 3: Preparation of isopropyl 6-methyl-5-(1-morpholinylethyl)-2-(4-morpholinylphenyl)indolizine-7-carboxylate: yield of two steps was 83%. MS (ESI) m/z 492 [M+H]⁺.

Step 4: Preparation of 6-methyl-5-(1-morpholinylethyl)-2-(4-morpholinylphenyl)indolizine-7-carboxylic acid: MS (ESI) m/z 409 [M+H]⁺.

Step 5: Preparation of N-((4,6-dimethyl-2-oxo-1,2-dihydropyridin-3-yl)methyl)-6-methyl-5-(1-morpholinylethyl)-2-(4-morpholinylphenyl)indolizine-7-carboxamide: yield of two steps was 20%. $^1$H NMR (MeOD, 400 MHz) δ 7.68-7.66 (m, 3H), 7.49 (s, 1H), 7.13-7.11 (m, 3H), 6.14 (s, 1H), 4.48 (s, 2H), 3.89-3.83 (m, 10H), 3.26 (s, 6H), 2.38 (s, 9H), 2.26 (s, 3H), 1.81-1.76 (m, 2H); MS (ESI) m/z 584 [M+H]⁺.

Example 33: Preparation of N-((4,6-dimethyl-2-oxo-1,2-dihydropyridin-3-yl)methyl)-6-methyl-5-(1-morpholinylethyl)-2-(pyridin-3-yl)indolizine-7-carboxamide

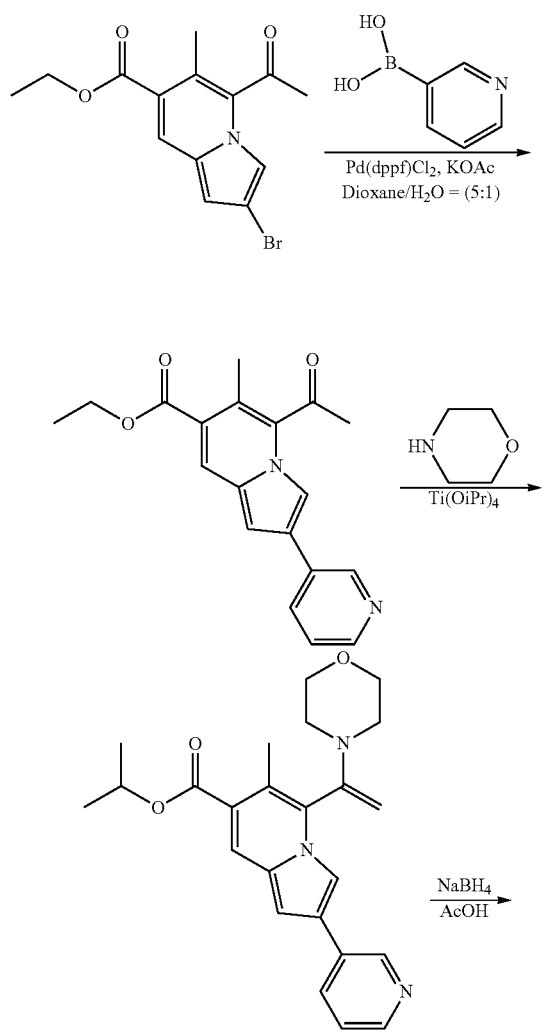

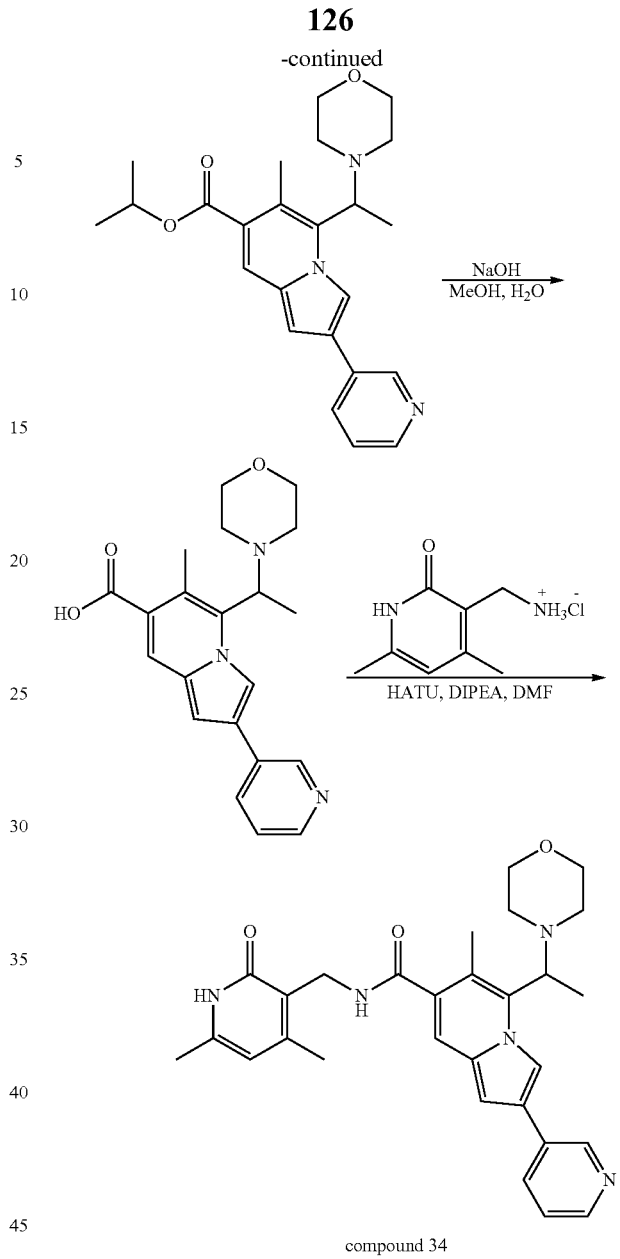

compound 34

N-((4,6-dimethyl-2-oxo-1,2-dihydropyridin-3-yl)methyl)-6-methyl-5-(1-morpholinylethyl)-2-(-3-morpholinylphenyl)indolizine-7-carboxamide was prepared by a method similar to example 31.

Step 1: Preparation of ethyl 5-acetyl-6-methyl-2-(pyridin-3-yl)indolizine-7-carboxylate: Yield 39%. MS (ESI) m/z 323 [M+H]⁺.

Step 2: Preparation of isopropyl 6-methyl-5-(1-morpholinylvinyl)-2-(pyridin-3-yl)indolizine-7-carboxylate: MS (ESI) m/z 406 [M+H]⁺.

Step 3: Preparation of isopropyl 6-methyl-5-(1-morpholinylethyl)-2-(pyridin-3-yl)indolizine-7-carboxylate: yield of two steps was 83%. MS (ESI) m/z 408 [M+H]⁺.

Step 4: Preparation of 6-methyl-5-(1-morpholinylethyl)-2-(pyridin-3-yl)indolizine-7-carboxylic acid. MS (ESI) m/z 366 [M+H]⁺.

Step 5: Preparation of N-((4,6-dimethyl-2-oxo-1,2-dihydropyridin-3-yl)methyl)-6-methyl-5-(1-morpholinylethyl)-2-(pyridin-3-yl)indolizine-7-carboxamide: yield of two steps was 20%. ¹H NMR (400 MHz, CDCl₃) δ ppm 11.48 (brs, 1H), 8.95 (s, 1H), 8.79 (brs, 1H), 8.44 (d, J=2.8 Hz, 1H), 8.20 (s, 1H), 8.08 (d, J=2.8 Hz, 1H), 7.43 (d, J=2.8 Hz, 1H), 7.30 (s, 1H), 6.92 (s, 1H), 5.87 (s, 1H), 4.26 (d, J=6.4 Hz, 2H), 4.06 (q, J=6.8 Hz, 1H), 3.59 (brs, 4H), 2.66 (brs, 2H), 2.26 (s, 3H), 2.20-2.16 (m, 5H), 2.11 (s, 3H), 1.47 (d, J=6.8 Hz, 1H); MS (ESI) m/z 500 [M+H]⁺.

Example 34: Preparation of N-((4,6-dimethyl-2-oxo-1,2-dihydropyridin-3-yl)methyl)-6-methyl-5-(1-morpholinylethyl)-2-(pyridin-4-yl)indolizine-7-carboxamide

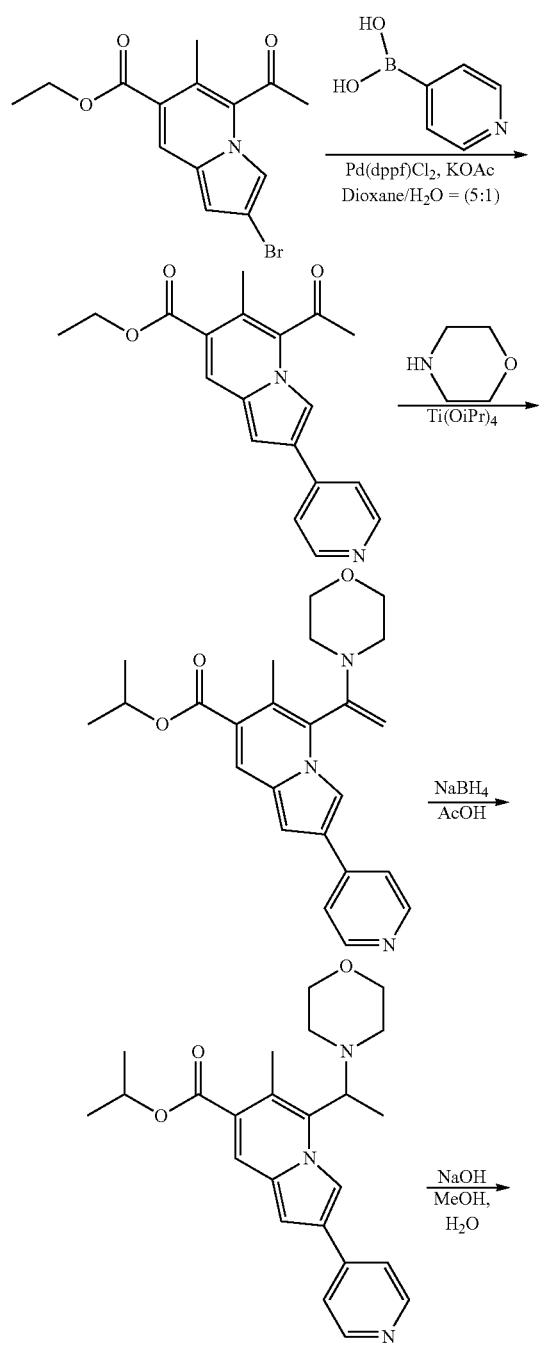

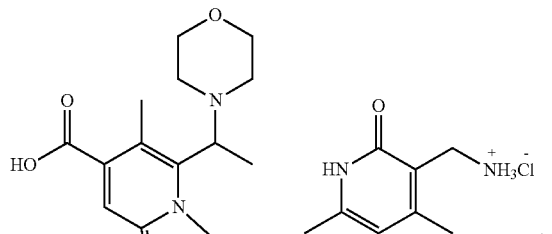

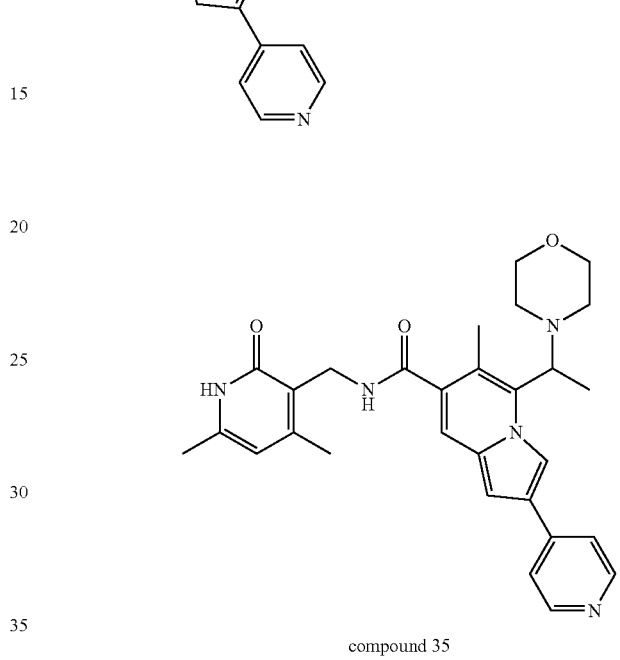

compound 35

N-((4,6-dimethyl-2-oxo-1,2-dihydropyridin-3-yl)methyl)-6-methyl-5-(1-morpholinylethyl)-2-(pyridin-4-yl)indolizine-7-carboxamide was prepared by a method similar to example 31.

Step 1: Preparation of ethyl 5-acetyl-6-methyl-2-(pyridin-4-yl)indolizine-7-carboxylate: Yield 34%. MS (ESI) m/z 323 [M+H]⁺.

Step 2: Preparation of isopropyl 6-methyl-5-(1-morpholinylvinyl)-2-(pyridin-4-yl)indolizine-7-carboxylate. MS (ESI) m/z 406 [M+H]⁺.

Step 3: Preparation of isopropyl 6-methyl-5-(1-morpholinylethyl)-2-(pyridin-4-yl)indolizine-7-carboxylate: two-step yield was 82%. MS (ESI) m/z 408 [M+H]⁺.

Step 4: Preparation of 6-methyl-5-(1-morpholinylethyl)-2-(pyridin-4-yl)indolizine-7-carboxylic acid. MS (ESI) m/z 366 [M+H]⁺.

Step 5: Preparation of N-((4,6-dimethyl-2-oxo-1,2-dihydropyridin-4-yl)methyl)-6-methyl-5-(1-morpholinylethyl)-2-(pyridin-3-yl)indolizine-7-carboxamide: yield of two steps was 20%. ¹H NMR (400 MHz, CDCl₃) δ ppm 8.87 (brs, 1H), 8.54 (d, J=7.8 Hz, 2H), 8.22 (s, 1H), 7.67 (d, J=7.8 Hz, 2H), 7.30 (s, 1H), 6.98 (s, 1H), 5.87 (s, 1H), 4.26 (d, J=6.4 Hz, 2H), 4.06 (q, J=6.8 Hz, 1H), 3.59 (brs, 4H), 2.66-2.62 (m, 2H), 2.26 (s, 3H), 2.20-2.17 (m, 5H), 2.16 (s, 3H), 1.46 (d, J=6.8 Hz, 1H); MS (ESI) m/z 500 [M+H]⁺.

Example 35: Preparation of N-((4,6-dimethyl-2-oxo-1,2-dihydropyridin-3-yl)methyl)-6-methyl-5-(1-morpholinylethyl)-2-phenylindolizine-7-carboxamide

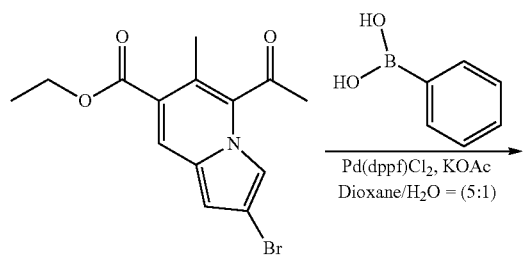

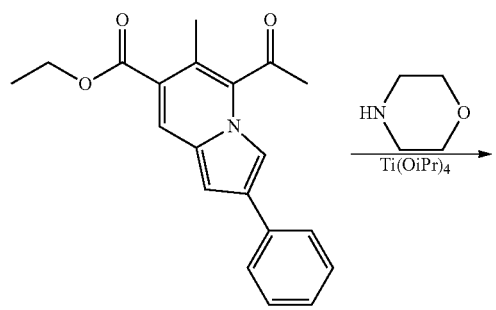

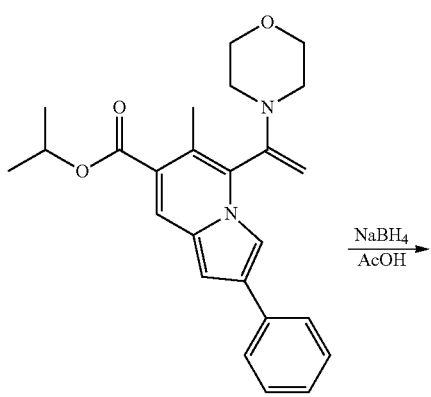

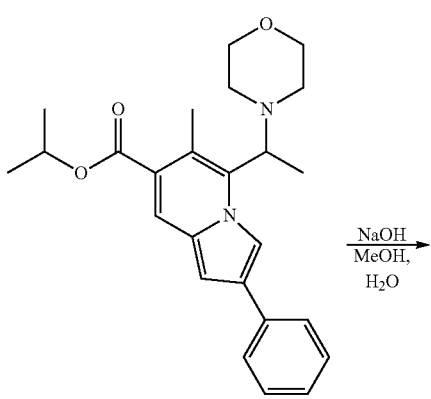

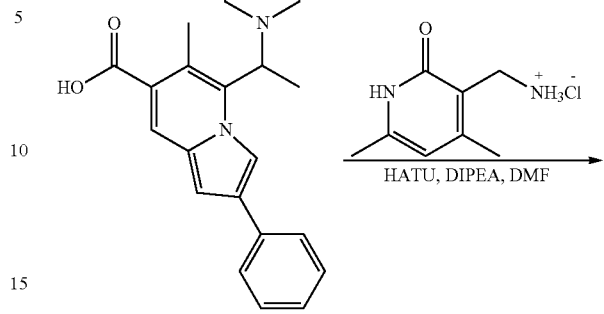

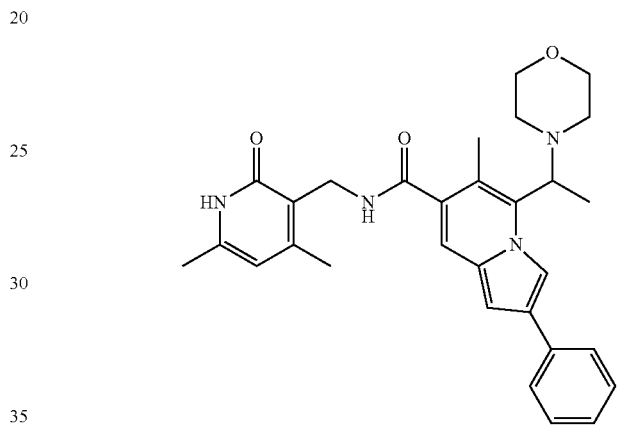

compound 36

N-((4,6-dimethyl-2-oxo-1,2-dihydropyridin-3-yl)methyl)-6-methyl-5-(1-morpholinylethyl)-2-phenylindolizine-7-carboxamide was prepared by a method similar to example 31.

Step 1: Preparation of ethyl 5-acetyl-6-methyl-2-phenylindolizine-7-carboxylate: Yield 40%. MS (ESI) m/z 322 [M+H]$^+$.

Step 2: Preparation of isopropyl 6-methyl-5-(1-morpholinylvinyl)-2-phenylindolizine-7-carboxylate. MS (ESI) m/z 405 [M+H]$^+$.

Step 3: Preparation of isopropyl 6-methyl-5-(1-morpholinylethyl)-2-phenylindolizine-7-carboxylate: yield of two steps was 42%. MS (ESI) m/z 407 [M+H]$^+$.

Step 4: Preparation of 6-methyl-5-(1-morpholinylethyl)-2-phenylindolizine-7-carboxylic acid. MS (ESI) m/z 365 [M+H]$^+$.

Step 5: Preparation of N-((4,6-dimethyl-2-oxo-1,2-dihydropyridin-3-yl)methyl)-6-methyl-5-(1-morpholinylethyl)-2-phenylindolizine-7-carboxamide: yield of two steps was 39%. $^1$H NMR (400 MHz, DMSO-d$_6$) δ ppm 11.47 (s, 1H), 8.71 (brs, 1H), 8.18 (s, 1H), 7.69 (d, J=7.8 Hz, 2H), 7.40 (t, J=7.8 Hz, 2H), 7.28-7.22 (m, 2H), 6.84 (s, 1H), 5.87 (s, 1H), 4.26 (d, J=6.4 Hz, 2H), 4.05 (q, J=6.8 Hz, 1H), 3.56 (brs, 4H), 2.66-2.61 (m, 2H), 2.26 (s, 3H), 2.20 (s, 3H) 2.20-2.17 (m, 5H), 2.11 (s, 3H), 1.45 (d, J=6.8 Hz, 1H); MS (ESI) m/z 499 [M+H]$^+$.

Example 36: Preparation of N-((4,6-dimethyl-2-oxo-1,2-dihydropyridin-3-yl)methyl)-6-methyl-5-(1-morphinolinylethyl)-2-(3-morphinolinylphenyl)indolizine-7-carboxamide

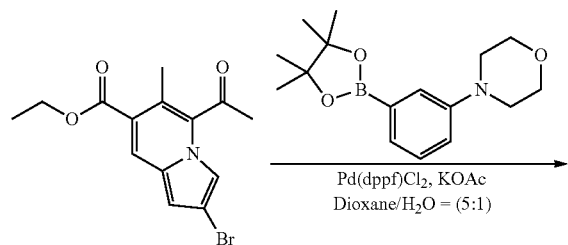

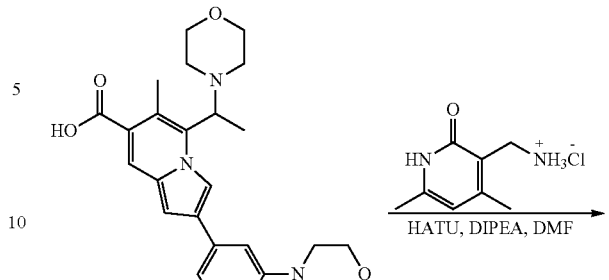

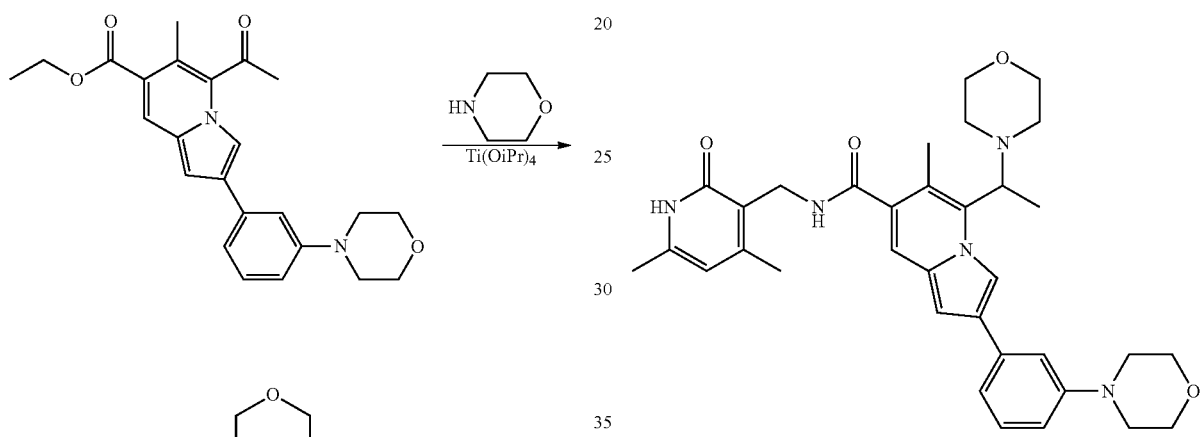

compound 37

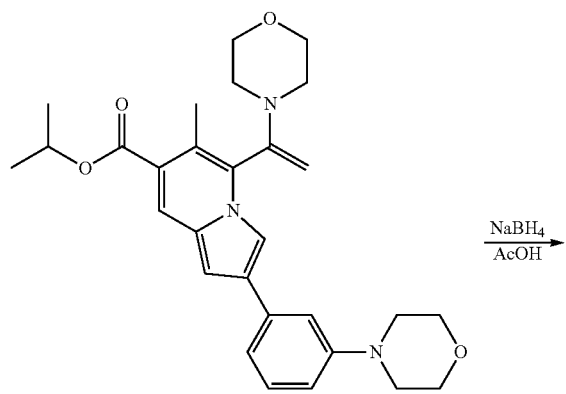

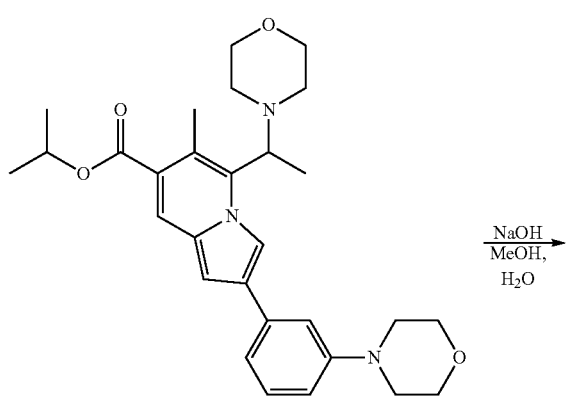

N-((4,6-dimethyl-2-oxo-1,2-dihydropyridin-3-yl)methyl)-6-methyl-5-(1-morphinolinylethyl)-2-(3-morphinolinylphenyl)indolizine-7-carboxamide was prepared by a method similar to example 31.

Step 1: Preparation of ethyl 5-acetyl-6-methyl-2-(3-morphinolinylphenyl)indolizine-7-carboxylate: Yield 56%. MS (ESI) m/z 407 [M+H]$^+$.

Step 2: Preparation of isopropyl 6-methyl-5-(1-morphinolinylvinyl)-2-(3-morphinolinylphenyl)indolizine-7-carboxylate. MS (ESI) m/z 490 [M+H]$^+$.

Step 3: Preparation of isopropyl 6-methyl-5-(1-morphinolinylethyl)-2-(3-morphinolinylphenyl)indolizine-7-carboxylate: yield of two steps was 83%. MS (ESI) m/z 492 [M+H]$^+$.

Step 4: Preparation of 6-methyl-5-(1-morphinolinylethyl)-2-(3-morphinolinylphenyl)-7-carboxylic acid. MS (ESI) m/z 450 [M+H]$^+$.

Step 5: Preparation of N-((4,6-dimethyl-2-oxo-1,2-dihydropyridin-3-yl)methyl)-6-methyl-5-(1-morphinolinylethyl)-2-(3-morphinolinylphenyl)indolizine-7-carboxamide: yield of two steps was 39%. $^1$H NMR (400 MHz, DMSO-d$_6$) δ ppm 11.50 (s, 1H), 8.61 (brs, 1H), 8.21 (s, 1H), 7.38-7.26 (m, 2H), 6.88-6.85 (m, 2H), 5.89 (s, 1H), 4.33 (s, 2H), 4.05 (q, J=6.8 Hz, 1H), 3.89-3.83 (m, 8H), 3.25-3.18 (m, 4H), 2.46 (s, 3H), 2.45-2.20 (m, 4H), 2.26 (s, 3H), 2.20 (s, 3H), 2.11 (s, 3H), 1.38 (d, J=6.8 Hz, 3H); MS (ESI) m/z 584 [M+H]$^+$.

Example 37: Preparation of N-((4,6-dimethyl-2-oxo-1,2-dihydropyridin-3-yl)methyl)-6-methyl-5-(1-morpholinylethyl)-2-(3,4,5-trimethoxyphenyl)indolizine-7-carboxamide

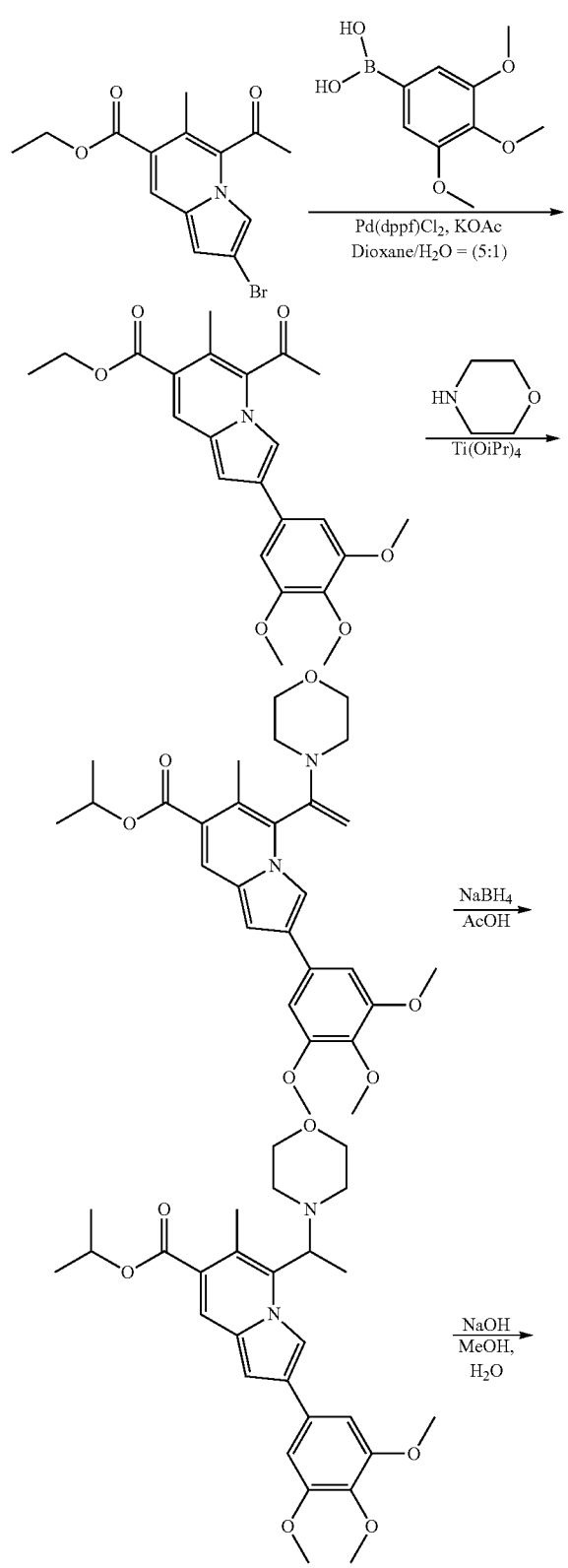

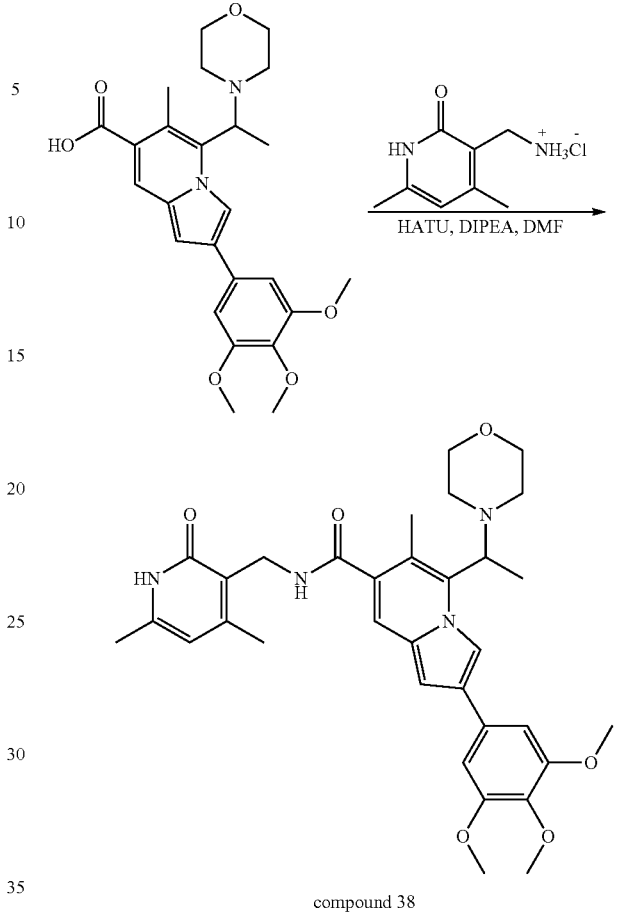

compound 38

N-((4,6-dimethyl-2-oxo-1,2-dihydropyridin-3-yl)methyl)-6-methyl-5-(1-morpholinylethyl)-2-(3,4,5-trimethoxyphenyl)indolizine-7-carboxamide was prepared by a method similar to example 31.

Step 1: Preparation of ethyl 5-acetyl-6-methyl-2-(3,4,5-trimethoxyphenyl)indolizine-7-carboxylate: Yield 47%. MS (ESI) m/z 412 [M+H]$^+$.

Step 2: Preparation of isopropyl 6-methyl-5-(1-morphinolinylvinyl)-2-(3,4,5-trimethoxyphenyl)indolizine-7-carboxylate. MS (ESI) m/z 495 [M+H]$^+$.

Step 3: Preparation of isopropyl 6-methyl-5-(1-morphinolinylethyl)-2-(3,4,5-trimethoxyphenyl)indolizine-7-carboxylate: yield of two steps was 81%. MS (ESI) m/z 497 [M+H]$^+$.

Step 4: Preparation of 6-methyl-5-(1-morpholinylethyl)-2-(3,4,5-trimethoxyphenyl)indolizine-7-carboxylic acid. MS (ESI) m/z 455 [M+H]$^+$.

Step 5: Preparation of N-((4,6-dimethyl-2-oxo-1,2-dihydropyridin-3-yl)methyl)-6-methyl-5-(1-morpholinylethyl)-2-(3,4,5-trimethoxyphenyl)indolizine-7-carboxamide: yield of two steps was 69%. $^1$H NMR (400 MHz, DMSO-d$_6$) δ ppm 11.48 (brs, 1H), 8.68 (brs, 1H), 8.18 (brs, 1H), 7.27 (s, 1H), 6.93 (s, 2H), 5.88 (s, 1H), 4.28 (s, 2H), 4.08 (q, J=6.8 Hz, 1H), 3.87 (s, 6H), 3.68 (s, 3H), 3.60 (brs, 4H), 2.75-2.68 (m, 2H), 2.27 (s, 3H), 2.21 (s, 5H), 2.12 (s, 3H), 1.47 (d, J=6.8 Hz, 3H); MS (ESI) m/z 589 [M+H]$^+$.

Example 38: Preparation of 2-(2,4-dimethoxyphenyl)-N-((4,6-dimethyl-2-oxo-1,2-dihydropyridin-3-yl)methyl)-6-methyl-5-(1-morpholinylethyl)indolizine-7-carboxamide

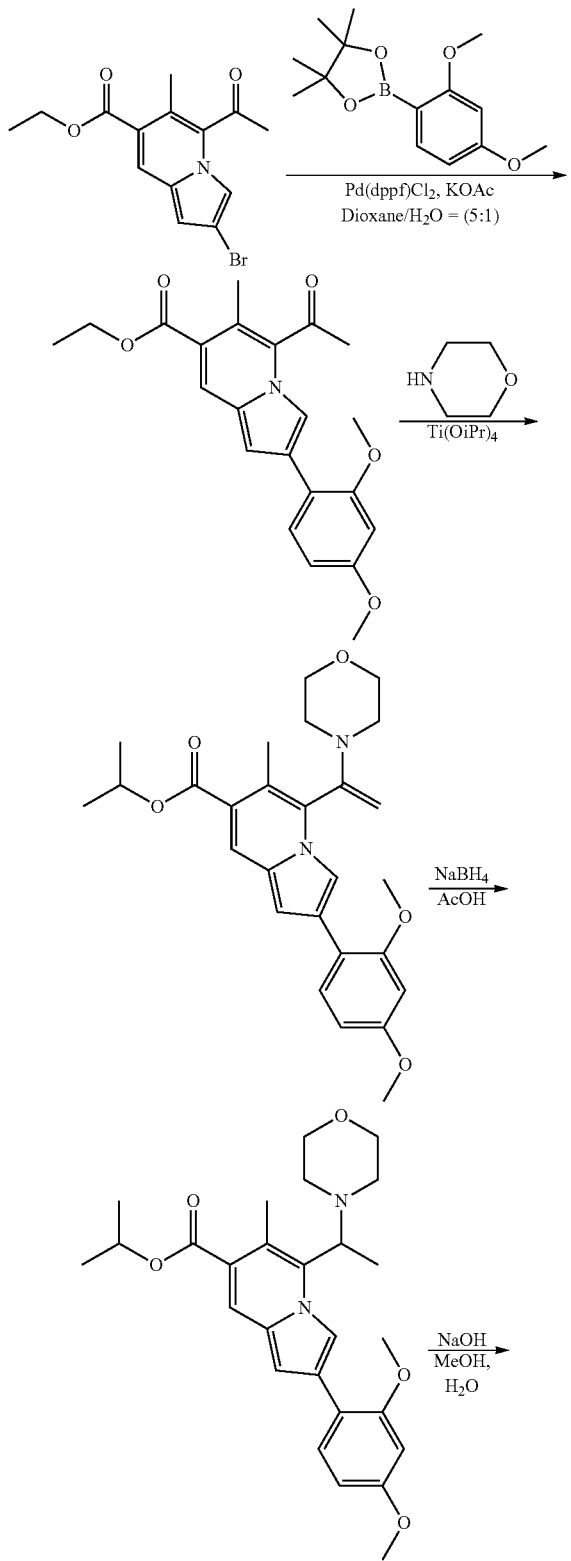

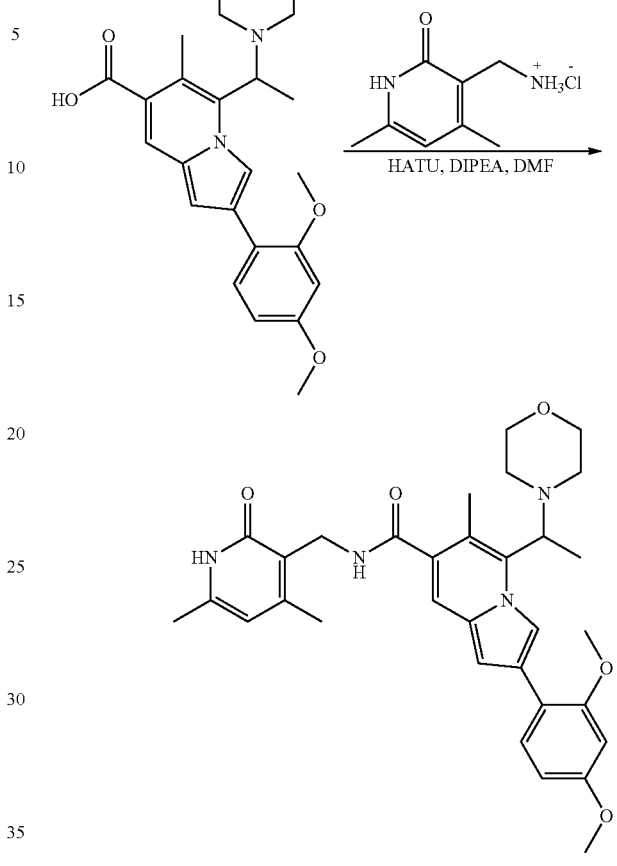

compound 39

2-(2,4-dimethoxyphenyl)-N-((4,6-dimethyl-2-oxo-1,2-dihydropyridin-3-yl)methyl)-6-methyl-5-(1-morpholinylethyl)indolizine-7-carboxamide was prepared by a method similar to example 31.

Step 1: Preparation of ethyl 5-acetyl-2-(2,4-dimethoxyphenyl)-6-methylindolizine-7-carboxylate: Yield 47%. MS (ESI) m/z 382 [M+H]$^+$.

Step 2: Preparation of isopropyl 2-(2,4-dimethoxyphenyl)-6-methyl-5-(1-morpholinylvinyl)indolizine-7-carboxylate. MS (ESI) m/z 465 [M+H]$^+$.

Step 3: Preparation of isopropyl 2-(2,4-dimethoxyphenyl)-6-methyl-5-(1-morpholinylethyl)indolizine-7-carboxylate: yield of two steps was 65%. MS (ESI) m/z 467 [M+H]$^+$.

Step 4: Preparation of 2-(2,4-dimethoxyphenyl)-6-methyl-5-(1-morpholinylethyl)indolizine-7-carboxylic acid. MS (ESI) m/z 425 [M+H]$^+$.

Step 5: Preparation of 2-(2,4-dimethoxyphenyl)-N-((4,6-dimethyl-2-oxo-1,2-dihydropyridin-3-yl)methyl)-6-methyl-5-(1-morpholinylethyl)indolizine-7-carboxamide: yield of two steps was 18%. $^1$H NMR (400 MHz, DMSO-d$_6$) δ ppm 11.46 (s, 1H), 8.81 (s, 1H), 8.12 (s, 1H), 7.57-7.55 (m, 1H), 7.25 (s, 1H), 6.77 (s, 1H), 6.64-6.59 (m, 2H), 5.86 (s, 1H), 4.26 (s, 2H), 4.03 (q, J=6.8 Hz, 1H), 3.90 (s, 3H), 3.79 (s, 3H), 3.60 (brs, 4H), 2.64-2.59 (m, 2H). 2.24 (s, 3H), 2.17 (s, 3H), 2.16-2.15 (m, 2H), 2.11 (s, 3H), 1.43 (d, J=6.8 Hz, 3H); MS (ESI) m/z 559 [M+H]$^+$.

Example 39: Preparation of N-((4,6-dimethyl-2-oxo-1,2-dihydropyridin-3-yl)methyl)-6-methyl-5-(1-morpholinylethyl)-2-(4-(morpholinylmethyl)phenyl)indolizine-7-carboxamide
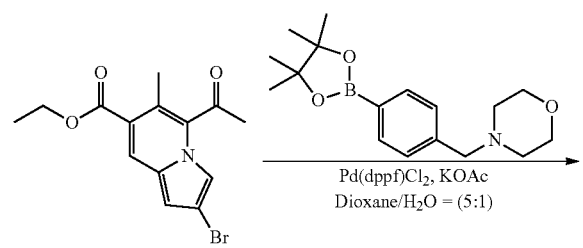
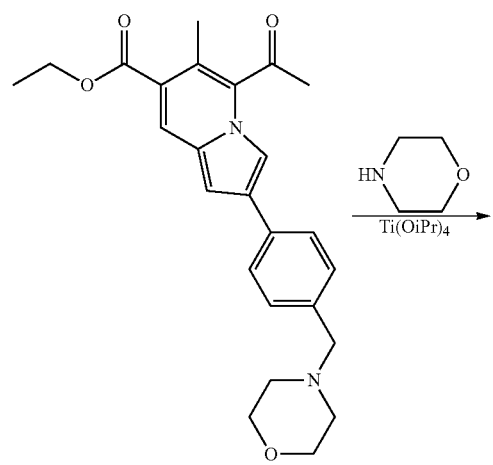
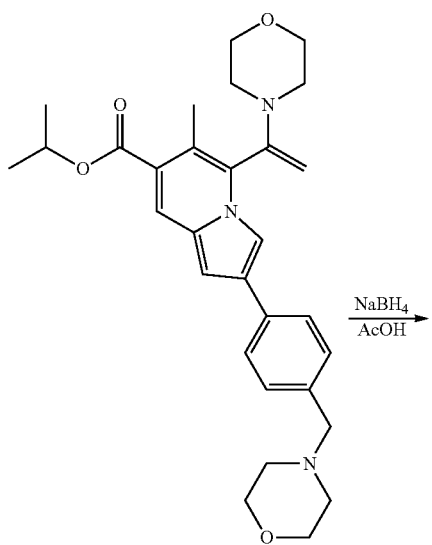
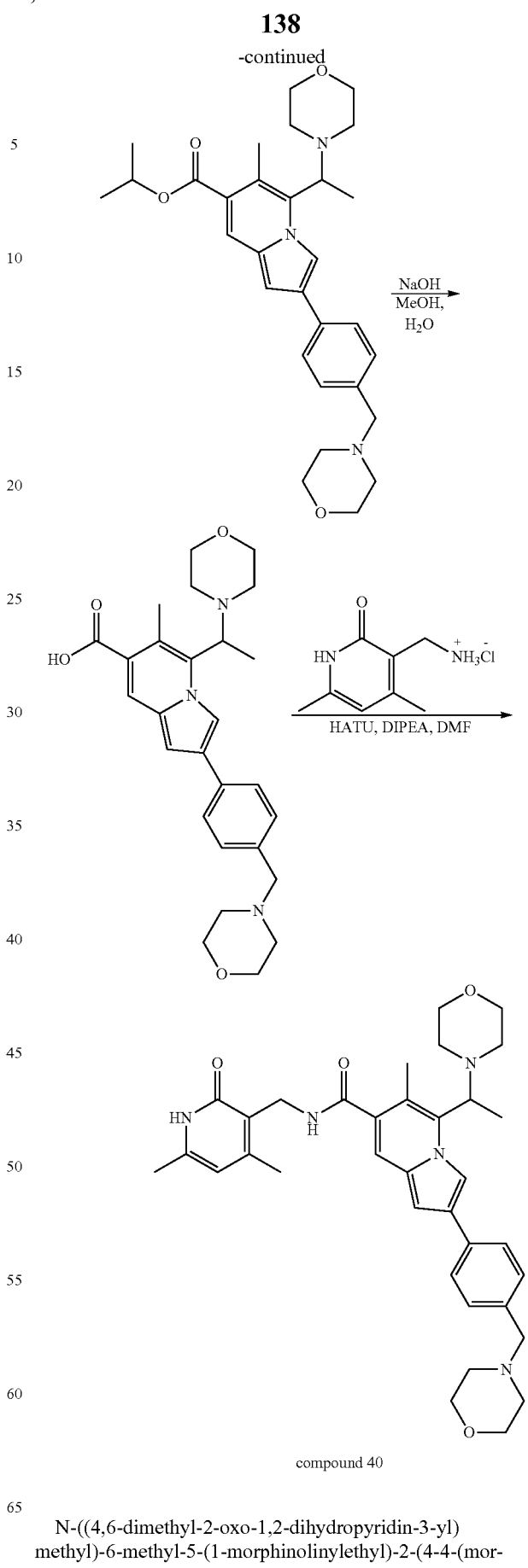
compound 40
N-((4,6-dimethyl-2-oxo-1,2-dihydropyridin-3-yl)methyl)-6-methyl-5-(1-morpholinylethyl)-2-(4-4-(morphinolinylmethyl)phenyl)indolizine-7-carboxamide was prepared by a method similar to example 31.

Step 1: Preparation of ethyl 5-acetyl-6-methyl-2-(4-(morpholinylmethyl)phenyl)indolizine-7-carboxylate: Yield 62%. MS (ESI) m/z 421 [M+H]+.

Step 2: Preparation of isopropyl 6-methyl-2-(4-(morpholinylmethyl)phenyl)-5-(1-morpholinylvinyl)indolizine-7-carboxylate. MS (ESI) m/z 504 [M+H]+.

Step 3: Preparation of isopropyl 6-methyl-5-(1-morpholinylethyl)-2-(4-(morpholinylmethyl)phenyl)indolizine-7-carboxylate: yield of two steps was 41%. MS (ESI) m/z 506 [M+H]+.

Step 4: Preparation of 6-methyl-5-(1-morpholinylethyl)-2-(4-(morpholinylmethyl)phenyl)indolizine-7-carboxylic acid. MS (ESI) m/z 464 [M+H]+.

Step 5: Preparation of N-((4,6-dimethyl-2-oxo-1,2-dihydropyridin-3-yl)methyl)-6-methyl-5-(1-morpholinylethyl)-2-(4-(morpholinylmethyl)phenyl)indolizine-7-carboxamide: yield of two steps was 43%. $^1$H NMR (MeOD, 400 MHz) δ ppm 7.84 (d, J=7.6 Hz, 2H), 7.53 (d, J=7.6 Hz, 2H), 7.49-7.45 (m, 2H), 6.14 (s, 2H), 4.47 (s, 2H), 4.44 (s, 2H), 4.06-4.02 (m, 2H), 3.88-3.86 (m, 2H), 3.78-3.74 (m, 3H), 3.41-3.37 (m, 2H), 3.23-3.21 (m, 2H), 2.38-2.34 (m, 8H), 2.27 (s, 6H), 1.80 (brs, 3H); MS (ESI) m/z 598 [M+H]+.

Example 40: Preparation of tert-butyl 7-cyano-5-(7-((4,6-dimethyl-2-oxo-1,2-dihydropyridin-3-yl)methyl)carbamoyl)-6-methyl-5-(1-morpholineyl-ethyl)indolizine-2-yl)indoline-1-carbamate

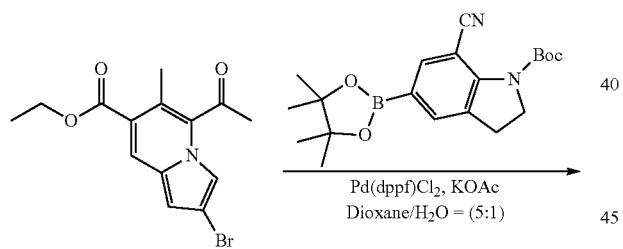

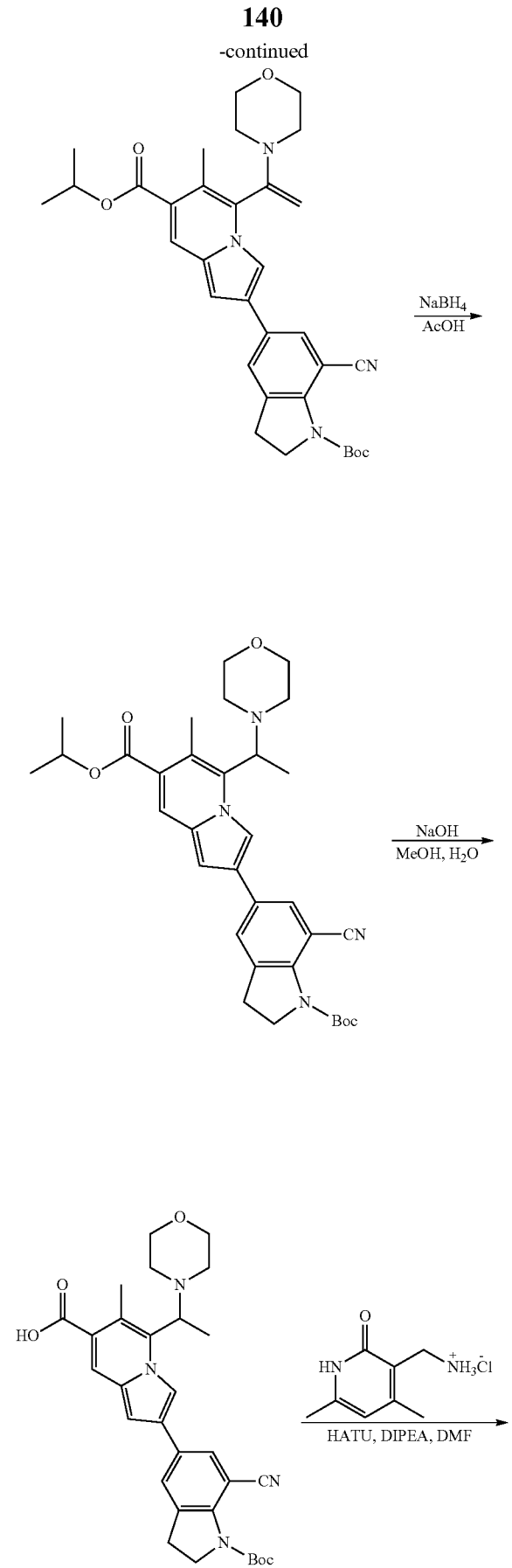

-continued

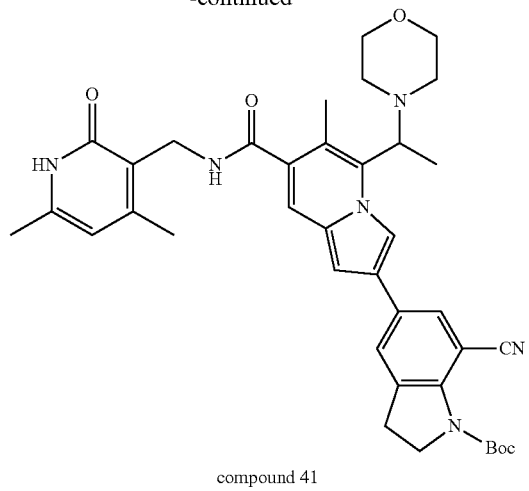

compound 41

Tert-butyl 7-cyano-5-(7-((4,6-dimethyl-2-oxo-1,2-dihydropyridin-3-yl)methyl)carbamoyl)-6-methyl-5-(1-morpholineylethyl)indolizine-2-yl)indoline-1-carbamate was prepared by a method similar to example 31.

Step 1: Preparation of tert-butyl 5-(5-acetyl-7-(ethoxycarbonyl)-6-methylindolizine-2-yl)-7-cyanoindoline-1-carbamate: Yield 66%. MS (ESI) m/z 488 [M+H]+.

Step 2: Preparation of tert-butyl 7-cyano-5-(7-(isopropoxycarbonyl)-6-methyl-5-(1-morpholinolinylvinyl)indolizine-2-yl)indoline-1-carboxylate: MS (ESI) m/z 571 [M+H]+.

Step 3: Preparation of tert-butyl 7-cyano-5-(7-(isopropoxycarbonyl)-6-methyl-5-(1-morpholinolinylethyl)indolizine-2-yl)indoline-1-carboxylate: yield of two steps was 30%. MS (ESI) m/z 573 [M+H]+.

Step 4: Preparation of 2-(1-(tert-butoxycarbonyl)-7-cyanoporphyrin-5-yl)-6-methyl-5-(1-morpholinolinylethyl)indolizine-7-carboxylic acid. MS (ESI) m/z 531 [M+H]+.

Step 5: Preparation of tert-butyl 7-cyano-5-(7-((4,6-dimethyl-2-oxo-1,2-dihydropyridin-3-yl)methyl)carbamoyl)-6-methyl-5-(1-morpholineylethyl)indolizine-2-yl)indoline-1-carbamate: yield of two steps was 35%. $^1$H NMR (400 MHz, DMSO-$d_6$) δ ppm 11.48 (s, 1H), 8.61 (s, 1H), 8.20 (s, 1H), 7.87 (s, 1H), 7.24 (s, 1H), 6.80 (s, 1H), 5.87 (s, 1H), 4.26 (d, J=6.4 Hz, 2H), 4.09-4.05 (m, 3H), 3.15-3.11 (m, 4H), 2.29 (brs, 2H), 2.21 (s, 6H), 2.12 (s, 3H), 1.54 (s, 9H), 1.24 (brs, 3H); MS (ESI) m/z 665 [M+H]+.

Example 41: Preparation of N-((4,6-dimethyl-2-oxo-1,2-dihydropyridin-3-yl)methyl)-6-methyl-2-(1-methyl-1H-pyrazol-5-yl)-5-(1-morpholineylethyl)indolizine-7-carboxamide

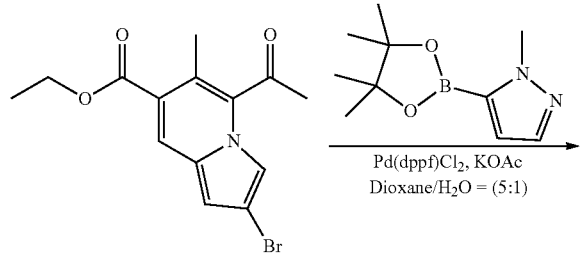

-continued

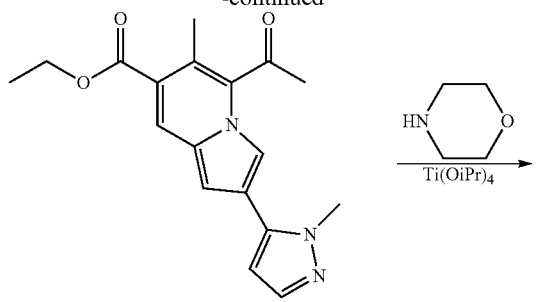

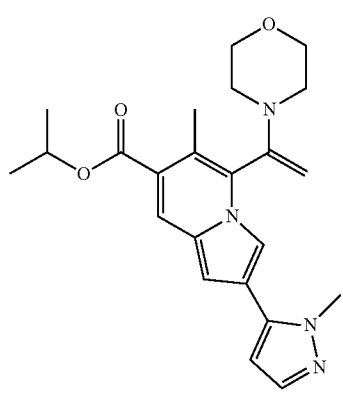

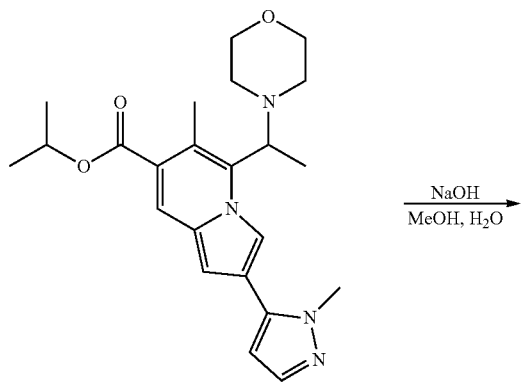

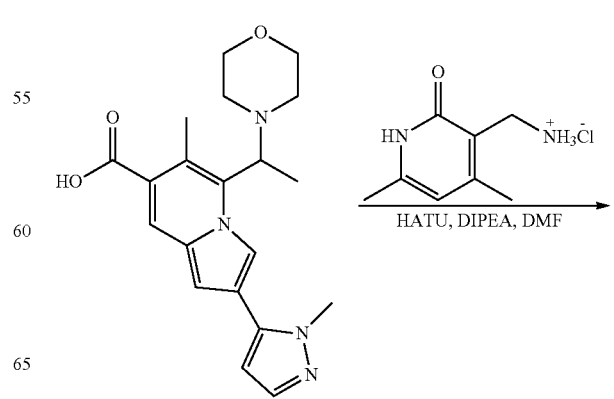

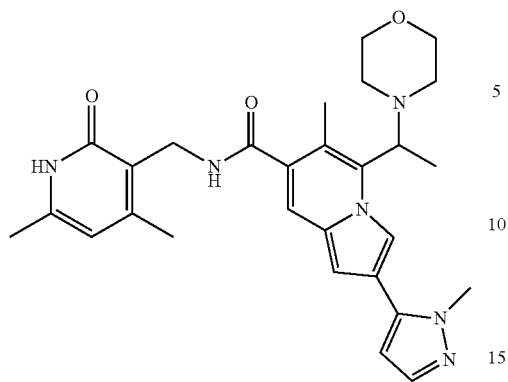

compound 42

N-((4,6-dimethyl-2-oxo-1,2-dihydropyridin-3-yl)methyl)-6-methyl-2-(1-methyl-1H-pyrazol-5-yl)-5-(1-morpholineylethyl)indolizine-7-carboxamide was prepared by a method similar to example 31.

Step 1: Preparation of ethyl 5-acetyl-6-methyl-2-(1-methyl-1H-pyrazol-5-yl)indolizine-7-carboxylate: Yield 55%. MS (ESI) m/z 326 [M+H]$^+$.

Step 2: Preparation of isopropyl 6-methyl-2-(1-methyl-1H-pyrazol-5-yl)-5-(1-morpholinylvinyl)indolizine-7-carboxylate: MS (ESI) m/z 409 [M+H]$^+$.

Step 3: Preparation of isopropyl 6-methyl-2-(1-methyl-1H-pyrazol-5-yl)-5-(1-morphinolinylethyl)indolizine-7-carboxylate: yield of two steps was 54%. MS (ESI) m/z 411 [M+H]$^+$.

Step 4: Preparation of 6-methyl-2-(1-methyl-1H-pyrazol-5-yl)-5-(1-morphinolinylethyl)indolizine-7-carboxylic acid: MS (ESI) m/z 369 [M+H]$^+$.

Step 5: Preparation of N-((4,6-dimethyl-2-oxo-1,2-dihydropyridin-3-yl)methyl)-6-methyl-2-(1-methyl-1H-pyrazol-5-yl)-5-(1-morphinolinylethyl)indolizine-7-carboxamide: Yield of two steps was 32%. $^1$H NMR (400 MHz, DMSO-d$_6$) δ ppm 11.48 (s, 1H), 8.65 (s, 1H), 8.21 (s, 1H), 7.43 (s, 1H), 7.32 (s, 1H), 6.73 (s, 1H), 6.46 (s, 1H), 5.87 (s, 1H), 4.45 (brs, 2H), 3.84 (brs, 2H), 3.72 (s, 3H), 3.48 (brs, 4H), 2.84 (s, 3H), 2.38 (s, 3H), 2.31 (s, 3H), 1.55 (s, 3H); MS (ESI) m/z 503 [M+H]$^+$.

Example 42: Preparation of N-((4,6-dimethyl-2-oxo-1,2-dihydropyridin-3-yl)methyl)-6-methyl-2-(1-methyl-1H-pyrazol-4-yl)-5-(1-morpholinylethyl)indolizine-7-carboxamide

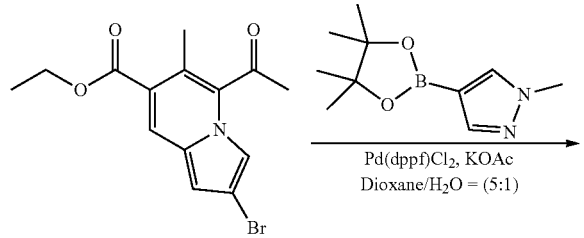

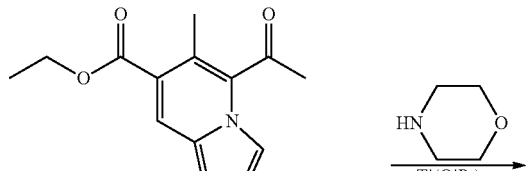

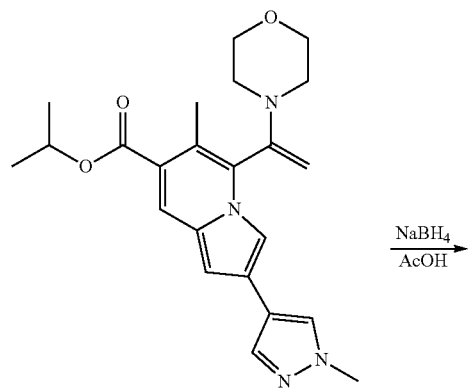

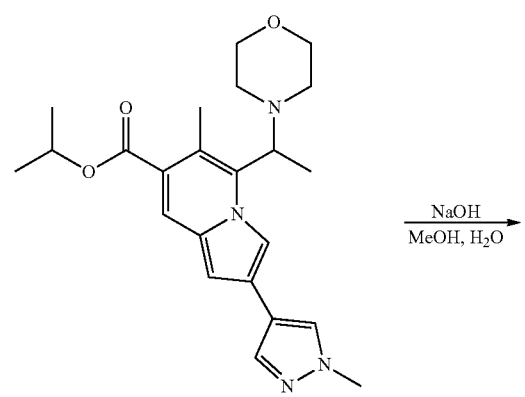

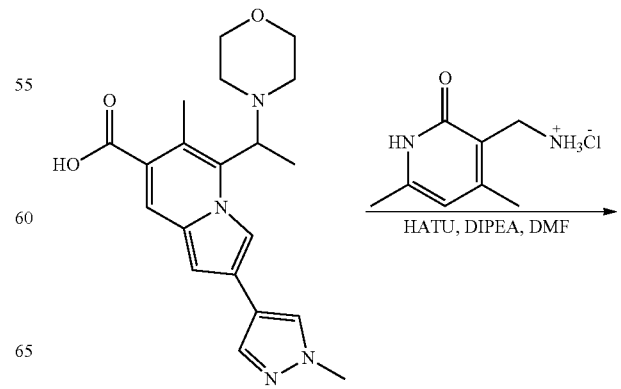

145
-continued

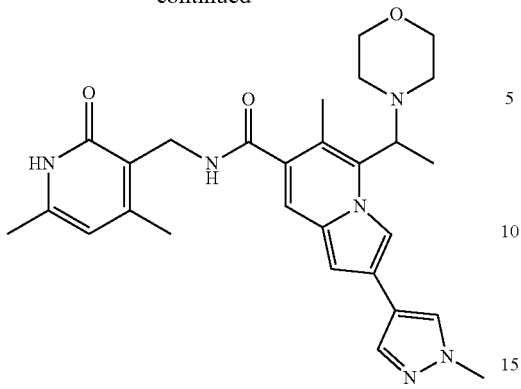

compound 43

N-((4,6-dimethyl-2-oxo-1,2-dihydropyridin-3-yl)methyl)-6-methyl-2-(1-methyl-1H-pyrazol-4-yl)-5-(1-morpholineylethyl)indolizine-7-carboxamide was prepared by a method similar to example 31.

Step 1: Preparation of ethyl 5-acetyl-6-methyl-2-(1-methyl-1H-pyrazol-4-yl)indolizine-7-carboxylate: Yield 74%. MS (ESI) m/z 326 [M+H]⁺.

Step 2: Preparation of isopropyl 6-methyl-2-(1-methyl-1H-pyrazol-4-yl)-5-(1-morphinolinylvinyl)indolizine-7-carboxylate: MS (ESI) m/z 409 [M+H]⁺.

Step 3: Preparation of isopropyl 6-methyl-2-(1-methyl-1H-pyrazol-4-yl)-5-(1-morphinolinylethyl)indolizine-7-carboxylate: yield of two steps was 30%. MS (ESI) m/z 411 [M+H]⁺.

Step 4: Preparation of 6-methyl-2-(1-methyl-1H-pyrazol-4-yl)-5-(1-morphinolinylethyl)indolizine-7-carboxylic acid: MS (ESI) m/z 369 [M+H]⁺.

Step 5: Preparation of N-((4,6-dimethyl-2-oxo-1,2-dihydropyridin-3-yl)methyl)-6-methyl-2-(1-methyl-1H-pyrazol-4-yl)-5-(1-morphinolinylethyl)indolizine-7-carboxamide: Yield 11%. ¹H NMR (400 MHz, MeOD) δ ppm 7.83 (s, 1H), 7.69 (s, 1H), 7.31 (s, 1H), 6.61 (s, 1H), 6.11 (s, 1H), 6.46 (s, 1H), 4.57 (s, 2H), 4.45 (brs, 2H), 4.07 (q, J=6.8 Hz, 1H), 3.68 (brs, 4H), 2.70-2.67 (m, 2H), 2.37 (s, 3H), 2.30 (s, 2H), 2.24-2.19 (m, 6H), 1.52 (d, J=6.8 Hz, 3H); MS (ESI) m/z 503 [M+H]⁺.

Example 43: Preparation of N-((4,6-dimethyl-2-oxo-1,2-dihydropyridin-3-yl)methyl)-2-(2-fluoro-4-methoxyphenyl)-6-methyl-5-(1-morpholinylethyl)indolizine-7-carboxamide

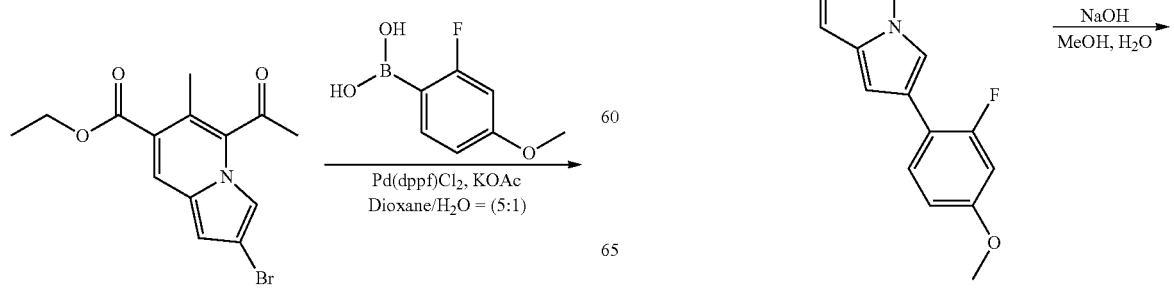

146
-continued

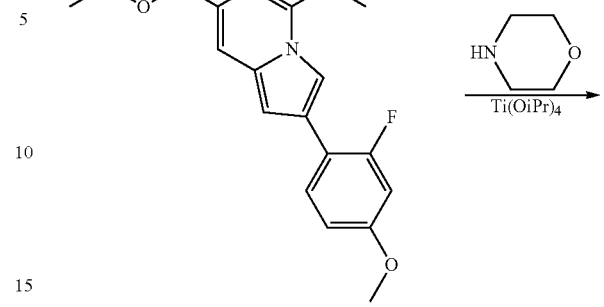

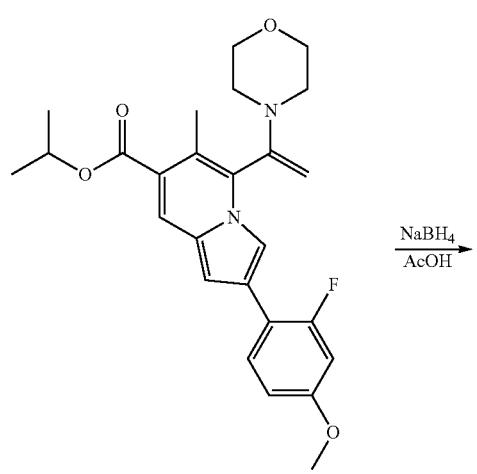

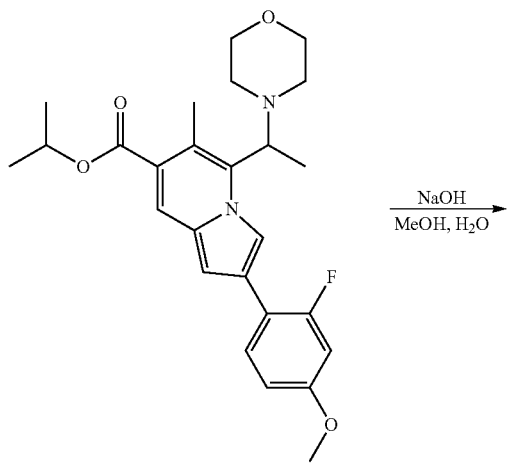

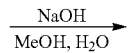

147

-continued

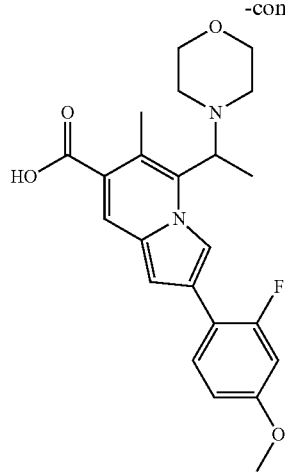

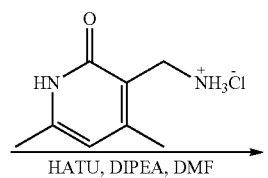

HATU, DIPEA, DMF compound 44

N-((4,6-dimethyl-2-oxo-1,2-dihydropyridin-3-yl)methyl)-2-(2-fluoro-4-methoxyphenyl)-6-methyl-5-(1-morphinolinylethyl)indolizine-7-carboxamide was prepared by a method similar to example 31.

Step 1: Preparation of ethyl 5-acetyl-2-(2-fluoro-4-dimethoxyphenyl)-6-methylindolizine-7-carboxylate: Yield 70%. MS (ESI) m/z 370 [M+H]$^+$.

Step 2: Preparation of isopropyl 2-(2-fluoro-4-methoxyphenyl)-6-methyl-5-(1-morphinolinylvinyl)indolizine-7-carboxylate: MS (ESI) m/z 453 [M+H]$^+$.

Step 3: Preparation of isopropyl 2-(2-fluoro-4-methoxyphenyl)-6-methyl-5-(1-morphinolinylethyl)indolizine-7-carboxylate: yield of two steps was 72%. MS (ESI) m/z 455 [M+H]$^+$.

Step 4: Preparation of 2-(2-fluoro-4-methoxyphenyl)-6-methyl-5-(1-morphinolinylethyl)indolizine-7-carboxylic acid: MS (ESI) m/z 413 [M]$^+$.

Step 5: Preparation of N-((4,6-dimethyl-2-oxo-1,2-dihydropyridin-3-yl)methyl)-2-(2-fluoro-4-methoxyphenyl)-6-methyl-5-(1-morphinolinylethyl)indolizine-7-carboxamide: Yield of the two steps was 28%. $^1$H NMR (400 MHz, DMSO-d$_6$) δ ppm 11.53 (s, 1H), 8.26 (s, 1H), 8.23 (t, J=2.8 Hz, 1H), 7.75 (t, J=7.8 Hz, 1H), 7.35 (s, 1H), 6.99-6.90 (m, 2H), 6.87 (s, 1H), 5.93 (s, 1H), 4.32 (d, J=6.4 Hz, 1H), 4.11 (q, J=6.8 Hz, 1H), 3.86 (s, 3H), 3.63 (brs, 4H), 2.71-2.69 (m, 2H), 2.31 (s, 3H), 2.28 (s, 3H), 2.28-2.18 (m, 2H), 2.17 (s, 3H), 1.49 (d, J=6.8 Hz, 1H); MS (ESI) m/z 547 [M+H]$^+$.

148

Example 44: Preparation of N-((4,6-dimethyl-2-oxo-1,2-dihydropyridin-3-yl)methyl)-6-methyl-5-(1-morphinolinylethyl)-2-(1-(piperidin-4-yl)-1H-pyrazol-4-yl)indolizine-7-carboxamide

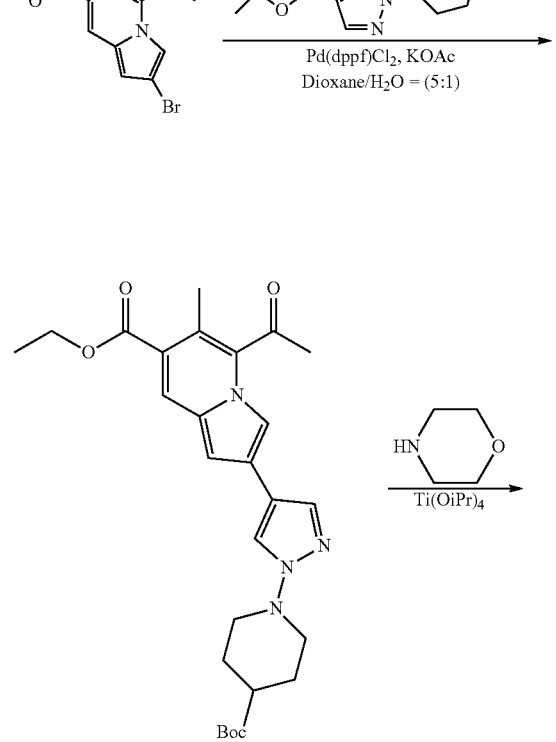

Pd(dppf)Cl$_2$, KOAc
Dioxane/H$_2$O = (5:1)

Ti(OiPr)$_4$

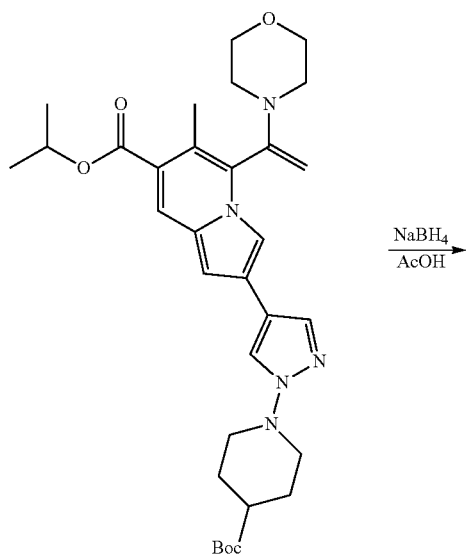

NaBH$_4$
AcOH

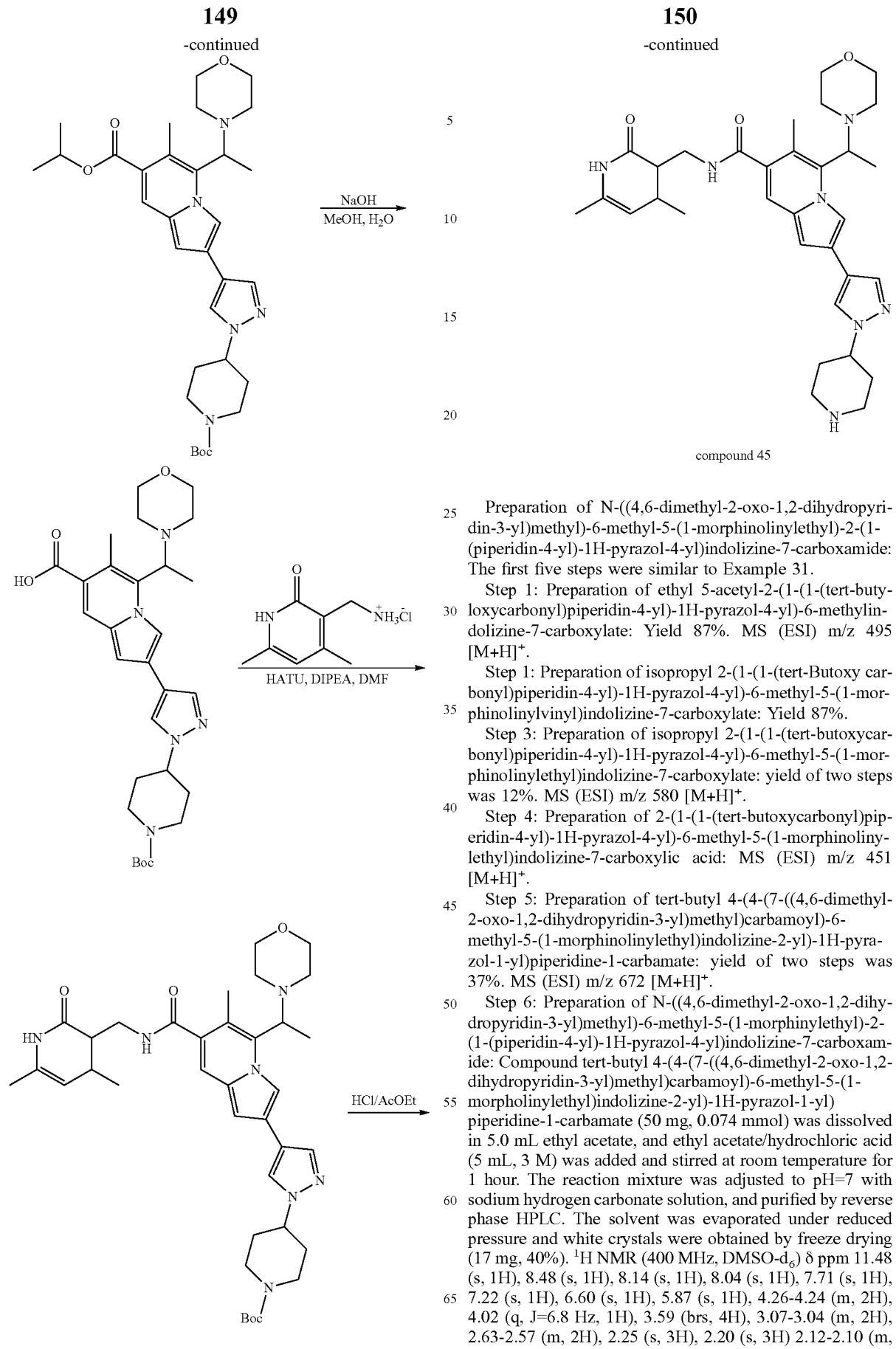

compound 45

Preparation of N-((4,6-dimethyl-2-oxo-1,2-dihydropyridin-3-yl)methyl)-6-methyl-5-(1-morpholinylethyl)-2-(1-(piperidin-4-yl)-1H-pyrazol-4-yl)indolizine-7-carboxamide: The first five steps were similar to Example 31.

Step 1: Preparation of ethyl 5-acetyl-2-(1-(1-(tert-butyloxycarbonyl)piperidin-4-yl)-1H-pyrazol-4-yl)-6-methylindolizine-7-carboxylate: Yield 87%. MS (ESI) m/z 495 [M+H]$^+$.

Step 1: Preparation of isopropyl 2-(1-(1-(tert-Butoxy carbonyl)piperidin-4-yl)-1H-pyrazol-4-yl)-6-methyl-5-(1-morpholinylvinyl)indolizine-7-carboxylate: Yield 87%.

Step 3: Preparation of isopropyl 2-(1-(1-(tert-butoxycarbonyl)piperidin-4-yl)-1H-pyrazol-4-yl)-6-methyl-5-(1-morpholinylethyl)indolizine-7-carboxylate: yield of two steps was 12%. MS (ESI) m/z 580 [M+H]$^+$.

Step 4: Preparation of 2-(1-(1-(tert-butoxycarbonyl)piperidin-4-yl)-1H-pyrazol-4-yl)-6-methyl-5-(1-morpholinylethyl)indolizine-7-carboxylic acid: MS (ESI) m/z 451 [M+H]$^+$.

Step 5: Preparation of tert-butyl 4-(4-(7-((4,6-dimethyl-2-oxo-1,2-dihydropyridin-3-yl)methyl)carbamoyl)-6-methyl-5-(1-morpholinylethyl)indolizine-2-yl)-1H-pyrazol-1-yl)piperidine-1-carbamate: yield of two steps was 37%. MS (ESI) m/z 672 [M+H]$^+$.

Step 6: Preparation of N-((4,6-dimethyl-2-oxo-1,2-dihydropyridin-3-yl)methyl)-6-methyl-5-(1-morphinylethyl)-2-(1-(piperidin-4-yl)-1H-pyrazol-4-yl)indolizine-7-carboxamide: Compound tert-butyl 4-(4-(7-((4,6-dimethyl-2-oxo-1,2-dihydropyridin-3-yl)methyl)carbamoyl)-6-methyl-5-(1-morpholinylethyl)indolizine-2-yl)-1H-pyrazol-1-yl)piperidine-1-carbamate (50 mg, 0.074 mmol) was dissolved in 5.0 mL ethyl acetate, and ethyl acetate/hydrochloric acid (5 mL, 3 M) was added and stirred at room temperature for 1 hour. The reaction mixture was adjusted to pH=7 with sodium hydrogen carbonate solution, and purified by reverse phase HPLC. The solvent was evaporated under reduced pressure and white crystals were obtained by freeze drying (17 mg, 40%). $^1$H NMR (400 MHz, DMSO-d$_6$) δ ppm 11.48 (s, 1H), 8.48 (s, 1H), 8.14 (s, 1H), 8.04 (s, 1H), 7.71 (s, 1H), 7.22 (s, 1H), 6.60 (s, 1H), 5.87 (s, 1H), 4.26-4.24 (m, 2H), 4.02 (q, J=6.8 Hz, 1H), 3.59 (brs, 4H), 3.07-3.04 (m, 2H), 2.63-2.57 (m, 2H), 2.25 (s, 3H), 2.20 (s, 3H) 2.12-2.10 (m, 5H), 1.98-1.95 (m, 2H), 1.83-1.80 (m, 2H), 1.44-1.43 (m, 3H); MS (ESI) m/z 572 [M+H]⁺.

Example 45: Preparation of N-((4,6-dimethyl-2-oxo-1,2-dihydropyridin-3-yl)methyl)-6-methyl-5-(1-morphinolinylethyl)-2-(1,2,3,6-tetrahydropyridin-4-yl)indolizine-7-carboxamide

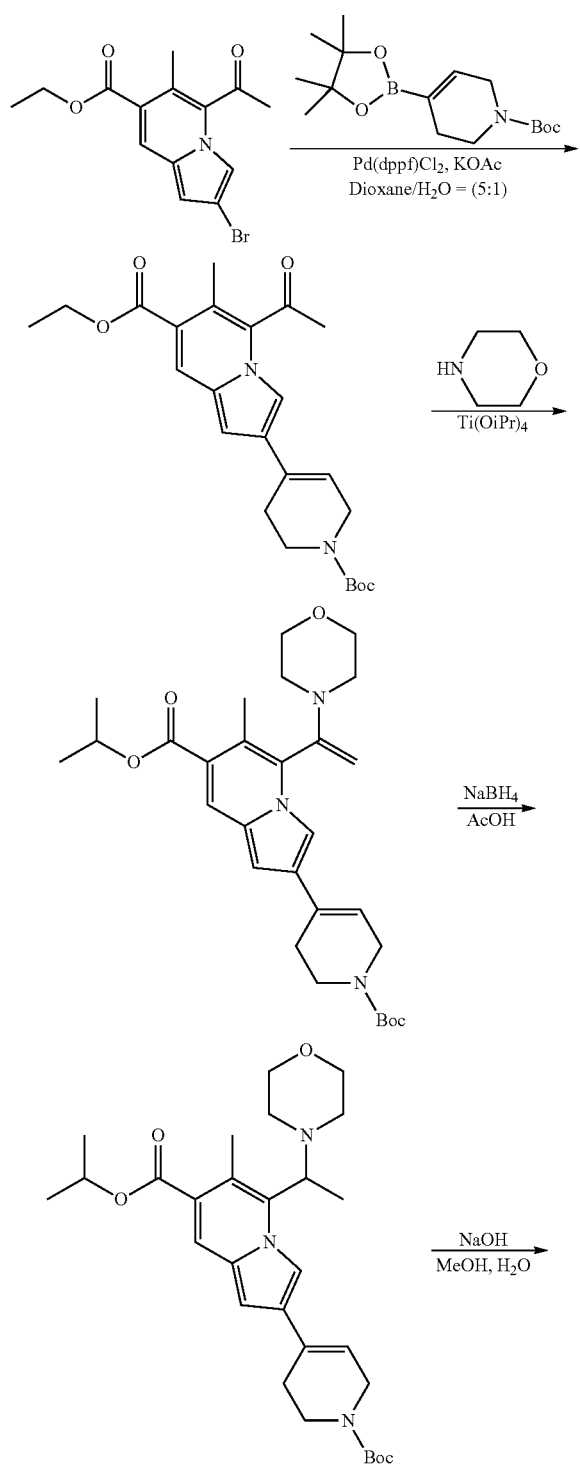

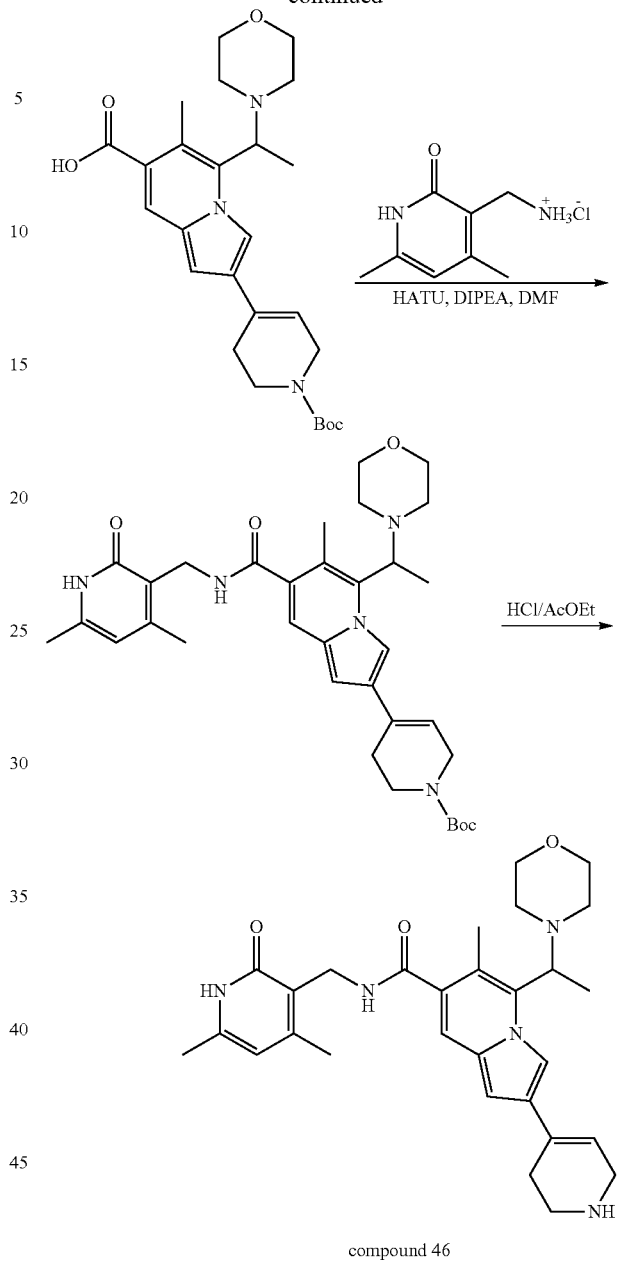

compound 46

N-((4,6-dimethyl-2-oxo-1,2-dihydropyridin-3-yl)methyl)-6-methyl-5-(1-morphinolinylethyl)-2-(1,2,3,6-tetrahydropyridin-4-yl)indolizine-7-carboxamide was prepared by a method similar to example 44.

Step 1: Preparation of ethyl 5-acetyl-2-(1-(tert-butyloxycarbonyl)-1,2,3,6-tetrahydropyridin-4-yl)-6-methylindolizine-7-carboxylate: Yield 65%. MS (ESI) m/z 427 [M+H]⁺.

Step 2: Preparation of isopropyl 2-(1-(1-(tert-Butoxy carbonyl)-1,2,3,6-tetrahydropyridin-4-yl)-6-methyl-5-(1-morphinolinylvinyl)indolizine-7-carboxylate: MS (ESI) m/z 510 [M+H]⁺.

Step 3: Preparation of isopropyl 2-(1-(tert-butoxycarbonyl)-1,2,3,6-tetrahydropyridin-4-yl)-6-methyl-5-(1-morphinolinylethyl) indolizine-7-carboxylate: yield of two steps was 54%. MS (ESI) m/z 512 [M+H]⁺.

Step 4: Preparation of 2-(1-(tert-butoxycarbonyl)-1,2,3,6-tetrahydropyridin-4-yl)-6-methyl-5-(1-morphinolinylethyl) indolizine-7-carboxylic acid: MS (ESI) m/z 470 [M+H]⁺.

Step 5: Preparation of tert-butyl 4-(7-((4,6-dimethyl-2-oxo-1,2-dihydropyridin-3-yl)methyl)carbamoyl)-6-methyl-5-(1-morpholinylethyl)indolizine-2-yl)-3,6-dihydropyridine-1(2H)-carboxylate: yield of two steps was 33%. MS (ESI) m/z 604 [M+H]+.

Step 6: Preparation of N-((4,6-dimethyl-2-oxo-1,2-dihydropyridin-3-yl)methyl)-6-methyl-5-(1-morphinolinylethyl)-2-(1,2,3,6-tetrahydropyridin-4-yl)indolizine-7-carboxamide: yield 40%. $^1$H NMR (400 MHz, MeOD) δ ppm 7.36 (s, 1H), 6.68 (s, 1H), 6.19 (s, 1H), 6.12 (s, 1H), 4.45 (s, 2H), 3.84 (s, 2H), 3.72 (s, 4H), 3.48 (s, 2H), 2.84 (s, 4H), 2.38 (s, 3H), 2.31 (s, 3H), 2.25 (s, 5H), 1.55 (s, 3H); MS (ESI) m/z 504 [M+H]+.

Example 46: Preparation of N-((4,6-dimethyl-2-oxo-1,2-dihydropyridin-3-yl)methyl)-6-methyl-5-(1-morphinolinylethyl)-2-(piperidin-4-yl)indolizine-7-carboxamide

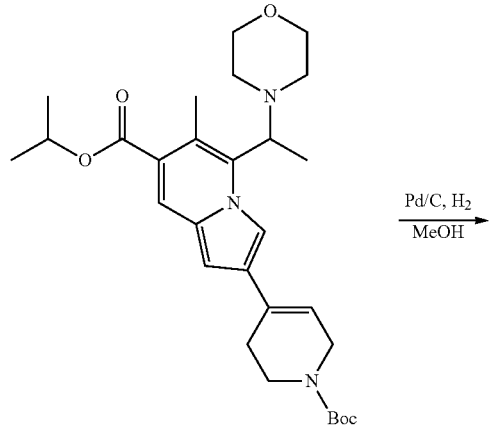

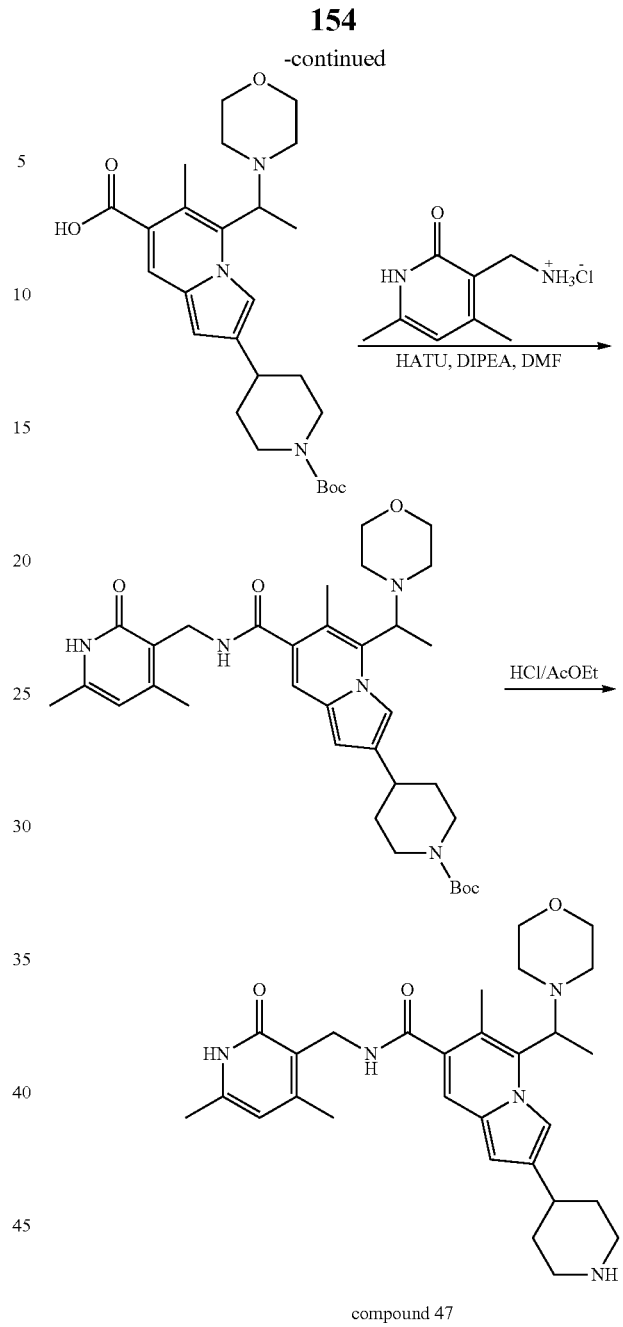

compound 47

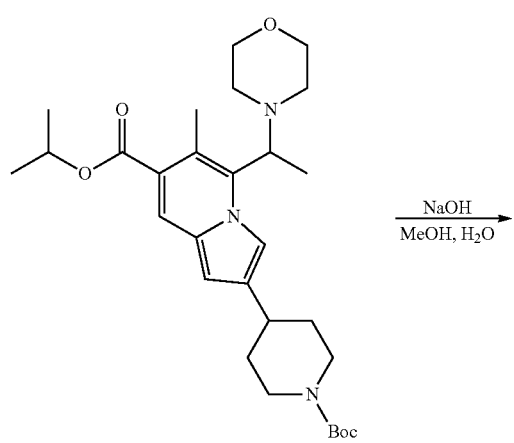

Step 1: Preparation of isopropyl 2-(1-(tert-Butoxycarbonyl)piperidin-4-yl)-6-methyl-5-(1-morphinolinylethyl)indolizine-7-carboxylate: isopropyl 2-(1-(tert-butyloxycarbonyl)-1,2,3,6-tetrahydropyridin-4-yl)-6-methyl-5-(1-morphinolinylethyl)indolizine-7-carboxylate (95 mg, 0.186 mmol)), Pd/C (10 mg) and 10 ml of methanol were added sequentially to a 25 mL single-necked flask, exchanged with hydrogen and stirred at room temperature for 2 hours, and filtered. The organic phase was concentrated to provide a product as yellow oil (90 mg, yield: 95%). MS (ESI) m/z 514 [M+H]+.

Step 2: Preparation of 2-(1-(tert-butoxycarbonyl)piperidin-4-yl)-6-methyl-5-(1-morphinolinylethyl)indolizine-7-carboxylic acid: 2-(1-(tert-butoxycarbonyl)piperidin-4-yl)-6-methyl-5-(1-morphinolinylethyl)indolizine-7-carboxylic acid was prepared by a method similar to step 5 of example 1. MS (ESI) m/z 472 [M+H]+.

Step 3: Preparation of tert-butyl 4-(7-((4,6-Dimethyl-2-oxo-1,2-dihydropyridin-3-yl)methyl)carbamoyl)-6-methyl-5-(1-morpholinylethyl)indolizine-2-yl)piperidine-1-carboxylate: tert-butyl 4-(7-((4,6-Dimethyl-2-oxo-1,2-dihydropyridin-3-yl)methyl)carbamoyl)-6-methyl-5-(1-morpholinylethyl)indolizine-2-yl)piperidine-1-carboxylate was prepared by a method similar to Step 6 of Example 1, yield of the two steps was 32%. MS (ESI) m/z 606 [M+H]+.

Step 4: Preparation of N-((4,6-dimethyl-2-oxo-1,2-dihydropyridin-3-yl)methyl)-6-methyl-5-(1-morpholinylethyl)-2-(piperidin-4-yl)indolizine-7-carboxamide: N-((4,6-dimethyl-2-oxo-1,2-dihydropyridin-3-yl)methyl)-6-methyl-5-(1-morpholinylethyl)-2-(piperidin-4-yl)indolizine-7-carboxamide was prepared by a method similar to Step 6 of Example 1, yield 47%. ¹H NMR (400 MHz, MeOD) δ ppm 7.36 (s, 1H), 6.13 (s, 1H), 4.46 (s, 3H), 3.84 (s, 1H), 3.76 (s, 4H), 3.49-3.49 (m, 3H), 3.23-3.16 (m, 7H), 2.38 (s, 3H), 2.31 (s, 5H), 2.33 (s, 3H), 2.25 (s, 6H), 1.94-1.85 (m, 3H); MS (ESI) m/z 506 [M+H]+.

Example 47: Preparation of 2-(3,6-dihydro-2H-pyran-4-yl)-N-((4,6-dimethyl-2-oxo-1,2-dihydropyridin-3-yl)-6-methyl-5-(1-morpholinylethyl)indolizine-7-carboxamide

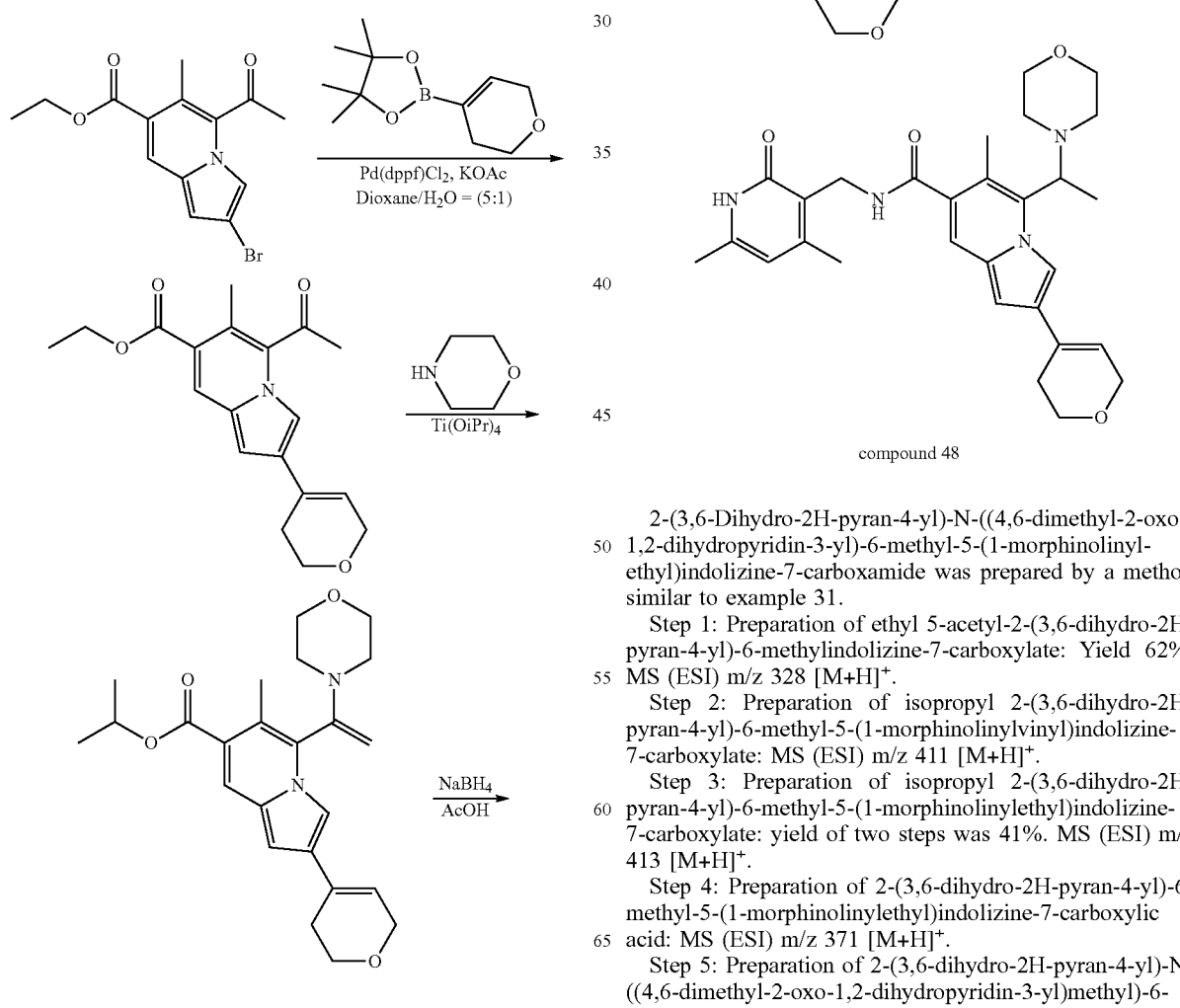

compound 48

2-(3,6-Dihydro-2H-pyran-4-yl)-N-((4,6-dimethyl-2-oxo-1,2-dihydropyridin-3-yl)-6-methyl-5-(1-morpholinylethyl)indolizine-7-carboxamide was prepared by a method similar to example 31.

Step 1: Preparation of ethyl 5-acetyl-2-(3,6-dihydro-2H-pyran-4-yl)-6-methylindolizine-7-carboxylate: Yield 62%. MS (ESI) m/z 328 [M+H]+.

Step 2: Preparation of isopropyl 2-(3,6-dihydro-2H-pyran-4-yl)-6-methyl-5-(1-morpholinylvinyl)indolizine-7-carboxylate: MS (ESI) m/z 411 [M+H]+.

Step 3: Preparation of isopropyl 2-(3,6-dihydro-2H-pyran-4-yl)-6-methyl-5-(1-morpholinylethyl)indolizine-7-carboxylate: yield of two steps was 41%. MS (ESI) m/z 413 [M+H]+.

Step 4: Preparation of 2-(3,6-dihydro-2H-pyran-4-yl)-6-methyl-5-(1-morpholinylethyl)indolizine-7-carboxylic acid: MS (ESI) m/z 371 [M+H]+.

Step 5: Preparation of 2-(3,6-dihydro-2H-pyran-4-yl)-N-((4,6-dimethyl-2-oxo-1,2-dihydropyridin-3-yl)methyl)-6- methyl-5-(1-morpholinylethyl)indolizine-7-carboxamide: yield of two steps was 43%. ¹H NMR (400 MHz, MeOD) δ ppm 7.46 (s, 1H), 6.21 (s, 1H), 6.15 (s, 1H), 4.46 (s, 2H), 4.29 (s, 2H), 3.93-3.84 (m, 7H), 2.54 (s, 2H), 2.39-2.38 (m, 8H), 2.38-2.35 (m, 6H), 1.80 (s, 3H); MS (ESI) m/z 505 [M+H]⁺.

Example 48: Preparation of N-((4,6-dimethyl-2-oxo-1,2-dihydropyridin-3-yl)methyl)-6-methyl-5-(1-morpholinylethyl)-2-(tetrahydro-2H-pyran-4-yl)indolizine-7-carboxamide

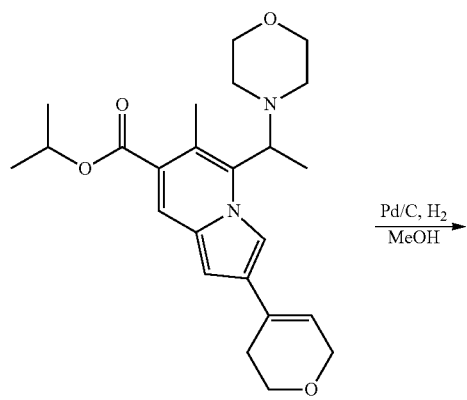

Pd/C, H₂
MeOH

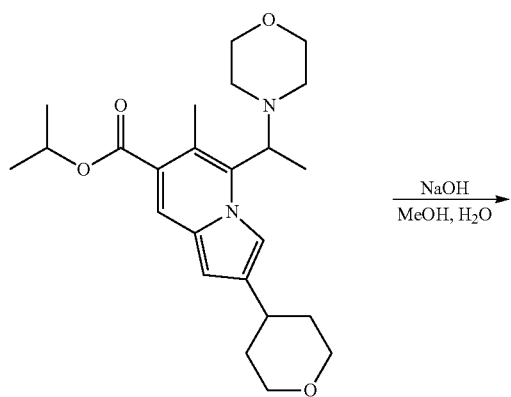

NaOH
MeOH, H₂O

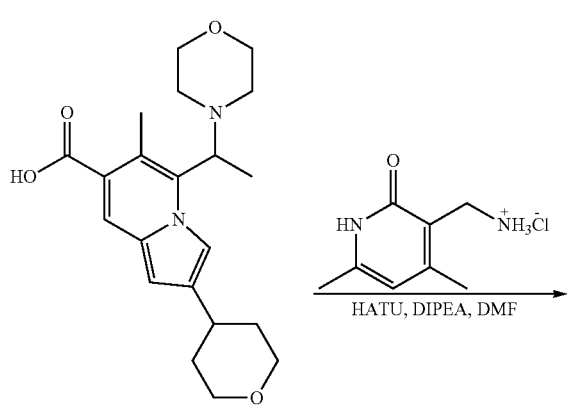

HATU, DIPEA, DMF

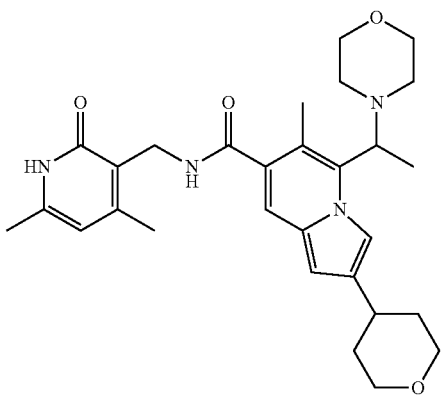

compound 49

Preparation of N-((4,6-dimethyl-2-oxo-1,2-dihydropyridin-3-yl)methyl)-6-methyl-5-(1-morpholinylethyl)-2-(tetrahydro-2H-pyran-4-yl)indolizine-7-carboxamide was similar to the first three steps of Example 46.

Step 1: Preparation of isopropyl 6-methyl-5-(1-morpholinylethyl)-2-(tetrahydro-2H-pyran-4-yl)indolizine-7-carboxylate: yield 94%. MS (ESI) m/z 415 [M+H]⁺.

Step 2: Preparation of 6-methyl-5-(1-morpholinylethyl)-2-(tetrahydro-2H-pyran-4-yl)indolizine-7-carboxylic acid: MS (ESI) m/z 373 [M+H]⁺.

Step 3: Preparation of N-((4,6-dimethyl-2-oxo-1,2-dihydropyridin-3-yl)methyl)-6-methyl-5-(1-morpholinylethyl)-2-(tetrahydro-2H-pyran-4-yl)indolizine-7-carboxamide: yield of two steps was 65%. ¹H NMR (400 MHz, MeOD) δ ppm 7.42 (s, 1H), 6.15 (s, 1H), 4.46 (s, 2H), 4.01 (d, J=4.8 Hz, 2H), 3.87-3.82 (m, 4H), 3.57 (t, J=11.6 Hz, 2H), 3.20-3.01 (m, 2H), 3.00-2.92 (m, 1H), 2.38-2.33 (m, 6H), 2.25 (s, 3H), 1.94-1.90 (m, 2H), 1.81-1.75 (m, 5H); MS (ESI) m/z 507 [M+H]⁺.

Example 49: Preparation of N-((4,6-dimethyl-2-oxo-1,2-dihydropyridin-3-yl)methyl)-5-(1-(4-(dimethylamino)piperidin-1-yl)ethyl)-6-methyl-2-(pyridin-3-yl)indolizine-7-carboxamide

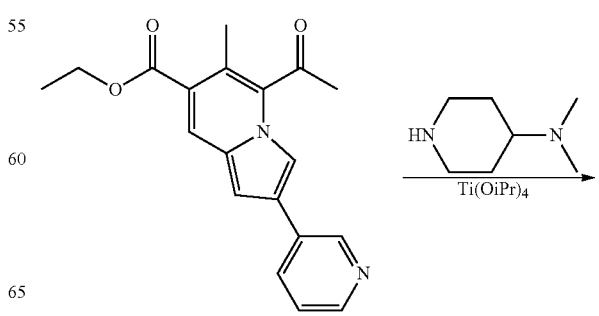

Ti(OiPr)₄

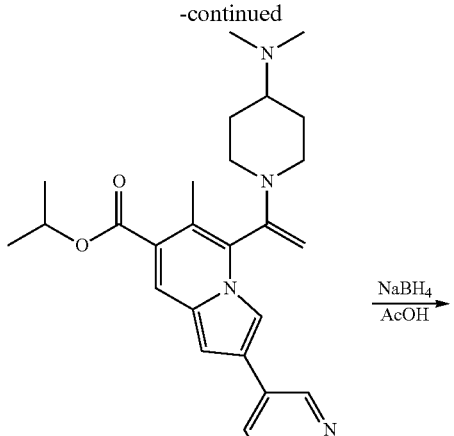

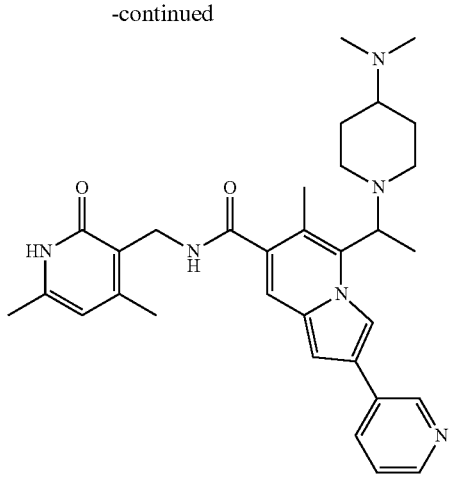

compound 50

N-((4,6-dimethyl-2-oxo-1,2-dihydropyridin-3-yl)methyl)-5-(1-(4-(dimethylamino)piperidin-1-yl)ethyl)-6-methyl-2-(pyridin-3-yl)indolizine-7-carboxamide was prepared by a method similar to example 31.

Step 1: Preparation of isopropyl 5-(1-(4-(dimethylamino)piperidin-1-yl)vinyl)-6-methyl-2-(pyridin-3-yl)indolizine-7-carboxylate: MS (ESI) m/z 447 [M+H]⁺.

Step 2: Preparation of isopropyl 5-(1-(4-(Dimethylamino)piperidin-1-yl)ethyl)-6-methyl-2-(pyridin-3-yl)indolizine-7-carboxylate: yield of two steps was 52%. MS (ESI) m/z 449 [M+H]⁺.

Step 3: Preparation of 5-(1-(4-(dimethylamino)piperidin-1-yl)ethyl)-6-methyl-2-(pyridin-3-yl)indolizine-7-carboxylic acid: MS (ESI) m/z 407 [M+H]⁺.

Step 4: Preparation of N-((4,6-dimethyl-2-oxo-1,2-dihydropyridin-3-yl)methyl)-5-(1-(4-(dimethylamino)piperidine-1-yl)ethyl)-6-methyl-2-(pyridin-3-yl)indolizine-7-carboxamide: Yield of the two steps was 27%. $^1$H NMR (400 MHz, DMSO-$d_6$) δ ppm 11.46 (brs, 1H), 9.60 (brs, 1H), 9.17 (s, 1H), 8.74 (brs, 1H), 8.65 (s, 1H), 8.55 (brs, 1H), 8.27 (brs, 1H), 7.78 (brs, 1H), 7.38 (s, 1H), 7.08 (s, 1H), 5.89 (s, 1H), 4.04 (s, 2H), 3.69-3.57 (m, 2H), 3.17 (s, 1H), 2.74 (s, 6H), 2.38 (s, 3H), 2.22 (s, 3H), 2.13 (s, 3H), 1.89-1.81 (m, 4H), 1.49 (brs, 3H); MS (ESI) m/z 541 [M+H]⁺.

Example 50: Preparation of N-((4,6-dimethyl-2-oxo-1,2-dihydropyridin-3-yl)methyl)-6-methyl-5-(1-morpholinylethyl)-2-(thiazol-2-yl)indolizine-7-carboxamide

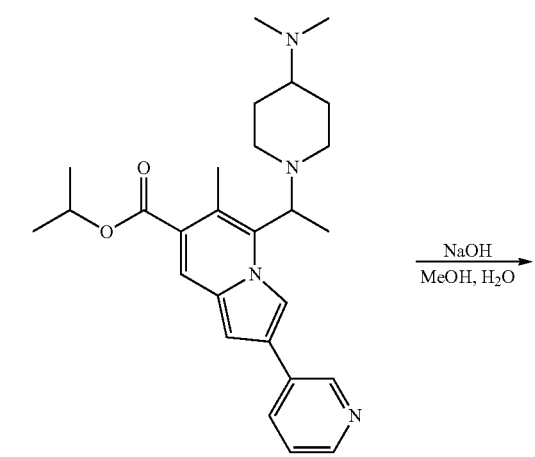

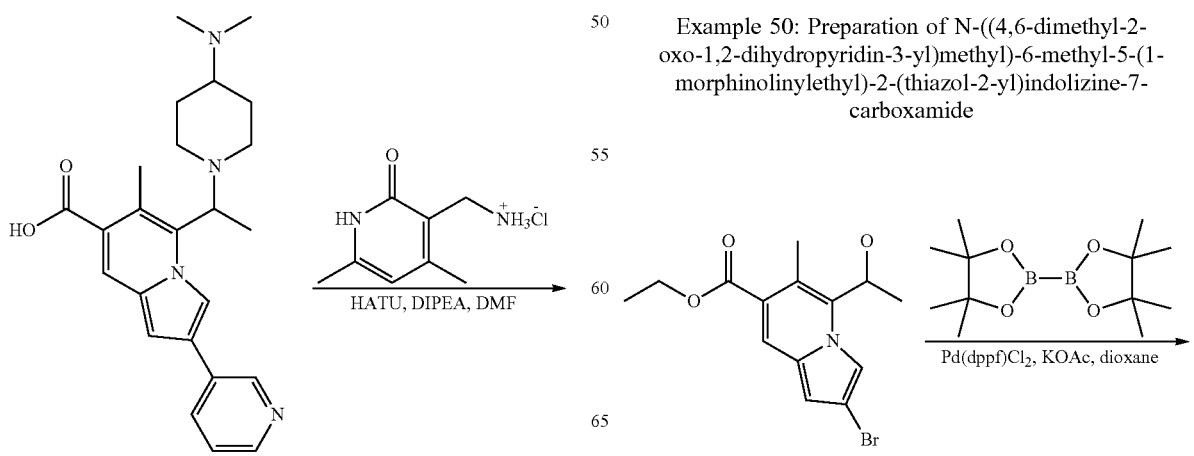

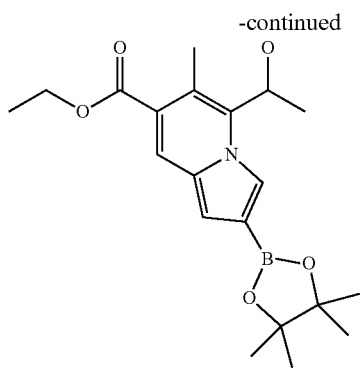 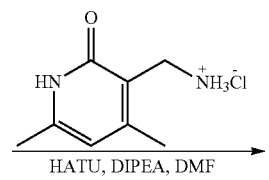 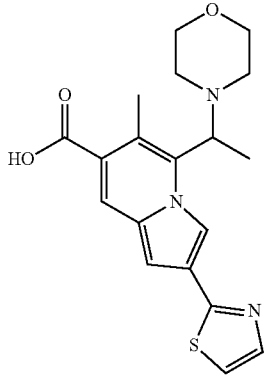

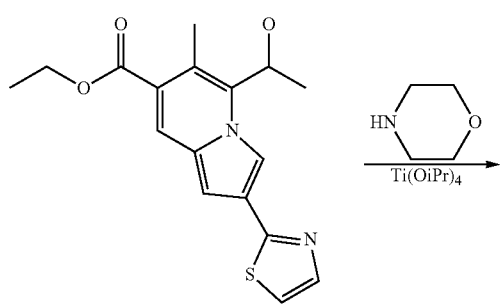 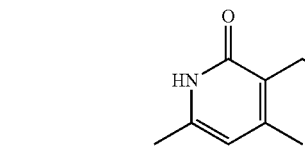

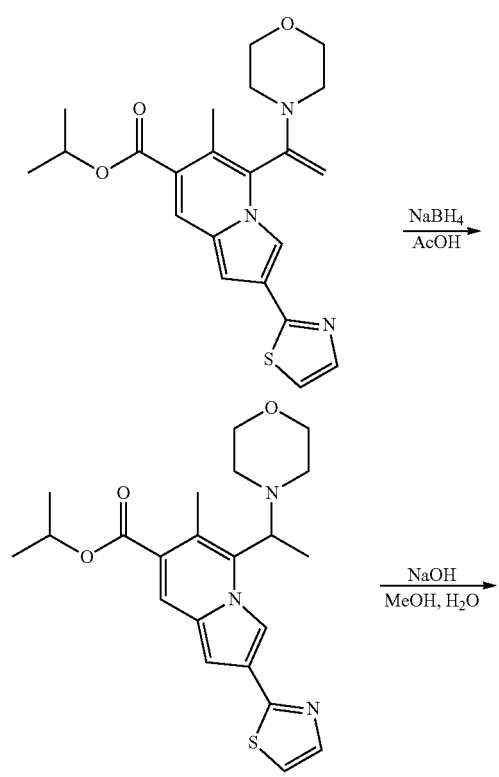

compound 51

Step 1: Preparation of ethyl 5-acetyl-6-methyl-2-(4,4,5,5-tetramethyl-1,3,2-dioxaborolan-2-yl)indolizine-7-carboxylate: ethyl 5-acetyl-2-bromo-6-methylindolizine-7-carboxylate (2.0 g, 6.2 mmol), Pd (dppf)Cl$_2$ (454 mg, 0.62 mmol), pinacol borate (3.15 g, 12.4 mmol) and potassium acetate (1.22 g, 12.4 mmol) were added into a dry 50 mL three-necked flask successively, dissolved in 1.4-dioxane (50 mL), and stirred under 110° C. overnight. After the reaction was completed, the reaction mixture was extracted with ethyl acetate (100 mL×3), washed with water (30 mL×2) and saturated brine (30 mL). The organic phase was dried over anhydrous sodium sulfate, filtered and concentrated to provide a crude product. After purified by column chromatography (petroleum ether:ethyl acetate=10:1), ethyl 5-acetyl-6-methyl-2-(4,4,5,5-tetramethyl-1,3,2-dioxaborolan-2-yl)indolizine-7-carboxylate (1.60 g, yield: 70%) was provided. MS (ESI) m/z 372 [M+H]$^+$.

Step 2: Preparation of ethyl 5-acetyl-6-methyl-2-(thiazole-2-yl)indolizine-7-carboxylate: the procedure was the same as step 1 of example 21. Yield: 32%. MS (ESI) m/z 329 [M+H]$^+$.

Step 3: Preparation of isopropyl 6-methyl-5-(1-morphinolinylvinyl)-2-(thiazol-2-yl)indolizine-7-carboxylate: isopropyl 6-methyl-5-(1-morphinolinylvinyl)-2-(thiazol-2-yl)indolizine-7-carboxylate was prepared by a method similar to step 1 of example 26. MS (ESI) m/z 412 [M+H]$^+$.

Step 4: Preparation of isopropyl 6-methyl-5-(1-morphinolinylethyl)-2-(thiazol-2-yl)indolizine-7-carboxylate: isopropyl 6-methyl-5-(1-morphinolinylethyl)-2-(thiazol-2-yl)indolizine-7-carboxylate was prepared by a method similar to step 2 of example 26, yield of two steps was 63%. MS (ESI) m/z 414 [M+H]$^+$.

Step 5: Preparation of 6-methyl-5-(1-morphinolinylethyl)-2-(thiazol-2-yl)indolizine-7-carboxylic acid:

6-methyl-5-(1-morpholinylethyl)-2-(thiazol-2-yl)indolizine-7-carboxylic acid was prepared by a method similar to step 5 of example 1. MS (ESI) m/z 372 [M+H]$^+$.

Step 6: Preparation of N-((4,6-dimethyl-2-oxo-1,2-dihydropyridin-3-yl)methyl)-6-methyl-5-(1-morpholinylethyl)-2-(thiazol-2-yl)indolizine-7-carboxamide: N-((4,6-Dimethyl-2-oxo-1,2-dihydropyridin-3-yl)methyl)-6-methyl-5-(1-morpholinylethyl)-2-(thiazol-2-yl)indolizine-7-carboxamide was prepared by a method similar to Step 6 of Example 1, yield 15%. $^1$H NMR (400 MHz, DMSO-d$_6$) δ ppm 11.48 (brs, 1H), 8.82 (brs, 1H), 8.24 (s, 1H), 7.83 (s, 1H), 7.66 (s, 1H), 7.36 (s, 1H), 6.91 (s, 1H), 5.87 (s, 1H), 4.27 (s, 2H), 4.14-4.12 (m, 1H), 3.60-3.57 (m, 4H), 2.67-2.62 (m, 2H), 2.40-2.36 (m, 5H). 2.11 (s, 3H), 2.05 (s, 3H), 1.43 (brs, 3H); MS (ESI) m/z 506 [M+H]$^+$.

Example 51: Preparation of N-((4,6-dimethyl-2-oxo-1,2-dihydropyridin-3-yl)methyl)-6-methyl-5-(1-morpholinylethyl)-2-(pyridin-2-yl)indolizine-7-carboxamide

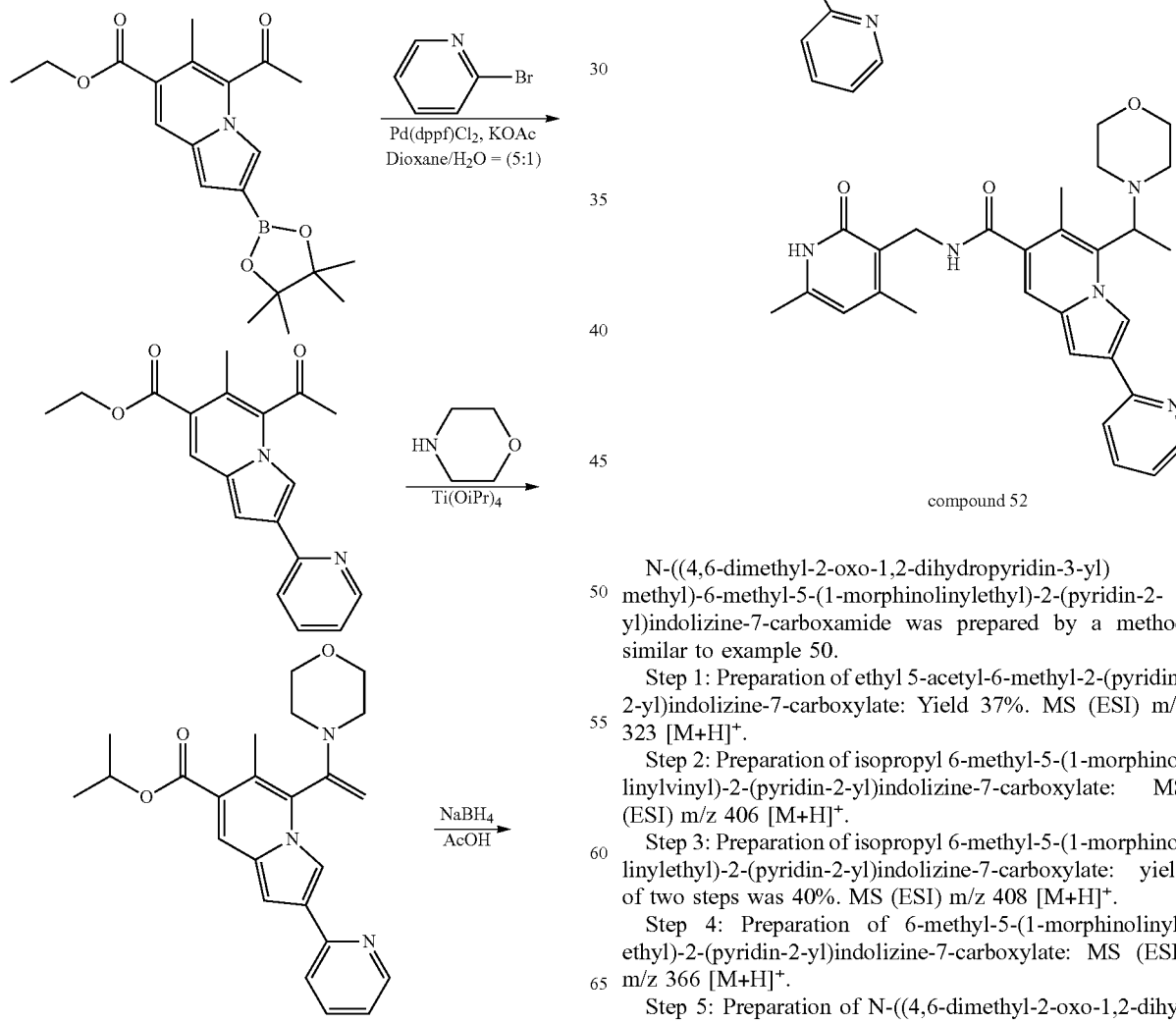

compound 52

N-((4,6-dimethyl-2-oxo-1,2-dihydropyridin-3-yl)methyl)-6-methyl-5-(1-morpholinylethyl)-2-(pyridin-2-yl)indolizine-7-carboxamide was prepared by a method similar to example 50.

Step 1: Preparation of ethyl 5-acetyl-6-methyl-2-(pyridin-2-yl)indolizine-7-carboxylate: Yield 37%. MS (ESI) m/z 323 [M+H]$^+$.

Step 2: Preparation of isopropyl 6-methyl-5-(1-morpholinylvinyl)-2-(pyridin-2-yl)indolizine-7-carboxylate: MS (ESI) m/z 406 [M+H]$^+$.

Step 3: Preparation of isopropyl 6-methyl-5-(1-morpholinylethyl)-2-(pyridin-2-yl)indolizine-7-carboxylate: yield of two steps was 40%. MS (ESI) m/z 408 [M+H]$^+$.

Step 4: Preparation of 6-methyl-5-(1-morpholinylethyl)-2-(pyridin-2-yl)indolizine-7-carboxylate: MS (ESI) m/z 366 [M+H]$^+$.

Step 5: Preparation of N-((4,6-dimethyl-2-oxo-1,2-dihydropyridin-3-yl)methyl)-6-methyl-5-(1-morpholinylethyl)-2-(pyridin-2-yl)indolizine-7-carboxamide: yield 28%. $^1$H NMR (400 MHz, DMSO-d$_6$) δ ppm 8.87 (brs, 1H), 8.57 (d, J=4.8 Hz, 1H), 8.21 (t, J=4.8 Hz, 1H), 7.79-7.78 (m, 2H), 7.30 (s, 1H), 7.21 (dd, J=7.8, 7.4 Hz, 1H), 7.01 (s, 1H), 5.87 (s, 1H), 4.27 (d, J=6.4 Hz, 2H), 4.06 (q, J=6.8 Hz, 1H), 3.58 (brs, 4H), 2.67-2.64 (m, 2H), 2.42 (s, 3H), 2.32-2.20 (m, 5H), 2.16 (s, 3H), 1.46 (d, J=6.8 Hz, 3H); MS (ESI) m/z 500 [M+H]$^+$.

Example 52: Preparation of N-((4,6-dimethyl-2-oxo-1,2-dihydropyridin-3-yl)methyl)-6-methyl-2-(1-methyl-1H-imidazole-4-yl)-5-(1-morpholineylethyl)indolizine-7-carboxamide

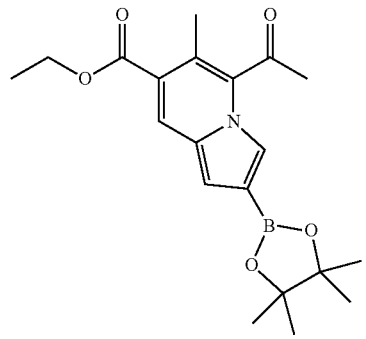

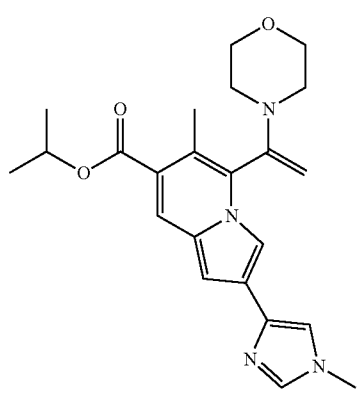

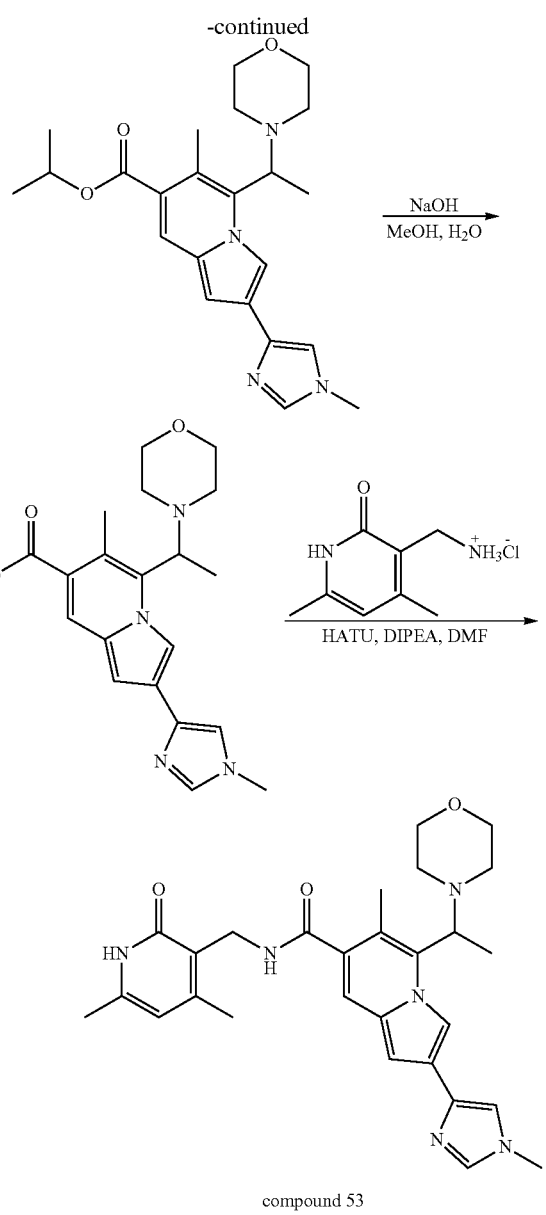

compound 53

N-((4,6-dimethyl-2-oxo-1,2-dihydropyridin-3-yl)methyl)-6-methyl-2-(1-methyl-1H-imidazole-4-yl)-5-(1-morpholineylethyl)indolizine-7-carboxamide was prepared by similar method in example 50.

Step 1: Preparation of ethyl 5-acetyl-6-methyl-2-(1-methyl-1H-imidazol-4-yl)indolizine-7-carboxylate: Yield 53%. MS (ESI) m/z 326 [M+H]$^+$.

Step 2: Preparation of isopropyl 6-methyl-2-(1-methyl-1H-imidazol-4-yl)-5-(1-morphinolinylvinyl)indolizine-7-carboxylate: MS (ESI) m/z 409 [M+H]$^+$.

Step 3: Preparation of isopropyl 6-methyl-2-(1-methyl-1H-imidazol-4-yl)-5-(1-morpholinylethyl)indolizine-7-carboxylate: yield of two steps was 63%. MS (ESI) m/z 411 [M+H]$^+$.

Step 4: Preparation of 6-methyl-2-(1-methyl-1H-imidazol-4-yl)-5-(1-morphinolinylethyl)indolizine-7-carboxylic acid: MS (ESI) m/z 369 [M+H]$^+$.

Step 5: Preparation of N-((4,6-dimethyl-2-oxo-1,2-dihydropyridin-3-yl)methyl)-6-methyl-2-(1-methyl-1H-imidazol-4-yl)-5-(1-morpholinylethyl)indolizine-7-carboxamide: Yield 5%. $^1$H NMR (400 MHz, MeOD) δ ppm 8.87 (s, 1H), 7.80 (s, 1H), 7.47 (s, 1H), 6.66 (s, 1H), 6.16 (s, 1H), 4.48 (s, 2H), 3.97 (s, 3H), 3.88-3.85 (m, 1H), 3.75 (brs, 4H), 3.23-3.22 (m, 2H), 2.39 (s, 3H), 2.35 (s, 3H), 2.28-2.26 (m, 5H), 1.64-1.62 (m, 3H); MS (ESI) m/z 503 [M+H]$^+$.
Example 53: Preparation of N-((4,6-dimethyl-2-oxo-1,2-dihydropyridin-3-yl)methyl)-6-methyl-5-(1-morphinolinylethyl)-2-(4,5,6,7-tetrahydrothiazolo[5,4-c]pyridin-2-yl)indolizine-7-carboxamide
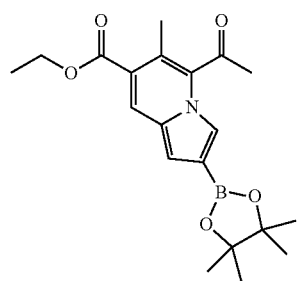
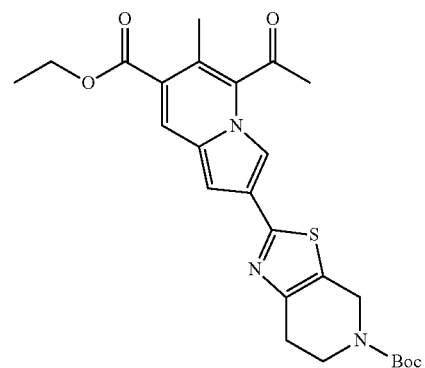
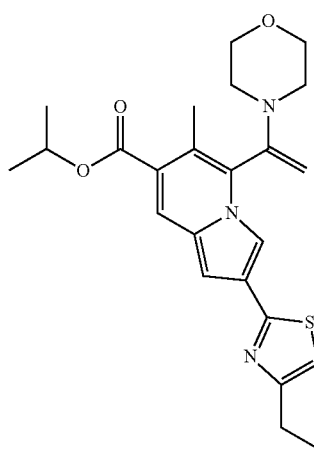
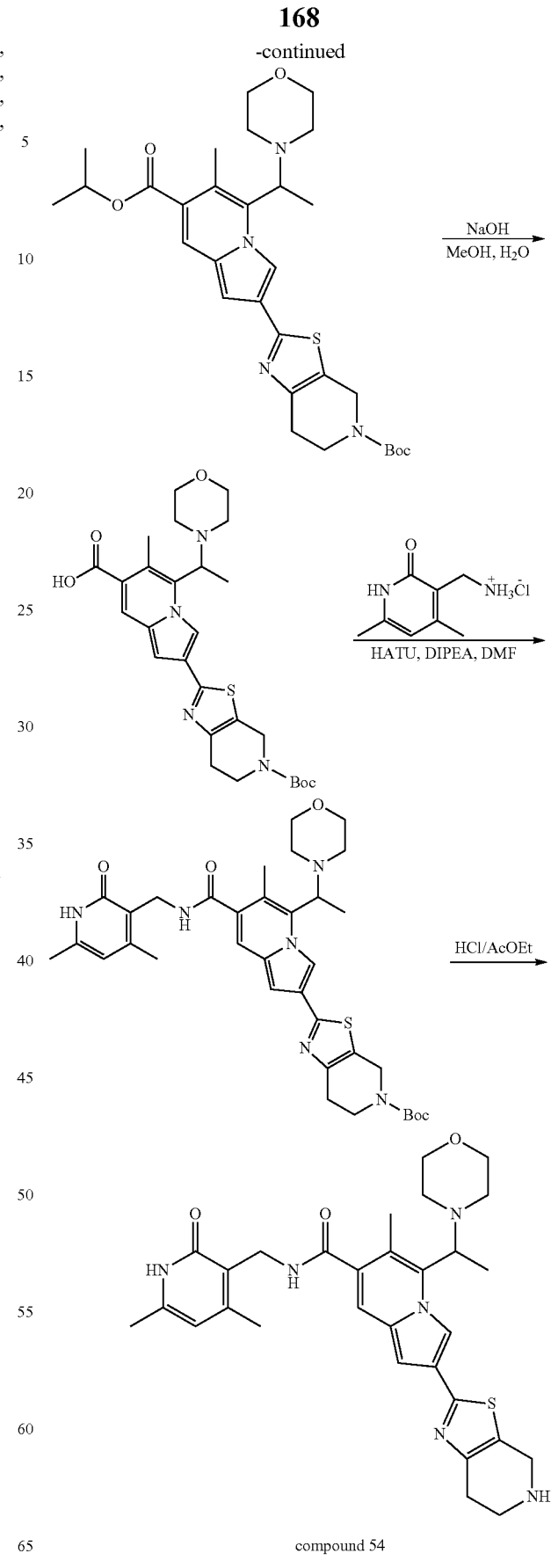
compound 54

The first five steps of the preparation method of N-((4,6-dimethyl-2-oxo-1,2-dihydropyridin-3-yl)methyl)-6-methyl-5-(1-morpholinylethyl)-2-(4,5,6,7-tetrahydrothiazolo[5,4-c]pyridin-2-yl)indolizine-7-carboxamide are similar to that of example 50, and the last deprotection step is the same as that in step 6 of example 44.

Step 1: Preparation of tert-butyl 2-(5-acetyl-7-(ethoxycarbonyl)-6-methylindolizin-2-yl)-6,7-dihydrothiazolo[5,4-c]pyridine-5 (4H)-carboxylate: Yield 26%. MS (ESI) m/z 484 [M+H]⁺.

Step 2: Preparation of tert-butyl 2-(7-(isopropoxycarbonyl)-6-methyl-5-(1-morpholinylvinyl)indolizin-2-yl)-6,7-dihydrothiazolo[5,4-c]-pyridin-5(4H)-carboxylate: MS (ESI) m/z 567 [M+H]⁺.

Step 3: Preparation of tert-butyl 2-(7-(isopropoxycarbonyl)-6-methyl-5-(1-morpholinylethyl)indolizin-2-yl)-6,7-dihydrothiazolo[5,4-c]pyridine-5(4H)-carboxylate: yield of two steps was 44%. MS (ESI) m/z 569 [M+H]⁺.

Step 4: Preparation of 2-(5-(tert-butoxycarbonyl)-4,5,6,7-tetrahydrothiazolo[5,4-c]pyridin-2-yl)-6-methyl-5-(1-morpholinylethyl)indolizine-7-carboxylic acid: MS (ESI) m/z 527 [M+H]⁺.

Step 5: Preparation of tert-butyl 2-(7-(((4,6-dimethyl-2-oxo-1,2-dihydropyridin-3-yl)methyl)carbamoyl)-6-methyl-5-(1-morpholinylethyl)indolizin-2-yl)-6,7-dihydrothiazolo[5,4-c]pyridine-5(4H)-carboxylate: yield of two steps was 49%. MS (ESI) m/z 661 [M+H]⁺.

Step 6: Preparation of N-((4,6-dimethyl-2-oxo-1,2-dihydropyridin-3-yl)methyl)-6-methyl-5-(1-morpholinylethyl)-2-(4,5,6,7-tetrahydrothiazolo[5,4-c]pyridin-2-yl)indolizine-7-carboxamide: yield 49%. ¹H NMR (400 MHz, DMSO-d₆) δ ppm 11.47 (brs, 1H), 8.78 (brs, 1H), 8.21 (t, J=2.6 Hz, 1H), 7.32 (s, 1H), 6.82 (s, 1H), 5.87 (s, 1H), 4.27 (t, J=6.2 Hz, 2H), 4.06 (q, J=6.8 Hz, 1H), 3.94 (m, 2H), 3.57 (brs, 4H), 3.09 (t, J=7.2 Hz, 2H), 2.73 (brs, 2H), 2.66-2.64 (m, 2H), 2.26 (s, 3H), 2.20-2.17 (m, 5H), 2.16 (s, 3H), 1.46 (d, J=6.8 Hz, 3H); MS (ESI) m/z 561 [M+H]⁺.

Example 54: Preparation of 1-bromo-N-((4,6-dimethyl-2-oxo-1,2-dihydropyridin-3-yl)methyl)-6-methyl-5-(1-morpholinylethyl)indolizine-7-carboxamide

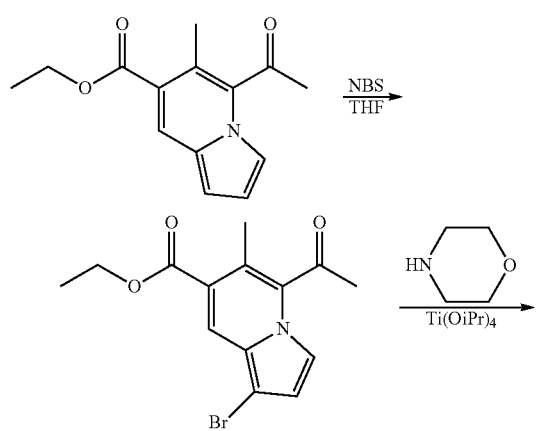

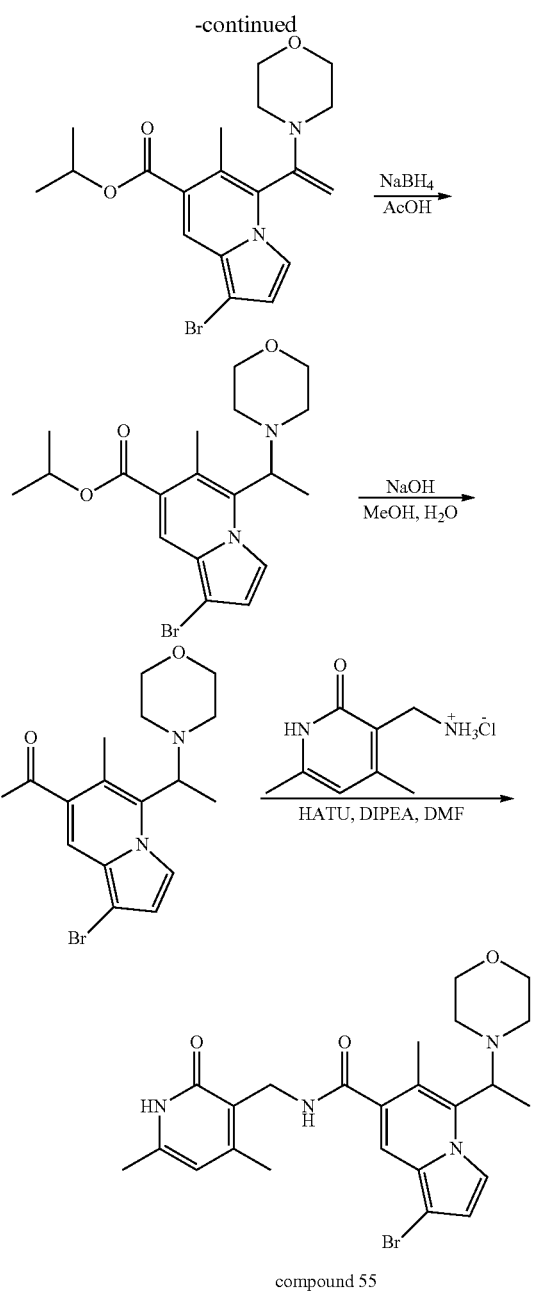

compound 55

Step 1: Preparation of ethyl 5-acetyl-1-bromo-6-methylindolizine-7-carboxylate: in a 100 ml dry single-mouth bottle, ethyl 5-acetyl-6-methylindolizine-7-carboxylate (500 mg, 2 mmol) was dissolved in 20 mL of tetrahydrofuran, bromosuccinimide (320 mg, 1.8 mmol) was added portionwise at 0° C., and the mixture was stirred at 0° C. for 20 min. The solvent was evaporated under reduced pressure to dry to provide a crude product, which was purified by column chromatography (petroleum ether:ethyl acetate=20:1) to obtain 141 mg of yellow oil, yield 26%. ¹H NMR (CDCl₃, 400 MHz) δ ppm 8.15 (s, 1H), 7.17 (d, J=2.8 Hz, 1H), 6.89 (d, J=2.8 Hz, 1H), 4.37 (q, J=14 Hz, 2H), 2.63 (s, 3H), 2.44 (s, 3H), 1.42 (t, J=14 Hz, 3H).

Step 2: Preparation of isopropyl 1-bromo-6-methyl-5-(1-morpholinylvinyl)indolizine-7-carboxylate: isopropyl 1-bromo-6-methyl-5-(1-morpholinylvinyl)indolizine-7- carboxylate was prepared by a method similar to Step 1 of example 26. MS (ESI) m/z 407 [M+H]⁺.

Step 3: Preparation of isopropyl 1-bromo-6-methyl-5-(1-morphinolinylethyl)indolizine-7-carboxylate: isopropyl 1-bromo-6-methyl-5-(1-morphinolinylethyl)indolizine-7-carboxylate was prepared by similar method in Step 2 of example 26, yield 84%. Yield of two steps was 50%. MS (ESI) m/z 323 [M−87+H]⁺.

Step 4: Preparation of 1-bromo-6-methyl-5-(1-morphinolinylethyl)indolizine-7-carboxylic acid: 1-bromo-6-methyl-5-(1-morphinolinylethyl)indolizine-7-carboxylic acid was prepared by a method similar to step 3 of example 26. MS (ESI) m/z 280 [M−87+H]⁺.

Step 5: Preparation of 1-bromo-N-((4,6-dimethyl-2-oxo-1,2-dihydropyridin-3-yl)methyl)-6-methyl-5-(1-morphinolinylethyl)indolizine-7-carboxamide: 1-bromo-N-((4,6-dimethyl-2-oxo-1,2-dihydropyridin-3-yl)methyl)-6-methyl-5-(1-morphinolinylethyl)indolizine-7-carboxamide was prepared by a method similar to Step 4 of Example 26, yield of two steps was 25%.

¹H NMR (400 MHz, CDCl₃) δ ppm 11.52 (brs, 1H), 8.40 (brs, 1H), 8.34 (s, 1H), 7.15 (s, 1H), 6.87 (s, 1H), 5.88 (s, 1H), 4.27 (t, J=6.2 Hz, 2H), 4.03 (q, J=6.8 Hz, 1H), 3.55 (brs, 4H), 2.62-2.58 (m, 2H), 2.25 (s, 3H), 2.20 (s, 3H) 2.17-2.11 (m, 5H), 1.40 (d, J=6.8 Hz, 3H); MS (ESI) m/z 501 [M+H]⁺.

Example 55: Preparation of N-((4,6-dimethyl-2-oxo-1,2-dihydropyridin-3-yl)methyl)-6-methyl-5-(methyl(tetrahydro-2H-pyran-4-yl)amino)indolizine-7-carboxamide

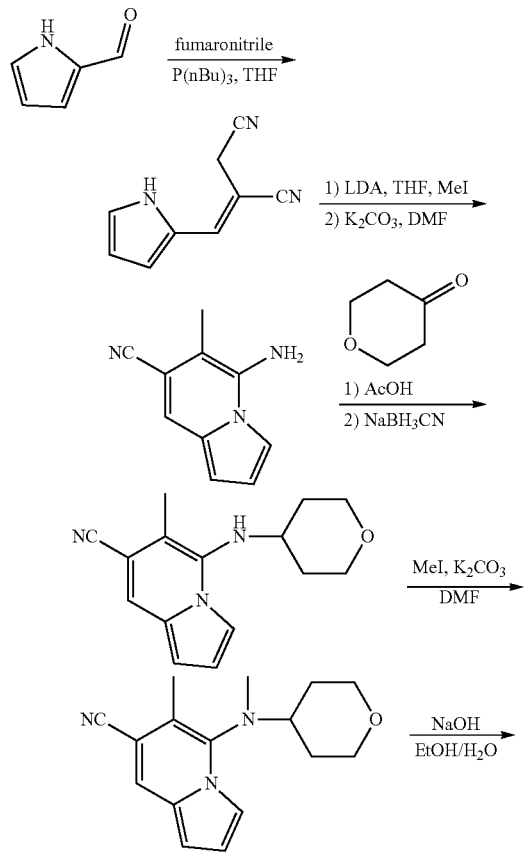

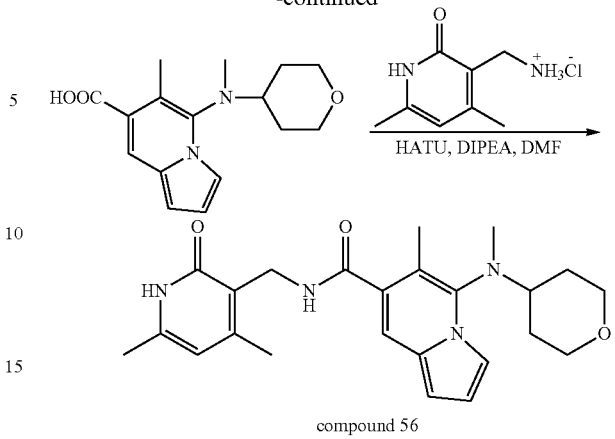

compound 56

Step 1: Preparation of (E)-2-((1H-pyrrol-2-yl)methylene) succinonitrile: pyrrole-2-carbaldehyde (3 g, 31.5 mmol), fumaronitrile (3.1 g, 39.4 mmol), tributylphosphine (5.8 ml, 37.8 mmol) and anhydrous tetrahydrofuran (80 mL) were added successively into a dry 100 mL round bottom flask at room temperature, heated to reflux under nitrogen and stirred for 8 hours. After the reaction was monitored to have been finished by TLC, the mixture was concentrated under reduced pressure, 30 mL of water was added, and extracted with ethyl acetate (40 mL×3), the organic phases were combined. The mixture was washed with saturated brine (30 mL×1), dried over anhydrous sodium sulfate, filtered and the filtrate was concentrated under reduced pressure, purified by column chromatography (pure dichloromethane) to provide yellow solids 1.85 g, yield 37%. ¹H NMR (CDCl₃, 400 MHz) δ ppm 7.49 (1H), 7.27 (d, J=8.9 Hz, 1H), 7.01 (t, J=3.9 Hz, 1H), 6.73 (d, J=3.9 Hz, 1H), 5.97 (s, 1H), 4.26 (s, 2H).

Step 2: Preparation of 5-amino-6-methylindolizine-7-carbonitrile: (E)-2-((1H-pyrrol-2-yl)methylene) succinonitrile (1.8 g, 11.7 mmol) and THF (60 mL) were added to a dry 100 mL round bottom flask at room temperature, and LDA (11.7 mL, 23.4 mmol) was added under −78° C., stirred at this temperature for half an hour, then methyl iodide (1.6 g, 11.7 mmol) was added, warmed to 0° C. and stirred for half an hour, then quenched with saturated aqueous ammonium chloride, extracted with ethyl acetate (40 mL×3), combined organic phase was dried over sodium sulfate, filtered, and the filtrate was evaporated, and the residue was dissolved in DMF (60 mL), and potassium carbonate (6.4 g, 46.8 mmol) was added, then the reaction was heated to 70° C. and stirred for 16 hours. After the reaction was completed, 30 mL of water was added and extracted with ethyl acetate (40 mL×3), organic phases were combined, washed with saturated brine (30 mL×1), dried over anhydrous sodium sulfate, filtered, and the filtrate was concentrated under reduced pressure to obtain yellow solids (1.76 g, yield 88%). ¹H NMR (CDCl₃, 400 MHz) δ ppm 7.51 (s, 1H), 7.19 (brs, 1H), 6.96 (t, J=2.8 Hz, 1H), 6.67 (d, J=2.8 Hz, 1H), 4.17 (s, 2H), 2.36 (s, 3H).

Step 3: Preparation of 6-methyl-5-((tetrahydro-2H-pyran-4-yl)amino)indolizine-7-carbonitrile: in a dry 50 mL round bottom flask, 5-amino-6-methylindolizine-7-carbonitrile (300 mg, 1.75 mmol), tetrahydropyranone (350 mg, 3.50 mmol) and acetic acid (3 mL) were added successively at room temperature. After heated to 50° C. and stirred for 1 hour, sodium cyanoborohydride (330 mg, 5.25 mmol) was added and stirred at 50° C. After TLC monitored that the reaction was completed, the mixture was neutralized with saturated aqueous solution of sodium hydrogencarbonate, and then extracted with ethyl acetate (20 mL×3), and washed with saturated brine (10 mL). The organic phase was dried over anhydrous sodium sulfate, filtered, and the filtrate was concentrated under reduced pressure. The residue obtained was purified by column chromatography (dichloromethane) to afford yellow solids (140 mg, yield 31%). $^1$H NMR (CDCl$_3$, 400 MHz) δ ppm 7.63 (s, 1H), 7.45 (s, 1H), 6.90 (brs, 1H), 6.69 (brs, 1H), 4.01 (d, J=9.8 Hz, 2H), 3.39-3.36 (m, 3H), 2.40 (s, 3H), 1.91-1.88 (m, 2H), 1.65-1.63 (m, 3H).

Step 4: Preparation of 6-methyl-5-(methyl(tetrahydro-2H-pyran-4-yl)amino)indolizine-7-carbonitrile: in a dry 25 mL round bottom flask, 6-methyl-5-((tetrahydro-2H-pyran-4-yl)amino)indolizine-7-carbonitrile (100 mg, 0.39 mmol), potassium carbonate (108 mg, 0.78 mmol), iodine methane (111 mg, 0.78 mmol) and DMF (2 ml) were added successively at room temperature, and replaced with nitrogen for three times, stirred and warmed to 80° C. for 16 hours. After the reaction was monitored to have been finished by TLC, 10 mL of saturated brine was added, and extracted with ethyl acetate (10 mL×3), and the organic phases were combined. The mixture was washed with saturated brine (10 mL×1), dried over anhydrous sodium sulfate and filtered. The filtrate was concentrated under reduced pressure to provide crude product 4 (50 mg, yellow sticky liquid), which can be directly used in the next step, yield: 47%. MS (ESI) m/z 270 [M+H]$^+$.

Step 5: Preparation of 6-methyl-5-(methyl(tetrahydro-2H-pyran-4-yl)amino)indolizine-7-carboxylic acid: in a dry 25 mL round bottom flask, 6-methyl-5-(methyl(tetrahydro-2H-pyran-4-yl)amino)indolizine-7-carbonitrile (50 mg, 0.18 mmol), sodium hydroxide (400 mg, 10 mmol) and ethanol/water 1:1 mixture solvent (1 mL) were added successively at room temperature, heated to 100° C. and stirred for 16 hours. After TLC monitored that the reaction was completed, pH was adjusted to 1 by 6N hydrochloric acid, and extracted with ethyl acetate (10 mL×3). The organic phases were combined, dried over anhydrous sodium sulfate, filtered, and the filtrate was concentrated under reduced pressure to obtain a crude product (42 mg, dark green solid), which can be directly used in the next step, yield 81%. MS (ESI) m/z 289 [M+H]$^+$.

Step 6: Preparation of N-((4,6-dimethyl-2-oxo-1,2-dihydropyridin-3-yl)methyl)-6-methyl-5-(methyl(tetrahydro-2H-pyran-4-yl)amino)indolizine-7-carboxamide: N-((4,6-dimethyl-2-oxo-1,2-dihydropyridin-3-yl)methyl)-6-methyl-5-(methyl(tetrahydro-2H-pyran-4-yl)amino)indolizine-7-carboxamide was prepared by a method similar to Step 6 of Example 1, yield 6%. $^1$H NMR (CDCl$_3$, 400 MHz) δ ppm 7.40 (s, 1H), 7.33 (s, 1H), 6.74 (s, 1H), 6.47 (s, 1H), 5.94 (s, 1H), 4.52-4.49 (m, 2H), 3.95-3.89 (m, 2H), 3.39-3.35 (m, 2H), 3.14-3.10 (m, 1H), 2.86 (s, 3H), 2.39 (s, 3H), 2.27 (s, 3H), 2.20 (s, 3H), 1.77-1.54 (m, 4H); MS (ESI) m/z 423 [M+H]$^+$.

Example 56: Preparation of N-((4,6-dimethyl-2-oxo-1,2-dihydropyridin-3-yl)methyl)-6-methyl-5-(ethyl(tetrahydro-2H-pyran-4-yl)amino)indolizine-7-carboxamide

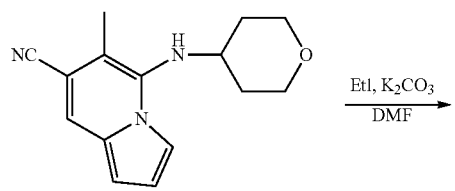

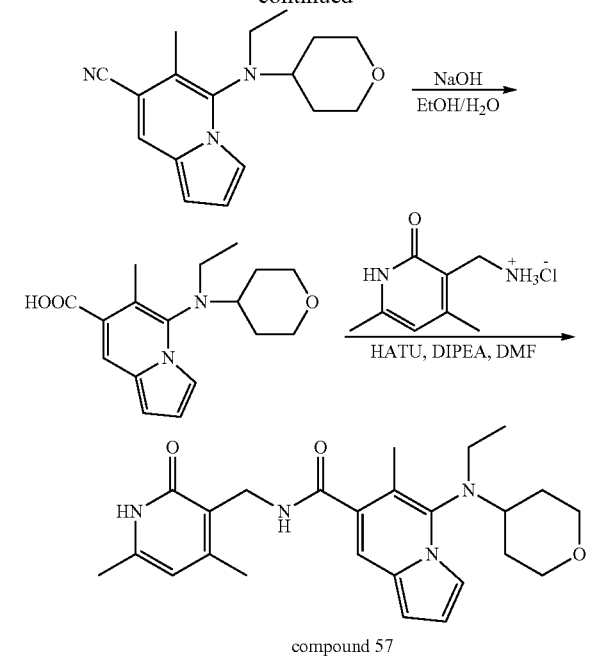

compound 57

N-((4,6-dimethyl-2-oxo-1,2-dihydropyridin-3-yl)methyl)-6-methyl-5-(ethyl(tetrahydro-2H-pyran-4-yl)amino)indolizine-7-carboxamide was prepared by a method similar to example 55.

Step 1: Preparation of 5-(ethyl(tetrahydro-2H-pyran-4-yl)amino)-6-methylindolizine-7-carbonitrile: Yield 46%. MS (ESI) m/z 284 [M+H]$^+$.

Step 2: Preparation of 5-(ethyl(tetrahydro-2H-pyran-4-yl)amino)-6-methylindolizine-7-carboxylic acid: Yield 78%. MS (ESI) m/z 303 [M+H]$^+$.

Step 3: Preparation of N-((4,6-dimethyl-2-oxo-1,2-dihydropyridin-3-yl)methyl)-6-methyl-5-(ethyl(tetrahydro-2H-pyran-4-yl)amino)indolizine-7-carboxamide: yield 8%. $^1$H NMR (CDCl$_3$, 400 MHz) δ ppm 7.35 (s, 1H), 7.28 (s, 1H), 6.65 (s, 1H), 6.39 (s, 1H), 5.88 (s, 1H), 4.45-4.44 (m, 2H), 3.85-3.82 (m, 2H), 3.31-3.19 (m, 4H), 3.14-3.11 (m, 1H), 2.32 (s, 3H), 2.24 (s, 3H), 2.17 (s, 3H), 1.74-1.71 (m, 4H), 0.90-0.87 (m, 3H); MS (ESI) m/z 437 [M+H]$^+$.

Example 57: Preparation of 2-bromo-N-((4,6-dimethyl-2-oxo-1,2-dihydropyridin-3-yl)methyl)-6-methyl-5-(methyl(tetrahydro)-2H-pyran-4-yl)amino)indolizine-7-carboxamide

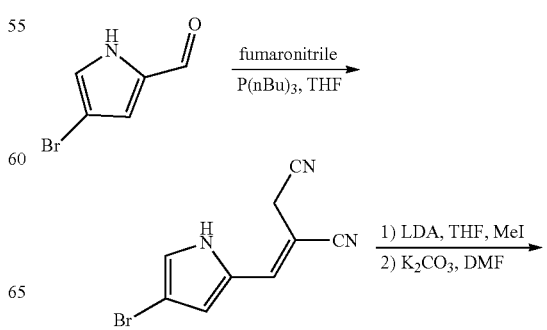

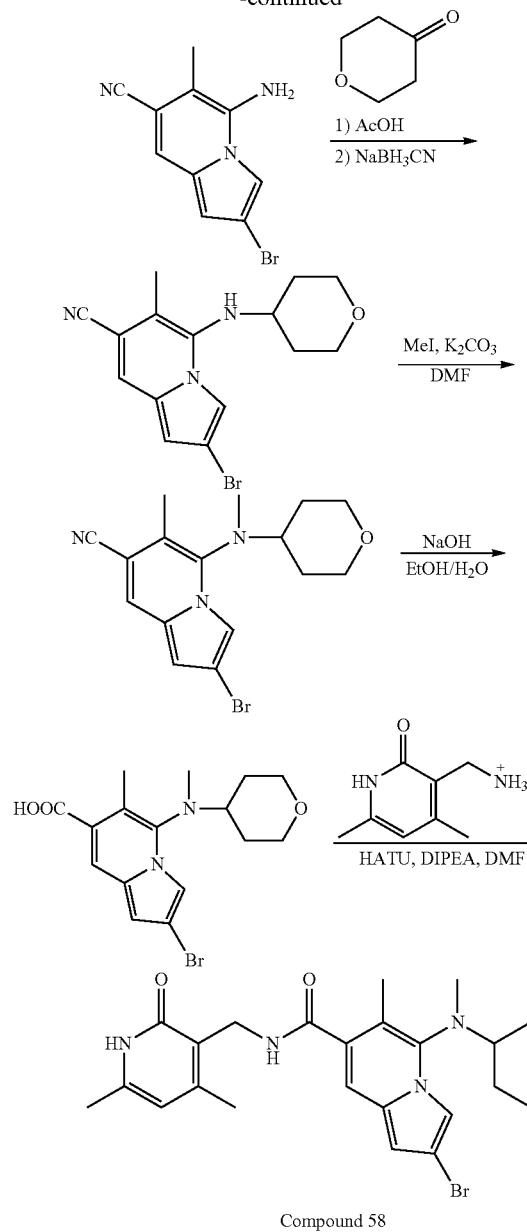

Compound 58

2-Bromo-N-((4,6-dimethyl-2-oxo-1,2-dihydropyridin-3-yl)methyl)-6-methyl-5-(methyl(tetrahydro-2H-pyran-4-yl)amino)indolizine-7-carboxamide was prepared by a method similar to example 55.

Step 1: Preparation of (E)-2-((4-bromo-1H-pyrrol-2-yl)methylene)succinonitrile: Yield 41%. MS (ESI) m/z 236 [M+H]+.

Step 2: Preparation of 5-amino-2-bromo-6-methylindolizine-7-carbonitrile: Yield 94%. MS (ESI) m/z 250 [M+H]+.

Step 3: Preparation of 2-bromo-6-methyl-5-((tetrahydro-2H-pyran-4-yl)amino)indolizine-7-carbonitrile: Yield 72%. 1H NMR (CDCl3, 400 MHz) δ ppm 7.54 (s, 1H), 7.42 (s, 1H), 6.72 (brs, 1H), 4.03-3.97 (m, 2H), 3.41-3.35 (m, 3H), 2.4 (s, 3H), 1.90-1.87 (m, 2H), 1.65-1.63 (m, 2H).

Step 4: Preparation of 2-bromo-6-methyl-5-(methyl(tetrahydro-2H-pyran-4-yl)amino)indolizine-7-carbonitrile: yield 53%. MS (ESI) m/z 348 [M+H]+.

Step 5: Preparation of 2-bromo-6-methyl-5-(methyl(tetrahydro-2H-pyran-4-yl)amino)indolizine-7-carboxylic acid: yield 81%. MS (ESI) m/z 367 [M+H]+.

Step 6: Preparation of 2-bromo-N-((4,6-dimethyl-2-oxo-1,2-dihydropyridin-3-yl)methyl)-6-methyl-5-(methyl(tetrahydro-2H-pyran-4-yl)amino)indolizine-7-carboxamide: yield 18%. 1H NMR (CDCl3, 400 MHz) δ ppm 11.31 (s, 1H), 7.40 (s, 1H), 7.23 (s, 1H), 6.48 (s, 1H), 5.96 (s, 1H), 4.50 (s, 2H), 3.98-3.89 (m, 2H), 3.39-3.30 (m, 3H), 2.83 (s, 3H), 2.32 (s, 3H), 2.24 (s, 3H), 2.17 (s, 3H), 1.78-1.59 (m, 4H); MS (ESI) m/z 501 [M+H]+.

Example 58: Preparation of 2-bromo-N-((4,6-dimethyl-2-oxo-1,2-dihydropyridin-3-yl)methyl)-5-(ethyl(tetrahydro-2H-pyran-4-yl)amino)-6-methylindolizine-7-carboxamide

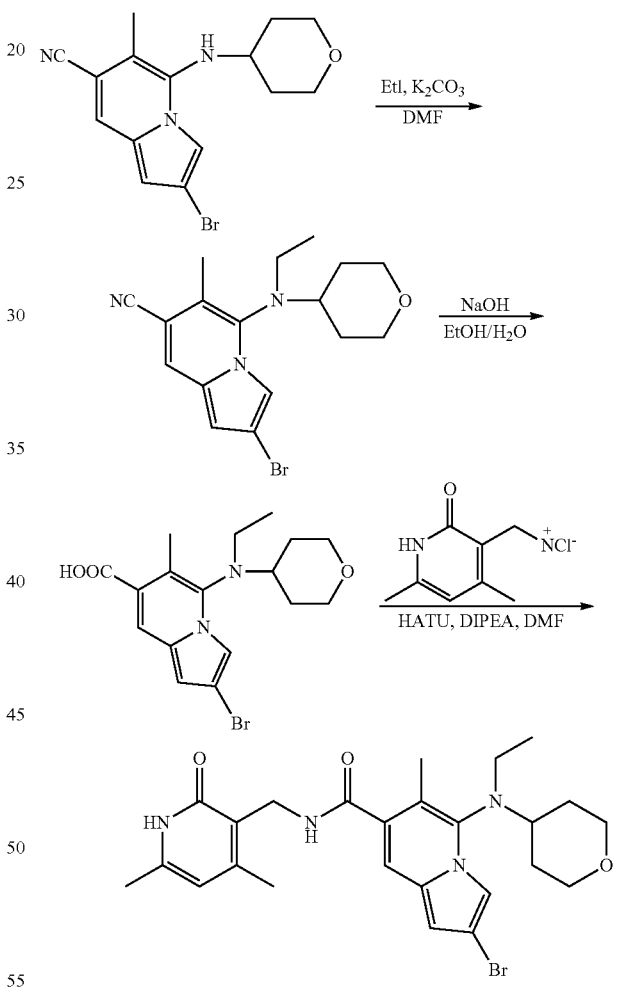

Compound 59

2-Bromo-N-((4,6-dimethyl-2-oxo-1,2-dihydropyridin-3-yl)methyl)-5-(ethyl(tetrahydro-2H-pyran-4-yl)amino)-6-methylindolizine-7-carboxamide was prepared by a method similar to example 55.

Step 1: Preparation of 2-bromo-5-(ethyl(tetrahydro-2H-pyran-4-yl)amino)-6-methylindolizine-7-carbonitrile: Yield 46%. MS (ESI) m/z 362 [M+H]+.

Step 2: Preparation of 2-bromo-5-(ethyl(tetrahydro-2H-pyran-4-yl)amino)-6-methylindolizine-7-carboxylic acid: Yield 79%. MS (ESI) m/z 381 [M+H]+.

Step 3: Preparation of 2-bromo-N-((4,6-dimethyl-2-oxo-1,2-dihydropyridin-3-yl)methyl)-5-(ethyl(tetrahydro-2H-pyran-4-yl)amino)-6-methylindolizine-7-carboxamide: yield 27%. $^1$H NMR (CDCl$_3$, 400 MHz) δ ppm 11.10 (s, 1H), 7.41 (s, 1H), 7.23 (s, 1H), 6.47 (s, 1H), 5.96 (s, 1H), 4.50 (s, 2H), 3.93-3.92 (m, 2H), 3.38-3.34 (m, 3H), 3.25-3.17 (m, 2H), 2.39 (s, 3H), 2.27 (s, 3H), 2.24 (s, 3H), 1.76-1.62 (m, 4H), 0.96 (t, J=7.2 Hz, 3H); MS (ESI) m/z 515 [M+H]$^+$.

Example 59: Preparation of 2-bromo-N-((4,6-dimethyl-2-oxo-1,2-dihydropyridin-3-yl)methyl)-5-(ethyl)oxetane-3)-yl)amino)-6-methylindolizine-7-carboxamide

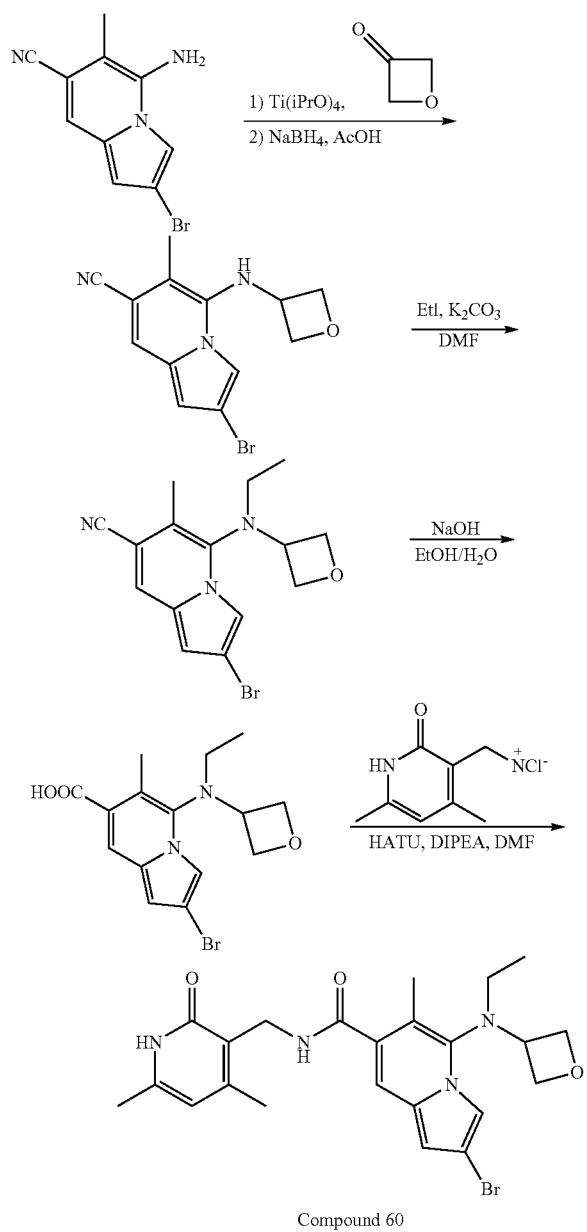

Compound 60

Step 1: Preparation of 5-(ethyl(tetrahydro-2H-pyran-4-yl)amino)-6-methylindolizine-7-carbonitrile: in a dry 50 mL three-necked flask, 5-amino-2-bromo-6-methylindolizine-7-carbonitrile (300 mg, 1.20 mmol) and oxetane (0.6 mL) were dissolved in tetraisopropyl titanium oxide (2 mL), and stirred overnight at 65° C. After the reaction was completed, 10 mL of dichloromethane was added, and a small amount of water was added thereto. The reaction liquid was concentrated under reduced pressure, and then large amount of floccule was precipitated. The solid was washed with dichloromethane (30 mL×3) and the organic phase was concentrated under reduced pressure. The resultant residue was redissolved in glacial acetic acid (10 mL) at 0° C., sodium borohydride (121 mg, 3.20 mmol) was slowly added, warmed to room temperature and stirred for another 1 hour. Water and sodium hydrogencarbonate were added to adjust the pH to 7, and extracted with ethyl acetate (30 mL×3). The combined organic phase was washed with water (10 mL×2) and saturated brine (10 mL). The organic phase was dried over anhydrous sodium sulfate and filted, and the filtrate was concentrated under reduced pressure to afford yellow oil (160 mg, yield 7%). MS (ESI) m/z 306 [M+H]$^+$.

Step 2: Preparation of 2-bromo-5-(ethyl(oxetan-3-yl)amino)-6-methylindolizine-7-carbonitrile: the procedure was same as step 4 in example 55. Yield: 51%. MS (ESI) m/z 334 [M+H]$^+$.

Step 3: Preparation of 2-bromo-5-(ethyl(oxetan-3-yl)amino)-6-methylindolizine-7-carboxylic acid: the procedure was same as step 5 of example 55. Yield: 68%. MS (ESI) m/z 353 [M+H]$^+$.

Step 4: Preparation of 2-bromo-N-((4,6-dimethyl-2-oxo-1,2-dihydropyridin-3-yl)methyl)-5-(ethyl(oxetane-3-yl)amino)-6-methylindolizine-7-carboxamide: the procedure was same as step 6 of example 55. Yield was 22%. $^1$H NMR (400 MHz, CDCl$_3$) δ ppm 9.24 (s, 1H), 7.38 (s, 1H), 7.18 (s, 1H), 6.52 (s, 1H), 5.92 (s, 1H), 5.35 (s, 2H), 4.73-4.67 (m, 3H), 4.65-4.47 (m, 3H), 3.29-3.20 (m, 2H), 2.39 (s, 3H), 2.24 (s, 3H), 2.19 (m, 3H), 1.03 (t, J=7.2 Hz, 3H); MS (ESI) m/z 487 [M+H]$^+$.

Example 60: Preparation of 5-(azetidin-3-yl(ethyl)amino)-2-bromo-N-((4,6-dimethyl-2-oxo-1,2-dihydropyridine-3-yl)methyl)-6-methylindolizine-7-carboxamide

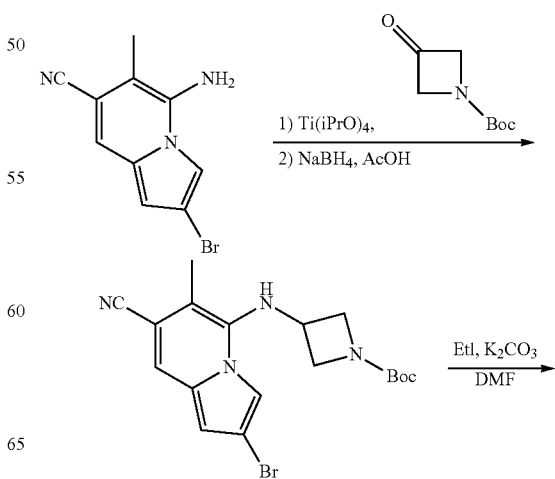

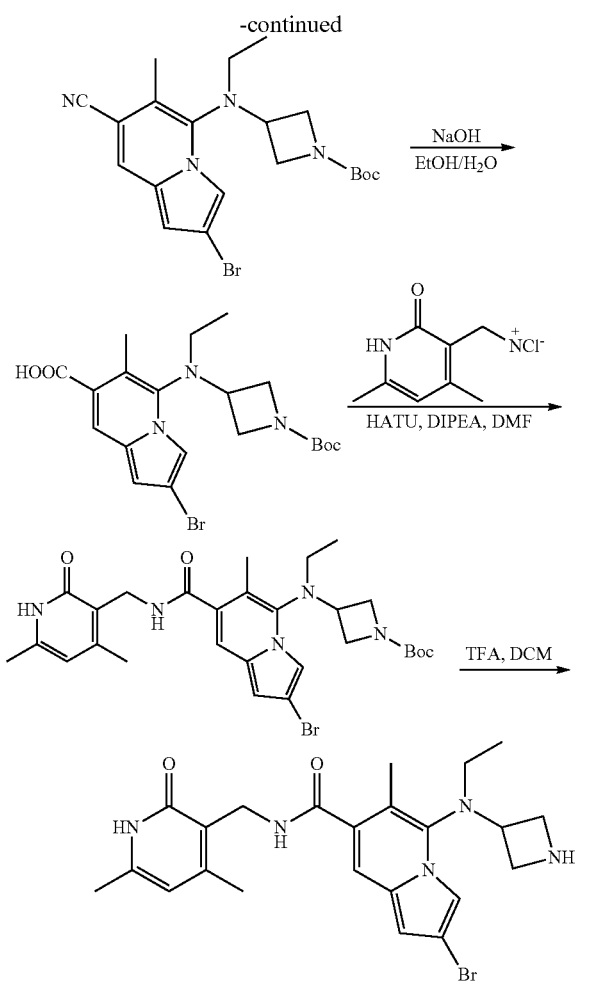

Compound 61

Preparation of 5-(azetidin-3-yl(ethyl)amino)-2-bromo-N-((4,6-dimethyl-2-oxo-1,2-dihydropyridine-3-yl)methyl)-6-methylindolizine-7-carboxamide: the procedure of first four steps are same as example 59.

Step 1: Preparation of tert-butyl 3-((2-bromo-7-cyano-6-methylindolizin-5-yl)amino)azetidin-1-carboxylate: Yield 49%. MS (ESI) m/z 405 [M+H]+.

Step 2: Preparation of tert-butyl 34(2-bromo-7-cyano-6-methylindolizin-5-yl)(ethyl)amino)azetidin-1-carboxylate: Yield 77%. MS (ESI) m/z 433 [M+H]+.

Step 3: Preparation of 2-bromo-5-((1-(tert-butoxycarbonyl)azetidin-3-yl)(ethyl)amino)-6-methylindolizine-7-carboxylic acid: Yield 74%. MS (ESI) m/z 452 [M+H]+.

Step 4: Preparation of tert-butyl 3-((2-bromo-7-((4,6-dimethyl-2-oxo-1,2-dihydropyridin-3-yl)methyl)carbamoyl)-6-methylindolizine-5-yl)(ethyl)amino)azetidin-1-carboxylate: yield 31%. MS (ESI) m/z 586 [M+H]+.

Step 5: Preparation of tert-butyl 5-(azetidin-3-yl(ethyl)amino)-2-bromo-N-((4,6-dimethyl-2-oxo-1,2-dihydropyridine)-3-yl)methyl)-6-methyl-7-carboxamide: 3-((2-bromo-7-((4,6-dimethyl-2-oxo-1,2-dihydropyridin-3-yl)methyl)carbamoyl)-6-methylindolizin-5-yl)(ethyl)amino)azetidine-1-carboxylate (20 mg, 0.034 mmol), trifluoroacetic acid (1 mL) were added to a dry 50 mL three-necked flask successively, and dissolved in dichloromethane (1 mL). Reaction was conducted for 1 hour at room temperature. The reaction mixture was directly concentrated, and purified by reverse phase HPLC to provide yellow oil (4 mg, yield 25%). $^1$H NMR (MeOD, 400 MHz) δ ppm 7.58 (s, 1H), 7.38 (s, 1H), 6.63 (s, 1H), 6.13 (s, 1H), 4.62-4.61 (m, 1H), 4.46 (s, 2H), 4.16-4.14 (m, 2H), 4.04-3.94 (m, 2H), 2.37 (s, 3H), 2.25 (s, 3H), 2.19 (s, 3H), 1.05-1.01 (m, 3H); MS (ESI) m/z 486 [M+H]+.

Example 61: Preparation of 2-bromo-N-((4,6-dimethyl-2-oxo-1,2-dihydropyridin-3-yl)methyl)-5-(ethyl(piperidin-4-yl)amino)-6-methylindolizine-7-carboxamide

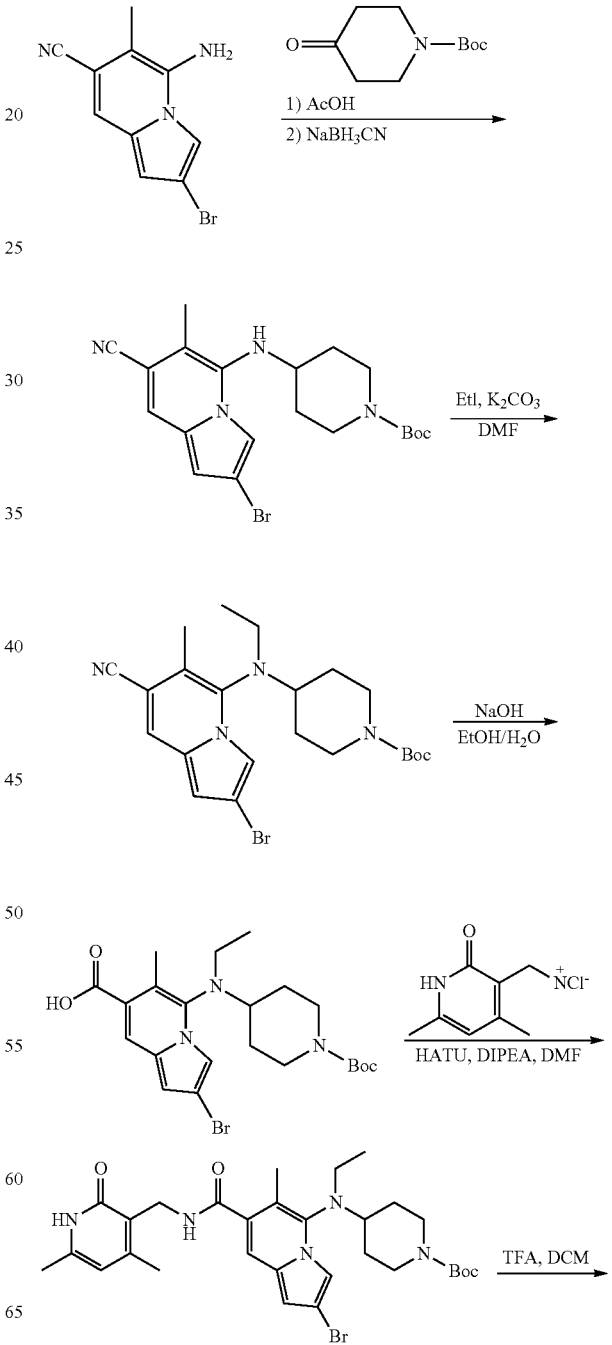

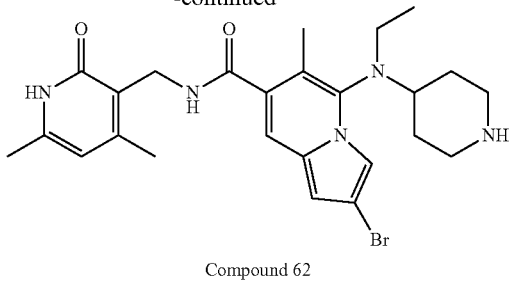

Compound 62

2-Bromo-N-((4,6-dimethyl-2-oxo-1,2-dihydropyridin-3-yl)methyl)-5-(ethyl(piperidin-4-yl)amino)-6-methylindolizine-7-carboxamide was prepared by a method similar to example 60.

Step 1: Preparation of tert-butyl 4-((2-bromo-7-cyano-6-methylindolizin-5-yl)amino)piperidin-1-carboxylate: Yield 28%. MS (ESI) m/z 433 [M+H]+.

Step 2: Preparation of tert-butyl 44(2-bromo-7-cyano-6-methylindolizin-5-yl)(ethyl)amino)piperidin-1-carboxylate: Yield 59%. MS (ESI) m/z 461 [M+H]+.

Step 3: Preparation of 2-bromo-5-((1-(tert-butoxycarbonyl)piperidin-4-yl)(ethyl)amino)-6-methylindolizine-7-carboxylic acid: Yield 64%. MS (ESI) m/z 614 [M+H]+.

Step 4: Preparation of tert-butyl 4,6-dimethyl-2-oxo-1,2-dihydropyridin-3-yl)methyl)carbamoyl)-6-methylindolizine-5-yl)(ethyl)amino)piperidine-1-carboxylate: yield 43%. MS (ESI) m/z 614 [M+H]+.

Step 5: Preparation of 2-bromo-N-((4,6-dimethyl-2-oxo-1,2-dihydropyridin-3-yl)methyl)-5-(ethyl(piperidin-4-yl)amino)-6-methylindolizine-7-carboxamide: Yield 35%. $^1$H NMR (MeOD, 400 MHz) δ ppm 7.55 (s, 1H), 7.33 (s, 1H), 6.58 (s, 1H), 6.12 (s, 1H), 4.45 (s, 2H), 3.10-2.98 (m, 4H), 2.37 (s, 3H), 2.25 (s, 6H), 2.10-2.02 (m, 2H), 1.72-1.30 (m, 2H), 0.91 (t, J=6.9 Hz, 3H); MS (ESI) m/z 514 [M+H]+.

Example 62: Preparation of 5-((1-acetylpiperidin-4-yl)(ethyl)amino)-2-bromo-N-((4,6-dimethyl-2-oxo-1,2-dihydropyridine-3-yl)methyl)-6-methylindolizine-7-carboxamide

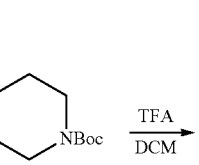

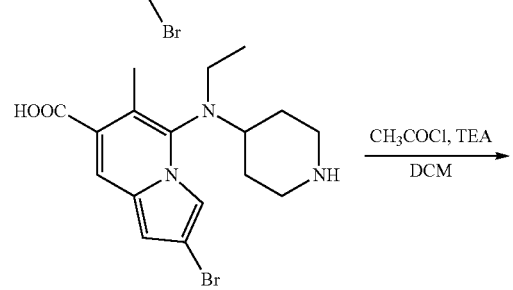

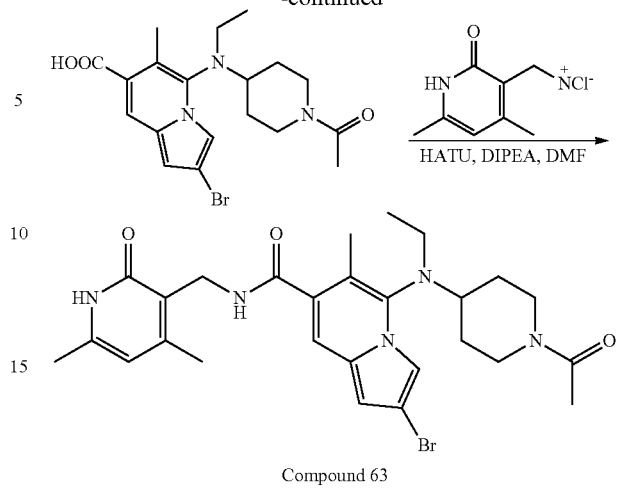

Compound 63

Step 1: Preparation of 2-bromo-5-(ethyl(piperidin-4-yl)amino)-6-methylindolizine-7-carboxylic acid: in a dry 50 mL round bottom flask, 2-bromo-5-((1-(tert-butoxycarbonyl)piperidin-4-yl)(ethyl)amino)-6-methylindolizine-7-carboxylic acid (80 mg, 0.16 mmol), dichloromethane (2 mL), and trifluoroacetic acid (1 mL) were added successively at room temperature. After stirred at room temperature for 1 hour, TLC monitored that the reaction was completed. MS (ESI) m/z 380 [M+H]+.

Step 2: Preparation of 54(1-acetylpiperidin-4-yl)(ethyl)amino)-2-bromo-6-methylindolizine-7-carboxylic acid: in a dry 25 mL round bottom flask, 2-bromo-5-(ethyl(piperidin-4-yl)amino)-6-methylindolizine-7-carboxylic acid (60 mg, 0.16 mmol), acetyl chloride (0.2 mL) and THF (1 mL) were added successively at room temperature, and stirred at room temperature for 1 h. After the reaction was monitored to have been finished by TLC, 10 mL of saturated sodium bicarbonate was added, and extracted with ethyl acetate (10 mL×3), and the organic phases were combined. The mixture was washed with saturated brine (10 mL×1), dried over anhydrous sodium sulfate, filtered and the filtrate was concentrated under reduced pressure to provide yellow sticky liquid 40 mg, which can be directly used in the next step. MS (ESI) m/z 422 [M+H]+.

Step 3: Preparation of 5-((1-acetylpiperidin-4-yl)(ethyl)amino)-2-bromo-N-((4,6-dimethyl-2-oxo-1,2-dihydropyridine)-3-yl)methyl)-6-methylindolizine-7-carboxamide:
5-((1-acetylpiperidin-4-yl)(ethyl)amino)-2-bromo-N-((4,6-dimethyl-2-oxo-1,2-dihydropyridine)-3-yl)methyl)-6-methylindolizine-7-carboxamide was prepared by a method similar to step 6 of example 1, yield 8%. $^1$H NMR (CDCl$_3$, 400 MHz) δ ppm 7.40 (s, 1H), 7.34 (s, 1H), 6.77 (s, 1H), 6.57 (s, 1H), 6.52 (s, 1H), 4.62-4.54 (m, 3H), 3.78-3.75 (m, 1H), 3.37-3.33 (m, 1H), 3.29-3.16 (m, 2H), 3.04-3.01 (m, 1H), 2.61 (s, 3H), 2.47 (s, 3H), 2.17 (s, 3H), 2.12 (s, 3H), 1.98-1.88 (m, 2H), 1.42-1.31 (m, 2H), 0.96 (t, J=6.9 Hz, 3H); MS (ESI) m/z 556 [M+H]+.

Example 63: Preparation of N-(4,6-dimethyl-2-oxo-1,2-dihydropyridin-3-yl)methyl)-5-(ethyl(tetrahydro-2H-pyran-4-yl)amino)-6-methyl-2-phenylindolizine-7-carboxamide

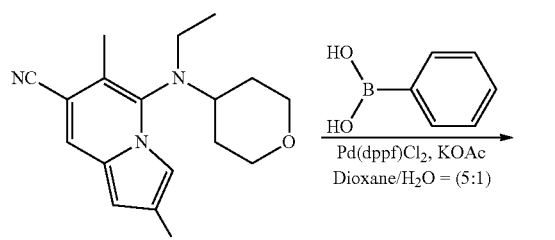

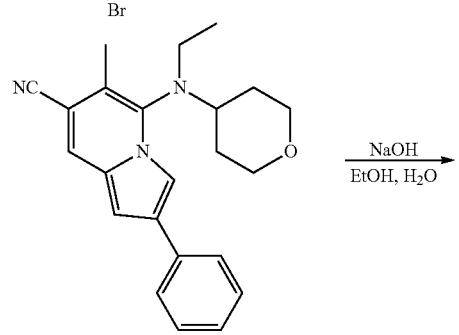

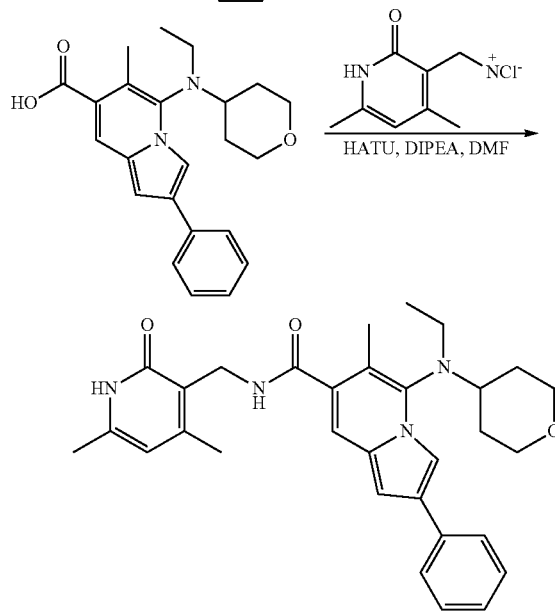

Compound 64

Step 1: Preparation of 5-(ethyl(tetrahydro-2H-pyran-4-yl)amino)-6-methyl-2-phenylindolizine-7-carbonitrile: the procedure was same as step 1 in example 31. Yield: 45%. MS (ESI) m/z 360 [M+H]⁺.

Step 2: Preparation of 5-(ethyl(tetrahydro-2H-pyran-4-yl)amino)-6-methyl-2-phenylindolizine-7-carboxylic acid: the procedure was same as step 5 of example 55. Yield was 68%. MS (ESI) m/z 379 [M+H]⁺.

Step 3: Preparation of N-(4,6-dimethyl-2-oxo-1,2-dihydropyridin-3-yl)methyl)-5-(ethyl(tetrahydro-2H-pyran-4-yl)amino)-6-methyl-2-phenylindolizine-7-carboxamide: N-(4,6-dimethyl-2-oxo-1,2-dihydropyridin-3-yl)methyl)-5-(ethyl(tetrahydro-2H-pyran-4-yl)amino)-6-methyl-2-phenylindolizine-7-carboxamide was prepared by a method similar to Step 6 of Example 1, yield 14%. ¹H NMR (CDCl₃, 400 MHz) δ ppm 11.35 (s, 1H), 7.69-7.64 (m, 3H), 7.38-7.33 (m, 4H), 6.72 (s, 1H), 5.95 (s, 1H), 4.52 (s, 2H), 3.99-3.92 (m, 2H), 3.36-3.23 (m, 4H), 3.22-3.17 (m, 1H), 2.40 (s, 3H), 2.31 (s, 3H), 2.24 (s, 3H), 1.60-1.45 (m, 4H), 0.87-0.83 (m, 3H); MS (ESI) m/z 513 [M+H]⁺.

Example 64: Preparation of N-((4,6-dimethyl-2-oxo-1,2-dihydropyridin-3-yl)methyl)-5-(ethyl(tetrahydro-2H-pyran-4-yl) amino)-6-methyl-2-(4-morpholinephenyl)indolizine-7-carboxamide

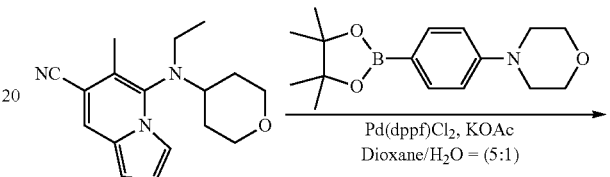

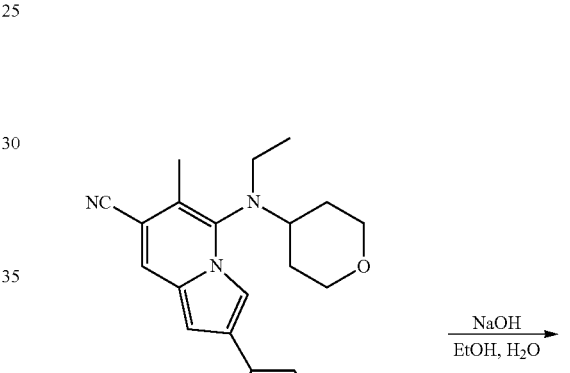

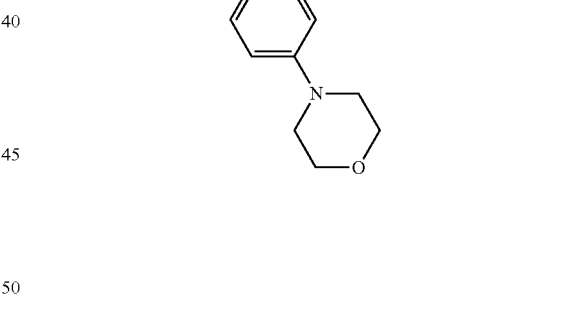

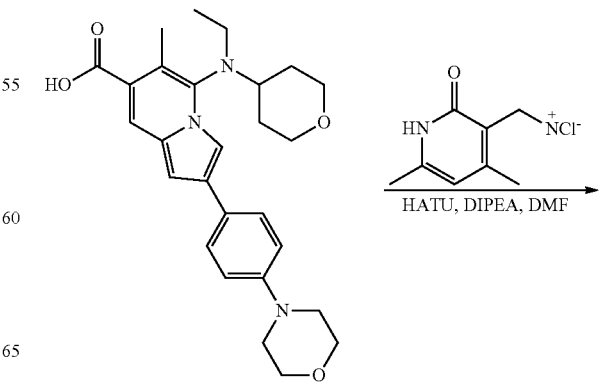

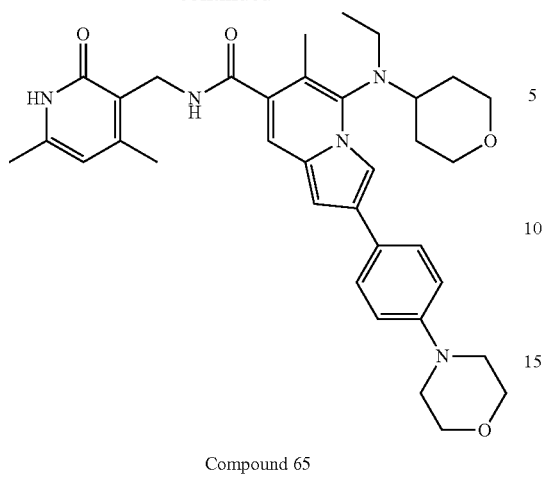

Compound 65

N-((4,6-Dimethyl-2-oxo-1,2-dihydropyridin-3-yl)methyl)-5-(ethyl(tetrahydro-2H-pyran-4-yl)amino)-6-methyl-2-(4-morpholinephenyl)indolizine-7-carboxamide was prepared by a method similar to example 63.

Step 1: Preparation of 5-(ethyl(tetrahydro-2H-pyran-4-yl)amino)-6-methyl-2-(4-morpholinephenyl)indolizine-7-carbonitrile: Yield 54%. MS (ESI) m/z 445 [M+H]$^+$.

Step 2: Preparation of 5-(ethyl(tetrahydro-2H-pyran-4-yl)amino)-6-methyl-2-(4-morpholinephenyl)indolizine-7-carboxylic acid: MS (ESI) m/z 464 [M+H]$^+$.

Step 3: Preparation of N-((4,6-dimethyl-2-oxo-1,2-dihydropyridin-3-yl)methyl)-5-(ethyl(tetrahydro-2H-pyran-4-yl)amino)-6-methyl-2-(4-morpholinephenyl)indolizine-7-carboxamide: Yield of the two steps was 31%. $^1$H NMR (CDCl$_3$, 400 MHz) δ ppm 11.30 (brs, 1H), 7.62 (s, 1H), 7.55 (d, J=7.8 Hz, 2H), 7.31 (s, 1H), 6.95 (d, J=7.8 Hz, 2H), 6.66 (s, 1H), 5.94 (s, 1H), 4.53 (brs, 2H), 3.93-3.88 (m, 6H), 3.41-3.31 (m, 4H), 3.24-3.18 (m, 5H), 2.40 (s, 3H), 2.30 (s, 3H), 2.24 (s, 3H), 1.67-1.61 (m, 2H), 0.99 (t, J=7.2 Hz, 3H); MS (ESI) m/z 598 [M+H]$^+$.

Example 65: Preparation of N-((4,6-dimethyl-2-oxo-1,2-dihydropyridin-3-yl)methyl)-5-(ethyl(tetrahydro-2H-pyran-4-yl) amino)-6-methyl-2-(1-methyl-1H-pyrazol-5-yl)indolizin-7-carboxamide

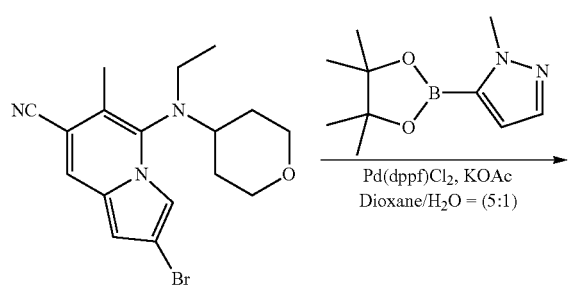

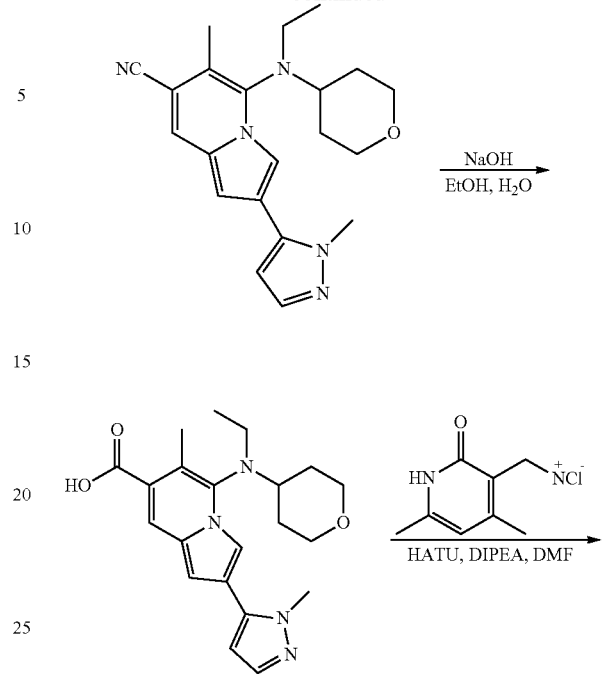

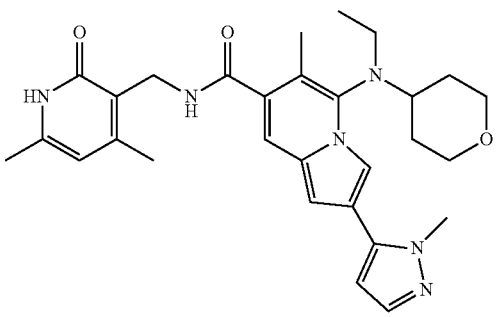

Compound 66

N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-pyrazol-5-yl)indolizin-7-carboxamide was prepared by a method similar to example 63.

Step 1: Preparation of 5-(ethyl(tetrahydro-2H-pyran-4-yl)amino)-6-methyl-2-(1-methyl-1H-pyrazol-5-yl)indolizin-7-carbonitrile: Yield 55%. MS (ESI) m/z 364 [M+H]$^+$.

Step 2: Preparation of 5-(ethyl(tetrahydro-2H-pyran-4-yl)amino)-6-methyl-2-(1-methyl-1H-pyrazol-5-yl)indolizine-7-carboxylic acid: yield 31%.

Step 3: Preparation of N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-pyrazol-5-yl)indolizin-7-carboxamide: yield of two step was 23%. $^1$H NMR (CDCl$_3$, 400 MHz) δ ppm 11.53 (brs, 1H), 7.58 (s, 1H), 7.49 (s, 1H), 7.34 (s, 1H), 6.57 (s, 1H), 6.36 (s, 1H), 5.96 (s, 1H), 4.53 (s, 2H), 4.19 (s, 3H), 3.95-3.90 (m, 2H), 3.39-3.36 (m, 3H), 3.26-3.19 (m, 2H), 3.02 (s, 1H), 2.48 (s, 3H), 2.40 (s, 3H), 2.25 (s, 3H), 1.53-1.78 (m, 4H), 1.12 (t, J=7.2 Hz, 3H); MS (ESI) m/z 517 [M+H]$^+$.

Example 66: Preparation of N-((4,6-dimethyl-2-oxo-1,2-dihydropyridin-3-yl)methyl)-5-(ethyl(tetrahydro-2H-pyran-4-yl) amino)-6-methyl-2-(1-methyl-1H-pyrazol-4-yl)indolizin-7-carboxamide

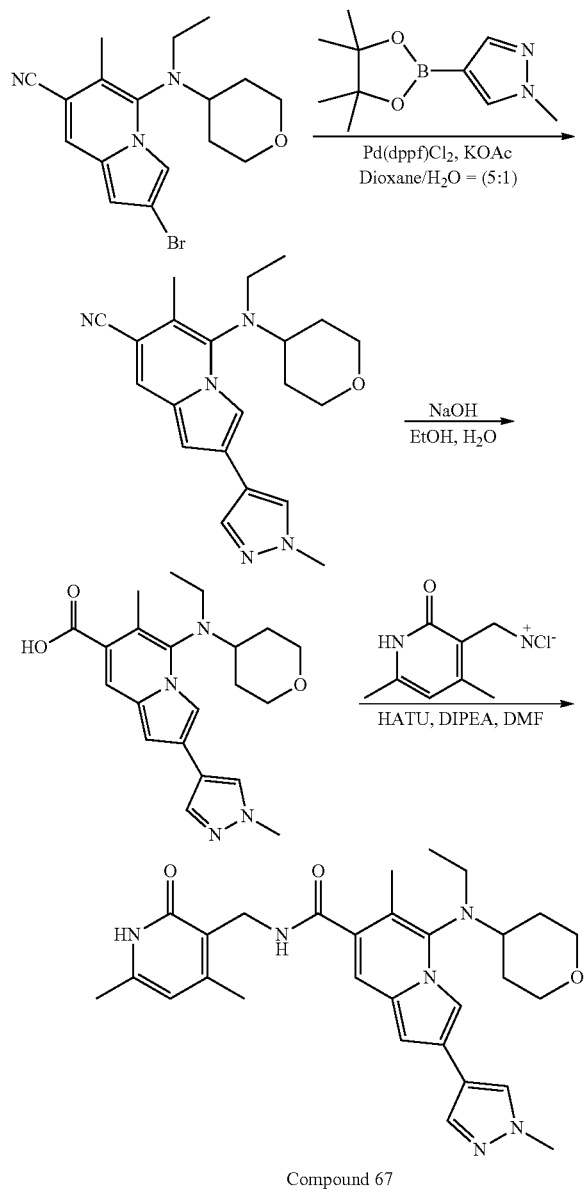

Compound 67

N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-pyrazol-4-yl)indolizin-7-carboxamide was prepared by a method similar to example 63.

Step 1: Preparation of 5-(ethyl(tetrahydro-2H-pyran-4-yl)amino)-6-methyl-2-(1-methyl-1H-pyrazol-4-yl)indolizin-7-carbonitrile: Yield 38%. MS (ESI) m/z 364 [M+H]$^+$.

Step 2: Preparation of 5-(ethyl(tetrahydro-2H-pyran-4-yl)amino)-6-methyl-2-(1-methyl-1H-pyrazol-4-yl)indolizine-7-carboxylic acid: yield 31%.

Step 3: Preparation of N-((4,6-dimethyl-2-dihydropyridin-3-yl)methyl)-5-(ethyl(tetrahydro-2H-pyran-4-yl)amino)-6-methyl-2-(1-methyl-1H-pyrazol-4-yl)indolizin-7-carboxamide: yield of two step was 53%. $^1$H NMR (CDCl$_3$, 400 MHz) δ ppm 12.31 (brs, 1H), 7.72 (s, 1H), 7.68 (s, 1H), 7.28 (s, 1H), 7.26 (s, 1H), 6.50 (s, 1H), 5.96 (s, 1H), 4.52 (s, 2H), 3.93-3.90 (m, 5H), 3.39-3.16 (m, 5H), 2.39 (s, 3H), 2.30 (s, 3H), 2.24 (s, 3H), 1.81-1.78 (m, 1H), 1.33-1.25 (m, 3H), 0.98 (t, J=7.0 Hz, 3H); MS (ESI) m/z 517 [M+H]$^+$.

Example 67: Preparation of N-((4,6-dimethyl-2-oxo-1,2-dihydropyridin-3-yl)methyl)-5-(ethyl(tetrahydro-2H-pyran-4-yl) amino)-6-methyl-2-(thiazol-2-yl)indolizin-7-carboxamide

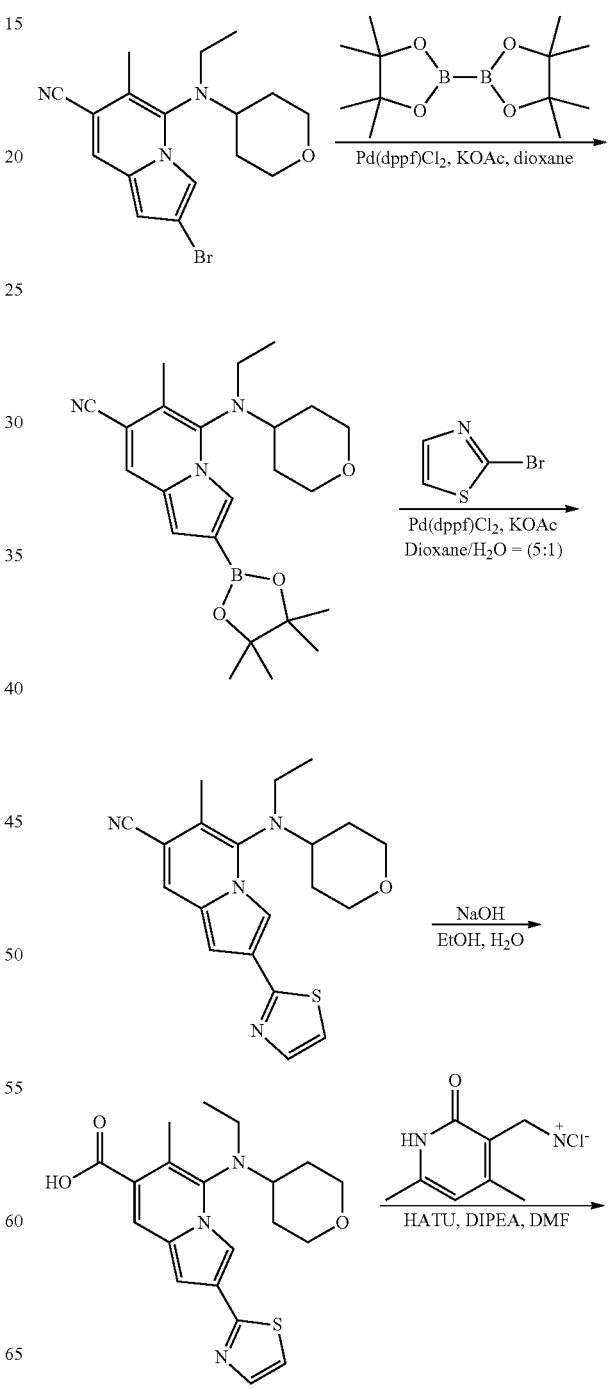

189
-continued

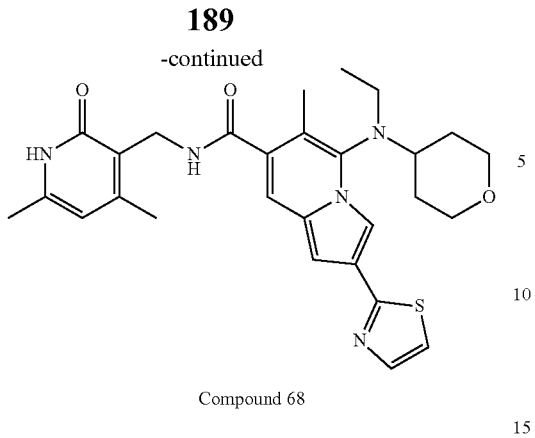

Compound 68

Step 1: Preparation of 5-(ethyl(tetrahydro-2H-pyran-4-yl)amino)-6-methyl-2-(4,4,5,5-tetramethyl-1,3,2-dioxane-2-yl)indolizine-7-carbonitrile: the procedure was same as step 1 in example 50. Yield: 48%. MS (ESI) m/z 410 [M+H]+.

Step 2: Preparation of 5-(ethyl(tetrahydro-2H-pyran-4-yl)amino)-6-methyl-2-(thiazol-2-yl)indolizine-7-carbonitrile: the procedure is same as step 1 of example 31. Yield: 66%. MS (ESI) m/z 367 [M+H]+.

Step 3: Preparation of 5-(ethyl(tetrahydro-2H-pyran-4-yl)amino)-6-methyl-2-(thiazol-2-yl)indolizine-7-carboxylic acid: the procedure was same as step 5 of example 55. MS (ESI) m/z 386 [M+H]+.

Step 4: Preparation of N-((4,6-dimethyl-2-oxo-1,2-dihydropyridin-3-yl)methyl)-5-(ethyl(tetrahydro-2H-pyran-4-yl)amino)-6-methyl-2-(thiazol-2-yl)indolizine-7-carboxamide: the procedure was same as step 6 in example 1. Yield of two steps was 21%. 1H NMR (CDCl3, 400 MHz) δ ppm 8.03 (s, 1H), 7.80 (s, 1H), 7.44 (s, 1H), 7.31 (s, 1H), 7.26 (s, 1H), 6.83 (s, 1H), 6.21 (s, 1H), 4.46 (s, 2H), 3.96-3.88 (m, 3H), 3.41-3.19 (m, 4H), 2.69 (s, 3H), 2.26 (s, 6H), 1.78-1.75 (m, 1H), 1.66-1.57 (m, 3H), 0.99 (t, J=7.0 Hz, 3H); MS (ESI) m/z 520 [M+H]+.

Example 68: Preparation of N-((4,6-dimethyl-2-oxo-1,2-dihydropyridin-3-yl)methyl)-6-methyl-5-(methyl(tetrahydro-2H-pyran-4-yl)amino)imidazo[1,5-a]pyridine-7-carboxamide

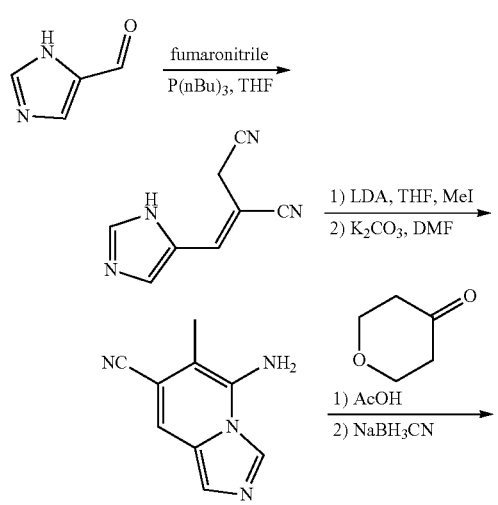

190
-continued

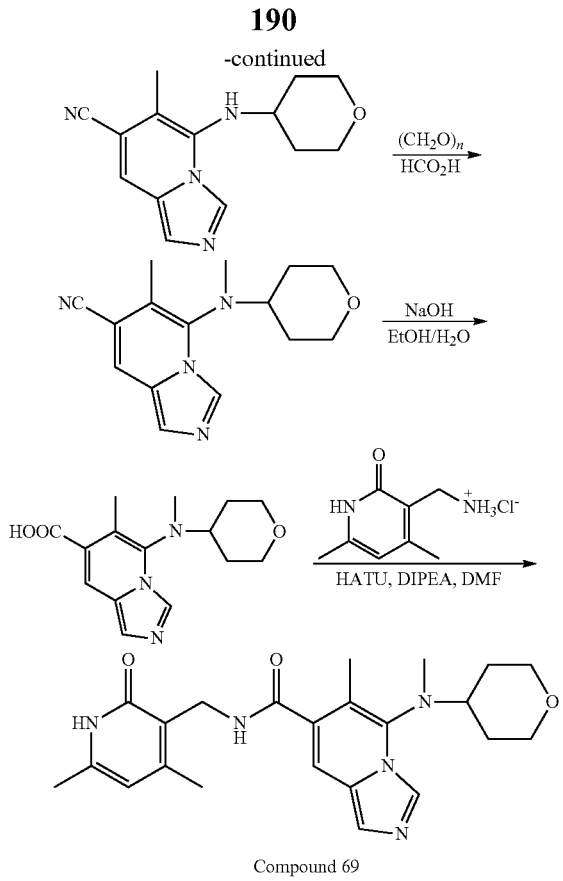

Compound 69

N-((4,6-Dimethyl-2-oxo-1,2-dihydropyridin-3-yl)methyl)-6-methyl-5-(methyl(tetrahydro-2H-pyran-4-yl)amino)imidazo[1,5-a]pyridine-7-carboxamide: the procedure was similar to example 55.

Step 1: Preparation of (E)-2-((1H-imidazol-5-yl)methylene)succinonitrile: Yield 51%. MS (ESI) m/z 159 [M+H]+.

Step 2: Preparation of 5-amino-6-methylimidazo[1,5-a]pyridine-7-carbonitrile: Yield 38%. MS (ESI) m/z 173 [M+H]+.

Step 3: Preparation of 6-methyl-5-((tetrahydro-2H-pyran-4-yl)amino)imidazo[1,5-a]pyridine-7-carbonitrile: Yield 7%. MS (ESI) m/z 257 [M+H]+.

Step 4: Preparation of 6-methyl-5-(methyl(tetrahydro-2H-pyran-4-yl)amino)imidazo[1,5-a]pyridine-7-carbonitrile: 6-Methyl-5-((tetrahydro-2H-pyran-4-yl)amino)imidazo[1,5-a]pyridine-7-carbonitrile (80 mg, 0.31 mmol), paraformaldehyde (93 mg, 3.12 mmol) were added successively to a dried 25 mL three-neck flask, dissolved in formic acid (2 mL), and heated to reflux for 3 hours. After the reaction was completed, yellow solids (30 mg) were obtained by thin-layer chromatography plate, yield 36%. MS (ESI) m/z 271 [M+H]+.

Step 5: Preparation of 6-methyl-5-(methyl(tetrahydro-2H-pyran-4-yl)amino)imidazo[1,5-a]pyridine-7-carboxylic acid: MS (ESI) m/z 290 [M+H]+.

Step 6: Preparation of N-((4,6-dimethyl-2-oxo-1,2-dihydropyridin-3-yl)methyl)-6-methyl-5-(methyl(tetrahydro-2H-pyran-4-yl)amino)imidazo[1,5-a]pyridine-7-carboxamide: two step yield was 9%. 1H NMR (CDCl3, 400 MHz) δ ppm 11.65 (s, 1H), 8.15 (s, 1H), 7.45 (s, 1H), 7.39-7.37 (m, 2H), 5.95 (s, 1H), 4.52 (d, J=6.2 Hz, 2H), 3.95 (t, J=6.9 Hz, 2H), 3.39-3.29 (m, 3H), 2.88 (s, 3H), 2.38 (s, 3H), 2.25 (s, 3H), 2.23 (s, 3H), 1.78-1.59 (m, 4H); MS (ESI) m/z 424 [M+H]⁺.

Example 69: Preparation of 2-chloro-N-((4,6-dimethyl-2-oxo-1,2-dihydropyridin-3-yl)methyl)-6-methyl-5-(1-morphinolinylethyl)indolizine-7-carboxamide

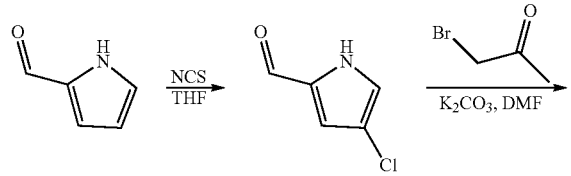

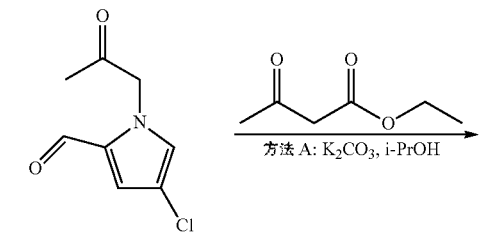

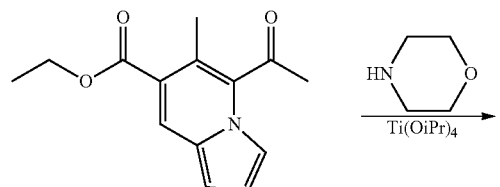

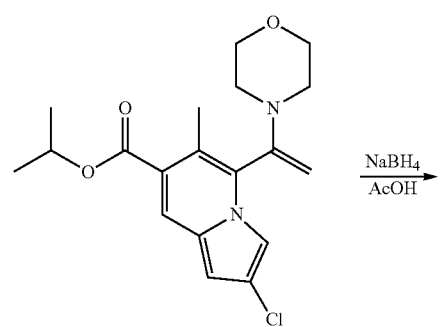

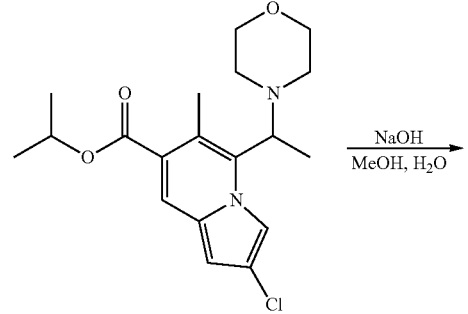

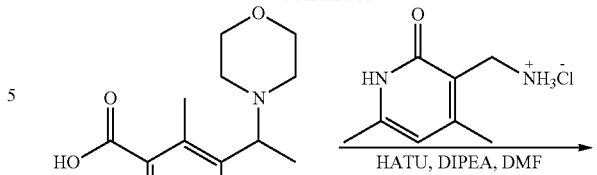

-continued

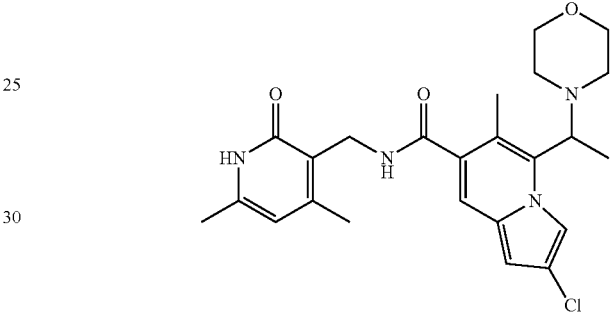

Compound 70

2-Chloro-N-((4,6-dimethyl-2-oxo-1,2-dihydropyridin-3-yl)methyl)-6-methyl-5-(1-morphinolinylethyl)indolizine-7-carboxamide was prepared by a method similar to example 29.

Step 1: Preparation of 4-chloro-1H-pyrrole-2-carbaldehyde: Yield 34%. MS (ESI) m/z 130 [M+H]⁺.

Step 2: Preparation of 4-chloro-1-(2-oxopropyl)-1H-pyrrole-2-carbaldehyde: yield 56%. MS (ESI) m/z 186 [M+H]⁺.

Step 3: Preparation of ethyl 5-acetyl-2-chloro-6-methylindolizine-7-carboxylate: Yield 58%. MS (ESI) m/z 280 [M+H]⁺.

Step 4: Preparation of isopropyl 2-chloro-6-methyl-5-(1-morphinolinylvinyl)indolizine-7-carboxylate: MS (ESI) m/z 363 [M+H]⁺.

Step 5: Preparation of isopropyl 2-chloro-6-methyl-5-(1-morphinolinylethyl)indolizine-7-carboxylate: yield of two steps was 50%. MS (ESI) m/z 365 [M+H]⁺.

Step 6: Preparation of 2-chloro-6-methyl-5-(1-morphinolinylethyl)indolizine-7-carboxylic acid: Yield 75%. MS (ESI) m/z 323 [M+H]⁺.

Step 7: Preparation of 2-chloro-N-((4,6-dimethyl-2-oxo-1,2-dihydropyridin-3-yl)methyl)-6-methyl-5-(1-morphinolinylethyl)indolizine-7-carboxamide: yield 25%. ¹H NMR (400 MHz, DMSO-d₆) δ 7.33 (s, 1H), 6.49 (s, 1H), 6.13 (s, 1H), 4.44 (s, 2H), 4.23 (d, J=5.6 Hz, 1H), 3.64 (d, J=10.4 Hz, 1H), 2.85 (s, 8H), 2.37 (s, 3H), 2.29 (s, 3H), 2.24 (s, 3H), 1.55 (d, J=6.4 Hz, 3H); MS (ESI) m/z 457 [M+H]⁺.

Example 70: Preparation of 2-chloro-N-((4,6-dimethyl-2-oxo-1,2-dihydropyridin-3-yl)methyl)-5-(1-(4-(dimethylamino)) piperidine)ethyl)-6-methylindolizine-7-carboxamide

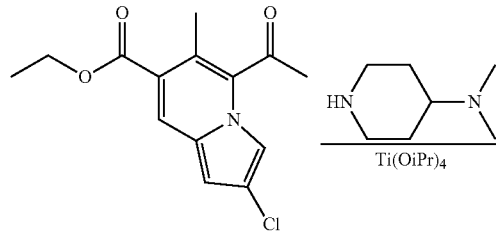

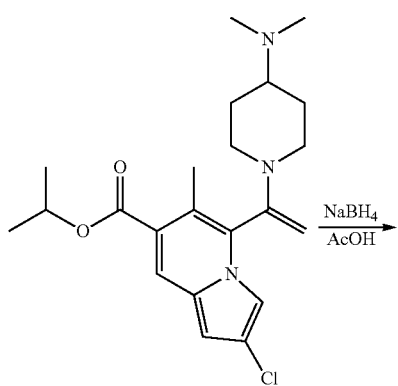

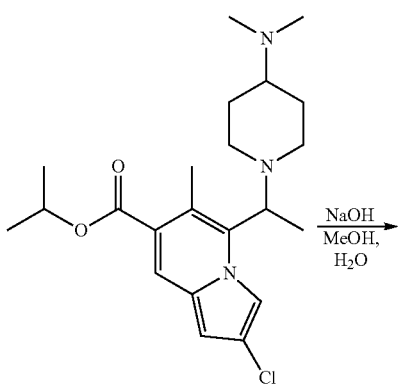

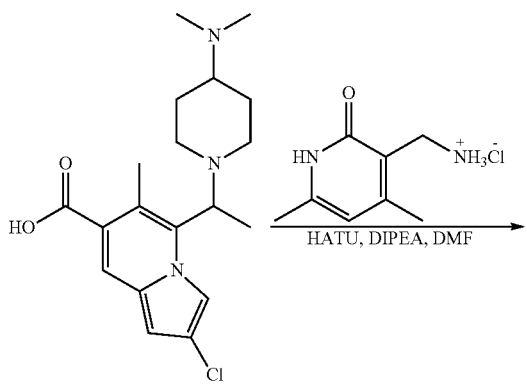

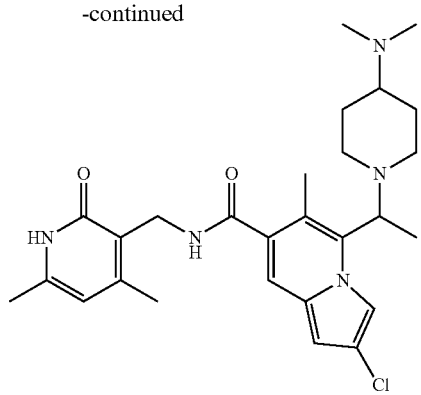

Compound 71

2-Chloro-N-((4,6-dimethyl-2-oxo-1,2-dihydropyridin-3-yl)methyl)-5-(1-(4-(dimethylamino))piperidine)ethyl)-6-methylindolizine-7-carboxamide was prepared by the same procedure as that in example 29.

Step 1: Preparation of isopropyl 2-chloro-5-(1-(4-(dimethylamino)piperidin-1-yl)vinyl)-6-methylindolizine-7-carboxylate: MS (ESI) m/z 404 [M+H]$^+$.

Step 2: Preparation of isopropyl 2-chloro-5-(1-(4-(dimethylamino)piperidin-1-yl)ethyl)-6-methylindolizine-7-carboxylate: yield 36%. MS (ESI) m/z 406 [M+H]$^+$.

Step 3: Preparation of 2-chloro-5-(1-(4-(dimethylamino)piperidin-1-yl)ethyl)-6-methylindolizine-7-carboxylic acid: yield 97%. MS (ESI) m/z 364 [M+H]$^+$.

Step 4: Preparation of 2-chloro-N-((4,6-dimethyl-2-oxo-1,2-dihydropyridin-3-yl)methyl)-5-(1-(4-(dimethylamino))piperidin-1-yl)ethyl)-6-methylindolizine-7-carboxamide: yield 15%. $^1$H NMR (400 MHz, DMSO-d$_6$) δ 11.50 (s, 1H), 9.40 (s, 1H), 8.25 (m, 2H), 7.25 (s, 1H), 6.55 (s, 1H), 5.87 (s, 1H), 4.25 (m, 3H), 4.03 (s, 1H), 3.41 (s, 1H), 3.09 (s, 1H), 2.74 (m, 8H), 2.45 (s, 1H), 2.23 (s, 3H), 2.19 (s, 3H), 2.10 (s, 6H), 1.41 (d, J=5.4 Hz, 3H); MS (ESI) m/z 498 [M+H]$^+$.

Example 71: Preparation of N-((4,6-dimethyl-2-oxo-1,2-dihydropyridin-3-yl)methyl)-6-methyl-5-(1-morpholinylethyl)imidazo[1,5-a]pyridine-7-carboxamide

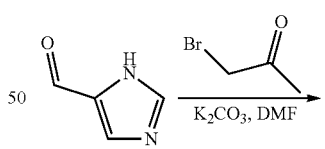

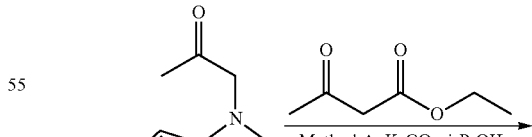

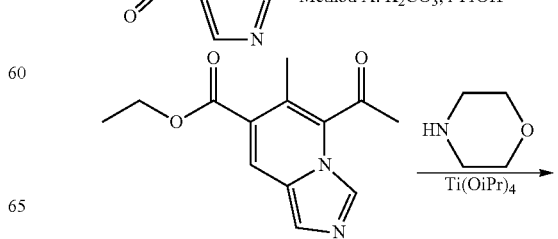

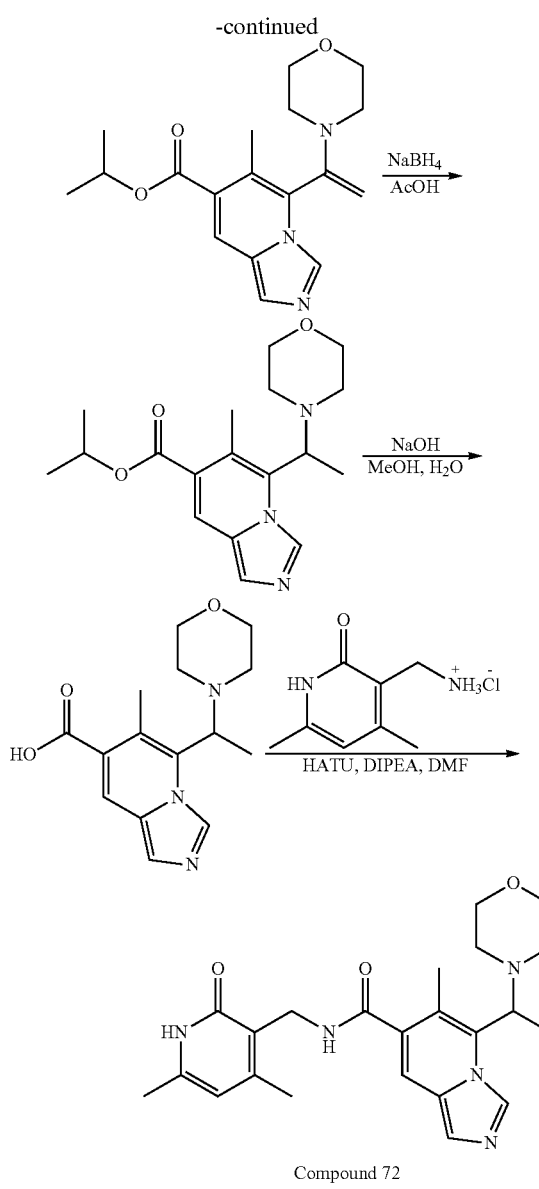

Compound 72

N-((4,6-dimethyl-2-oxo-1,2-dihydropyridin-3-yl) methyl)-6-methyl-5-(1-morphinolinylethyl)imidazo[1,5-a] pyridine-7-carboxamide was prepared by a method similar to example 26, while the intermediate ethyl 5-acetyl-6-methylimidazo[1,5-a]pyridine-7-carboxylate was prepared according to step 2, method A of Example 1.

Step 1: Preparation of 1-(2-oxopropyl)-1H-imidazole-5-formaldehyde: yield 8%. MS (ESI) m/z 153 [M+H]+.

Step 2: Preparation of ethyl 5-acetyl-6-methylimidazo[1,5-a]pyridine-7-carboxylate: Yield 31%. MS (ESI) m/z 247 [M+H]+.

Step 3: Preparation of isopropyl 6-methyl-5-(1-morphinolinylvinyl)imidazo[1,5-a]pyridine-7-carboxylate: MS (ESI) m/z 330 [M+H]+.

Step 4: Preparation of isopropyl 6-methyl-5-(1-morphinolinylethyl)imidazo[1,5-a]pyridine-7-carboxylate: yield of two steps was 32%. MS (ESI) m/z 332 [M+H]+.

Step 5: Preparation of 6-methyl-5-(1-morphinolinylethyl) imidazo[1,5-a]pyridine-7-carboxylic acid: yield 66%. MS (ESI) m/z 290 [M+H]+.

Step 6: Preparation of N-((4,6-dimethyl-2-oxo-1,2-dihydropyridin-3-yl)methyl)-6-methyl-5-(1-morphinolinylethyl) imidazo[1,5-a]pyridine-7-carboxamide: yield 18%. 1H NMR (400 MHz, DMSO-$d_6$) δ 11.54 (brs, 1H), 10.04 (brs, 1H), 8.50 (t, J=4.9 Hz, 1H), 8.14 (s, 1H), 7.68 (s, 1H), 5.89 (s, 1H), 4.29 (t, J=7.2 Hz, 2H), 3.57 (brs, 4H), 2.66 (brs, 2H), 2.29 (s, 3H), 2.21 (s, 3H), 2.12 (s, 3H), 1.45 (d, J=6.5 Hz, 3H); MS (ESI) m/z 424 [M+H]+.

Example 72: Preparation of N-((4,6-dimethyl-2-oxo-1,2-dihydropyridin-3-yl)methyl)-6-methyl-5-(1-morphinolinylethyl)imidazo[1,2-a]pyridine-7-carboxamide

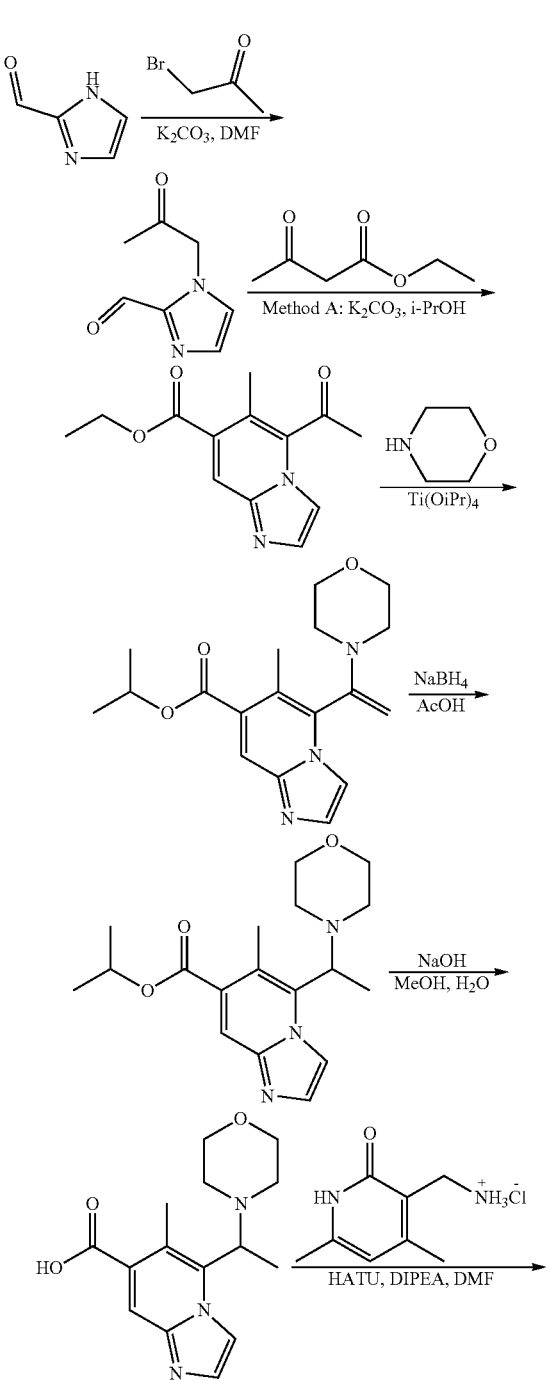

-continued

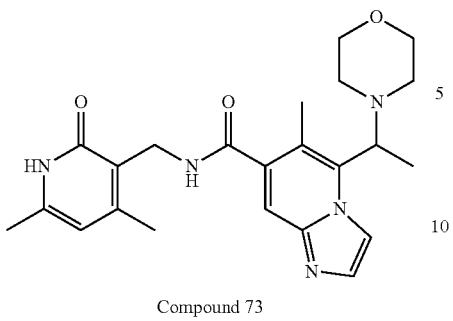

Compound 73

N-((4,6-dimethyl-2-oxo-1,2-dihydropyridin-3-yl)methyl)-6-methyl-5-(1-morpholinylethyl)imidazo[1,2-a]pyridine-7-carboxamide was prepared by a method similar to example 72.

Step 1: Preparation of 1-(2-oxopropyl)-1H-imidazole-2-formaldehyde: yield 10%. MS (ESI) m/z 153 [M+H]⁺.

Step 2: Preparation of ethyl 5-acetyl-6-methylimidazo[1,2-a]pyridine-7-carboxylate: Yield 17%. MS (ESI) m/z 247 [M+H]⁺.

Step 3: Preparation of isopropyl 6-methyl-5-(1-morpholinylvinyl)imidazo[1,2-a]pyridine-7-carboxylate: MS (ESI) m/z 330 [M+H]⁺.

Step 4: Preparation of isopropyl 6-methyl-5-(1-morpholinylethyl)imidazo[1,2-a]pyridine-7-carboxylate: yield of two steps was 50%. MS (ESI) m/z 332 [M+H]⁺.

Step 5: Preparation of 6-methyl-5-(1-morpholinylethyl)imidazo[1,2-a]pyridine-7-carboxylic acid: yield 82%. MS (ESI) m/z 290 [M+H]⁺.

Step 6: Preparation of N-((4,6-dimethyl-2-oxo-1,2-dihydropyridin-3-yl)methyl)-6-methyl-5-(1-morpholinylethyl)imidazo[1,2-a]pyridine-7-carboxamide: yield 18%. ¹H NMR (400 MHz, DMSO-d₆) δ 11.56 (brs, 1H), 8.97 (brs, 1H), 8.62 (t, J=2.1 Hz, 1H), 8.22 (d, J=2.0 Hz, 1H), 7.73 (s, 1H), 5.90 (s, 1H), 4.32 (d, J=5.1 Hz, 2H), 3.57 (s, 8H), 2.36 (s, 3H), 2.23 (s, 3H), 2.12 (s, 3H), 1.44 (d, J=6.6 Hz, 3H); MS (ESI) m/z 424 [M+H]⁺.

Example 73: Preparation of N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-imidazol-4-yl)indolizin-7-carboxamide

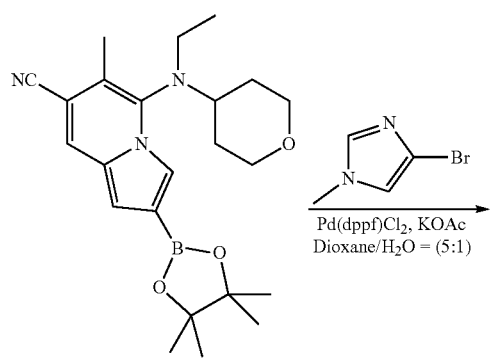

-continued

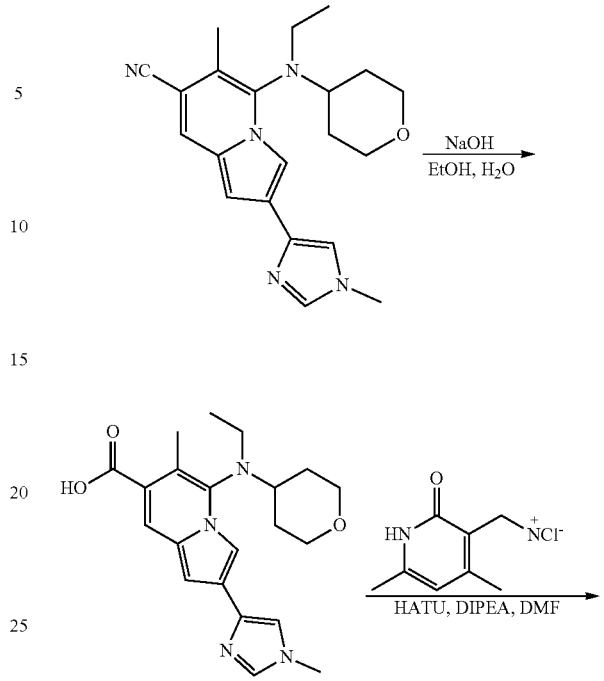

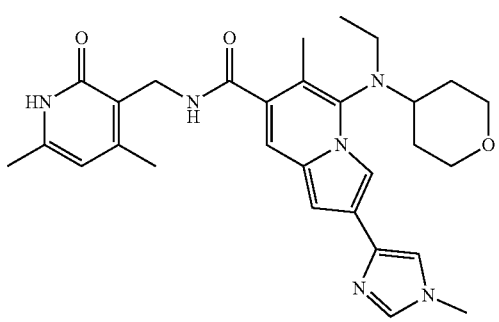

Compound 74

N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-imidazol-4-yl)indolizin-7-carboxamide was prepared by same method as that in example 67.

Step 1: Preparation of 5-(ethyl(tetrahydro-2H-pyran-4-yl)amino)-6-methyl-2-(1-methyl-1H-imidazol-4-yl)indolizin-7-carbonitrile: Yield 43%. MS (ESI) m/z 364 [M+H]⁺.

Step 2: Preparation of 5-(ethyl(tetrahydro-2H-pyran-4-yl)amino)-6-methyl-2-(1-methyl-1H-imidazol-4-yl)indolizine-7-carboxylic acid: MS (ESI) m/z 383 [M+H]⁺.

Step 3: Preparation of N-((4,6-dimethyl-2-oxo-1,2-dihydropyridin-3-yl)methyl)-5-(ethyl(tetrahydro-2H-pyran-4-yl)amino)-6-methyl-2-(1-methyl-1H-imidazol-4-yl)indolizine-7-carb oxamide: Yield of the two steps was 21%. ¹H NMR (CDCl₃, 400 MHz) δ ppm 8.86 (s, 1H), 8.01 (s, 1H), 7.80 (s, 1H), 7.38 (s, 1H), 6.82 (s, 1H), 6.12 (s, 1H), 4.46 (s, 2H), 3.96 (s, 3H), 3.89-3.84 (m, 2H), 3.49-3.40 (m, 4H), 3.25-3.21 (m, 1H), 2.56 (s, 3H), 2.41 (s, 6H), 2.25-2.20 (m, 2H), 1.82-1.67 (m, 2H), 0.99 (t, J=7.0 Hz, 3H); MS (ESI) m/z 517 [M+H]⁺.

Example 74: Preparation of N-((4,6-dimethyl-2-oxo-1,2-dihydropyridin-3-yl)methyl)-2-(3-((dimethylamino)methyl)phen yl))-6-methyl-5-(1-morpholineethyl)indolizine-7-amide

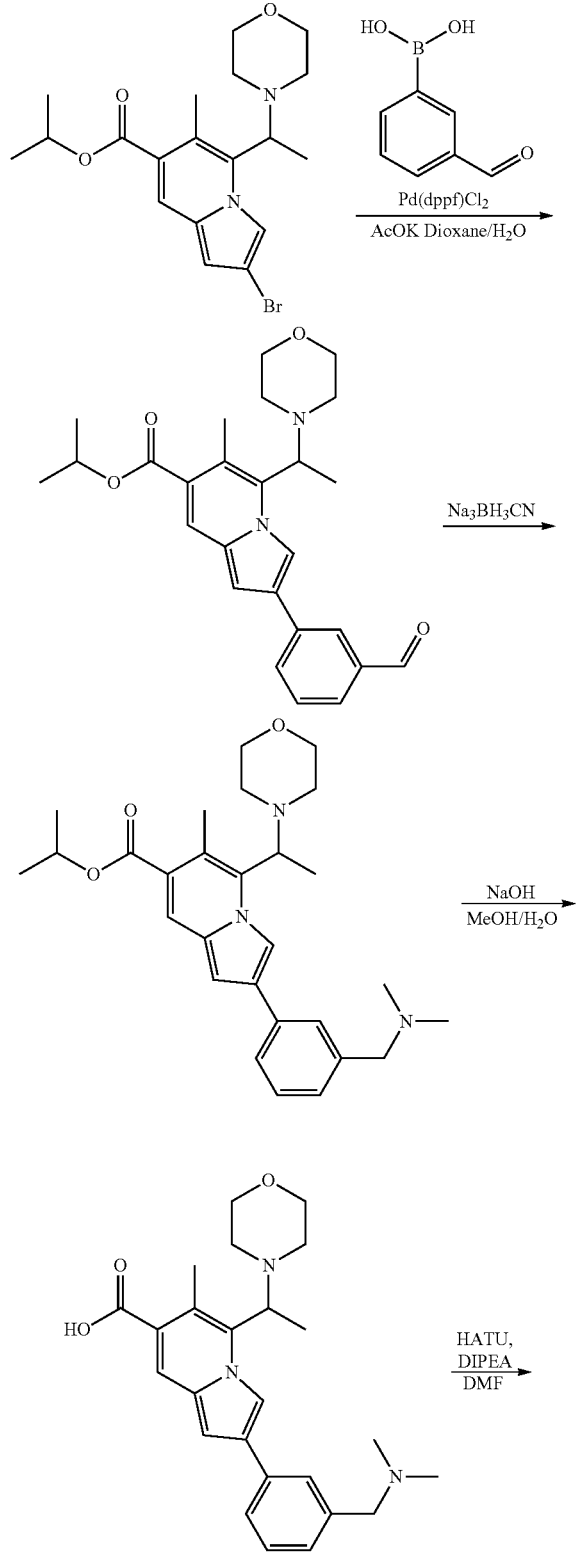

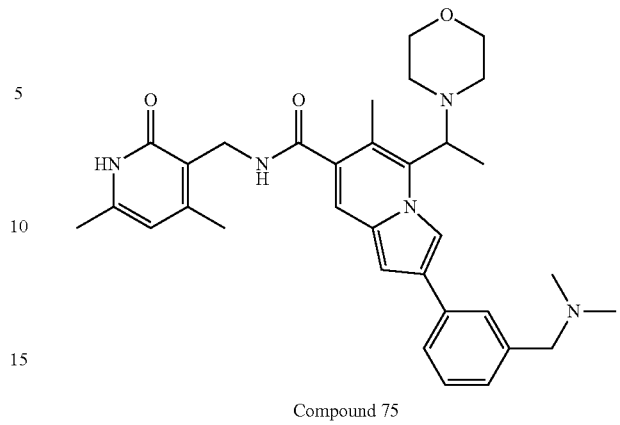

Compound 75

Step 1: Preparation of isopropyl 2-(3-formylphenyl)-6-methyl-5-(1-morpholinylethyl)indolizine-7-formate: similar to step 1 of example 31, yield 25%. MS (ESI) m/z 348 [M+H]$^+$.

Step 2: Preparation of isopropyl 2-(3-((dimethyl)methyl)phenyl)-6-methyl-5-(1-morpholinylethyl)indolizine-7-carboxylate: isopropyl 2-(3-((dimethyl)methyl)phenyl)-6-methyl-5-(1-morpholinylethyl)indolizine-7-carboxylate (100 mg, 0.23 mmol), dimethylamine hydrochloride (56 mg, 0.69 mmol), triethylamine (69 mg, 0.69 mmol), sodium cyanoborohydride (36 mg, 0.58 mmol) and dichloromethane (5 ml) were added successively to dry 50 mL round bottom flask at room temperature. After stirred at room temperature for 3 h, TLC monitored that the reaction was completed, the mixture was neutralized with saturated aqueous solution of sodium hydrogencarbonate, and then extracted with ethyl acetate (20 mL×3), and washed with saturated brine (10 mL). The organic phase was dried over anhydrous sodium sulfate, filtered, and the filtrate was concentrated under reduced pressure. The obtained residue was purified by column chromatography (petroleum ether:ethyl acetate=1:1) to afford product, isopropyl 2-(3-((dimethylamine)methyl)phenyl)-6-methyl-5-(1-morpholinylethyl)indolizine-7-carboxylate, yield 52%. MS (ESI) m/z 464 [M+H]$^+$.

Step 3: Preparation of 2-(3-((Dimethylamino)methyl)phenyl)-6-methyl-5-(1-morpholinylethyl)indolizine-7-carboxylic acid: similar to step 4 of example 31. MS (ESI) m/z 335 [M+H]$^+$.

Step 4: Preparation of N-((4,6-dimethyl-2-oxo-1,2-dihydropyridin-3-yl)methyl)-2-(3-((dimethylamino)methyl) phen yl)-6-methyl-5-(1-morpholinylethyl)indolizine-7-amide: similar to step 5 of Example 31, yield of the two steps was 18%. $^1$H NMR (DMSO-d$_6$, 400 MHz) δ11.47 (s, 1H), 8.70 (s, 1H), 8.17 (m, 1H), 7.58-7.60 (m, 2H), 7.34-7.36 (m, 1H), 7.29 (s, 1H), 7.17-7.18 (m, 1H), 6.83 (s, 1H), 5.88 (s, 1H), 4.26-4.28 (m, 2H), 4.06-4.07 (m, 1H), 3.59 (m, 2H), 2.65-2.67 (m, 2H), 2.26 (s, 3H), 2.18-2.22 (m, 11H), 2.12 (s, 3H), 1.45-1.47 (m, 3H); MS(ESI) m/z 556 [M+H]$^+$.

Example 75: Preparation of N-((4,6-dimethyl-2-oxo-1,2-dihydropyridin-3-yl)methyl)-2-(4-((dimethylamino)methyl)phen yl))-6-methyl-5-(1-morpholinoethyl)indolizine-7-carboxamide

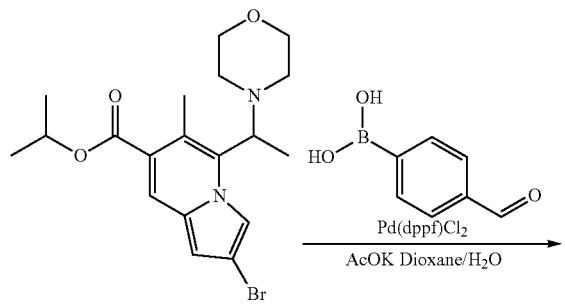

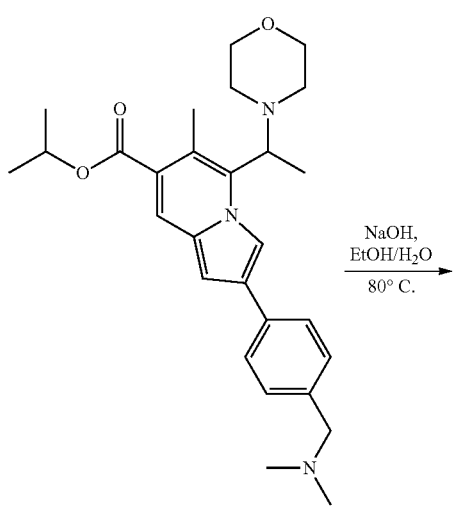

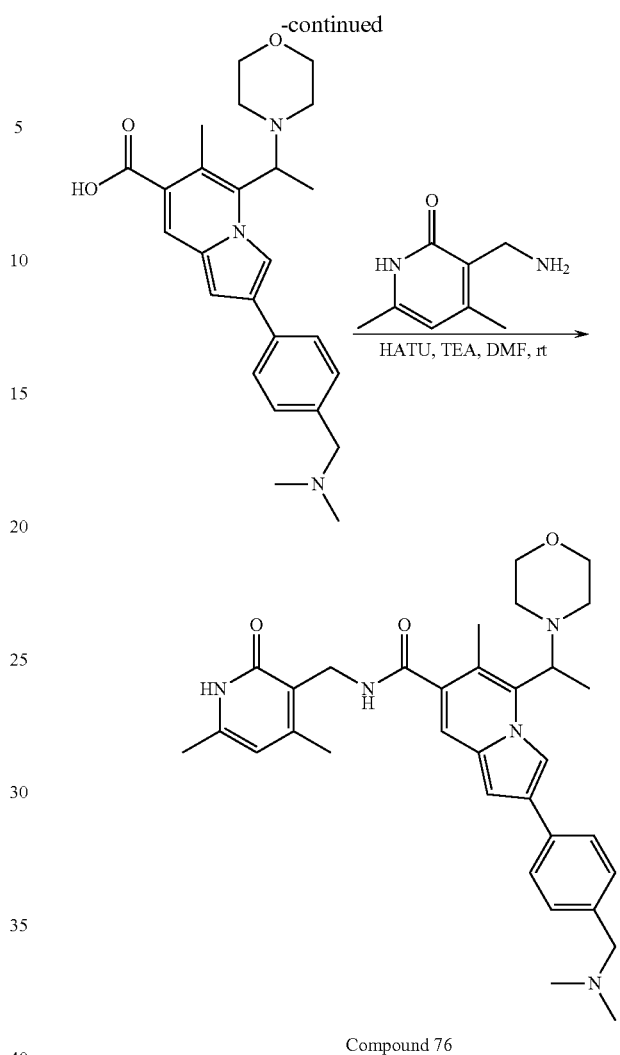

Compound 76

Preparation of N-((4,6-dimethyl-2-oxo-1,2-dihydropyridin-3-yl)methyl)-2-(4-(((dimethylamino)methyl)phen yl))-6-methyl-5-(1-morpholinoethyl)indolizine-7-carboxamide: same as example 74.

Step 1: Preparation of isopropyl 2-(4-formylphenyl)-6-methyl-5-(1-morpholinoethyl)indolizine-7-carboxylate: yield 34%. MS (ESI) m/z 348 [M+H]$^+$. Step 2: Preparation of isopropyl 2-(4-((dimethylamino)methyl)phenyl)-6-methyl-5-(1-morpholinoethyl)indolizine-7-carboxylate: yield 47%. MS (ESI) m/z 464 [M+H]$^+$.

Step 3: Preparation of 2-(4-((dimethylamino)methyl)phenyl)-6-methyl-5-(1-morpholinoethyl)indolizine-7-carboxylic acid: MS (ESI) m/z 422 [M]$^+$.

Step 3: Preparation of N-((4,6-dimethyl-2-oxo-1,2-dihydropyridin-3-yl)methyl)-2-(4-((dimethylamino)methyl) phen yl))-6-methyl-5-(1-morpholinoethyl)indolizine-7-carboxamide: Yield of the two steps was 11%. $^1$H-NMR (CDCl$_3$, 400 MHz) δ7.91 (s, 2H), 7.89 (s, 1H), 7.60 (s, 1H), 7.56 (s, 2H), 7.54 (s, 1H), 6.24 (s, 1H), 4.96 (s, 2H), 4.33 (s, 2H), 3.91-3.86 (m, 4H), 3.87-3.85 (m, 1H), 2.99-2.98 (m, 1H), 2.88 (s, 6H), 2.41 (s, 6H), 2.28 (s, 3H), 1.96-1.94 (m, 2H), 1.38-1.32 (m, 3H); MS(ESI) m/z 556 [M+H]$^+$.

Example 76: Preparation of 2-(7-cyanoindol-5-yl)-N-((4,6-dimethyl-2-oxo-1,2-dihydropyridin-3-yl)methyl)-6-methyl-5-(1-morpholinoethyl)indolizin-7-carboxamide

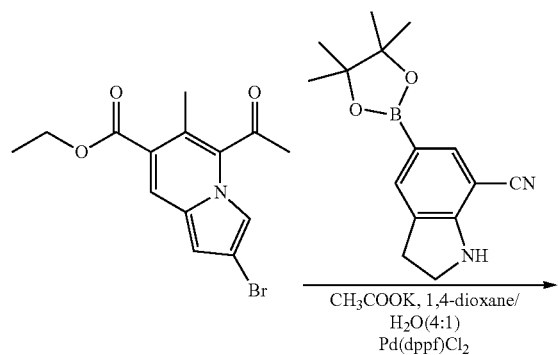

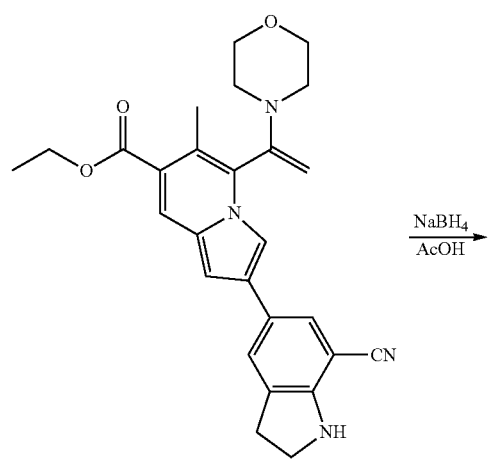

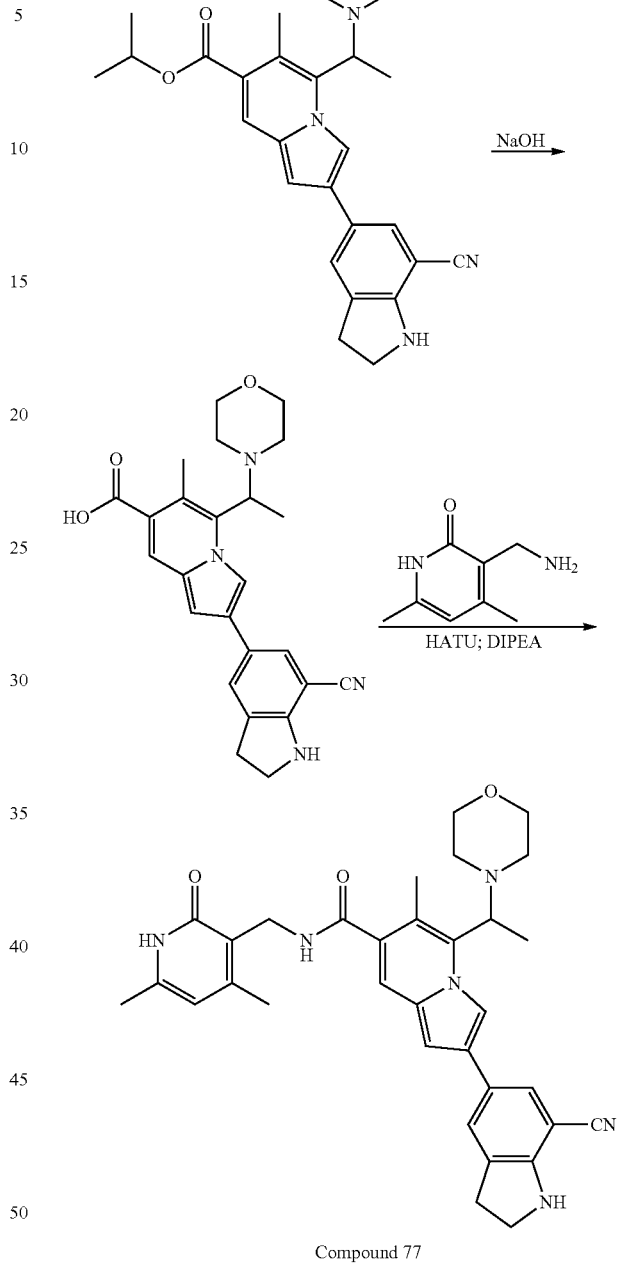

Compound 77

2-(7-Cyanoindol-5-yl)-N-((4,6-dimethyl-2-oxo-1,2-dihydropyridin-3-yl)methyl)-6-methyl-5-(1-morpholinoethyl)indolizin-7-carboxamide was prepared according to example 31.

Step 1: Preparation of ethyl 5-acetyl-2-(7-cyanoindole-5-yl)-6-methylindolizin-7-carboxylate: Yield 52%. MS (ESI) m/z 388 [M+H]$^+$.

Step 2: Preparation of ethyl isopropyl-2-(7-cyanoindol-5-yl)-6-methyl-5-(1-morpholinovinyl)indolizine-7-carboxylate: MS (ESI) m/z 471 [M+H]$^+$.

Step 3: Preparation of ethyl isopropyl-2-(7-cyanoindol-5-yl)-6-methyl-5-(1-morpholino-ethyl)indolizine-7-carboxylate: yield of two steps was 69%. MS (ESI) m/z 473 [M+H]$^+$.

Step 4: Preparation of 2-(7-cyanoindol-5-yl)-6-methyl-5-(1-morpholino)indolizine-7-carboxylic acid: MS (ESI) m/z 431 [M+H]⁺.

Step 5: Preparation of 2-(7-cyanoindol-5-yl)-N-((4,6-dimethyl-2-oxo-1,2-dihydropyridin-3-yl)methyl)-6-methyl-5-(1-morpholinoethyl)indolizine-7-carboxamide: yield of two steps was 10%. ¹H-NMR (CDCl₃, 400 MHz) δ 12.19 (s, 1H), 8.56 (s, 1H), 7.47 (s, 1H), 7.40 (s, 1H), 7.30 (s, 1H), 6.54 (s, 1H), 5.96 (s, 1H), 4.53-4.52 (m, 2H), 4.06-4.01 (m, 1H), 3.77-3.69 (m, 6H), 3.17-3.13 (m, 2H), 2.66-2.65 (m, 2H), 2.40 (s, 3H), 2.34 (s, 3H), 2.26-2.18 (m, 5H), 1.50-1.49 (m, 3H); MS(ESI) m/z 565 [M+H]⁺.

Example 77: Preparation of N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-pyrazol-3-yl)indolizin-7-carboxamide

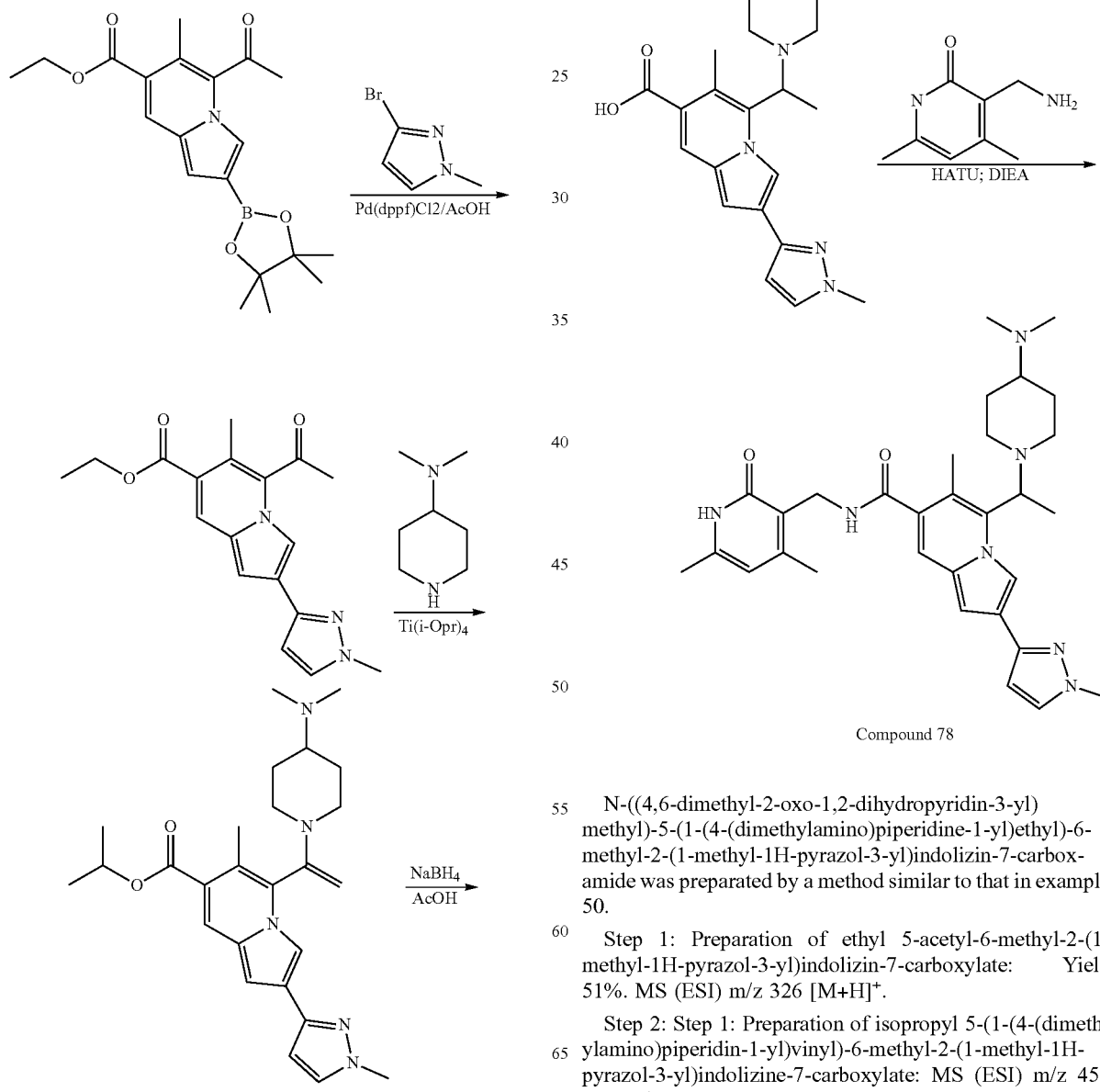

Compound 78

N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-pyrazol-3-yl)indolizin-7-carboxamide was preparated by a method similar to that in example 50.

Step 1: Preparation of ethyl 5-acetyl-6-methyl-2-(1-methyl-1H-pyrazol-3-yl)indolizin-7-carboxylate: Yield 51%. MS (ESI) m/z 326 [M+H]⁺.

Step 2: Step 1: Preparation of isopropyl 5-(1-(4-(dimethylamino)piperidin-1-yl)vinyl)-6-methyl-2-(1-methyl-1H-pyrazol-3-yl)indolizine-7-carboxylate: MS (ESI) m/z 450 [M+H]⁺.

Step 2: Preparation of isopropyl 5-(1-(4-(dimethylamino) piperidin-1-yl)ethyl)-6-methyl-2-(1-methyl-1H-pyrazol-3-yl)indolizine-7-carboxylate: yield of two steps was 56%. MS (ESI) m/z 452 [M+H]+.

Step 3: Step 3: Preparation of 5-(1-(4-(dimethylamino) piperidin-1-yl)ethyl)-6-methyl-2-(1-methyl-1H-pyrazol-3-yl)indolizine-7-carboxylic acid: MS (ESI) m/z 410 [M+H]+.

Step 4: Preparation of N-((4,6-dimethyl-2-oxo-1,2-dihydropyridin-3-yl)methyl)-5-(1-(4-(dimethyl amino)piperidine-1-yl)ethyl)-6-methyl-2-(1-methyl-1H-pyrazol-3-yl)indolizine-7-carboxamide: Yield of the two steps was 4%. $^1$H-NMR (DMSO-$d_6$, 400 MHz) δ 8.75 (s, 1H), 7.73-7.71 (m, 1H), 7.54-7.49 (m, 2H), 7.34 (s, 1H), 7.14 (s, 1H), 6.52 (s, 1H), 5.93 (s, 1H), 4.52-4.50 (m, 2H), 4.00 (m, 1H), 3.75 (s, 3H), 3.37-3.35 (m, 1H), 2.39 (s, 3H), 2.36-2.35 (m, 2H). 2.25-2.23 (m, 6H), 2.22-2.21 (m, 3H), 2.20-2.17 (m, 2H), 1.98-1.94 (m, 4H), 1.49-1.45 (m, 3H), 0.99-0.96 (m, 3H); MS(ESI) m/z 544 [M+H]+.

Example 78: Preparation of N-((4,6-dimethyl-2-oxo-1,2-dihydropyridin-3-yl)methyl)-6-methyl-5-(1-morpholinylethyl)-1-(3-cyanophenyl)indolizin-7-amide

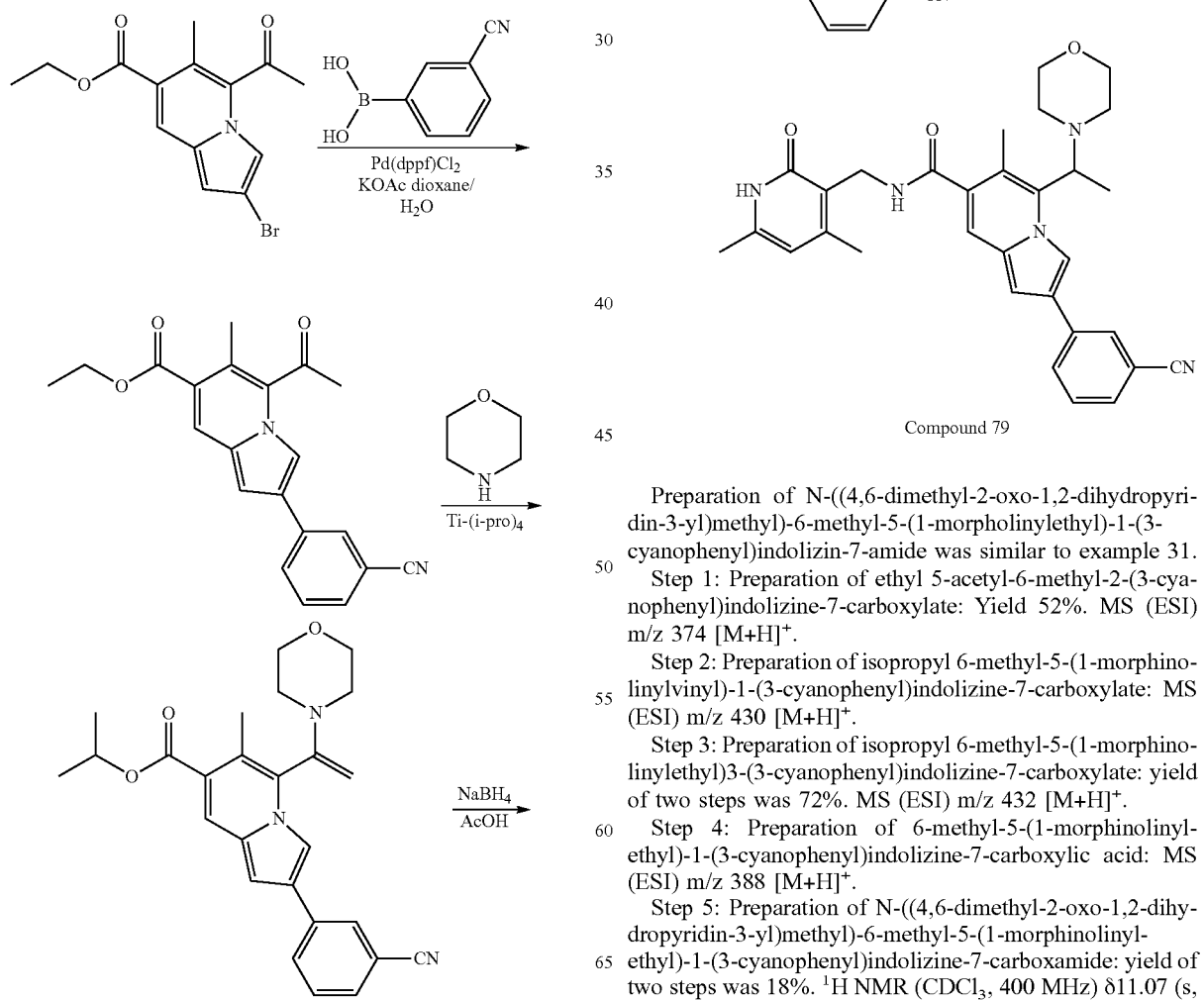

Compound 79

Preparation of N-((4,6-dimethyl-2-oxo-1,2-dihydropyridin-3-yl)methyl)-6-methyl-5-(1-morpholinylethyl)-1-(3-cyanophenyl)indolizin-7-amide was similar to example 31.

Step 1: Preparation of ethyl 5-acetyl-6-methyl-2-(3-cyanophenyl)indolizine-7-carboxylate: Yield 52%. MS (ESI) m/z 374 [M+H]+.

Step 2: Preparation of isopropyl 6-methyl-5-(1-morphinolinylvinyl)-1-(3-cyanophenyl)indolizine-7-carboxylate: MS (ESI) m/z 430 [M+H]+.

Step 3: Preparation of isopropyl 6-methyl-5-(1-morphinolinylethyl)3-(3-cyanophenyl)indolizine-7-carboxylate: yield of two steps was 72%. MS (ESI) m/z 432 [M+H]+.

Step 4: Preparation of 6-methyl-5-(1-morpholinylethyl)-1-(3-cyanophenyl)indolizine-7-carboxylic acid: MS (ESI) m/z 388 [M+H]+.

Step 5: Preparation of N-((4,6-dimethyl-2-oxo-1,2-dihydropyridin-3-yl)methyl)-6-methyl-5-(1-morphinolinylethyl)-1-(3-cyanophenyl)indolizine-7-carboxamide: yield of two steps was 18%. $^1$H NMR (CDCl$_3$, 400 MHz) δ11.07 (s, 1H), 8.74 (s, 1H), 7.89 (s, 1H), 7.85-7.83 (d, J=7.2 Hz, 1H), 7.53-7.47 (m, 2H), 7.34 (s, 1H), 6.68 (s, 1H), 5.96 (s, 1H), 4.53-4.52 (m, 2H), 4.09-4.03 (m, 1H), 3.71 (m, 4H), 2.68 (s, 2H), 2.40 (s, 3H), 2.34 (s, 3H), 2.28-2.24 (m, 5H), 1.52-1.50 (m, 3H); MS(ESI) m/z 437 [M+H]$^+$.

Example 79: Preparation of N-((4,6-dimethyl-2-oxo-1,2-dihydropyridin-3-yl)methyl)-6-methyl-2-(1-methyl-1H-imidazole-2-yl)-5-(1-morpholinoethyl)indolizine-7-carboxamide

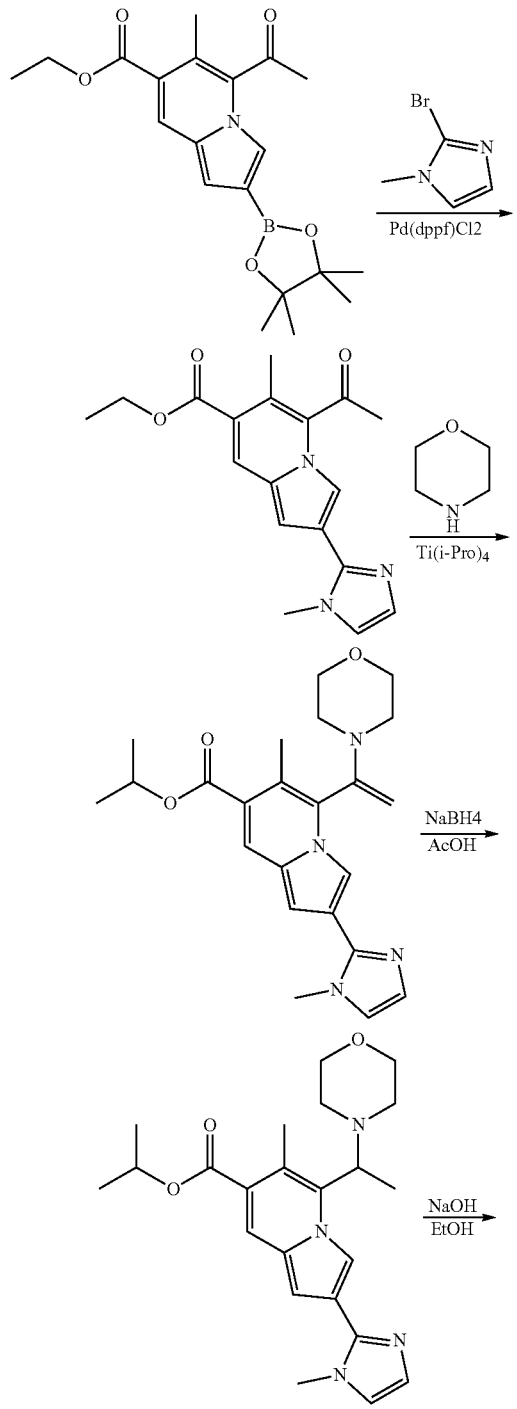

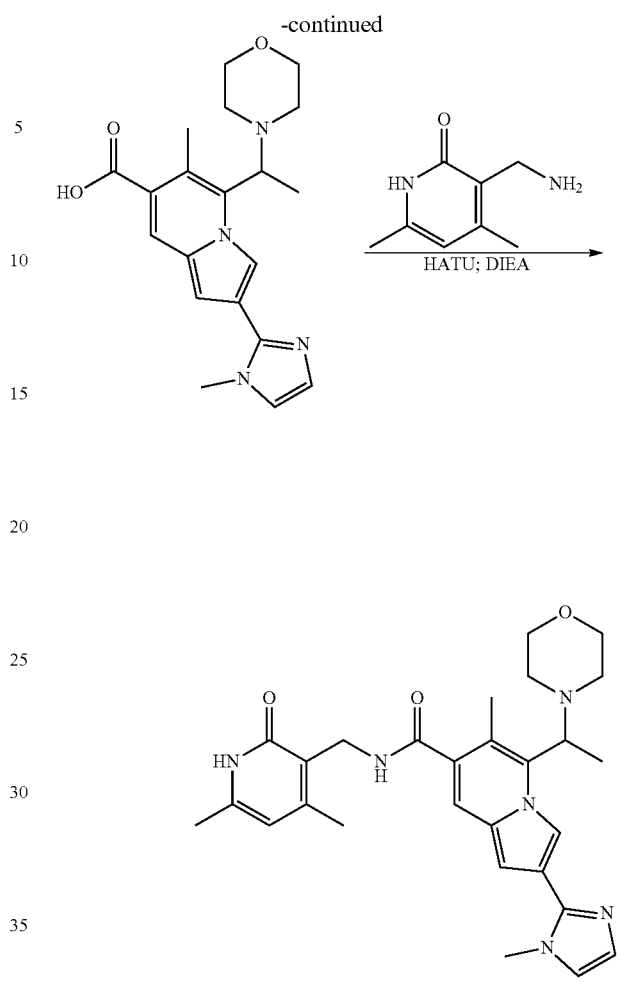

Compound 80

Preparation of N-((4,6-dimethyl-2-oxo-1,2-dihydropyridin-3-yl)methyl)-6-methyl-2-(1-methyl-1H-imidazole-2-yl)-5-(1-morpholinoethyl)indolizine-7-carboxamide was similar to example 50.

Step 1: Preparation of ethyl 5-acetyl-6-methyl-2-(1-methyl-1H-imidazol-2-yl)indolizine-7-carboxylate: Yield 49%. MS (ESI) m/z 326 [M+H]$^+$.

Step 2: Preparation of ethyl isopropyl-6-methyl-2-(1-methyl-1H-imidazol-2-yl)-5-(1-morpholinovinyl)indolizine-7-carboxylate: MS (ESI) m/z 409 [M+H]$^+$.

Step 3: Preparation of ethyl isopropyl-6-methyl-2-(1-methyl-1H-imidazol-2-yl)-5-(1-morpholinoethyl)indolizine-7-carboxylate: yield 65%. MS (ESI) m/z 411 [M+H]$^+$.

Step 4: Preparation of 6-methyl-2-(1-methyl-1H-imidazol-2-yl)-5-(1-morphinoethyl)indolizine-7-carboxylic acid: MS (ESI) m/z 369 [M+H]$^+$.

Step 5: Preparation of N-((4,6-dimethyl-2-oxo-1,2-dihydropyridin-3-yl)methyl)-6-methyl-2-(1-methyl-1H-imidazol-2-yl)-5-(1-morphinolinylethyl)indolizine-7-carboxamide, yield 22%. $^1$H-NMR (DMSO-d$_6$, 400 MHz) δ 11.48 (s, 1H), 8.89 (s, 1H), 8.31-8.28 (m, 1H), 7.78-7.76 (m, 2H), 7.45 (s, 1H), 7.09-7.07 (m, 1H), 5.88 (s, 1H), 4.44 (s, 2H), 4.24-4.22 (m, 1H), 4.18 (s, 3H), 3.63-3.58 (m, 4H), 2.67-2.64 (m, 2H), 2.27-2.17 (m, 6H), 2.15-2.13 (m, 2H), 2.11 (s, 3H), 1.48-1.47 (m, 3H); MS(ESI) m/z 503 [M+H]$^+$.

Example 80: Preparation of N-((4,6-dimethyl-2-oxo-1,2-dihydropyridin-3-yl)methyl)-5-(1-morpholine-1-ethyl)-6-methyl-2-(3-(morpholinemethylene)phenyl)indolizin-7-amide

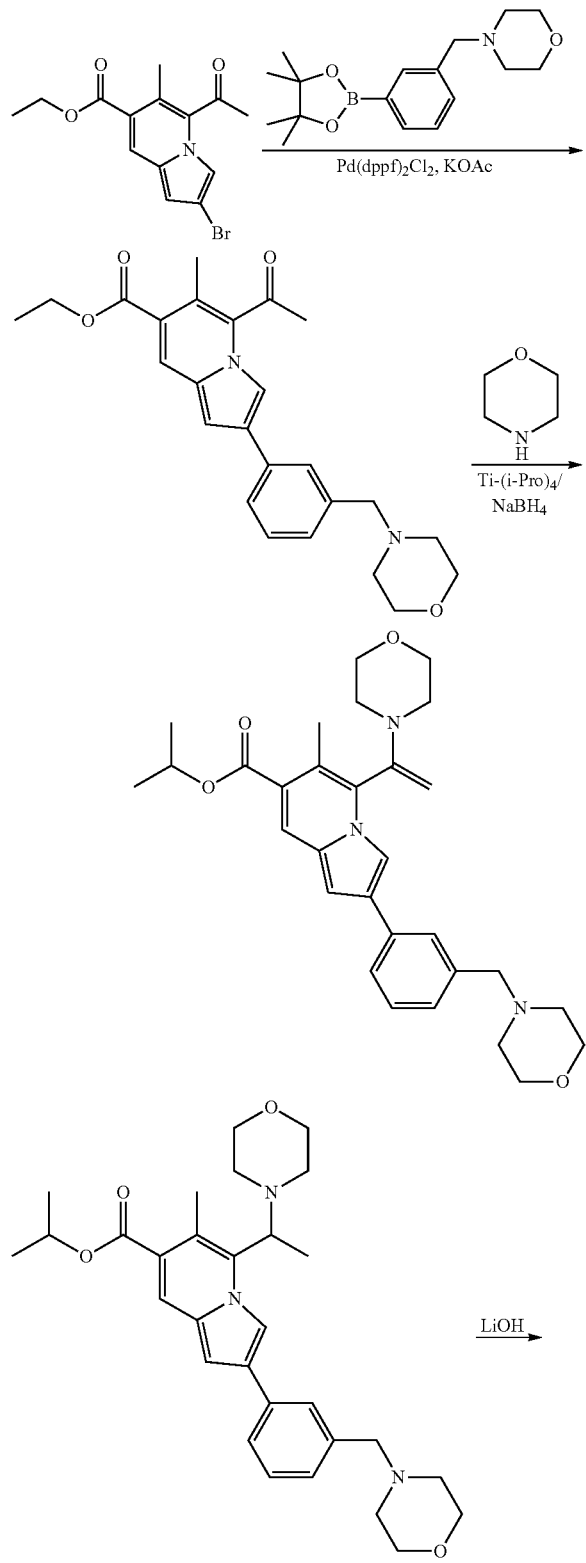

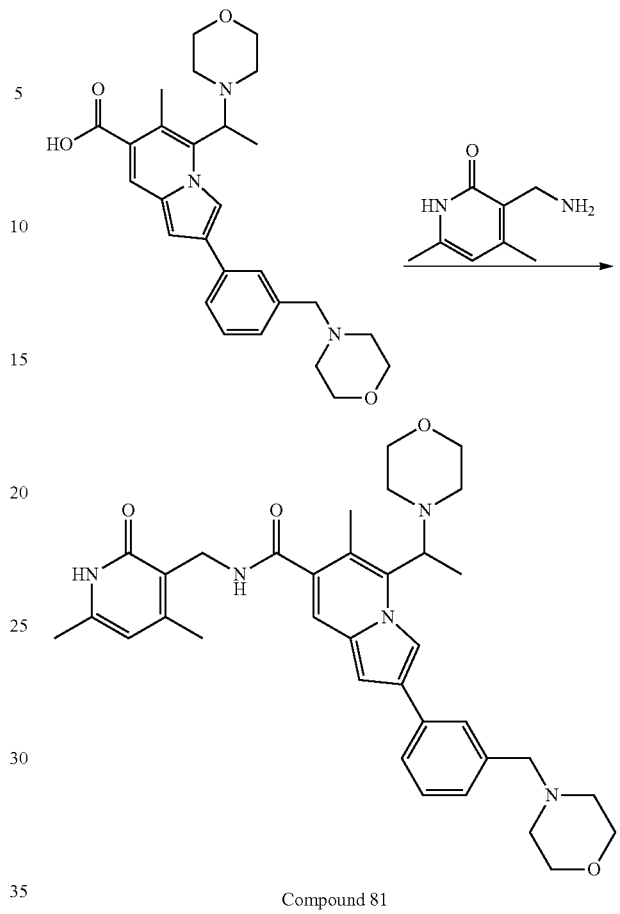

Compound 81

Preparation of N-((4,6-dimethyl-2-oxo-1,2-dihydropyridin-3-yl)methyl)-5-(1-morpholino-1-ethyl)-6-methyl-2-(3-(morpholinomethylene)phenyl)indolizine-7-carboxamide was similar to example 31.

Step 1: Preparation of ethyl 5-acetyl-6-methyl-2-(3-(morpholinemethylene)phenyl)indolizine-7-carboxylate: yield 46%. MS (ESI) m/z 420 [M+H]$^+$.

Step 2: Preparation of isopropyl 5-(1-morpholine-1-vinyl)-6-methyl-2-(3-(morpholinemethylene)phenyl)indolizine-7-carboxylate: MS (ESI) m/z 504 [M+H]$^+$.

Step 3: Preparation of isopropyl 5-(1-morpholine-1-ethyl)-6-methyl-2-(3-(morpholinemethylene)phenyl)indolizine-7-carboxylate: yield of two steps was 80%. MS(ESI) m/z 506 [M+H]$^+$.

Step 4: Step 4: Preparation of 5-(1-morpholine-1-ethyl)-6-methyl-2-(3-(morphinolinylmethylene)phenyl)indolizine-7-carboxylic acid: MS (ESI) m/z 377 [M+H]$^+$.

Step 5: Step 5: Preparation of N-((4,6-dimethyl-2-oxo-1,2-dihydropyridin-3-yl)methyl)-5-(1-morpholine-1-ethyl)-6-methyl-2-(3-(morpholinemethylene)phenyl)indolizine-7-amide: yield of two steps was 19%. $^1$H NMR (CDCl$_3$, 400 MHz) δ 8.67 (s, 1H), 7.57 (s, 1H), 7.50-7.48 (d, J=7.6, 1H), 7.31-7.23 (m, 1H), 7.13-7.10 (m, 1H), 6.67 (s, 1H), 5.89 (s, 1H), 4.46-4.44 (m, 2H), 3.40-4.39 (m, 1H), 3.69 (s, 4H), 3.64 (s, 4H), 3.56 (s, 2H), 2.61 (s, 2H), 2.50 (s, 4H), 2.34 (s, 3H), 2.27 (s, 3H), 2.23-2.20 (m, 2H), 2.18 (s, 3H), 1.46-1.44 (d, J=6.8 Hz, 3H); MS(ESI) m/z 620 [M+Na]$^+$.

Example 81: Preparation of N-((4,6-dimethyl-2-oxo-1,2-dihydropyridin-3-yl)methyl)-6-methyl-1-(1-methyl-1H-pyrazol-5-yl)-5-(1-morpholinylethyl)indolizin-7-amide

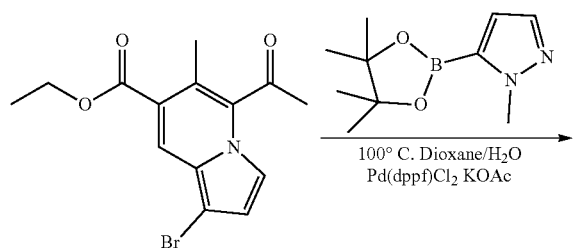

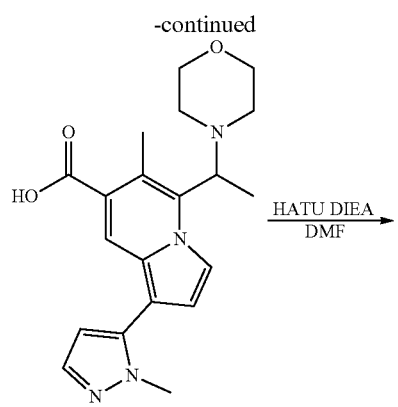

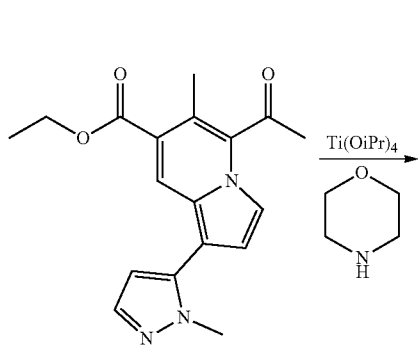

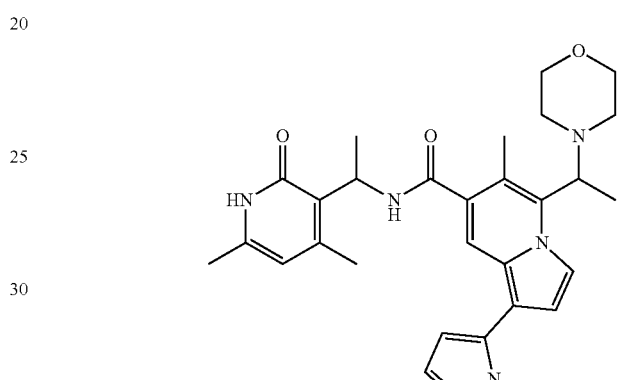

Compound 82

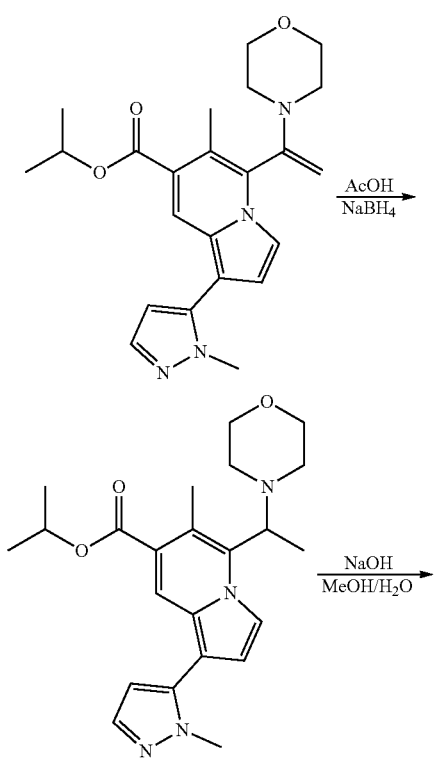

Preparation of N-((4,6-dimethyl-2-oxo-1,2-dihydropyridin-3-yl)methyl)-6-methyl-1-(1-methyl-1H-pyrazol-5-yl)-5-(1-morpholinylethyl)indolizine-7-amide was similar to example 31.

Step 1: Preparation of ethyl 5-acetyl-6-methyl-1-(1-methyl-1H-pyrazol-5-yl)indolizine-7-formate: Yield 33%. MS (ESI) m/z 326 [M+H]$^+$.

Step 2: Preparation of isopropyl 6-methyl-1-(1-methyl-1H-pyrazol-5-yl)-5-(1-morphinolinylvinyl)indolizine-7-formate: MS (ESI) m/z 409 [M+H]$^+$.

Step 3: Step 3: Preparation of isopropyl 6-methyl-1-(1-methyl-1H-pyrazol-5-yl)-5-(1-morphinolinylethyl)indolizine-7-formate: yield of two steps was 30%. MS (ESI) m/z 411 [M+H]$^+$.

Step 4: Preparation of 6-methyl-1-(1-methyl-1H-pyrazol-5-yl)-5-(1-morphinolinylethylene)indolizine-7-formic acid: MS (ESI) m/z 369 [M+H]$^+$.

Step 5: Preparation of N-((4,6-dimethyl-2-oxo-1,2-dihydropyridin-3-yl)methyl)-6-methyl-1-(1-methyl-1H-pyrazol-5-yl)-5-(1-morphinolinylethyl)indolizine-7-carboxamide: Yield of two steps was 16%. $^1$H NMR (400 MHz, CDCl$_3$) δ 11.46 (s, 1H), 8.50 (s, 1H), 8.27 (s, 1H), 7.47 (s, 1H), 7.31 (s, 1H), 7.03-7.02 (d, J=2.8 Hz, 1H), 6.40 (s, 1H), 5.85 (s, 1H), 4.25-4.24 (m, 2H), 4.09-4.07 (m, 1H), 3.83 (s, 3H), 3.58 (m, 4H), 2.67-2.62 (m, 2H), 2.28 (s, 3H), 2.18-2.14 (m, 5H), 2.10 (s, 3H), 1.45-1.43 (m, 3H); MS(ESI) m/z 503 [M+H]$^+$.

Example 82: Preparation of N-((4,6-dimethyl-2-oxo-1,2-dihydropyridin-3-yl)methyl)-6-methyl-5-(1-morphinolinylethyl)-1-phenylindolizine-7-carboxamide

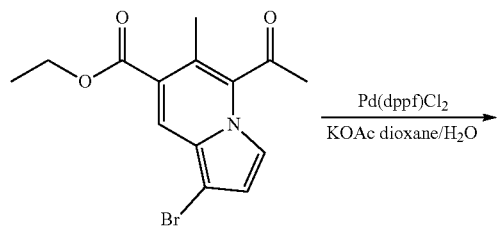

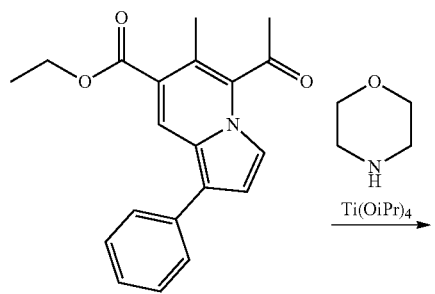

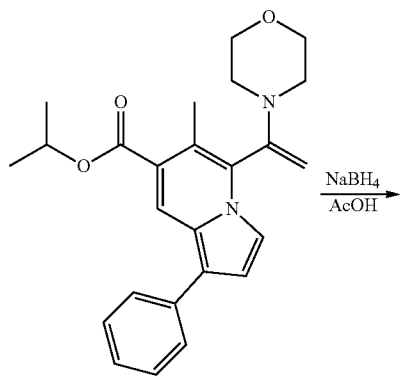

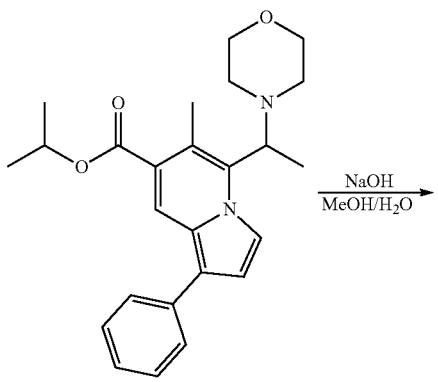

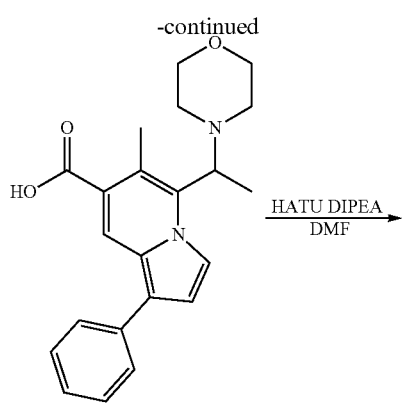

Compound 83

Preparation of N-((4,6-dimethyl-2-oxo-1,2-dihydropyridin-3-yl)methyl)-6-methyl-5-(1-morphinolinylethyl)-1-phenylindolizine-7-carboxylate was similar to example 31.

Step 1: Preparation of ethyl 5-acetyl-6-methyl-1-phenylindolizine-7-carboxylate: yield 14%. MS (ESI) m/z 322 [M+H]$^+$.

Step 2: Preparation of isopropyl 6-methyl-5-(1-morphinolinylvinyl)-1-phenylindolizine-7-carboxylate: MS (ESI) m/z 405 [M+H]$^+$.

Step 3: Preparation of isopropyl 6-methyl-5-(1-morphinolinylethyl)-1-phenylindolizine-7-carboxylate: yield of two steps was 38%. MS (ESI) m/z 320 [M+H]$^+$.

Step 4: Preparation of 6-methyl-5-(1-morpholinylethyl)-1-phenylindolizine-7-carboxylic acid: MS (ESI) m/z 278 [M+H]$^+$.

Step 5: Preparation of N-((4,6-dimethyl-2-oxo-1,2-dihydropyridin-3-yl)methyl)-6-methyl-5-(1-morphinolinylethyl)-1-phenylindolizine-7-carboxamide: yield of two steps was 17. $^1$H NMR (400 MHz, CDCl$_3$) δ ppm 11.46 (s, 1H), 8.44 (s, 1H), 8.27-8.30 (s, 1H), 7.57-7.59 (m, 3H), 7.40-7.43 (m, 2H), 7.20-7.23 (m, 1H), 7.01-7.02 (d, J=2.8 Hz, 1H), 5.86 (s, 1H), 4.26-4.27 (m, 2H), 4.03-4.08 (m, 1H), 3.55 (brs, 4H), 2.58-2.67 (m, 2H), 2.35 (s, 3H), 2.11-2.17 (m, 5H), 2.07 (s, 3H), 1.39-1.41 (m, 3H); MS(ESI) m/z 499 [M+H]$^+$.

Example 83: Preparation of N-((4-methoxy-6-methyl-2-oxo-1,2-dihydropyridin-3-yl)methyl)-6-methyl-2-(1-methyl-1H-pyrazol-5-yl)-5-(1-(4-(2,2,2-trifluoroethyl)piperazin-1-yl)ethyl)indolizine-7-carboxamide

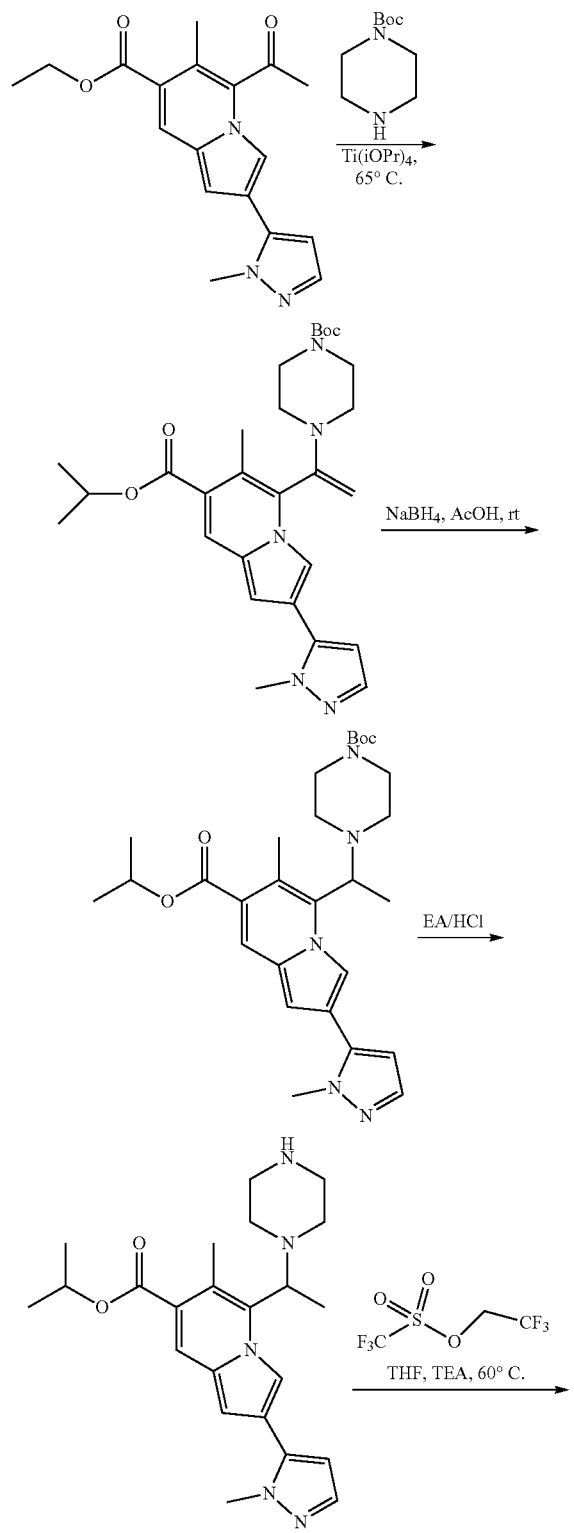

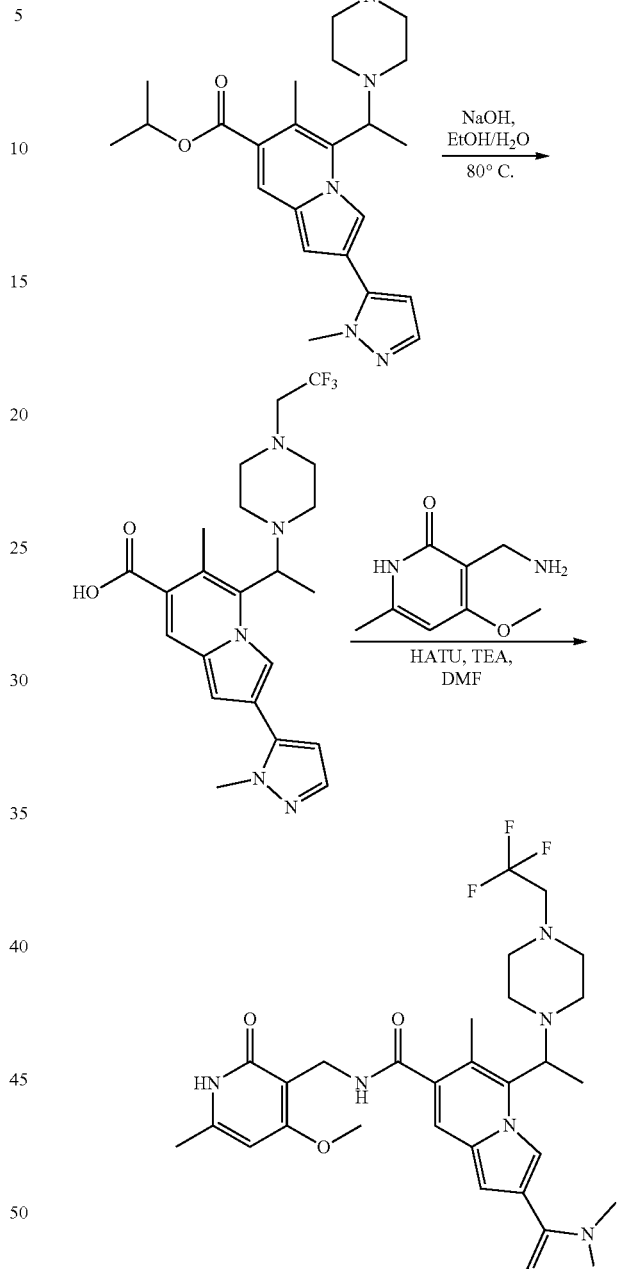

Compound 84

Step 1: Preparation of isopropyl 5-(1-(4-(tert-Butoxy carbonyl)piperazin-1-yl)vinyl)-6-methyl-2-(1-methyl-1H-pyrazol-5-yl)indolizine-7-formate: similar to step 2 of example 31. MS (ESI) m/z 508 [M+H]⁺.

Step 2: Preparation of isopropyl 5-(1-(4-(tert-butoxycarbonyl)piperazin-1-yl)ethyl)-6-methyl-2-(1-methyl-1H-pyrazol-5-yl)indolizine-7-formate: similar to step 3 of example 31. MS (ESI) m/z 510 [M+H]⁺.

Step 3: Synthesis of isopropyl 6-Methyl-2-(1-methyl-1H-pyrazol-5-yl)-5-(1-(piperazin-1-yl)ethyl)indolizine-7-formate: isopropyl 5-(1-(4-(tert-butoxycarbonyl)piperazin-1- yl)ethyl)-6-methyl-2-(1-methyl-1H-pyrazol-5-yl)indolizine-7-carboxylate (360 mg (crude), 0.7 mmol) was dissolved in 2 mL of dichloromethane) in a 100 ml dry single-mouth bottle, and trifluoroacetic acid (1 ml) was added at 0 degree. The mixture was stirred at room temperature for 2 hours. After the reaction was monitored to have been completed by TLC, NaHCO₃ solution was added and extracted with dichloromethane (50×3 mL). The organic phases were combined and dried over anhydrous sodium sulfate, filtered and the solvent was removed under reduced pressure to provide yellow oil, which was used in the next step without purification. MS (ESI) m/z 410 [M+H]⁺.

Step 4: Synthesis of isopropyl 6-methyl-2-(1-methyl-1H-pyrazol-5-yl)-5-(1-(4-(2,2,2-trifluoroethyl)piperazine-1-yl)ethyl)indolizine-7-carboxylate: isopropyl 6-methyl-2-(1-methyl-1H-pyrazol-5-yl)-5-(1-(piperazin-1-yl)ethyl)indolizine-7-carboxylate (300 mg (crude), 0.73 mmol) was dissolved in tetrahydrofuran (5 mL) in 100 ml dry single-mouth bottle, and 2,2,2-trifluoroethyl trifluoromethane-sulfonate (172 mg, 0.74 mmol), triethylamine (206 mg, 2.0 mmol) were added. The mixture was stirred at 60° C. for 4 hrs, water was added and extracted by ethyl acetate (50×3 mL). The organic phases were combined and dried over anhydrous sodium sulfate. After filtered, the solvent was removed by evaporation under reduced pressure to give yellow oil, which was purified through column (ethyl ether: petroleum ether=1:3) to provide 210 mg pure product (yield-58%). MS (ESI) m/z 492 [M+H]⁺.

Step 5: Synthesis of 6-methyl-2-(1-methyl-1H-pyrazol-5-yl)-5-(1-(4-(2,2,2-trifluoroethyl)piperazin-1-yl)ethyl)indolizine-7-formic acid: same as step 4 of example 31. MS (ESI) m/z 450 [M+H]⁺.

Step 6: Synthesis of N-((4-methoxy-6-methyl-2-oxo-1,2-dihydropyridin-3-yl)methyl)-6-methyl-2-(1-methyl-1H-pyrazol-5-yl)-5-(1-(4-(2,2,2-trifluoroethyl)piperazin-1-yl)ethyl)indolizine-7-carboxamide: same as step 5 of example 31. Yield of two steps was 9%. ¹H-NMR (CDCl₃, 400 MHz) δ ppm 8.51 (s, 1H), 7.64 (s, 1H), 7.45 (s, 1H), 6.84 (s, 1H), 6.74 (s, 1H), 6.56 (s, 1H), 6.41 (s, 1H), 4.62-4.61 (m, 2H), 4.48-4.46 (m, 1H), 4.10 (s, 3H), 4.07 (s, 3H), 3.31-3.26 (m, 2H), 3.20-3.14 (m, 2H), 3.07-2.91 (m, 4H), 2.68-2.67 (m, 2H), 2.53 (s, 3H), 2.39 (s, 3H), 1.77 (d, 3H, J=6.9 Hz); MS(ESI) m/z 600 [M+H]⁺.

Example 84: Preparation of N-((4,6-dimethyl-2-oxo-1,2-dihydropyridin-3-yl)methyl)-6-methyl-2-(1-methyl-1H-pyrazole-5-yl)-5-(1-(4-(2,2,2-trifluoroethyl)piperazin-1-yl)ethyl)indolizine-7-carboxamide

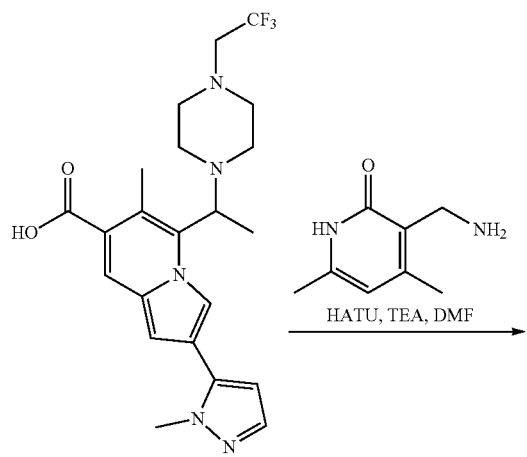

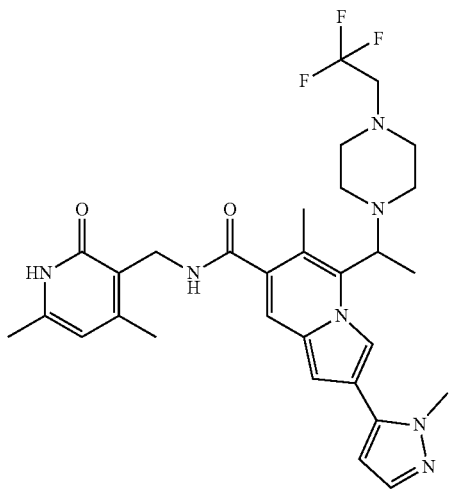

Compound 85

Step 1: Synthesis of N-((4,6-dimethyl-2-oxo-1,2-dihydropyridin-3-yl)methyl)-6-methyl-2-(1-methyl-1H-pyrazole-5-yl)-5-(1-(4-(2,2,2-trifluoroethyl)piperazin-1-yl)ethyl)indolizine-7-carboxamide: same as step 5 of example 31. Yield: 8%. ¹H-NMR (CDCl₃, 400 MHz): 8.51 (s, 1H), 7.66 (s, 1H), 7.45 (s, 1H), 6.93 (s, 1H), 6.75 (s, 1H), 6.57-6.53 (m, 1H), 4.78 (s, 2H), 4.50 (m, 1H), 4.11 (s, 3H), 3.25-3.21 (m, 4H), 2.94 (m, 4H), 2.69 (m, 2H), 2.62 (s, 3H), 2.56 (s, 3H), 2.39 (s, 3H), 1.68 (d, 3H, J=6.9 Hz); MS(ESI) m/z 584 [M+H]⁺.

Example 85: Preparation of N-((4,6-dimethyl-2-oxo-1,2-dihydropyridin-3-yl)methyl)-6-methyl-2-(1-methyl-1H-pyrazole-3-yl)-5-(1-morpholino)indolizine-7-carboxamide

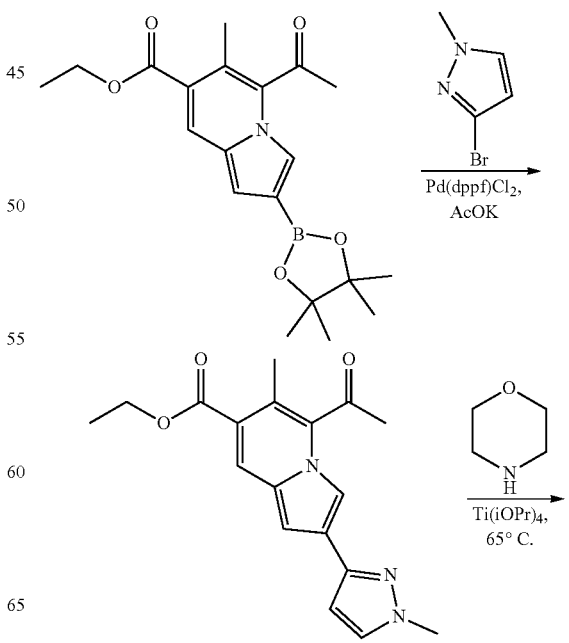

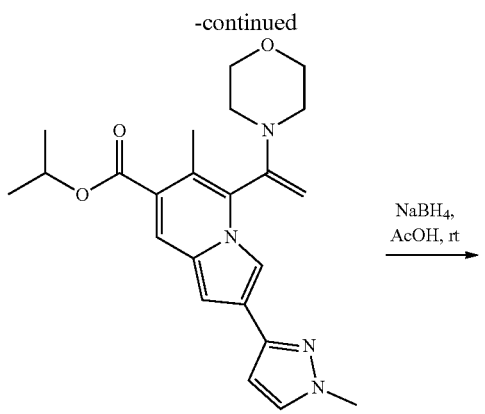

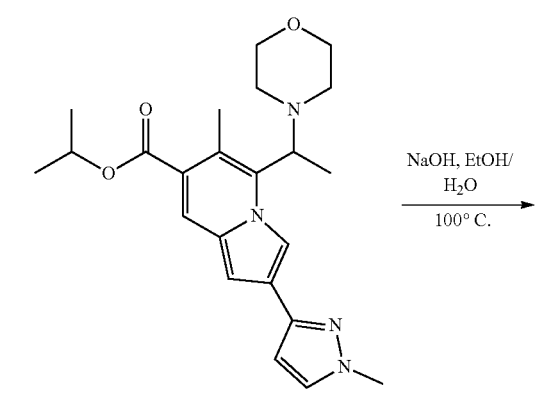

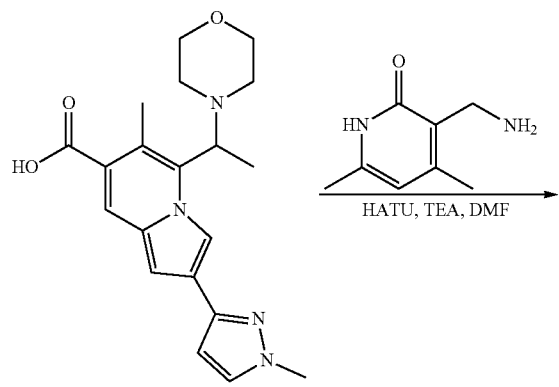

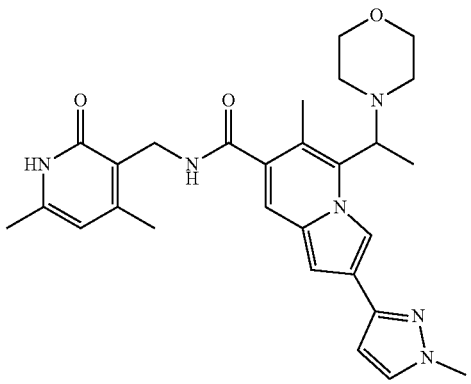

Compound 86

Preparation of N-((4,6-dimethyl-2-oxo-1,2-dihydropyridin-3-yl)methyl)-6-methyl-2-(1-methyl-1H-pyrazole-3-yl)-5-(1-morpholino)indolizine-7-carboxamide was same as example 31.

Step 1: Preparation of ethyl 5-acetyl-6-methyl-2-(1-methyl-1H-pyrazol-3-yl)indolizine-7-formate: Yield 39%. MS (ESI) m/z 326 [M+H]$^+$.

Step 2: Preparation of isopropyl 6-methyl-2-(1-methyl-1H-pyrazol-3-yl)-5-(1-morpholinovinyl)indolizine-7-carboxylate: MS (ESI) m/z 409 [M+H]$^+$.

Step 3: Preparation of isopropyl 6-methyl-2-(1-methyl-1H-pyrazol-3-yl)-5-(1-morpholinoethyl)indolizine-7-carboxylate: yield of two steps was 37%. MS (ESI) m/z 411 [M+H]$^+$.

Step 4: Preparation of 6-methyl-2-(1-methyl-1H-pyrazol-3-yl)-5-(1-morpholinoethyl)indolizine-7-carboxylic acid: yield 84%. MS (ESI) m/z 369 [M+H]$^+$.

Step 5: Preparation of N-((4,6-dimethyl-2-oxo-1,2-dihydropyridin-3-yl)methyl)-6-methyl-2-(1-methyl-1H-pyrazole-3-yl)-5-(1-morpholinoethyl)indolizine-7-carboxamide: Yield 7%. $^1$H-NMR (MeOD, 400 MHz): 7.57 (s, 1H), 7.35 (s, 1H), 6.77 (s, 1H), 6.49 (s, 1H), 6.14 (s, 1H), 4.46 (s, 2H), 4.08-4.02 (m, 1H), 3.92 (s, 3H), 3.34-3.30 (m, 4H), 2.69-2.67 (m, 2H), 2.37 (s, 3H), 2.29 (s, 3H), 2.26 (s, 3H), 2.25-2.18 (m, 2H), 1.35-1.28 (m, 3H); MS(ESI) m/z 503 [M+H]$^+$.

Example 86: Preparation of N-((4,6-dimethyl-2-oxo-1,2-dihydropyridin-3-yl)methyl)-6-methyl-2-(1-methyl-1H-imidazole-5-yl)-5-(1-morpholinoethyl)indolizine-7-carboxamide: Same as Example 50

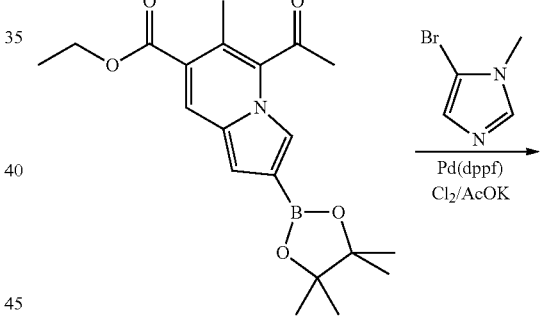

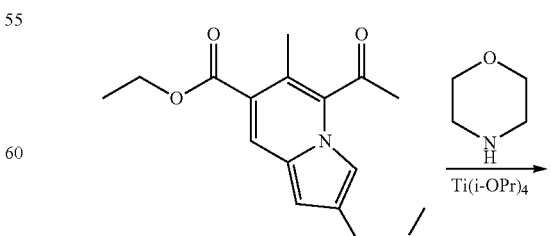

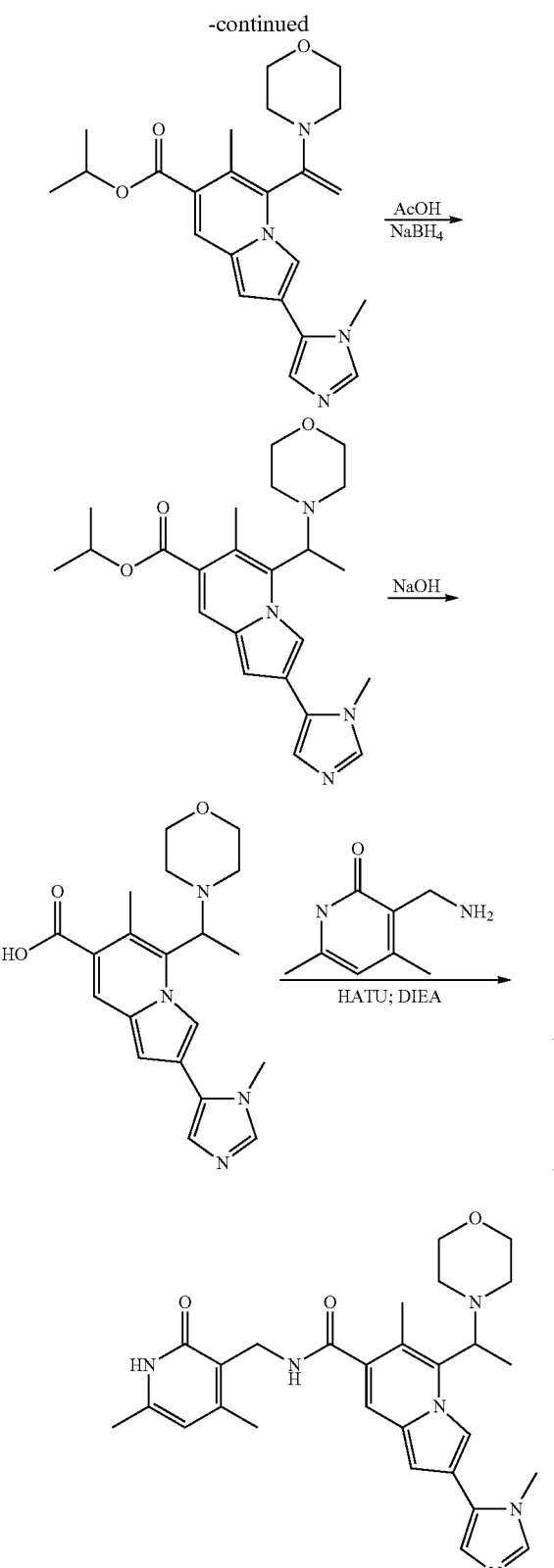

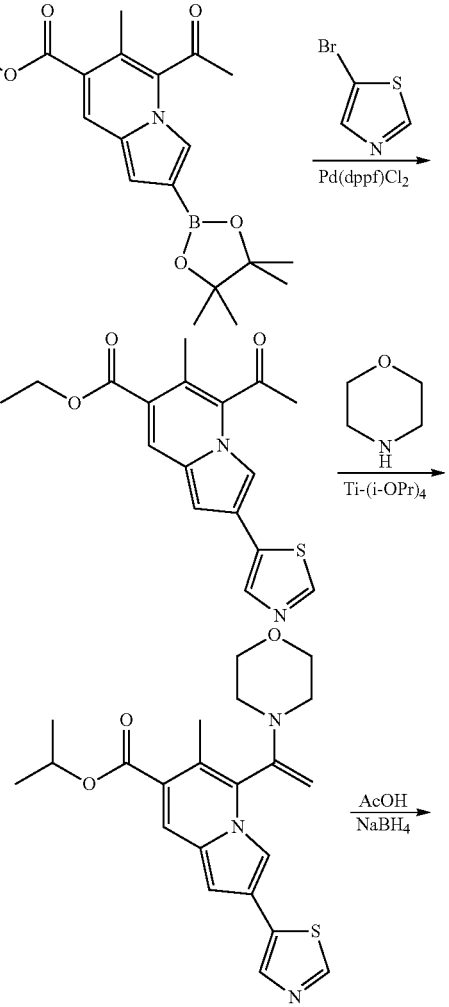

Step 2: Preparation of isopropyl 6-methyl-2-(1-methyl-1H-imidazol-5-yl)-5-(1-morpholinovinyl)indolizine-7-carboxylate: MS (ESI) m/z 409 [M+H]⁺.

Step 3: Preparation of isopropyl 6-methyl-2-(1-methyl-1H-imidazol-5-yl)-5-(1-morpholinoethyl)indolizine-7-carboxylate: yield 48%. MS (ESI) m/z 411 [M+H]⁺.

Step 4: Preparation of 6-methyl-2-(1-methyl-1H-imidazol-5-yl)-5-(1-morpholinoethyl)indolizine-7-carboxylic acid: MS (ESI) m/z 369 [M+H]⁺.

Step 5: Preparation of N-((4,6-dimethyl-2-oxo-1,2-dihydropyridin-3-yl)methyl)-6-methyl-2-(1-methyl-1H-imidazol-5-yl)-5-(1-morphinolinylethyl)indolizine-7-carboxamide, yield 10%. I—H-NMR (DMSO-$d_6$, 400 MHz): 11.48 (s, 1H), 9.17-9.15 (m, 1H), 8.75 (s, 1H), 8.25 (s, 1H), 7.95-7.93 (m, 1H), 7.38 (s, 1H), 6.86-6.85 (m, 1H), 5.90-5.88 (m, 1H), 4.62 (s, 2H), 3.99-3.97 (m, 3H), 3.77-3.76 (m, 1H), 3.60-3.59 (m, 4H), 2.70-2.67 (m, 2H), 2.42-2.41 (m, 3H), 2.39-2.34 (m, 5H), 2.14-2.12 (m, 3H), 1.54-1.48 (m, 3H). MS(ESI) m/z 503.2 [M+H]⁺.

Example 87: Preparation of N-((4,6-dimethyl-2-oxo-1,2-dihydropyridin-3-yl)methyl)-6-methyl-5-(1-morpholinoethyl)-2-(thiazol-5-yl)indolizine-7-carboxamide: Same as Example 50

Step 1: Preparation of ethyl 5-acetyl-6-methyl-2-(1-methyl-1H-imidazol-5-yl)indolizine-7-carboxylate, yield 80%. MS (ESI) m/z 326 [M+H]⁺.

Compound 87

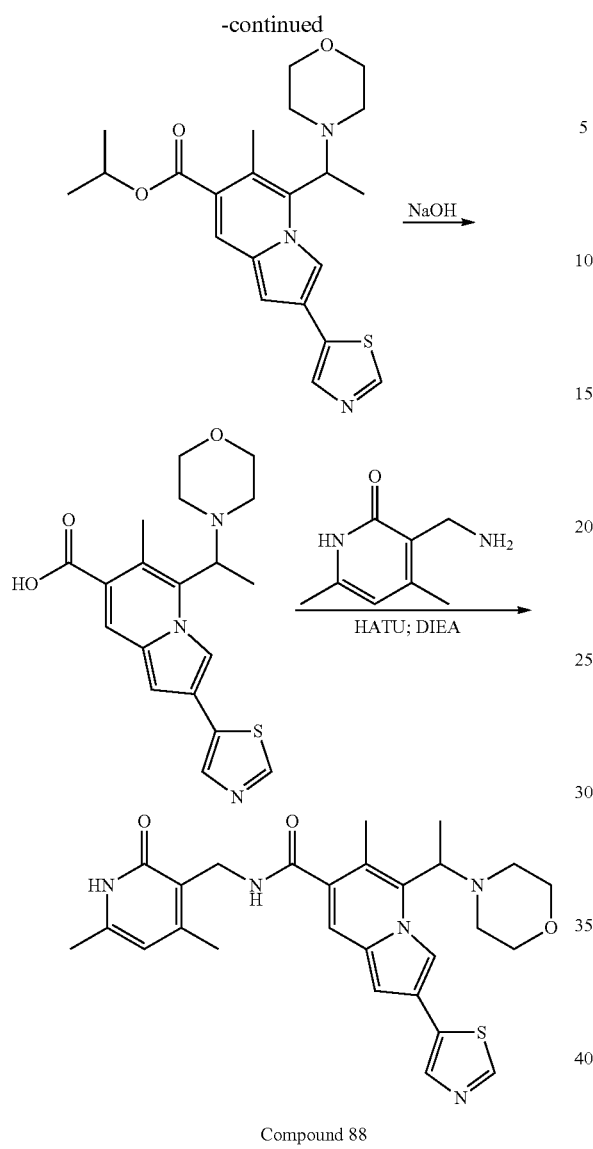

Compound 88

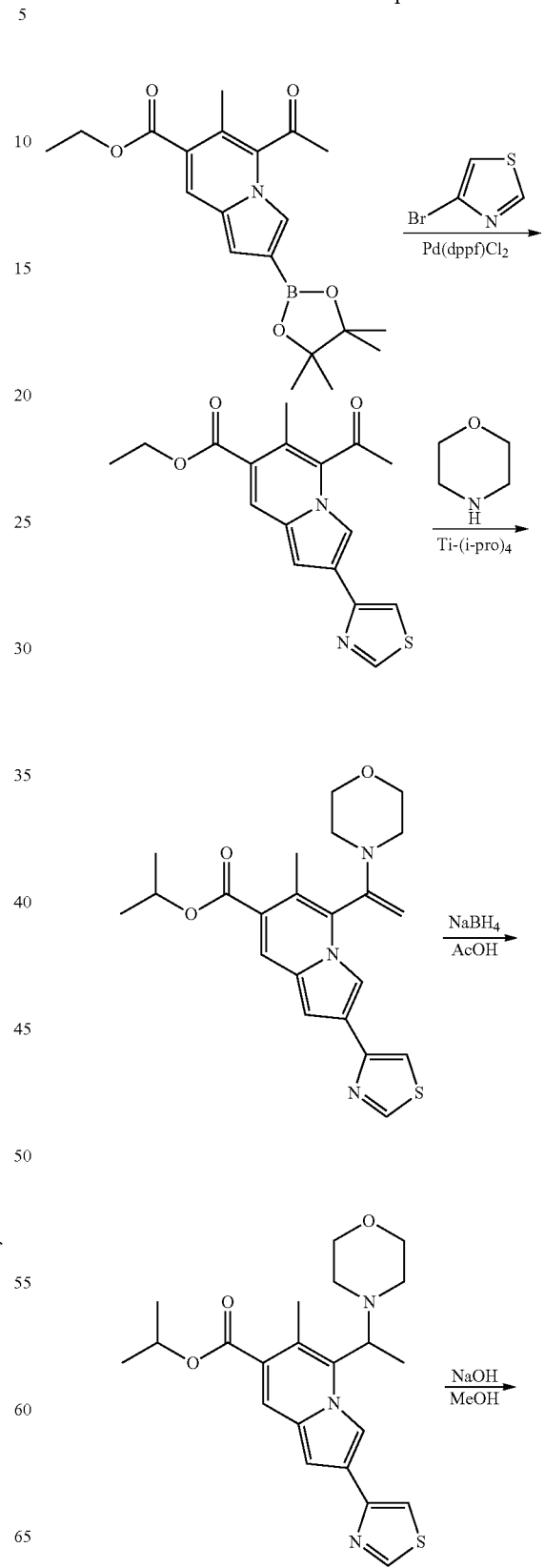

Example 88: Preparation of N-((4,6-dimethyl-2-oxo-1,2-dihydropyridin-3-yl)methyl)-6-methyl-5-(1-morpholinylethyl)-2-(thiazol-4-yl)indolizine-7-amide: Same as Example 50

Step 1: Preparation of ethyl 5-methyl-6-methyl-2-(thiazol-5-yl)indolizine-7-carboxylate: Yield 33%. MS (ESI) m/z 329 [M+H]$^+$.

Step 2: Preparation of isopropyl 6-methyl-5-(1-morpholinoethyl)-2-(thiazol-5-yl)indolizine-7-carboxylate: MS (ESI) m/z 412 [M+H]$^+$.

Step 3: Preparation of isopropyl 6-methyl-5-(1-morpholinoethyl)-2-(thiazol-5-yl)indolizine-7-carboxylate: yield of two steps was 63%. MS (ESI) m/z 414 [M+H]$^+$.

Step 4: Preparation of 6-methyl-5-(1-morpholinoethyl)-2-(thiazol-5-yl)indolizine-7-carboxylic acid: MS (ESI) m/z 372.3 [M+H]$^+$.

Step 5: Preparation of N-((4,6-dimethyl-2-oxo-1,2-dihydropyridin-3-yl)methyl)-6-methyl-5-(1-morpholinoethyl)-2-(thiazol-5-yl)indolizine-7-carboxamide: yield of two steps was 17%. 1—H-NMR (CDCl$_3$, 400 MHz): 11.83 (s, 1H), 8.69 (s, 2H), 7.99 (s, 1H), 7.28-7.30 (m, 2H), 6.59 (s, 1H), 6.96 (s, 1H), 4.53-4.52 (m, 2H), 4.06-4.01 (m, 1H), 3.69-3.68 (m, 4H), 2.65-2.64 (m, 2H), 2.39-2.34 (m, 6H), 2.26-2.23 (m, 5H). 1.50-1.49 (m, 3H); MS(ESI) m/z 506 [M+H]$^+$.

-continued

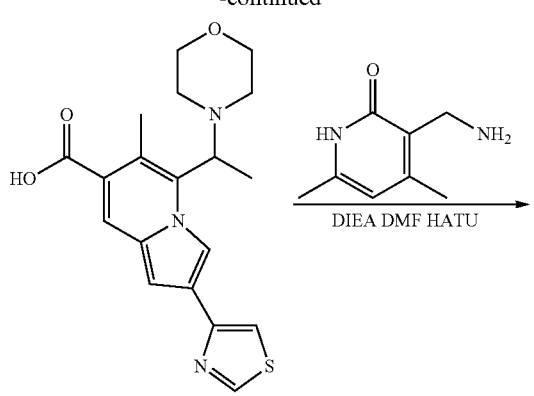

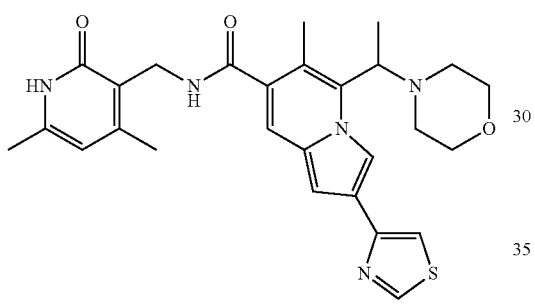

Compound 89

Step 1: Preparation of ethyl 5-acetyl-6-methyl-2-(thiazol-4-yl)indolizine-7-carboxylate: Yield 38%. MS (ESI) m/z 329 [M+H]+.

Step 2: Preparation of isopropyl 6-methyl-5-(1-morpholinylvinyl)-2-(thiazol-4-yl)indolizine-7-carboxylate: MS (ESI) m/z 406 [M+H]+.

Step 3: Preparation of isopropyl 6-methyl-5-(1-morpholinylethyl)-2-(thiazol-4-yl)indolizine-7-carboxylate: yield of two steps was 35%. MS (ESI) m/z 408 [M+H]+.

Step 4: Preparation of 6-methyl-5-(1-morpholineethyl)-2-(thiazol-4-yl)indolizine-7-carboxylic acid: MS (ESI) m/z 366 [M+H]+.

Step 5: Preparation of N-((4,6-dimethyl-2-oxo-1,2-dihydropyridin-3-yl)methyl)-6-methyl-5-(1-morpholinylethyl)-2-(thiazol-4-yl)indolizine-7-amide: 1H NMR (400 MHz, DMSO-d6) δ11.47 (s, 1H), 9.14-9.13 (d, J=1.6 Hz, 1H), 8.75 (s, 1H), 8.20-8.17 (m, 1H), 7.88 (d, J=1.2 Hz, 1H), 7.29 (s, 1H), 6.87 (s, 1H), 5.87 (s, 1H), 4.27-4.26 (m, 2H), 4.06-4.02 (m, 1H), 3.57 (m, 4H), 2.63 (m, 2H), 2.25 (s, 3H), 2.20-2.15 (m, 5H), 2.11 (s, 3H), 1.46-1.44 (m, 3H); MS(ESI) m/z 506 [M+H]+.

Example 89: Preparation of 2-(6-aminopyridin-3-yl)-N-((4,6-dimethyl-2-oxo-1,2-dihydropyridin-3-yl)methyl)-6-methyl-5-(1-morpholinylethyl)indolizine-7-amide: Same as Example 31

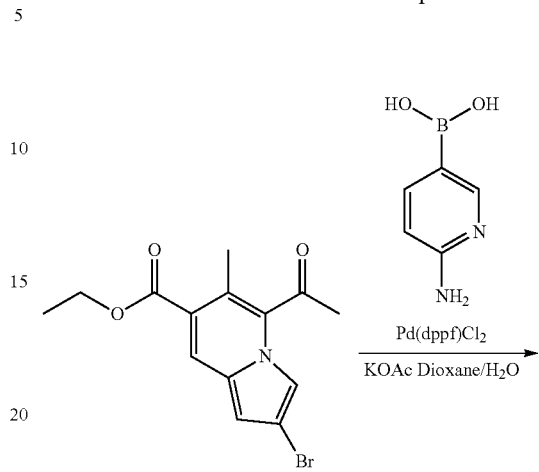

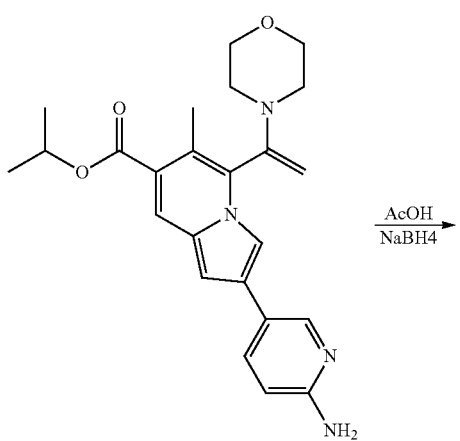

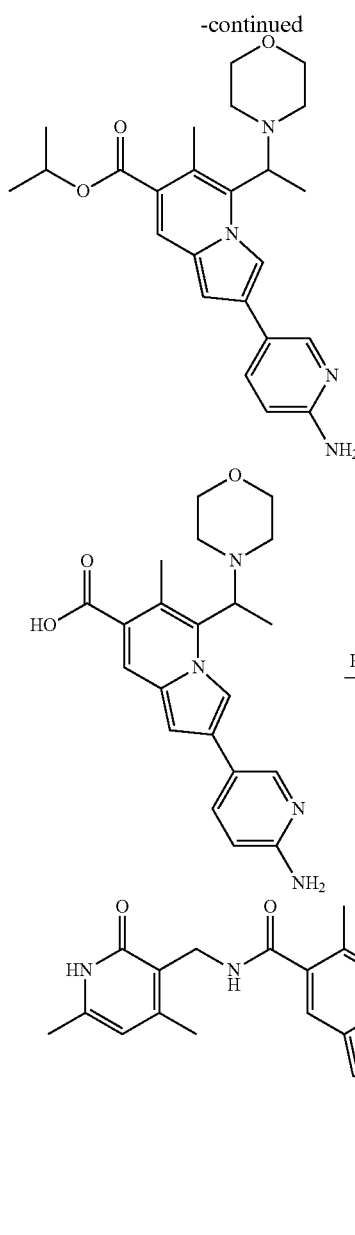

Compound 90

Step 1: Preparation of ethyl 5-acetyl-2-(6-aminopyridin-3-yl)-6-methylindolizine-7-carboxylate: Yield 71%. MS (ESI) m/z 338 [M+H]⁺.

Step 2: Preparation of isopropyl 2-(6-aminopyridin-3-yl)-6-methyl-5-(1-morphinolinylvinyl)indolizine-7-carboxylate: MS (ESI) m/z 421 [M+H]⁺.

Step 3: Preparation of isopropyl 2-(6-aminopyridin-3-yl)-6-methyl-5-(1-morphinolinylethyl)indolizine-7-carboxylate: yield of two steps was 50%. MS (ESI) m/z 423 [M+H]⁺.

Step 4: Preparation of 2-(6-aminopyridin-3-yl)-6-methyl-5-(1-morphinolinylethyl)indolizine-7-carboxylic acid: MS (ESI) m/z 381 [M+H]⁺.

Step 5: Preparation of 2-(6-aminopyridin-3-yl)-N-((4,6-dimethyl-2-oxo-1,2-dihydropyridin-3-yl)methyl)-6-methyl-5-(1-morpholinylethyl)indolizine-7-amide: ¹H NMR (400 MHz, DMSO-d₆) δ 11.47 (s, 1H), 8.69-8.67 (s, 1H), 8.32-8.26 (m, 2H), 8.20 (s, 1H), 7.96 (s, 2H), 7.28 (s, 1H), 7.07-7.05 (d, J=8.8 Hz, 1H), 6.84 (s, 1H), 5.87 (s, 1H), 4.27-4.26 (m, 2H), 4.07-4.05 (m, 1H), 3.59 (m, 4H), 2.26 (s, 3H), 2.33-2.20 (m, 5H), 2.11 (s, 3H), 1.48-1.46 (m, 3H); MS(ESI) m/z 515 [M+H]⁺.

Example 90: Preparation of N-((4,6-dimethyl-2-oxo-1,2-dihydropyridin-3-yl)methyl)-6-methyl-5-(1-morphinolinylethyl)-2-(6,-1-tetrahydropyridin-3-yl)indolizine-7-carboxamide: Same as Example 44

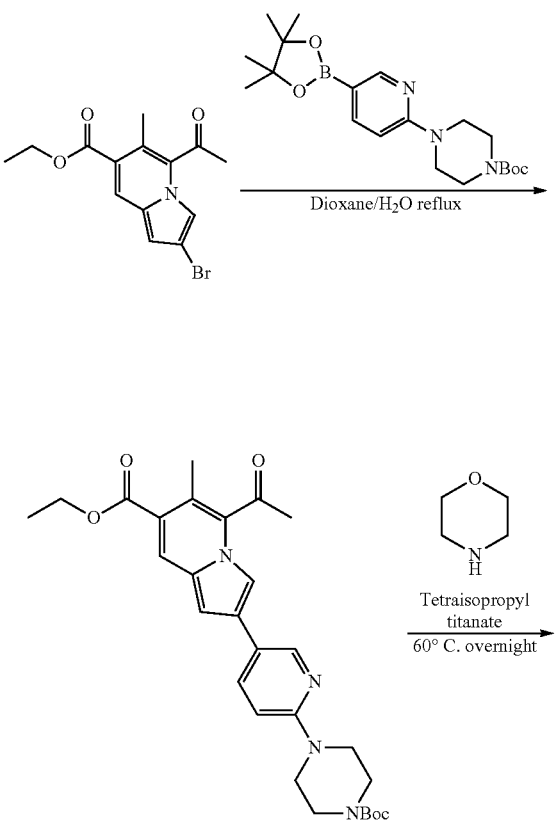

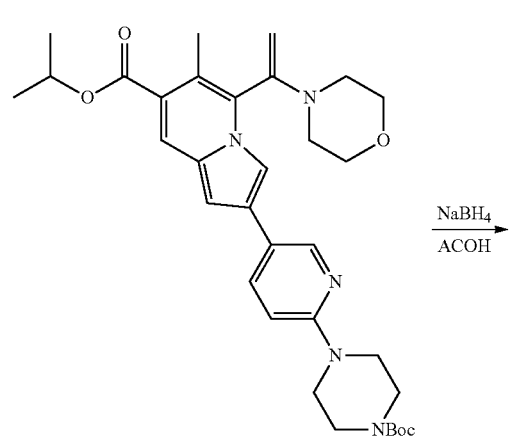

231

-continued

232

-continued

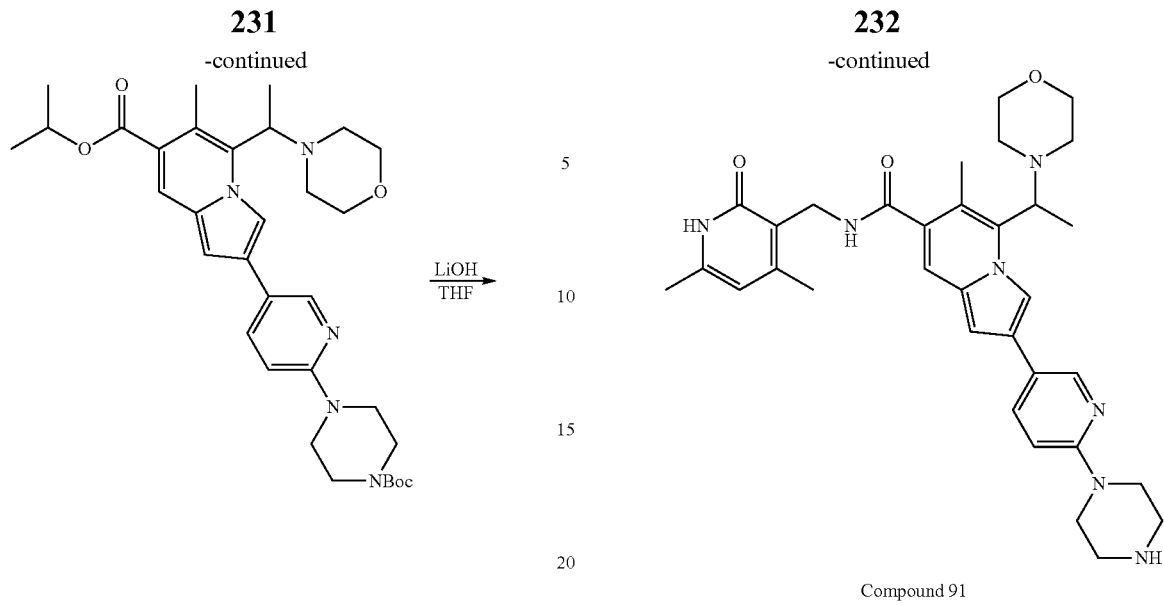

Compound 91

Step 1: Preparation of ethyl 5-acetyl-2-(6-(4-(tert-butoxy-carbonyl)piperazin-1-yl)pyridin-3-yl)-6-methylindolizine-7-carboxylate: Yield 65%. MS (ESI) m/z 507 [M+H]⁺.

Step 2: Preparation of isopropyl 2-(6-(4-(tert-butoxycarbonyl)piperazin-1-yl)pyridin-3-yl)-6-methyl-5-(1-morpholinovinyl)indolizine-7-carboxylate: MS (ESI) m/z 589 [M+H]⁺.

Step 3: Preparation of isopropyl 2-(6-(4-(tert-butoxycarbonyl)piperazin-1-yl)pyridin-3-yl)-6-methyl-5-(1-morpholinoethyl)indolizine-7-carboxylate: yield of two steps was 54%. MS (ESI) m/z 591 [M+H]⁺.

Step 4: Preparation of 2-(6-(4-(tert-butoxycarbonyl)piperazin-1-yl)pyridin-3-yl)-6-methyl-5-(1-morpholinoethyl)indolizine-7-formic acid: MS (ESI) m/z 549 [M+H]⁺.

Step 5: Preparation of tert-butyl 4-(5-(7-((4,6-dimethyl-2-oxo-1,2-dihydropyridin-3-yl)methyl)carbamoyl)-6-methyl-5-(1-morpholinoethyl)indol-2-yl)pyridin-2-yl)piperazine-1-carboxylic acid: MS (ESI) m/z 684 [M+H]⁺.

Step 6: Preparation of N-((4,6-dimethyl-2-oxo-1,2-dihydropyridin-3-yl)methyl)-6-methyl-5-(1-morpholinoethyl)-2-(6-(piperazin-1-yl)pyridin-3-yl)indolizine-7-carboxamide: three-step yield was 6%. MS (ESI) m/z 584 [M+H]⁺.

Example 91: Preparation of N-((4,6-dimethyl-2-oxo-1,2-dihydropyridin-3-yl)methyl)-6-methyl-2-(6-(4-methylpiperazine)-1-yl)pyridin-3-yl)-5-(1-morpholinoethyl)indolizine-7-carboxamide

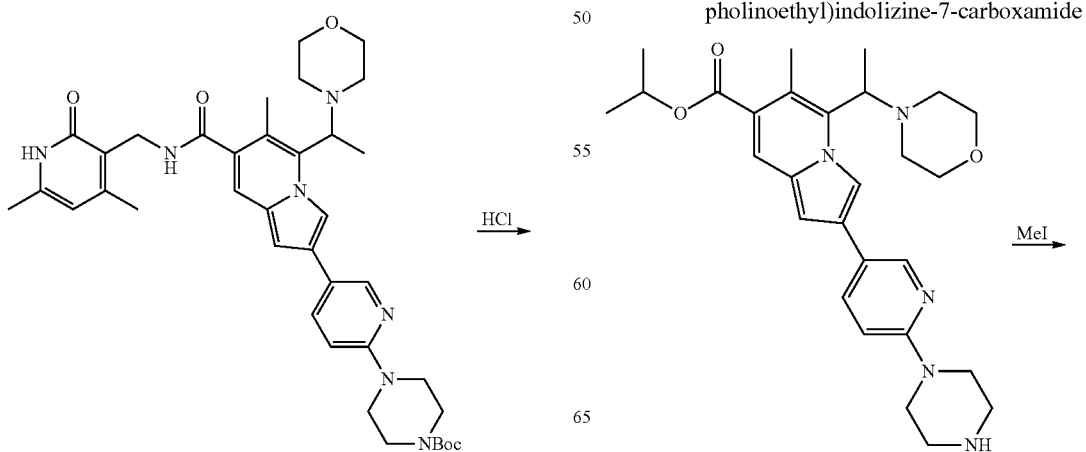

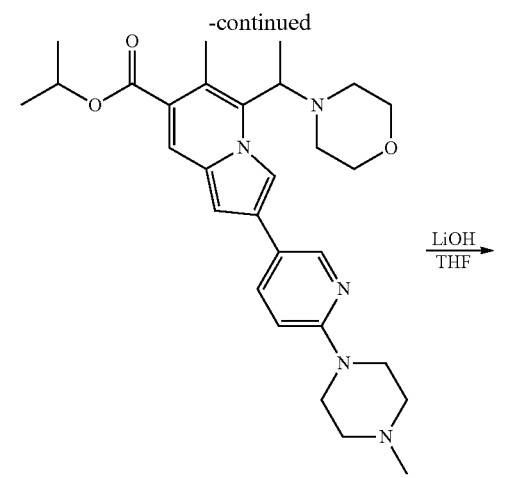

organic phase was separated and concentrated to provide a crude product (90 mg), which was used directly in the next step. MS (ESI) m/z 506 [M+H]+.

Step 2: Preparation of 6-methyl-2-(6-(4-methylpiperazin-1-yl)pyridin-3-yl)-5-(1-morpholinoethyl)indolizine-7-carboxylic acid: same as step 4 of example 31. MS (ESI) m/z 464 [M+H]+.

Example 3: Preparation of N-((4,6-dimethyl-2-oxo-1,2-dihydropyridin-3-yl)methyl)-6-methyl-2-(6-(4-methylpiperazine)-1-yl)pyridin-3-yl)-5-(1-morpholinoethyl)indolizine-7-carboxamide: Same as Step 5 of Example 31. Three-Step Yield was 3%

MS (ESI) m/z 598 [M+H]+.

Example 92: Preparation of N-((4,6-dimethyl-2-oxo-1,2-dihydropyridin-3-yl)methyl)-5-(1-(4-(dimethyl amino)piperidine-1-yl)ethyl)-6-methyl-2-(3,4,5-trimethoxyphenyl)-indolizine-7-carboxamide: Same as Example 31

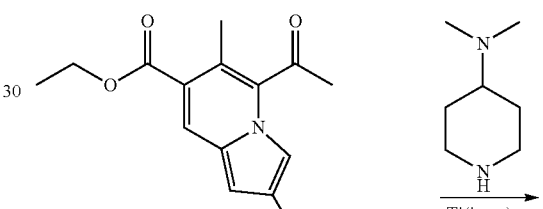

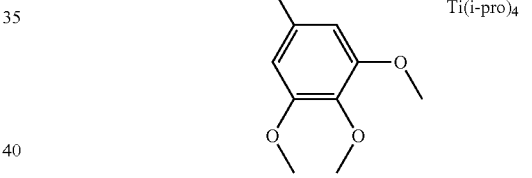

Compound 92

Step 1: Synthesis of isopropyl 6-methyl-2-(6-(4-methylpiperazin-1-yl)pyridin-3-yl)-5-(1-morpholinoethyl)indolizine-7-carboxylate: isopropyl 6-methyl-5-(1-morpholino)-2-(6-(piperazin-1-yl)pyridin-3-yl)indolizine-7-carboxylate (120 mg, 0.244 mmol) was added to a dry nitrogen-protected 100 ml single-mouth flask, cooled to 0° C., then NaH (24.4 mg, 0.61 mmol) was added, stirred at room temperature for 30 min, and then iodomethane (38.2 mg, 0.269 mmol) was added. The reaction was stirred at room temperature for 10 minutes, and 20 ml of ethyl acetate and 10 ml of water were added to the reaction system. The

235

-continued

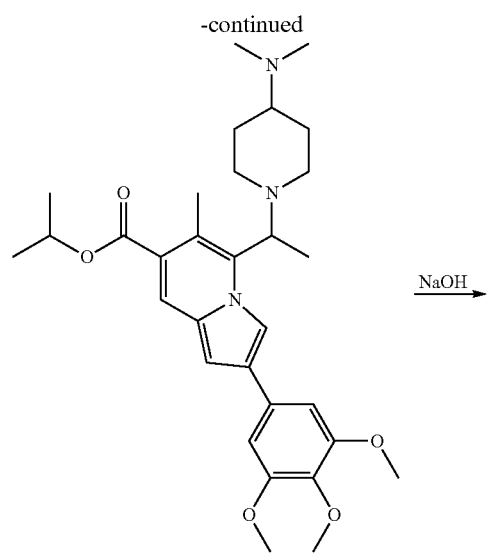

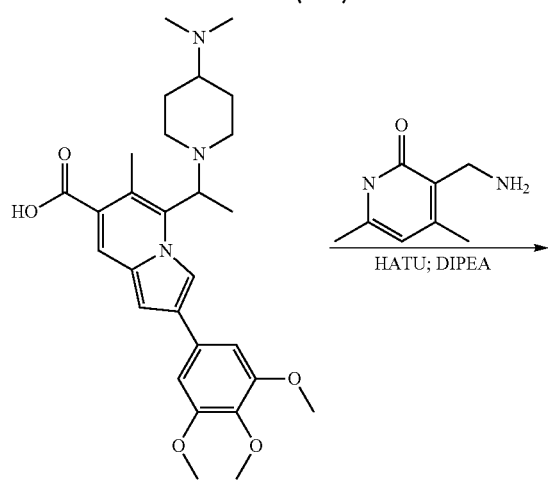

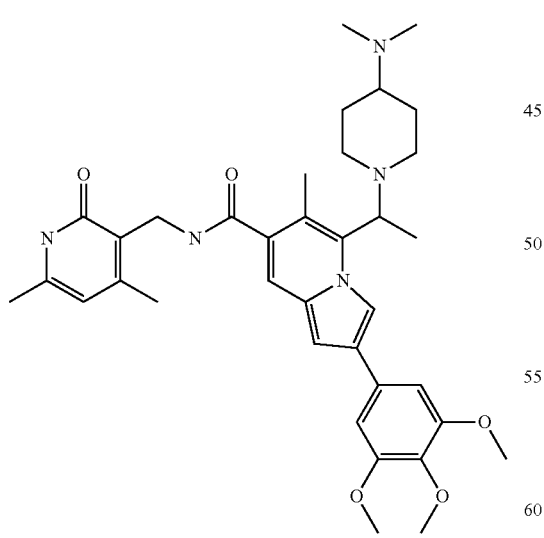

Compound 93

Step 1: Preparation of isopropyl 5-(1-(4-(dimethylamino) piperidin-1-yl)vinyl)-6-methyl-2-(3,4,5-trimethoxyphenyl)-indolizine-7-carboxylate: MS (ESI) m/z 536 [M+H]+.

236

Step 2: Preparation of isopropyl 5-(1-(4-(Dimethylamino) piperidin-1-yl)ethyl)-6-methyl-2-(3,4,5-trimethoxyphenyl)-indolizine-7-carboxylate: yield of two steps was 60%. MS (ESI) m/z 538 [M+H]+.

Step 3: Preparation of 5-(1-(4-(dimethylamino)piperidin-1-yl)ethyl)-6-methyl-2-(3,4,5-trimethoxyphenyl)-indolizine-7-carboxylic acid: MS (ESI) m/z 496.5 [M+H]+.

Step 4: Preparation of N-((4,6-dimethyl-2-oxo-1,2-dihydropyridin-3-yl)methyl)-5-(1-(4-(dimethyl amino)piperidine-1-yl)ethyl)-6-methyl-2-(3,4,5-trimethoxyphenyl)-indolizine-7-carboxamide: Yield of the two steps was 29%. $^1$H-NMR (CDCl$_3$, 400 MHz): 12.39 (s, 1H), 8.50 (s, 1H), 7.31-7.27 (m, 2H), 6.82-6.79 (m, 2H), 6.64 (s, 1H), 5.95 (s, 1H), 4.51 (s, 2H), 4.04-4.03 (m, 1H), 3.93 (s, 6H), 3.88 (s, 3H), 3.44 (s, 1H), 2.73-2.62 (m, 2H), 2.52 (s, 6H), 2.43 (s, 3H). 2.37 (s, 3H), 2.22 (m, 3H), 2.18-2.16 (m, 2H), 1.99-1.94 (m, 2H), 1.94-1.80 (m, 2H), 1.77-1.52 (m, 3H); MS(ESI) m/z 630 [M+H]+.

Example 93: Preparation of N-((4,6-dimethyl-2-oxo-1,2-dihydropyridin-3-yl)methyl)-5-(1-(4-(dimethyl amino)piperidine-1-yl)ethyl)-6-methyl-2-(pyridin-4-yl)indolizine-7-carboxamide: Same as Example 31

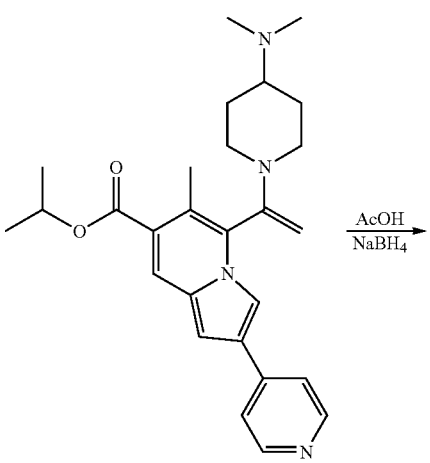

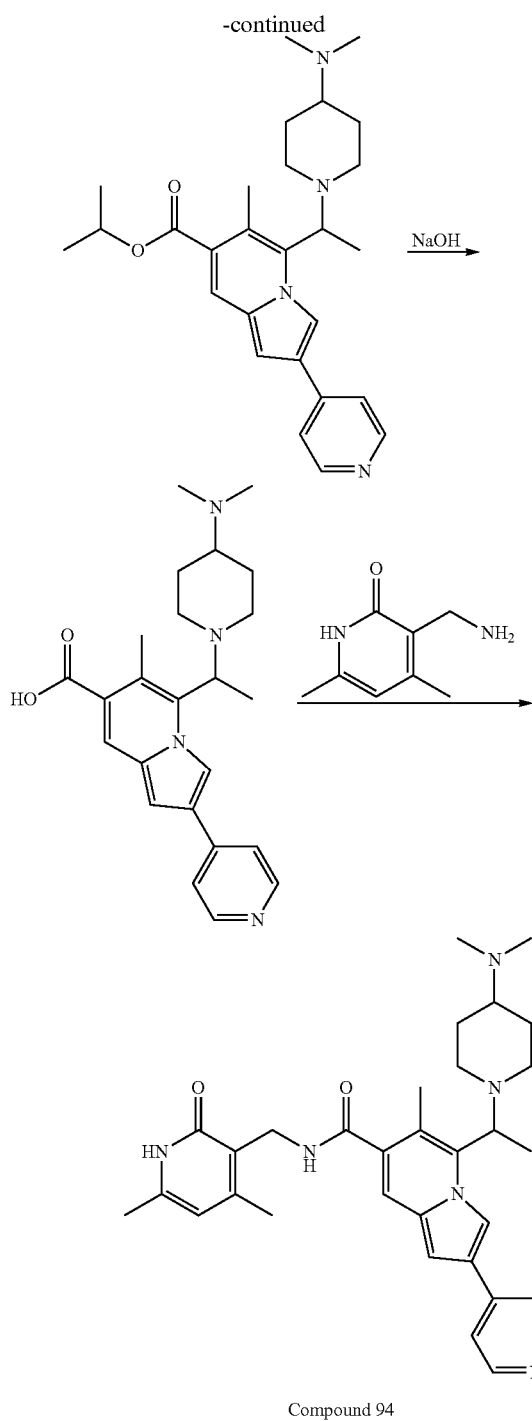

Compound 94

Step 1: Step 1: Preparation of isopropyl 5-(1-(4-(dimethylamino)piperidin-1-yl)ethylene)-6-methyl-2-(pyridin-4-yl)indolizine-7-carboxylate: MS (ESI) m/z 447 [M+H]⁺.

Step 2: Preparation of isopropyl 5-(1-(4-(dimethylamino)piperidin-1-yl)ethyl)-6-methyl-2-(pyridin-4-yl)indolizine-7-carboxylate: yield of two steps was 52%. MS (ESI) m/z 449 [M+H]⁺.

Step 3: Preparation of 5-(1-(4-(dimethylamino)piperidin-1-yl)ethyl)-6-methyl-2-(pyridin-4-yl)indolizine-7-carboxylic acid.

MS (ESI) m/z 407 [M+H]⁺.

Step 4: Preparation of N-((4,6-dimethyl-2-oxo-1,2-dihydropyridin-3-yl)methyl)-5-(1-(4-(dimethyl amino)piperidine-1-yl)ethyl)-6-methyl-2-(pyridin-4-yl)indolizine-7-carboxamide: yield of the two steps was 37%. I—H-NMR (MeOD, 400 MHz): 9.14 (s, 1H), 8.66-8.64 (m, 2H), 8.35-8.33 (m, 2H), 7.52 (s, 1H), 7.23 (s, 1H), 6.16 (s, 1H), 4.47 (s, 2H), 3.82-3.81 (s, 1H), 2.99-2.98 (m, 1H), 2.85-2.81 (m, 8H), 2.39 (s, 3H). 2.35 (s, 3H), 2.29-2.28 (m, 2H), 2.24-2.22 (m, 6H), 2.11-1.96 (m, 2H), 1.71-1.69 (m, 3H); MS(ESI) m/z 541.4 [M+H]⁺.

Example 94: Preparation of N-((4,6-dimethyl-2-oxo-1,2-dihydropyridin-3-yl)methyl)-6-methyl-5-(1-morpholinylethyl)-1-(3,5-dimethylphenyl)indolizine-7-amide: Same as Example 31

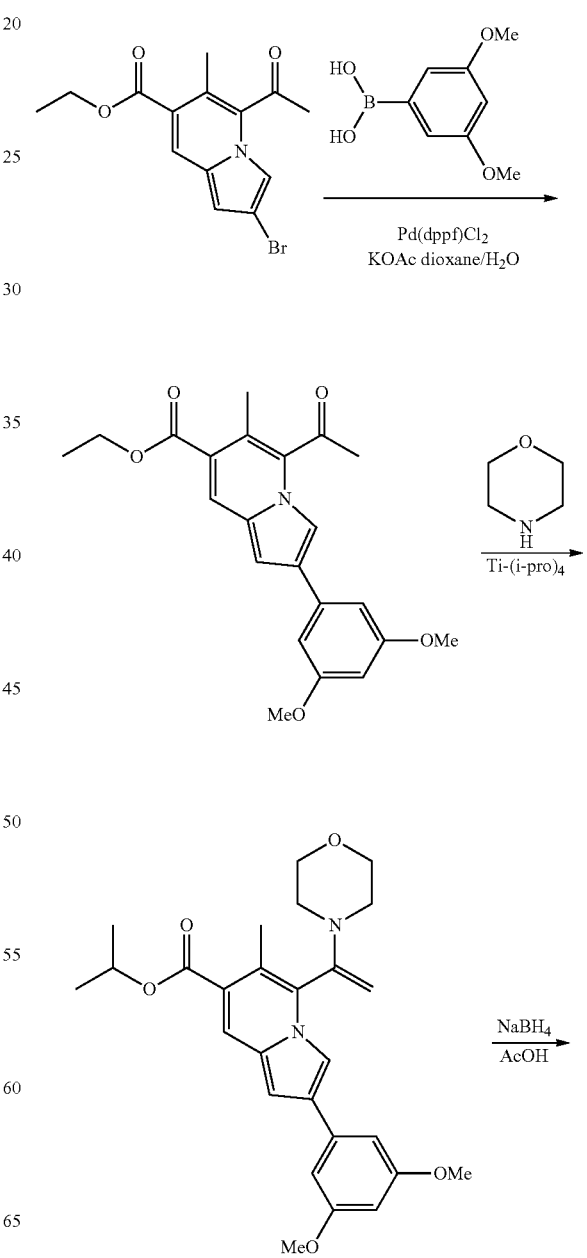

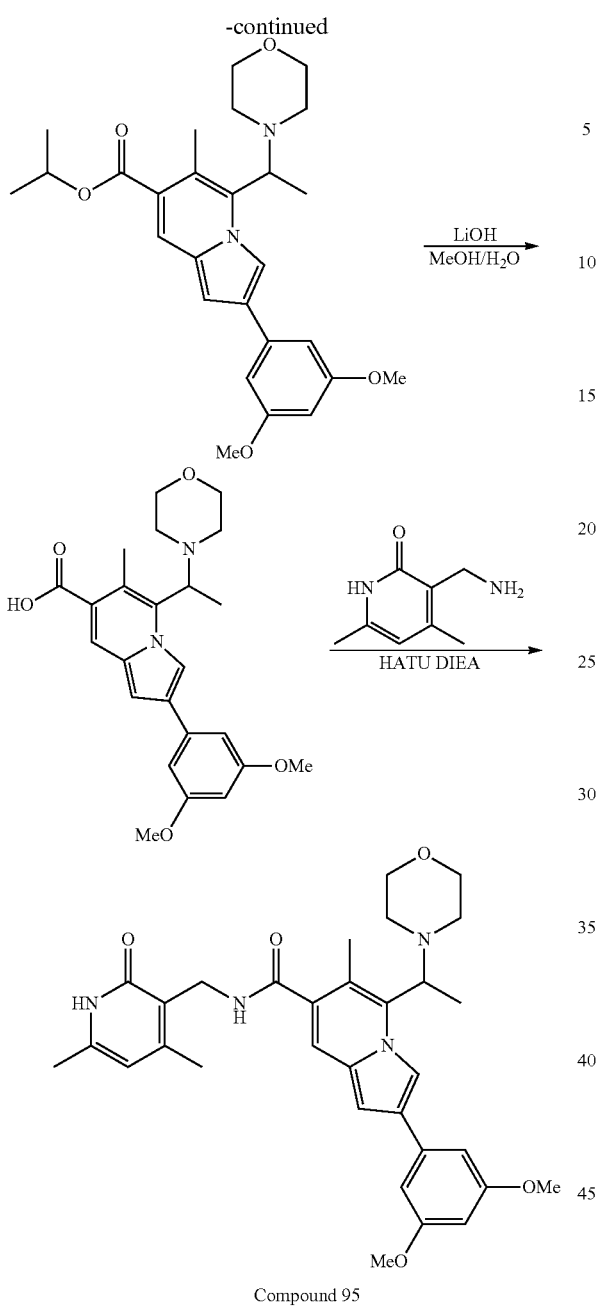

Compound 95

Step 1: Preparation of ethyl 5-acetyl-6-methyl-2-(3,5-dimethylphenyl)indolizine-7-carboxylate: yield 60%. MS (ESI) m/z 382 [M+H]+.

Step 2: Step 2: Preparation of isopropyl 6-methyl-5-(1-morpholinylvinyl)-1-(3,5-dimethylphenyl)indolizine-7-carboxylate. MS (ESI) m/z 465 [M+H]+.

Step 3: Step 3: Preparation of isopropyl 6-methyl-5-(1-morpholinylethyl)-1-(3,5-dimethylphenyl)indolizine-7-carboxylate: yield of two steps was 55%. MS (ESI) m/z 467 [M+H]+.

Step 4: Preparation of 6-methyl-5-(1-morpholinylethyl)-1-(3,5-dimethylphenyl)indolizine-7-carboxylic acid: MS (ESI) m/z 425 [M+H]+.

Step 5: Preparation of N-((4,6-dimethyl-2-oxo-1,2-dihydropyridin-3-yl)methyl)-6-methyl-5-(1-morpholinylethyl)-1-(3,5-dimethylphenyl)indolizine-7-carboxamide: yield of two steps was 6%. 1H NMR (400 MHz, CDCl3) δ11.56 (s, 1H), 8.62 (s, 1H), 7.66-7.64 (m, 1H), 7.47-7.45 (m, 1H), 6.73 (s, 2H), 6.60 (s, 1H), 6.32 (s, 1H), 5.88 (s, 1H), 4.45-4.44 (d, J=4.8 Hz, 2H), 4.03-4.01 (m, 1H), 3.79 (s, 6H), 3.62 (s, 4H), 2.58 (s, 2H), 2.32 (s, 3H), 2.27 (s, 3H), 2.20-2.13 (m, 5H), 1.43-1.41 (d, J=6.4 Hz, 2H); MS(ESI) m/z 559 [M+H]+.

Example 95: Preparation of N-((4,6-dimethyl-2-oxo-1,2-dihydropyridin-3-yl)methyl)-6-methyl-5-(1-morpholinylethyl)-1-(3,4-dimethylphenyl)indolizine-7-amide: Same as Example 31

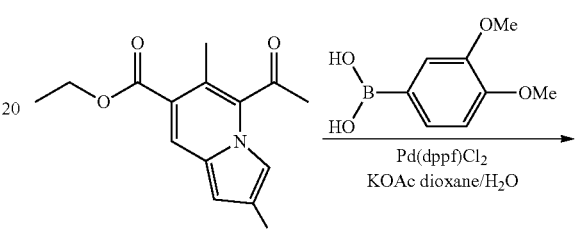

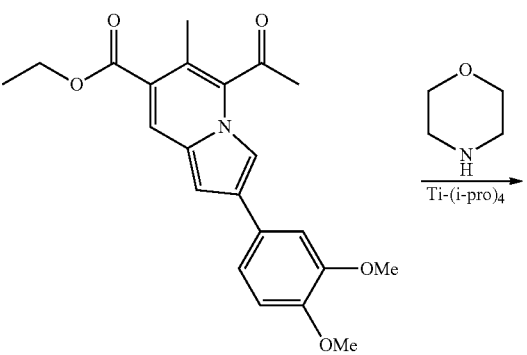

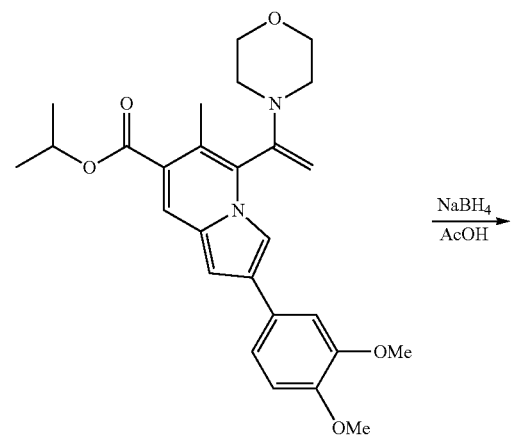

-continued

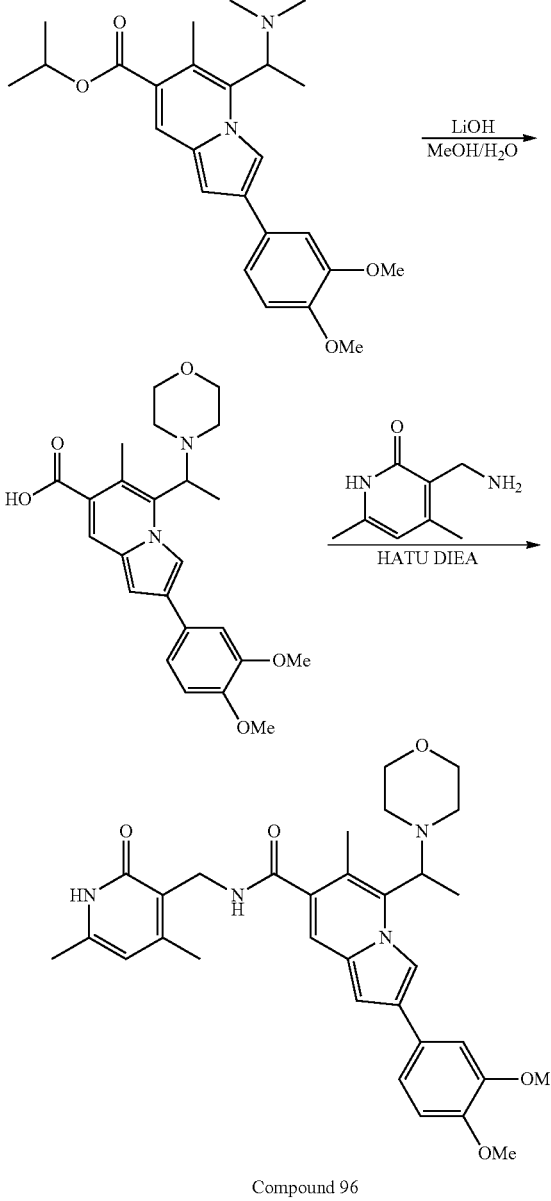

Compound 96

Step 1: Preparation of ethyl 5-acetyl-6-methyl-2-(3,4-dimethylphenyl)indolizine-7-carboxylate: yield 42%. MS (ESI) m/z 382 [M+H]+.

Step 2: Preparation of isopropyl 6-methyl-5-(1-morpholinylvinyl)-1-(3,4-dimethylphenyl)indolizine-7-carboxylate. MS (ESI) m/z 465 [M+H]+.

Step 3: Preparation of isopropyl 6-methyl-5-(1-morpholinylethyl)-1-(3,4-dimethylphenyl)indolizine-7-carboxylate: yield of two steps was 55%. MS (ESI) m/z 467 [M+H]+.

Step 4: Preparation of 6-methyl-5-(1-morphinolinyl-ethyl)-1-(3,4-dimethylphenyl)indolizine-7-carboxylic acid: MS (ESI) m/z 425 [M+H]+.

Step 5: Preparation of N-((4,6-dimethyl-2-oxo-1,2-dihydropyridin-3-yl)methyl)-6-methyl-5-(1-morpholinylethyl)-1-(3,4-dimethylphenyl)indolizine-7-carboxamide: yield of two steps was 13%. $^1$H NMR (400 MHz, CDCl$_3$) δ11.08 (s, 1H), 8.59 (s, 1H), 7.25 (s, 1H), 7.15-7.13 (m, 2H), 7.11 (s, 1H), 7.08 (s, 1H), 6.86-6.84 (d, J=8.4 Hz, 1H), 6.57 (s, 1H), 5.88 (s, 1H), 4.45-4.44 (d, J=4.4 Hz, 2H), 4.01-3.95 (m, 1H), 3.89 (s, 3H), 3.85 (s, 3H), 3.63 (s, 3H), 2.59 (s, 2H), 2.33 (s, 3H), 2.27 (s, 3H), 2.21-2.15 (m, 5H), 1.44-1.42 (d, J=6.4 Hz, 3H); MS(ESI) m/z 559 [M+H]+.

Example 96: Preparation of N-((4,6-dimethyl-2-oxo-1,2-dihydropyridin-3-yl)methyl)-2-(3-methoxyphenyl)-6-methyl-5-(1-morpholino)indolizine-7-carboxamide: Same as Example 31

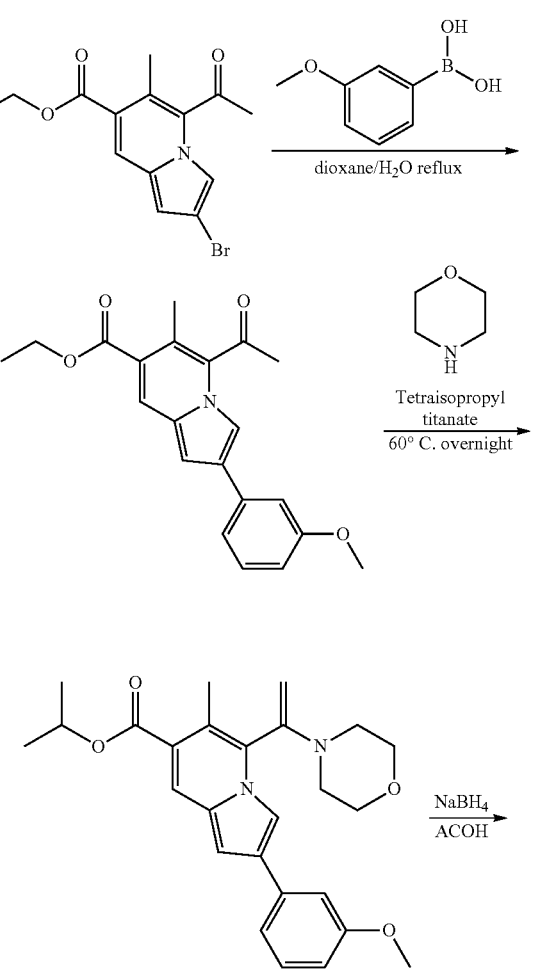

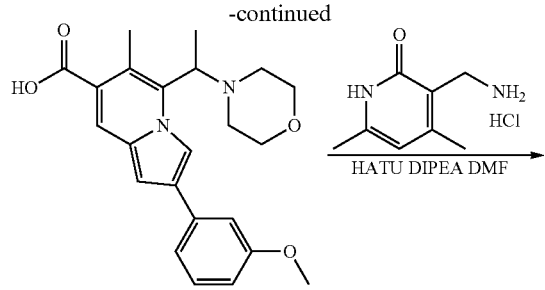

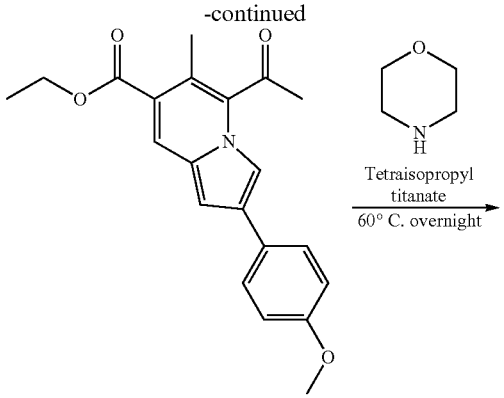

Compound 97

Step 1: Preparation of ethyl 5-acetyl-2-(3-methoxyphenyl)-6-methylindolizine-7-carboxylate: Yield 72%. MS(ESI) m/z 352 [M+H]⁺.

Step 2: Preparation of isopropyl 2-(3-methoxyphenyl)-6-methyl-5-(1-morpholinylvinyl)indolizine-7-carboxylate: MS (ESI) m/z 435 [M+H]⁺.

Step 3: Preparation of isopropyl 2-(3-methoxyphenyl)-6-methyl-5-(1-morpholinylethyl)indolizine-7-carboxylate: yield of two steps was 52%. MS (ESI) m/z 437 [M+H]⁺.

Step 4: Preparation of 2-(3-methoxyphenyl)-6-methyl-5-(1-morpholinylethyl)indolizine-7-carboxylic acid: MS (ESI) m/z 395 [M+H]⁺.

Step 5: Preparation of N-((4,6-dimethyl-2-oxo-1,2-dihydropyridin-3-yl)methyl)-2-(3-methoxyphenyl)-6-methyl-5-(1-morpholinylethyl)indolizine-7-carboxamide: Yield 50%. $^1$H-NMR (DMSO, 400 MHz): 11.48 (s, 1H), 8.23 (s, 1H), 8.19 (s, 1H), 7.35-7.23 (m, 4H), 6.85 (m, 2H), 5.88 (s, 1H), 4.28-4.27 (m, 2H), 3.85 (s, 6H), 3.60 (m, 5H), 2.28 (s, 3H), 2.21 (s, 3H), 2.19 (s, 3H), 1.55-1.54 (m, 3H); MS(ESI) m/z 529 [M+H]⁺.

Example 97: Preparation of N-((4,6-dimethyl-2-oxo-1,2-dihydropyridin-3-yl)methyl)-2-(4-methoxyphenyl)-6-methyl-5-(1-morpholinoethyl)indolizine-7-carboxamide: Same as Example 31

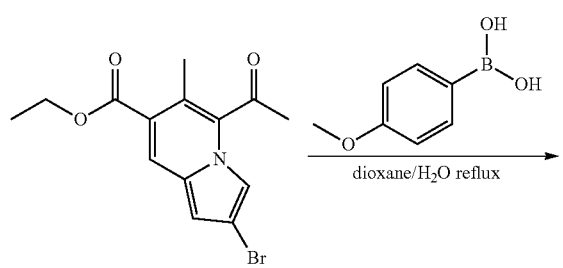

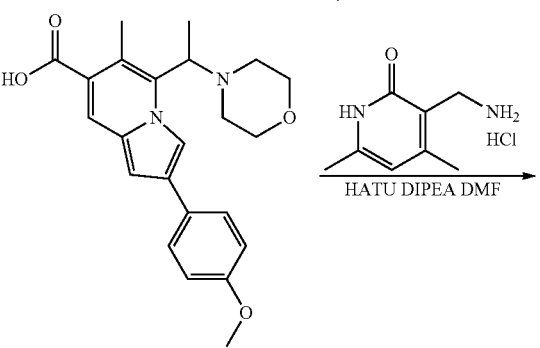

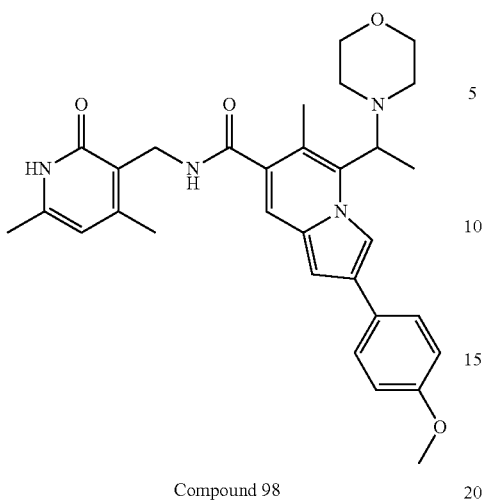

Compound 98

Step 1: Preparation of ethyl 5-acetyl-2-(4-methoxyphenyl)-6-methylindolizine-7-carboxylate: Yield 60%. MS (ESI) m/z 352 [M+H]⁺.

Step 2: Preparation of isopropyl 2-(4-methoxyphenyl)-6-methyl-5-(1-morpholinylvinyl)indolizine-7-carboxylate: MS (ESI) m/z 435 [M+H]⁺.

Step 3: Preparation of isopropyl 2-(4-methoxyphenyl)-6-methyl-5-(1-morpholinylethyl)indolizine-7-carboxylate: yield of two steps was 41%. MS (ESI) m/z 437 [M+H]⁺.

Step 4: Preparation of 2-(4-methoxyphenyl)-6-methyl-5-(1-morpholinylethyl)indolizine-7-carboxylic acid: MS (ESI) m/z 395 [M+H]⁺.

Step 5: Preparation of N-((4,6-dimethyl-2-oxo-1,2-dihydropyridin-3-yl)methyl)-2-(4-methoxyphenyl)-6-methyl-5-(1-morpholinylethyl)indolizine-7-carboxamide: Yield of two steps was 7%. 1H-NMR (CDCl₃, 400 MHz): 11.69 (s, 1H), 8.65 (s, 1H), 7.77 (s, 1H), 7.67-7.66 (m, 2H), 7.32 (s, 1H), 6.96-6.94 (m, 2H), 6.63 (s, 1H), 5.94 (s, 1H), 4.52 (m, 2H), 4.09 (m, 1H), 3.85 (s, 3H), 3.60 (m, 4H), 2.67 (s, 2H), 2.28 (s, 3H), 2.21 (s, 3H), 2.15 (m, 5H), 1.52 (m, 3H); MS(ESI) m/z 529 [M+H]⁺.

Example 98: Preparation of N-((4,6-dimethyl-2-oxo-1,2-dihydropyridin-3-yl)methyl)-6-methyl-5-(1-(4-methylpiperazine)-1-ethyl)-2-bromoindolizine-7-carboxamide: Same as Example 30

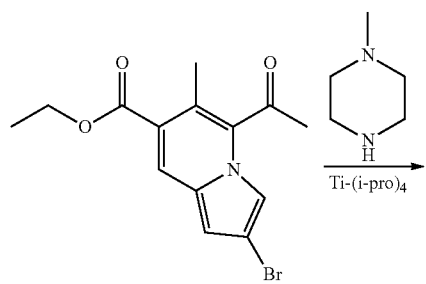

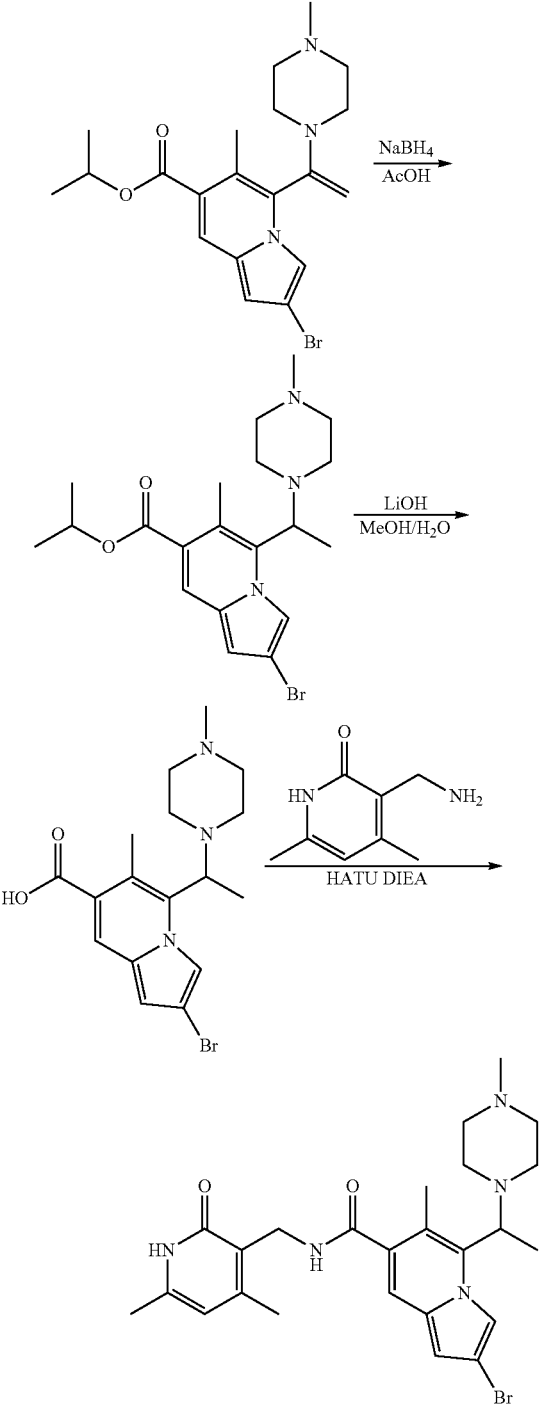

Compound 99

Step 1: Step 1: Preparation of isopropyl 6-methyl-5-(1-(4-methylpiperazine)-1-vinyl)-2-bromoindolizine-7-carboxylate: MS (ESI) m/z 420 [M+H]⁺.

Step 2: Step 6: Preparation of isopropyl 6-methyl-5-(1-(4-methylpiperazine)-1-ethyl)-2-bromoindolizine-7-carboxylate: yield of two steps was 87%. MS (ESI) m/z 424 [M+H]⁺.

Step 3: Step 1: Preparation of 6-methyl-5-(1-(4-methylpiperazine)-1-ethyl)-2-bromoindolizine-7-carboxylic acid: MS (ESI) m/z 380 [M+H]⁺.

Step 4: Preparation of N-((4,6-dimethyl-2-oxo-1,2-dihydropyridin-3-yl)methyl)-6-methyl-5-(1-(4-methylpiperazine)-1-ethyl)-2-bromoindolizine-7-carboxamide: yield 8%.
$^1$H NMR (400 MHz, CDCl$_3$) δ8.11 (s, 1H), 7.28-7.23 (m, 1H), 6.77 (s, 1H), 6.40 (s, 1H), 5.90 (s, 1H), 5.86 (s, 1H), 4.50-4.35 (m, 1H), 4.23-4.22 (d, J=5.6 HZ, 2H), 3.64-3.58 (m, 4H), 3.08-3.02 (m, 4H), 2.32 (s, 3H), 2.25 (s, 3H), 2.20 (s, 3H), 2.17 (s, 3H), 1.48-1.44 (m, 3H); MS(ESI) m/z 536 [M+H]$^+$.

Example 99: Preparation of N-((4,6-dimethyl-2-oxo-1,2-dihydropyridin-3-yl)methyl)-6-methyl-5-(1-(4-ethylpiperazine)-1-ethyl)-2-bromoindolizine-7-carboxamide: Same as Example 30

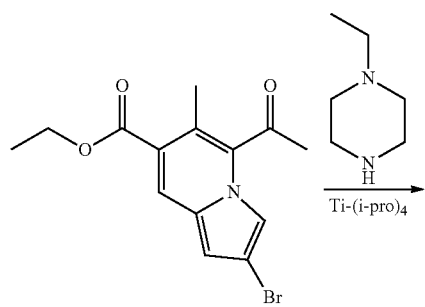

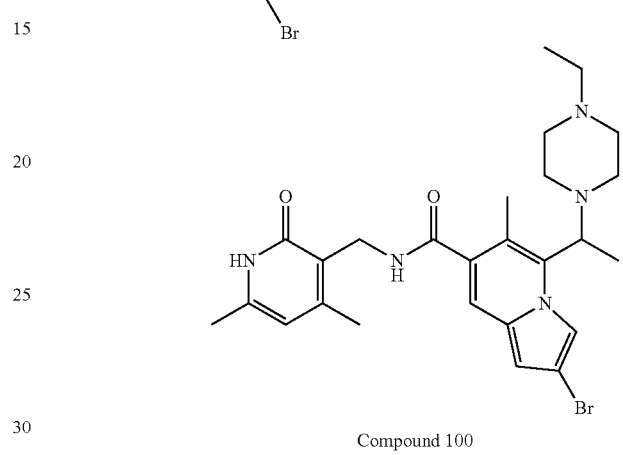

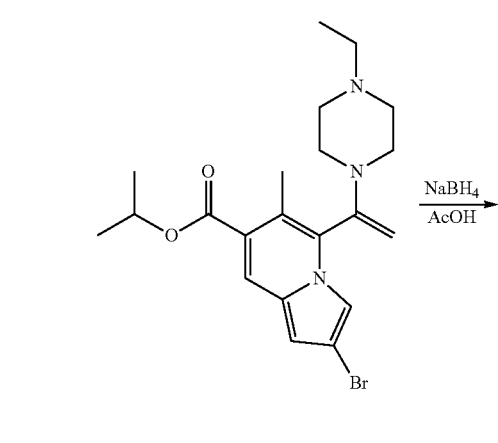

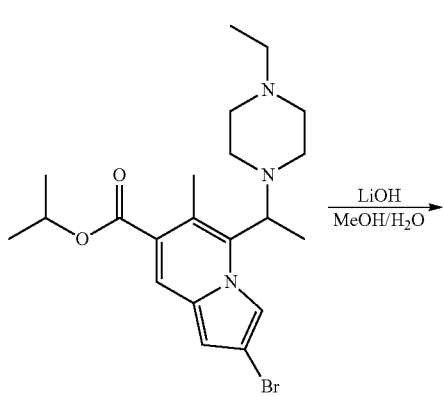

Compound 100

Step 1: Preparation of isopropyl 6-methyl-5-(1-(4-ethylpiperazine)-1-vinyl)-2-bromoindolizine-7-carboxylate: MS (ESI) m/z 434 [M+H]$^+$.

Step 2: Preparation of isopropyl 6-methyl-5-(1-(4-ethylpiperazine)-1-ethyl)-2-bromoindolizine-7-carboxylate: yield of two steps was 99%.
MS (ESI) m/z 436 [M+H]$^+$.

Step 3: Preparation of 6-methyl-5-(1-(4-ethylpiperazine)-1-ethyl)-2-bromoindolizine-7-carboxylic acid: MS (ESI) m/z 394 [M+H]$^+$.

Step 4: Preparation of N-((4,6-dimethyl-2-oxo-1,2-dihydropyridin-3-yl)methyl)-6-methyl-5-(1-(4-ethylpiperazine)-1-ethyl)-2-bromoindolizine-7-carboxamide: yield of two steps was 60%. $^1$H NMR (400 MHz, MeOD) δ 7.35 (s, 1H), 6.57 (s, 1H), 6.14 (s, 1H), 4.46 (s, 2H), 4.22-4.17 (m, 1H), 3.67-3.63 (d, J=13.2 Hz, 1H), 3.58-3.55 (m, 2H), 3.40-3.37 (d, J=12.4 Hz, 1H), 3.25-3.19 (m, 4H), 2.45-2.38 (m, 5H), 2.31 (s, 3H), 2.25 (s, 3H), 1.55-1.53 (d, J=6.8 Hz, 3H), 1.34-1.31 (t, J=7.6 Hz, 3H); MS(ESI) m/z 552 [M+H]$^+$.

Example 100: Preparation of 2-bromo-N-((4,6-dimethyl-2-oxo-1,2-dihydropyridin-3-yl)methyl)-6-methyl-5-(1-(piperazine)-1-yl)ethyl)indolizine-7-carboxamide

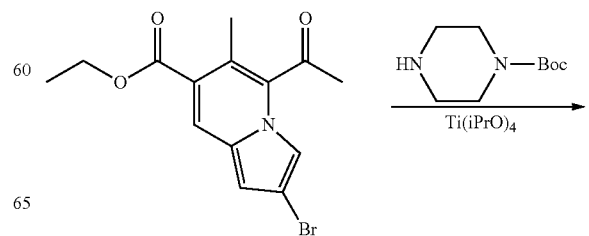

249
-continued

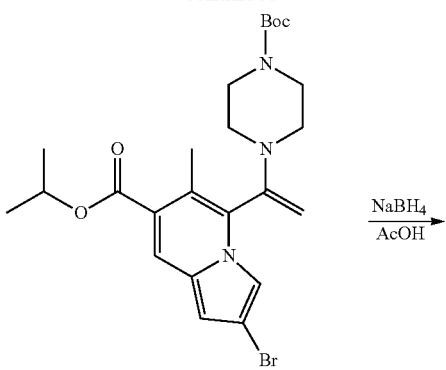

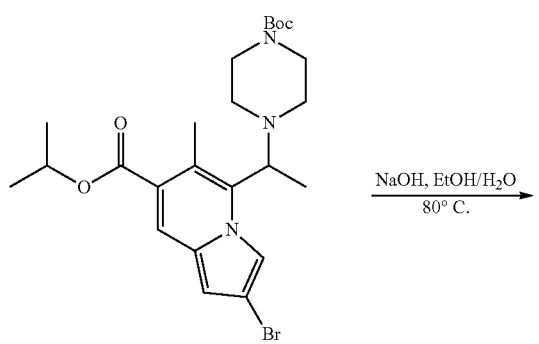

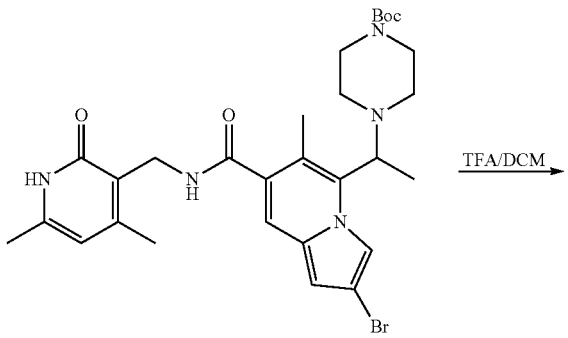

250
-continued

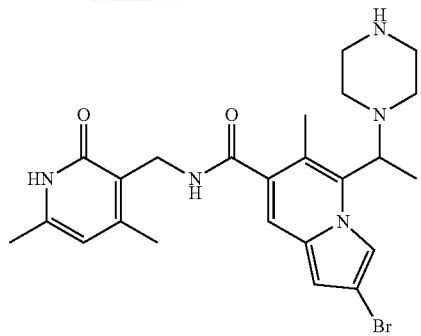

Compound 101

Step 1: Preparation of isopropyl 2-bromo-5-(1-(4-(tert-butoxycarbonyl)piperazin-1-yl)vinyl)-6-methylindolizine-7-carboxylate: same as step 1 of example 30. MS (ESI) m/z 506 [M+H]+.

Step 2: Preparation of isopropyl 2-bromo-5-(1-(4-(tert-butoxycarbonyl)piperazin-1-yl)ethyl)-6-methylindolizine-7-carboxylate: same as step 2 of example 30. Yield of two steps was 33%. MS (ESI) m/z 508 [M+H]+.

Step 3: Preparation of 2-bromo-5-(1-(4-(tert-butoxycarbonyl)piperazin-1-yl)ethyl)-6-methylindolizine-7-carboxylic acid: same as step 3 of example 30. MS (ESI) m/z 466 [M+H]+.

Step 4: Preparation of tert-butyl 4-(1-(2-(2,6-dimethyl-2-oxo-1,2-dihydropyridin-3-yl)methyl)aminocarbonyl)-6-methylindolizine-5-yl)ethyl)piperazine-1-carboxylate: same as step 4 of example 30. Yield of two steps was 40%. MS (ESI) m/z 600 [M+H]+.

Step 5: Preparation of 2-bromo-N-((4,6-dimethyl-2-oxo-1,2-dihydropyridin-3-yl)methyl)-6-methyl-5-(1-(piperazine)-1-yl)ethyl)indolizine-7-carboxamide: same as step 5 of example 60. Yield: 53%. 1H-NMR (CDCl3, 400 MHz): 7.34 (s, 1H), 6.57 (s, 1H), 6.12 (s, 1H), 4.64 (s, 2H), 4.19-4.18 (m, 1H), 3.22-3.17 (m, 4H), 2.93-2.90 (m, 2H), 2.55-2.45 (m, 2H), 2.41 (s, 3H), 2.30 (s, 3H), 2.24 (s, 3H), 1.51 (d, 3H, J=6.7 Hz); MS(ESI) m/z 500 [M+H]+.

Example 101: Preparation of 5-(1-(4-methylpiperazin-1-yl)ethyl)-2-bromo-N-((4,6-dimethyl-2-oxo-1,2-dihydropyridine-3-yl)methyl)-6-methylindolizine-7-carboxamide

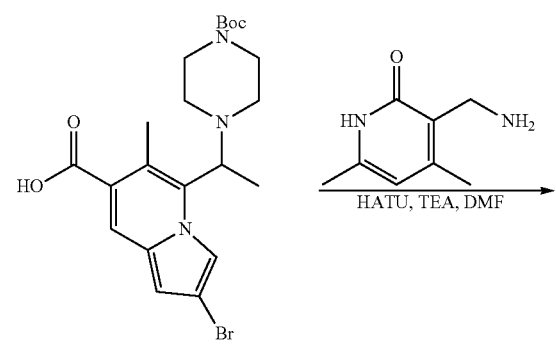

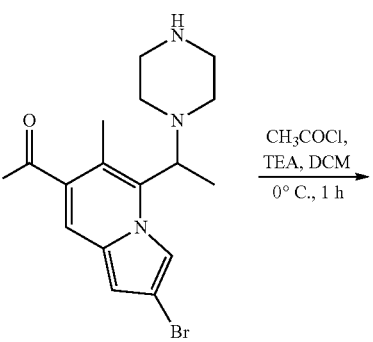

251

-continued

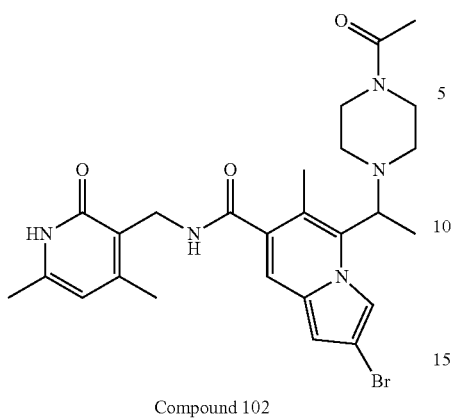

Compound 102

Step 1: Preparation of 5-(1-(4-methylpiperazin-1-yl) ethyl)-2-bromo-N-((4,6-dimethyl-2-oxo-1,2-dihydropyridin-3-yl)methyl)-6-methylindolizine-7-carboxamide: In a 50 ml dry single-mouth bottle, compound 2-bromo-N-((4,6-dimethyl-2-oxo-1,2-dihydropyridin-3-yl)methyl)-6-methyl-5-(1-(piperazin-1-yl)ethyl)indolizine-7-carboxamide (38 mg, 0.076 mmol) was dissolved in dichloromethane (3 mL), acetyl chloride (140 mg, 1.8 mmol), triethylamine (180 mg, 1.8 mmol) were added and stirred at room temperature for 1 hour. The reaction mixture was separated and purified by preparative purification. The solvent was evaporated under reduced pressure and lyophilized to afford white solids (32 mg, yield: 78%). $^1$H-NMR (CDCl$_3$, 400 MHz): 8.37 (br, 1H), 7.24 (s, 1H), 6.82 (s, 1H), 6.58 (s, 1H), 6.39 (s, 1H), 4.54-4.52 (m, 2H), 4.02-3.97 (m, 1H), 3.82-3.79 (m, 1H), 3.47-3.36 (m, 3H), 2.93-2.84 (m, 4H), 2.56 (s, 3H), 2.42 (s, 3H), 2.27 (s, 3H), 2.06 (s, 3H), 1.49 (d, J=6.7 Hz, 3H); MS(ESI) m/z 542 [M+H]$^+$.

Example 102: Preparation of 2-bromo-N-((4,6-dimethyl-2-oxo-1,2-dihydropyridin-3-yl)methyl)-5-(1-(4-(2-hydroxyacetyl) piperazin-1-yl)ethyl)-6-methylindolizine-7-carboxamide

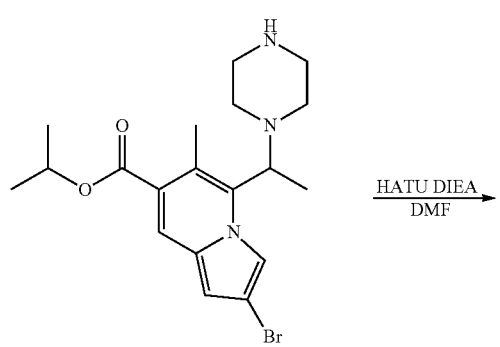

252

-continued

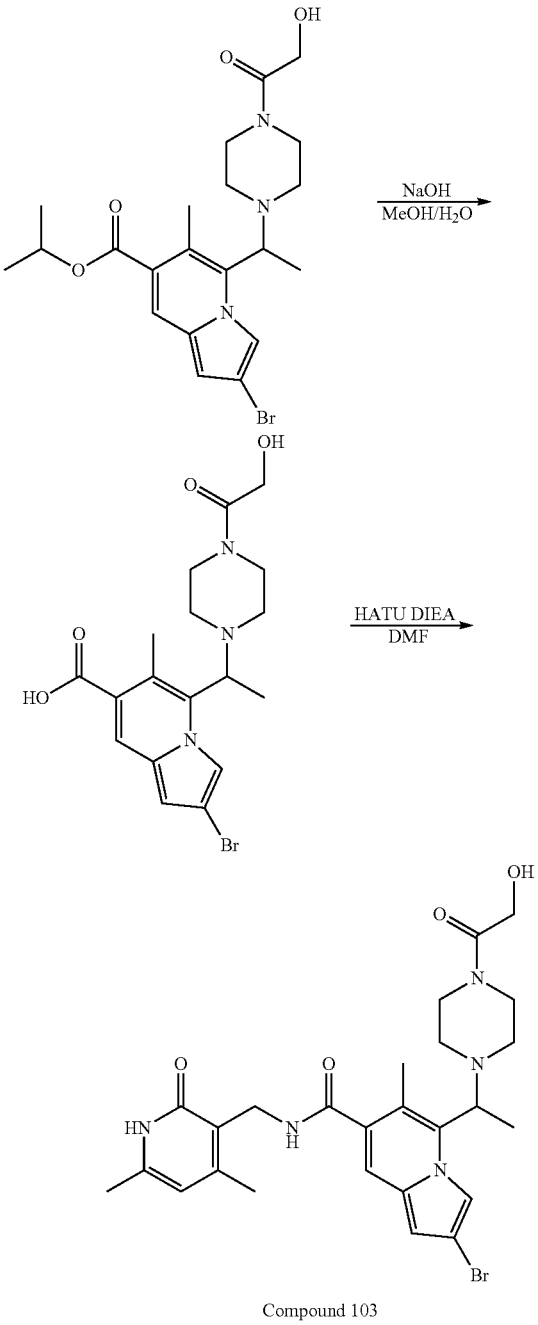

Compound 103

Step 1: Preparation of isopropyl 2-bromo-5-(1-(4-(2-hydroxyacetyl)piperazin-1-yl)ethyl)-6-methylindolizine-7-carboxylate: same as step 1 of example 102, yield: 48%. MS (ESI) m/z 466 [M+H]$^+$.

Step 2: Preparation of 2-bromo-5-(1-(4-(2-hydroxyacetyl) piperazin-1-yl)ethyl)-6-methylindolizine-7-carboxylic acid: same as step 4 of example 31. MS (ESI) m/z 424 [M+H]$^+$.

Step 3: Preparation of 2-bromo-N-((4,6-dimethyl-2-oxo-1,2-dihydropyridin-3-yl)methyl)-5-(1-(4-(2-hydroxyacetyl) piperazin-1-yl)ethyl)-6-methylindolizine-7-carboxamide: same as step 5 of example 31, yield 5%. $^1$H NMR (400 MHz, DMSO-d$_6$) δ ppm 8.41 (s, 1H), 7.31 (s, 1H), 6.54 (s, 1H), 6.10 (s, 1H), 4.75 (s, 2H), 4.58 (s, 2H), 4.20 (s, 1H), 3.58-3.71 (m, 3H), 3.19-3.24 (m, 2H), 2.36 (s, 3H), 2.28-2.20 (m, 8H), 2.11 (s, 3H), 1.37-1.32 (m, 3H); MS(ESI) m/z 560 [M+H]⁺.

Example 103: Preparation of 2-bromo-N-((4,6-dimethyl-2-oxo-1,2-dihydropyridin-3-yl)methyl)-6-methyl-5-(1-(4-(methylsulfonyl)piperazin-1-yl)ethyl)indolizine-7-carboxamide: Same as Example 102

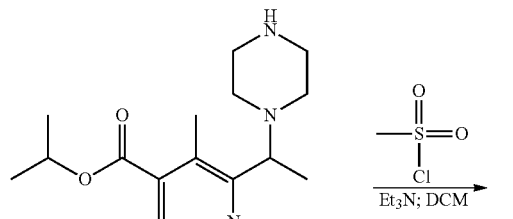

-continued

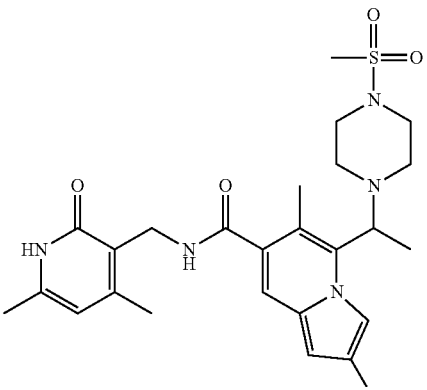

Compound 104

Step 1: Preparation of isopropyl 2-bromo-6-methyl-5-(1-(4-(methylsulfonyl)piperazin-1-yl)ethyl)indolizine-7-carboxylate: yield 91%. MS (ESI) m/z 488 [M+H]⁺.

Step 2: 2-bromo-6-methyl-5-(1-(4-(methylsulfonyl)piperazin-1-yl)ethyl)indolizine-7-carboxylic acid: yield 91%. MS (ESI) m/z 444 [M+H]⁺.

Step 3: Preparation of 2-bromo-N-((4,6-dimethyl-2-oxo-1,2-dihydropyridin-3-yl)methyl)-6-methyl-5-(1-(4-(methylsulfonyl)piperazin-1-yl)ethyl)indolizine-7-carboxamide: yield 29%. ¹H-NMR (DMSO-d₆, 400 MHz): 8.28 (s, 1H), 8.24-8.21 (m, 1H), 7.27 (s, 1H), 6.61 (s, 1H), 5.88 (s, 1H), 4.27-4.26 (m, 2H), 4.11-4.10 (m, 1H), 3.12-3.11 (m, 4H), 2.89 (s, 3H), 2.89-2.88 (m, 2H), 2.24-2.21 (m, 5H). 2.21-2.20 (m, 3H), 2.12 (s, 3H), 1.44-1.42 (m, 3H); MS(ESI) m/z 580 [M+H]⁺.

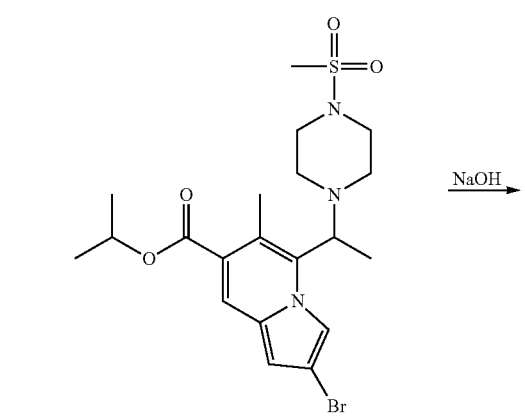

Example 104: Preparation of N-((4,6-dimethyl-2-oxo-1,2-dihydropyridin-3-yl)methyl)-6-methyl-5-(1-(4-ethylsulfonyl) piperazine)-1-ethyl)-2-bromoindolizine-7-carboxamide: Same As Example 102

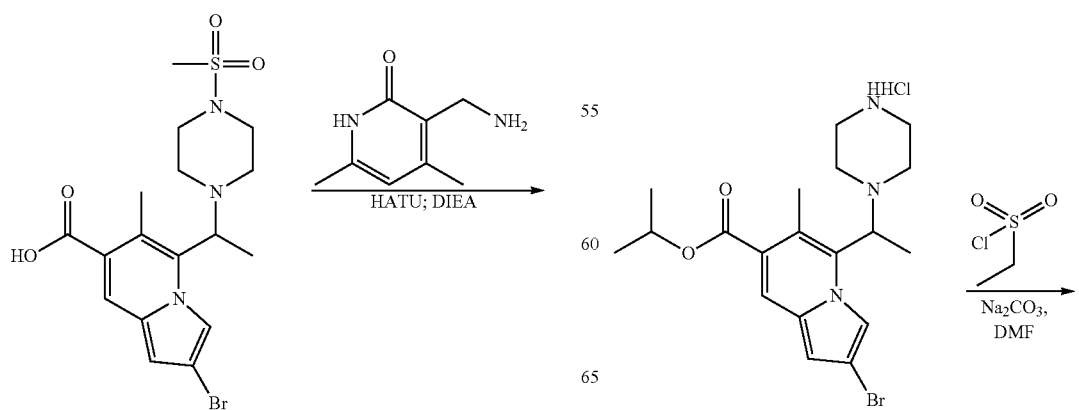

255
-continued

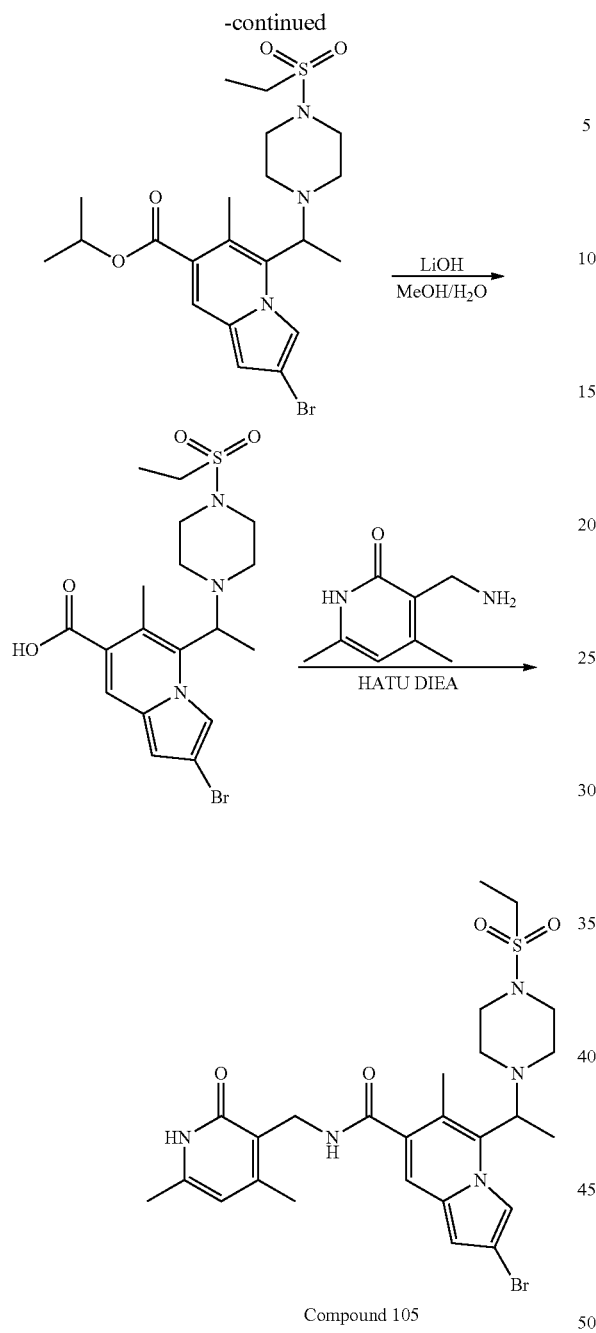

Compound 105

Step 1: Preparation of isopropyl 6-methyl-5-(1-(4-ethylsulfonylpiperazine)-1-ethyl)-2-bromoindolizine-7-carboxylate: yield 88%. MS (ESI) m/z 500 [M+H]+.

Step 2: Preparation of 6-methyl-5-(1-(4-ethylsulfonylpiperazine)-1-ethyl)-2-bromoindolizine-7-carboxylic acid: yield 76%. MS (ESI) m/z 458 [M+H]+.

Step 3: Preparation of N-((4,6-dimethyl-2-oxo-1,2-dihydropyridin-3-yl)methyl)-6-methyl-5-(1-(4-ethylsulfonylpiperazine)-1-ethyl)-2-bromoindolizine-7-carboxamide: yield 88%. $^1$H NMR (400 MHz, MeOD) δ 7.97 (s, 1H), 7.39 (s, 1H), 6.61 (s, 1H), 6.23 (s, 1H), 4.46 (s, 1H), 3.10-3.03 (m, 1H), 2.99 (s, 1H), 2.40 (s, 3H), 2.32 (m, 3H), 2.28 (s, 3H), 1.38-1.34 (m, 7H), 1.33-1.29 (m, 3H); MS(ESI) m/z 592 [M+H]+.

256

Example 105: Preparation of 2-bromo-N-((4,6-dimethyl-2-oxo-1,2-dihydropyridin-3-yl)methyl)-6-methyl-5-(1-(4-(3,3,3-trifluoropropyl)piperazin-1-yl)ethyl)indolizine-7-carboxamide

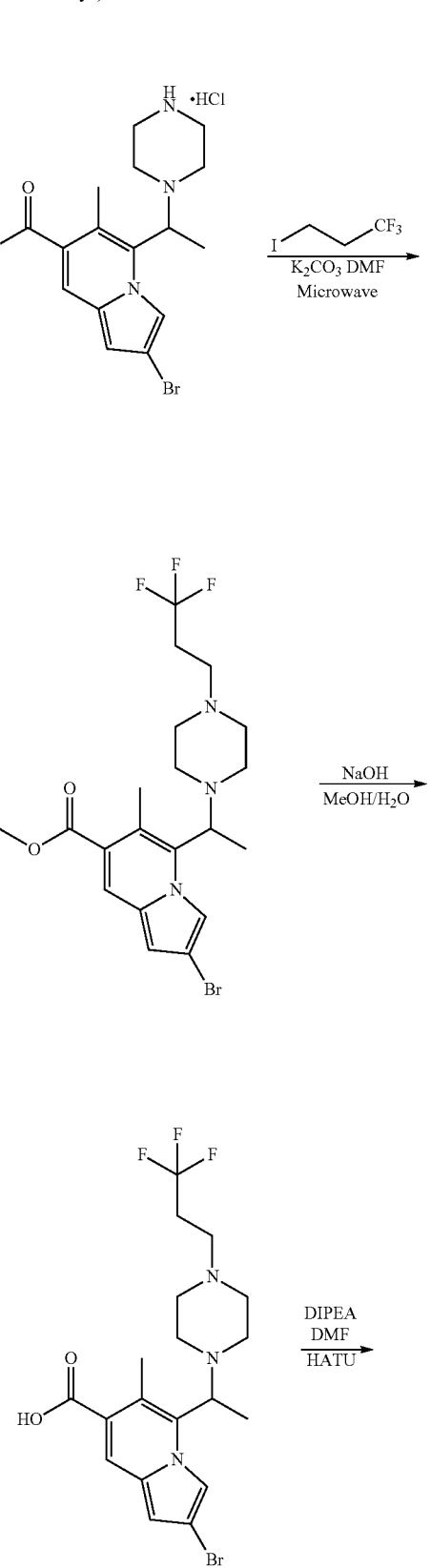

-continued

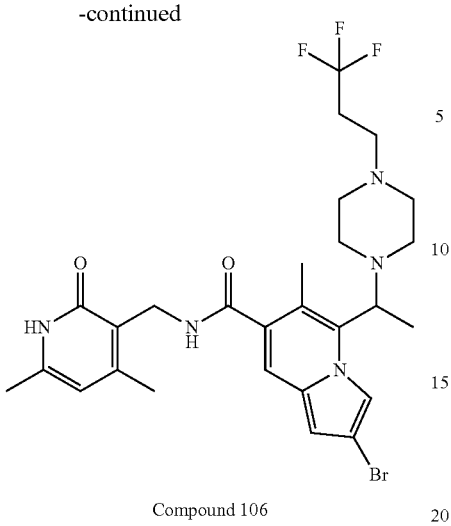

Compound 106

Step 1: Preparation of ethyl 2-bromo-6-methyl-5-(1-(4-(3,3,3-trifluoropropyl)piperazin-1-yl)ethyl)indolizine-7-carboxylate: in a 100 ml dry single-mouth flask, isopropyl 2-bromo-6-methyl-5-(1-(piperazine-1-ethyl)ethyl)indolizine-7-carboxylate hydrochloride (170 mg, 0.38 mmol) was dissolved in N,N-dimethylformamide (10 mL), and 1,1,1-trifluoro-3-iodopropane (170 mg, 0.76 mmol), potassium carbonate (157 mg, 1.14 mmol) were added, the mixture was microwave-stirred at 100° C. for 2 hours, water was added, and extracted with ethyl acetate (50×3 mL). The combined organic phase was dried over anhydrous sodium sulfate, filtrated, and solvent was removed under reduced pressure to give a yellow oil (120 mg, 63%), MS (ESI) m/z 504 [M+H]$^+$.

Step 2: Synthesis of 2-bromo-6-methyl-5-(1-(4-(3,3,3-trifluoropropyl)piperazin-1-yl)ethyl)indolizine-7-carboxylic acid: same as step 2 of example 102. MS (ESI) m/z 462 [M+H]$^+$.

Step 3: Preparation of 2-bromo-N-((4,6-dimethyl-2-oxo-1,2-dihydropyridin-3-yl)methyl)-6-methyl-5-(1-(4-(3,3,3-trifluoropropyl)piperazin-1-yl)ethyl)indolizine-7-carboxamide: same as step 3 of example 102. Yield: 56%. $^1$H NMR (400 MHz, DMSO-d$_6$) δ 11.47 (s, 1H), 8.24-8.20 (m, 2H), 7.29 (s, 1H), 6.63 (s, 1H), 5.88 (s, 1H), 4.27-4.26 (m, 2H), 4.15-4.13 (m, 1H), 3.59 (m, 3H), 3.48-3.42 (m, 2H), 3.33-2.81 (m, 4H), 2.26 (s, 3H), 2.35 (s, 3H), 2.25 (s, 6H), 2.12 (s, 3H), 1.45-1.44 (m, 3H); MS(ESI) m/z 596 [M+H]$^+$.

Example 106: Preparation of N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-pyrazol-5-yl)indolizine-7-carboxamide: Same as Example 31

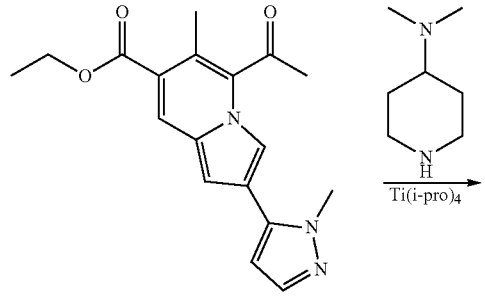

-continued

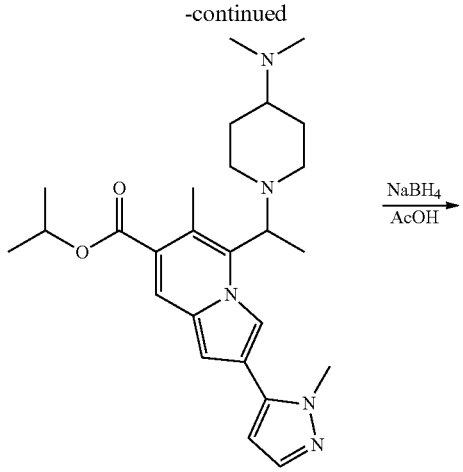

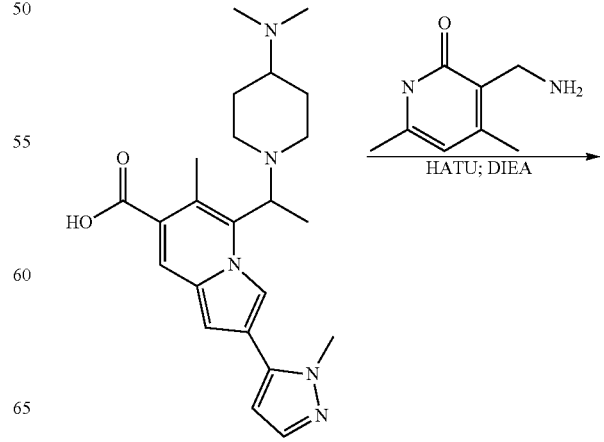

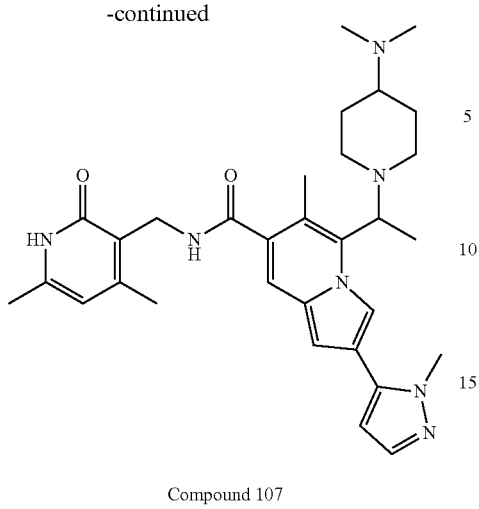

Compound 107

Step 1: Step 1: Preparation of isopropyl 5-(1-(4-(dimethylamino)piperidin-1-yl)vinyl)-6-methyl-2-(1-methyl-1H-pyrazol-5-yl)indolizine-7-carboxylate: MS (ESI) m/z 450 [M+H]$^+$.

Step 2: Preparation of isopropyl 5-(1-(4-(dimethylamino)piperidin-1-yl)ethyl)-6-methyl-2-(1-methyl-1H-pyrazol-5-yl)indolizine-7-carboxylate: yield of two steps was 51%. MS (ESI) m/z 452 [M+H]$^+$.

Step 3: Preparation of 5-(1-(4-(dimethylamino)piperidin-1-yl)ethyl)-6-methyl-2-(1-methyl-1H-pyrazol-5-yl)indolizine-7-carboxylic acid: MS (ESI) m/z 410.5 [M+H]$^+$.

Step 4: Preparation of N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-pyrazol-5-yl)indolizine-7-carboxamide: Yield of the two steps was 20%. $^1$H-NMR (DMSO-d$_6$, 400 MHz): 11.54 (s, 1H), 9.45-9.44 (m, 1H), 8.68-8.67 (m, 1H), 8.23 (s, 1H), 7.43-7.32 (m, 2H), 6.78-6.75 (m, 1H), 6.43 (s, 1H), 5.88 (s, 1H), 4.28-4.26 (m, 2H), 4.18 (m, 3H), 3.43-3.42 (m, 1H), 2.78-2.73 (m, 8H), 2.38-2.36 (m, 3H), 2.26-2.21 (m, 5H). 2.16-2.14 (m, 6H), 1.96-1.94 (m, 2H), 1.75-1.73 (m, 2H); MS(ESI) m/z 544 [M+H]$^+$.

Example 107: Preparation of N-((4,6-dimethyl-2-oxo-1,2-dihydropyridin-3-yl)methyl)-5-(1-(4-(dimethyl amino)piperidine-1-yl)ethyl)-6-methyl-2-(1-methyl-1H-pyrazol-2-yl)indolizine-7-carboxamide: Same as Example 50

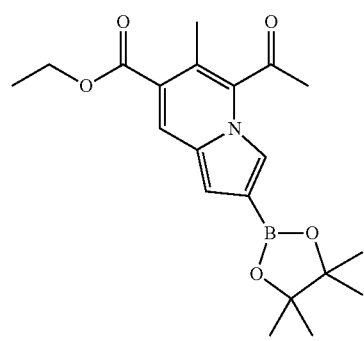

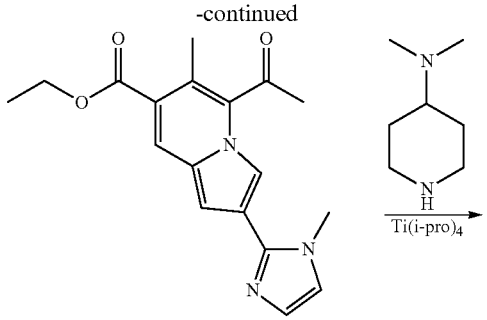 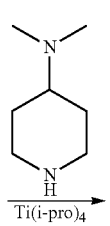

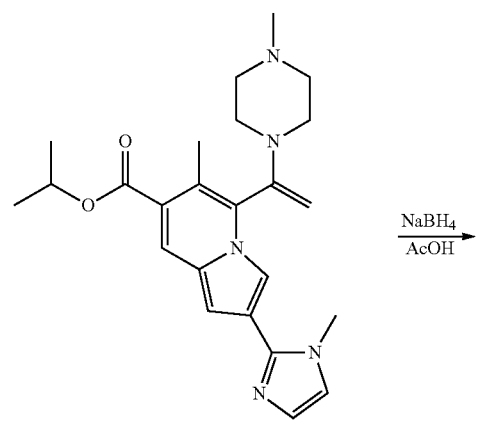

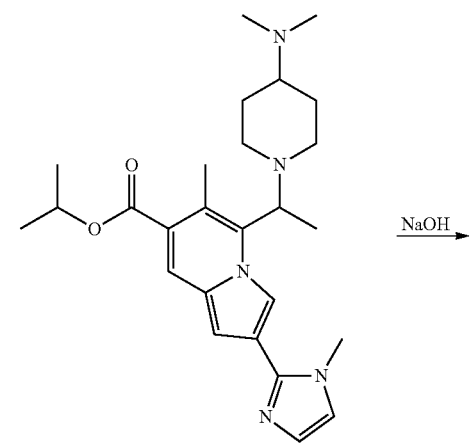

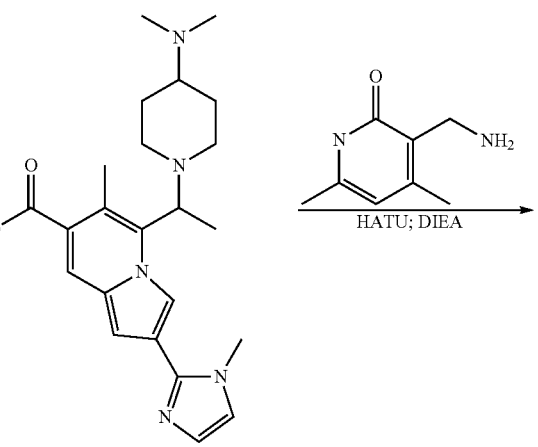

-continued

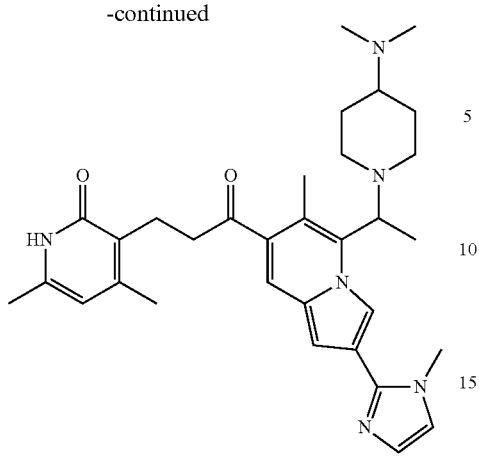

Compound 108

-continued

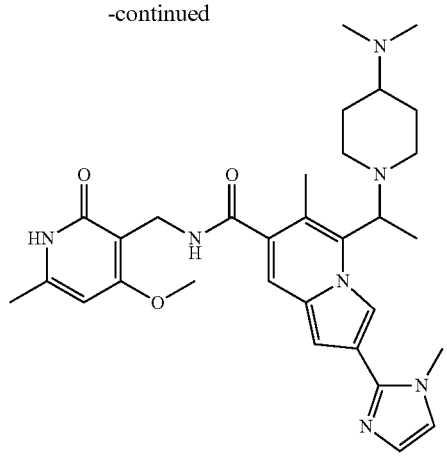

Compound 109

Step 1: Preparation of isopropyl 5-(1-(4-(dimethylamino)piperidin-1-yl)vinyl)-6-methyl-2-(1-methyl-1H-pyrazol-2-yl)indolizine-7-carboxylate: MS (ESI) m/z 450 [M+H]$^+$.

Step 2: Preparation of isopropyl 5-(1-(4-(dimethylamino)piperidin-1-yl)ethyl)-6-methyl-2-(1-methyl-1H-pyrazol-2-yl)indolizine-7-carboxylate: yield of two steps was 45%. MS (ESI) m/z 452 [M+H]$^+$.

Step 3: Preparation of 5-(1-(4-(dimethylamino)piperidin-1-yl)ethyl)-6-methyl-2-(1-methyl-1H-pyrazol-2-yl)indolizine-7-carboxylic acid: MS (ESI) m/z 410 [M+H]$^+$.

Step 4: Preparation of N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-pyrazol-2-yl)indolizine-7-carboxamide: Yield of the two steps was 55%. $^1$H-NMR (MeOD, 400 MHz): 8.96 (s, 1H), 7.62 (s, 1H), 7.58 (s, 2H), 7.07 (s, 1H), 6.19 (s, 1H), 4.49 (s, 2H), 4.47 (s, 1H), 4.07 (s, 3H), 3.69-3.67 (m, 1H), 2.96 (s, 6H), 2.41 (s, 3H), 2.37 (s, 3H), 2.28-2.26 (m, 5H). 1.98-1.95 (m, 2H), 1.69-1.67 (m, 2H); MS(ESI) m/z 544 [M+H]$^+$.

Example 108: Preparation of 5-(1-(4-(dimethylamino)piperidin-1-yl)ethyl)-N-((4-methoxy-6-methyl-2-oxo-1,2-dihydropyridin-3-yl)methyl)-6-methyl-2-(1-methyl-1H-imidazol-2-yl)indolizine-7-carboxamide: Same as Step 5 in Example 31, Wherein the Desired 3-(aminomethyl)-4-methoxy-6-methylpyridine-2(1H)-one was Synthesized According to (WO2015023915)

Step 5: Preparation of 5-(1-(4-(dimethylamino)piperidin-1-yl)ethyl)-N-((4-methoxy-6-methyl-2-oxo-1,2-dihydropyridin-3-yl)methyl)-6-methyl-2-(1-methyl-1H-imidazol-2-yl)indolizine-7-carboxamide, yield 55%. $^1$H-NMR (MeOD, 400 MHz): 8.96 (s, 1H), 7.61-7.60 (m, 1H), 7.59-7.55 (m, 2H), 7.06 (s, 1H), 6.39 (s, 1H), 4.46 (s, 2H), 4.33 (s, 1H), 4.06 (s, 3H), 3.96 (s, 3H), 3.69-3.67 (m, 1H), 3.23-3.02 (m, 2H), 2.91 (s, 6H), 2.78-2.77 (m, 2H), 2.36 (s, 6H), 2.26-2.23 (m, 2H).

1.96-1.93 (m, 2H), 1.65-1.63 (m, 3H); MS(ESI) m/z 560 [M+H]$^+$.

Example 109: Preparation of N-((4-methoxy-6-methyl-2-oxo-1,2-dihydropyridin-3-yl)methyl)-6-methyl-2-(1-methyl-1H-imidazol-2-yl)-5-(1-(4-(2,2,2-trifluoroethyl)piperazin-1-yl)ethyl)indolizine-7-carboxamide: Same as Example 83

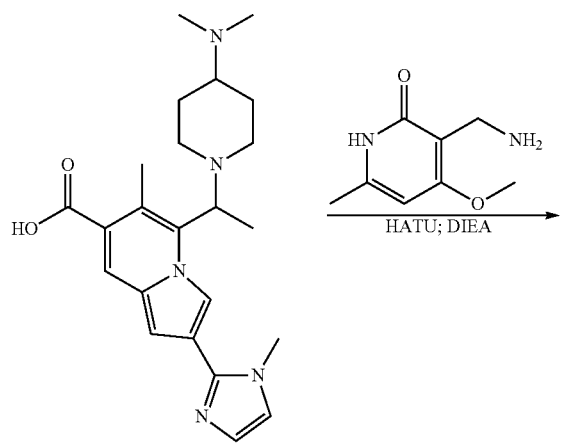

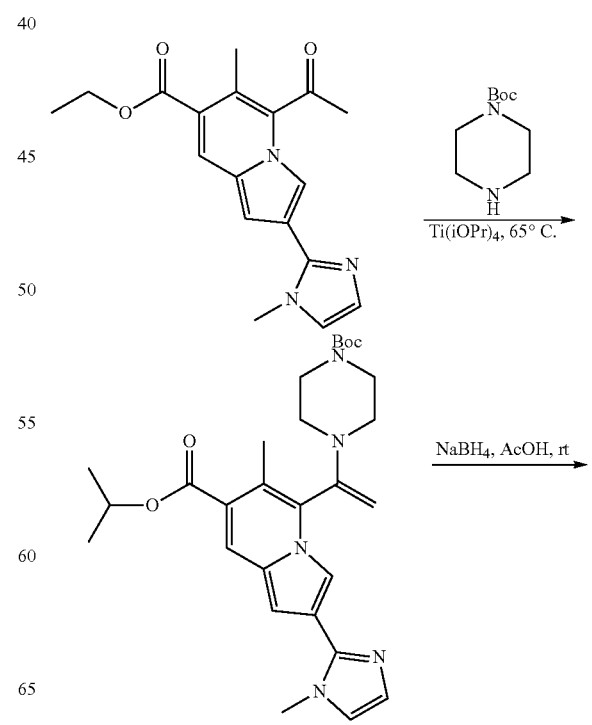

263
-continued

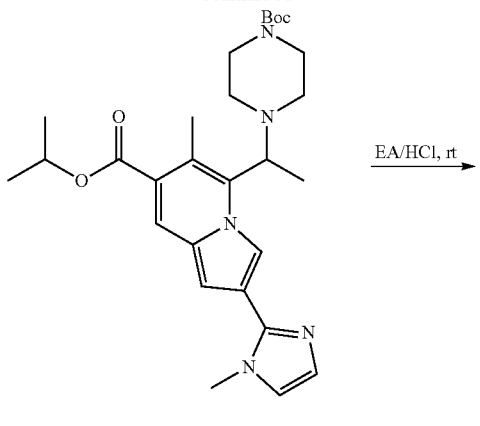

EA/HCl, rt →

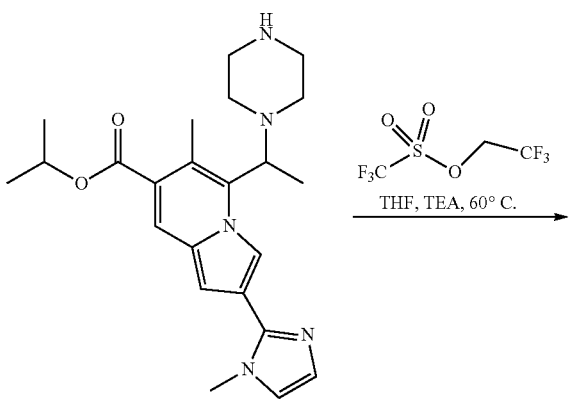

THF, TEA, 60° C. →

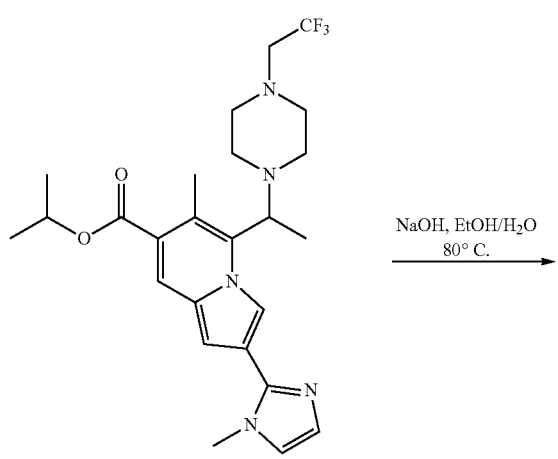

NaOH, EtOH/H₂O
80° C. →

264
-continued

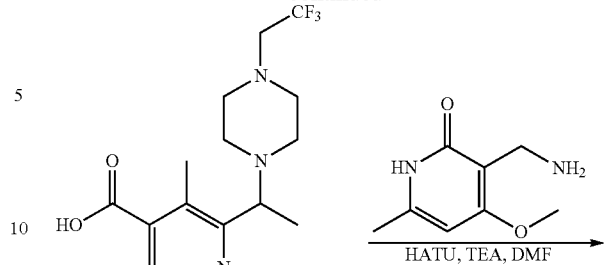

HATU, TEA, DMF →

Compound 110

Step 1: Synthesis of isopropyl 5-(1-(4-(tert-butoxycarbonyl)piperazin-1-yl)vinyl)-6-methyl-2-(1-methyl-1H-imidazol-2-yl)indolizine-7-formate: MS(ESI) m/z 508 [M+H]⁺.

Step 2: Synthesis of isopropyl 5-(1-(4-(tert-butoxycarbonyl)piperazin-1-yl)ethyl)-6-methyl-2-(1-methyl-1H-imidazol-2-yl)indolizine-7-formate: yield of the two steps was 45%. MS (ESI) m/z 510 [M+H]⁺.

Step 3: Preparation of isopropyl 6-methyl-2-(1-methyl-1H-pyrazol-5-yl)-5-(1-(piperazin-1-yl)ethyl)indolizine-7-carboxylate: yield 87%. MS (ESI) m/z 410 [M+H]⁺.

Step 4: Preparation of isopropyl 6-methyl-2-(1-methyl-1H-imidazol-2-yl)-5-(1-(4-(2,2,2-trifluoroethyl)piperazin-1-yl)ethyl)indolizine-7-formate: yield 63%. MS (ESI) m/z 492 [M+H]⁺.

Step 5: Preparation of 6-methyl-2-(1-methyl-1H-imidazol-2-yl)-5-(1-(4-(2,2,2-trifluoroethyl)piperazin-1-yl)indolizine-7-formic acid: MS (ESI) m/z 450 [M+H]⁺.

Step 6: Preparation of N-((4-methoxy-6-methyl-2-oxo-1,2-dihydropyridin-3-yl)methyl)-6-methyl-2-(1-methyl-1H-imidazol-2-yl)-5-(1-(4-(2,2,2-trifluoroethyl)piperazin-1-yl)ethyl)indolizine-7-carboxamide: yield of the two steps was 4%. ¹H-NMR (CDCl₃, 400 MHz): 8.82 (s, 1H), 7.72-7.57 (m, 4H), 7.16 (s, 1H), 6.91 (s, 1H), 4.52 (s, 2H), 4.10 (s, 3H), 4.05 (s, 3H), 3.24-3.12 (m, 6H), 2.98-2.95 (m, 1H), 2.54-2.52 (m, 2H), 2.51 (s, 3H), 2.40 (s, 2H), 1.78 (d, J=6.9 Hz, 3H); MS(ESI) m/z 600 [M+H]⁺.

Example 110: Preparation of N-((4-methoxy-6-methyl-2-oxo-1,2-dihydropyridin-3-yl)methyl)-6-methyl-2-(1-methyl-1H-imidazol-2-yl)-5-(1-(4-(2,2,2-trifluoroethyl)piperazin-1-yl)ethyl)indolizine-7-carboxamide: same as step 5 in example 31

Example 111: Preparation of N-((4,6-dimethyl-2-oxo-1,2-dihydropyridin-3-yl)methyl)-5-(1-(4-(dimethylamino)piperidine-1-yl)ethyl)-6-methyl-2-(1-methyl-1H-imidazol-2-yl)indolizine-7-carboxamide: Same as Example 50

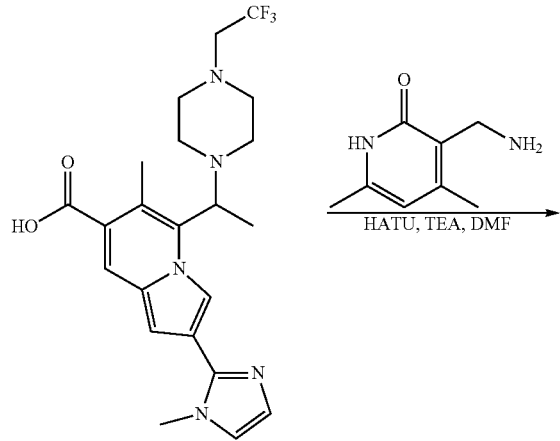
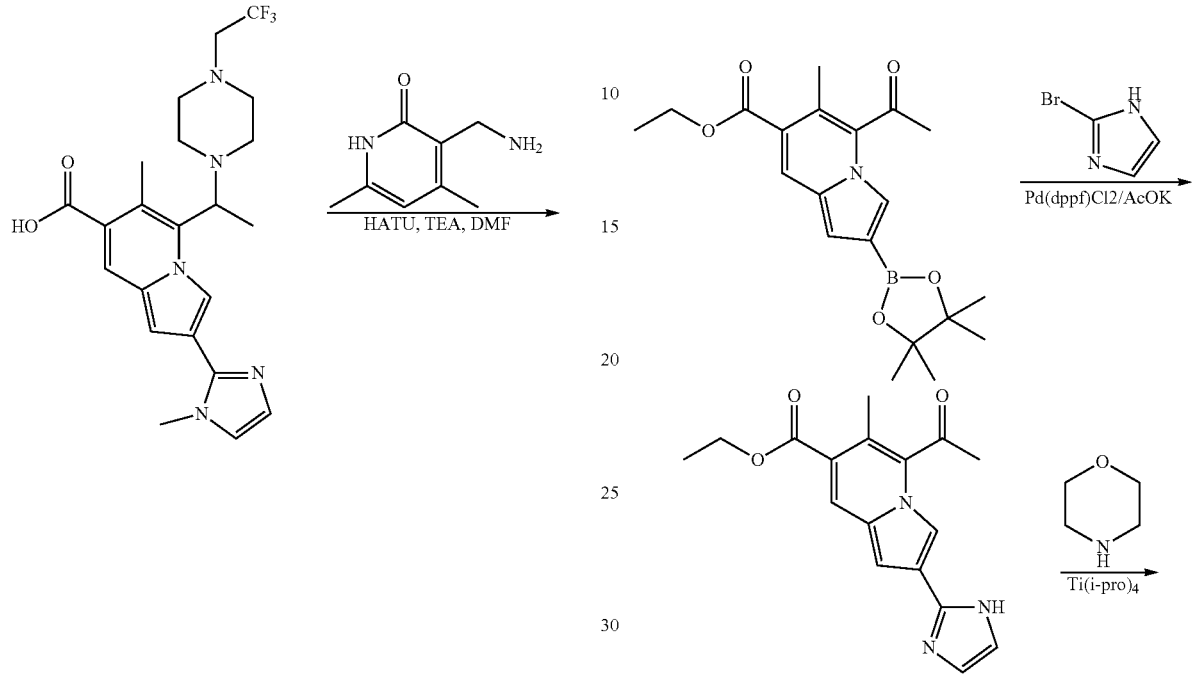

Compound 111

Step 1: Preparation of N-((4-methoxy-6-methyl-2-oxo-1,2-dihydropyridin-3-yl)methyl)-6-methyl-2-(1-methyl-1H-imidazol-2-yl)-5-(1-(4-(2,2,2-trifluoroethyl)piperazin-1-yl)ethyl)indolizine-7-carboxamide: yield 4%. $^1$H-NMR (CDCl$_3$, 400 MHz): 8.86 (s, 1H), 7.71-7.54 (s, 4H), 7.12 (s, 1H), 6.44 (s, 1H), 4.52 (s, 2H), 4.05 (s, 3H), 3.86-3.84 (m, 1H), 3.78-3.71 (m, 2H), 3.24-3.12 (m, 6H), 2.98-2.95 (m, 2H), 2.46 (s, 3H), 2.38 (s, 3H), 2.34 (s, 3H), 1.78 (d, J=6.9 Hz, 3H); MS(ESI) m/z 584 [M+H]$^+$.

-continued

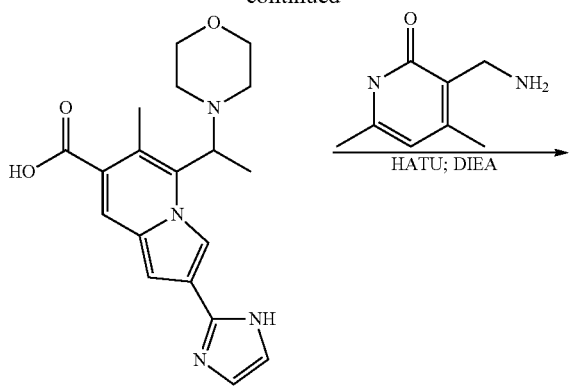

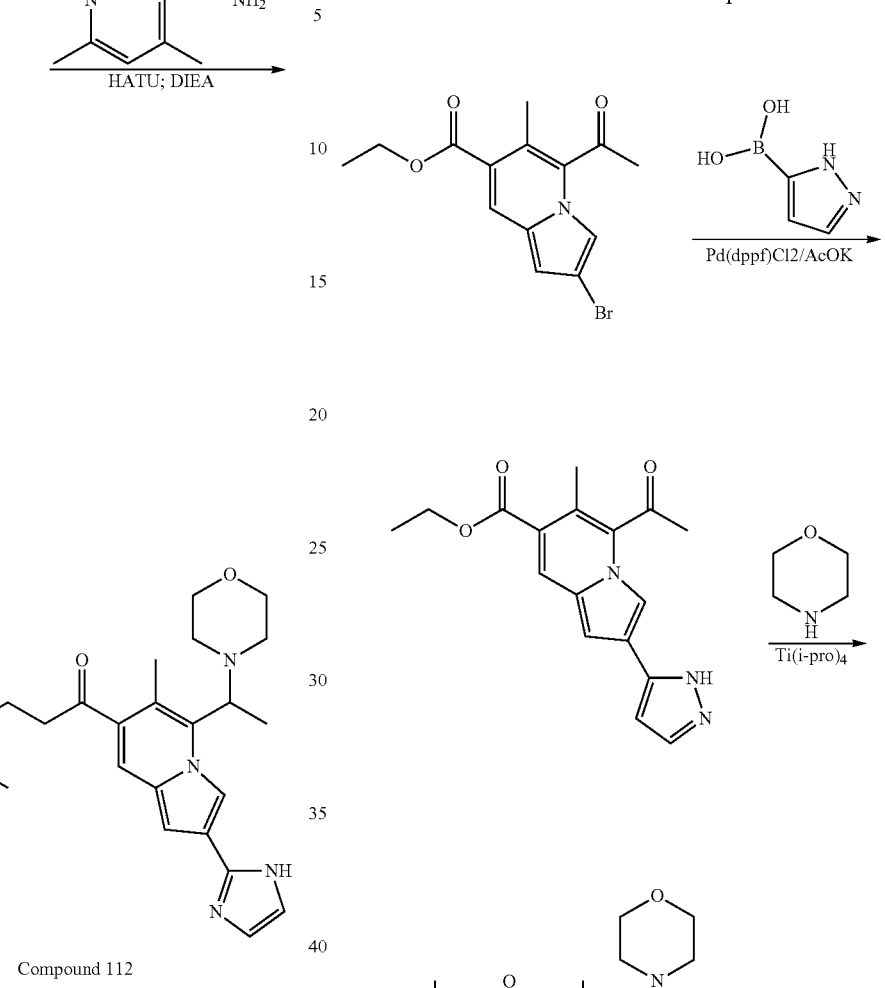

Compound 112

Step 1: Preparation of ethyl 5-methyl-2-(1H-imidazol-2-yl)-6-methylindolizine-7-carboxylate: Yield 89%. MS (ESI) m/z 312 [M+H]$^+$.

Step 1: Preparation of isopropyl 5-(1-(4-(dimethylamino)piperidin-1-yl)vinyl)-2-(1H-imidazol-2-yl)-6-methylindolizine-7-carboxylate: MS (ESI) m/z 395 [M+H]$^+$.

Step 3: Preparation of isopropyl 5-(1-(4-(dimethylamino)piperidin-1-yl)ethyl)-2-methyl-2-(imidazol-2-yl)-6-methyl-indolizine-7-carboxylate: yield of two steps was 55%. MS (ESI) m/z 397 [M+H]$^+$.

Step 4: Preparation of 5-(1-(4-(dimethylamino)piperidin-1-yl)ethyl)-2-(1H-imidazol-2-yl)-6-methylindolizine-7-carboxylic acid: MS (ESI) m/z 355 [M+H]$^+$.

Step 5: Preparation of N-((4,6-dimethyl-2-oxo-1,2-dihydropyridin-3-yl)methyl)-5-(1-(4-(dimethyl amino)piperidine-1-yl)ethyl)-6-methyl-2-(1-methyl-1H-imidazol-2-yl)indolizine-7-carboxamide: Yield of the two steps was 13%. $^1$H-NMR (MeOD, 400 MHz): 9.13 (s, 1H), 7.55-7.47 (m, 4H), 7.04 (s, 1H), 6.13 (s, 1H), 4.46 (s, 2H), 4.26-4.25 (m, 1H), 3.88-3.85 (m, 1H), 3.71 (s, 4H), 3.23-3.21 (m, 2H), 2.91-2.81 (m, 2H), 2.38 (s, 3H), 2.31 (s, 3H). 2.19 (s, 3H), 1.61-1.59 (m, 3H); MS(ESI) m/z 489.3 [M+H]$^+$.

Example 112: Preparation of N-((4,6-dimethyl-2-oxo-1,2-dihydropyridin-3-yl)methyl)-6-methyl-5-(1-morpholinoethyl)-2-(pyrazol-5-yl)indolizine-7-carboxamide: Same as Example 31

269

-continued

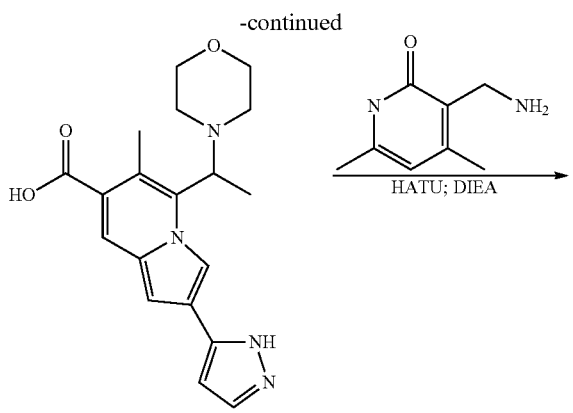

HATU; DIEA

Compound 113

Step 1: Preparation of ethyl 5-acetyl-6-methyl-2-(1H-pyrazol-5-yl)indolizine-7-carboxylate: Yield 31%. MS (ESI) m/z 312.1 [M+H]+.

Step 2: Preparation of isopropyl 6-methyl-5-(1-morpholinovinyl)-2-(1H-pyrazol-5-yl)indolizine-7-carboxylate: MS (ESI) m/z 395 [M+H]+.

Step 3: Step 3: Preparation of isopropyl 6-methyl-5-(1-morpholinoethyl)-2-(1H-pyrazol-5-yl)indolizine-7-carboxylate: yield of two steps was 53%. MS (ESI) m/z 397 [M+H]+.

Step 4: Step 4: Preparation of 6-methyl-5-(1-morpholinoethyl)-2-(1H-pyrazol-5-yl)indolizine-7-carboxylic acid: MS (ESI) m/z 355 [M+H]+.

Step 5: Preparation of N-((4,6-dimethyl-2-oxo-1,2-dihydropyridin-3-yl)methyl)-6-methyl-5-(1-morpholinoethyl)-2-(1H-pyrazol-5-yl)indolizine-7-carboxamide: yield 14%. ¹H-NMR (MeOD, 400 MHz): 7.90 (s, 1H), 7.62 (s, 1H), 6.80 (s, 1H), 6.30 (s, 1H), 4.50 (s, 2H), 3.89-3.88 (m, 4H), 3.21-3.19 (m, 2H), 2.43-2.42 (m, 6H), 2.30-2.26 (m, 5H), 1.94-1.92 (m, 3H); MS(ESI) m/z 489 [M+H]+.

270

Example 113: Preparation of N-((4,6-dimethyl-2-oxo-1,2-dihydropyridin-3-yl)methyl)-6-methyl-5-(1-morpholinylethyl)-2-(1-ethyl-1H-pyrazole)indolizine-7-carboxamide

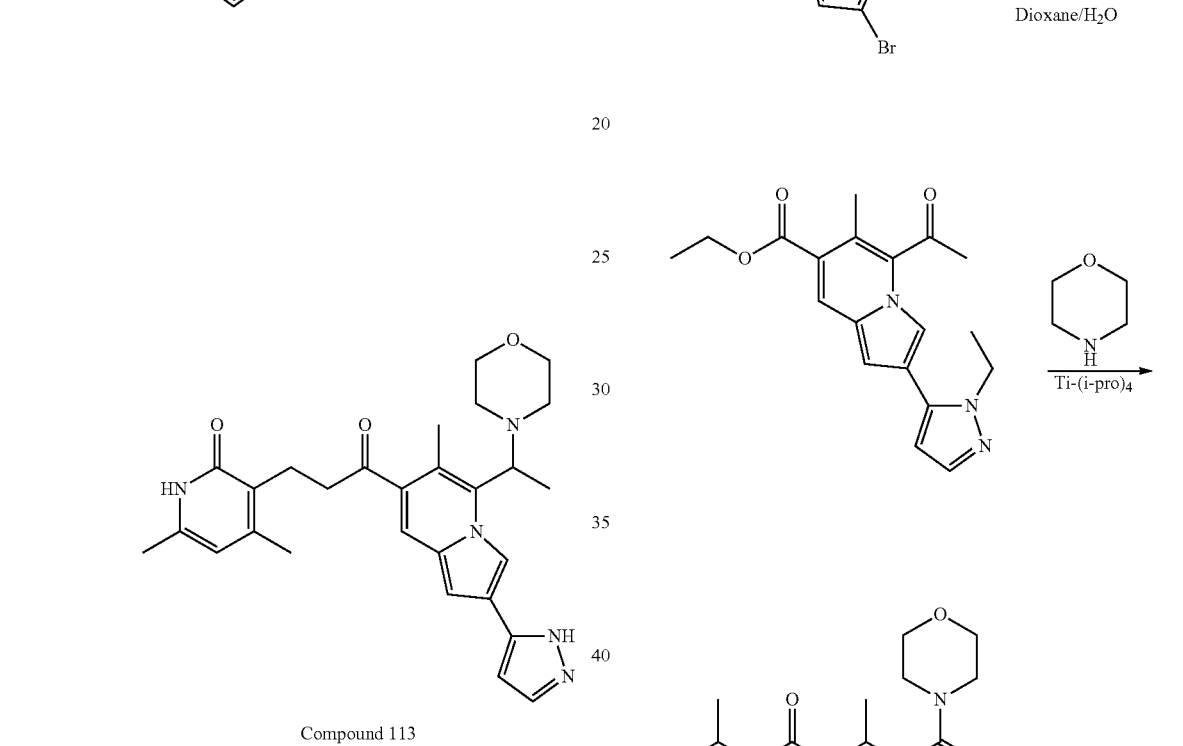

-continued

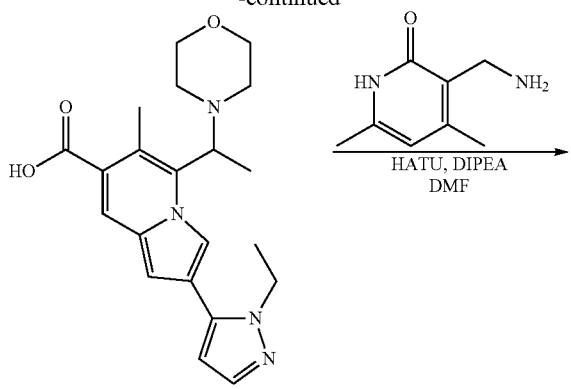

HATU, DIPEA
DMF

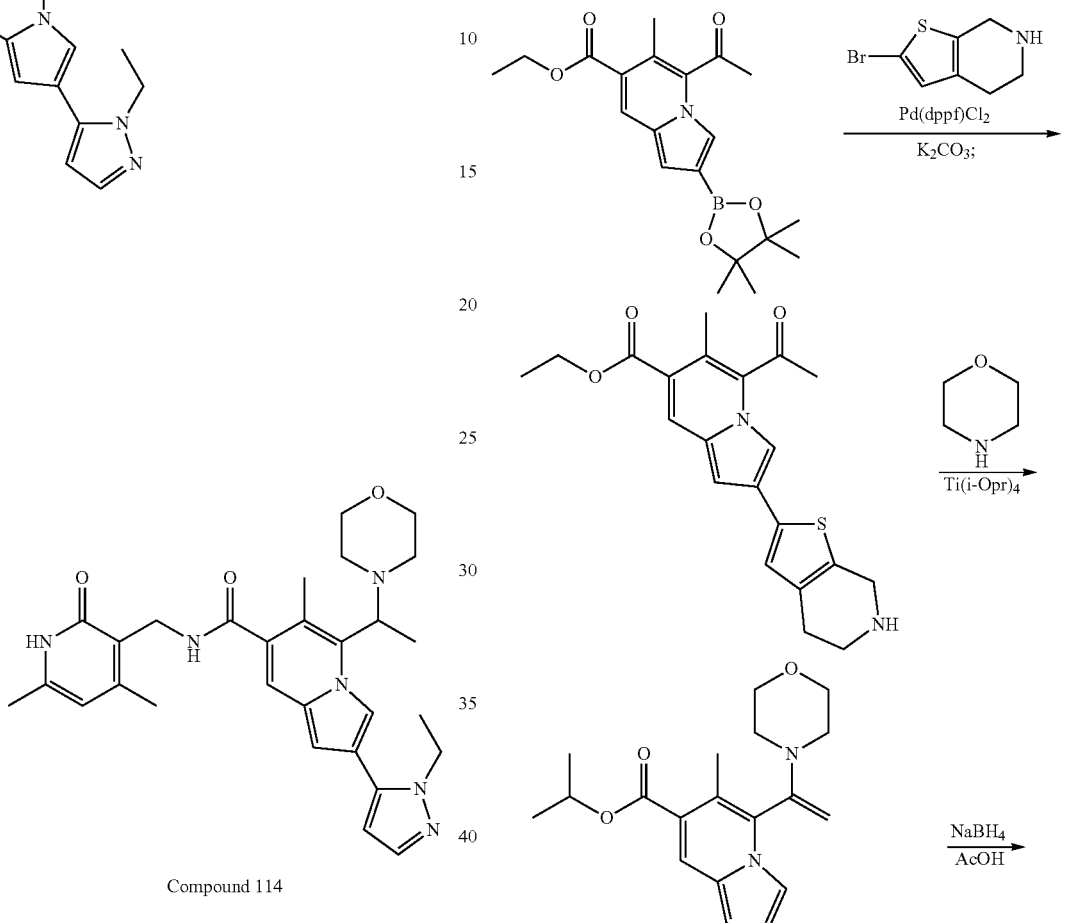

Compound 114

Step 1: Preparation of ethyl 5-acetyl-6-methyl-2-(1-ethyl-1H-pyrazole)indolizine-7-carboxylate: yield 43%. MS (ESI) m/z 340 [M+H]+.

Step 2: Preparation of isopropyl 6-methyl-5-(1-morpholinylvinyl)-2-(1-ethyl-1H-pyrazole)indolizine-7-carboxylate: MS (ESI) m/z 423 [M+H]+.

Step 3: Preparation of isopropyl 6-methyl-5-(1-morpholinylethyl)-2-(1-ethyl-1H-pyrazole)indolizine-7-carboxylate: yield of two steps was 40%. MS (ESI) m/z 425 [M+H]+.

Step 4: Preparation of 6-methyl-5-(1-morpholinylethyl)-2-(1-ethyl-1H-pyrazole)indolizine-7-carboxylate: MS (ESI) m/z 383 [M+H]+.

Step 5: Preparation of N-((4,6-dimethyl-2-oxo-1,2-dihydropyridin-3-yl)methyl)-6-methyl-5-(1-morpholinylethyl)-2-(1-ethyl-1H-pyrazole)indolizine-7-carboxamide: yield of two steps was 42%. $^1$H NMR (400 MHz, DMSO-$d_6$) δ ppm 11.52 (s, 1H), 8.56 (s, 1H), 8.17 (s, 1H), 7.46 (s, 1H), 7.35 (s, 1H), 6.72 (s, 1H), 6.43 (s, 1H), 5.88 (s, 1H), 4.27-4.32 (m, 9H), 3.60 (s, 3H), 2.28 (s, 3H), 2.21 (s, 3H), 2.12 (s, 3H), 1.49 (s, 2H), 1.38 (t, J=6.8 Hz, 3H), 1.24 (s, 2H); MS(ESI) m/z 539 [M+H]+.

Example 114: Preparation of N-((4,6-dimethyl-2-oxo-1,2-dihydropyridin-3-yl)methyl)-6-methyl-5-(1-morpholinoethyl)-2-(4,5,6,7-tetrahydro[2,3-c]pyridin-2-yl)indolizine-7-carboxamide: the First Four Steps are Similar to Those of Example 31

273

-continued

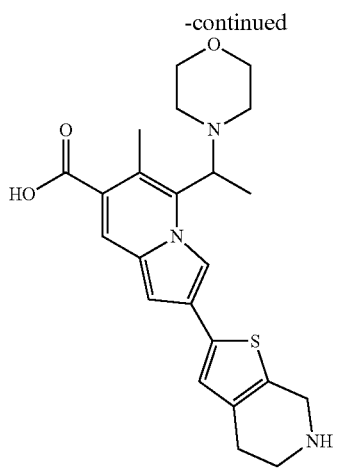

(Boc)₂O / DCM →

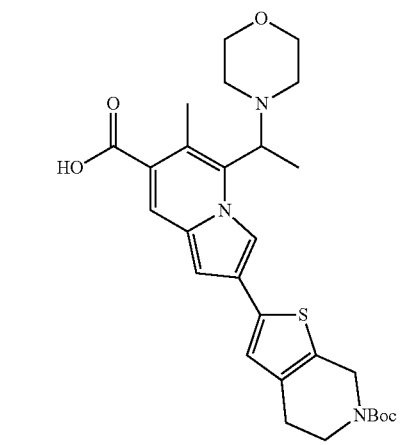

HATU →

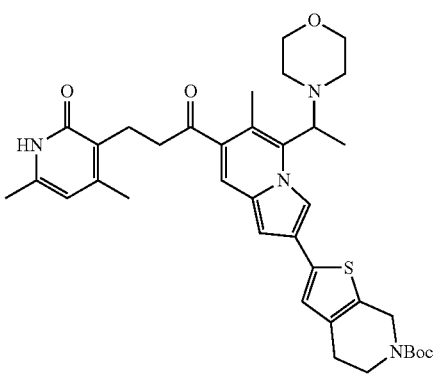

HCl/AcOEt →

274

-continued

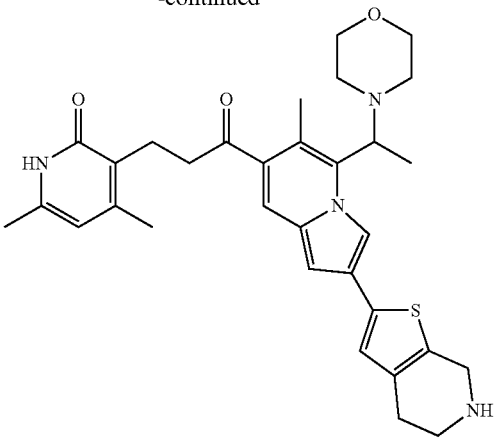

Compound 115

Step 1: Synthesis of ethyl 5-acetyl-6-methyl-2-(4,5,6,7-tetrahydrothieno[2,3-c]pyridin-2-yl)indolizine-7-formate, yield 53%. MS (ESI) m/z 383 [M+H]⁺.

Step 2: Synthesis of ethyl isopropyl-6-methyl-5-(1-morpholinovinyl)-2-(4,5,6,7-tetrahydrothieno[2,3-c]pyridine-2-yl)indolizine-7-carboxylate: MS (ESI) m/z 466 [M+H]⁺.

Step 3: Synthesis of ethyl isopropyl-6-methyl-5-(1-morpholinoethyl)-2-(4,5,6,7-tetrahydrothieno[2,3-c]pyridine-2-yl)indolizine-7-carboxylate: two-step yield of 68%. MS (ESI) m/z 468 [M+H]⁺.

Step 4: Synthesis of 6-methyl-5-(1-morpholinoethyl)-2-(4,5,6,7-tetrahydrothieno[2,3-c]pyridin-2-yl)indolizine-7-formic acid: yield 63%. MS (ESI) m/z 426 [M+H]⁺.

Step 5: Synthesis of 2-(6-(tert-butoxycarbonyl)-4,5,6,7-tetrahydrothieno[2,3-c]pyridin-2-yl)-6-methyl-5-(1-morpholinoethyl)indolizine-7-carboxylic acid: To a dry 25 mL three-necked flask, crude product 6-methyl-5-(1-morpholinoethyl)-2-(4,5,6,7-tetrahydrothieno[2,3-c]pyridin-2-yl)indolizine-7-carboxylic acid (120 mg, 0.28 mmol), Di-tert-butyl dicarbonate (123 mg, 0.56 mmol), sodium hydroxide (22 mg, 0.56 mmol) were added successively, dissolved in 1.4-dioxane/water (1:1) (3 mL), and stirred for 2 hours at room temperature. After the reaction was completed, 1N diluted hydrochloric acid was added to the reaction mixture to adjust pH=7, and product was extracted with ethyl acetate (130 mg, yellow solid), yield: 88%. MS (ESI) m/z 526 [M+H]⁺.

Step 6: Preparation of tert-butyl 2-(7-((4,6-dimethyl-2-oxo-1,2-dihydropyridin-3-yl)methyl)carbamoyl)-6-methyl-5-(1-morpholinoethyl)indol-2-yl)-4,5-dihydro-thieno[2,3-c]pyridine-6(2H)-carboxylate: Same as Step 5 in example 31. Yield: 24%. MS (ESI) m/z 660 [M+H]⁺.

Step 7: Preparation of N-((4,6-dimethyl-2-oxo-1,2-dihydropyridin-3-yl)methyl)-6-methyl-5-(1-morpholinoethyl)-2-(4,5,6,7-tetrahydro[2,3-c]pyridin-2-yl)indolizine-7-carboxamide: same as step 6 in example 44. Yield: 74%.

¹H-NMR (MeOD, 400 MHz): 8.74 (s, 1H), 7.33 (s, 1H), 7.04 (s, 1H), 6.67 (s, 1H), 6.11 (s, 1H), 4.55 (s, 2H), 4.45-4.42 (m, 4H), 4.10-4.08 (m, 1H), 3.67 (s, 4H), 3.54-3.51 (m, 2H), 3.03-3.00 (m, 2H), 2.69-2.67 (m, 2H), 2.37 (s, 3H), 2.30 (s, 3H), 2.22 (s, 3H), 1.51-1.49 (m, 3H). MS(ESI) m/z 560 [M+H]⁺.

Example 115: Preparation of N-((4,6-dimethyl-2-oxo-1,2-dihydropyridin-3-yl)methyl)-6-methyl-5-(1-morpholinoethyl)-2-(4,5,6,7-tetrahydrothieno[3,2-c]pyridin-2-yl)indolizine-7-carboxamide: Same as Example 53

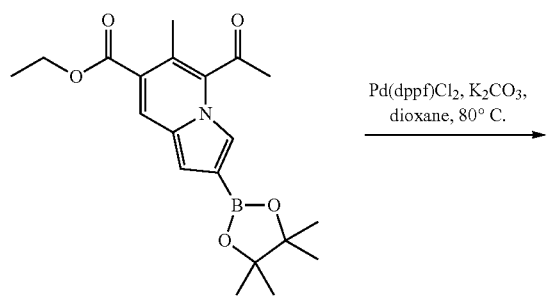

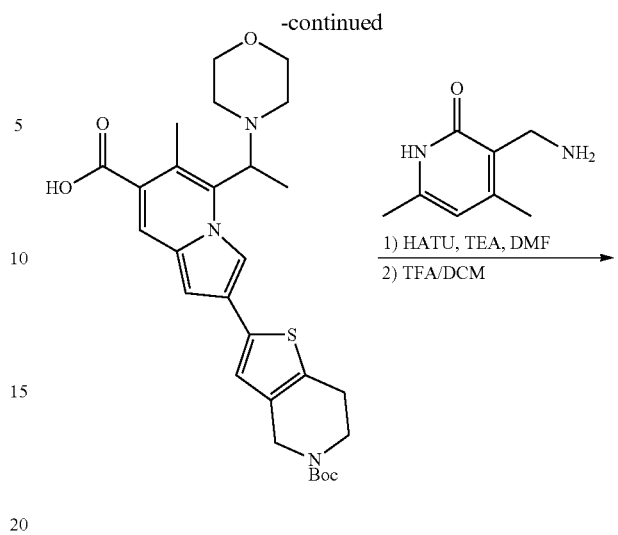

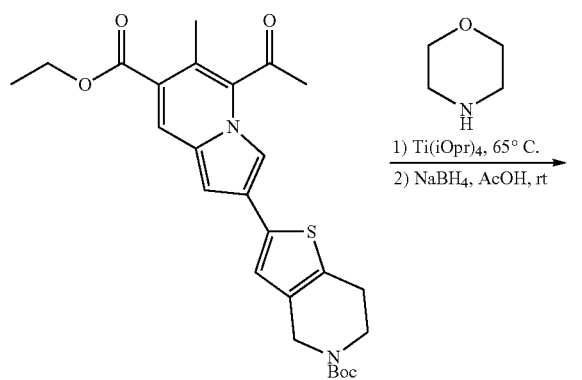

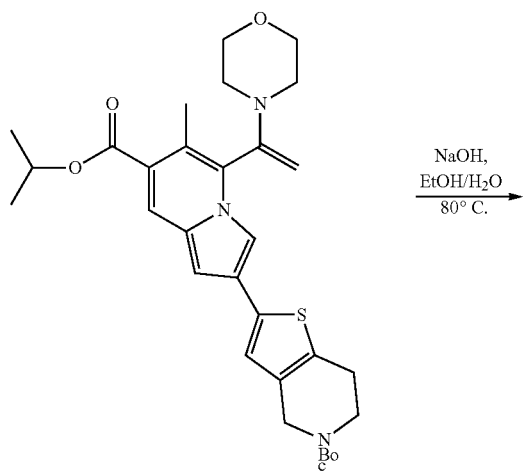

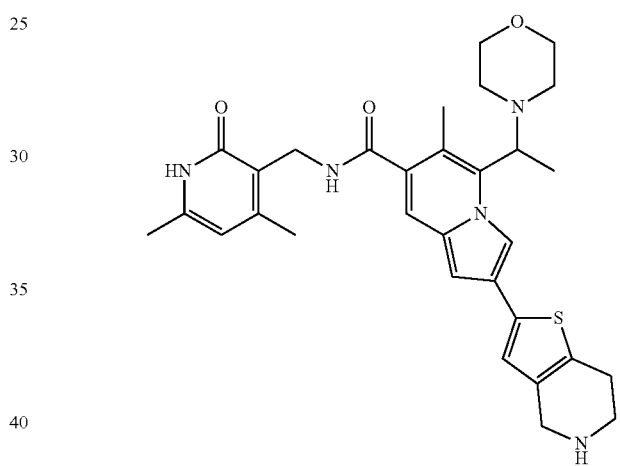

Compound 116

Step 1: Synthesis of tert-butyl 2-(5-acetyl-7-(ethoxycarbonyl)-6-methylindolizine-2-yl)-6,7-tetrahydrothieno[3,2-c]pyridine-5(4H)-formate, yield 29%. MS (ESI) m/z 483 [M+H]$^+$.

Step 2: Synthesis of tert-butyl 2-(7-(isopropoxycarbonyl)-6-methyl-5-(1-morpholinoethyl)indolizine-2-yl)-6,7-tetrahydrothieno[3,2-c]pyridine-5(4H)-carboxylate, yield of two steps was 72%. MS (ESI) m/z 568 [M+H]$^+$.

Step 3: Synthesis of 2-(5-(tert-butoxycarbonyl)-4,5,6,7-tetrahydrothieno[3,2-c]pyridin-2-yl)-6-methyl-5-(1-morpholinoethyl)indolizine-7-carboxylic acid, yield 72%. MS (ESI) m/z 526 [M+H]$^+$.

Step 4: Preparation of N-((4,6-dimethyl-2-oxo-1,2-dihydropyridin-3-yl)methyl)-6-methyl-5-(1-morpholinoethyl)-2-(4,5,6,7-tetrahydrothieno[3,2-c]pyridin-2-yl)indolizine-7-carboxamide: yield of two steps was 6%. $^1$H-NMR (CDCl$_3$, 400 MHz): 7.36 (s, 1H), 7.05 (s, 1H), 6.12 (s, 1H), 4.59 (s, 2H), 4.28 (s, 2H), 3.85 (s, 1H), 3.71 (s, 4H), 3.58-3.55 (m, 2H), 3.23-3.21 (m, 2H), 3.17-3.15 (m, 2H), 2.77 (s, 2H), 2.38 (s, 3H), 2.31 (s, 3H), 2.19 (s, 3H), 1.58 (d, J=6.9 Hz, 3H); MS(ESI) m/z 560 [M+H]$^+$.

Example 116: Preparation of N-((4,6-dimethyl-2-oxo-1,2-dihydropyridin-3-yl)methyl)-1-(3-(dimethylamine)phenyl)-6-methyl-5-(1-morpholinylethyl)indolizine-7-carboxamide: Same as Example 31

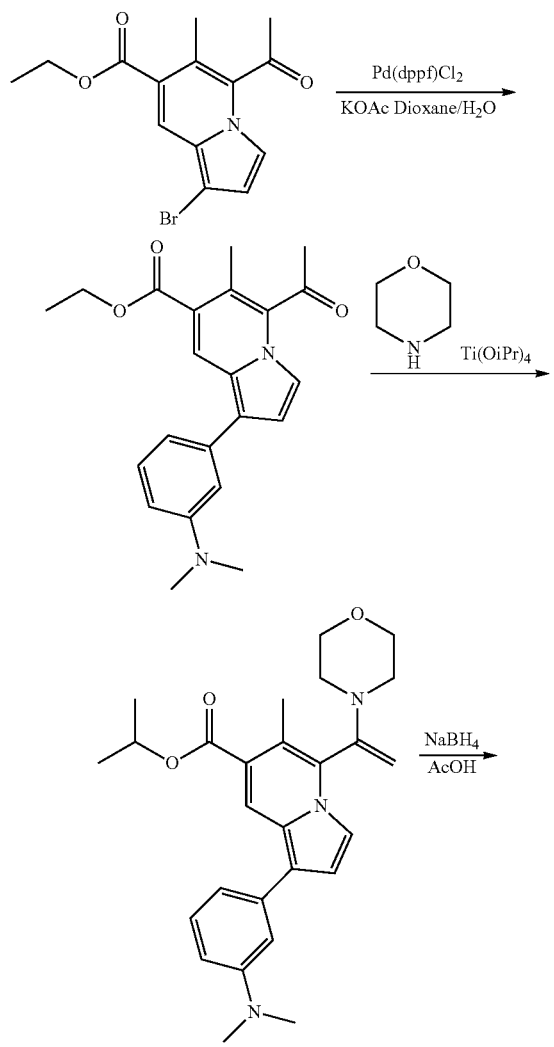

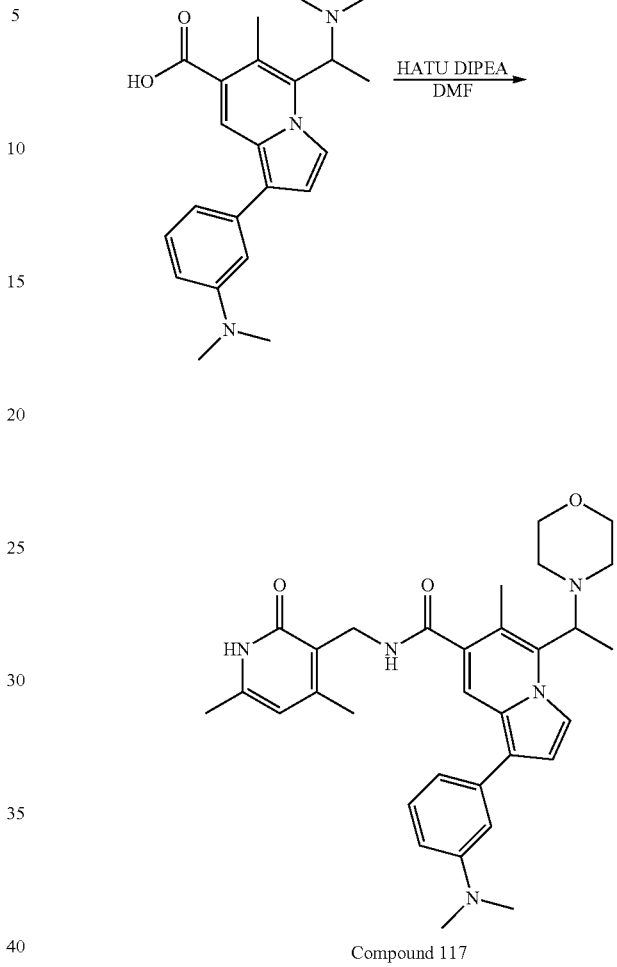

Compound 117

Step 1: Preparation of ethyl 5-acetyl-1-(3-(dimethylamine)phenyl)-6-methylindolizine-7-carboxylate: yield 25%. MS (ESI) m/z 365 [M+H]+.

Step 2: Preparation of isopropyl 1-(3-(dimethylamine)phenyl)-6-methyl-5-(1-morpholinevinyl)indolizine-7-carboxylate: MS (ESI) m/z 448 [M+H]+.

Step 3: Preparation of isopropyl 1-(3-(dimethylamine)phenyl)-6-methyl-5-(1-morphinolinylethyl)indolizine-7-carboxylate: yield of two steps was 42%. MS (ESI) m/z 450 [M+H]+.

Step 4: Preparation of 1-(3-(dimethylamine)phenyl)-6-methyl-5-(1-morpholinylethyl)indolizine-7-carboxylic acid: MS (ESI) m/z 408 [M+H]+.

Step 5: Preparation of N-((4,6-dimethyl-2-oxo-1,2-dihydropyridin-3-yl)methyl)-1-(3-(dimethylamine)phenyl)-6-methyl-5-(1-morpholinylethyl)indolizine-7-carboxamide: yield 27%. $^1$H NMR (400 MHz, CDCl$_3$) δ ppm 11.47 (s, 1H), 8.41 (s, 1H), 8.24-8.26 (m, 1H), 7.57 (s, 1H), 7.19-7.23 (m, 1H), 6.97-6.98 (d, J=2.8 Hz, 1H), 6.61 (m, 2H), 5.85 (s, 1H), 4.25-4.26 (m, 2H), 4.05-4.07 (m, 1H), 3.58 (m, 4H), 2.88 (s, 6H), 2.63-2.66 (m, 2H), 2.31 (s, 3H), 2.11-2.17 (m, 5H), 2.11 (s, 3H), 1.43-1.44 (m, 3H); MS(ESI) m/z 542 [M+H]+.

Example 117: Preparation of N-((4,6-dimethyl-2-oxo-1,2-dihydropyridin-3-yl)methyl)-6-methyl-5-(1-morpholinylethyl)-1-(3-morpholinylphenyl)indolizine-7-carboxamide: Same as Example 31

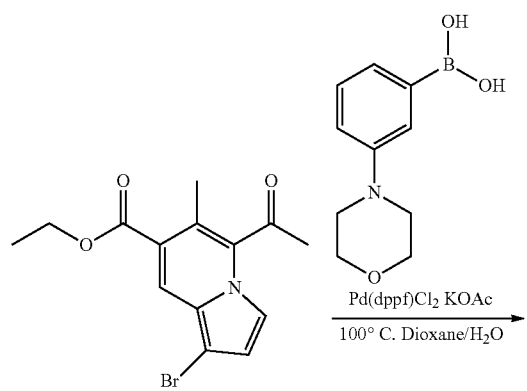

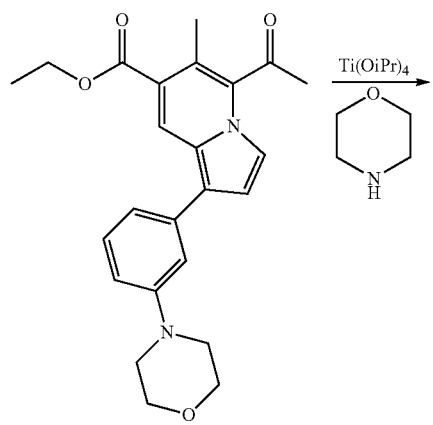

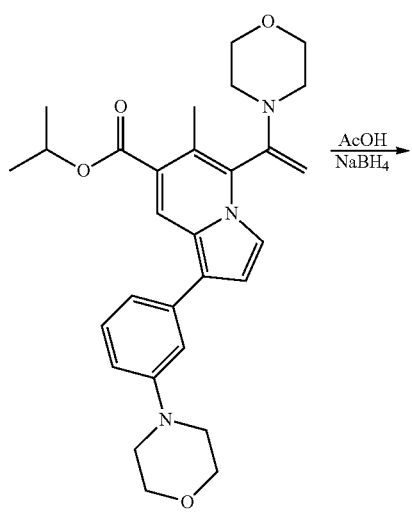

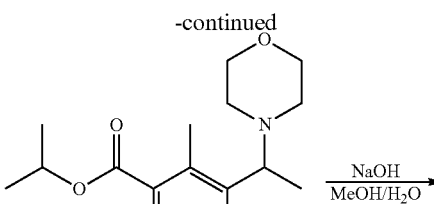

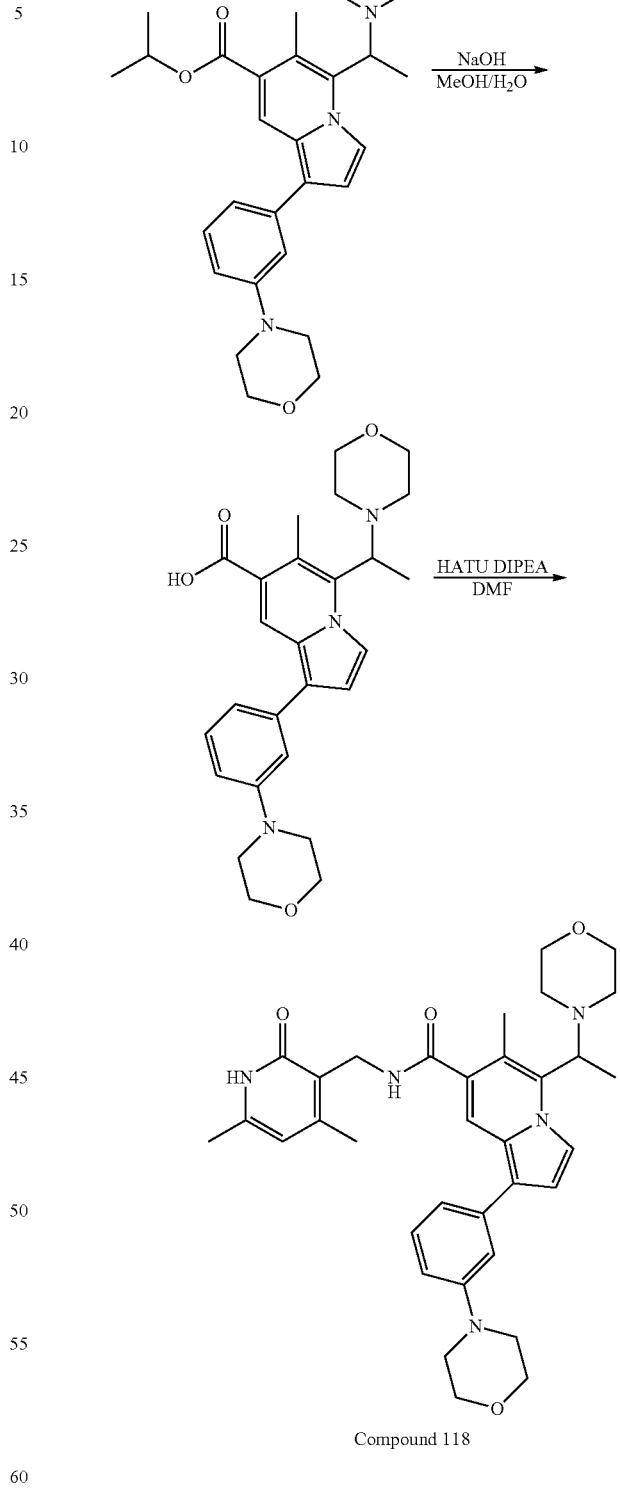

Compound 118

Step 1: Preparation of ethyl 5-acetyl-6-methyl-1-(3-morpholinylphenyl)indolizine-7-carboxylate: Yield 21%. MS (ESI) m/z 406 [M+H]+.

Step 2: Preparation of isopropyl 6-methyl-1-(3-morpholinylphenyl)-5-(1-morpholinylvinyl)indolizine-7-carboxylate: MS (ESI) m/z 490 [M+H]+.

281

Step 3: Preparation of isopropyl 6-methyl-1-(3-morphino-linylphenyl)-5-(1-morphinolinylethyl)indolizine-7-carboxylate: MS (ESI) m/z 492 [M+H]+.

Step 4: Preparation of 6-methyl-1-(3-morphinolinylphenyl)-5-(1-morphinolinylethyl)indolizine-7-carboxylic acid: yield of two steps was 46%. MS (ESI) m/z 450 [M+H]+.

Step 6: Preparation of N-((4,6-dimethyl-2-oxo-1,2-dihydropyridin-3-yl)methyl)-6-methyl-5-(1-morpholinylethyl)-1-(3-morphinolinylphenyl)indolizine-7-carboxamide: yield 40%. $^1$H NMR (400 MHz, CDCl$_3$) δ ppm 11.44 (s, 1H), 8.42-8.41 (s, 1H), 8.29 (s, 1H), 7.54 (s, 1H), 7.29-7.25 (m, 1H), 7.07 (s, 1H), 7.03-6.99 (m, 2H), 6.82-6.80 (d, J=6.0 Hz, 1H), 5.86 (s, 1H), 4.27-4.26 (m, 2H), 4.08-4.04 (m, 1H), 3.73-3.70 (m, 4H), 3.58-3.49 (m, 4H), 3.19-3.13 (m, 4H), 2.68-2.63 (m, 2H), 2.29 (s, 3H), 2.18-2.14 (m, 5H), 2.11 (s, 3H), 1.45-1.44 (m, 3H); MS(ESI) m/z 584 [M+H]+.

Example 118: Preparation of N-((4,6-dimethyl-2-oxo-1,2-dihydropyridin-3-yl)methyl)-1-(4-(dimethylamine)phenyl)-6-methyl-5-(1-morpholinylethyl)indolizine-7-carboxamide: Same as Example 31

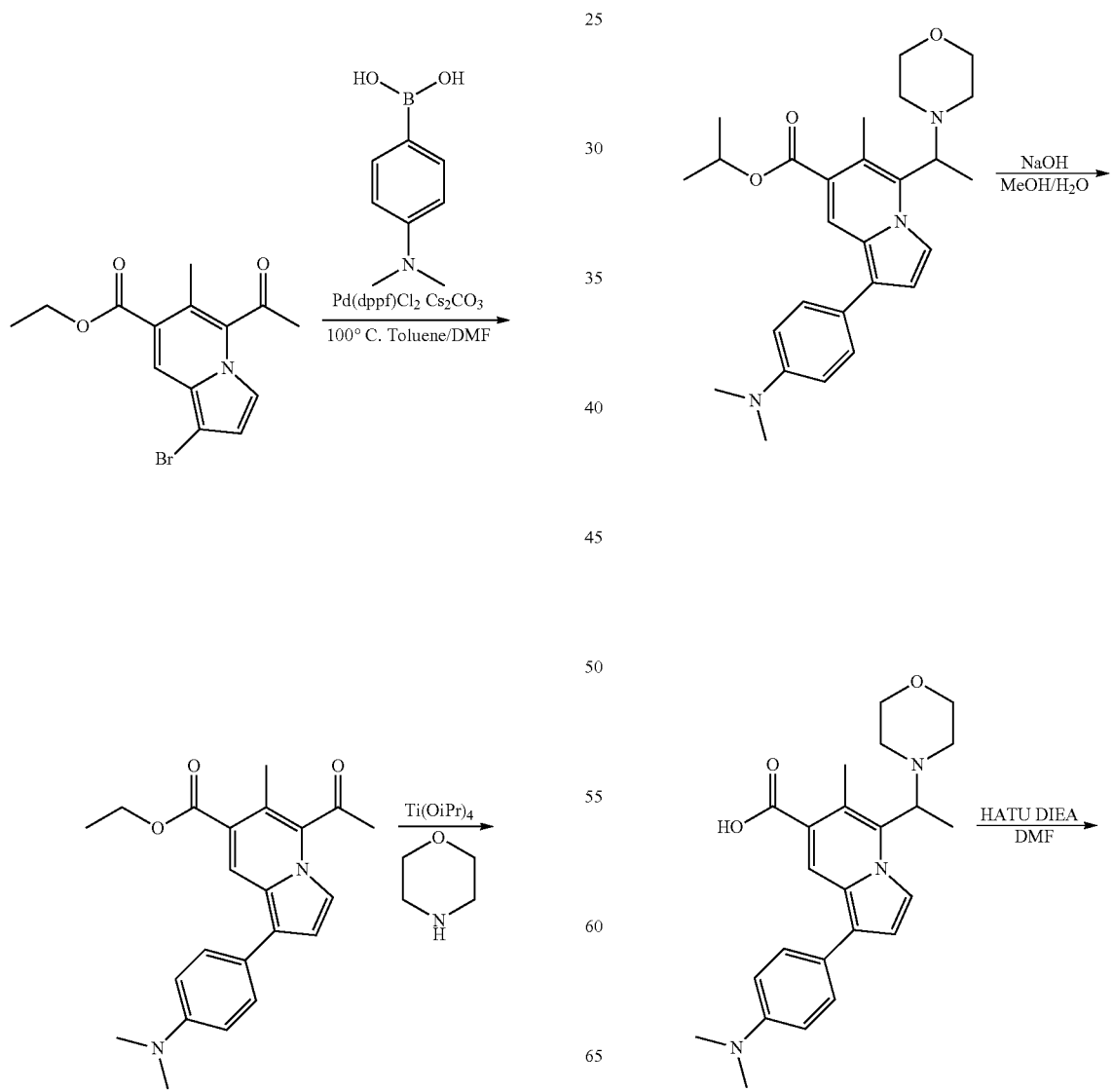

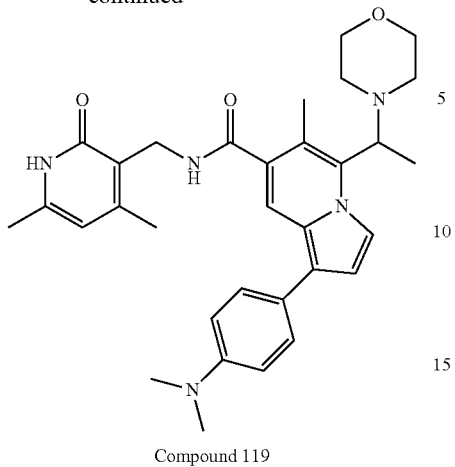

Compound 119

Step 1: Preparation of ethyl 5-acetyl-1-(4-(dimethylamino)phenyl)-6-methylindolizine-7-carboxylate: Yield 5%. MS (ESI) m/z 365 [M+H]$^+$.

Step 2: Preparation of isopropyl 1-(4-(dimethylamine)phenyl)-6-methyl-5-(1-morpholinevinyl)indolizine-7-carboxylate: MS (ESI) m/z 448 [M+H]$^+$.

Step 3: Preparation of isopropyl 1-(4-(dimethylamine)phenyl)-6-methyl-5-(1-morphinolinylethyl)indolizine-7-carboxylate: yield of two steps was 25%. MS (ESI) m/z 450 [M+H]$^+$.

Step 4: Preparation of 1-(4-(dimethylamine)phenyl)-6-methyl-5-(1-morpholinylethyl)indolizine-7-carboxylic acid: MS (ESI) m/z 408 [M+H]$^+$.

Step 5: Preparation of N-((4,6-dimethyl-2-oxo-1,2-dihydropyridin-3-yl)methyl)-1-(4-(dimethylamine)phenyl)-6-methyl-5-(1-morpholinylethoxy)indolizine-7-carboxamide: yield 38%. 41 NMR (400 MHz, CDCl$_3$) δ ppm 8.45 (s, 1H), 7.59 (s, 1H), 7.41-7.39 (m, 2H), 6.87-6.84 (m, 1H), 6.10 (s, 1H), 5.85 (s, 1H), 4.66 (s, 2H), 4.10-4.08 (m, 1H), 3.67 (m, 4H), 2.94 (s, 6H), 2.69-2.68 (m, 2H), 2.36 (s, 3H), 2.30-2.23 (m, 5H), 2.20 (s, 3H), 1.52-1.50 (m, 3H); MS(ESI) m/z 542 [M+H]$^+$.

Example 119: Preparation of N-((4,6-dimethyl-2-oxo-1,2-dihydropyridin-3-yl)methyl)-6-methyl-5-(1-morpholinylethyl)-1-(4-morpholinylphenyl)indolizine-7-carboxamide: Same as Example 31

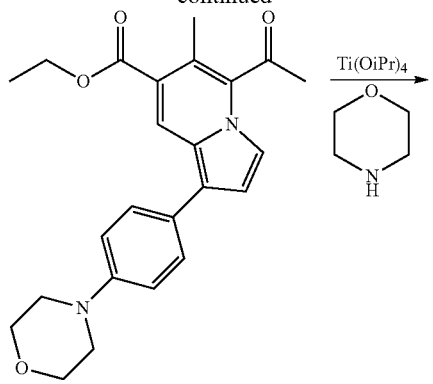

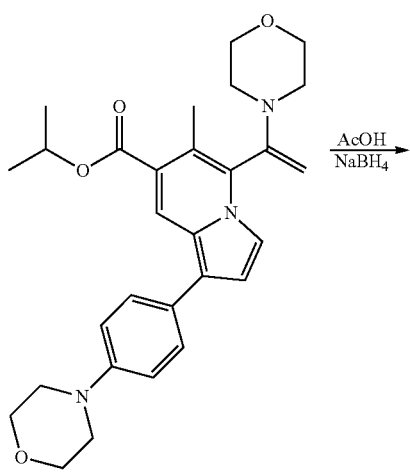

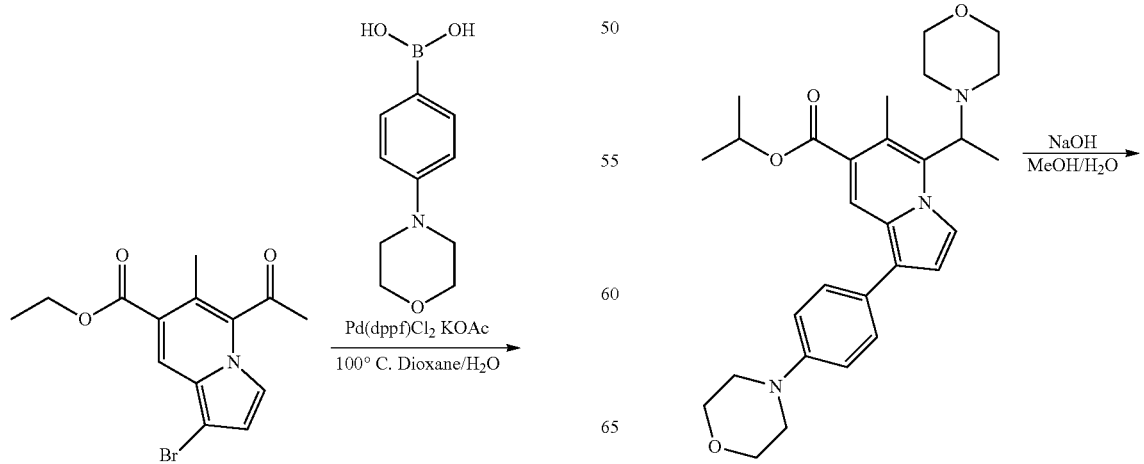

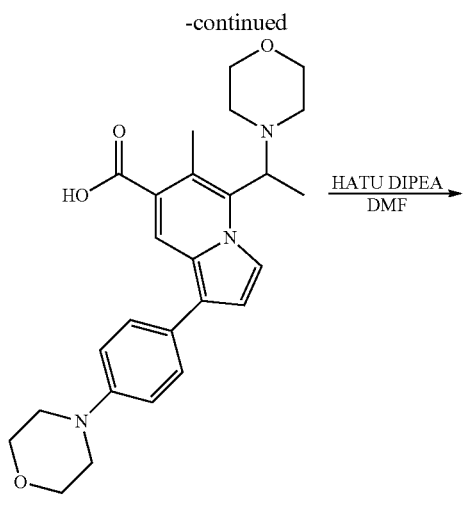

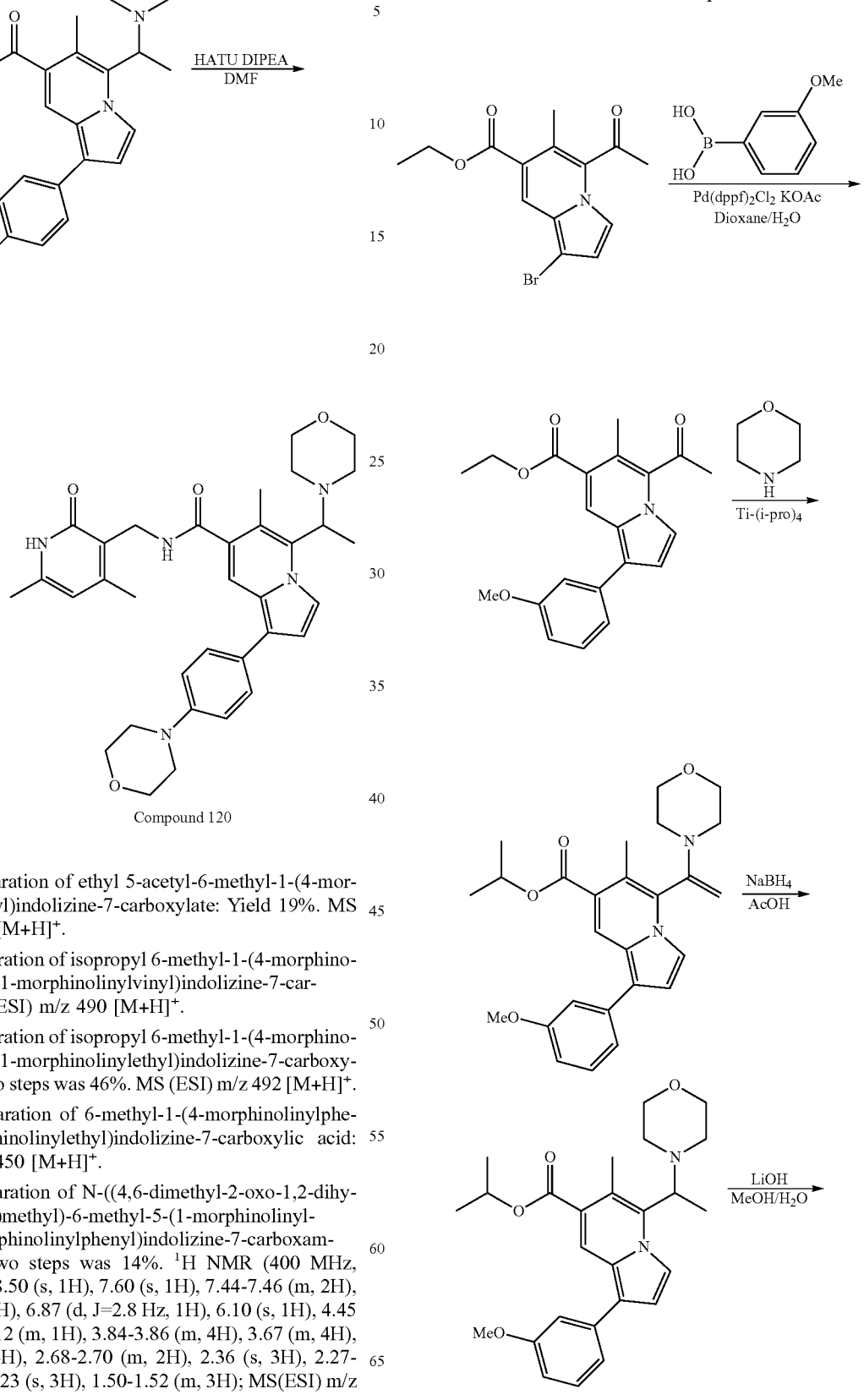

Compound 120

Step 1: Preparation of ethyl 5-acetyl-6-methyl-1-(4-morpholinylphenyl)indolizine-7-carboxylate: Yield 19%. MS (ESI) m/z 407 [M+H]+.

Step 2: Preparation of isopropyl 6-methyl-1-(4-morpholinylphenyl)-5-(1-morpholinylvinyl)indolizine-7-carboxylate: MS (ESI) m/z 490 [M+H]+.

Step 3: Preparation of isopropyl 6-methyl-1-(4-morpholinylphenyl)-5-(1-morpholinylethyl)indolizine-7-carboxylate: yield of two steps was 46%. MS (ESI) m/z 492 [M+H]+.

Step 4: Preparation of 6-methyl-1-(4-morpholinylphenyl)-5-(1-morpholinylethyl)indolizine-7-carboxylic acid: MS (ESI) m/z 450 [M+H]+.

Step 5: Preparation of N-((4,6-dimethyl-2-oxo-1,2-dihydropyridin-3-yl)methyl)-6-methyl-5-(1-morpholinylethyl)-1-(4-morpholinylphenyl)indolizine-7-carboxamide: yield of two steps was 14%. $^1$H NMR (400 MHz, CDCl$_3$) δ ppm 8.50 (s, 1H), 7.60 (s, 1H), 7.44-7.46 (m, 2H), 7.01-7.04 (m, 2H), 6.87 (d, J=2.8 Hz, 1H), 6.10 (s, 1H), 4.45 (s, 2H), 4.07-4.12 (m, 1H), 3.84-3.86 (m, 4H), 3.67 (m, 4H), 3.14-3.17 (m, 4H), 2.68-2.70 (m, 2H), 2.36 (s, 3H), 2.27-2.31 (m, 5H), 2.23 (s, 3H), 1.50-1.52 (m, 3H); MS(ESI) m/z 584 [M+H]+.

Example 120: Preparation of N-((4,6-dimethyl-2-oxo-1,2-dihydropyridin-3-yl)methyl)-6-methyl-5-(1-morpholinylethyl)-1-(3-methoxyphenyl)indolizine-7-amide: Same as Example 31

-continued

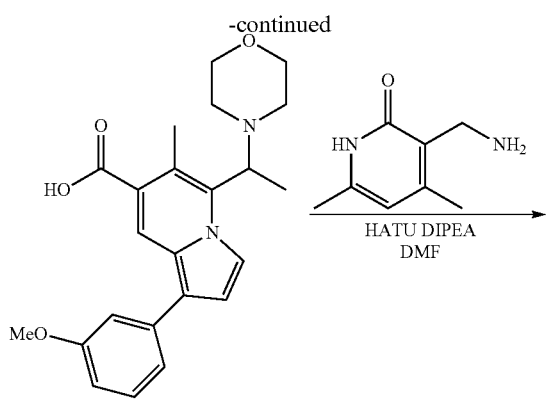

Example 121: Preparation of N-((4,6-dimethyl-2-oxo-1,2-dihydropyridin-3-yl)methyl)-6-methyl-5-(1-morpholinylethyl)-1-(4-methoxyphenyl)indolizine-7-carboxamide

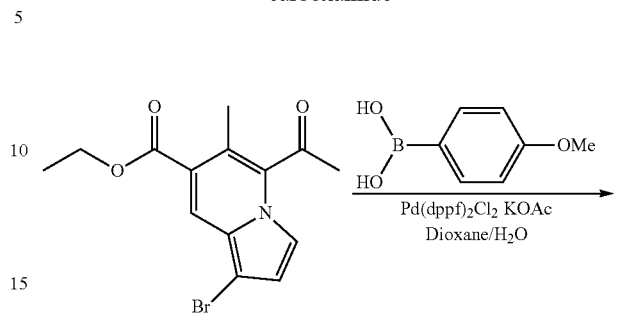

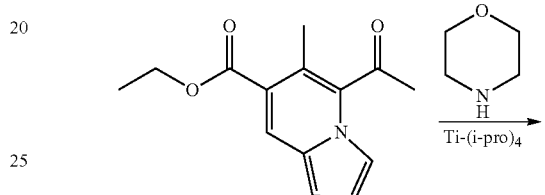

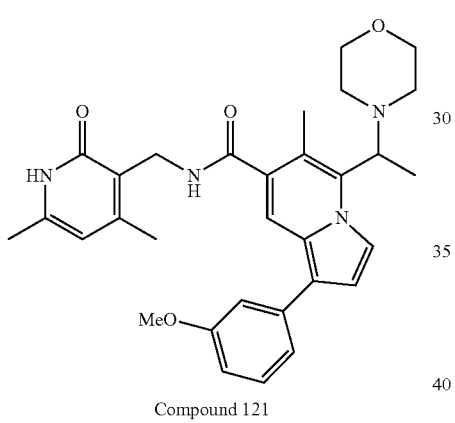

Compound 121

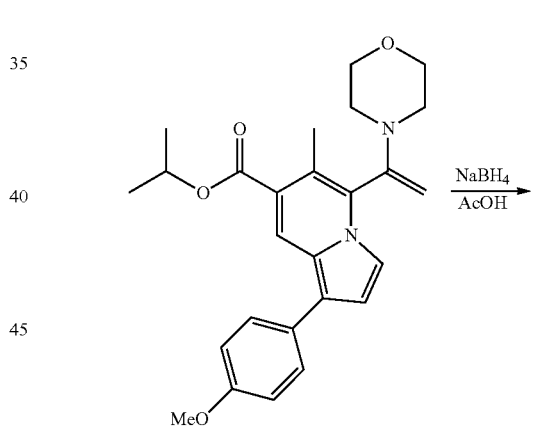

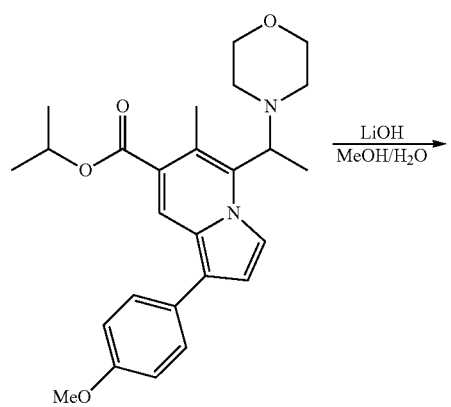

Step 1: Preparation of ethyl 5-acetyl-6-methyl-2-(3-methoxyphenyl)indolizine-7-carboxylate: Yield 14%. MS (ESI) m/z 352 [M+H]⁺.

Step 2: Preparation of isopropyl 6-methyl-5-(1-morpholinylvinyl)-1-(3-methoxyphenyl)indolizine-7-carboxylate: MS (ESI) m/z 435 [M+H]⁺.

Step 3: Preparation of isopropyl 6-methyl-5-(1-morpholinylethyl)-1-(3-methoxyphenyl)indolizine-7-carboxylate: yield of two steps was 79%. MS (ESI) m/z 437 [M+H]⁺.

Step 4: Preparation of 6-methyl-5-(1-morpholinylethyl)-1-(3-methoxyphenyl)indolizine-7-carboxylic acid: MS (ESI) m/z 395 [M+H]⁺.

Step 5: Preparation of N-((4,6-dimethyl-2-oxo-1,2-dihydropyridin-3-yl)methyl)-6-methyl-5-(1-morpholinylethyl)-1-(3-methoxyphenyl)indolizine-7-carboxamide: yield of two steps was 9%. $^1$H NMR (400 MHz, CDCl$_3$) δ ppm 11.16 (s, 1H), 8.41 (s, 1H), 7.61 (s, 1H), 7.22-7.20 (m, 2H), 7.06-7.04 (m, 2H), 7.00 (s, 1H), 6.83 (s, 1H), 6.67-6.65 (m, 1H), 5.81 (s, 1H), 4.44-4.42 (d, J=5.2 Hz, 2H), 4.02-3.96 (m, 1H), 3.74 (s, 3H), 3.62 (s, 4H), 2.58 (s, 2H), 2.31 (s, 3H), 2.27 (s, 3H), 2.21-2.18 (m, 2H), 2.04 (s, 3H), 1.43-1.41 (d, J=6.8 Hz, 3H); MS(ESI) m/z 551 [M+H]⁺.

289
-continued

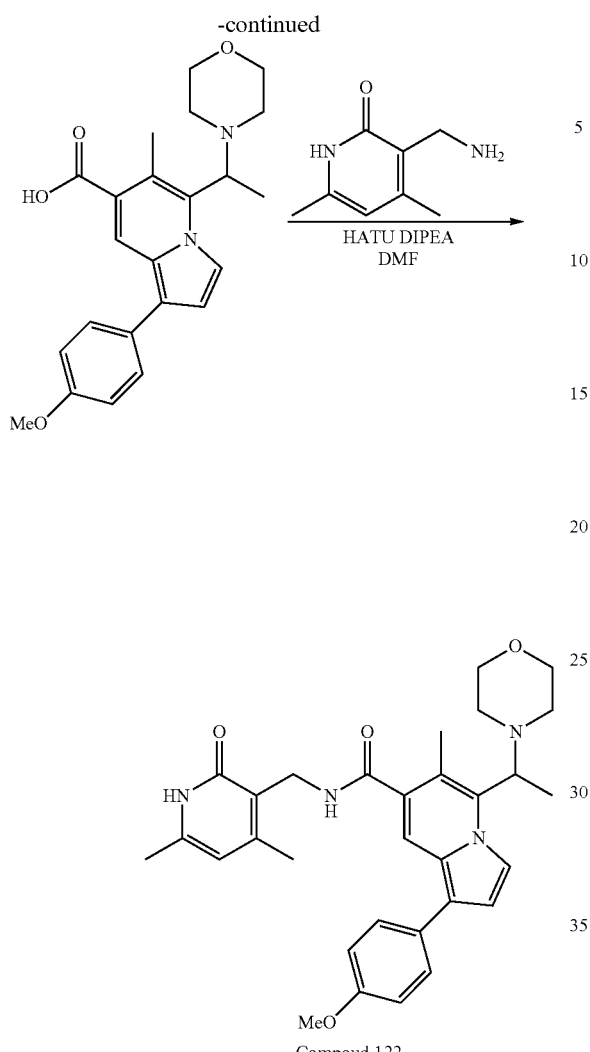

Compoud 122

Step 1: Preparation of ethyl 5-acetyl-6-methyl-2-(4-methoxyphenyl)indolizine-7-carboxylate: Yield 11%. MS (ESI) m/z 352 [M+H]+.

Step 2: Preparation of isopropyl 6-methyl-5-(1-morphinolinylvinyl)-1-(4-methoxyphenyl)indolizine-7-carboxylate: MS (ESI) m/z 435 [M+H]+.

Step 3: Preparation of isopropyl 6-methyl-5-(1-morphinolinylethyl)-1-(4-methoxyphenyl)indolizine-7-carboxylate: yield 78%. MS (ESI) m/z 437 [M+H]+.

Step 4: Preparation of 6-methyl-5-(1-morpholinylethyl)-1-(4-methoxyphenyl)indolizine-7-carboxylic acid: MS (ESI) m/z 395 [M+H]+.

Step 5: Preparation of N-((4,6-dimethyl-2-oxo-1,2-dihydropyridin-3-yl)methyl)6-methyl-5-(1-morpholinylethyl)-1-(4-methoxyphenyl)indolizine-7-carboxamide: $^1$H NMR (400 MHz, CDCl$_3$) δ ppm 8.38 (s, 1H), 7.61 (s, 1H), 7.68-7.64 (m, 1H), 7.55 (s, 1H), 7.48-7.45 (m, 1H), 7.39-7.36 (d, J=8.8 Hz, 2H), 7.11-7.09 (m, 1H), 6.87-6.84 (d, J=8.8 Hz, 2H), 6.79-6.78 (m, 1H), 4.44-4.42 (d, J=5.6 Hz, 2H), 4.03-4.01 (d, J=6.8 Hz, 1H), 3.72 (s, 3H), 3.62 (s, 4H), 2.32 (s, 3H), 2.26 (s, 3H), 2.17-2.13 (t, J=7.6 Hz, 2H), 1.97-1.92 (m, 2H), 1.42-1.44 (d, J=6.4 Hz, 3H). MS (ESI) m/z 551 [M+H]+.

290

Example 122: Preparation of 2-bromo-N-((4,6-dimethyl-2-oxo-1,2-dihydropyridin-3-yl)methyl)-6-methyl-5-(1-(pyrrole-1-yl)ethyl)indolizine-7-carboxamide: Same as Example 30

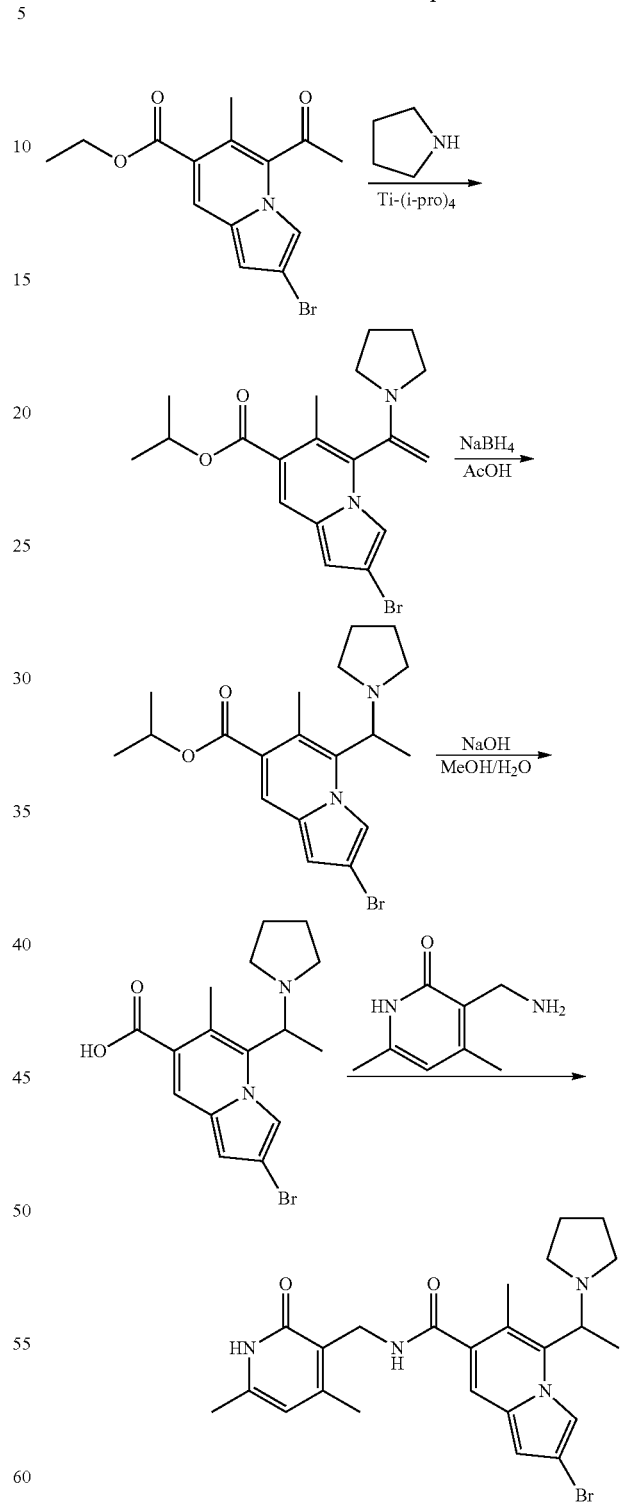

Compound 123

Step 1: Step 2: Preparation of isopropyl 2-bromo-6-methyl-5-(1-(pyrrol-1-yl)vinyl)indolizine-7-carboxylate: MS (ESI) m/z 391 [M+H]+.

Step 2: Preparation of isopropyl 2-bromo-6-methyl-5-(1-(pyrrol-1-yl)ethyl)indolizine-7-carboxylate: yield of two steps was 59%. MS (ESI) m/z 393 [M+H]+.

Step 3: Preparation of 2-bromo-6-methyl-5-(1-(pyrrol-1-yl)ethyl)indolizine-7-carboxylic acid: MS (ESI) m/z 351 [M+H]+.

Step 4: Preparation of 2-bromo-N-((4,6-dimethyl-2-oxo-1,2-dihydropyridin-3-yl)methyl)-6-methyl-5-(1-(pyrrol-1-yl)ethyl)indolizine-7-carboxamide: Yield 4%. 1H NMR (400 MHz, DMSO-d6) δ ppm 8.47 (s, 1H), 7.28 (s, 1H), 6.84 (s, 1H), 6.51 (s, 1H), 6.10 (s, 1H), 4.57 (m, 2H), 4.05-4.04 (m, 1H), 2.69-2.67 (m, 2H), 2.36 (s, 3H), 2.29-2.19 (m, 5H), 2.18 (s, 3H), 1.78-1.77 (m, 4H), 1.49-1.47 (m, 3H); MS(ESI) m/z 485 [M+H]+.

Example 123: Preparation of 2-bromo-5-(1-(4,4-difluoropiperidin-1-yl)ethyl)-N-((4,6-dimethyl-2-oxo-1,2-dihydropyridin-3-yl)methyl)-6-methylindolizine-7-carboxamide: Same as Example 30

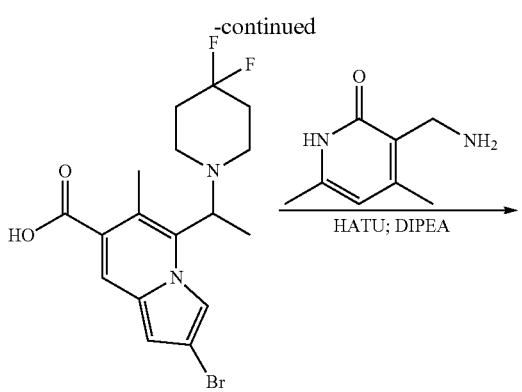

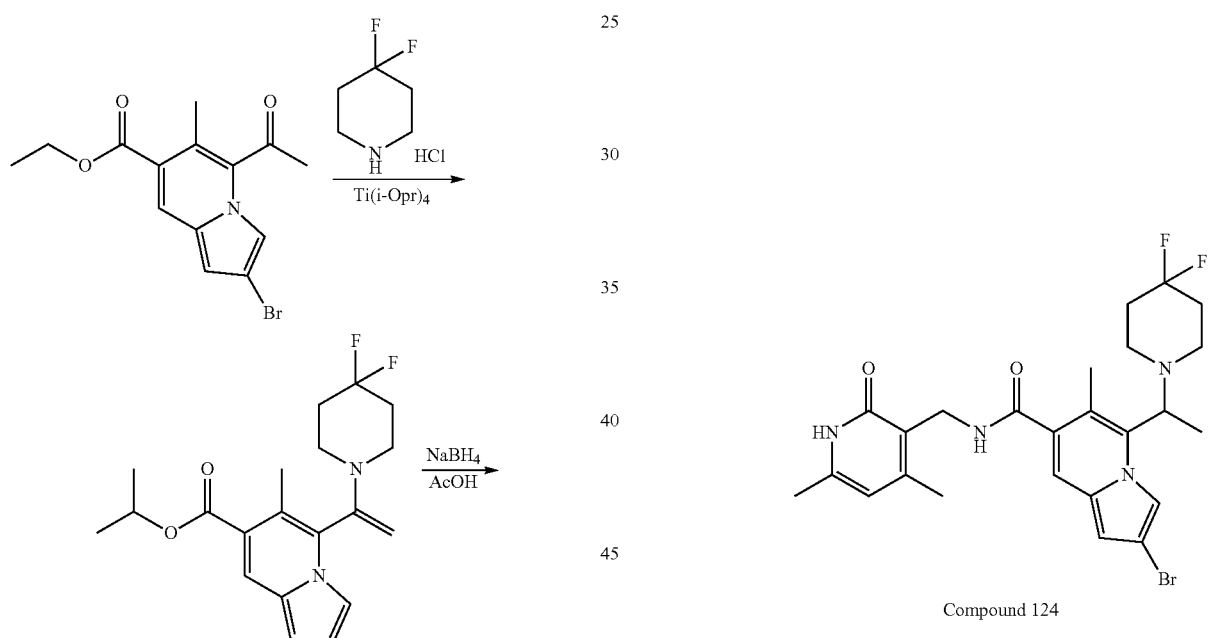

Compound 124

Step 1: Preparation of isopropyl 2-bromo-5-(1-(4,4-difluoropiperidin-1-yl)vinyl)-6-methylindolizine-7-carboxylate: MS (ESI) m/z 441 [M+H]+.

Step 2: Preparation of isopropyl 2-bromo-5-(1-(4,4-difluoropiperidin-1-yl)ethyl)-6-methylindolizine-7-carboxylate: yield of two steps was 7%. MS (ESI) m/z 443 [M+H]+.

Step 3: Preparation of 2-bromo-5-(1-(4,4-difluoropiperidin-1-yl)ethyl)-6-methylindolizine-7-carboxylic acid: MS (ESI) m/z 401 [M+H]+.

Step 4: Preparation of 2-bromo-5-(1-(4,4-difluoropiperidin-1-yl)ethyl)-N-((4,6-dimethyl-2-oxo-1,2-dihydropyridin-3-yl)methyl)-6-methylindolizine-7-carboxamide: yield of two steps was 51%. 1H-NMR (MeOD, 400 MHz): 7.36 (s, 1H), 6.59 (s, 1H), 6.14 (s, 1H), 4.48 (s, 2H), 4.39 (s, 1H), 2.96-2.95 (m, 2H), 2.55-2.53 (m, 2H), 2.37 (s, 3H), 2.30 (s, 3H), 2.35 (s, 3H), 2.03-2.02 (m, 4H). 1.60-1.58 (m, 3H); MS(ESI) m/z 535 [M+H]+.

Example 124: Preparation of N-((4,6-dimethyl-2-oxo-1,2-dihydropyridin-3-yl)methyl)-2-(2-fluoro-5-methoxyphenyl)-6-methyl-5-(1-morpholinoethyl)indolizine-7-carboxamide: Same as Example 31

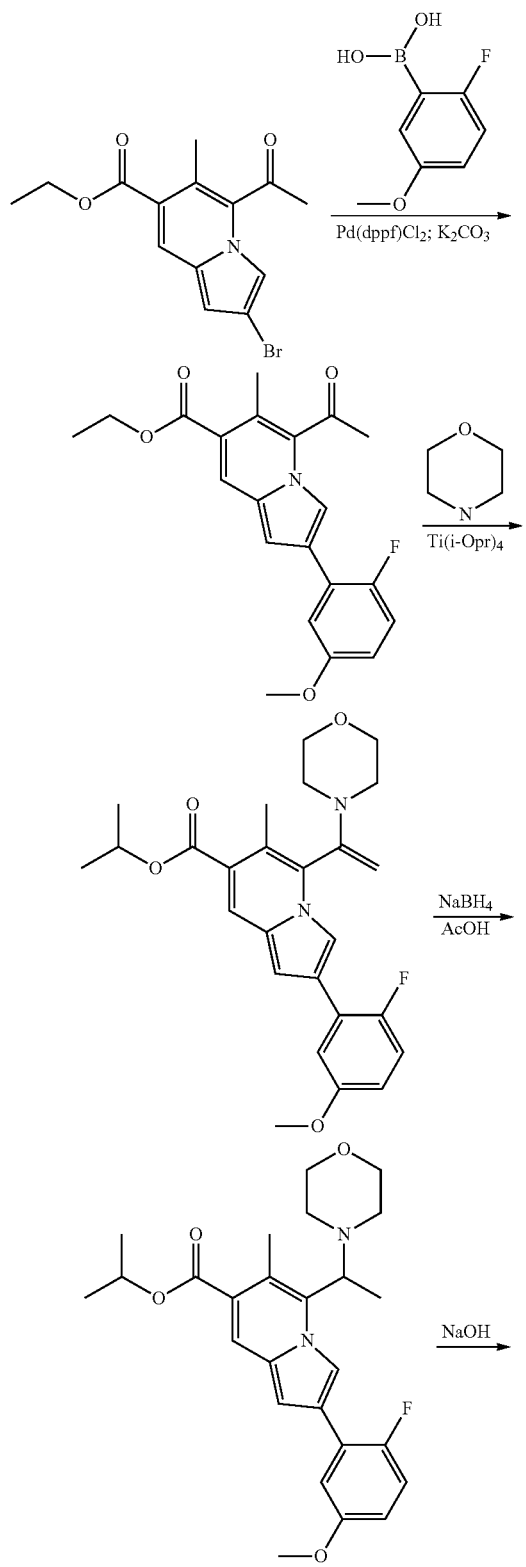

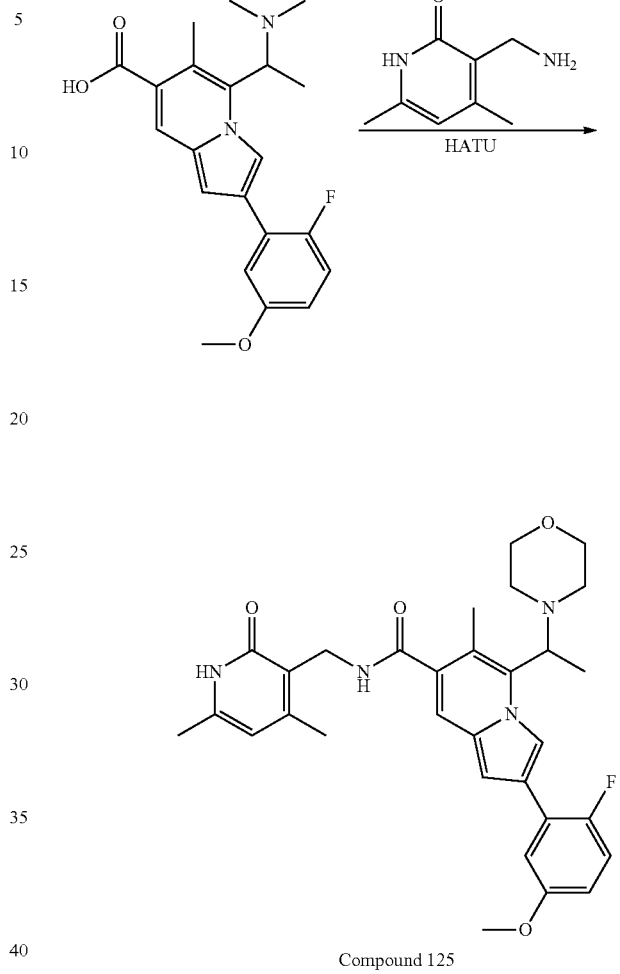

Compound 125

Step 1: Preparation of ethyl 5-acetyl-2-(2-fluoro-5-methoxyphenyl)-6-methylindolizine-7-carboxylate: Yield 66%. MS (ESI) m/z 370 [M+H]$^+$.

Step 2: Preparation of isopropyl 2-(2-fluoro-5-methoxyphenyl)-6-methyl-5-(1-morphinolinylvinyl)indolizine-7-carboxylate. MS (ESI) m/z 453 [M+H]$^+$.

Step 3: Preparation of isopropyl 2-(2-fluoro-5-methoxyphenyl)-6-methyl-5-(1-morpholinylethyl)indolizine-7-carboxylate: yield of two steps was 65%. MS (ESI) m/z 455 [M+H]$^+$.

Step 4: Preparation of 2-(2-fluoro-5-methoxyphenyl)-6-methyl-5-(1-morpholinylethyl)indolizine-7-carboxylic acid: MS (ESI) m/z 413 [M+H]$^+$.

Step 5: Preparation of N-((4,6-dimethyl-2-oxo-1,2-dihydropyridin-3-yl)methyl)-2-(2-fluoro-5-methoxyphenyl)-6-methyl-5-(1-morpholinylethyl)indolizine-7-carboxamide: yield of two steps was 32%. $^1$H-NMR (CDCl$_3$, 400 MHz): 12.78 (s, 1H), 8.88 (s, 1H), 7.35 (s, 2H), 7.18-7.15 (m, 1H), 7.07-7.03 (m, 1H), 6.74-6.72 (m, 2H), 5.98 (s, 1H), 4.54-4.52 (m, 2H), 4.07-4.02 (m, 1H), 3.83 (s, 3H), 3.69-3.68 (m, 4H), 2.65-2.64 (m, 2H), 2.39 (s, 3H), 2.35 (s, 3H), 2.27-2.22 (m, 2H), 2.04 (s, 3H), 1.50-1.48 (m, 3H); MS(ESI) m/z 547 [M+H]$^+$.

Example 125: Preparation of methyl 7-(((4,6-dimethyl-2-oxo-1,2-dihydropyridin-3-yl)methyl)carbamoyl)-6-methyl-5-(1-morpholinylethyl)indolizine-2-carboxylate

Example 126: Preparation of N-((4,6-dimethyl-2-oxo-1,2-dihydropyridin-3-yl)methyl)-6-methyl-2-(morpholin-4-carbonyl)-5-(1-morpholinoethyl)indolizine-7-carboxamide

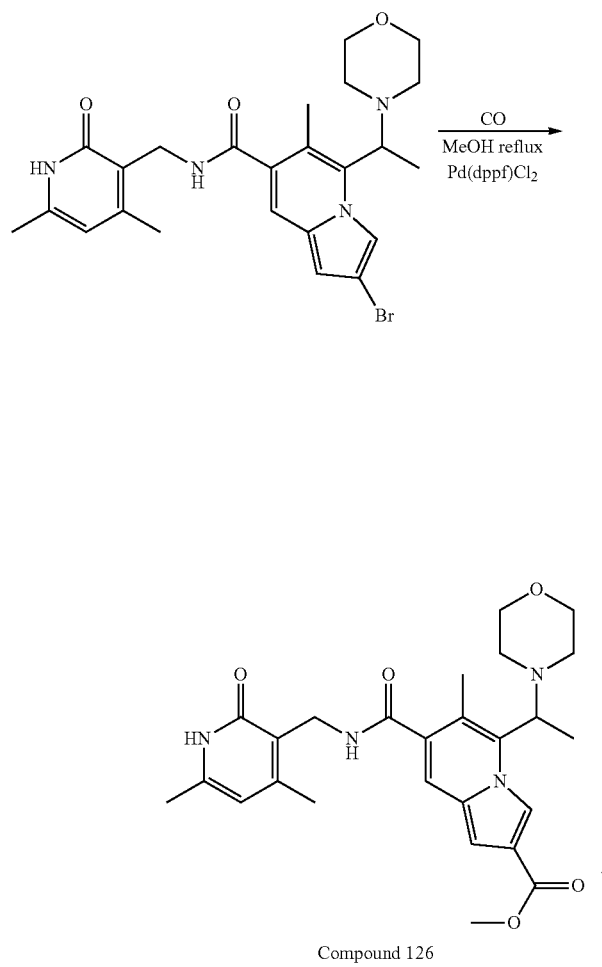

Compound 126

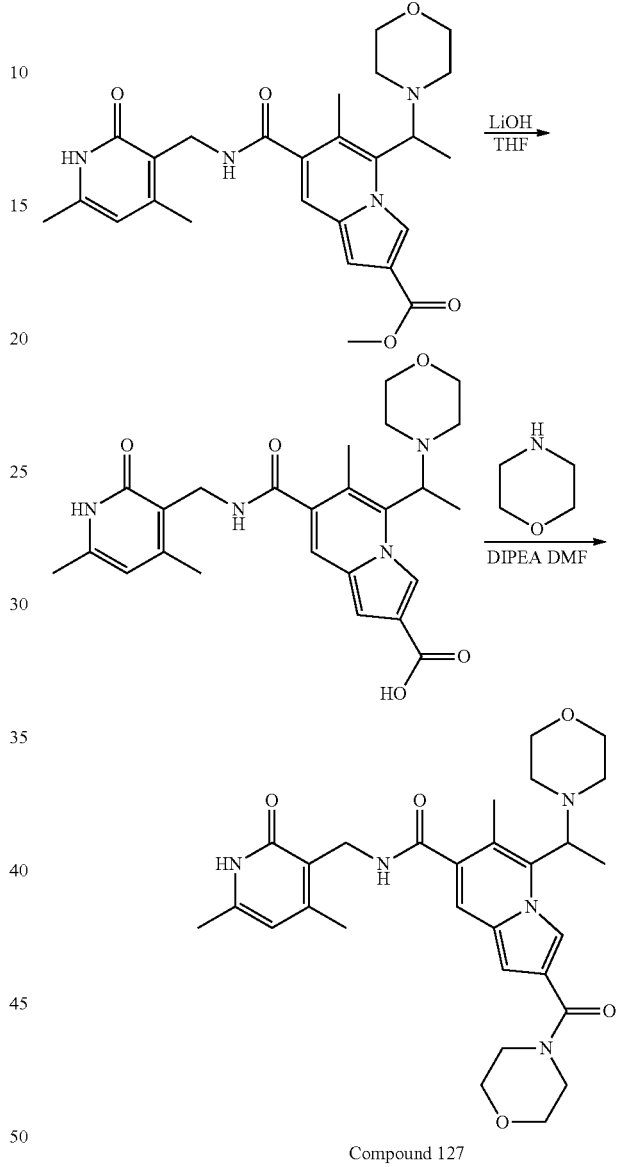

Compound 127

Step 1: Synthesis of methyl 7-(((4,6-dimethyl-2-oxo-1,2-dihydropyridin-3-yl)methyl)carbamoyl)-6-methyl-5-(1-morpholinoethyl)indolizine-2-carboxylate: 2-bromo-N-((4,6-dimethyl-2-oxo-1,2-dihydropyridin-3-yl)methyl)-6-methyl-5-(1-morpholino) indolizine-7-carboxamide (170 mg, 0.34 mmol), Pd(dppf)Cl$_2$ (17 mg), triethylamine (69 mg, 0.68 mmol) and 30 ml of methanol were added successively into a 25 mL CO-protected single-mouth flask, stirred to reflux overnight, and then 50 ml of ethyl acetate and 20 ml of water were added. The organic phase was separated and concentrated to provide a crude product, which was purified through column chromatography (petroleum ether: ethyl acetate=5:1) to provide a product as yellow solids (13 mg, yield: 8%). $^1$H-NMR (DMSO, 400 MHz): 11.48 (s, 1H), 8.77 (s, 1H), 8.25 (s, 1H), 7.48-7.47 (m, 1H), 6.85 (m, 1H), 5.85 (s, 1H), 4.39-4.37 (m, 3H), 3.85 (s, 3H), 3.60 (m, 5H), 2.28 (s, 3H), 2.21 (s, 5H), 2.19 (s, 5H), 1.55-1.54 (m, 3H). MS (ESI) m/z 481 [M+H]$^+$.

Step 1: Preparation of 7-(((4,6-dimethyl-2-oxo-1,2-dihydropyridin-3-yl)methyl)carbamoyl)-6-methyl-5-(1-morpholinoethyl)indolizine-2-carboxylic acid: methyl 74(4,6-dimethyl-2-oxo-1,2-dihydropyridine-3-yl)methyl)carbamoyl)-6-methyl-5-(1-morpholinoethyl)indolizine-2-carboxylate (50 mg (crude), 0.104 mmol), lithium hydroxide (17.5 mg, 0.417 mmol) and 20 ml of THF/15 ml of water were added successively to a 50 mL single-necked flask, stirred to reflux overnight, 2N hydrochloric acid was added to adjust pH to 6-7, and 100 ml of ethyl acetate was added to the reaction system. The organic phase was separated and evaporated to provide a crude product (50 mg), which was used directly in the next step.

Step 2: Preparation of N-((4,6-dimethyl-2-oxo-1,2-dihydropyridin-3-yl)methyl)-6-methyl-2-(morpholin-4-carbonyl)-5-(1-morpholinoethyl)indolizine-7-carboxamide: yield 21%. ¹H-NMR (MeOD, 400 MHz): 8.47 (s, 1H), 7.54 (s, 1H), 6.78 (s, 1H), 6.16 (s, 1H), 4.47 (s, 3H), 3.79-3.72 (m, 13H), 3.28 (m, 2H), 2.39 (s, 6H), 2.26 (s, 3H), 1.74 (s, 3H); MS(ESI) m/z 536 [M+H]⁺.

Example 127: Preparation of N-((4,6-dimethyl-2-oxo-1,2-dihydropyridin-3-yl)methyl)-6-methyl-5-(4-dimethylaminopiperidinylethyl)-1-phenylindolizine-7-carboxamide: Same as Example 31

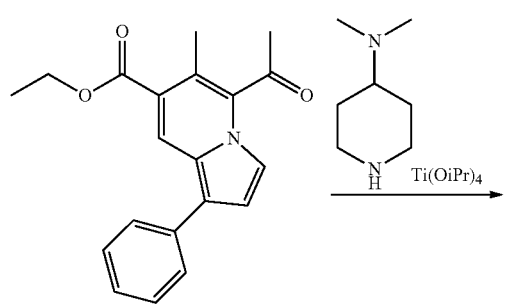

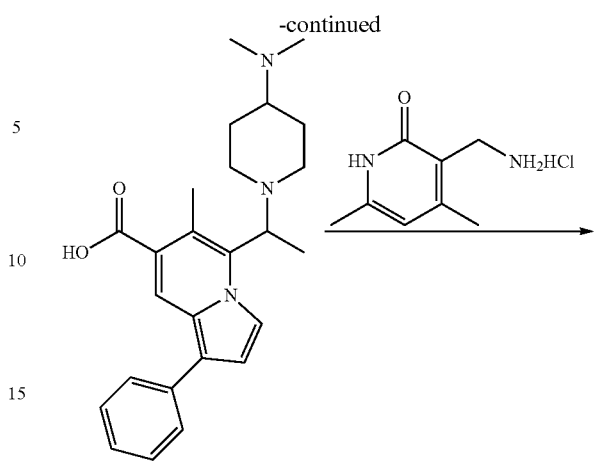

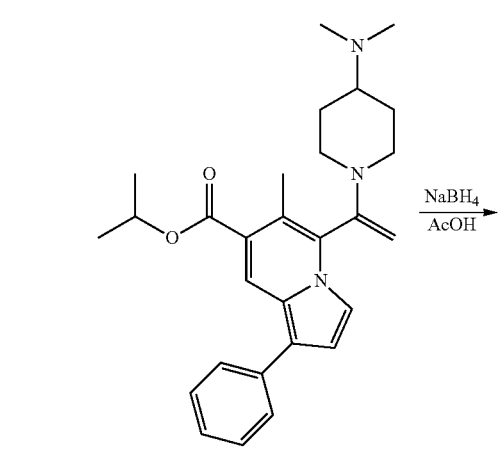

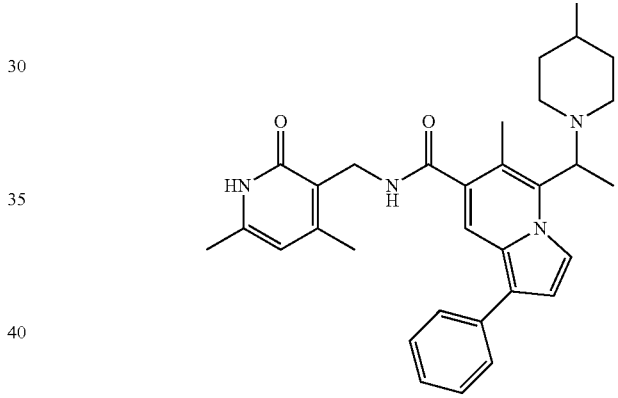

Compound 128

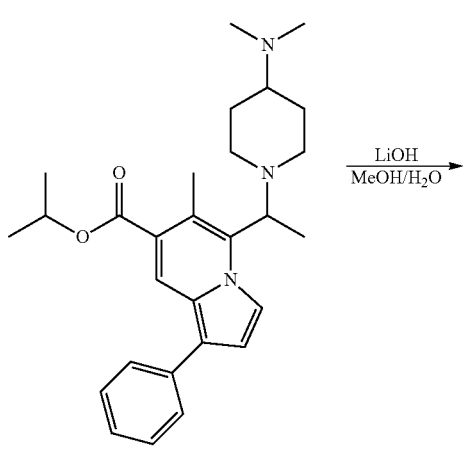

Step 1: Preparation of isopropyl 6-methyl-5-(4-dimethylamidopiperidinylvinyl)-1-phenylindolizine-7-carboxylate: MS (ESI) m/z 446 [M+H]⁺.

Step 2: Preparation of isopropyl 6-methyl-5-(4-dimethylamidopiperidinylvinyl)-1-phenylindolizine-7-carboxylate: yield of two steps was 91%. MS(ESI) m/z 320 [M+H-$C_7H_{16}N_2$]⁺.

Step 3: Preparation of 6-methyl-5-(4-dimethylamidopiperidinylvinyl)-1-phenylindolizine-7-carboxylic acid: MS (ESI) m/z 406 [M+H]⁺.

Step 4: Preparation of N-((4,6-dimethyl-2-oxo-1,2-dihydropyridin-3-yl)methyl)-6-methyl-5-(4-dimethylaminopiperidinylethyl)-1-phenylindolizine-7-carboxamide: yield of two steps was 27%. ¹H NMR (400 MHz, MeOD) δ ppm 7.73 (s, 1H), 7.547 (d, J=7.2 Hz, 2H), 7.41 (t, J=7.6 Hz, 2H), 7.236 (t, J=7.6 Hz, 1H), 7.02 (s, 1H), 6.18 (s, 1H), 4.47 (s, 2H), 3.83 (s, 1H), 3.60 (d, J=12.8 Hz, 1H), 2.92 (s, 2H), 2.88 (s, 6H), 2.38-2.36 (m, 6H), 2.30 (s, 2H), 2.26 (s, 3H), 2.21-2.16 (m, 2H), 2.04-2.00 (m, 2H), 1.73 (d, J=6.0 Hz, 3H); MS(ESI) m/z 562 [M+H]⁺.

299

Example 128: Preparation of N-((4-methoxy-6-methyl-2-oxo-1,2-dihydropyridin-3-yl)methyl)-6-methyl-5-(4-dimethylaminopiperidinylethyl)-1-phenylindolizine-7-carboxamide: Same as Example 108

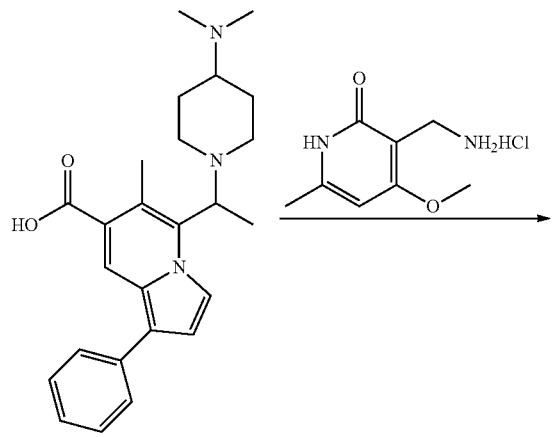

Compound 129

Step 1: Preparation of N-((4-methoxy-6-methyl-2-oxo-1,2-dihydropyridin-3-yl)methyl)-6-methyl-5-(4-dimethylaminopiperidinylethylene)-1-phenylindolizine-7-carboxamide: yield 31%. $^1$H NMR (400 MHz, d$^6$-DMSO) δ ppm 11.44 (s, 1H), 8.37 (s, 1H), 8.10 (s, 1H), 7.60-7.56 (m, 3H), 7.42 (t, J=7.2 Hz, 2H), 7.24-7.21 (m, 1H), 7.00 (s, 1H), 6.11 (s, 1H), 4.42 (d, J=4 Hz, 2H), 4.11-4.06 (m, 1H), 3.80 (s, 3H), 3.03 (d, J=6.8 Hz, 2H), 2.86 (t, J=10 Hz, 2H), 2.66 (s, 6H), 2.60-2.57 (m, 1H), 2.38 (s, 3H), 2.28 (s, 3H), 2.18 (s, 4H), 1.47 (d, J=3.4 Hz, 3H); MS(ESI) m/z 556 [M+H]$^+$.

300

Example 129: Preparation of N-((4,6-dimethyl-2-oxo-1,2-dihydropyridin-3-yl)methyl)-5-(1-(4-(dimethylamine)piperidine-1-yl)ethyl)-6-methyl-1-(1-methyl-1H-pyrazol-5-yl)indolizine-7-carboxamide

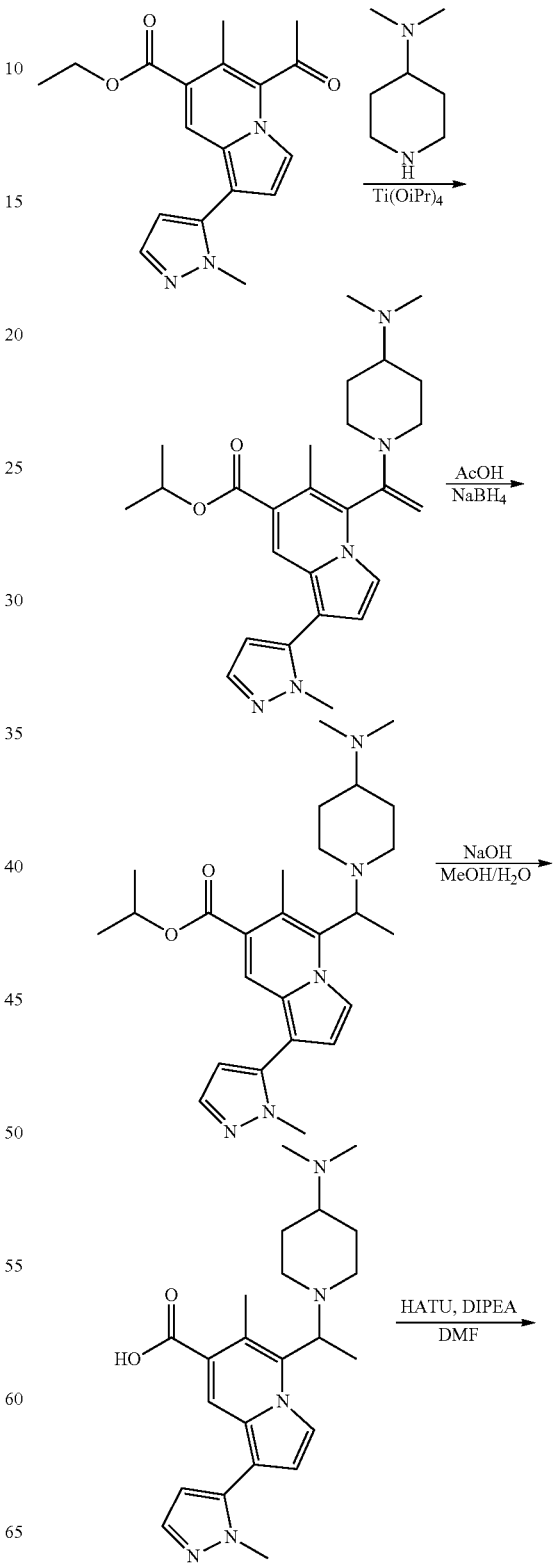

-continued

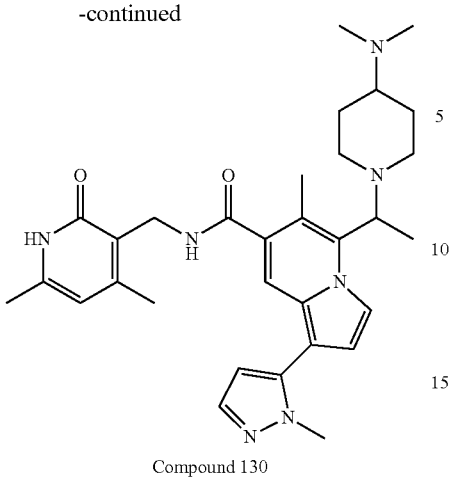

Compound 130

Step 1: Preparation of isopropyl 5-(1-(4-(dimethylamine) piperidin-1-yl)vinyl)-6-methyl-1-(1-methyl-1H-pyrazol-5-yl)indolizine-7-carboxylate: MS (ESI) m/z 450 [M+H]$^+$.

Step 2: Preparation of isopropyl 5-(1-(4-(dimethylamine) piperidin-1-yl)ethyl)-6-methyl-1-(1-methyl-1H-pyrazol-5-yl)indolizine-7-carboxylate: yield of two steps was 35%. MS (ESI) m/z 452 [M+H]$^+$.

Step 3: Preparation of 5-(1-(4-(dimethylamine)piperidin-1-yl)ethyl)-6-methyl-1-(1-methyl-1H-pyrazol-5-yl)indolizine-7-formic acid: MS(ESI) m/z 282 [M+H-C$_7$H$_{16}$N$_2$]$^+$.

Step 4: Preparation of N-((4,6-dimethyl-2-oxo-1,2-dihydropyridin-3-yl)methyl)-5-(1-(4-(dimethylamine)piperidine-1-yl)ethyl)-6-methyl-1-(1-methyl-1H-pyrazol-5-yl)indolizine-7-carboxamide: yield of the two steps was 16%. $^1$H NMR (400 MHz, CDCl$_3$) δ ppm 8.48 (s, 1H), 8.27 (s, 1H), 7.47 (s, 1H), 7.29 (s, 1H), 7.01 (d, J=2.4 Hz, 1H), 6.40 (s, 1H), 5.85 (s, 1H), 4.25-4.24 (m, 2H), 4.03-4.02 (m, 1H), 3.83 (s, 3H), 2.26 (m, 2H), 2.17-2.02 (m, 13H), 1.99-1.86 (m, 5H), 1.61-1.59 (m, 1H), 1.41-1.39 (m, 3H); MS(ESI) m/z 544 [M+H]$^+$.

Example 130: Preparation of 2-chloro-5-(1-(4-(dimethylamino)piperidin-1-yl)ethyl)-N-((4-methoxy-6-methyl-2-oxo-1,2-di hydropyridin-3-yl)methyl)-6-methylindolizine-7-carboxamide: Same as Example 108

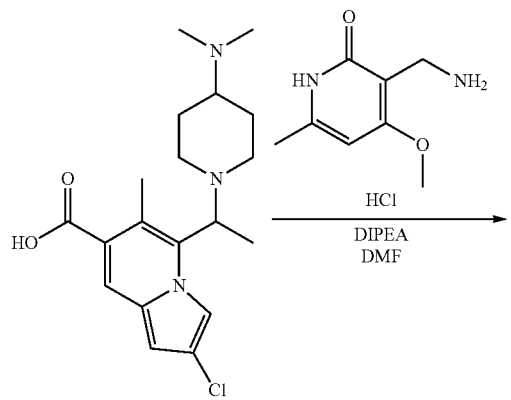

-continued

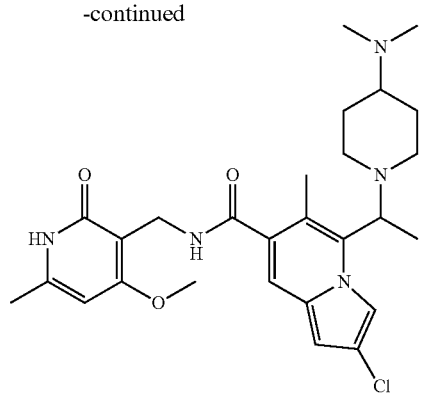

Compound 131

Step 1: Preparation of 2-chloro-5-(1-(4-(dimethylamino) piperidin-1-yl)ethyl)-N-((4-methoxy-6-methyl-2-oxo-1,2-di hydropyridin-3-yl)methyl)-6-methylindolizine-7-carboxamide: Yield 12%. $^1$H-NMR (DMSO-d$_6$, 400 MHz): 11.48 (s, 1H), 9.50 (s, 1H), 8.25 (s, 1H), 8.05 (s, 1H), 7.28 (s, 1H), 6.58 (s, 1H), 6.13 (s, 1H), 4.22-4.21 (m, 2H), 3.99 (s, 6H), 3.20 (m, 2H), 2.77-2.76 (m, 8H), 2.28 (s, 3H), 2.21-2.19 (m, 7H), 1.55-1.54 (m, 3H); MS(ESI) m/z 514 [M+H]$^+$.

Example 131: Preparation of N-((4-methoxy-6-methyl-2-oxo-1,2-dihydropyridin-3-yl)methyl)-6-methyl-5-(1-morpholinyl ethyl)-1-phenylindolizine-7-carboxamide: Same as Example 108

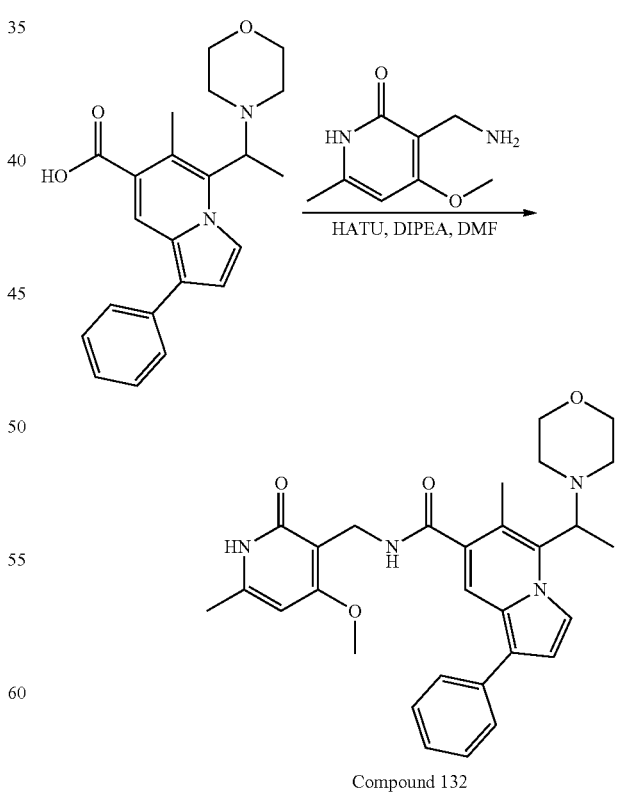

Compound 132

Step 1: Preparation of N-((4-methoxy-6-methyl-2-oxo-1, 2-dihydropyridin-3-yl)methyl)-6-methyl-5-(1-morpholinyl ethyl)-1-phenylindolizine-7-carboxamide: yield of two steps was 24%. ¹H NMR (400 MHz, MeOD) δ ppm 7.68 (s, 1H), 7.54 (d, J=7.6 Hz, 2H), 7.439 (t, J=7.6 Hz, 2H), 7.22 (t, J=7.2 Hz, 1H), 6.98 (s, 1H), 6.29 (s, 1H), 4.44 (s, 2H), 3.91 (s, 3H), 3.88-3.86 (m, 1H), 3.74 (s, 4H), 3.23-3.18 (m, 2H), 2.37 (s, 3H), 2.32 (s, 3H), 1.64 (d, J=6.4 Hz, 3H), 1.31 (s, 2H); MS(ESI) m/z 515 [M+H]⁺.

Example 132: Preparation of N-((4-methoxy-6-methyl-2-oxo-1,2-dihydropyridin-3-yl)methyl)-6-methyl-1-(1-methyl-1H-pyrazol-5-yl)-5-(1-morpholinylethyl)indolizine-7-carboxamide: Same to Example 108

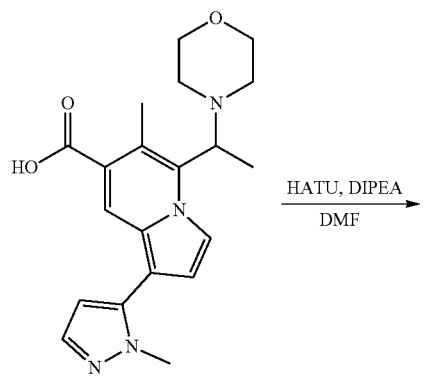

Example 133: Preparation of N-((4N-((4-methoxy-6-methyl-2-oxo-1,2-dihydropyridin-3-yl)methyl)-6-methyl)-2-(1-methyl-1H-imidazol-5-yl)-5-(1-morpholinoethyl)indolizine-7-carboxamide: Same as Example 108

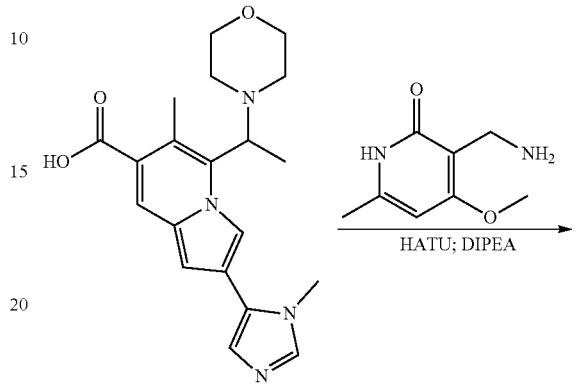

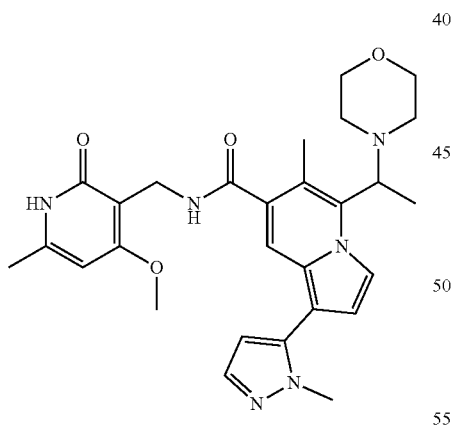

Compound 133

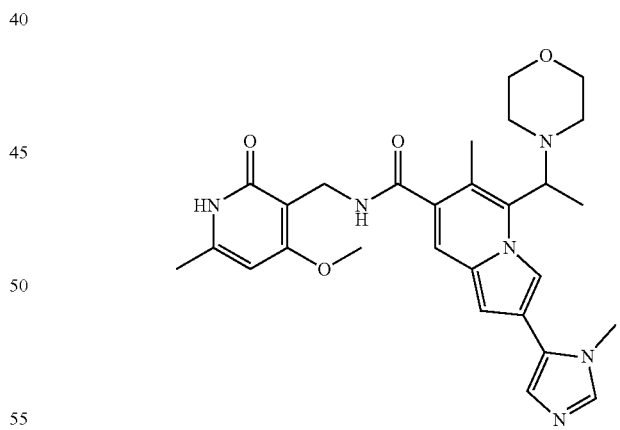

Compound 134

Step 1: Preparation of N-((4-Methoxy-6-methyl-2-oxo-1,2-dihydropyridin-3-yl)methyl)-6-methyl-1-(1-methyl-1H-pyrazol-5-yl)-5-(1-morpholinylethyl)indolizine-7-carboxamide: Yield 21%. ¹H NMR (400 MHz, CDCl₃) δ ppm 11.40 (s, 1H), 8.47 (s, 1H), 8.05-8.06 (d, J=3.6 Hz, 1H), 7.46 (d, J=1.2 Hz, 1H), 7.02 (d, J=2.8 Hz, 1H), 6.08 (s, 1H), 6.38 (s, 1H), 4.19-4.20 (m, 2H), 4.05-4.09 (m, 1H), 3.78 (s, 3H), 3.82 (s, 3H), 3.65 (m, 4H), 2.63-2.70 (m, 2H), 2.37 (s, 3H), 2.00 (m, 5H), 1.45-1.44 (m, 3H); MS(ESI) m/z 542 [M+H]⁺.

Step 1: Synthesis of N-((4N-((4-methoxy-6-methyl-2-oxo-1,2-dihydropyridin-3-yl)methyl)-6-methyl-2-(1-methyl-1H-imidazol-5-yl)-5-(1-morpholinoethyl)indolizine-7-carboxamide, yield 37%. ¹H-NMR (MeOD, 400 MHz): 8.91 (s, 1H), 7.68 (s, 1H), 7.58 (s, 1H), 6.93 (s, 1H), 6.48 (s, 1H), 4.47 (s, 2H), 4.03-3.97 (m, 6H), 3.85-3.74 (m, 1H), 3.79 (s, 4H), 3.23-3.20 (m, 2H), 2.75-2.68 (m, 2H), 2.39 (s, 6H), 1.76-1.75 (m, 3H); MS(ESI) m/z 519.5 [M+H]⁺.

Example 134: Preparation of N-((4,6-dimethyl-2-oxo-1,2-dihydropyridin-3-yl)methyl)-5-(1-(4-(dimethylamino)piperidin-1-yl)ethyl)-6-methyl-2-(1-methyl-1H-imidazol-5-yl)indolizine-7-carboxamide: Same as Example 31

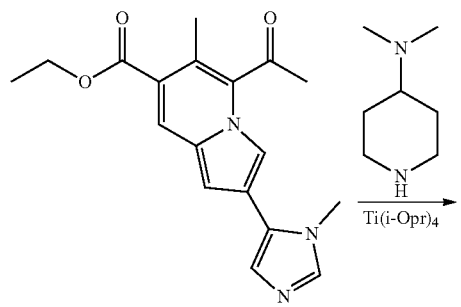

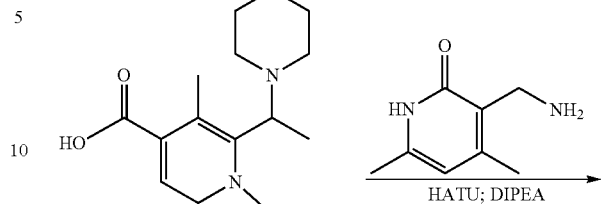

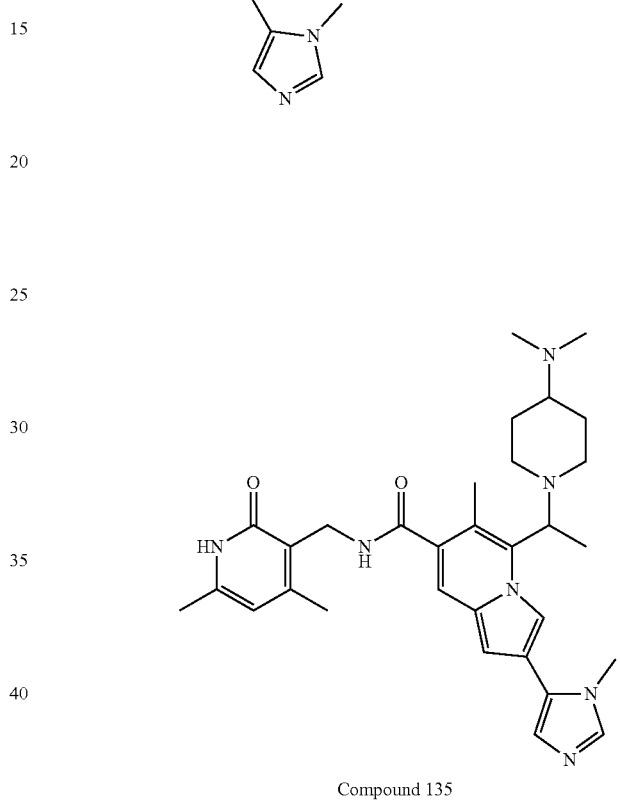

Compound 135

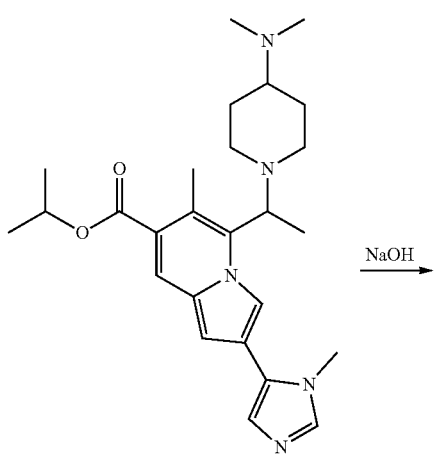

Step 1: Synthesis of isopropyl 5-(1-(4-(dimethylamino)piperidin-1-yl)vinyl)-6-methyl-2-(1-methyl-1H-imidazol-5-yl)indolizine-7-formate: MS (ESI) m/z 450 [M+H]$^+$.

Step 2: Synthesis of isopropyl 5-(1-(4-(dimethylamino)piperidin-1-yl)ethyl)-6-methyl-2-(1-methyl-1H-imidazol-5-yl)indolizine-7-formate: yield of two steps was 29%. MS (ESI) m/z 452 [M+H]$^+$.

Step 3: Synthesis of 5-(1-(4-(dimethylamino)piperidin-1-yl)ethyl)-6-methyl-2-(1-methyl-1H-imidazol-5-yl)indolizine-7-formic acid: MS (ESI) m/z 410 [M+H]$^+$.

Step 4: Synthesis of N-((4,6-dimethyl-2-oxo-1,2-dihydropyridin-3-yl)methyl)-5-(1-(4-(dimethyl amino)piperidin-1-yl)ethyl)-6-methyl-2-(1-methyl-1H-imidazol-5-yl)indolizine-7-carboxamide: yield of two steps was 40%. $^1$H-NMR (MeOD, 400 MHz): 8.69 (s, 1H), 8.59 (s, 1H), 7.56 (s, 1H), 7.43 (s, 1H), 6.78 (s, 1H), 6.12 (s, 1H), 4.52-4.46 (s, 2H), 4.17-4.13 (m, 1H), 3.98 (s, 3H), 3.58-3.56 (m, 1H), 3.30 (s, 4H), 2.84 (s, 6H), 2.37 (s, 3H), 2.32 (s, 3H), 2.25 (s, 3H) 2.10-2.07 (m, 2H), 1.98-1.89 (m, 2H), 1.62-1.54 (m, 3H); MS(ESI) m/z 544 [M+H]$^+$.

Example 135: Preparation of 5-(1-(4-(dimethyl-amino)piperidin-1-yl)ethyl)-N-((4-methoxy-6-methyl-2-oxo-1,2-dihydropyridin-3-yl)methyl)-6-methyl-2-(1-methyl-1H-imidazol-5-yl)indolizine-7-carboxamide: Same as Example 108

Example 136: Preparation of N-((4,6-dimethyl-2-oxo-1,2-dihydropyridin-3-yl)methyl)-6-methyl-2-(1-methyl-1H-imidazol-5-yl)-5-(1-(4-(2,2,2-trifluoro-ethyl)piperazin-1-yl)ethyl)indolizine-7-carboxamide: Same as Example 83

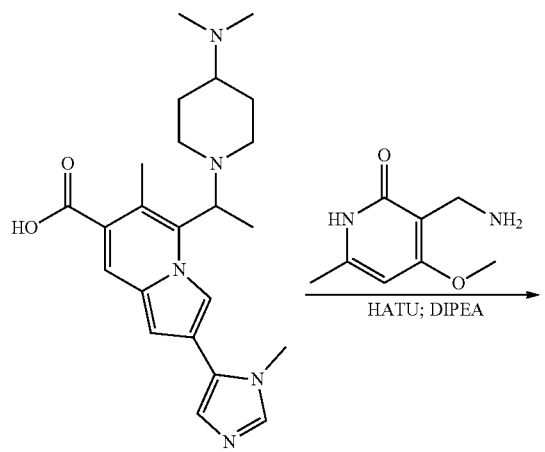

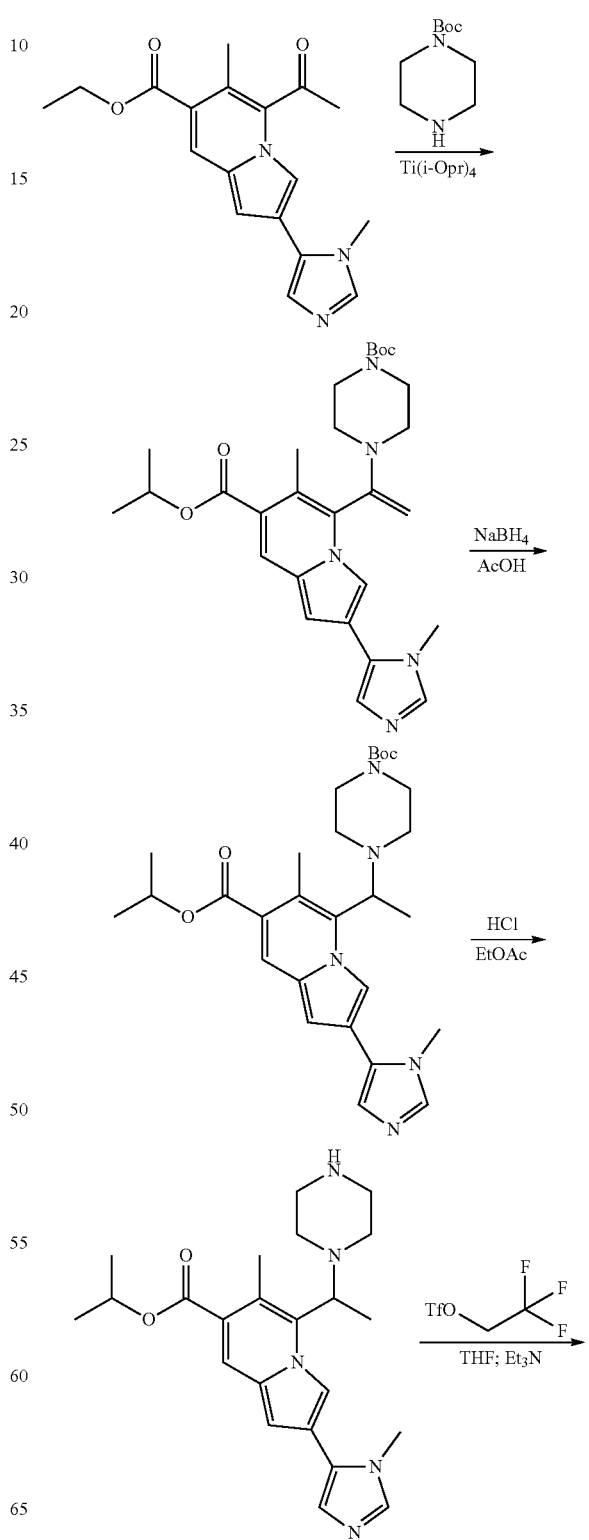

Compound 136

Step 1: Synthesis of 5-(1-(4-(dimethylamino)piperidin-1-yl)ethyl)-N-((4-methoxy-6-methyl-2-oxo-1,2-dihydropyridin-3-yl)methyl)-6-methyl-2-(1-methyl-1H-imidazol-5-yl)indolizine-7-carboxamide: Yield 32%. (CDCl$_3$, 400 MHz): 8.59 (s, 1H), 7.48 (s, 1H), 7.42 (s, 1H), 7.34 (s, 1H), 7.15 (s, 1H), 6.49 (s, 1H), 5.93 (s, 1H), 4.56-4.55 (m, 2H), 4.01-3.99 (m, 1H), 3.89 (s, 3H), 3.75 (s, 3H), 3.37-3.34 (m, 1H), 2.53 (s, 3H), 2.37-2.36 (m, 3H), 2.35 (s, 6H), 2.02-1.94 (m, 4H), 1.63-1.57 (m, 2H), 1.55-1.47 (m, 3H); MS(ESI) m/z 560 [M+H]$^+$.

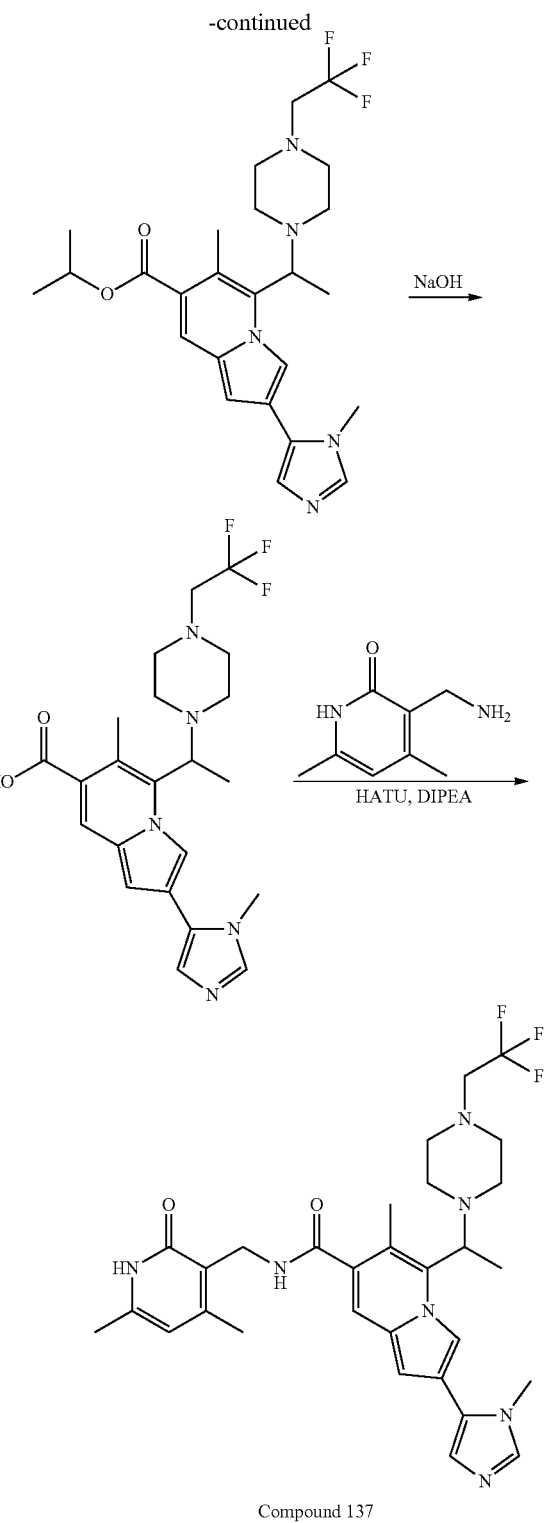

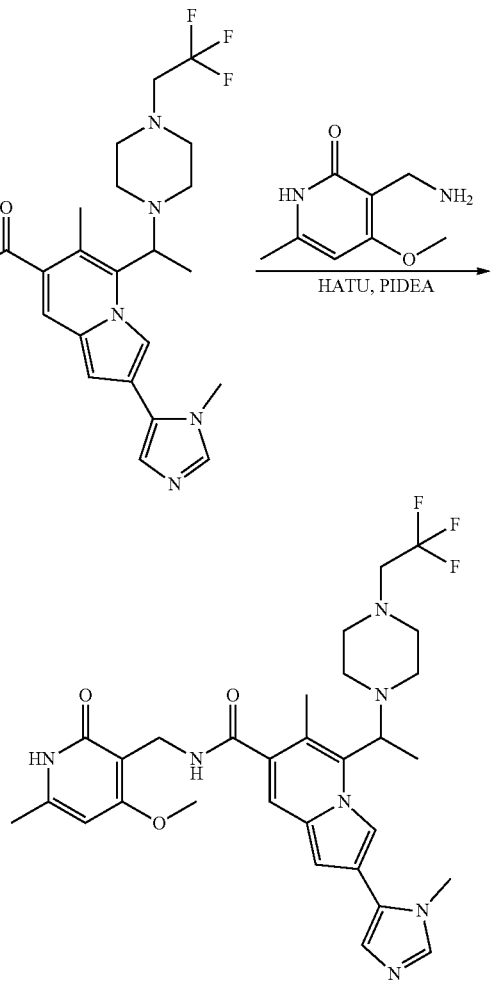

6-methyl-2-(1-methyl-1H-imidazol-5-yl)-5-(1-(piperazin-1-yl)ethyl)indolizine-7-carboxylate: MS (ESI) m/z 410 [M+H]⁺.

Step 4: Synthesis of isopropyl 6-methyl-2-(1-methyl-1H-imidazol-5-yl)-5-(1-(4-(2,2,2-trifluoroethyl)piperazine-1-yl)ethyl)indolizine-7-carboxylate: yield 33%. MS (ESI) m/z 492 [M+H]⁺.

Step 5: Synthesis of 6-methyl-2-(1-methyl-1H-imidazol-5-yl)-5-(1-(4-(2,2,2-trifluoroethyl)piperazine-1-yl)ethyl)indolizine-7-carboxylic acid: MS (ESI) m/z 450 [M+H]⁺.

Step 6: Synthesis of N-((4,6-dimethyl-2-oxo-1,2-dihydropyridin-3-yl)methyl)-6-methyl-2-(1-methyl-1H-imidazo-5-yl)-5-(1-(4-(2,2,2-trifluoroethyl)piperazin-1-yl)ethyl)indolizine-7-carboxamide: yield of two steps was 70%. ¹H-NMR (MeOD, 400 MHz): 8.96 (s, 1H), 7.70 (s, 1H), 7.61 (s, 1H), 6.18 (s, 1H), 4.49 (s, 2H), 4.01 (s, 3H), 3.35-3.34 (m, 1H), 3.05-2.99 (m, 4H), 2.94-2.93 (m, 2H), 2.41-2.38 (m, 6H), 2.29-2.27 (m, 5H). 1.87-1.85 (m, 3H); MS(ESI) m/z 584 [M+H]⁺.

Example 137: Preparation of N-((4-Methoxy-6-methyl-2-oxo-1,2-dihydropyridin-3-yl)methyl)-6-methyl-2-(1-methyl-1H-imidazol-5-yl)-5-(1-(4-(2,2,2-trifluoroethyl)piperazin-1-yl)ethyl)indolizine-7-carboxamide Step 1: Synthesis of isopropyl 5-(1-(4-(tert-butoxycarbonyl)piperazin-1-yl)vinyl)-6-methyl-2-(1-methyl-1H-imidazole-5-yl) indolizine-7-carboxylate: MS (ESI) m/z 508 [M+H]⁺.

Step 2: Synthesis of isopropyl 5-(1-(4-(tert-butoxycarbonyl)piperazin-1-yl)vinyl)-6-methyl-2-(1-methyl-1H-imidazole-5-yl) indolizine-7-formate: yield of two steps was 35%. MS (ESI) m/z 510 [M+H]⁺. Step 3: Synthesis of isopropyl Step 1: Synthesis of N-((4-methoxy-6-methyl-2-oxo-1,2-dihydropyridin-3-yl)methyl)-6-methyl-2-(1-methyl-1H-imidazole-5-yl)-5-(1-(4-(2,2,2-trifluoroethyl)piperazin-1-yl)ethyl)indolizine-7-carboxamide: yield 62%. $^1$H-NMR (CDCl$_3$, 400 MHz): 8.96 (s, 1H), 7.71 (s, 1H), 7.62 (s, 1H), 6.47 (s, 1H), 4.49 (s, 2H), 4.01-3.99 (m, 6H), 3.31-3.30 (m, 1H), 3.30-3.29 (m, 2H), 3.07-3.04 (m, 4H), 2.94-2.93 (m, 2H), 2.42-2.39 (m, 8H), 1.89-1.86 (m, 3H); MS(ESI) m/z 600.5 [M+H]$^+$.

Example 138: Preparation of N-((4-methoxy-6-methyl-2-oxo-1,2-dihydropyridin-3-yl)methyl)-6-methyl-5-(1-morpholinoethyl)-2-(thiazol-5-yl)indolizine-7-carboxamide: Same as Example 50

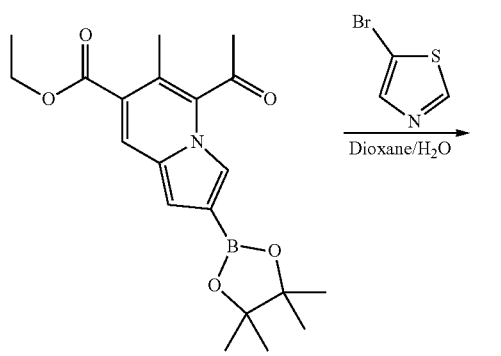

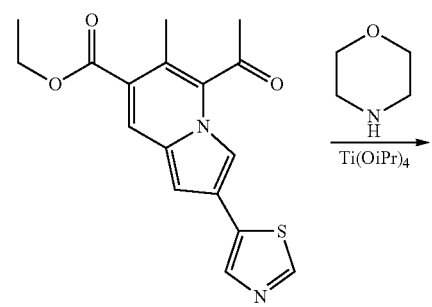

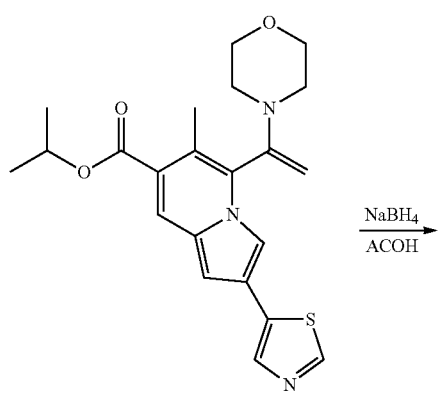

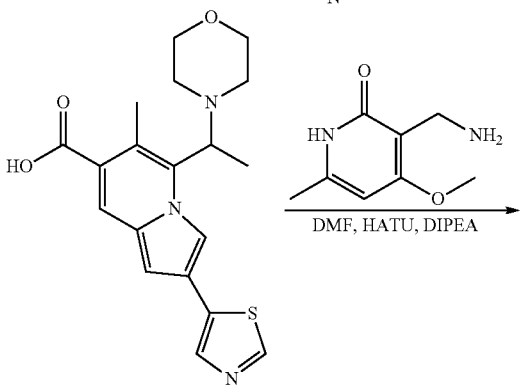

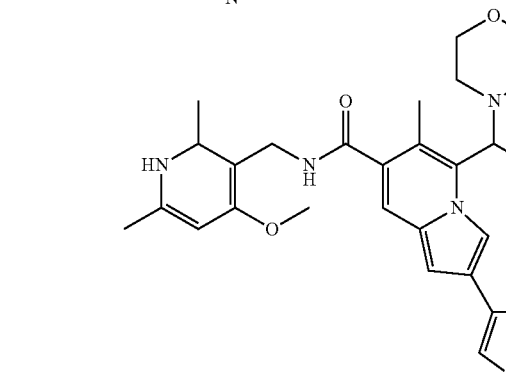

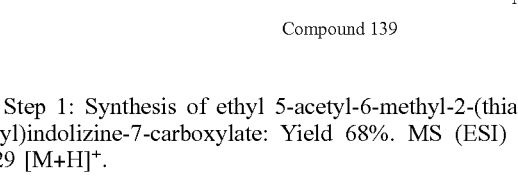

Compound 139

Step 1: Synthesis of ethyl 5-acetyl-6-methyl-2-(thiazol-5-yl)indolizine-7-carboxylate: Yield 68%. MS (ESI) m/z 329 [M+H]$^+$.

Step 2: Synthesis of isopropyl 6-methyl-5-(1-morpholinovinyl)-2-(thiazol-5-yl)indolizine-7-carboxylate: MS (ESI) m/z 412 [M+H]$^+$.

Step 3: Synthesis of isopropyl 6-methyl-5-(1-morpholinoethyl)-2-(thiazol-5-yl)indolizine-7-carboxylate: yield of two steps was 47%. MS (ESI) m/z 414 [M+H]$^+$.

Step 4: Synthesis of 6-methyl-5-(1-morpholinoethyl)-2-(thiazol-5-yl)indolizine-7-carboxylic acid: MS (ESI) m/z 372 [M+H]$^+$.

Step 5: Synthesis of N-((4-methoxy-6-methyl-2-oxo-1,2-dihydropyridin-3-yl)methyl)-6-methyl-5-(1-morphoethyl)-2-(thiazol-5-yl)indolizine-7-carboxamide: yield of two steps was 24%. $^1$H-NMR (MeOD, 400 MHz): 8.96 (s, 1H), 8.15 (s, 1H), 7.56 (s, 1H), 6.49 (s, 1H), 4.47 (s, 1H), 3.99 (s, 3H), 3.87-3.86 (m, 4H), 3.24-3.20 (m, 4H), 2.41-2.39 (m, 6H), 1.83 (m, 3H); MS(ESI) m/z 522 [M+H]$^+$.

Example 139: Preparation of N-((4,6-dimethyl-2-oxo-1,2-dihydropyridin-3-yl)methyl)-5-(1-(4-(dimethylamino)piperidin-1-yl)ethyl)-6-methyl-2-(thiazol-5-yl)indolizine-7-carboxamide: Same as Example 31

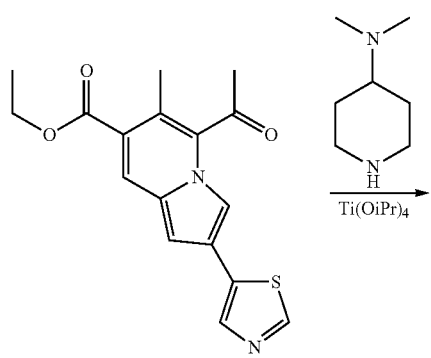

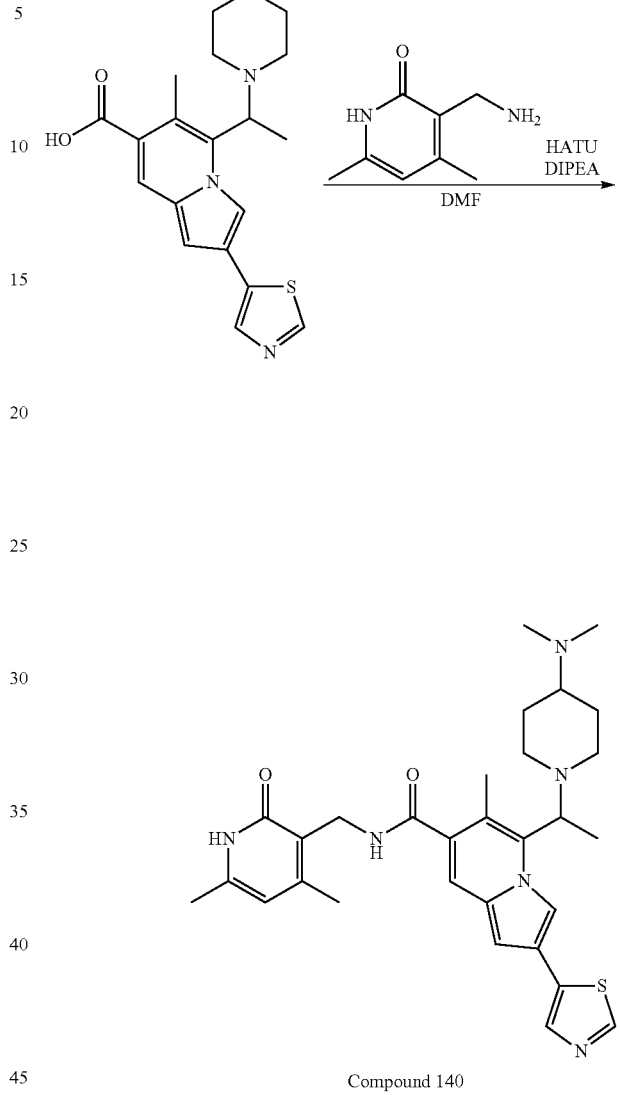

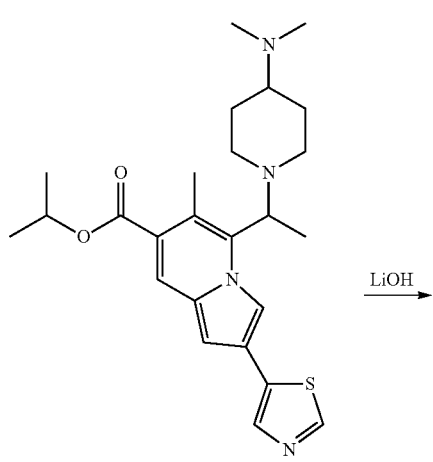

Compound 140

Step 1: Synthesis of isopropyl 5-(1-(4-(dimethylamino)piperidin-1-yl)vinyl)-6-methyl-2-(thiazol-5-yl)indolizine-7-carboxylate: MS (ESI) m/z 453 [M+H]$^+$.

Step 2: Synthesis of isopropyl 5-(1-(4-(dimethylamino)piperidin-1-yl)ethyl)-6-methyl-2-(thiazol-5-yl)indolizine-7-carboxylate: yield of two steps was 44%. MS (ESI) m/z 455 [M+H]$^+$.

Step 3: Synthesis of 5-(1-(4-(dimethylamino)piperidin-1-yl)ethyl)-6-methyl-2-(thiazol-5-yl)indolizine-7-carboxylic acid: MS (ESI) m/z 413 [M+H]$^+$.

Step 4: Synthesis of N-((4,6-dimethyl-2-oxo-1,2-dihydropyridin-3-yl)methyl)-5-(1-(4-(dimethyl amino))piperidin-1-yl)ethyl)-6-methyl-2-(thiazol-5-yl)indolizine-7-carboxamide, two-step yield: 10%. $^1$H-NMR (MeOD, 400 MHz): 8.89 (s, 1H), 8.05 (s, 1H), 7.39 (s, 1H), 6.77 (s, 1H), 6.14 (s, 1H), 4.47 (s, 2H), 3.99 (s, 2H), 2.92 (s, 1H), 2.85 (s, 6H), 2.38 (s, 3H), 2.32 (s, 3H), 2.28-2.25 (m, 5H), 1.60-1.59 (m, 3H). MS (ESI) m/z 547 [M+H]$^+$.

Example 140: Preparation of 5-(1-(4-(dimethyl-amino)piperidin-1-yl)ethyl)-N-((4-methoxy-6-methyl-2-oxo)-1,2-dihydropyridin-3-yl)methyl)-6-methyl-2-(thiazol-5-yl)indolizine-7-carboxamide: Same as Example 108

Example 141: Preparation of N-((4,6-dimethyl-2-oxo-1,2-dihydropyridin-3-yl)methyl)-6-methyl-2-(thiazole-5-yl)-5-(1-(4-(2,2,2-trifluoroethyl)piperazin-1-yl)ethyl)indolizine-7-carboxamide: Same as Example 83

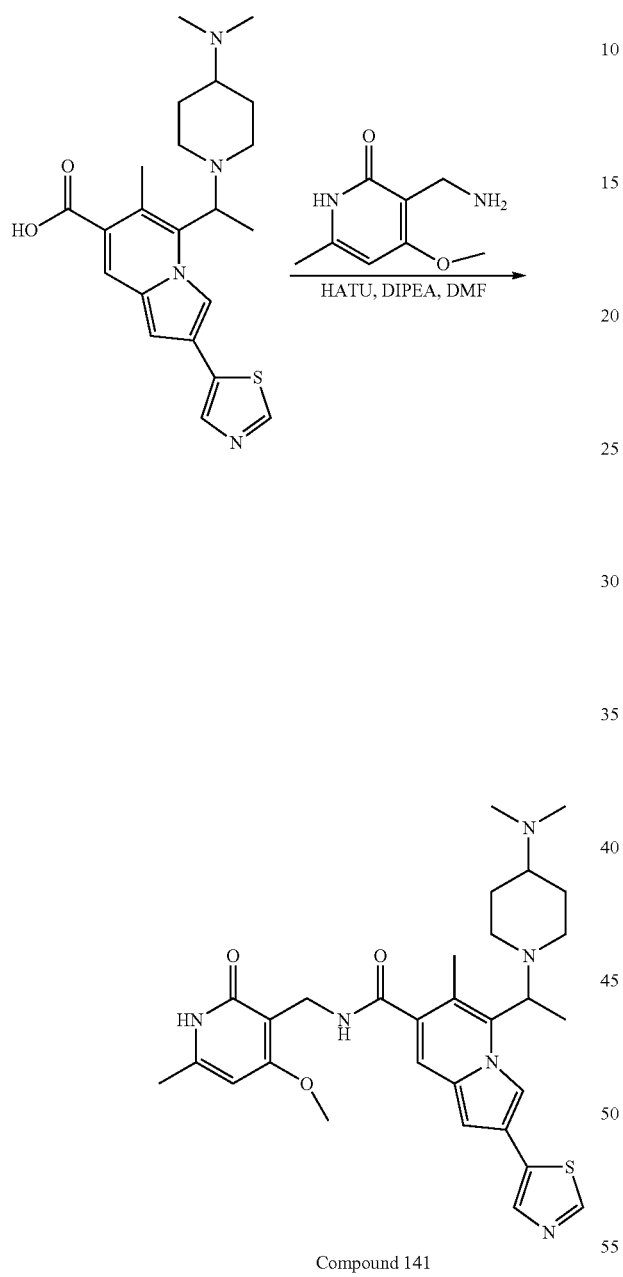

Compound 141

Step 1: Synthesis of 5-(1-(4-(dimethylamino)piperidin-1-yl)ethyl)-N-((4-methoxy-6-methyl-2-oxo-1,2-dihydropyridin-3-yl)methyl)-6-methyl-2-(thiazol-5-yl)indolizine-7-carboxamide: Yield 11%.

$^1$H-NMR (MeOD, 400 MHz): 8.89 (s, 1H), 8.05 (s, 1H), 7.39 (s, 1H), 6.74 (s, 1H), 6.29 (s, 1H), 4.44 (s, 2H), 4.16-4.14 (s, 1H), 3.95 (s, 3H), 3.62-3.59 (s, 1H), 3.22 (m, 2H), 2.85 (s, 6H), 2.69-2.67 (m, 1H), 2.17 (s, 6H), 2.25-2.28 (m, 6H), 1.60-1.59 (m, 3H); MS(ESI) m/z 563 [M+H]$^+$.

-continued

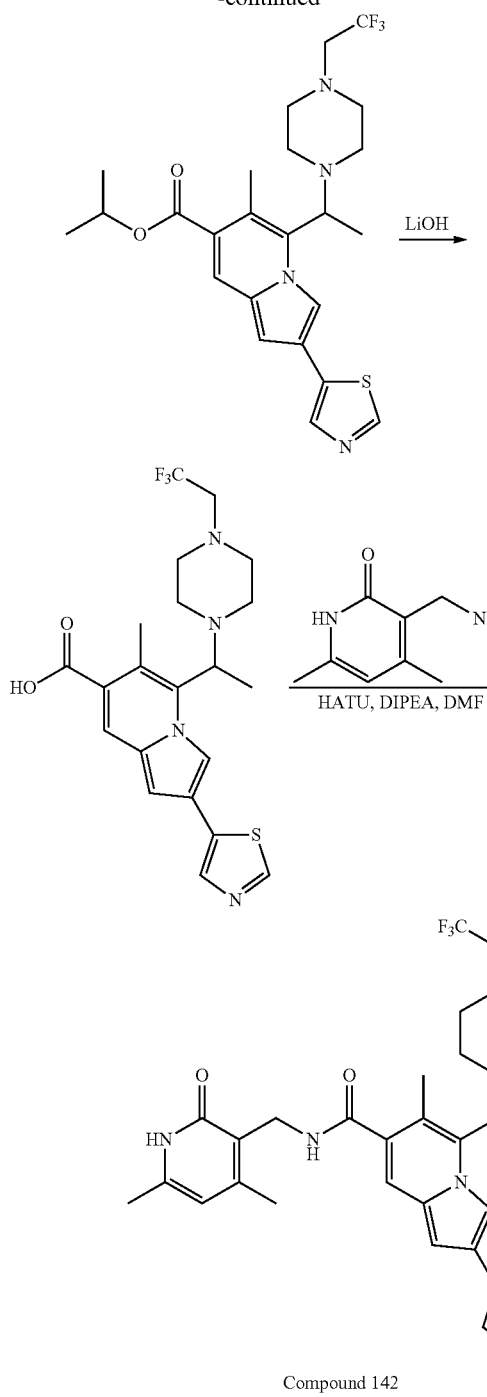

Compound 142

Step 1: Synthesis of isopropyl 5-(1-(4-(tert-butoxycarbonyl)piperazin-1-yl)vinyl)-6-methyl-2-(thiazole-5-yl)indolizine-7-carboxylate: MS (ESI) m/z 511 [M+H]⁺.

Step 2: Synthesis of isopropyl 5-(1-(4-(tert-butoxycarbonyl)piperazin-1-yl)ethyl)-6-methyl-2-(thiazole-5-yl)indolizine-7-formate: yield of two steps was 34%. MS (ESI) m/z 513 [M+H]⁺.

Step 3: Synthesis of isopropyl 6-methyl-5-(1-(piperazin-1-yl)ethyl)-2-(thiazol-5-yl)indolizine-7-carboxylate hydrochloride: MS (ESI) m/z 413 [M+H]⁺.

Step 4: Synthesis of isopropyl 6-methyl-2-(thiazol-5-yl)-5-(1-(4-(2,2,2-trifluoroethyl)piperazin-1-yl)ethyl)indolizine-7-formate: yield of two steps was 25%. MS (ESI) m/z 495 [M+H]⁺.

Step 5: Synthesis of 6-Methyl-2-(thiazol-5-yl)-5-(1-(4-(2,2,2-trifluoroethyl)piperazin-1-yl)ethyl)indolizine-7-carboxylic acid: MS (ESI) m/z 453 [M+H]⁺.

Step 6: Synthesis of N-((4,6-dimethyl-2-oxo-1,2-dihydropyridin-3-yl)methyl)-6-methyl-2-(thiazol-5-yl)-5-(1-(4-(2,2,2-trifluoroethyl)piperazin-1-yl)ethyl)indolizine-7-carboxamide: yield of two steps was 46%. ¹H-NMR (MeOD, 400 MHz): 8.92 (s, 1H), 8.09 (s, 1H), 7.50 (s, 1H), 6.13 (s, 1H), 4.47 (s, 3H), 3.26-3.22 (m, 6H), 2.94 (m, 4H), 2.38 (s, 3H), 2.34 (s, 3H), 2.25 (s, 3H), 1.77-1.76 (m, 3H); MS(ESI) m/z 587 [M+H]⁺.

Example 142: Preparation of N-((4-methoxy-6-methyl-2-oxo-1,2-dihydropyridin-3-yl)methyl)-6-methyl-2-(thiazole-5-yl)-5-(1-(4-(2,2,2-trifluoroethyl)piperazin-1-yl)ethyl)indolizine-7-carboxamide: Same to Example 108

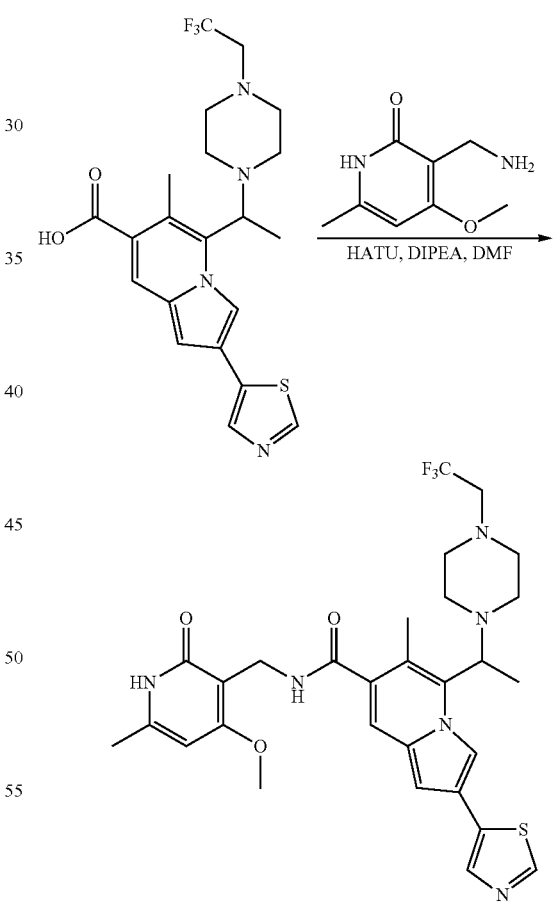

Compound 143

Step 1: Synthesis of N-((4-methoxy-6-methyl-2-oxo-1,2-dihydropyridin-3-yl)methyl)-6-methyl-2-(thiazol-5-yl)-5-(1-(4-(2,2,2-trifluoroethyl)piperazin-1-yl)ethyl)indolizine-7-carboxamide: yield 38.7%. ¹H-NMR (MeOD, 400 MHz): 8.93 (s, 1H), 8.09 (s, 1H), 7.50 (s, 1H), 6.34 (s, 1H), 4.52 (s, 2H), 3.96 (s, 3H), 3.26-3.22 (m, 6H), 2.94 (m, 4H), 2.38 (s, 3H), 2.34 (s, 3H), 1.77-1.76 (m, 3H); MS(ESI) m/z 603 [M+H]⁺.

Example 143: Preparation of 2-Bromo-N-((4,6-dimethyl-2-oxo-1,2-dihydropyridin-3-yl)methyl)-6-methyl-5-(1-(4-methoxypiperidin-1-yl)ethyl)indolizine-7-carboxamide: Same as Example 30

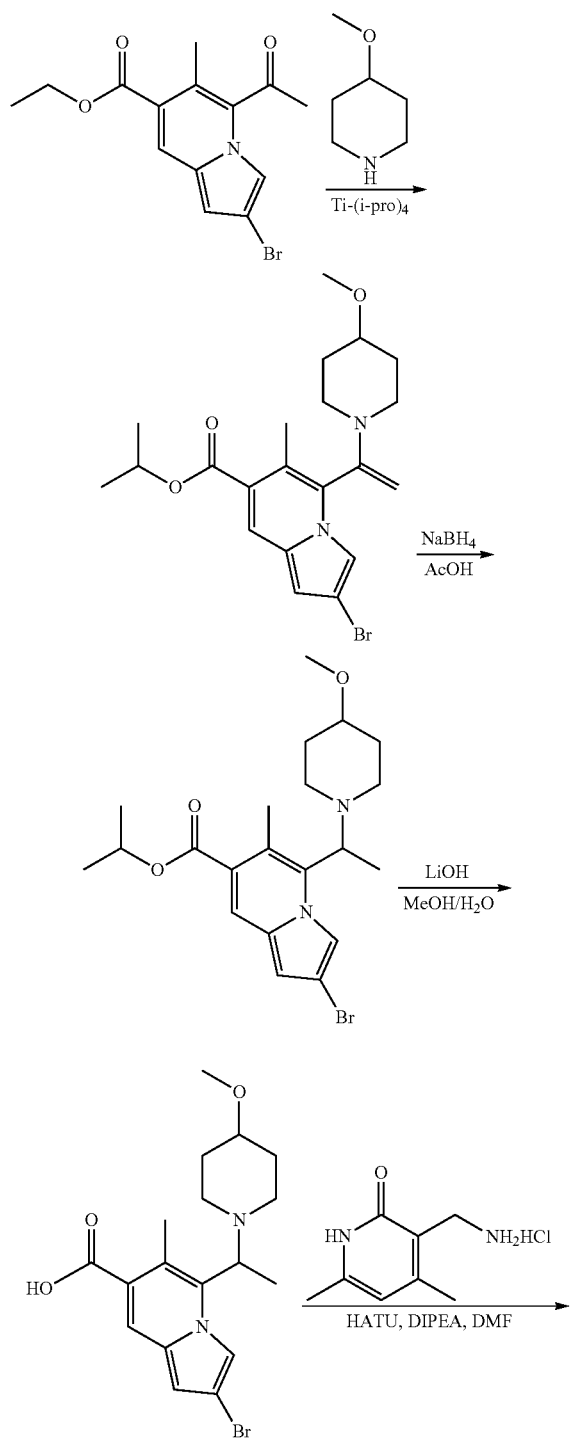

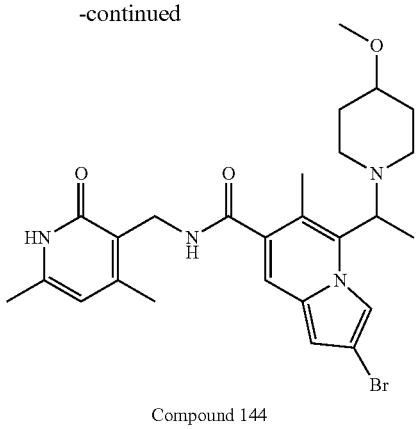

Compound 144

Step 1: Preparation of isopropyl 2-bromo-6-methyl-5-(1-(4-methoxypiperidin-1-yl)vinyl)indolizine-7-carboxylate: MS (ESI) m/z 436 [M+H]⁺.

Step 2: Preparation of isopropyl 2-bromo-6-methyl-5-(1-(4-methoxypiperidin-1-yl)ethyl)indolizine-7-carboxylate: yield of two steps was 74%. MS (ESI) m/z 438 [M+H]⁺.

Step 3: Preparation of 2-bromo-6-methyl-5-(1-(4-methoxypiperidin-1-yl)ethyl)indolizine-7-carboxylic acid: MS (ESI) m/z 396 [M+H]⁺.

Step 4: Preparation of 2-bromo-N-((4,6-dimethyl-2-oxo-1,2-dihydropyridin-3-yl)methyl)-6-methyl-5-(1-(4-methoxypiperidin-1-yl)ethyl)indolizine-7-carboxamide: yield of two steps was 57%. ¹H NMR (400 MHz, MeOD-d₄) δ ppm 7.54 (s, 1H), 6.78 (s, 1H), 6.13 (s, 1H), 5.18-5.14 (m, 1H), 4.46 (s, 2H), 3.58 (s, 1H), 3.52 (s, 3H), 3.31 (s, 4H), 2.38-2.37 (m, 6H), 2.25 (s, 3H), 2.13-2.08 (m, 2H), 1.90 (d, J=6.8 Hz, 3H), 1.29 (s, 2H); MS(ESI) m/z 552 [M+H]⁺.

Example 144: Preparation of 2-bromo-N-((4,6-dimethyl-2-oxo-1,2-dihydropyridin-3-yl)methyl)-5-(1-(4-hydroxypiperidin-1-yl)ethyl)-6-indolizine-7-carboxamide: Same as Example 30

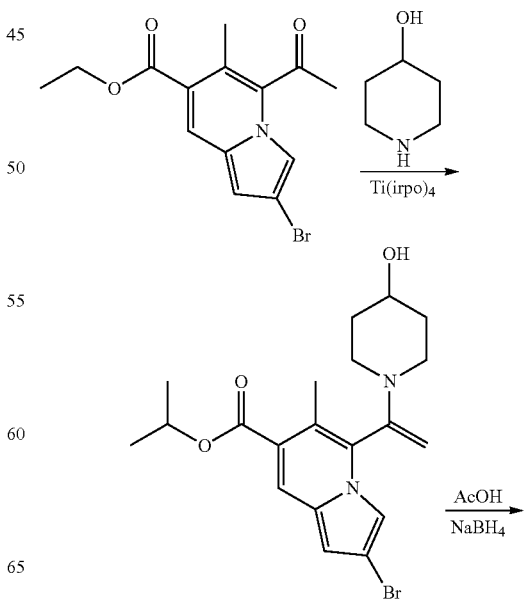

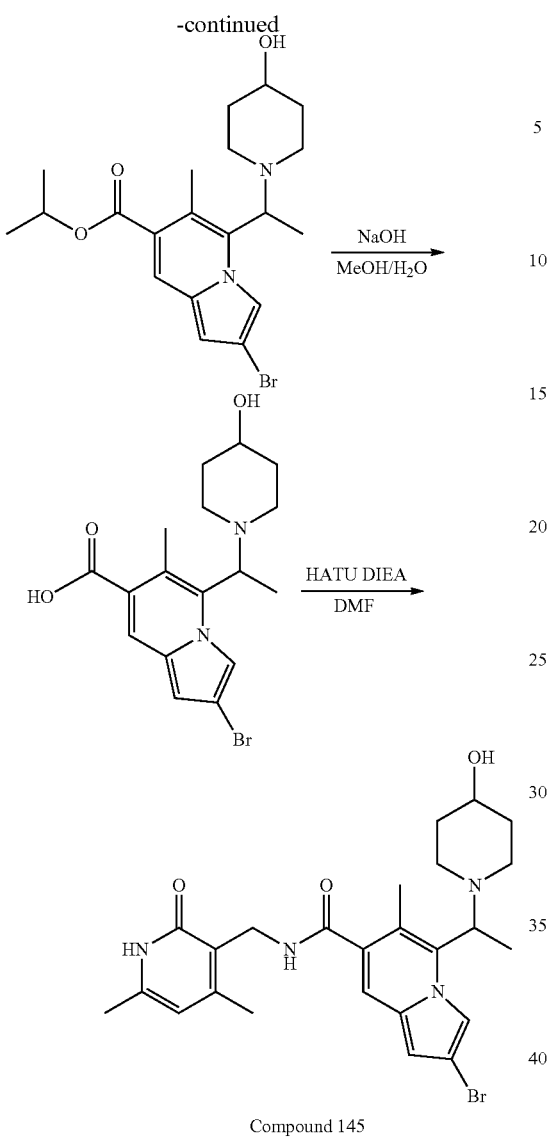

Compound 145

Step 1: Preparation of isopropyl 2-bromo-5-(1-(4-hydroxypiperidin-1-yl)vinyl)-6-methylindolizine-7-carboxylate: MS (ESI) m/z 421 [M+H]+.

Step 2: Preparation of isopropyl 2-bromo-5-(1-(4-hydroxypiperidin-1-yl)ethyl)-6-methylindolizine-7-carboxylate: yield of two steps was 41%. MS (ESI) m/z 423 [M+H]+.

Step 3: Preparation of 2-bromo-5-(1-(4-hydroxypiperidin-1-yl)ethyl)-6-methylindolizine-7-carboxylic acid: MS (ESI) m/z 381 [M+H]+.

Step 4: Preparation of 2-bromo-N-((4,6-dimethyl-2-oxo-1,2-dihydropyridin-3-yl)methyl)-5-(1-(4-hydroxypiperidine-1-yl)ethyl)-6-indolizine-7-carboxamide, yield of two steps was 23%. $^1$H NMR (400 MHz, DMSO-$d_6$) δ ppm 11.45 (s, 1H), 8.39 (s, 1H), 8.21-8.20 (d, J=2.4 Hz, 1H), 7.23 (s, 1H), 6.58 (s, 1H), 5.87 (s, 1H), 4.56-4.55 (m, 1H), 4.26-4.25 (m, 2H), 3.97-3.96 (m, 1H), 3.02 (m, 1H), 2.41-2.38 (m, 2H), 2.32-2.28 (m, 6H), 2.21 (s, 3H), 2.01-1.93 (m, 2H), 1.78-1.77 (m, 1H), 1.65-1.64 (m, 1H), 1.46-1.44 (m, 4H). MS (ESI) m/z 517 [M+H]+.

Example 145: Preparation of 2-bromo-N-((4,6-dimethyl-2-oxo-1,2-dihydropyridin-3-yl)methyl)-6-methyl-5-(1-(4-(pyrrolidin-1-yl)piperidin-1-yl)ethyl)indolizine-7-carboxamide: Same as Example 30

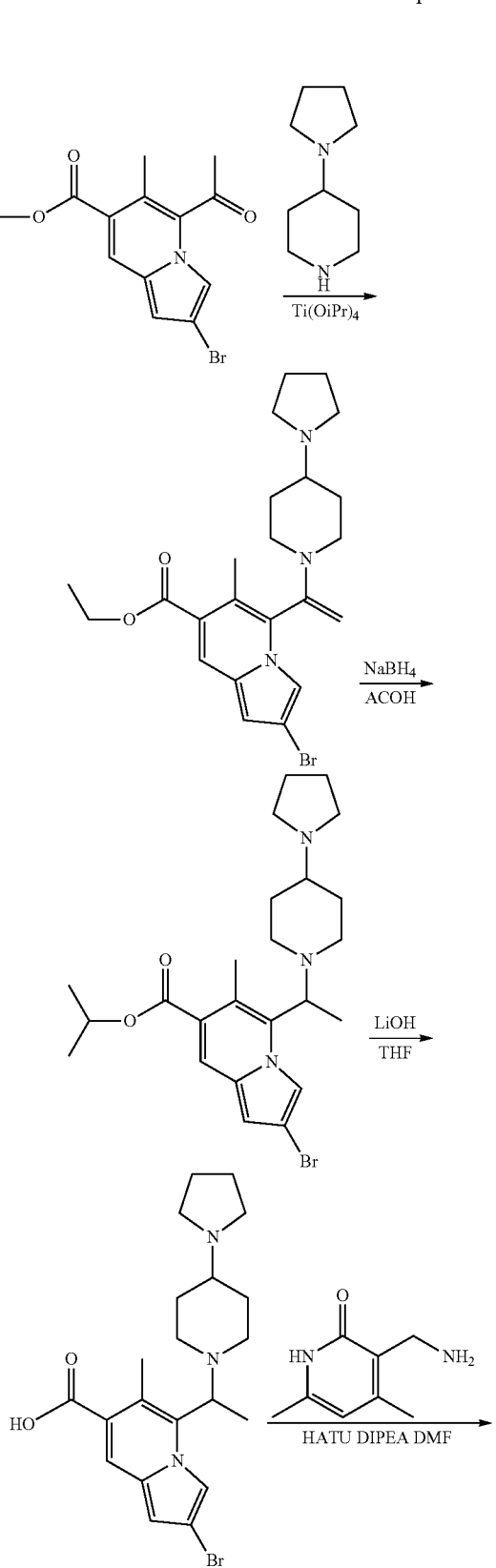

323
-continued

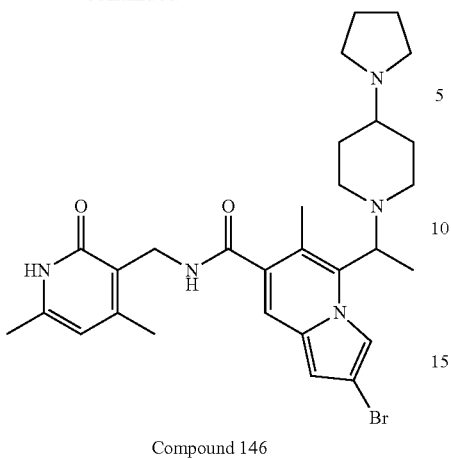

Compound 146

Step 1: Synthesis of isopropyl 2-bromo-6-methyl-5-(1-(4-(pyrrolidin-1-yl)piperidin-1-yl)vinyl)indolizine-7-carboxylate: MS (ESI) m/z 474 [M+H]⁺.

Step 2: Synthesis of isopropyl 2-bromo-6-methyl-5-(1-(4-(pyrrolidin-1-yl)piperidin-1-yl)ethyl)indolizine-7-carboxylate: yield of two steps was 69%. MS (ESI) m/z 476 [M+H]⁺.

Step 3: Synthesis of 2-bromo-6-methyl-5-(1-(4-(pyrrolidin-1-yl)piperidin-1-yl)ethyl)indolizine-7-carboxylic acid: MS (ESI) m/z 434 [M+H]⁺.

Step 4: Synthesis of 2-bromo-N-((4,6-dimethyl-2-oxo-1,2-dihydropyridin-3-yl)methyl)-6-methyl-5-(1-(4-(pyrrolidin-1-yl)piperidin-1-yl)ethyl)indolizine-7-carboxamide: yield of two steps was 12%. $^1$H-NMR (MeOD, 400 MHz): 8.07 (s, 1H), 6.83 (s, 1H), 3.68-3.61 (m, 4H), 3.12-3.08 (m, 5H), 2.81 (s, 2H), 2.57 (s, 4H), 2.47-2.42 (m, 2H), 2.39 (m, 5H), 2.08 (m, 5H), 1.55-1.54 (m, 5H). MS (ESI) m/z 570 [M+H]⁺.

Example 146: Preparation of 2-bromo-5-(1-(4-cyanopiperidin-1-yl)ethyl)-N-((4,6-dimethyl-2-oxo-1,2-dihydropyridin-3-yl) methyl)-6-methylindolizine-7-carboxamide: Same as Example 30

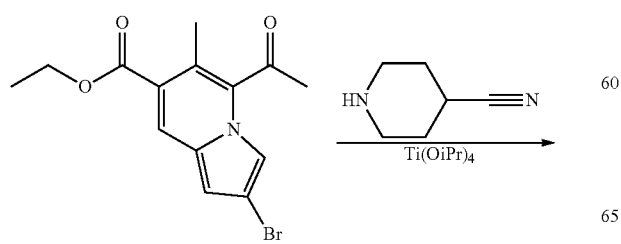

324
-continued

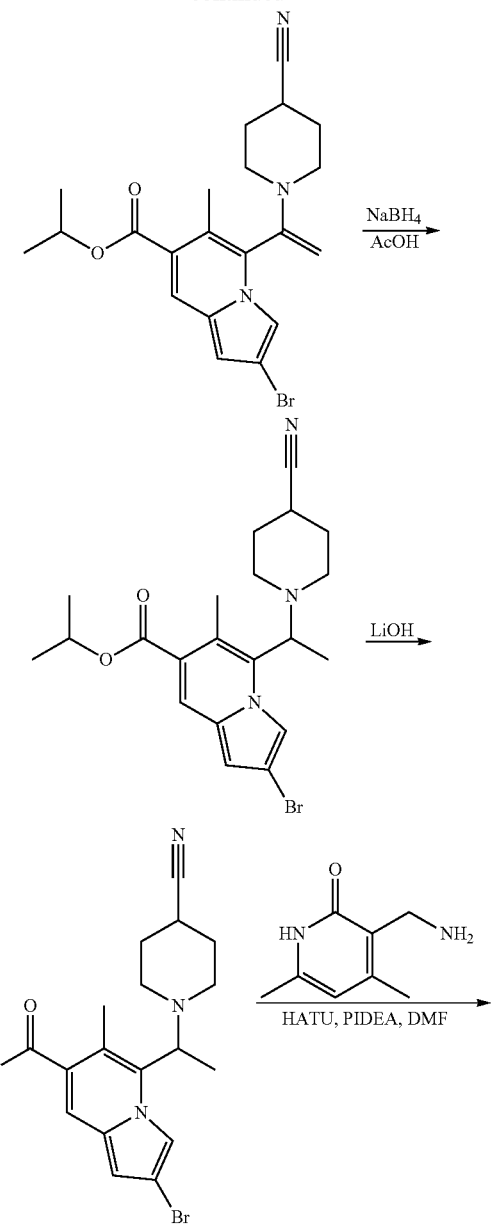

Compound 147

Step 1: Synthesis of isopropyl 2-bromo-5-(1-(4-cyanopiperidin-1-yl)vinyl)-6-methylindolizine-7-carboxylate: MS (ESI) m/z 430 [M+H]⁺.

Step 2: Synthesis of isopropyl 2-bromo-5-(1-(4-cyanopiperidin-1-yl) ethyl)-6-methylindolizine-7-carboxylate: yield of two steps was 50%. MS (ESI) m/z 432 [M+H]⁺.

Step 3: Synthesis of 2-bromo-5-(1-(4-cyanopiperidin-1-yl)ethyl)-6-methylindolizine-7-carboxylic acid: MS (ESI) m/z 392 [M+H]⁺.

Step 4: Synthesis of 2-bromo-5-(1-(4-cyanopiperidin-1-yl)ethyl)-N-((4,6-dimethyl-2-oxo-1,2-dihydropyridin-3-yl)methyl)-6-methylindolizine-7-carboxamide, yield of two steps was 7%. ¹H-NMR (MeOD, 400 MHz): 7.39 (s, 1H), 6.62 (s, 1H), 6.12 (s, 1H), 4.45 (s, 2H), 2.92-2.90 (m, 2H), 2.37 (s, 3H), 2.32 (s, 3H), 2.24 (s, 3H), 1.94-1.93 (m, 2H). 1.91-1.88 (m, 2H), 1.63-1.61 (m, 3H); MS (ESI) m/z 526 [M+H]⁺.

Example 147: Preparation of 2-bromo-N-((4,6-dimethyl-2-oxo-1,2-dihydropyridin-3-yl)methyl)-5-(1-(3-(dimethylamino)azetidin-1-yl)ethyl)-6-methylindolizine-7-carboxamide: Same as Example 30

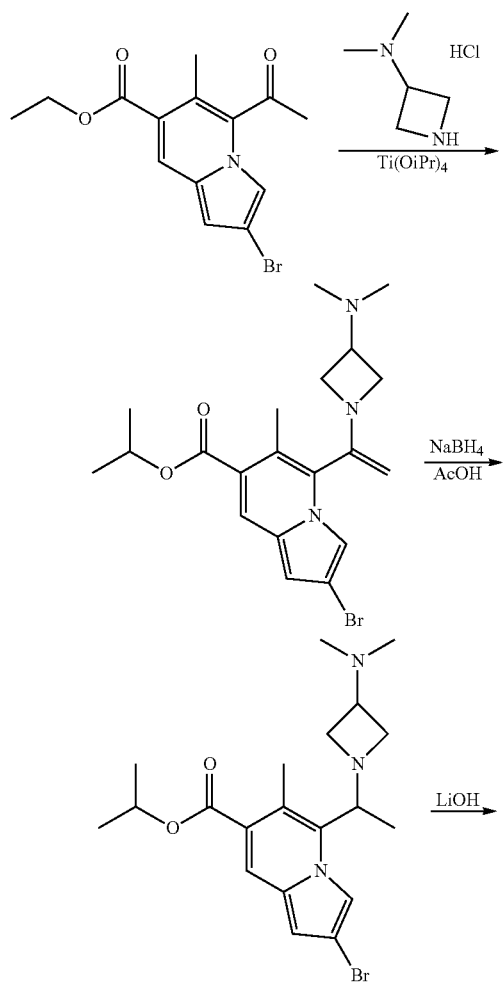

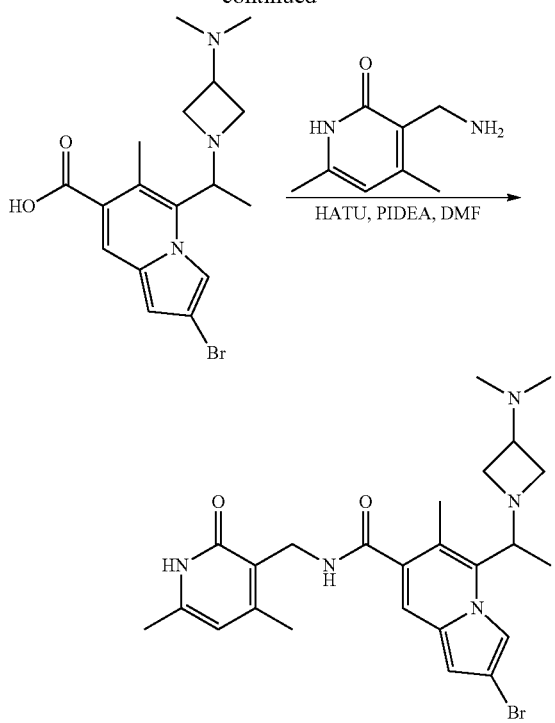

Compound 148

Step 1: Synthesis of isopropyl 2-bromo-5-(1-(3-(dimethylamino)azetidin-1-yl)vinyl)-6-methylindolizine-7-carboxylate: MS (ESI) m/z 420 [M+H]⁺.

Step 2: Synthesis of isopropyl 2-bromo-5-(1-(3-(dimethylamino)azetidin-1-yl) ethyl)-6-methylindolizine-7-carboxylate: yield of two steps was 8%. MS (ESI) m/z 422 [M+H]⁺.

Step 3: Synthesis of 2-bromo-5-(1-(3-(dimethylamino)azetidin-1-yl)ethyl)-6-methylindolizine-7-carboxylic acid: MS (ESI) m/z 380 [M+H]⁺.

Step 4: Synthesis of 2-bromo-N-((4,6-dimethyl-2-oxo-1,2-dihydropyridin-3-yl)methyl)-5-(1-(3-(dimethylamino)azetidin-1-yl)ethyl)-6-methylindolizine-7-carboxamide, yield of two-steps was 65%. MS (ESI) m/z 514 [M+H]⁺.

Example 148: Preparation of 2-(3,5-dimethoxy-4-(morphinylmethyl)phenyl)-N-((4,5-dimethyl-2-oxo-1,2-dihydropyridin-3-yl)methyl)-6-methyl-5-(1-morpholinethyl)indolizine-7-carboxamide: Same as Example 74

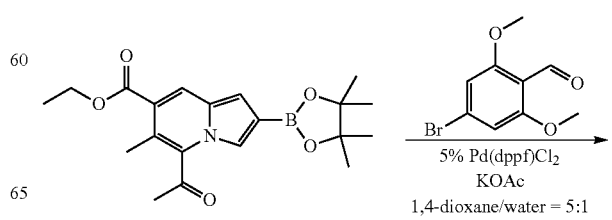

327
-continued

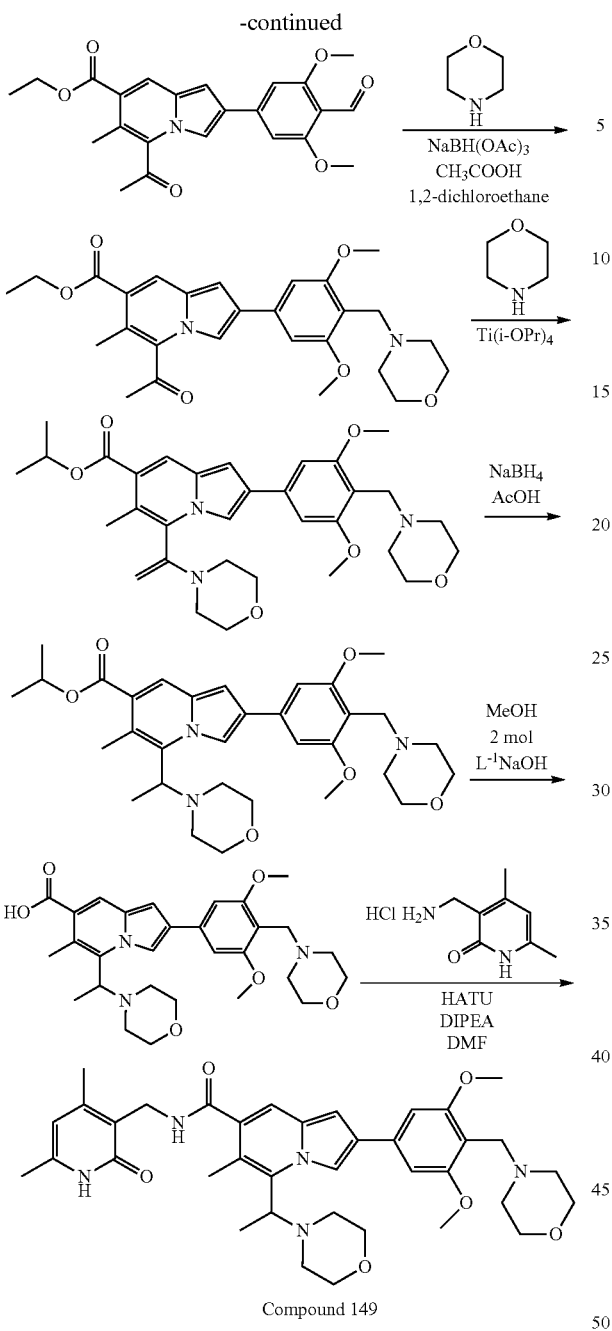

Compound 149

Step 1: Preparation of ethyl 5-acetyl-2-(4-formyl-3,5-dimethoxyphenyl)-6-methylindolizine-7-carboxylate: yield 53%. MS (ESI) m/z 410 [M+H]$^+$.

Step 2: Preparation of ethyl 5-acetyl-2-(3,5-dimethoxy-4-(morpholinomethyl)phenyl)-6-methylindolizine-7-carboxylate: yield 84%. MS (ESI) m/z 394 [M+H-C$_4$H$_9$NO]$^+$.

Step 3: Preparation of isopropyl 2-(3,5-dimethoxy-4-((morpholinomethyl)phenyl)-6-methyl-5-(1-morphinylvinyl)indolizine-7-carboxylate: MS (ESI) m/z 564 [M+H]$^+$.

Step 4: Preparation of isopropyl 2-(3,5-dimethoxy-4-((morpholinylmethyl)phenyl)-6-methyl-5-(1-morpholinoethyl)indolizine-7-carboxylate: yield: 97%. MS (ESI) m/z 479 [M+H-C$_4$H$_9$NO]$^+$.

Step 5: Preparation of 2-(3,5-dimethoxy-4-((morpholinylmethyl)phenyl)-6-methyl-5-(1-morpholinoethyl)indolizine-7-carboxylic acid: MS (ESI) m/z 524 [M+H]$^+$.

328

Step 6: Preparation of 2-(3,5-dimethoxy-4-(morphinylmethyl)phenyl)-N-((4,5-dimethyl-2-oxo-1,2-dihydropyridine)-3-yl)methyl)-6-methyl-5-(1-morpholinoethyl)indolizine-7-carboxamide: yield 5%. $^1$H NMR (400 MHz, DMSO) δ 11.49 (s, 1H), 9.47 (s, 1H), 8.81 (s, 1H), 8.21 (s, 1H), 7.33 (s, 1H), 7.03 (s, 2H), 5.87 (s, 1H), 4.25 (s, 2H), 3.91 (s, 6H), 3.89 (brs, 2H), 3.77-3.50 (m, 8H), 3.36-3.22 (m, 2H), 3.19-3.03 (m, 2H), 2.35-2.25 (m, 2H), 2.19 (s, 3H), 2.10 (s, 3H), 1.53-1.50 (m, 3H); MS(ESI) m/z 571 [M+H-C$_4$H$_9$NO]$^+$.

Example 149: Preparation of 2-bromo-N-((4,6-dimethyl-2-oxo-1,2-dihydropyridin-3-yl)methyl)-6-methyl-7-(1-morpholino propyl)indolizine-5-carboxamide: Same as Example 29

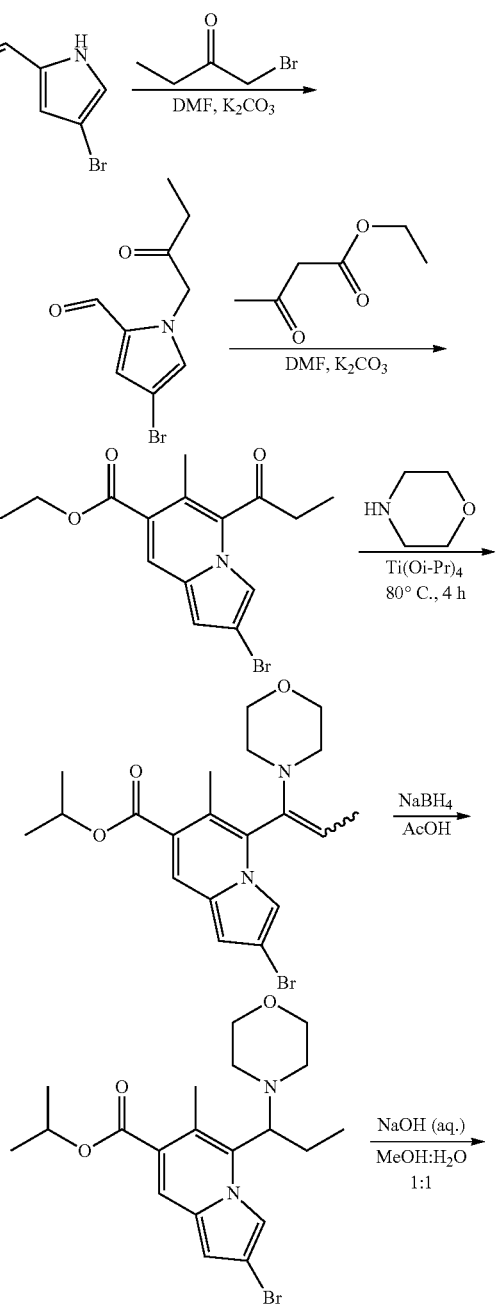

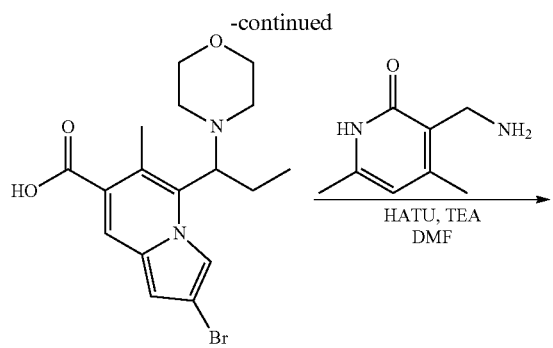

Step 1: Preparation of 4-bromo-1-(2-oxobutyl)-1H-pyrrole-2-carbaldehyde: yield: 86%. MS(ESI) m/z 216[M+H-CO]⁺.

Step 2: Preparation of ethyl 2-bromo-6-methyl-7-propionylindolizine-5-carboxylate: yield: 46%. MS (ESI) m/z 338 [M+H]⁺.

Step 3: Preparation of (Z) or (E)-isopropyl 2-bromo-6-methyl-7-(1-morpholinyl-1-propen-1-yl)indolizine-5-carboxylate: yield: 75%. MS (ESI) m/z 421 [M+H]⁺.

Step 4: Preparation of isopropyl 2-bromo-6-methyl-7-(1-morpholinylpropyl)indolizine-5-carboxylate: yield: 81%. MS (ESI) m/z 423 [M+H]⁺.

Step 5: Preparation of 2-bromo-6-methyl-7-(1-morpholinylpropyl)indolizine-5-carboxylic acid: yield: 91%. MS (ESI) m/z 381 [M+H]⁺.

Step 6: Preparation of 2-bromo-N-((4,6-dimethyl-2-oxo-1,2-dihydropyridin-3-yl)methyl)-6-methyl-7-(1-morpholinylpropyl)indolizine-5-carboxamide: Yield: 99%. ¹H NMR (400 MHz, CDCl₃) δ 10.93 (s, 1H), 8.35 (s, 1H), 7.32 (s, 1H), 6.48 (s, 1H), 5.96 (s, 1H), 4.50 (s, 1H), 3.90 (s, 4H), 3.67 (s, 6H), 2.75 (s, 2H), 2.65 (s, 2H), 2.39 (s, 3H), 2.34 (s, 3H), 2.25 (s, 3H), 1.38 (m, 2H), 0.62 (t, J=7.3 Hz, 3H); MS (ESI) m/z 515 [M+H]⁺.

Example 150: Preparation of N-((4,6-dimethyl-2-oxo-1,2-dihydropyridin-3-yl)methyl)-7-(1-methoxymethyl)-6-methyl-2-(3,4,5-trimethoxyphenyl)indolizine-5-carboxamide: Same as Example 1

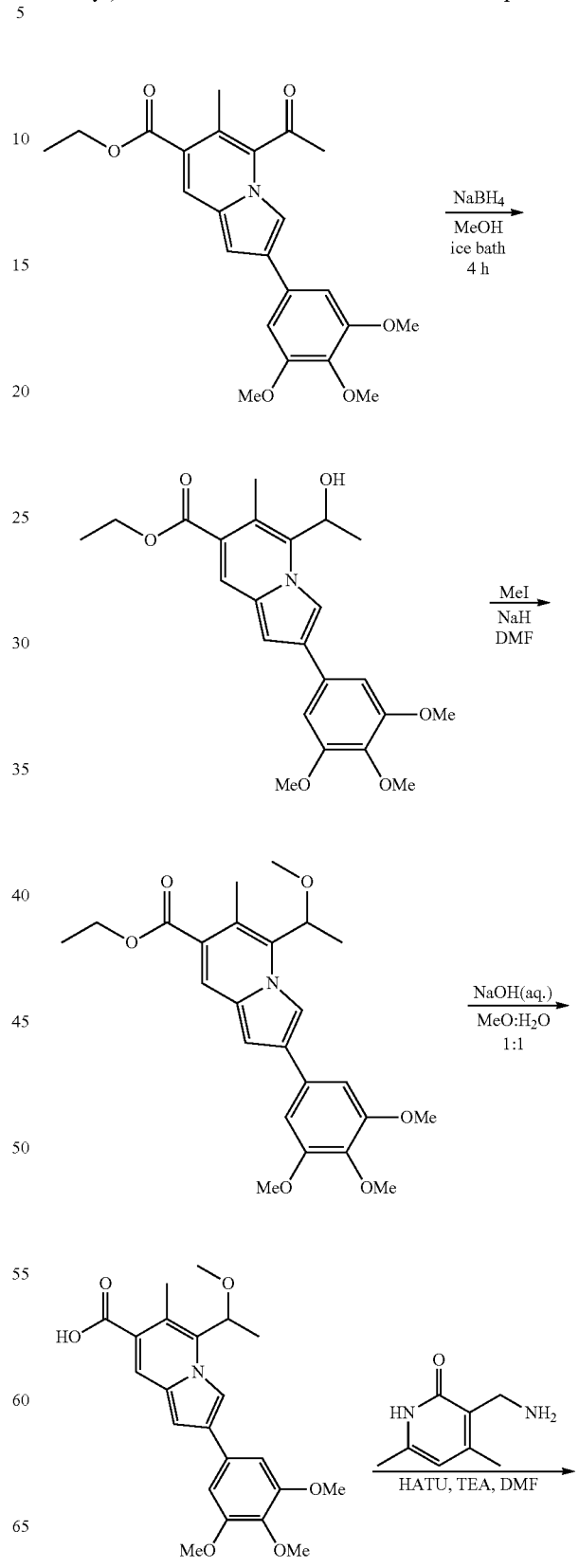

-continued

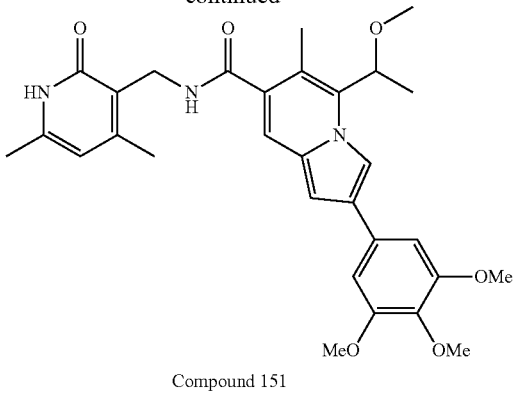

Compound 151

Step 1: Preparation of ethyl 7-(1-hydroxyethyl)-6-methyl-2-(3,4,5-trimethoxyphenyl)indolizine-5-carboxylate: Yield: 91%. MS (ESI) m/z 414 [M+H]$^+$.

Step 2: Preparation of ethyl 7-(1-methoxymethyl)-6-methyl-2-(3,4,5-trimethoxyphenyl)indolizine-5-carboxylate: Yield: 95%. MS (ESI) m/z 428 [M+H]$^+$.

Step 3: Preparation of 7-(1-methoxymethyl)-6-methyl-2-(3,4,5-trimethoxyphenyl)indolizine-5-carboxylic acid: Yield: 83%. MS (ESI) m/z 400 [M+H]$^+$.

Step 4: Preparation of N-((4,6-dimethyl-2-oxo-1,2-dihydropyridin-3-yl)methyl)-7-(1-methoxymethyl)-6-methyl-2-(3,4,5-trimethoxyphenyl)indolizine-5-carboxamide: yield: 92%. $^1$H NMR (400 MHz, CDCl$_3$) δ 11.00 (brs, 1H), 8.18 (s, 1H), 7.37 (s, 1H), 6.85 (s, 2H), 6.73 (s, 1H), 6.07 (s, 1H), 5.13 (q, J=6.8 Hz, 1H), 4.53 (s, 1H), 3.94 (s, 6H), 3.87 (s, 3H), 3.23 (s, 2H), 2.80 (s, 3H), 2.46 (s, 3H), 2.33 (s, 3H), 2.30 (s, 3H), 1.65 (d, J=6.8 Hz, 3H); MS (ESI) m/z 534 [M+H]$^+$.

Example 151: Biological Activity Assay

1. Determination of the Activity of a Compound to PRC2 Complex (EZH2Y641F):

Detection Method: Homogeneous Time-Resolved Fluorescence (HTRF)

MATERIALS: The PRC2 complex (EZH2 Y641F/EED/SUZ12/RbAp48/AEBP2) histone methyltransferase was purchased from Cisbio; the substrate H3(1-50) K27me1 was a product of GL Biochem; methyl donor S-(5-Adenosyl)-L-methionine chloride dihydrochloride (SAM) was purchased from Sigma-aldrich; Eu-labeled H3K27me3, Streptavidin-XL665 and the buffer required for the reaction were purchased from Cisbio.

Experimental method: PRC2 complex (EZH2 Y641F/EED/SUZ12/RbAp48/AEBP2), H3(1-50) me1 substrate, methyl donor SAM and a compound were added into each well. The total reaction system was 10⁴. Reaction was conducted in darkness at room temperature for 4 h. 5υl Eu-labeled H3K27 Me3 antibody and 5υl Streptavidin-XL665 were added into each well, mixed well and incubated for 1 h at room temperature, and fluorescence was measured at 620 nm and 665 nm with multi-label microplate assay system (PerkinElmer Envision), and the HTRF signal ratio per well (665 nm/620 nm) was calculated. The IC50 values of the compounds were calculated using SoftMax Pro 5.4.1 software.

2. Determination of the Activity of a Compound to PRC2 Complex (EZH2 Wild Type):

Detection Method: Enzyme-Linked Immunosorbent Assay (ELISA)

MATERIALS: The PRC2 complex (EZH2/EED/SUZ12/RbAp48/AEBP2) histone methyltransferase was purchased from BPS; the substrate Biotin H3 (21-44) me0 was produced by AnaSpec; SAM was purchased from Sigma, which is GL Biochem product; methyl donor SAM was purchased from Sigma-aldrich; H3K27me3 antibody was purchased from BPS.

Experimental method: avdin of a final concentration of 100 nM was used to coat 96-well plate at 10 μL/well, placed in a wet box and shaken overnight, and then 100 μL 3% BSA per well was added and blocked for 1 h at room temperature. PRC2 complex (EZH2/EED/SUZ12/RbAp48/AEBP2), H3 (21-44) me0 substrate, methyl donor SAM and compound were added into each well of the blocked 96-well plate. The total reaction system was 100 μL, placed in a wet box and allowed to react for 1 h on shaker at room temperature. The plate was washed with TBS-T [20 mM Tris-HCl (pH 7.2-7.4, room temperature), 150 mM NaCl, 0.1% (v/v) Tween-20] for 3 times, blocked with 3% BSA for 10 min, and anti-H3K27me3 antibody was added and incubated for 1 h in a wet box on shaker at room temperature. The plate was washed again with TBS-T for 3 times, and blocked with 3% BSA per well for 10 min. Horseradish peroxidase-labeled secondary antibody was added and reacted in a wet box at room temperature for 1 h, and finally, washed with TBS-T for 3 times. 2 mg/ml OPD color developing solution (1004/well) was added for coloring, and the reaction was stopped with 2M H$_2$SO$_4$ (50 μL/well). The plate was read by a plate reader at 490 nm and IC50 of the compound was calculated using SoftMax Pro 5.4.1 software.

The results are shown below:

Table 1 shows the IC50 values of some of the compounds of the present invention.

The letter A represents IC50≤100 nm;
The letter B represents IC50 of >100 nm to ≤1000 nm;
The letter C represents IC50 of >1 uM to ≤10 uM;
The letter D represents IC50>10 uM

| Compound | IC$_{50}$ (EZH2_Y641F, nM) | IC$_{50}$ (EZH2 wild type, nM) | Compound | IC$_{50}$ (EZH2_Y641F, nM) | IC$_{50}$ (EZH2 wild type, nM) |
|---|---|---|---|---|---|
| 1 | B | / | 2 | C | / |
| 3 | B | / | 4 | B | B |
| 5 | B | / | 6 | C | / |
| 7 | B | / | 8 | B | / |
| 9 | B | / | 10 | B | B |
| 11 | B | B | 12 | B | B |
| 13 | B | B | 14 | B | B |
| 15 | B | / | 16 | B | / |
| 17 | A | / | 18 | A | B |
| 19 | B | B | 20 | B | B |
| 21 | A | A | 22 | C | / |

-continued

| Compound | IC$_{50}$ (EZH2_Y641F, nM) | IC$_{50}$ (EZH2 wild type, nM) | Compound | IC$_{50}$ (EZH2_Y641F, nM) | IC$_{50}$ (EZH2 wild type, nM) |
|---|---|---|---|---|---|
| 23 | B | / | 24 | D | / |
| 25 | B | A | 26 | A | A |
| 27 | A | A | 28 | A | / |
| 29 | B | / | 30 | A | / |
| 31 | A | / | 32 | B | / |
| 33 | A | / | 34 | A | / |
| 35 | A | / | 36 | B | / |
| 37 | A | / | 38 | A | / |
| 39 | A | / | 40 | A | / |
| 41 | A | / | 42 | A | / |
| 43 | A | / | 44 | A | / |
| 45 | A | / | 46 | C | / |
| 47 | A | / | 48 | B | / |
| 49 | A | / | 50 | A | / |
| 51 | A | / | 52 | A | / |
| 53 | B | / | 54 | A | / |
| 55 | A | / | 56 | B | B |
| 57 | A | / | 58 | B | A |
| 59 | B | / | 60 | C | / |
| 61 | C | / | 62 | B | / |
| 63 | A | / | 64 | B | / |
| 65 | B | / | 66 | A | / |
| 67 | A | / | 68 | B | / |
| 69 | A | / | 70 | A | / |
| 71 | A | / | 72 | A | / |
| 73 | A | / | 74 | A | / |
| 75 | A | / | 76 | B | / |
| 77 | B | / | 78 | A | / |
| 79 | B | / | 80 | A | / |
| 81 | B | / | 82 | A | / |
| 83 | A | / | 84 | A | / |
| 85 | B | / | 86 | B | / |
| 87 | A | / | 88 | B | / |
| 89 | B | / | 90 | A | / |
| 91 | C | / | 92 | A | / |
| 93 | A | / | 94 | A | / |
| 95 | A | / | 96 | A | / |
| 97 | A | / | 98 | B | / |
| 99 | B | / | 100 | B | / |
| 101 | B | / | 102 | B | / |
| 103 | C | / | 104 | B | / |
| 105 | B | / | 106 | C | / |
| 107 | A | / | 108 | A | / |
| 109 | A | / | 110 | B | / |
| 111 | B | / | 112 | B | / |
| 113 | A | / | 114 | A | / |
| 115 | B | / | 116 | A | / |
| 117 | A | / | 118 | A | / |
| 119 | A | / | 120 | A | / |
| 121 | A | / | 122 | B | / |
| 123 | B | / | 124 | C | / |
| 125 | B | / | 126 | B | / |
| 127 | A | / | 128 | A | / |
| 129 | A | / | 130 | A | / |
| 131 | A | / | 132 | A | / |
| 133 | A | / | 134 | A | / |
| 135 | A | / | 136 | A | / |
| 137 | A | / | 138 | A | / |
| 139 | A | / | 140 | A | / |
| 141 | B | / | 142 | B | / |
| 143 | A | / | 144 | B | / |
| 145 | B | / | 146 | B | / |
| 147 | B | / | 149 | A | / |
| 150 | B | / | 151 | A | / |
| 152 | 2.65 | / | 153 | 2.15 | / |
| 154 | A | A | 155 | B | A |
| 156 | 3.10 | 3.81 | 157 | A | / |
| 158 | A | A | 159 | A | A |
| 160 | A | A | 161 | A | / |
| 162 | A | / | 163 | A | / |
| 164 | B | / | 165 | A | / |
| 166 | A | / | 167 | A | / |
| 168 | B | / | 169 | A | / |
| 170 | A | / | 171 | A | / |
| 172 | B | / | 173 | A | / |

-continued

| Compound | IC$_{50}$ (EZH2_Y641F, nM) | IC$_{50}$ (EZH2 wild type, nM) | Compound | IC$_{50}$ (EZH2_Y641F, nM) | IC$_{50}$ (EZH2 wild type, nM) |
|---|---|---|---|---|---|
| 174 | A | / | 175 | B | / |
| 176 | A | / | 177 | A | / |
| 178 | B | / | 179 | A | / |
| 180 | A | / | 181 | A | / |
| 182 | B | / | 183 | A | / |
| 184 | A | / | 185 | A | / |
| 186 | A | / | 187 | A | / |
| 188 | B | / | 189 | B | / |
| 190 | A | / | 191 | A | / |
| 192 | A | / | 193 | A | / |
| 194 | A | / | 195 | B | / |
| 196 | A | / | 197 | A | / |
| 198 | A | / | 199 | A | / |
| 200 | A | / | 201 | A | / |
| 202 | A | / | 203 | A | / |
| 204 | A | / | 205 | A | / |
| 206 | A | / | 207 | A | / |

Note:
"/" means "not determined"

Example 152: Preparation of N-((4-Methoxy-6-methyl-2-oxo-1,2-dihydropyridin-3-yl)methyl)-6-methyl-5-(1-morpholinyl ethyl)-1-(1H-pyrazol-4-yl)indolizine-7-carboxamide: Same as Example 31

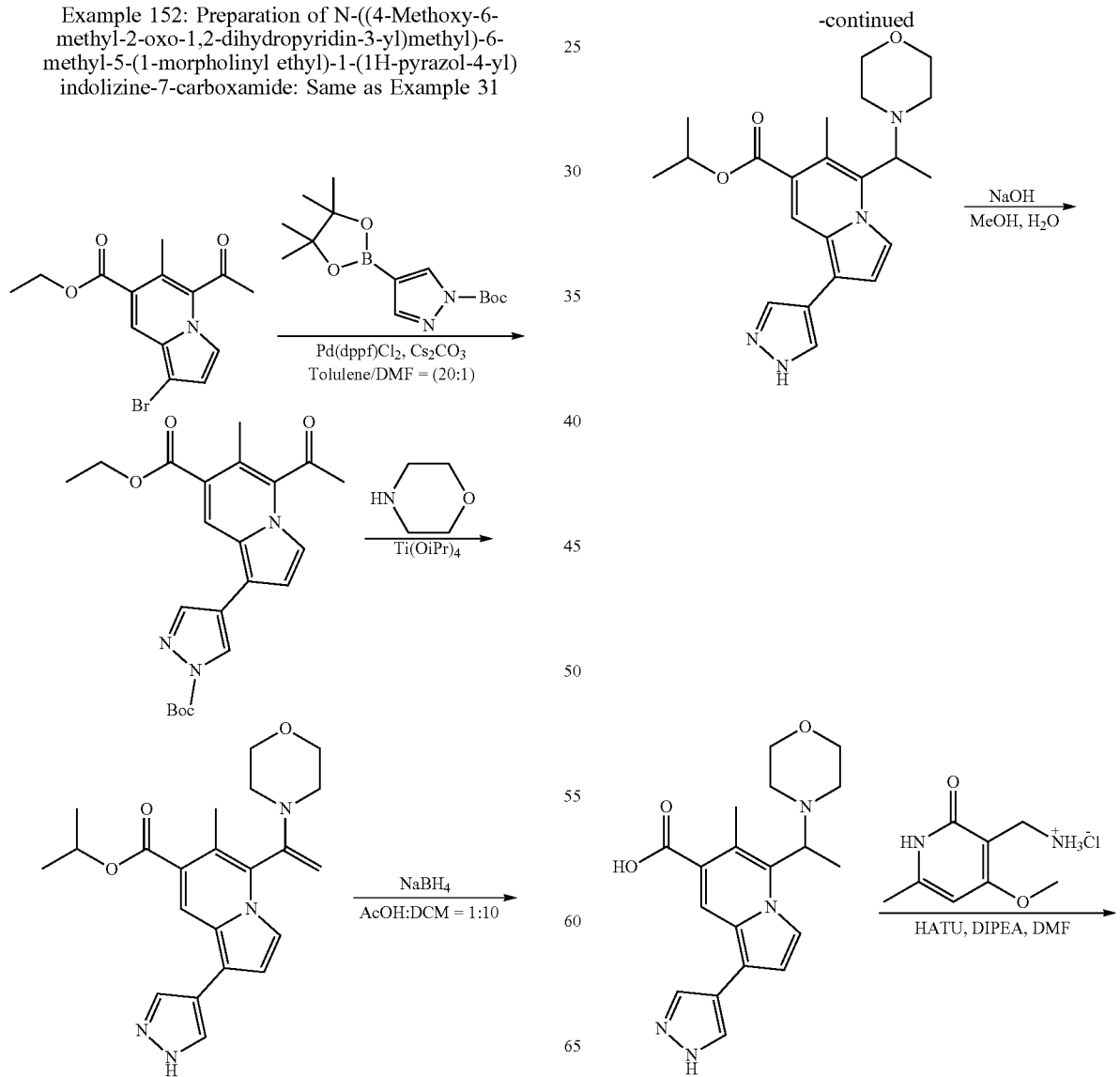

337
-continued

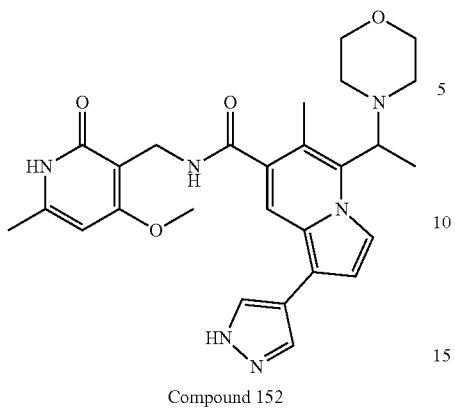

Compound 152

Step 1: Preparation of ethyl 5-acetyl-1-(1-(tert-butyloxy-carbonyl)-1H-pyrazol-4-yl)-6-methylindolizine-7-carboxylate: Yield 43%. MS (ESI) m/z 412 [M+H]⁺.

Step 2: Preparation of isopropyl 6-methyl-5-(1-morpholinylvinyl)-1-(1H-pyrazol-4-yl)indolizine-7-carboxylate: MS (ESI) m/z 395 [M+H]⁺.

Step 3: Preparation of isopropyl 6-methyl-5-(1-morpholinylethyl)-1-(1H-pyrazol-4-yl)indolizine-7-carboxylate: yield of two steps was 49%. MS (ESI) m/z 397 [M+H]⁺.

Step 4: Preparation of 6-methyl-5-(1-morpholinylethyl)-1-(1H-pyrazol-4-yl)indolizine-7-carboxylic acid: yield 43%. MS (ESI) m/z 355 [M+H]⁺.

Step 5: Preparation of N-((4-methoxy-6-methyl-2-oxo-1,2-dihydropyridin-3-yl)methyl)-6-methyl-5-(1-morpholinylethyl)-1-(1H-pyrazol-4-yl)indolizine-7-carboxamide: Yield 50%. $^1$H NMR (400 MHz, CDCl$_3$) δ ppm 8.43 (s, 1H), 7.86 (s, 1H), 7.80 (s, 1H), 7.68 (t, J=4.8 Hz, 1H), 7.62 (s, 1H), 7.51 (d, J=3.8 Hz, 1H), 7.38 (t, J=8.0 Hz, 1H), 6.82 (d, J=1.4 Hz, 1H), 5.91 (s, 1H), 4.62-4.51 (m, 2H), 4.09-4.03 (m, 1H), 3.87 (s, 3H), 3.69 (s, 4H), 2.85 (s, 2H), 2.42 (s, 3H), 2.27-2.23 (m, 5H), 1.49 (d, J=6.8 Hz, 3H); MS (ESI) m/z 505 [M+H]⁺.

Example 153: Preparation of N-((4-Methoxy-6-methyl-2-oxo-1,2-dihydropyridin-3-yl)methyl)-6-methyl-5-(1-morpholinyl ethyl)-1-(1H-pyrazol-5-yl)indolizine-7-carboxamide: Same to Example 31

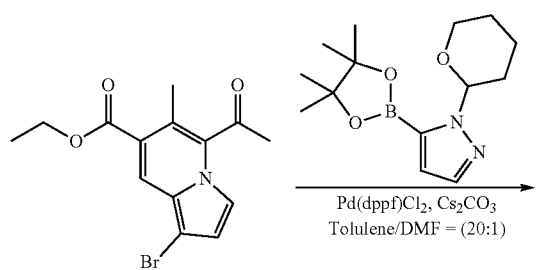

338
-continued

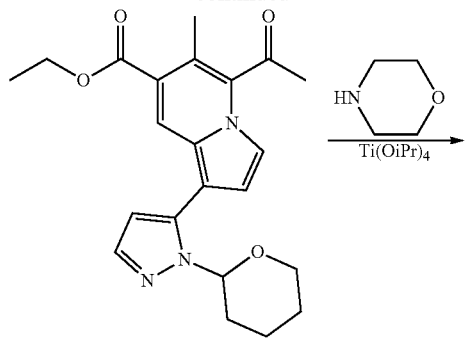

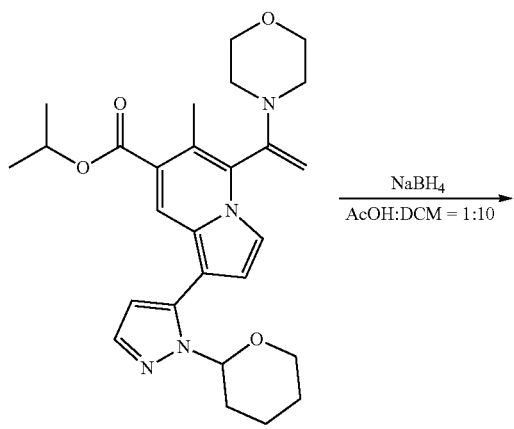

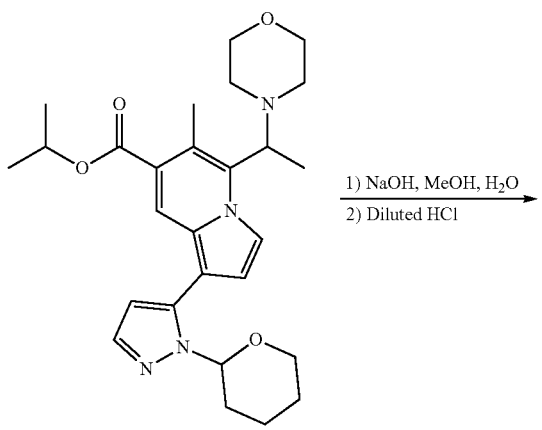

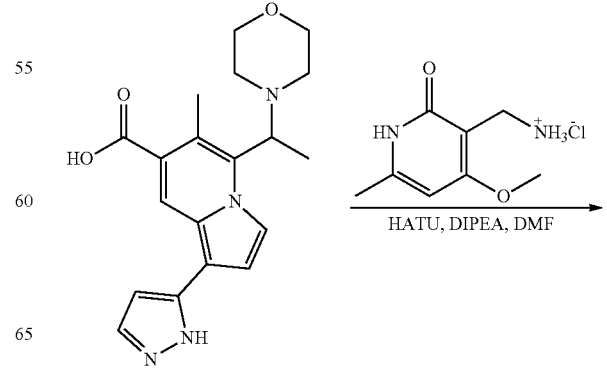

339
-continued

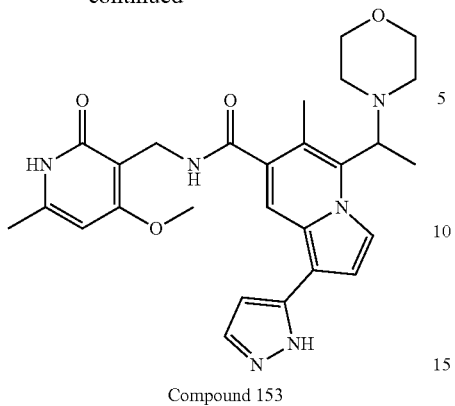

Compound 153

Step 1: Preparation ethyl 5-acetyl-6-methyl-1-(1-(tetrahydro-2H-pyran-2-yl)-1H-pyrazol-5-yl)indolizine-7-carboxylate: Yield 82%. MS (ESI) m/z 396 [M+H]+.

Step 2: Preparation of isopropyl 6-methyl-5-(1-morphinolinylvinyl)-1-(1-(tetrahydro-2H-pyran-2-yl)-1H-pyrazol-5-yl)indolizine-7-carboxylate: MS (ESI) m/z 479 [M+H]+.

Step 3: Preparation of isopropyl 6-methyl-5-(1-morphinolinylethyl)-1-(1-(tetrahydro-2H-pyran-2-yl)-1H-pyrazol-5-yl)indolizine-7-carboxylate: yield of two steps was 44%. MS (ESI) m/z 481 [M+H]+.

Step 4: Preparation of 6-methyl-5-(1-morphinolinylethyl)-1-(1H-pyrazol-5-yl)indolizine-7-carboxylic acid: MS (ESI) m/z 355 [M+H]+.

Step 5: Preparation of N-((4-methoxy-6-methyl-2-oxo-1,2-dihydropyridin-3-yl)methyl)-6-methyl-5-(1-morpholinylethyl)-1-(1H-pyrazol-5-yl)indolizine-7-carboxamide: yield of two steps was 10%. $^1$H NMR (400 MHz, CDCl$_3$) δ ppm 12.60 (s, 1H), 11.43 (s, 1H), 8.37 (s, 1H), 8.00 (s, 1H), 7.05 (s, 1H), 6.50 (s, 1H), 6.10 (s, 1H), 5.87 (s, 1H), 4.30-4.24 (m, 2H), 4.05-4.02 (m, 1H), 4.02 (s, 3H), 3.63-3.44 (m, 4H), 2.66-2.54 (m, 2H), 2.33-2.11 (m, 8H), 1.44 (d, J=6.8 Hz, 3H); MS (ESI) m/z 505 [M+H]+.

Example 154: Preparation of N-((4-methoxy-6-methyl-2-oxo-1,2-dihydropyridin-3-yl)methyl)-6-methyl-1-(1H-pyrazol-5-yl)-5-(1-(4-(2,2,2-trifluoroethyl)piperazin-1-yl)ethyl)indolizine-7-carboxamide: Same as Example 31

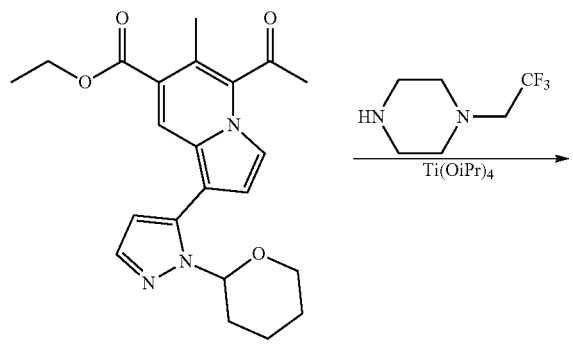

340
-continued

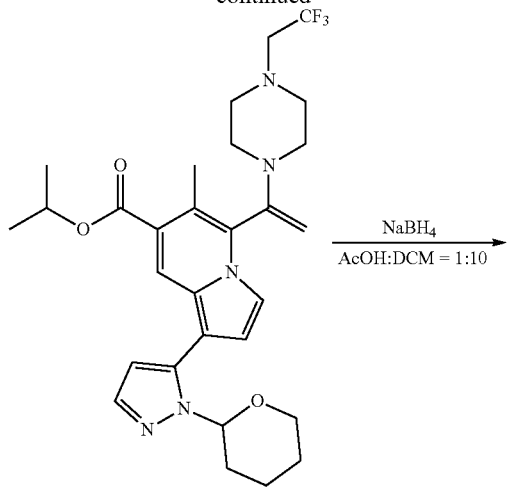

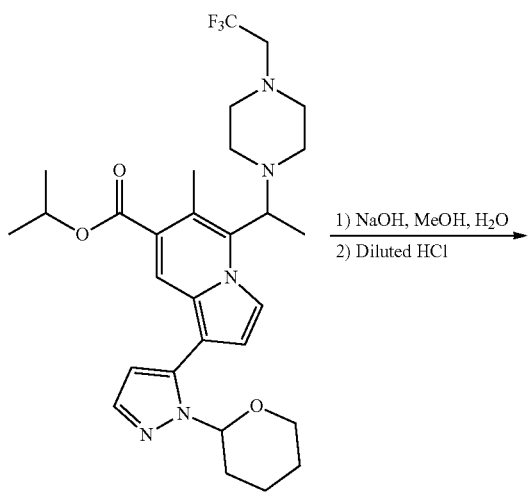

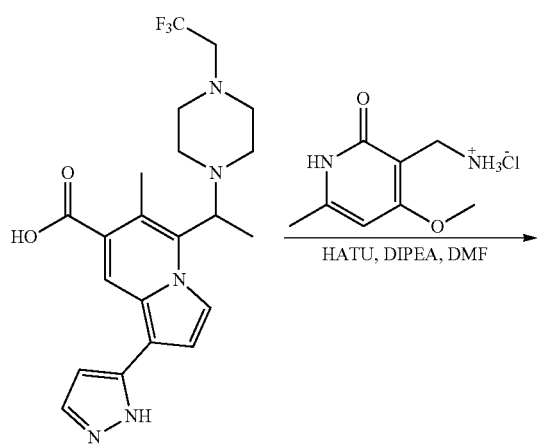

-continued

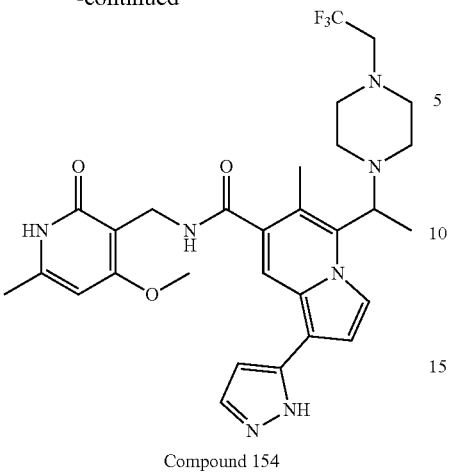

Compound 154

Step 1: Preparation of isopropyl 6-methyl-1-(1-(tetrahydro-2H-pyran-2-yl)-1H-pyrazol-5-yl)-5-(1-(4-(2,2,2-trifluoroethyl)piperazin-1-yl)vinyl)indolizine-7-carboxylate: MS (ESI) m/z 560 [M+H]+.

Step 2: Preparation of isopropyl 6-methyl-1-(1-(tetrahydro-2H-pyran-2-yl)-1H-pyrazol-5-yl)-5-(1-(4-(2,2,2-trifluoroethyl)piperazin-1-yl)ethyl)indolizine-7-carboxylate: yield of two steps was 32%. MS (ESI) m/z 562 [M+H]+.

Step 3: Preparation of 6-methyl-1-(1H-pyrazol-5-yl)-5-(1-(4-(2,2,2-trifluoroethyl)piperazin-1-yl)indolizine-7-formic acid: yield 77%. MS (ESI) m/z 436 [M+H]+.

Step 5: Preparation of N-((4-methoxy-6-methyl-2-oxo-1,2-dihydropyridin-3-yl)methyl)-6-methyl-1-(1H-pyrazol-5-yl)-5-(1-(4-(2,2,2-trifluoroethyl)piperazin-1-yl)ethyl)indolizine-7-carboxamide: yield 25%. $^1$H NMR (DMSO-$d_6$, 400 MHz): 11.46 (brs, 1H), 8.36 (brs, 1H), 8.02 (s, 1H), 7.72 (s, 1H), 7.54 (s, 1H), 7.04 (s, 1H), 6.50 (s, 1H), 6.11 (s, 1H), 4.23 (d, J=4.0 Hz, 2H), 4.04 (q, J=6.8 Hz, 1H), 3.82 (s, 3H), 3.16-3.11 (m, 2H), 2.61 (brs, 6H), 2.32 (s, 3H), 2.19-2.18 (m, 5H), 1.43 (d, J=6.8 Hz, 3H); MS (ESI) m/z 586 [M+H]+.

Example 155: Preparation of (S)—N-((4-methoxy-6-methyl-2-oxo-1,2-dihydropyridin-3-yl)methyl)-6-methyl-1-(1H-pyrazol-5-yl)-5-(1-(4-(2,2,2-trifluoroethyl)piperazin-1-yl)ethyl)indolizine-7-carboxamide or (R)—N-((4-methoxy-6-methyl-2-oxo-1,2-dihydropyridin-3-yl)methyl)-6-methyl-1-(1H-pyrazol-5-yl)-5-(1-(4-(2,2,2-trifluoroethyl)piperazin-1-yl)ethyl)indolizine-7-carboxamide: Compound 154 was Separated by Chiral Preparative Liquid Chromatography to Provide Compound 155 and Compound 156

The separation conditions were: column type: OD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 155: $^1$H-NMR (DMSO-$d_6$, 400 MHz): 11.46 (brs, 1H), 8.36 (brs, 1H), 8.02 (s, 1H), 7.72 (s, 1H), 7.54 (s, 1H), 7.04 (s, 1H), 6.50 (s, 1H), 6.11 (s, 1H), 4.23 (d, J=4.0 Hz, 2H), 4.04 (q, J=6.8 Hz, 1H), 3.82 (s, 3H), 3.16-3.11 (m, 2H), 2.61 (brs, 6H), 2.32 (s, 3H), 2.19-2.18 (m, 5H), 1.43 (d, J=6.8 Hz, 3H); MS (ESI) m/z 586 [M+H]+; $t_R$=4.398 min.

Compound 156: $^1$H-NMR (DMSO-$d_6$, 400 MHz): 11.46 (brs, 1H), 8.36 (brs, 1H), 8.02 (s, 1H), 7.72 (s, 1H), 7.54 (s, 1H), 7.04 (s, 1H), 6.50 (s, 1H), 6.11 (s, 1H), 4.23 (d, J=4.0 Hz, 2H), 4.04 (q, J=6.8 Hz, 1H), 3.82 (s, 3H), 3.16-3.11 (m, 2H), 2.61 (brs, 6H), 2.32 (s, 3H), 2.19-2.18 (m, 5H), 1.43 (d, J=6.8 Hz, 3H); MS (ESI) m/z 586 [M+H]+; $t_R$=4.806 min.

Example 156: Preparation of 1-(6-aminopyridin-3-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: Similar to Example 83

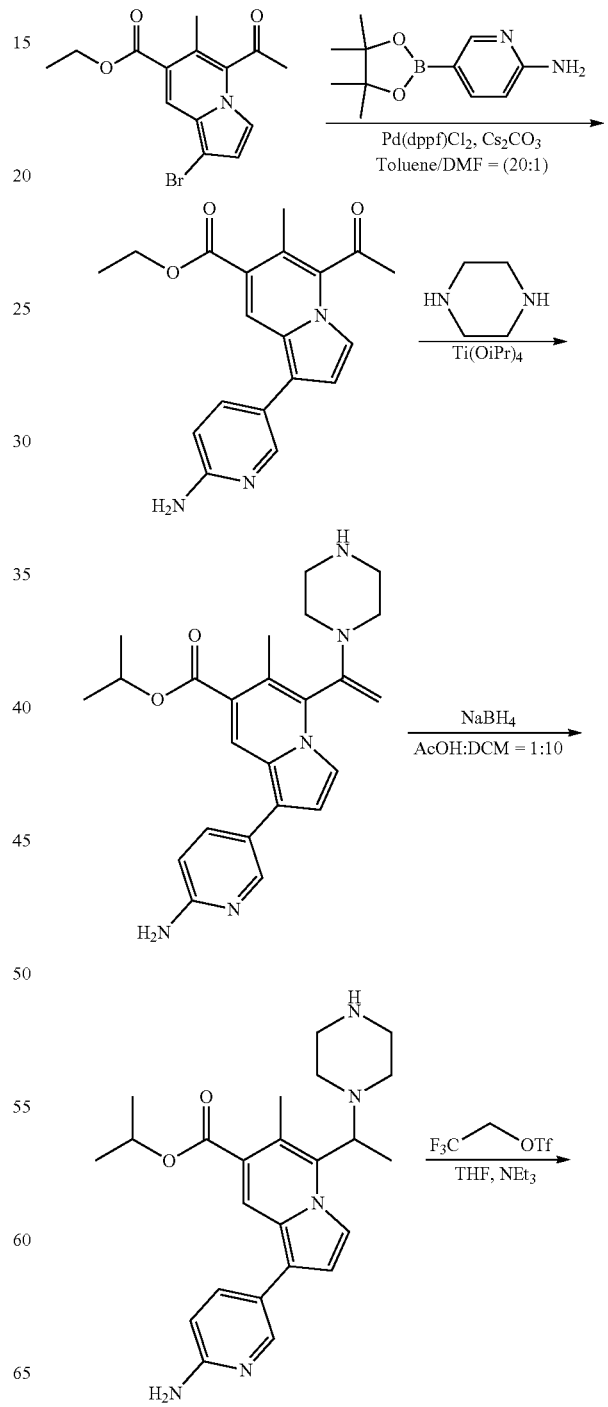

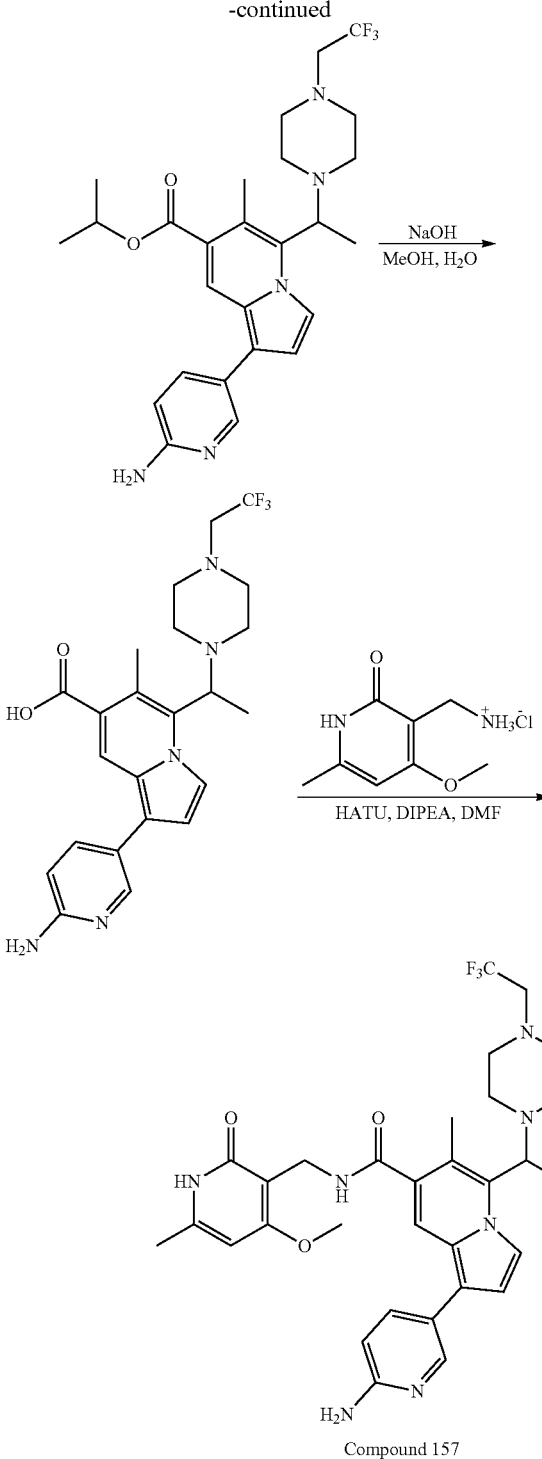

Compound 157

Step 1: Preparation of ethyl 5-acetyl-1-(6-aminopyridin-3-yl)-6-methylindolizine-7-carboxylate: yield 67%. MS (ESI) m/z 338 [M+H]⁺.

Step 2: Preparation of isopropyl 1-(6-aminopyridin-3-yl)-6-methyl-5-(1-(piperazin-1-yl)vinyl)indolizine-7-carboxylate: MS (ESI) m/z 420 [M+H]⁺.

Step 3: Preparation of isopropyl 1-(6-aminopyridin-3-yl)-6-methyl-5-(1-(piperazin-1-yl)ethyl)indolizine-7-carboxylate: yield of two steps was 99%. MS (ESI) m/z 422 [M+H]⁺.

Step 4: Preparation of isopropyl 1-(6-aminopyridin-3-yl)-6-methyl-5-(1-(4-(2,2,2-trifluoroethyl)piperazin-1-yl)ethyl)indolizine-7-carboxylate: yield of two steps was 67%. MS (ESI) m/z 504 [M+H]⁺.

Step 5: Preparation of 1-(6-aminopyridin-3-yl)-6-methyl-5-(1-(4-(2,2,2-trifluoroethyl)piperazin-1-yl)ethyl)indolizine-7-carboxylic acid: yield of two steps was 95%. MS (ESI) m/z 562 [M+H]⁺.

Step 6: Preparation of 1-(6-aminopyridin-3-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: yield 42%. ¹H-NMR (DMSO-d₆, 400 MHz) ppm 11.43 (brs, 1H), 8.37 (s, 1H), 8.15 (s, 1H), 8.06 (s, 1H), 7.59 (d, J=4.4 Hz, 1H), 7.42 (s, 1H), 6.88 (d, J=1.4 Hz, 1H), 6.53 (d, J=4.2 Hz, 1H), 6.10 (s, 1H), 5.83 (s, 2H), 4.21 (d, J=2.2 Hz, 2H), 4.04 (q, J=6.8 Hz, 1H), 3.81 (s, 3H), 3.16-3.13 (m, 2H), 3.63 (s, 6H), 2.27 (s, 3H), 2.18 (s, 5H), 1.43 (d, J=6.8 Hz, 3H); MS (ESI) m/z 634 [M+Na]⁺.

Example 157: Preparation of 1-(6-aminopyridin-3-yl)-N-((4,6-dimethyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Similar to Example 156

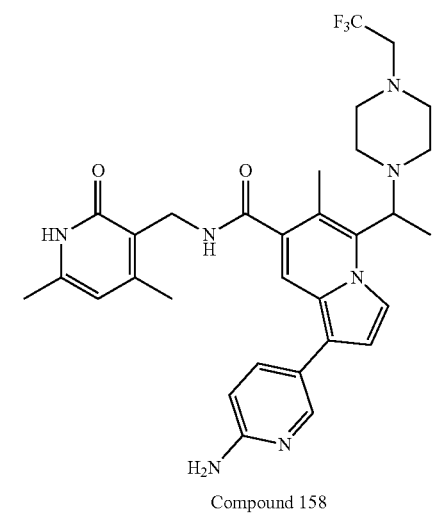

Compound 158

Step 1: Preparation of 1-(6-aminopyridin-3-yl)-N-((4,6-dimethyl-2-oxo-1,2-dihydropyridin-3-yl)methyl)-6-methyl-5-(1-(4-(2,2,2-trifluoroethyl)piperazin-1-yl)ethyl)indolizine-7-carboxamide: yield 28%. ¹H NMR (400 MHz, CDCl₃) ppm 12.10 (brs, 1H), 8.43 (s, 1H), 8.22 (s, 1H), 7.58-7.54 (m, 2H), 7.46 (t, J=5.6 Hz, 1H), 6.80 (d, J=1.4 Hz, 1H), 6.43 (d, J=4.2 Hz, 1H), 4.65 (brs, 2H), 4.53-4.44 (m, 2H), 4.05 (q, J=6.8 Hz, 1H), 2.94 (q, J=9.6 Hz, 2H), 2.68-2.63 (m, 8H), 2.39 (s, 3H), 2.35 (s, 3H), 2.10 (s, 3H), 1.49 (d, J=6.8 Hz, 3H); MS (ESI) m/z 618 [M+Na]⁺.

Example 158: Preparation of (S)-1-(6-aminopyridin-3-yl)-N-((4,6-dimethyl-2-oxo-1,2-dihydropyridin-3-yl)methyl)-6-methyl-5-(1-(4-(2,2,2-trifluoroethyl)piperazin-1-yl)ethyl)indolizine-7-carboxamide or (R) 1-(6-aminopyridin-3-yl)-N-((4,6-dimethyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Compound 158 was Separated by Chiral Preparative Liquid Chromatography to Provide Compound 159 and Compound 160

The separation conditions were: column type: OD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 159: ¹H NMR (400 MHz, CDCl₃) ppm 12.10 (brs, 1H), 8.43 (s, 1H), 8.22 (s, 1H), 7.58-7.54 (m, 2H), 7.46 (t, J=5.6 Hz, 1H), 6.80 (d, J=1.4 Hz, 1H), 6.43 (d, J=4.2 Hz, 1H), 4.65 (brs, 2H), 4.53-4.44 (m, 2H), 4.05 (q, J=6.8 Hz, 1H), 2.94 (q, J=9.6 Hz, 2H), 2.68-2.63 (m, 8H), 2.39 (s, 3H), 2.35 (s, 3H), 2.10 (s, 3H), 1.49 (d, J=6.8 Hz, 3H); MS (ESI) m/z 618 [M+Na]⁺; t_R=4.586 min.

Compound 160: ¹H NMR (400 MHz, CDCl₃) ppm 12.10 (brs, 1H), 8.43 (s, 1H), 8.22 (s, 1H), 7.58-7.54 (m, 2H), 7.46 (t, J=5.6 Hz, 1H), 6.80 (d, J=1.4 Hz, 1H), 6.43 (d, J=4.2 Hz, 1H), 4.65 (brs, 2H), 4.53-4.44 (m, 2H), 4.05 (q, J=6.8 Hz, 1H), 2.94 (q, J=9.6 Hz, 2H), 2.68-2.63 (m, 8H), 2.39 (s, 3H), 2.35 (s, 3H), 2.10 (s, 3H), 1.49 (d, J=6.8 Hz, 3H); MS (ESI) m/z 618 [M+Na]⁺; t_R=4.948 min.

Example 159: Preparation of 1-(3,5-dimethylisoxazol-4-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: Similar to Example 83

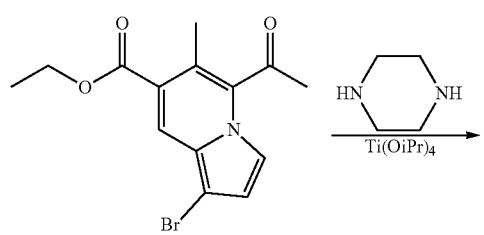

-continued

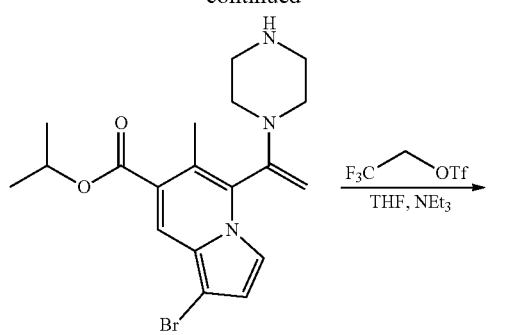

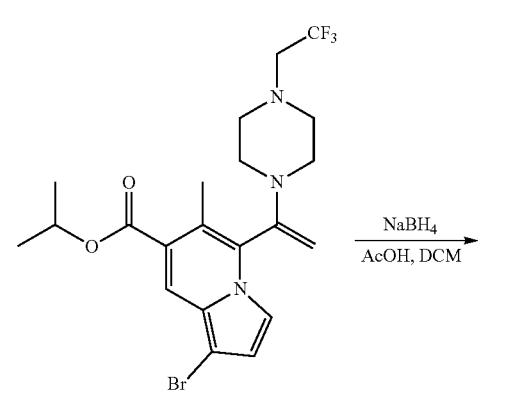

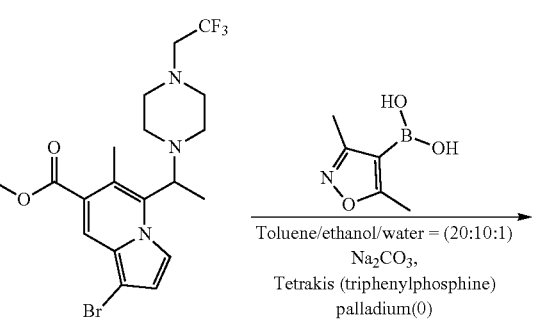

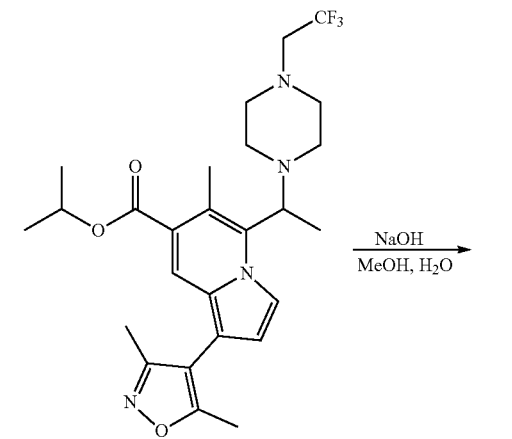

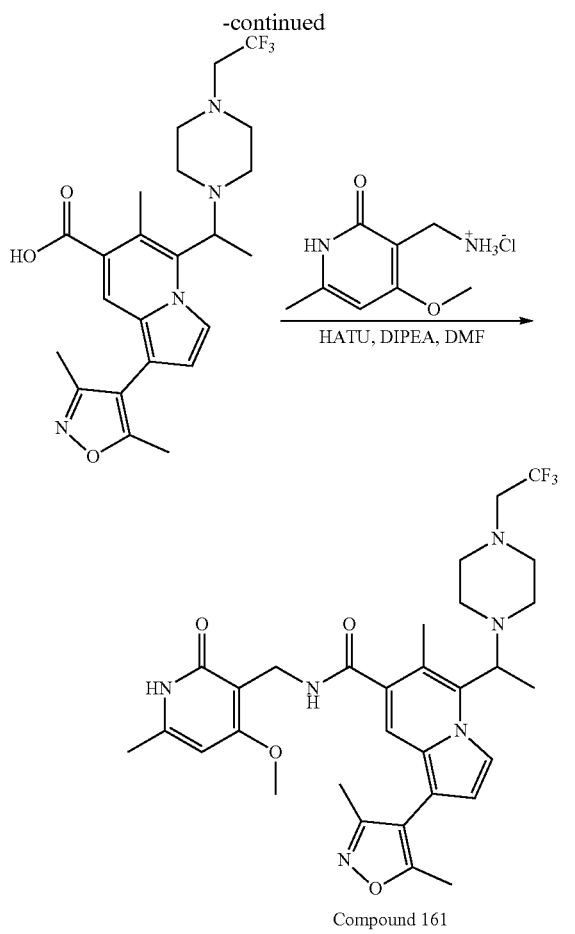

Compound 161

Step 1: Preparation of isopropyl 1-bromo-6-methyl-5-(1-(piperazin-1-yl)vinyl)indolizine-7-carboxylate: MS (ESI) m/z 406 [M+H]⁺.

Step 2: Preparation of isopropyl 1-bromo-6-methyl-5-(1-(4-(2,2,2-trifluoroethyl)piperazin-1-yl)vinyl)indolizine-7-carboxylate: yield of two steps was 99%. MS (ESI) m/z 488 [M+H]⁺.

Step 3: Preparation of isopropyl 1-bromo-6-methyl-5-(1-(4-(2,2,2-trifluoroethyl)piperazin-1-yl)ethyl)indolizine-7-carboxylate: yield 91%. MS (ESI) m/z 490 [M+H]⁺.

Step 4: Preparation of isopropyl 1-(3,5-dimethylisoxazol-4-yl)-6-methyl-5-(1-(4-(2,2,2-trifluoroethyl)piperazin-1-yl)ethyl)indolizine-7-carboxylate: yield was 70%. MS (ESI) m/z 507 [M+H]⁺.

Step 5: Preparation of 1-(3,5-dimethylisoxazol-4-yl)-6-methyl-5-(1-(4-(2,2,2-trifluoroethyl)piperazine-1-yl)ethyl)indolizine-7-carboxylic acid: MS (ESI) m/z 465 [M+H]⁺.

Step 6: Preparation of 1-(3,5-dimethylisoxazol-4-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: yield 32%. ¹H NMR (400 MHz, DMSO-d₆) δ ppm 11.42 (brs, 1H), 8.42 (s, 1H), 8.02 (s, 1H), 6.99 (s, 1H), 6.83 (s, 1H), 6.08 (s, 1H), 6.10 (s, 1H), 4.19 (brs, 2H), 4.06 (q, J=6.8 Hz, 1H), 3.77 (s, 3H), 3.16-3.13 (m, 2H), 2.63 (brs, 6H), 2.29 (brs, 6H), 2.24-2.21 (m, 9H), 1.44 (d, J=6.8 Hz, 3H); MS (ESI) m/z 615 [M+H]⁺.

Example 160: Preparation of 1-(4-fluorophenyl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Same as Example 159

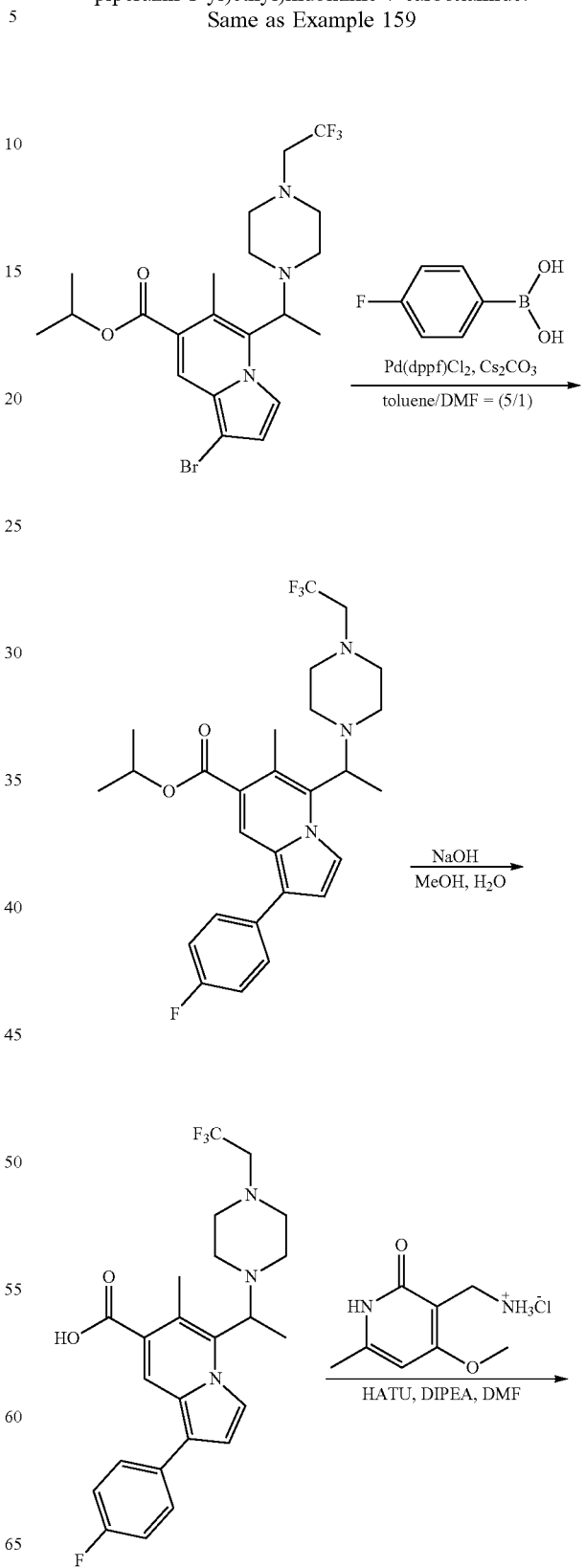

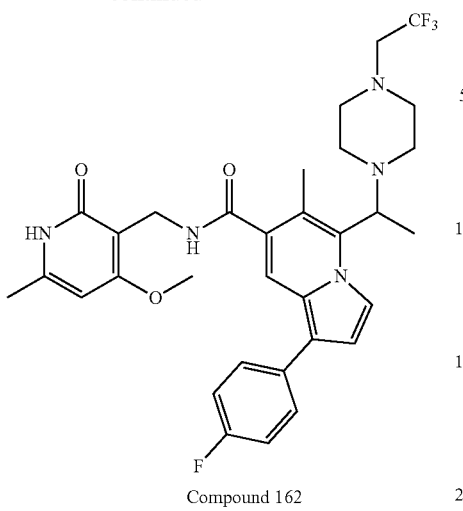

Compound 162

Step 1: Preparation of isopropyl 1-(4-fluorophenyl)-methyl-5-(1-(4-(2,2,2-trifluoroethyl)piperazin-1-yl)ethyl) indolizine-7-carboxylate: yield 56%. MS (ESI) m/z 338 [M-C$_6$H$_{11}$F$_3$N$_2$+H]$^+$.

Step 2: Preparation of 1-(4-fluorophenyl)-methyl-5-(1-(4-(2,2,2-trifluoroethyl)piperazin-1-yl)ethyl)indolizine-7-carboxylic acid: yield 73%. MS (ESI) m/z 464 [M+H]$^+$.

Step 3: Preparation of 1-(4-fluorophenyl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: yield 56%. $^1$H-NMR (MeOD, 400 MHz) δ ppm 7.57-7.52 (m, 3H), 7.17-7.10 (m, 2H), 6.89 (d, J=2.8 Hz, 1H), 6.24 (s, 1H), 4.42 (s, 2H), 4.11 (q, J=6.8 Hz, 1H), 3.90 (s, 3H), 3.04-3.01 (m, 2H), 2.74-2.66 (m, 6H), 2.33-2.30 (m, 9H), 1.51 (d, J=6.8 Hz, 3H); MS (ESI) m/z 614 [M+H]$^+$.

Example 161: Preparation of N-((4-methoxy-6-methyl-2-oxo-1,2-dihydropyridin-3-yl)methyl)-6-methyl-1-(6-(methylamino)pyridin-3-yl)-5-(1-(4-(2,2,2-trifluoroethyl)piperazin-1-yl)ethyl)indolizine-7-carboxamide: Same as Example 159

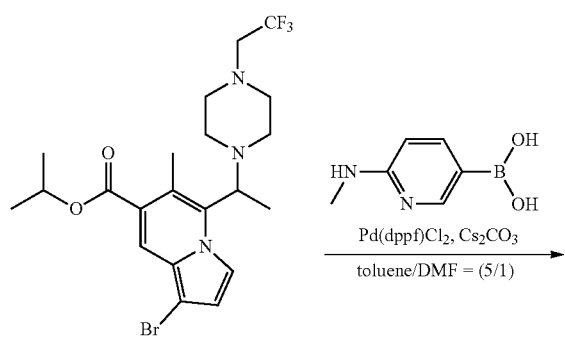

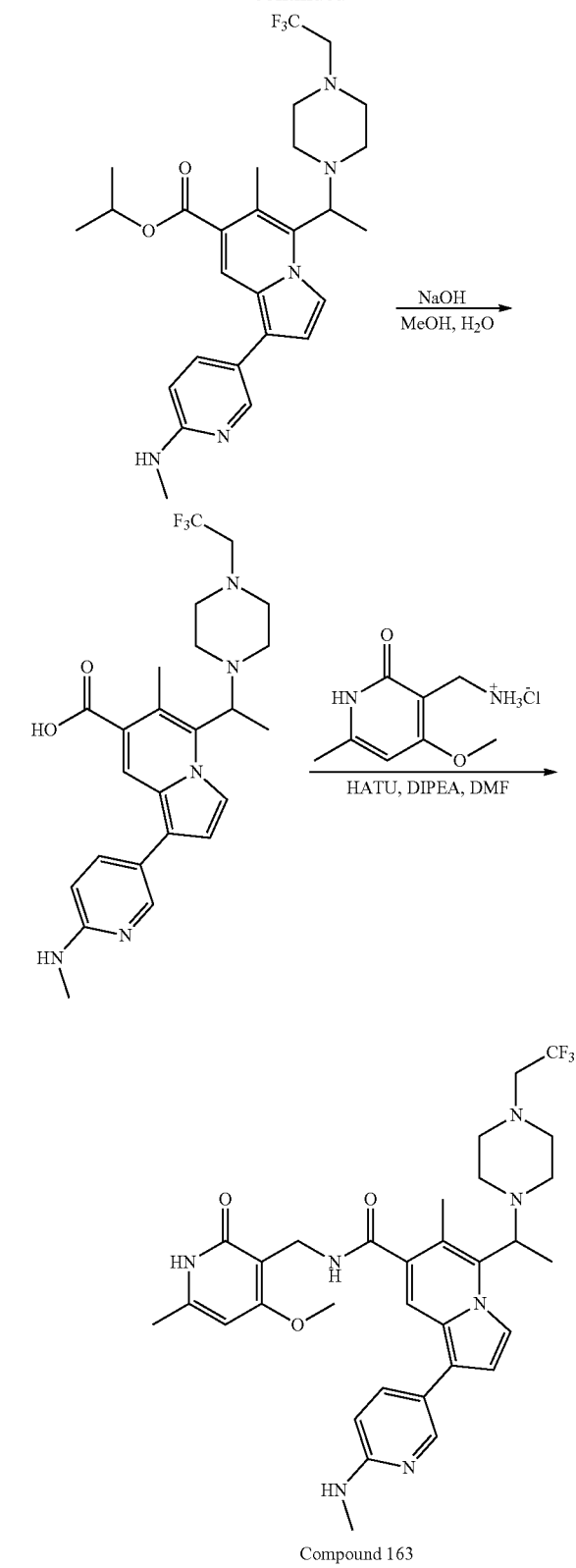

Compound 163

Step 1: Preparation of isopropyl 6-methyl-1-(6-(methylamino)pyridin-3-yl)-5-(1-(4-(2,2,2-trifluoroethyl)piperazin-1-yl)ethyl) indolizine-7-carboxylate: yield 33%. MS (ESI) m/z 518 [M+H]$^+$.

Step 2: Preparation of 6-methyl-1-(6-(methylamino)pyridin-3-yl)-5-(1-(4-(2,2,2-trifluoroethyl)piperazine-1-yl)ethyl) indolizine-7-carboxylic acid: MS (ESI) m/z 476 [M+H]⁺.

Step 3: Preparation of N-((4-methoxy-6-methyl-2-oxo-1,2-dihydropyridin-3-yl)methyl)-6-methyl-1-(6-(methylamino)pyridin-3-yl)-5-(1-(4-(2,2,2-trifluoroethyl)piperazin-1-yl)ethyl)indolizine-7-carboxamide: yield of two steps was 34%. ¹H-NMR (MeOD, 400 MHz) δ ppm 8.44 (s, 1H), 8.11 (d, J=2.0 Hz, 1H), 7.65 (dd, J=8.8, 2.4 Hz, 1H), 7.50 (s, 1H), 6.82 (d, J=2.8 Hz, 1H), 6.59 (d, J=8.8 Hz, 1H), 6.24 (s, 1H), 4.42 (s, 2H), 4.09 (q, J=6.8 Hz, 1H), 3.90 (s, 3H), 3.02 (q, J=10.0 Hz, 2H), 2.89 (s, 3H), 2.68-2.66 (m, 4H), 2.33 (s, 3H), 2.30-2.29 (m, 4H), 1.50 (d, J=6.8 Hz, 3H); MS (ESI) m/z 626 [M+H]⁺.

Example 162: Preparation of (S)—N-((4-methoxy-6-methyl-2-oxo-1,2-dihydropyridin-3-yl)methyl)-6-methyl-1-(6-(methylamino)pyridin-3-yl)-5-(1-(4-(2,2,2-trifluoroethyl)piperazin-1-yl)ethyl)indolizine-7-formamide or (R)—N-((4-methoxy-6-methyl-2-oxo-1,2-dihydropyridin-3-yl)methyl)-6-methyl-1-(6-(methylamino)pyridin-3-yl)-5-(1-(4-(2,2,2-trifluoroethyl)piperazin-1-yl)ethyl)indolizine-7-formamide: Compound 163 was Separated by Chiral Preparative Liquid Chromatography to Provide Compound 164 and Compound 165

The separation conditions were: column type: AD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C. Compound 164: ¹H-NMR (MeOD, 400 MHz) δ ppm 8.44 (s, 1H), 8.11 (d, J=2.0 Hz, 1 H), 7.65 (dd, J=8.8, 2.4 Hz, 1H), 7.50 (s, 1H), 6.82 (d, J=2.8 Hz, 1H), 6.59 (d, J=8.8 Hz, 1H), 6.24 (s, 1H), 4.42 (s, 2H), 4.09 (q, J=6.8 Hz, 1H), 3.90 (s, 3H), 3.02 (q, J=10.0 Hz, 2H), 2.89 (s, 3H), 2.68-2.66 (m, 4H), 2.33 (s, 3H), 2.30-2.29 (m, 4H), 1.50 (d, J=6.8 Hz, 3H); MS (ESI) m/z 626 [M+H]⁺; $t_R$=2.319 min.

Compound 165: ¹H-NMR (MeOD, 400 MHz) δ ppm 8.44 (s, 1H), 8.11 (d, J=2.0 Hz, 1H), 7.65 (dd, J=8.8, 2.4 Hz, 1H), 7.50 (s, 1H), 6.82 (d, J=2.8 Hz, 1H), 6.59 (d, J=8.8 Hz, 1H), 6.24 (s, 1H), 4.42 (s, 2H), 4.09 (q, J=6.8 Hz, 1H), 3.90 (s, 3H), 3.02 (q, J=10.0 Hz, 2H), 2.89 (s, 3H), 2.68-2.66 (m, 4H), 2.33 (s, 3H), 2.30-2.29 (m, 4H), 1.50 (d, J=6.8 Hz, 3H); MS (ESI) m/z 626 [M+H]⁺; $t_R$=6.490 min.

Example 163: Preparation of N-((4-methoxy-6-methyl-2-oxo-1,2-dihydropyridin-3-yl)methyl)-6-methyl-1-(2-(methylpyridin-3-yl)-5-(1-(4-(2,2,2-trifluoroethyl)piperazin-1-yl)ethyl)indolizine-7-carboxamide: Same as Example 159

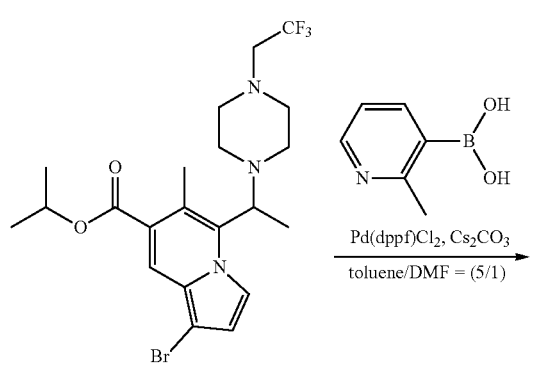

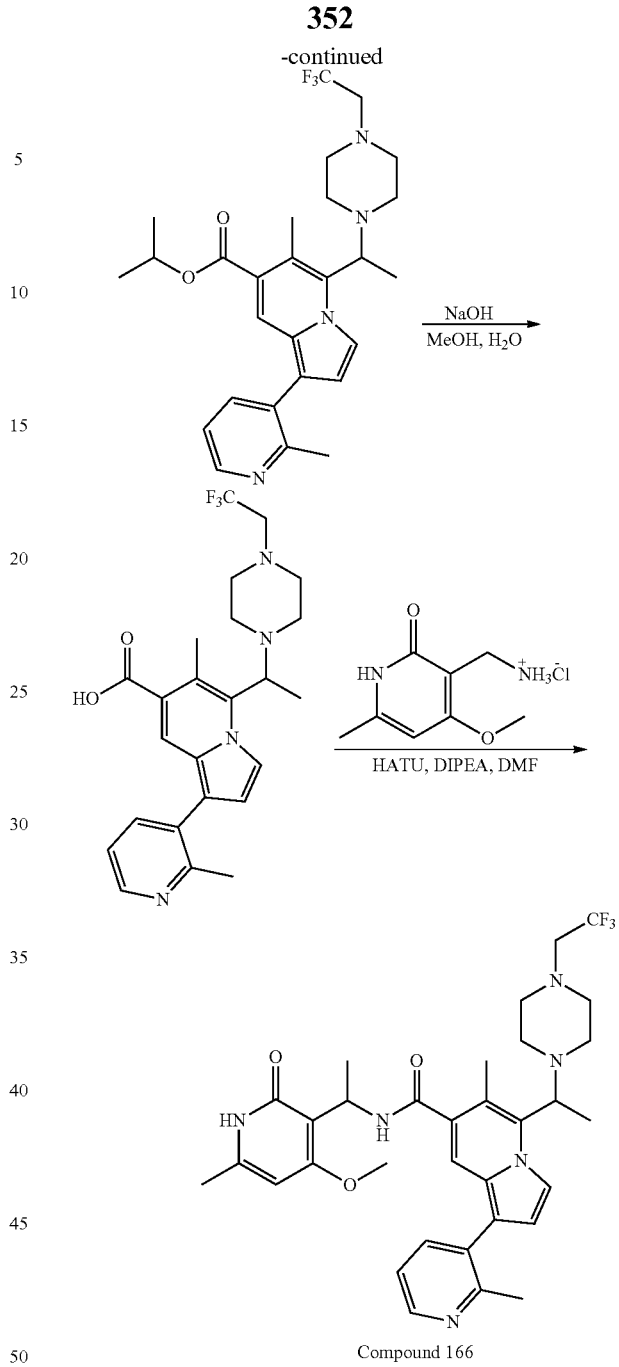

Compound 166

Step 1: Preparation of isopropyl 6-methyl-1-(2-methylpyridin-3-yl)-5-(1-(4-(2,2,2-trifluoroethyl)piperazin-1-yl)ethyl)indolizine-7-carboxylate: yield 44%. MS (ESI) m/z 503 [M+H]⁺.

Step 2: Preparation of 6-methyl-1-(2-methylpyridin-3-yl)-5-(1-(4-(2,2,2-trifluoroethyl)piperazine-1-yl)ethyl)indolizine-7-carboxylic acid: MS (ESI) m/z 461 [M+H]⁺.

Step 3: Preparation of N-((4-methoxy-6-methyl-2-oxo-1,2-dihydropyridin-3-yl)methyl)-6-methyl-1-(2-methylpyridin-3-yl)-5-(1-(4-(2,2,2-trifluoroethyl)piperazin-1-yl)ethyl)indolizine-7-carboxamide: yield of two steps was 35%. ¹H-NMR (MeOD, 400 MHz) δ ppm 8.55 (s, 1H), 8.33 (dd, J=4.8, 1.2 Hz, 1H), 7.75 (dd, J=7.6, 1.2 Hz, 1H), 7.30 (dd, J=7.6, 4.8 Hz, 1H), 7.16 (s, 1H), 6.85 (d, J=2.4 Hz, 1H), 6.22 (s, 1H), 4.38 (s, 2H), 4.13 (q, J=6.8 Hz, 1H), 3.04 (q, J=10.0

Hz, 2H), 2.74-2.67 (m, 6H), 2.49 (s, 3H), 2.34-2.30 (m, 6H), 2.29 (s, 3H), 1.53 (d, J=6.8 Hz, 3H); MS (ESI) m/z 611 [M+H]⁺.

Example 164: Preparation of 1-(2-chloropyridin-4-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Same as Example 159

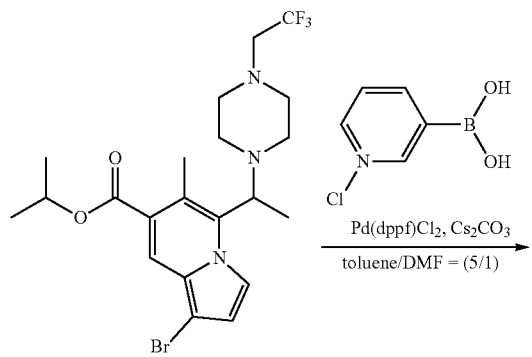

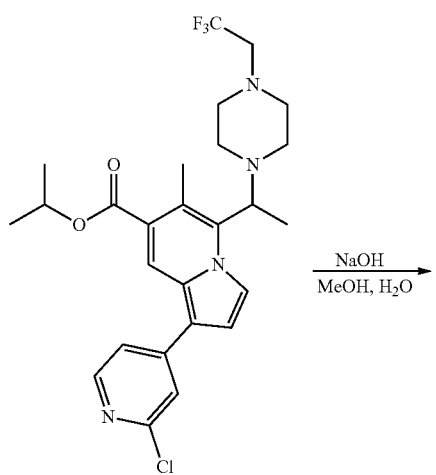

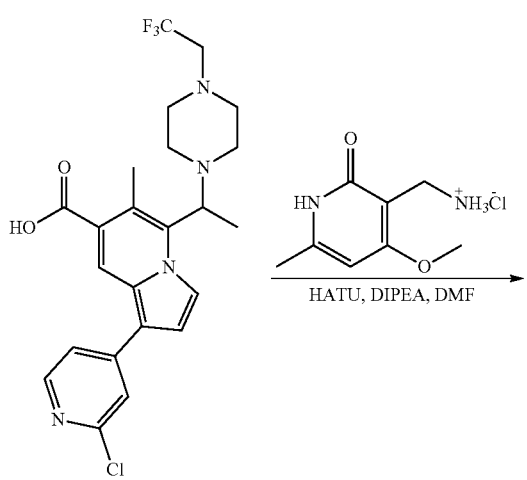

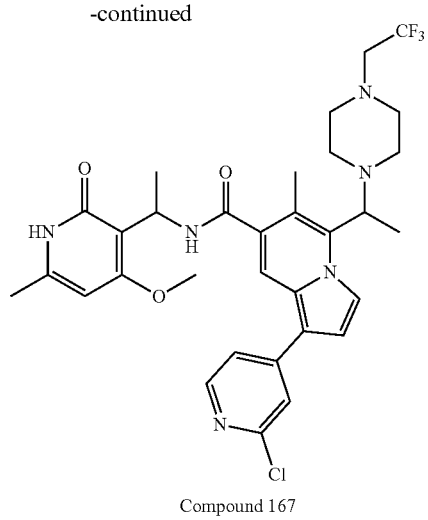

Compound 167

Step 1: Preparation of isopropyl 1-(2-chloropyridin-4-yl)-6-methyl-5-(1-(4-(2,2,2-trifluoroethyl)piperazin-1-yl)ethyl)indolizine-7-carboxylate: yield 35%. MS (ESI) m/z 523 [M+H]⁺.

Step 2: Preparation of 1-(2-chloropyridin-4-yl)-6-methyl-5-(1-(4-(2,2,2-trifluoroethyl)piperazin-1-yl)ethyl)indolizine-7-carboxylic acid: yield was 97%. MS (ESI) m/z 481 [M+H]⁺.

Step 3: Preparation of 1-(2-chloropyridin-4-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: yield 30%. ¹H-NMR (CDCl₃, 400 MHz) δ ppm 8.49 (s, 1H), 8.20 (d, J=8.2 Hz, 1H), 7.75 (s, 1H), 7.71 (t, J=5.6 Hz, 1H), 7.38 (s, 1H), 7.32 (d, J=5.2 Hz, 1H), 6.93 (d, J=4.3 Hz, 1H), 5.87 (s, 1H), 4.57 (t, J=5.2 Hz, 2H), 4.09 (q, J=6.8 Hz, 1H), 3.89 (s, 3H), 2.95 (q, J=6.8 Hz, 2H), 2.67-2.61 (m, 6H), 2.41 (s, 3H), 2.29-2.28 (m, 2H), 2.17 (s, 3H), 1.48 (d, J=6.8 Hz, 3H); MS (ESI) m/z 631 [M+H]⁺.

Example 165: Preparation of (S)-1-(2-chloropyridin-4-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide or (R) 1-(2-chloropyridin-4-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide: Compound 167 was Separated by Chiral Preparative Liquid Chromatography to Provide Compound 168 and Compound 169

The separation conditions were: column type: AD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 168: ¹H-NMR (CDCl₃, 400 MHz) δ ppm 8.49 (s, 1H), 8.20 (d, J=8.2 Hz, 1H), 7.75 (s, 1H), 7.71 (t, J=5.6 Hz, 1H), 7.38 (s, 1H), 7.32 (d, J=5.2 Hz, 1H), 6.93 (d, J=4.3 Hz, 1H), 5.87 (s, 1H), 4.57 (t, J=5.2 Hz, 2H), 4.09 (q, J=6.8 Hz, 1H), 3.89 (s, 3H), 2.95 (q, J=6.8 Hz, 2H), 2.67-2.61 (m, 6H), 2.41 (s, 3H), 2.29-2.28 (m, 2H), 2.17 (s, 3H), 1.48 (d, J=6.8 Hz, 3H); MS (ESI) m/z 631 [M+H]⁺; $t_R$=3.461 min.

Compound 169: $^1$H-NMR (CDCl$_3$, 400 MHz) δ ppm 8.49 (s, 1H), 8.20 (d, J=8.2 Hz, 1H), 7.75 (s, 1H), 7.71 (t, J=5.6 Hz, 1H), 7.38 (s, 1H), 7.32 (d, J=5.2 Hz, 1H), 6.93 (d, J=4.3 Hz, 1H), 5.87 (s, 1H), 4.57 (t, J=5.2 Hz, 2H), 4.09 (q, J=6.8 Hz, 1H), 3.89 (s, 3H), 2.95 (q, J=6.8 Hz, 2H), 2.67-2.61 (m, 6H), 2.41 (s, 3H), 2.29-2.28 (m, 2H), 2.17 (s, 3H), 1.48 (d, J=6.8 Hz, 3H); MS (ESI) m/z 631 [M+H]$^+$; $t_R$=5.255 min.

Example 166: Preparation of 1-(2-(dimethylamino) pyridin-4-yl)-N-((4-methoxy-6-methyl-2-oxo-1,2-dihydropyridin-3-yl) methyl)-6-methyl-5-(1-(4-(2,2,2-trifluoroethyl)piperazin-1-yl)ethyl)indolizine-7-carboxamide: Same as Example 159

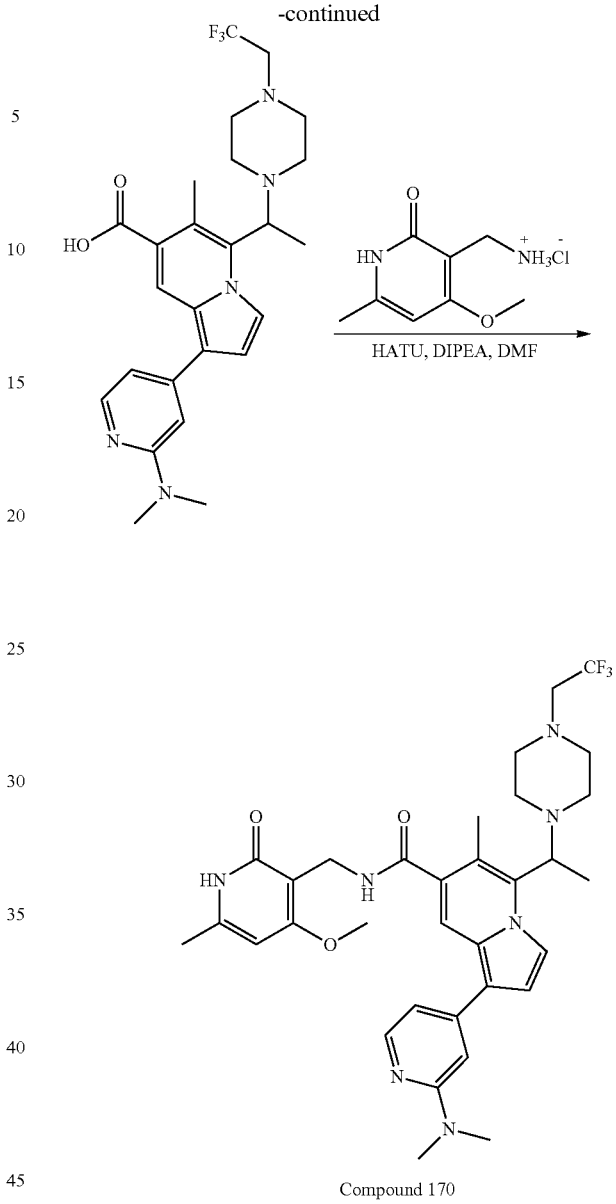

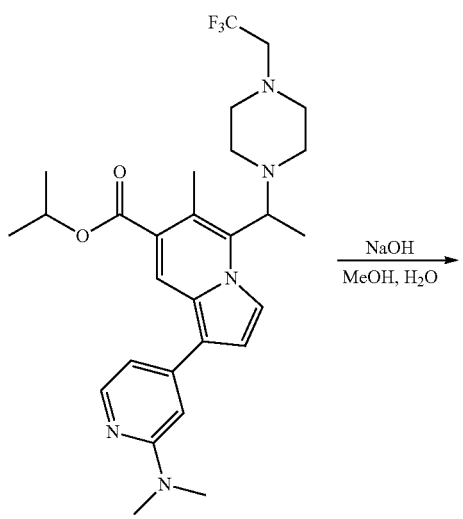

Step 1: Preparation of isopropyl 1-(2-(dimethylamino) pyridin-4-yl)-6-methyl-5-(1-(4-(2,2,2-trifluoroethyl)piperazin-1-yl)ethyl) indolizine-7-carboxylate: yield of two steps was 49%. MS (ESI) m/z 532 [M+H]$^+$.

Step 2: Preparation of 1-(2-(dimethylamino)pyridin-4-yl)-6-methyl-5-(1-(4-(2,2,2-trifluoroethyl)piperazin-1-yl) ethyl) indolizine-7-carboxylic acid: yield 88%. MS (ESI) m/z 490 [M+H]$^+$.

Step 3: Preparation of 1-(2-(dimethylamino)pyridin-4-yl)-N-((4-methoxy-6-methyl-2-oxo-1,2-dihydropyridin-3-yl) methyl)-6-methyl-5-(1-(4-(2,2,2-trifluoroethyl)piperazin-1-yl)ethyl)indolizine-7-carboxamide: yield 24%. $^1$H NMR (400 MHz, DMSO-d$_6$) δ ppm 8.44 (s, 1H), 8.12 (t, J=4.4 Hz, 1H) 8.06 (d, J=5.2 Hz, 1H), 7.63 (s, 1H), 7.12 (d, J=2.1 Hz, 1H), 6.81 (d, J=5.2 Hz, 1H), 6.73 (s, 1H), 6.18 (s, 1H), 4.25 (brs, 2H), 4.07 (q, J=6.8 Hz, 1H), 3.85 (s, 3H), 3.10 (q, J=9.8 Hz, 2H), 3.02 (s, 6H), 2.63-2.51 (m, 6H), 2.30 (s, 3H), 2.36 (s, 6H), 1.48 (d, J=6.8 Hz, 3H); MS (ESI) m/z 640 [M+H]$^+$.

Example 167: Preparation of (S)-1-(2-(dimethyl-amino)pyridin-4-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide or (R) 1-(2-(dimethylamino)pyridin-4-yl)-N-((4-methoxy-6-methyl-2-oxo-1,2-dihydropyridine-3-yl) methyl)-6-methyl-5-(1-(4-(2,2,2-trifluoroethyl)piperazin-1-yl)ethyl)indolizine-7-carboxamide: Compound 170 was Separated by Chiral Preparative Liquid Chromatography to Provide Compound 171 and Compound 172

The separation conditions were: column type IC-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 171: $^1$H NMR (400 MHz, DMSO-d$_6$) δ ppm 8.44 (s, 1H), 8.12 (t, J=4.4 Hz, 1H) 8.06 (d, J=5.2 Hz, 1H), 7.63 (s, 1H), 7.12 (d, J=2.1 Hz, 1H), 6.81 (d, J=5.2 Hz, 1H), 6.73 (s, 1H), 6.18 (s, 1H), 4.25 (brs, 2H), 4.07 (q, J=6.8 Hz, 1H), 3.85 (s, 3H), 3.10 (q, J=9.8 Hz, 2H), 3.02 (s, 6H), 2.63-2.51 (m, 6H), 2.30 (s, 3H), 2.36 (s, 6H), 1.48 (d, J=6.8 Hz, 3H); MS (ESI) m/z 640 [M+H]$^+$; t$_R$=24.811 min.

Compound 172: $^1$H NMR (400 MHz, DMSO-d$_6$) δ ppm 8.44 (s, 1H), 8.12 (t, J=4.4 Hz, 1H) 8.06 (d, J=5.2 Hz, 1H), 7.63 (s, 1H), 7.12 (d, J=2.1 Hz, 1H), 6.81 (d, J=5.2 Hz, 1H), 6.73 (s, 1H), 6.18 (s, 1H), 4.25 (brs, 2H), 4.07 (q, J=6.8 Hz, 1H), 3.85 (s, 3H), 3.10 (q, J=9.8 Hz, 2H), 3.02 (s, 6H), 2.63-2.51 (m, 6H), 2.30 (s, 3H), 2.36 (s, 6H), 1.48 (d, J=6.8 Hz, 3H); MS (ESI) m/z 640 [M+H]$^+$; t$_R$=30.994 min.

Example 168: Preparation of 1-(2-(2,6-dimethylpyridin-4-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Same as Example 159

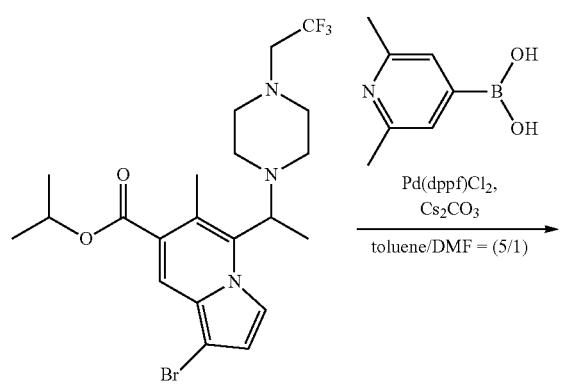

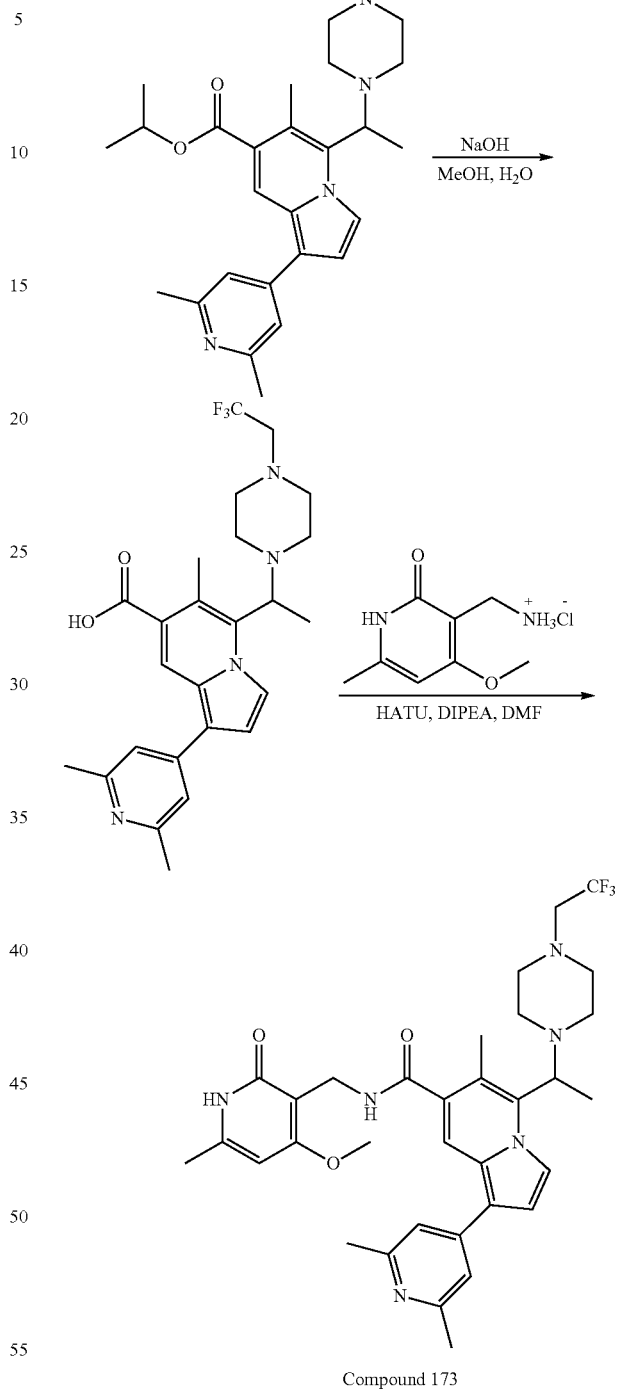

Compound 173

Step 1: Preparation of isopropyl 1-(2-dimethylpyridin-4-yl)-6-methyl-5-(1-(4-(2,2,2-trifluoroethyl)piperazin-1-yl)ethyl)indolizine-7-carboxylate: yield 60%. MS (ESI) m/z 517 [M+H]$^+$.

Step 2: Preparation of 1-(2,6-dimethylpyridin-4-yl)-6-methyl-5-(1-(4-(2,2,2-trifluoroethyl)piperazine-1-yl)ethyl) indolizine-7-carboxylic acid: MS (ESI) m/z 475 [M+H]$^+$.

Step 3: Preparation of 1-(2,6-dimethylpyridin-4-yl)-N-((4-methoxy-6-methyl-2-oxo)-1,2-dihydropyridin-3-yl)

methyl)-6-methyl-5-(1-(4-(2,2,2-trifluoroethyl)piperazin-1-yl)ethyl)indolizine-7-carboxamide: yield of two steps was 6%. ¹H-NMR (MeOD, 400 MHz) δ ppm 8.54 (s, 1H), 7.75 (s, 1H), 7.30 (s, 2H), 7.08 (d, J=2.8 Hz, 1H), 6.26 (s, 1H), 4.45 (brs, 2H), 4.13 (q, J=6.8 Hz, 1H), 3.91 (s, 3H), 3.02 (q, J=9.8 Hz, 2H), 2.78-2.67 (m, 6H), 2.50 (s, 6H), 2.36 (s, 3H), 2.92-2.30 (m, 5H), 1.51 (d, J=6.8 Hz, 3H); MS (ESI) m/z 625 [M+H]⁺.

Example 169: Preparation of (S)-1-(2,6-dimethylpyridin-4-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide or (R) 1-(2,6-dimethylpyridin-4-yl)-N-((4-methoxy-6-methyl-2-oxo-1,2-dihydropyridine-3-yl)methyl)-6-methyl-5-(1-(4-(2,2,2-trifluoroethyl) piperazin-1-yl)ethyl)indolizine-7-carboxamide: Compound 173 was Separated by Chiral Preparative Liquid Chromatography to Provide Compound 174 and Compound 175

The separation conditions were: column type IC-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 174: ¹H-NMR (MeOD, 400 MHz) δ ppm 8.54 (s, 1H), 7.75 (s, 1H), 7.30 (s, 2H), 7.08 (d, J=2.8 Hz, 1H), 6.26 (s, 1H), 4.45 (brs, 2H), 4.13 (q, J=6.8 Hz, 1H), 3.91 (s, 3H), 3.02 (q, J=9.8 Hz, 2H), 2.78-2.67 (m, 6H), 2.50 (s, 6H), 2.36 (s, 3H), 2.92-2.30 (m, 5H), 1.51 (d, J=6.8 Hz, 3H); MS (ESI) m/z 625 [M+H]⁺; $t_R$=9.681 min.

Compound 175: ¹H-NMR (MeOD, 400 MHz) δ ppm 8.54 (s, 1H), 7.75 (s, 1H), 7.30 (s, 2H), 7.08 (d, J=2.8 Hz, 1H), 6.26 (s, 1H), 4.45 (brs, 2H), 4.13 (q, J=6.8 Hz, 1H), 3.91 (s, 3H), 3.02 (q, J=9.8 Hz, 2H), 2.78-2.67 (m, 6H), 2.50 (s, 6H), 2.36 (s, 3H), 2.92-2.30 (m, 5H), 1.51 (d, J=6.8 Hz, 3H); MS (ESI) m/z 625 [M+H]⁺; $t_R$=11.694 min.

Example 170: Preparation of 1-(2-(2,6-dimethylpyridin-3-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Same as Example 159

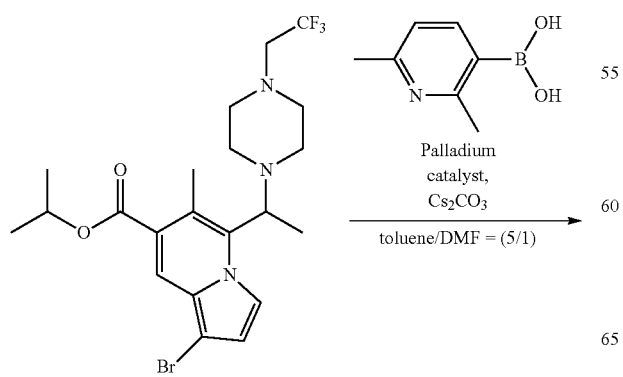

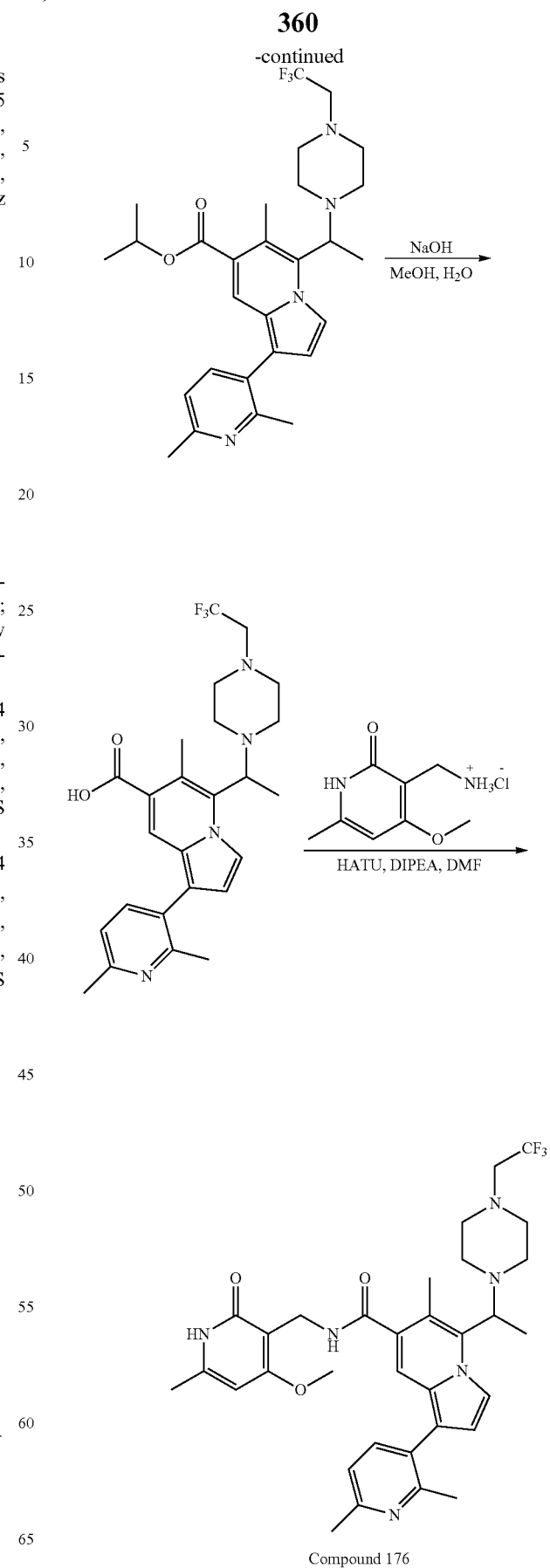

Compound 176

361

-continued

Palladium catalyst = 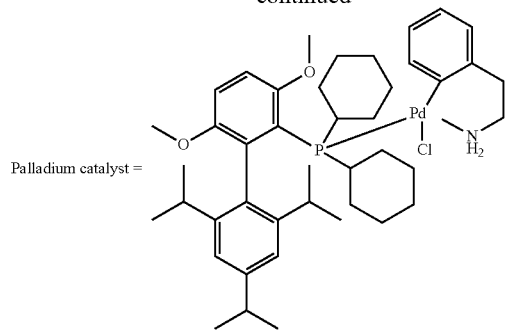

Step 1: Preparation of isopropyl 1-(2-dimethylpyridin-3-yl)-6-methyl-5-(1-(4-(2,2,2-trifluoroethyl)piperazin-1-yl)ethyl)indolizine-7-carboxylate: yield 25%. MS (ESI) m/z 517 [M+H]$^+$.

Step 2: Preparation of 1-(2,6-dimethylpyridin-3-yl)-6-methyl-5-(1-(4-(2,2,2-trifluoroethyl)piperazin-1-yl)ethyl)indolizine-7-carboxylic acid: yield 68%. MS (ESI) m/z 475 [M+H]$^+$.

Step 3: Preparation of 1-(2,6-dimethylpyridin-3-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: yield 18%. $^1$H-NMR (CDCl$_3$, 400 MHz) δ ppm 8.42 (s, 1H), 7.46 (d, J=7.6 Hz, 1H), 7.27-7.26 (m, 2H), 6.97 (d, J=8.0 Hz, 1H), 6.75 (s, 1H), 5.87 (s, 1H), 4.50 (d, J=5.2 Hz, 1H), 4.06 (q, J=6.4 Hz, 1H), 3.85 (s, 3H), 2.95 (q, J=8.8 Hz, 2H), 2.68-2.58 (m, 6H), 2.52 (s, 3H), 2.47 (s, 3H), 2.37-2.31 (m, 5H), 2.10 (s, 3H), 1.50 (d, J=6.4 Hz, 3H); MS (ESI) m/z 625 [M+H]$^+$.

Example 171: Preparation of (S)-1-(2,6-dimethylpyridin-3-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide or (R) 1-(2,6-dimethylpyridin-3-yl)-N-((4-methoxy-6-methyl-2-oxo-1,2-dihydropyridine-3-yl)methyl)-6-methyl-5-(1-(4-(2,2,2-trifluoroethyl)piperazin-1-yl)ethyl)indolizine-7-carboxamide: Compound 176 was Separated by Chiral Preparative Liquid Chromatography to Provide Compound 177 and Compound 178

The separation conditions were: column type IC-H; column size: 0.46 cm ID×15 cm L; injection volume: 2 μL; mobile phase: EtOH (0.1% DEA)=100; flow rate: 0.5 ml/min; detection conditions: UVλ=254 nm; column temperature: 25° C.

Compound 177: $^1$H-NMR (CDCl$_3$, 400 MHz) δ ppm 8.42 (s, 1H), 7.46 (d, J=7.6 Hz, 1H), 7.27-7.26 (m, 2H), 6.97 (d, J=8.0 Hz, 1H), 6.75 (s, 1H), 5.87 (s, 1H), 4.50 (d, J=5.2 Hz, 1H), 4.06 (q, J=6.4 Hz, 1H), 3.85 (s, 3H), 2.95 (q, J=8.8 Hz, 2H), 2.68-2.58 (m, 6H), 2.52 (s, 3H), 2.47 (s, 3H), 2.37-2.31 (m, 5H), 2.10 (s, 3H), 1.50 (d, J=6.4 Hz, 3H); MS (ESI) m/z 625 [M+H]$^+$; t$_R$=12.450 min.

Compound 178: $^1$H-NMR (CDCl$_3$, 400 MHz) δ ppm 8.42 (s, 1H), 7.46 (d, J=7.6 Hz, 1H), 7.27-7.26 (m, 2H), 6.97 (d, J=8.0 Hz, 1H), 6.75 (s, 1H), 5.87 (s, 1H), 4.50 (d, J=5.2 Hz, 1H), 4.06 (q, J=6.4 Hz, 1H), 3.85 (s, 3H), 2.95 (q, J=8.8 Hz, 2H), 2.68-2.58 (m, 6H), 2.52 (s, 3H), 2.47 (s, 3H), 2.37-2.31 (m, 5H), 2.10 (s, 3H), 1.50 (d, J=6.4 Hz, 3H); MS (ESI) m/z 625 [M+H]$^+$; t$_R$=17.820 min.

362

Example 172: Preparation of 1-(2-(dimethylamino)pyridin-3-yl)-N-((4-methoxy-6-methyl-2-oxo-1,2-dihydropyridin-3-yl) methyl)-6-methyl-5-(1-(4-(2,2,2-trifluoroethyl)piperazin-1-yl)ethyl)indolizine-7-carboxamide

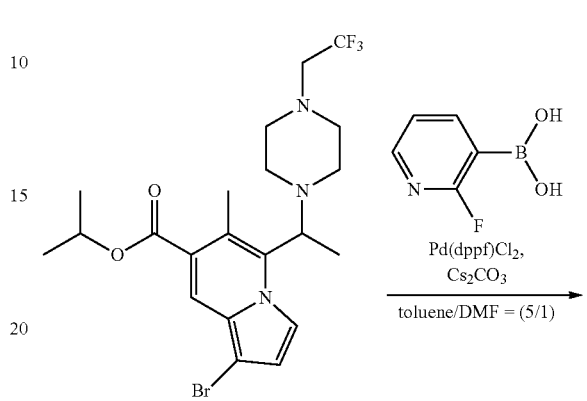

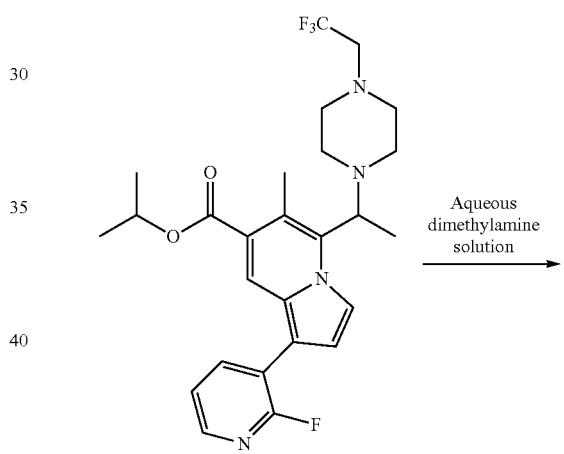

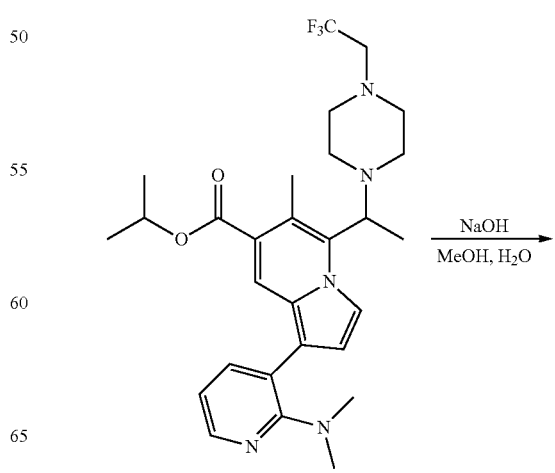

-continued

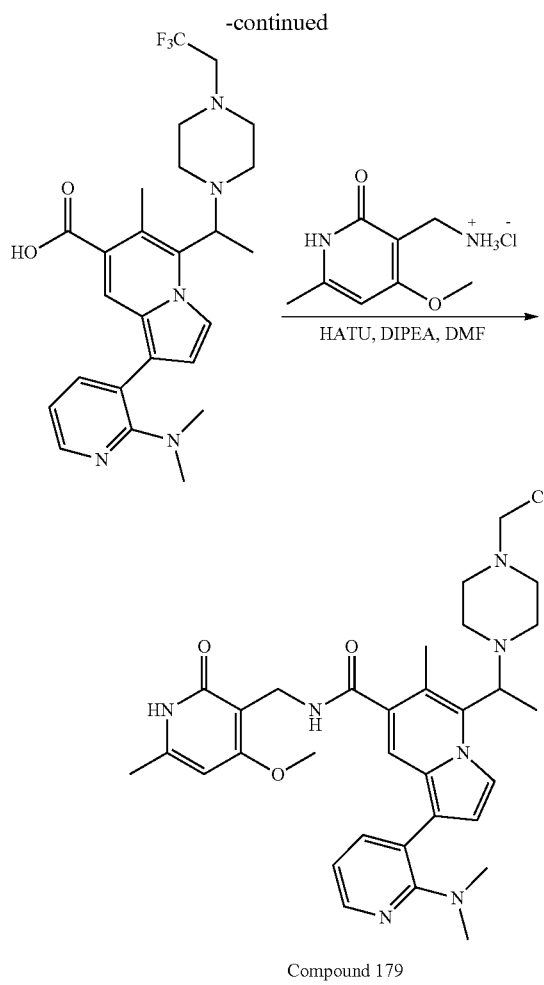

Compound 179

Step 1: Preparation of isopropyl 1-(2-fluoropyridin-3-yl)-6-methyl-5-(1-(4-(2,2,2-trifluoroethyl)piperazin-1-yl)ethyl) indolizine-7-carboxylate: same as step 1 of example 160. Yield was 43%. MS (ESI) m/z 339 [M-C$_6$H$_{11}$F$_3$N$_2$+H]$^+$.

Step 2: Preparation of isopropyl 1-(2-(dimethylamino)pyridin-3-yl)-6-methyl-5-(1-(4-(2,2,2-trifluoroethyl)piperazine-1-yl)ethyl) indolizine-7-carboxylate: In a dry 25 mL sealed tube, compound isopropyl 1-(2-fluoropyridin-3-yl)-6-methyl-5-(1-(4-(2,2,2-trifluoroethyl)piperazin-1-yl)ethyl) indolizine-7-carboxylate (330 mg, 0.59 mmol), dimethylamine aqueous solution (25 ml) was added successively, and dissolved in tetrahydrofuran (5 ml), 85° C. reacted for 2 days. The reaction solution was extracted with dichloromethane (200 mL), washed with water (100 mL×2) and saturated brine (100 mL). The organic layer was dried over anhydrous sodium sulfate, filtered and concentrated to provide a crude product. After purified by column chromatography (dichloromethane:methanol=20:1), yellow oil 280 mg was afforded, yield 81%. MS (ESI) m/z 532 [M+H]$^+$.

Step 3: Preparation of 1-(2-(dimethylamino)pyridine-3-yl)-6-methyl-5-(1-(4-(2,2,2-trifluoroethyl)piperazin-1-yl) ethyl) indolizine-7-carboxylic acid: same as step 2 of example 160. MS (ESI) m/z 490 [M+H]$^+$.

Step 4: Preparation of 1-(2-(dimethylamino)pyridin-3-yl)-N-((4-methoxy-6-methyl-2-oxo-1,2-dihydropyridin-3-yl) methyl)-6-methyl-5-(1-(4-(2,2,2-trifluoroethyl)piperazin-1-yl)ethyl)indolizine-7-carboxamide: same as step 3 of example 160. Yield of two steps was 8%. $^1$H-NMR (CDCl$_3$, 400 MHz) δ ppm 8.45 (s, 1H), 8.08 (d, J=3.2 Hz, 1H), 7.48 (dd, J=7.2, 1.6 Hz, 1H), 7.36 (s, 1H), 7.18 (t, J=7.2 Hz, 1H), 6.85 (d, J=2.8 Hz, 1H), 6.74 (dd, J=7.2, 2.4 Hz, 1H), 5.87 (s, 1H), 4.52 (d, J=5.2 Hz, 2H), 4.05 (q, J=6.4 Hz, 1H), 3.86 (s, 3H), 2.95 (q, J=9.6 Hz, 2H), 2.68-2.66 (m, 6H), 2.64 (s, 6H), 2.35 (s, 3H), 2.32-2.29 (m, 2H), 2.15 (s, 3H), 1.50 (d, J=6.4 Hz, 3H); MS (ESI) m/z 640 [M+H]$^+$.

Example 173: Preparation of N-((4-methoxy-6-methyl-2-oxo-1,2-dihydropyridin-3-yl)methyl)-6-methyl-1-(2-(methylamino)pyridin-4-yl)-5-(1-(4-(2,2,2-trifluoroethyl)piperazin-1-yl)ethyl)indolizine-7-carboxamide: Same as Example 172

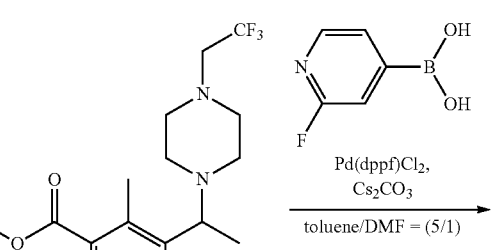

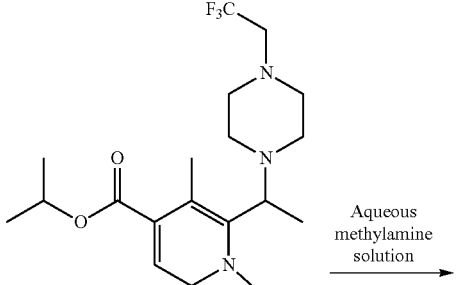

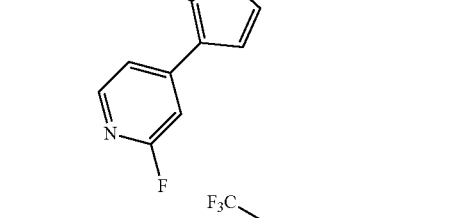

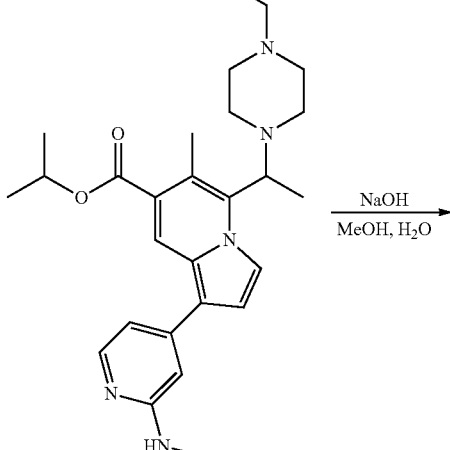

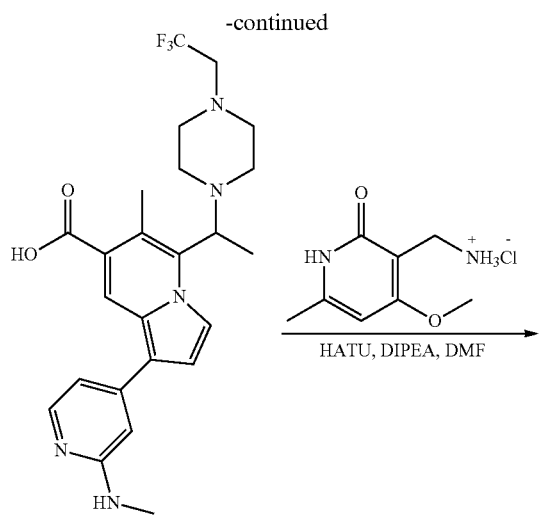

Compound 180

Step 1: Preparation of isopropyl 1-(2-fluoropyridin-4-yl)-6-methyl-5-(1-(4-(2,2,2-trifluoroethyl)piperazin-1-yl)ethyl)indolizine-7-carboxylate: yield 65%. MS (ESI) m/z 507 [M+H]$^+$.

Step 2: Preparation of isopropyl 6-methyl-1-(2-(methylamino)pyridin-4-yl)-5-(1-(4-(2,2,2-trifluoroethyl)piperazin-1-yl)ethyl) indolizine-7-carboxylate: yield 39%. MS (ESI) m/z 518 [M+H]$^+$.

Step 3: Preparation of 6-methyl-1-(2-(methylamino)pyridin-4-yl)-5-(1-(4-(2,2,2-trifluoroethyl)piperazin-1-yl)ethyl)indolizine-7-carboxylic acid: yield 63%. MS (ESI) m/z 476 [M+H]$^+$.

Step 4: Preparation of N-((4-methoxy-6-methyl-2-oxo-1,2-dihydropyridin-3-yl)methyl)-6-methyl-1-(2-(methylamino)pyridin-4-yl)-5-(1-(4-(2,2,2-trifluoroethyl)piperazin-1-yl)ethyl)indolizine-7-carboxamide: yield 15%. $^1$H-NMR (MeOD, 400 MHz) δ ppm 8.55 (brs, 1H), 7.86 (d, J=4.8 Hz, 1H), 7.76 (s, 1H), 7.05 (d, J=3.2 Hz, 1H), 6.88 (d, J=5.6 Hz, 1H), 6.80 (s, 1H), 6.25 (s, 1H), 4.57 (s, 2H), 4.44 (s, 2H), 4.14 (q, J=6.4 Hz, 1H), 3.95 (s, 3H), 3.13 (q, J=9.6 Hz, 2H), 2.98 (s, 3H), 2.68-2.64 (m, 6H), 2.35 (s, 3H), 2.34-2.32 (m, 6H), 1.50 (d, J=6.4 Hz, 3H); MS (ESI) m/z 626 [M+H]$^+$.

Example 174: Preparation of (S)—N-((4-methoxy-6-methyl-2-oxo-1,2-dihydropyridin-3-yl)methyl)-6-methyl-1-(2-(methylamino)pyridin-4-yl)-5-(1-(4-(2,2,2-trifluoroethyl)piperazin-1-yl)ethyl)indolizine-7-formamide or (R)—N-((4-methoxy-6-methyl-2-oxo-1,2-dihydropyridin-3-yl)methyl)-6-methyl-1-(2-(methylamino)pyridin-4-yl)-5-(1-(4-(2,2,2-trifluoroethyl)piperazin-1-yl)ethyl)indolizine-7-formamide: Compound 180 was Separated by Chiral Preparative Liquid Chromatography to Provide Compound 181 and Compound 182

The separation conditions were: column type: AD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C. Compound 181: $^1$H-NMR (CDCl$_3$, 400 MHz) δ ppm 8.44 (s, 1H), 7.39 (d, J=4.4 Hz, 1H), 7.59 (d, J=7.2 Hz, 2H), 7.28 (s, 1H), 7.19 (s, 1H), 7.14 (t, J=4.8 Hz, 1H), 6.78 (s, 1H), 5.88 (s, 1H), 4.50 (d, J=4.0 Hz, 1H), 4.07 (q, J=6.8 Hz, 1H), 3.86 (s, 3H), 2.96 (q, J=9.6 Hz, 2H), 2.75-2.66 (m, 6H), 2.52 (s, 3H), 2.37-2.31 (m, 5H), 2.14 (s, 3H), 1.51 (d, J=6.4 Hz, 3H); MS (ESI) m/z 626 [M+H]$^+$; MS (ESI) m/z 626 [M+H]$^+$; t$_R$=10.432 min. Compound 182: $^1$H-NMR (CDCl$_3$, 400 MHz) δ ppm 8.44 (s, 1H), 7.39 (d, J=4.4 Hz, 1 H), 7.59 (d, J=7.2 Hz, 2H), 7.28 (s, 1H), 7.19 (s, 1H), 7.14 (t, J=4.8 Hz, 1H), 6.78 (s, 1H), 5.88 (s, 1H), 4.50 (d, J=4.0 Hz, 1H), 4.07 (q, J=6.8 Hz, 1H), 3.86 (s, 3H), 2.96 (q, J=9.6 Hz, 2H), 2.75-2.66 (m, 6H), 2.52 (s, 3H), 2.37-2.31 (m, 5H), 2.14 (s, 3H), 1.51 (d, J=6.4 Hz, 3H); MS (ESI) m/z 626 [M+H]$^+$; t$_R$=17.440 min.

Example 175: Preparation of N-((4-methoxy-6-methyl-2-oxo-1,2-dihydropyridin-3-yl)methyl)-6-methyl-1-(1-methyl-1H-1,2,4-triazol-5-yl)-5-(1-(4-(2,2,2-trifluoroethyl)piperazin-1-yl)ethyl)indolizine-7-carboxamide: Similar to Example 50

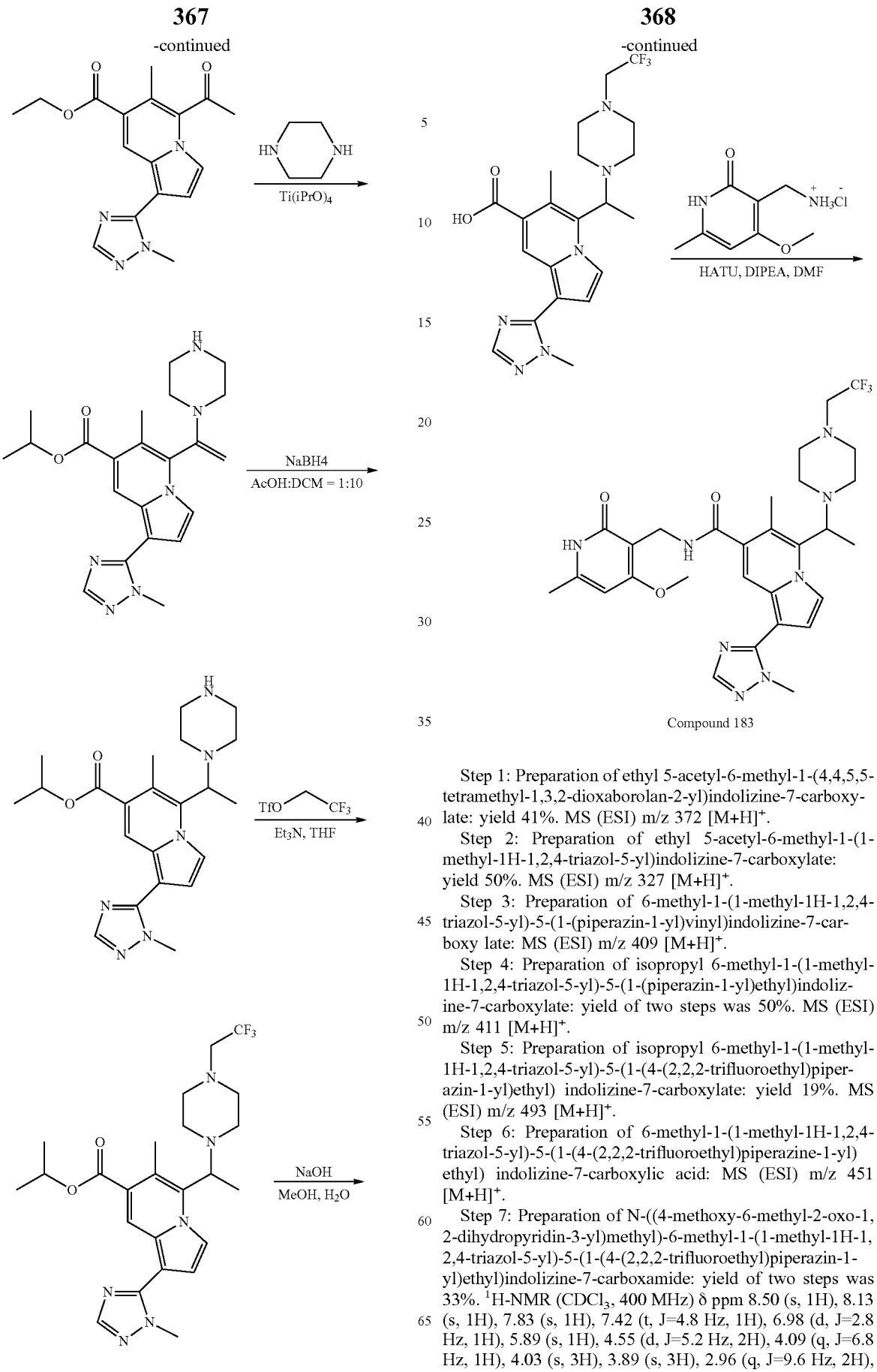

Step 1: Preparation of ethyl 5-acetyl-6-methyl-1-(4,4,5,5-tetramethyl-1,3,2-dioxaborolan-2-yl)indolizine-7-carboxylate: yield 41%. MS (ESI) m/z 372 [M+H]⁺.

Step 2: Preparation of ethyl 5-acetyl-6-methyl-1-(1-methyl-1H-1,2,4-triazol-5-yl)indolizine-7-carboxylate: yield 50%. MS (ESI) m/z 327 [M+H]⁺.

Step 3: Preparation of 6-methyl-1-(1-methyl-1H-1,2,4-triazol-5-yl)-5-(1-(piperazin-1-yl)vinyl)indolizine-7-carboxylate: MS (ESI) m/z 409 [M+H]⁺.

Step 4: Preparation of isopropyl 6-methyl-1-(1-methyl-1H-1,2,4-triazol-5-yl)-5-(1-(piperazin-1-yl)ethyl)indolizine-7-carboxylate: yield of two steps was 50%. MS (ESI) m/z 411 [M+H]⁺.

Step 5: Preparation of isopropyl 6-methyl-1-(1-methyl-1H-1,2,4-triazol-5-yl)-5-(1-(4-(2,2,2-trifluoroethyl)piperazin-1-yl)ethyl) indolizine-7-carboxylate: yield 19%. MS (ESI) m/z 493 [M+H]⁺.

Step 6: Preparation of 6-methyl-1-(1-methyl-1H-1,2,4-triazol-5-yl)-5-(1-(4-(2,2,2-trifluoroethyl)piperazine-1-yl) ethyl) indolizine-7-carboxylic acid: MS (ESI) m/z 451 [M+H]⁺.

Step 7: Preparation of N-((4-methoxy-6-methyl-2-oxo-1,2-dihydropyridin-3-yl)methyl)-6-methyl-1-(1-methyl-1H-1,2,4-triazol-5-yl)-5-(1-(4-(2,2,2-trifluoroethyl)piperazin-1-yl)ethyl)indolizine-7-carboxamide: yield of two steps was 33%. ¹H-NMR (CDCl₃, 400 MHz) δ ppm 8.50 (s, 1H), 8.13 (s, 1H), 7.83 (s, 1H), 7.42 (t, J=4.8 Hz, 1H), 6.98 (d, J=2.8 Hz, 1H), 5.89 (s, 1H), 4.55 (d, J=5.2 Hz, 2H), 4.09 (q, J=6.8 Hz, 1H), 4.03 (s, 3H), 3.89 (s, 3H), 2.96 (q, J=9.6 Hz, 2H), 2.68-2.64 (m, 6H), 2.38 (s, 3H), 2.31-2.29 (m, 2H), 2.21 (s, 3H), 1.50 (d, J=6.8 Hz, 3 H); MS (ESI) m/z 601 [M+Na]$^+$.

Example 176: Preparation of 1-(6-aminopyridin-3-yl)-N-((2,6-dimethyl-4-oxo-1,4-dihydropyridin-3-yl)methyl)-6-methyl-5-(1-(4-(2,2,2-trifluoroethyl)piperazin-1-yl)ethyl)indolizine-7-carboxamide: Procedures are the Same as in Example 108. The Desired 3-(aminomethyl)-2,6-lutidine-4(1H)-one hydrochloride was Synthesized as Described in Reference (WO2015200650)

Example 177: Preparation of 1-(6-aminopyridin-3-yl)-6-methyl-N-((6-methyl-2-oxo-4-propyl-1,2-dihydropyridine-3-yl)-5-(1-(4-(2,2,2-trifluoroethyl)piperazin-1-yl)ethyl)indolizine-7-carboxamide: procedure was similar to example 108. The desired 3-(aminomethyl)-6-methyl-4-lutidine-2(1H)-one hydrochloride was Synthesized as Described in Reference (WO2014177982)

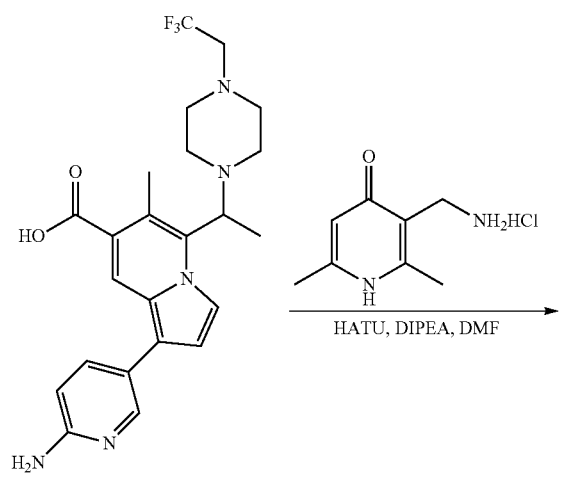

Compound 184

Compound 185

Step 1: Preparation of 1-(6-aminopyridin-3-yl)-N-((2,6-dimethyl-4-oxo-1,4-dihydropyridin-3-yl)methyl)-6-methyl-5-(1-(4-(2,2,2-trifluoroethyl)piperazin-1-yl)ethyl)indolizine-7-carboxamide: yield 12%. $^1$H NMR (400 MHz, CDCl$_3$) ppm 8.41 (s, 1H), 8.10 (s, 1H), 7.65 (s, 1H), 7.56 (d, J=4.0 Hz, 1H), 7.45 (s, 1H), 6.75 (s, 1H), 6.59 (d, J=4.2 Hz, 1H), 6.08 (s, 1H), 4.43 (s, 2H), 4.02 (q, J=6.8 Hz, 1H), 2.95 (q, J=9.6 Hz, 2H), 2.66 (brs, 6H), 2.47 (s, 3H), 2.30 (brs, 5H), 2.16 (s, 3H), 1.46 (d, J=6.4 Hz, 3H); MS (ESI) m/z 618 [M+Na]$^+$.

Step 1: Preparation of 1-(6-aminopyridin-3-yl)-6-methyl-N-((6-methyl-2-oxo-4-propyl-1,2-dihydropyridine-3-yl)methyl)-5-(1-(4-(2,2,2-trifluoroethyl)piperazin-1-yl)ethyl)indolizine-7-carboxamide: yield 27%. $^1$H NMR (400 MHz, DMSO-d$_6$) δ ppm 11.46 (brs, 1H), 8.36 (s, 1H), 8.25 (t, J=2.0 Hz, 2H), 8.14 (s, 1H), 7.58 (d, J=2.0 Hz, 1H), 7.42 (s, 1H), 6.86 (d, J=2.4 Hz, 1H), 6.50 (d, J=5.6 Hz, 1H), 5.88 (s, 1H), 5.81 (s, 2H), 4.26 (d, J=4.8 Hz, 2H), 4.03 (q, J=6.8 Hz, 1H), 3.14 (q, J=9.6 Hz, 2H), 2.66-2.62 (m, 6H), 2.25 (s, 3H), 2.21-2.11 (m, 5H), 1.46 (q, J=8.0 Hz, 2H), 1.42 (d, J=6.8 Hz, 3H), 0.89 (t, J=8.0 Hz, 3H); MS (ESI) m/z 624 [M+H]$^+$.

Example 178: Preparation of 1-(6-aminopyridin-3-yl)-6-methyl-N-((6-methyl-2-oxo-4-(trifluoromethyl)-1,2-dihydropyridine-3-yl)-5-(1-(4-(2,2,2-trifluoroethyl)piperazin-1-yl)ethyl)indolizine-7-carboxamide: procedure was similar to example 108. The desired 3-(aminomethyl)-6-methyl-4-(trifluoromethyl)pyridin-2(1H)-one hydrochloride was Synthesized as Described in WO2014177982

Example 179: Preparation of 1-(6-aminopyridin-3-yl)-N-((5-methoxy-1-methyl-3-oxo-2,3-dihydro-1H-pyrazole-4-yl)methyl)-6-methyl-5-(1-(4-(2,2,2-trifluoroethyl)piperazin-1-yl)ethyl)indolizine-7-carboxamide: the Procedure was the Same as Example 108. The Desired 4-(aminomethyl)-5-methoxy-1-methyl-1H-pyrazole-3(1H)-one hydrochloride was Synthesized as Described in Reference (WO2015010049)

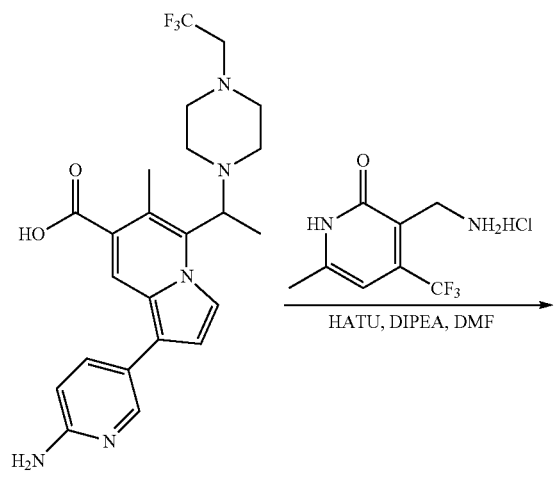

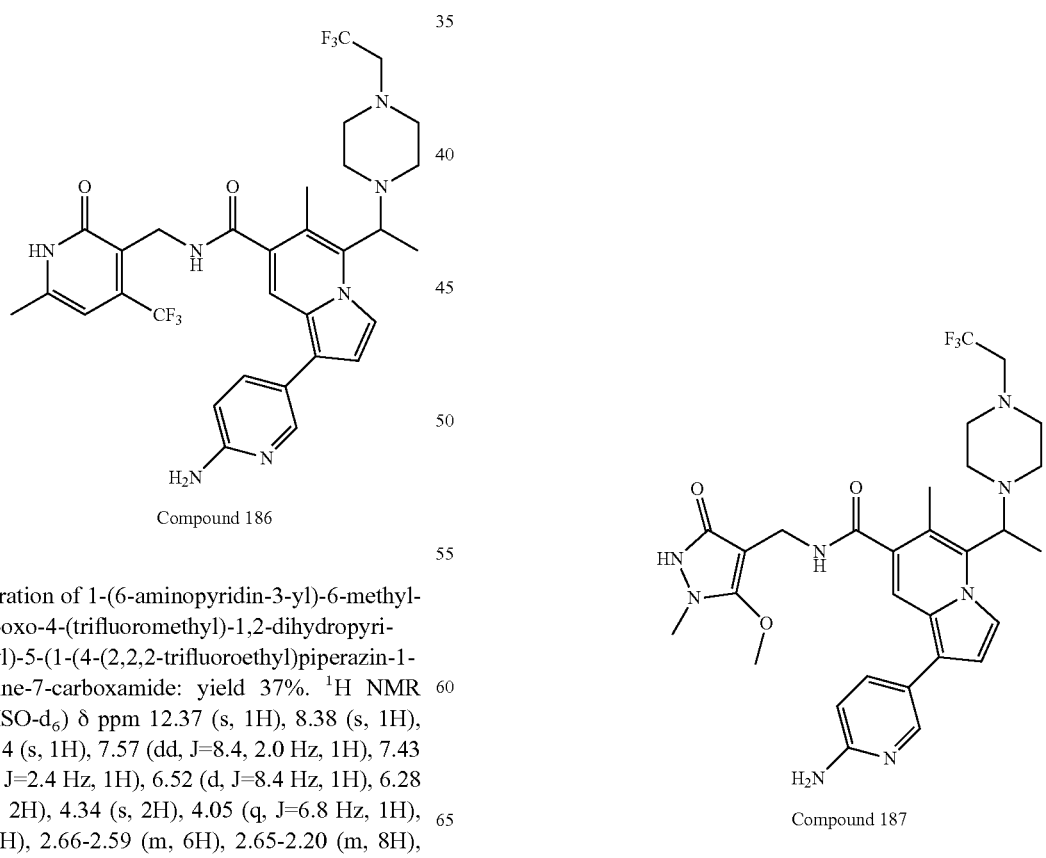

Compound 186

Step 1: Preparation of 1-(6-aminopyridin-3-yl)-6-methyl-N-((6-methyl-2-oxo-4-(trifluoromethyl)-1,2-dihydropyridine-3-yl)methyl)-5-(1-(4-(2,2,2-trifluoroethyl)piperazin-1-yl)ethyl)indolizine-7-carboxamide: yield 37%. $^1$H NMR (400 MHz, DMSO-$d_6$) δ ppm 12.37 (s, 1H), 8.38 (s, 1H), 8.29 (s, 1H), 8.14 (s, 1H), 7.57 (dd, J=8.4, 2.0 Hz, 1H), 7.43 (s, 1H), 6.89 (d, J=2.4 Hz, 1H), 6.52 (d, J=8.4 Hz, 1H), 6.28 (s, 1H), 5.85 (s, 2H), 4.34 (s, 2H), 4.05 (q, J=6.8 Hz, 1H), 3.17-3.11 (m, 2H), 2.66-2.59 (m, 6H), 2.65-2.20 (m, 8H), 1.43 (d, J=6.8 Hz, 3H); MS (ESI) m/z 650 [M+H]$^+$.

Compound 187

Step 1: Preparation of 1-(6-aminopyridin-3-yl)-N-((5-methoxy-1-methyl-3-oxo-2,3-dihydro-1H-pyrazole-4-yl)methyl)-6-methyl-5-(1-(4-(2,2,2-trifluoroethyl)piperazin-1-yl)ethyl)indolizine-7-carboxamide: yield 19%. ¹H NMR (400 MHz, MeOD) δ ppm 8.49 (s, 1H), 8.08 (s, 1H), 7.70 (dd, J=8.4, 2.4 Hz, 1H), 7.55 (s, 1H), 6.85 (d, J=2.8 Hz, 1H), 6.67 (d, J=8.4 Hz, 1H), 4.58 (s, 1H), 4.27 (s, 2H), 4.09 (q, J=6.8 Hz, 1H), 4.04 (s, 3H), 3.31 (s, 3H), 3.05 (q, J=7.2 Hz, 1H), 3.06-3.01 (m, 6H), 2.67-2.33 (m, 5H), 1.50 (d, J=6.8 Hz, 3H); MS (ESI) m/z 600 [M+H]⁺.

Example 180: Preparation of 1-(6-aminopyridin-3-yl)-N-((7-isobutyl-1-methyl-3-oxo-2,3,5,6,7,8-hexahydro-2,7-naphthyridin-4-yl)methyl)-6-methyl-5-(1-(4-(2,2,2-trifluoroethyl)piperazin-1-yl)ethyl)indolizine-7-carboxamide: the Procedure was the Same as Example 108. The Desired 4-(aminomethyl)-7-isobutyl-1-methyl-5,6,7,8-tetrahydro-2,7-naphthyridin-3(2H)-one hydrochloride was Synthesized as Described in Reference (WO2015110999)

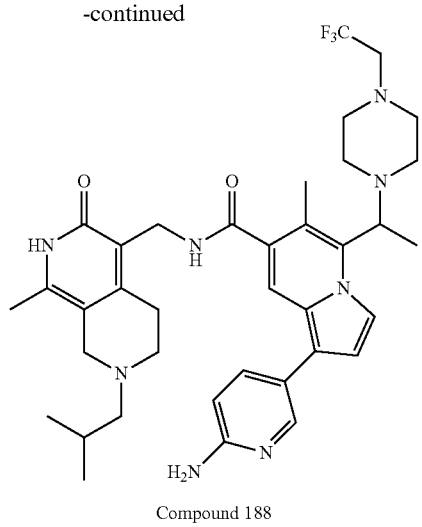

Compound 188

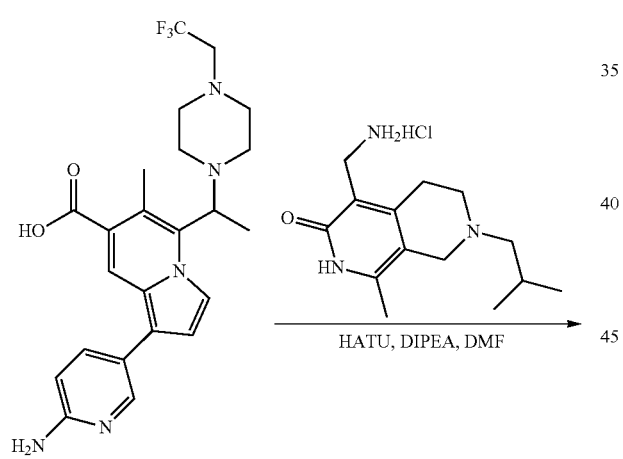

Step 1: Preparation of 1-(6-aminopyridin-3-yl)-N-((7-isobutyl-1-methyl-3-oxo-2,3,5,6,7,8-hexahydro-2,7-naphthyridin-4-yl)methyl)-6-methyl-5-(1-(4-(2,2,2-trifluoroethyl)piperazin-1-yl)ethyl)indolizine-7-carboxamide: yield 20%. ¹H NMR (400 MHz, DMSO-d₆) δ ppm 11.54 (brs, 1H), 8.38 (s, 1H), 8.29 (t, J=4.8 Hz, 1H), 8.15 (d, J=2.4 Hz, 1H), 7.60 (d, J=2.4 Hz, 1H), 7.43 (s, 1H), 6.88 (d, J=2.8 Hz, 1H), 6.52 (d, J=8.8 Hz, 1H), 5.84 (s, 2H), 4.26 (d, J=4.8 Hz, 2H), 4.04 (q, J=6.8 Hz, 1H), 3.21-3.10 (m, 6H), 2.83 (t, J=5.6 Hz, 2H), 2.67-2.62 (m, 6H), 2.26 (s, 3H), 2.18 (d, J=7.6 Hz, 4H), 2.09 (s, 3H), 1.86 (sept, J=6.8 Hz, 1H), 1.43 (d, J=6.8 Hz, 3H), 0.87 (d, J=6.8 Hz, 6H); MS (ESI) m/z 715 [M+Na]⁺.

Example 181: Preparation of 1-(6-(4-aminopiperidin-1-yl)pyridine-3-yl)-6-methyl-N-((1-methyl-3-oxo-2,3-dihydrogenisoquinolin-4-yl)methyl)-5-(1-(4-(2,2,2-trifluoroethyl)piperazin-1-yl)ethyl)indolizine-7-carboxamide: the Procedure was Similar to Example 156. The Desired tert-butyl (1-(5-(4,4,5,5-tetramethyl-1,3,2-dioxaborolan-2-yl)pyridin-2-yl)piperidine-4-yl)carbamate was Synthesized as Described in Reference (WO2008090181), and Synthesis of 4-(aminomethyl)-1-methylisoquinoline-3(2H)-one hydrochloride was Synthesized as Described in WO2015077193

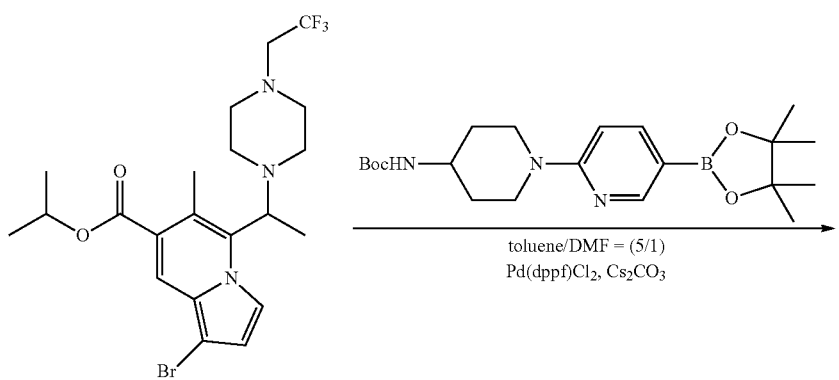

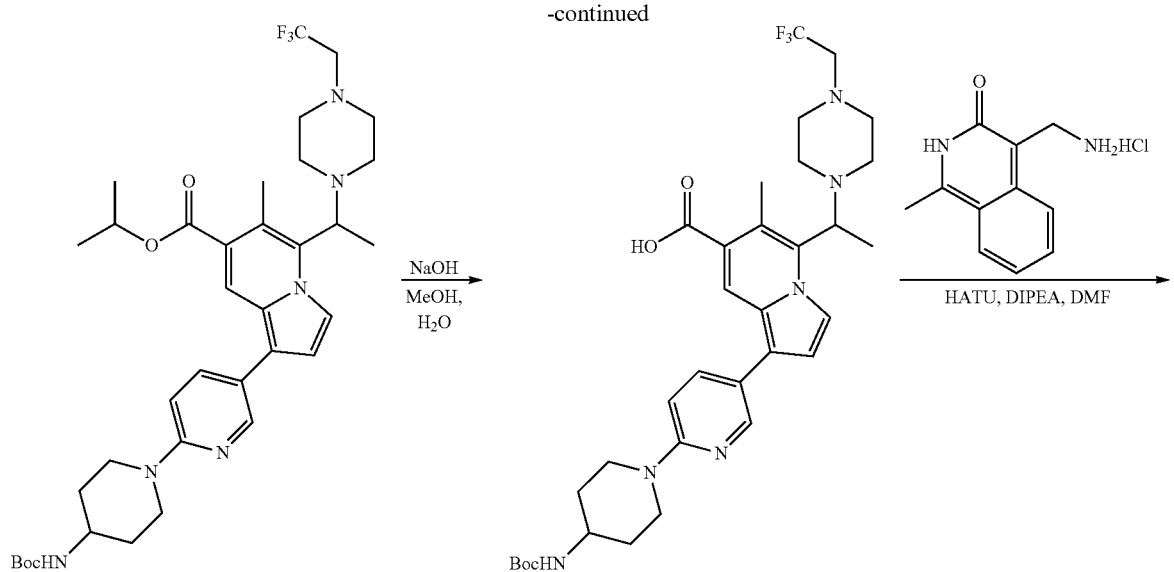

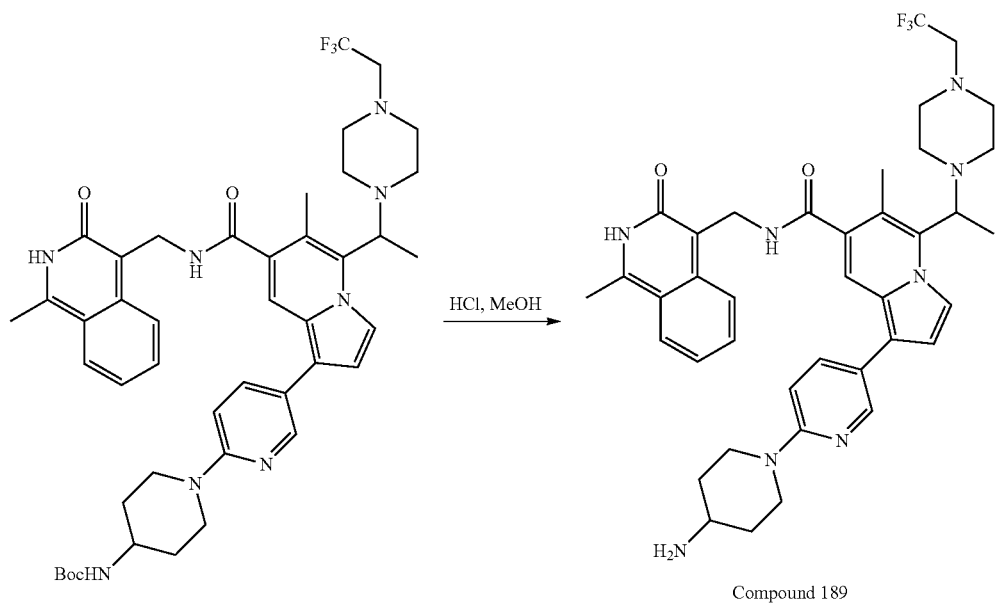

Compound 189

Step 1: Preparation of isopropyl 1-(6-(4-((tert-butoxycarbonyl)amino)piperidin-1-yl)pyridin-3-yl)-6-methyl-5-(1-(4-(2,2,2-trifluoroethyl)piperazin-1-yl)ethyl)indolizine-7-carboxylate: Yield 25%. MS (ESI) m/z 687 [M+H]⁺.

Step 4: Preparation of 1-(1-(6-(4-((tert-butoxycarbonyl)amino)piperidin-1-yl)pyridin-3-yl)-6-methyl-5-(1-(4-(2,2,2-trifluoroethyl)piperazin-1-yl)ethyl)indolizine-7-carboxylic acid: yield 77%. MS (ESI) m/z 645 [M+H]⁺.

Step 3: Tert-butyl (1-(5-(6-methyl-3-oxo-2,3-dihydroisoquinolin-4-yl)methyl)carbamoyl)-5-(1-(4-(2,2,2-trifluoroethyl)piperazin-1-yl)ethyl)indolizine-1-yl)pyridin-2-yl)piperidin-4-yl)carbamate: MS (ESI) m/z 815 [M+H]⁺.

Step 4: Preparation 1-(6-(4-aminopiperidin-1-yl)pyridine-3-yl)-6-methyl-N-((1-methyl-3-oxo-2,3-dihydroisoquinolin-4-yl)methyl)-5-(1-(4-(2,2,2-trifluoroethyl)piperazin-1-yl)ethyl)indolizine-7-carboxamide: yield of two steps was 18%. $^1$H-NMR (MeOD, 400 MHz) δ ppm 8.52-8.39 (m, 4H), 8.26 (s, 1H), 8.14-8.10 (m, 1H), 7.98 (s, 1H), 7.79-7.75 (m, 1H), 7.58-7.56 (m, 1H), 7.25 (s, 1H), 5.00 (s, 2H), 4.42-4.38 (m, 2H), 3.47-3.44 (m, 2H), 3.41-3.31 (m, 4H), 2.30-2.29 (m, 2H), 3.24-3.21 (m, 2H), 2.97-2.94 (m, 4H), 2.89-2.87 (m, 1H), 2.46 (s, 3H), 2.31-2.25 (m, 3H), 1.93-1.87 (m, 2H), 1.84-1.82 (m, 3H); MS (ESI) m/z 715 [M+H]⁺.

Example 182: Preparation of N-((4,6-dimethyl-2-oxo-1,2-dihydropyridin-3-yl)methyl)-6-methyl-1-(1-(tetrahydro-2H-pyran-4-yl)-1H-pyrazol-4-yl)-5-(1-(4-(2,2,2-trifluoroethyl)piperazin-1-yl)ethyl)indolizine-7-carboxamide: Similar to Example 83
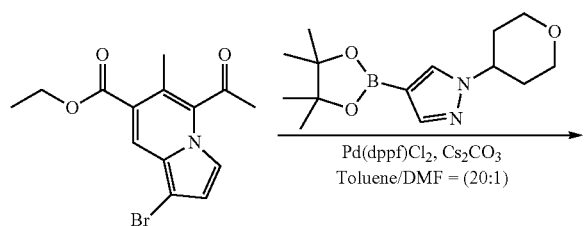
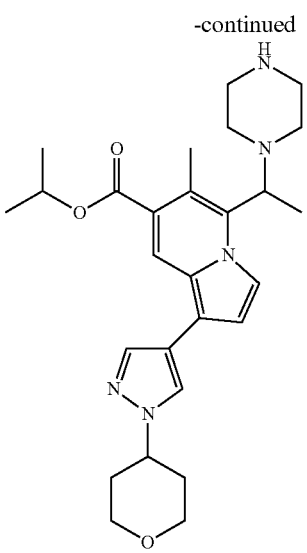
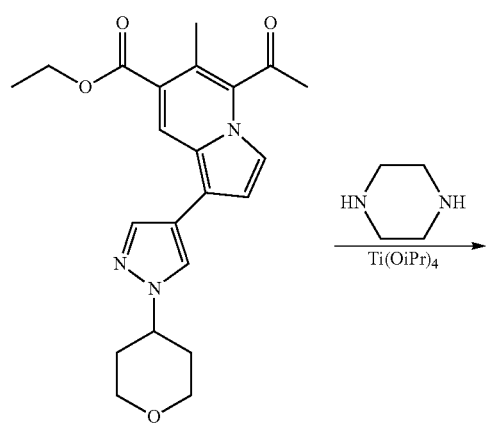
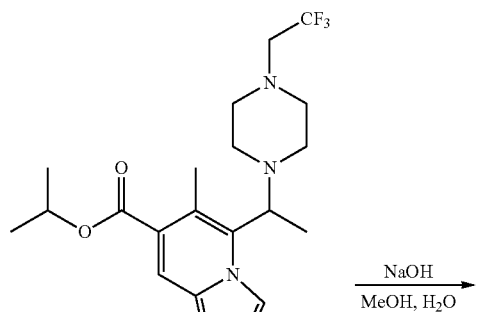
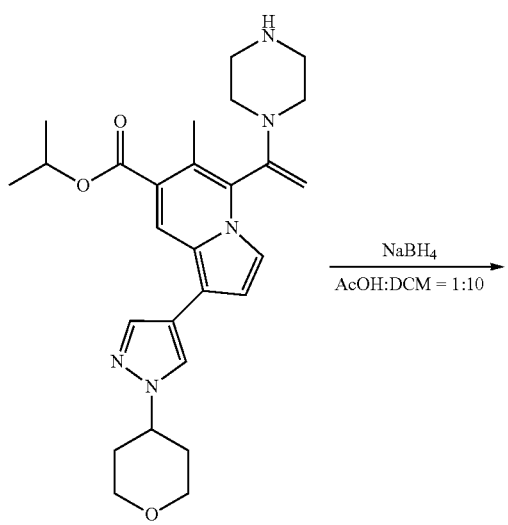
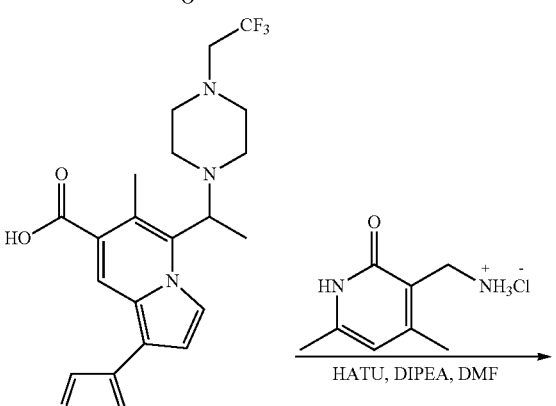

379

-continued

Compound 190

Step 1: Preparation ethyl 5-acetyl-6-methyl-1-(1-(tetrahydro-2H-pyran-4-yl)-1H-pyrazol-4-yl)indolizine-7-carboxylate: yield 27%. MS (ESI) m/z 396 [M+H]⁺.

Step 2: Preparation of isopropyl 6-methyl-5-(1-(piperazin-1-yl)vinyl)-1-(1-(tetrahydro-2H-pyran-4-yl)-1H-pyrazol-4-yl)indolizine-7-carboxylate: MS (ESI) m/z 478 [M+H]⁺.

Step 3: Preparation of isopropyl 6-methyl-5-(1-(piperazin-1-yl)ethyl)-1-(1-(tetrahydro-2H-pyran-4-yl)-1H-pyrazol-4-yl)indolizine-7-carboxylate: MS (ESI) m/z 480 [M+H]⁺.

Step 4: Preparation of isopropyl 6-methyl-1-(1-(tetrahydro-2H-pyran-4-yl)-1H-pyrazol-4-yl)-5-(1-(4-(2,2,2-trifluoroethyl)piperazin-1-yl)ethyl)indolizine-7-carboxylate: yield of three steps was 37%. MS (ESI) m/z 562 [M+H]⁺.

Step 5: Preparation of 6-methyl-1-(1-(tetrahydro-2H-pyran-4-yl)-1H-pyrazol-4-yl)-5-(1-(4-(2,2,2-trifluoroethyl)piperazin-1-yl)ethyl)indolizine-7-carboxylic acid: MS (ESI) m/z 520 [M+H]⁺.

Step 6: Preparation of N-((4,6-dimethyl-2-oxo-1,2-dihydropyridin-3-yl)methyl)-6-methyl-1-(1-(tetrahydro-2H-pyran-4-yl)-1H-pyrazol-4-yl)-5-(1-(4-(2,2,2-trifluoroethyl)piperazin-1-yl)ethyl)indolizine-7-carb oxamide: yield of two steps was 43%. ¹H-NMR (MeOD, 400 MHz) δ ppm 8.46 (s, 1H), 7.95 (s, 1H), 7.76 (s, 1H), 7.57 (s, 1H), 6.85 (d, J=2.4 Hz, 1H), 6.11 (s, 1H), 4.46-4.45 (m, 3H), 4.11-4.09 (m, 3H), 3.61 (d, J=10.8 Hz, 2H), 3.02 (q, J=6.8 Hz, 2H), 2.72-2.67 (m, 6H), 2.37 (s, 3H), 2.31 (s, 3H). 2.28-2.24 (m, 5H), 2.16-2.09 (m, 4H), 1.42 (d, J=6.8 Hz, 3H); MS (ESI) m/z 654 [M+H]⁺.

380

Example 183: Preparation of N-((4-methoxy-6-methyl-2-oxo-1,2-dihydropyridin-3-yl)methyl)-6-methyl-1-(1H-pyrazol-5-yl)-5-(1-(thiazol-2-yl-methoxy)ethyl)indolizine-7-carboxamide

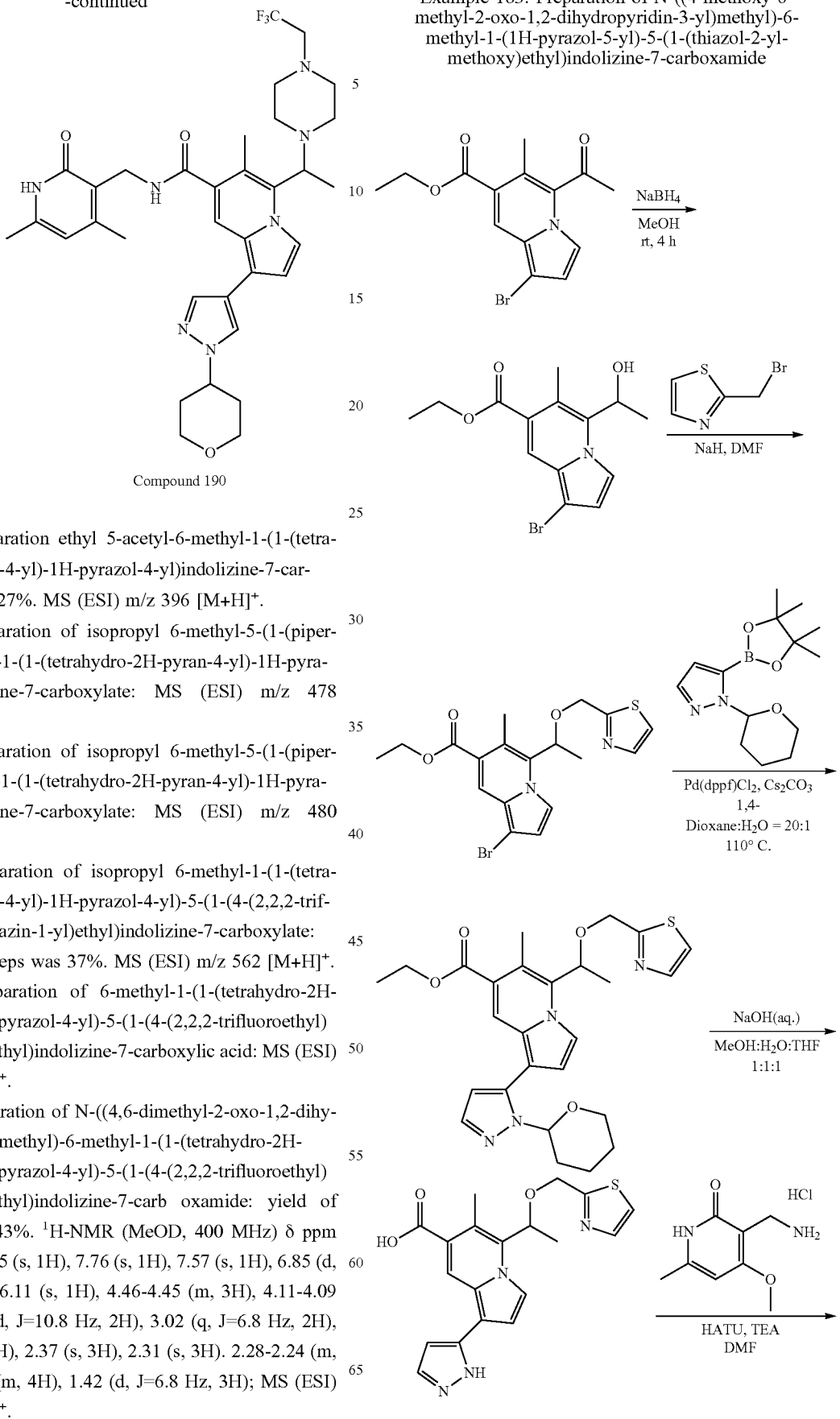

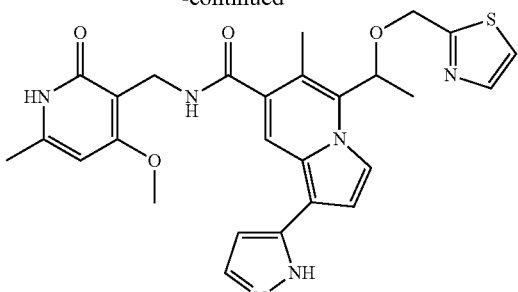

Compound 191

Step 1: Preparation of ethyl 1-bromo-5-(1-hydroxyethyl)-6-methylindolizine-7-carboxylate: compound ethyl 5-acetyl-1-bromo-6-methylindolizine-7-carboxylate (600 mg, 1.86 mmol) and 10 mL of methanol were added into a dry nitrogen-protected 50 mL single-necked flask, cooled to 0° C., and then sodium borohydride (1054 mg, 27.86 mmol) was added portionwise. The reaction was stirred at room temperature for 2 hours, and then the mixture was extracted with ethyl acetate (50 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=20:1), yellow solids (478 mg, yield: 79%) were obtained. MS (ESI) m/z 396 [M+H]$^+$.

Step 2: Preparation of ethyl 1-bromo-6-methyl-5-(1-(thiazol-2-ylmethoxy)ethyl)indolizine-7-carboxylate: in a 25 mL nitrogen-protected single-necked flask, compound ethyl 1-bromo-5-(1-hydroxyethyl)-6-methylindolizine-7-carboxylate (478 mg, 1.47 mmol) and sodium hydride (53 mg, 2.21 mmol) were added successively, and dissolved in 3 mL DMF. The mixture was stirred for 15 minutes in an ice bath, then 2-bromomethylthiazole (312 mg, 1.476 mmol) was added, and stirred at room temperature for 4 hr. The reaction was quenched with aqueous ammonia, extracted with ethyl acetate (50 mL), washed with water (50 mL×2) and saturated brine (50 mL), and organic phase was dried over anhydrous sodium sulfate. The organic phase was dried over anhydrous sodium sulfate, filtered and concentrated to provide a crude product. After purified by column chromatography (petroleum ether:EtOAc=10:1), yellow solids (480 mg, yield: 77%) were obtained. MS (ESI) m/z 423 [M+H]$^+$.

Step 3: Preparation of ethyl 6-methyl-1-(1-(tetrahydro-2H-pyran-2-yl)-1H-pyrazol-5-yl)-5-(1-(thiazol-2-ylmethoxy)ethyl) indolizine-7-carboxylate: In a dry nitrogen-protected 100 mL single-mouth flask, compound ethyl 1-bromo-6-methyl-5-(1-(thiazol-2-ylmethoxy)ethyl)indolizine-7-carboxylate (480 mg, 1.13 mmol), 1-(tetrahydro-2H-pyran-2-yl)-5-(4,4,5,5-tetramethyl-1,3,2-dioxoborolan-2-yl)-1H-pyrazole (630 mg, 2.27 mmol), [2-(dicyclohexylphosphino)-3,6-methoxy-2',4',6'-triisopropyl-1,1'-biphenyl][2-(2-aminoethyl) benzene]palladium chloride (45 mg, 0.057 mmol), Cs$_2$CO$_3$ (738 mg, 2.27 mmol) were added to 6 mL of toluene:DMF=10:1. The flask was exchanged with nitrogen for several times, connected to a balloon filled with nitrogen, and the mixture was stirred overnight in an oil bath at 110° C. The mixture was extracted with dichloromethane (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=10:1), yellow-green solids (223 mg, yield: 40%) were obtained. MS (ESI) m/z 495 [M+H]$^+$.

Step 4: Preparation of 6-methyl-1-(1-(tetrahydro-2H-pyran-2-yl)-1H-pyrazol-5-yl)-5-(1-(thiazol-2-ylmethoxy) ethyl) indolizine-7-carboxylic acid: in a 25 mL nitrogen-protected single-necked flask, compound ethyl 6-methyl-1-(1-(tetrahydro-2H-pyran-2-yl)-1H-pyrazol-5-yl)-5-(1-(thiazol-2-ylmethoxy)ethyl) indolizine-7-carboxylate (223 mg, 0.451 mmol), 2.5 mL THF, and 2.5 mL methanol were added, and overdose sodium hydroxide in 2.5 mL of water were added successively to the reaction system, warmed to 60° C. and stirred to reflux overnight. The reaction solution was neutralized with dilute hydrochloric acid to pH 5, extracted with dichloromethane (50 mL). The organic phase was dried with sodium sulfate, filtered and concentrated to provide pale yellow solids (140 mg, yield 81%). MS (ESI) m/z 383 [M+H]$^+$.

Step 5: Preparation of N-((4-methoxy-6-methyl-2-oxo-1,2-dihydropyridin-3-yl)methyl)-6-methyl-1-(1H-pyrazol-5-yl)-5-(1-(thiazol-2-ylmethoxy)ethyl)indolizine-7-carboxamide: 6-methyl-1-(1-(tetrahydro-2H-pyran-2-yl)-1H-pyrazol-5-yl)-5-(1-(thiazol-2-ylmethoxy)ethyl) indolizine-7-carboxylic acid (70 mg, 0.163 mmol), 3-(aminomethyl)-4-methoxy-6-methylpyridine-2(1H)-one hydrochloride (37 mg, 0.196 mmol), HATU (93 mg, 0.245 mmol), TEA (49 mg, 0.489 mmol) and DMF 2 mL were added successively in a 25 mL nitrogen-protected single-necked flask, and stirred at room temperature overnight. Yellow solids (1 mg, yield: 1%) were obtained through preparative purification. $^1$H NMR (400 MHz, CDCl$_3$) δ 12.11 (s, 1H), 8.20 (s, 1H), 8.12 (s, 1H), 8.06 (s, 1H), 7.73 (d, J=3.2 Hz, 1H), 7.44 (s, 1H), 7.32 (d, J=2.8 Hz, 1H), 6.99 (s, 1H), 6.39 (s, 1H), 5.84 (s, 1H), 5.45 (q, J=13.2, 6.0 Hz, 1H), 4.67 (s, 2H), 4.56 (s, 2H), 3.84 (s, 3H), 2.42 (s, 3H), 2.16 (s, 3H), 1.73 (d, J=6.5 Hz, 3H); MS (ESI) m/z 533 [M+H]$^+$.

Example 184: Preparation of N-((4-methoxy-6-methyl-2-oxo-1,2-dihydropyridin-3-yl)methyl)-6-methyl-1-(6-(methylpyridin-3-yl)-5-(1-(4-(2,2,2-trifluoroethyl)piperazin-1-yl)ethyl)indolizine-7-carboxamide: Same as Example 159

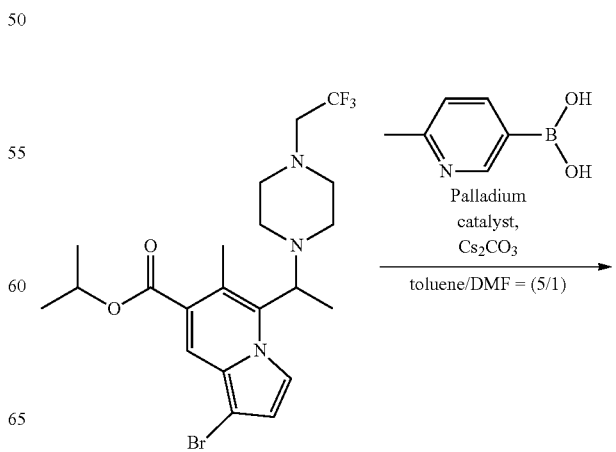

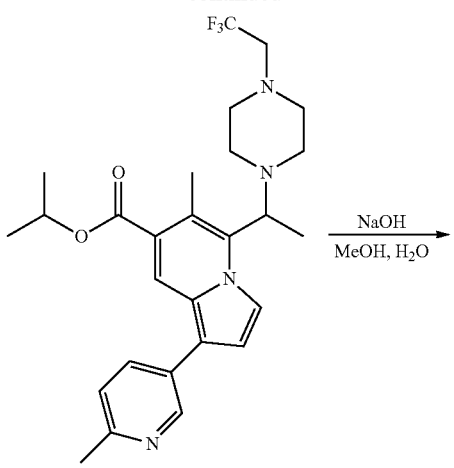

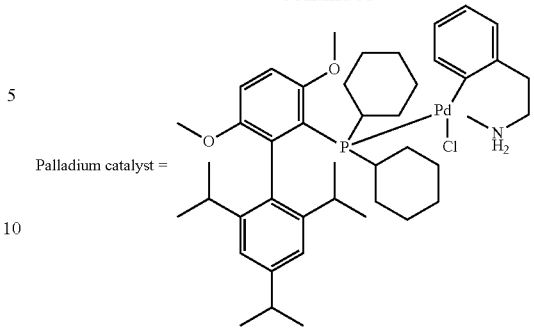

Step 1: Preparation of isopropyl 6-methyl-1-(6-methylpyridin-3-yl)-5-(1-(4-(2,2,2-trifluoroethyl)piperazin-1-yl) indolizine-7-carboxylate: yield 33%. MS (ESI) m/z 503 [M+H]⁺.

Step 2: Preparation of 6-methyl-1-(6-methylpyridin-3-yl)-5-(1-(4-(2,2,2-trifluoroethyl)piperazin-1-yl)ethyl)indolizine-7-carboxylic acid: yield 87%. MS (ESI) m/z 461 [M+H]⁺.

Step 3: Preparation of N-((4-methoxy-6-methyl-2-oxo-1,2-dihydropyridin-3-yl)methyl)-6-methyl-1-(6-methylpyridin-3-yl)-5-(1-(4-(2,2,2-trifluoroethyl)piperazin-1-yl)ethyl) indolizine-7-carboxamide: yield 17%. ¹H NMR (CDCl₃, 400 MHz) δ ppm 8.71 (s, 1H), 8.46 (s, 1H), 7.32 (dd, J=8.0, 2.4 Hz, 1H), 7.66 (d, J=7.7 Hz, 1H), 7.60 (t, J=2.4 Hz, 1H), 7.16 (d, J=8.0 Hz, 1H), 6.89 (s, 1H), 5.87 (s, 1H), 4.52 (d, J=5.2 Hz, 2H), 4.06 (q, J=6.4 Hz, 1H), 3.87 (s, 3H), 2.95 (q, J=9.6 Hz, 2H), 2.68-2.58 (m, 6H), 2.50 (s, 3H), 2.37 (s, 3H), 2.35-2.31 (m, 2H), 2.22 (s, 3H), 1.48 (d, J=6.4 Hz, 3H); MS (ESI) m/z 611 [M+H]⁺.

Example 185: Preparation of N-((4-methoxy-6-methyl-2-oxo-1,2-dihydropyridin-3-yl)methyl)-1-(2-methoxypyridine-4-yl)-6-methyl-5-(1-(4-(2,2,2-trifluoroethyl)piperazin-1-yl)ethyl)indolizine-7-carboxamide: Same as Example 159

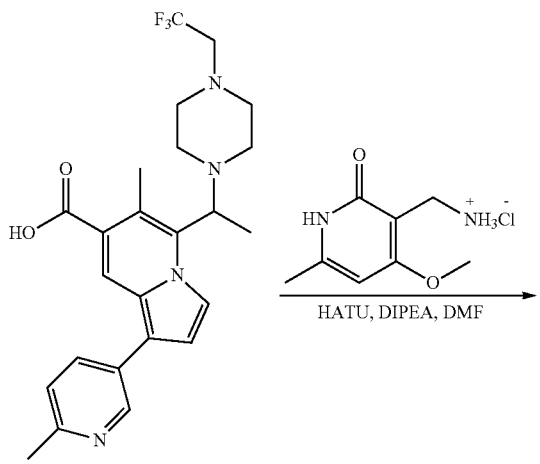

Compound 192

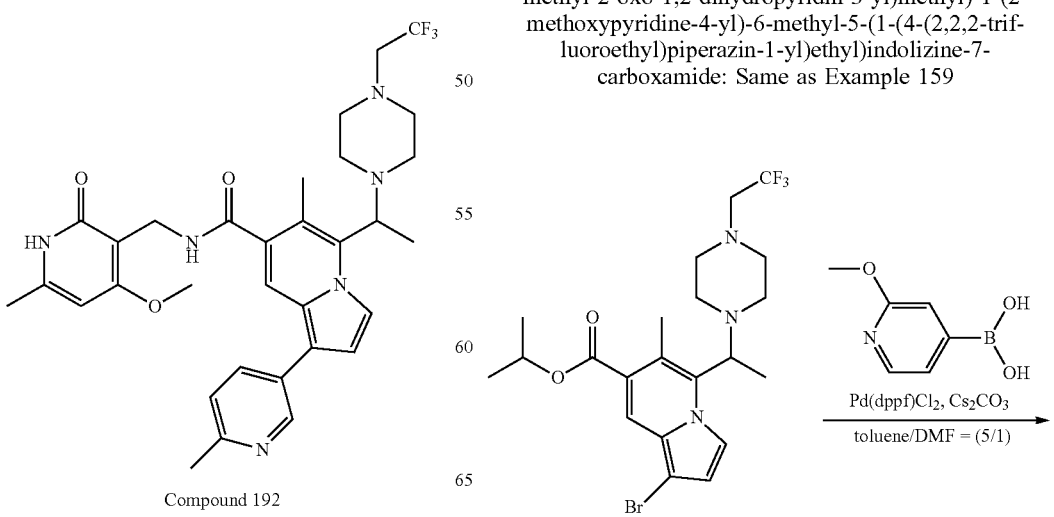

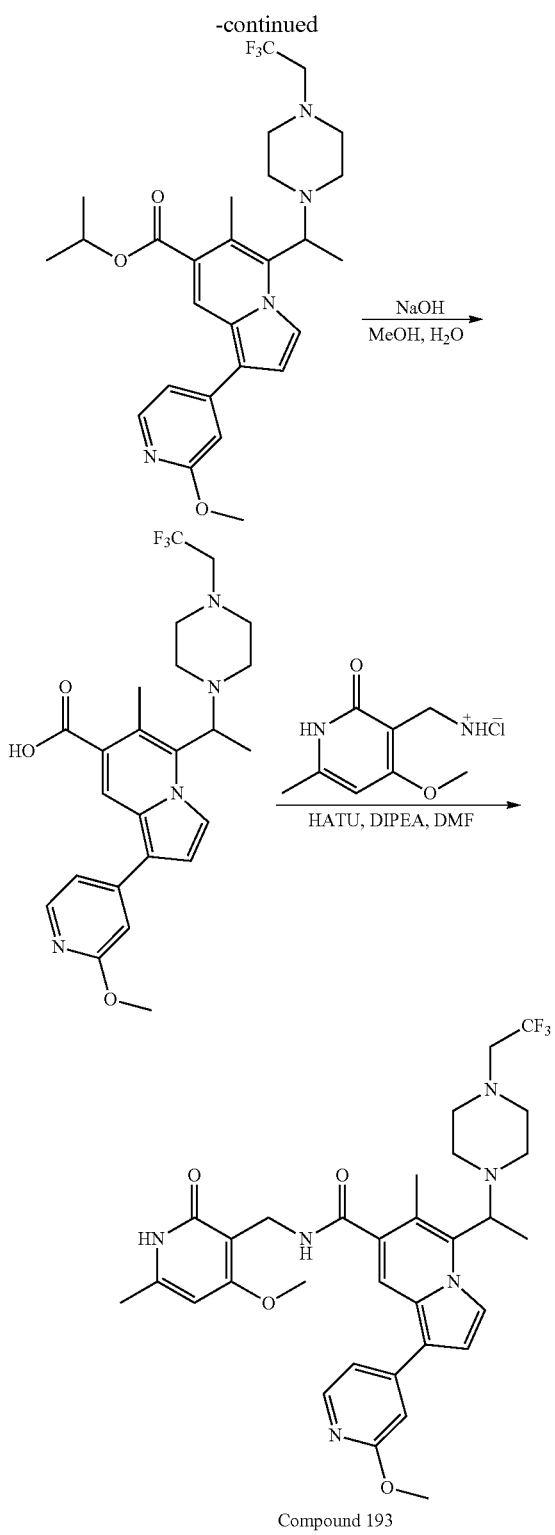

Compound 193

Step 1: Preparation of isopropyl 1-(2-methoxypyridin-4-yl)-6-methyl-5-(1-(4-(2,2,2-trifluoroethyl)piperazin-1-yl)ethyl)indolizine-7-carboxylate: yield of two steps was 80%. MS (ESI) m/z 519 [M+H]⁺.

Step 2: Preparation of 1-(2-methoxypyridin-4-yl)-6-methyl-5-(1-(4-(2,2,2-trifluoroethyl)piperazine-1-yl)ethyl)indolizine-7-carboxylic acid: MS (ESI) m/z 477 [M+H]⁺.

Step 3: Preparation of N-((4-methoxy-6-methyl-2-oxo-1,2-dihydropyridin-3-yl)methyl)-1-(2-methoxypyridin-4-yl)-6-methyl-5-(1-(4-(2,2,2-trifluoroethyl)piperazin-1-yl)ethyl)indolizine-7-carboxamide: yield of two steps was 53%. ¹H NMR (CDCl₃, 400 MHz) δ ppm 12.13 (brs, 1H), 8.50 (s, 1H), 8.06 (d, J=5.2 Hz, 1H), 7.76 (s, 1H), 7.64 (t, J=5.2 Hz, 1H), 7.06 (dd, J=6.8, 5.2 Hz, 1H), 6.95 (d, J=7.2 Hz, 1H), 6.90 (s, 1H), 5.87 (s, 1H), 4.56 (d, J=2.8 Hz, 2H), 4.07 (q, J=6.8 Hz, 1H), 3.92 (s, 3H), 3.89 (s, 3H), 2.95 (q, J=9.6 Hz, 2H), 2.68-2.58 (m, 6H), 2.38 (s, 3H), 2.33-2.29 (m, 2H), 2.18 (s, 3H), 1.48 (d, J=6.8 Hz, 3H); MS (ESI) m/z 627 [M+H]⁺.

Example 186: Preparation of (S)—N-((4-methoxy-6-methyl-2-oxo-1,2-dihydropyridin-3-yl)methyl)-1-(2-methoxypyridin-4-yl)-6-methyl-5-(1-(4-(2,2,2-trifluoroethyl)piperazin-1-yl)ethyl)indolizine-7-carboxamide or (R)—N-((4-methoxy-6-methyl-2-oxo-1,2-dihydropyridin-3-yl)methyl)-1-(2-methoxypyridin-4-yl)-6-methyl-5-(1-(4-(2,2,2-trifluoroethyl)piperazin-1-yl)ethyl)indolizine-7-carboxamide: Compound 193 was Separated by Chiral Preparative Liquid Chromatography to Provide Compound 194 and Compound 195

The separation conditions were: column type IC-H; column size: 0.46 cm I.D.×15 cm L; injection volume: 2 μL; mobile phase: EtOH (0.1% DEA); flow rate: 0.5 ml/min; detection conditions: UVλ=254 nm; column temperature: 25° C.

Compound 194: ¹H NMR (CDCl₃, 400 MHz) δ ppm 11.48 (brs, 1H), 8.50 (s, 1H), 8.06 (d, J=5.2 Hz, 1H), 7.76 (s, 1H), 7.64 (t, J=5.2 Hz, 1H), 7.06 (dd, J=6.8, 5.2 Hz, 1H), 6.95 (d, J=7.2 Hz, 1H), 6.90 (s, 1H), 5.87 (s, 1H), 4.56 (d, J=2.8 Hz, 2H), 4.07 (q, J=6.8 Hz, 1H), 3.92 (s, 3H), 3.89 (s, 3H), 2.95 (q, J=9.6 Hz, 2H), 2.68-2.58 (m, 6H), 2.38 (s, 3H), 2.33-2.29 (m, 2H), 2.18 (s, 3H), 1.48 (d, J=6.8 Hz, 3H); MS (ESI) m/z 627 [M+H]⁺; $t_R$=10.543 min.

Compound 195: ¹H NMR (CDCl₃, 400 MHz) δ ppm 12.51 (brs, 1H), 8.50 (s, 1H), 8.06 (d, J=5.2 Hz, 1H), 7.76 (s, 1H), 7.64 (t, J=5.2 Hz, 1H), 7.06 (dd, J=6.8, 5.2 Hz, 1H), 6.95 (d, J=7.2 Hz, 1H), 6.90 (s, 1H), 5.87 (s, 1H), 4.56 (d, J=2.8 Hz, 2H), 4.07 (q, J=6.8 Hz, 1H), 3.92 (s, 3H), 3.89 (s, 3H), 2.95 (q, J=9.6 Hz, 2H), 2.68-2.58 (m, 6H), 2.38 (s, 3H), 2.33-2.29 (m, 2H), 2.18 (s, 3H), 1.48 (d, J=6.8 Hz, 3H); MS (ESI) m/z 627 [M+H]⁺; $t_R$=12.384 min.

Example 187: Preparation of N-((4-methoxy-6-methyl-2-oxo-1,2-dihydropyridin-3-yl)methyl)-6-methyl-1-(2-methylpyrimidin-5-yl)-5-(1-(4-(2,2,2-trifluoroethyl)piperazin-1-yl)ethyl)indolizine-7-carboxamide: Same as Example 159

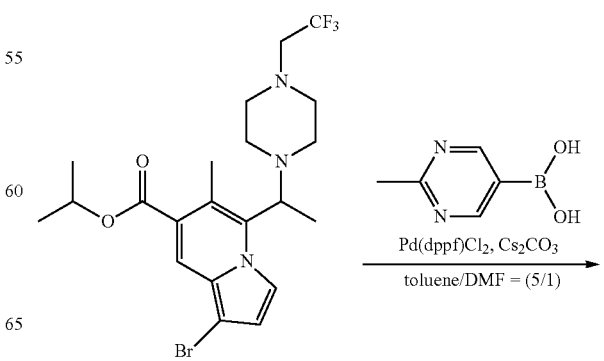

-continued

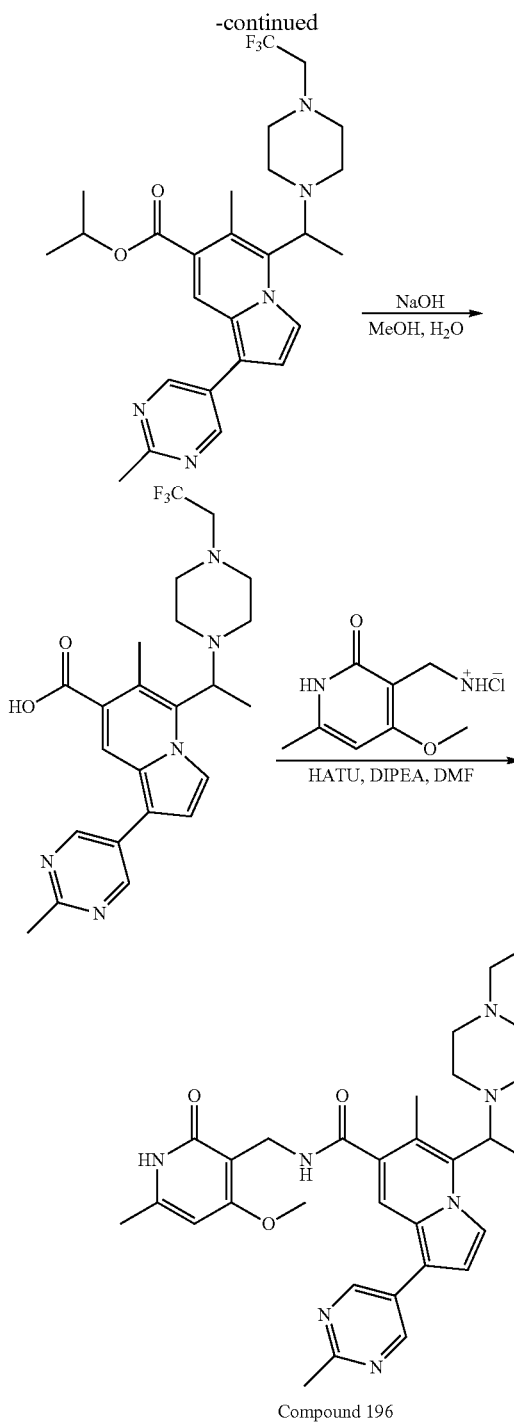

Compound 196

Step 1: Preparation of isopropyl 6-methyl-1-(2-methylpyrimidin-5-yl)-5-(1-(4-(2,2,2-trifluoroethyl)piperazin-1-yl)indolizine-7-carboxylate: yield 82%. MS (ESI) m/z 504 [M+H]⁺.

Step 2: Preparation of 6-methyl-1-(2-methylpyrimidin-5-yl)-5-(1-(4-(2,2,2-trifluoroethyl)piperazin-1-yl)ethyl)indolizine-7-carboxylic acid: yield 78%. MS (ESI) m/z 462 [M+H]⁺.

Step 3: Preparation of N-((4-methoxy-6-methyl-2-oxo-1,2-dihydropyridin-3-yl)methyl)-6-methyl-1-(2-methylpyrimidin-5-yl)-5-(1-(4-(2,2,2-trifluoroethyl)piperazin-1-yl)ethyl)indolizine-7-carboxamide: yield 30%. $^1$H NMR (CDCl$_3$, 400 MHz) δ ppm 8.83 (s, 2H), 8.51 (s, 1H), 7.66-7.62 (m, 2H), 6.92 (d, J=2.8 Hz, 1H), 5.89 (s, 1H), 4.53 (d, J=5.6 Hz, 2H), 4.08 (q, J=6.8 Hz, 1H), 3.89 (s, 3H), 2.95 (q, J=8.8 Hz, 2H), 2.78-2.23 (m, 8H), 2.39 (s, 3H), 2.33-2.29 (m, 2H), 2.21 (s, 3H), 1.48 (d, J=6.8 Hz, 3H); MS (ESI) m/z 612 [M+H]⁺.

Example 188: Preparation of (S)—N-((4-methoxy-6-methyl-2-oxo-1,2-dihydropyridin-3-yl)methyl)-6-methyl-1-(2-methylpyrimidin-5-yl)-5-(1-(4-(2,2,2-trifluoroethyl)piperazin-1-yl)ethyl)indolizine-7-formamide or (R)—N-((4-methoxy-6-methyl-2-oxo-1,2-dihydropyridin-3-yl)methyl)-6-methyl-1-(2-methylpyrimidin-5-yl)-5-(1-(4-(2,2,2-trifluoroethyl)piperazin-1-yl)ethyl)indolizine-7-formamide: Compound 196 was Separated by Chiral Preparative Liquid Chromatography to Provide Compound 197 and Compound 198

The separation conditions were: column type IC-H; column size: 0.46 cm I.D.×15 cm L; injection volume: 2 μL; mobile phase: EtOH (0.1% DEA); flow rate: 0.5 ml/min; detection conditions: UVλ=254 nm; column temperature: 25° C.

Compound 197: $^1$H NMR (CDCl$_3$, 400 MHz) δ ppm 8.83 (s, 2H), 8.51 (s, 1H), 7.66-7.62 (m, 2H), 6.92 (d, J=2.8 Hz, 1H), 5.89 (s, 1H), 4.53 (d, J=5.6 Hz, 2H), 4.08 (q, J=6.8 Hz, 1H), 3.89 (s, 3H), 2.95 (q, J=8.8 Hz, 2H), 2.78-2.23 (m, 8H), 2.39 (s, 3H), 2.33-2.29 (m, 2H), 2.21 (s, 3H), 1.48 (d, J=6.8 Hz, 3H); MS (ESI) m/z 612 [M+H]⁺; $t_R$=10.921 min.

Compound 198: $^1$H NMR (CDCl$_3$, 400 MHz) δ ppm 8.83 (s, 2H), 8.51 (s, 1H), 7.66-7.62 (m, 2H), 6.92 (d, J=2.8 Hz, 1H), 5.89 (s, 1H), 4.53 (d, J=5.6 Hz, 2H), 4.08 (q, J=6.8 Hz, 1H), 3.89 (s, 3H), 2.95 (q, J=8.8 Hz, 2H), 2.78-2.23 (m, 8H), 2.39 (s, 3H), 2.33-2.29 (m, 2H), 2.21 (s, 3H), 1.48 (d, J=6.8 Hz, 3H); MS (ESI) m/z 612 [M+H]⁺; $t_R$=12.259 min.

Example 189: Preparation of N-((4-methoxy-6-methyl-2-oxo-1,2-dihydropyridin-3-yl)methyl)-6-methyl-1-(6-methylpyrazin-3-yl)-5-(1-(4-(2,2,2-trifluoroethyl)piperazin-1-yl)ethyl)indolizine-7-carboxamide: Similar to Example 50

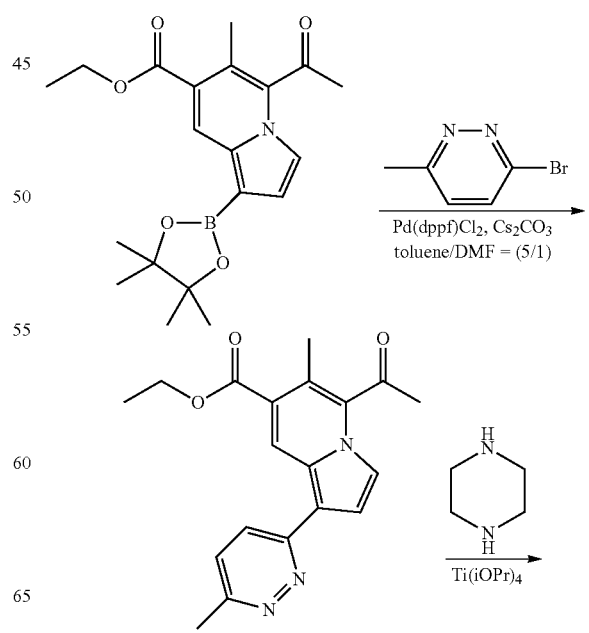

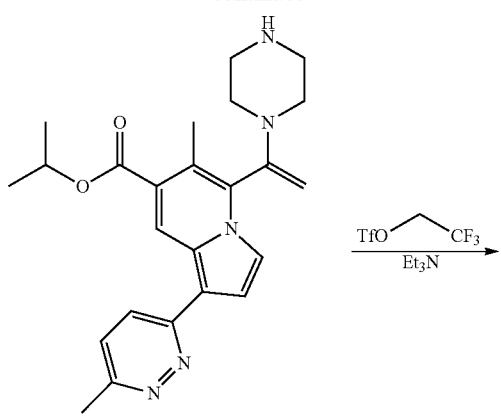

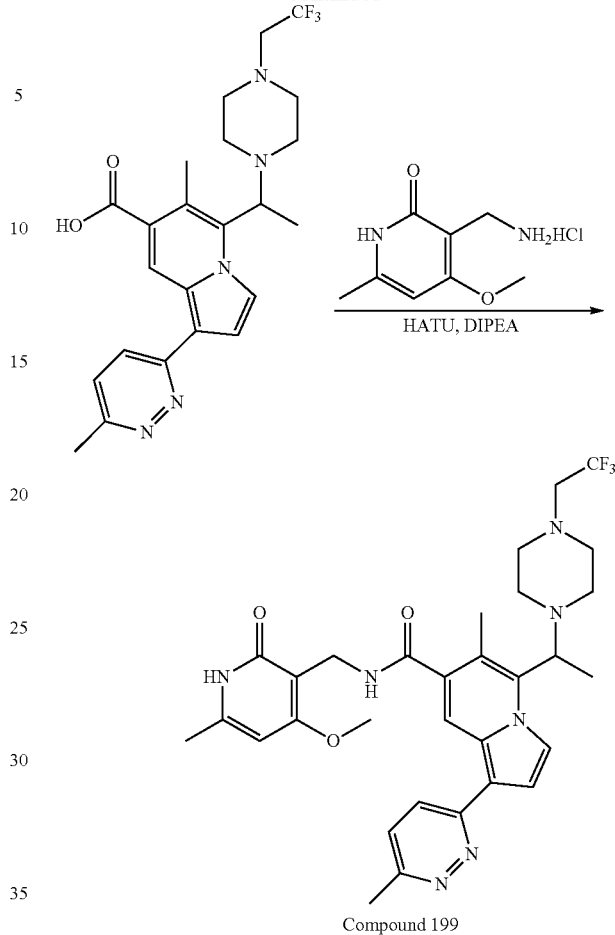

Compound 199

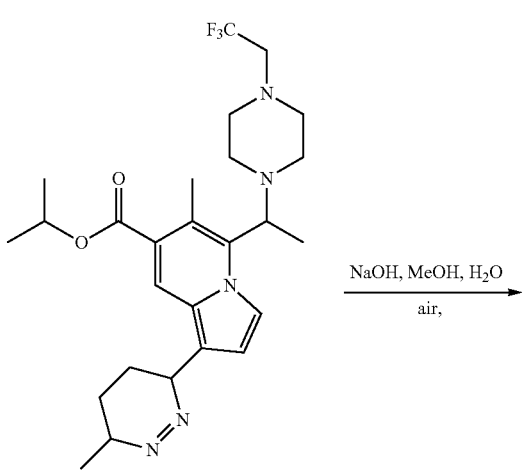

Step 1: Preparation of ethyl 5-acetyl-6-methyl-1-(6-methylpyridazin-3-yl)indolizine-7-carboxylate: yield 48%. MS (ESI) m/z 338 [M+H]+.

Step 2: Preparation of 6-methyl-1-(6-methylpyridazin-3-yl)-5-(1-(piperazin-1-yl)vinyl)indolizine-7-carboxylate: MS (ESI) m/z 420 [M+H]+.

Step 3: Preparation of isopropyl 6-Methyl-1-(6-methylpyridazin-3-yl)-5-(1-(4-(2,2,2-trifluoroethyl)piperazin-1-yl)vinyl)indolizine-7-carboxylate: MS (ESI) m/z 502 [M+H]+.

Step 4: Preparation of isopropyl 6-methyl-1-(6-methyl-3,4,5,6-tetrahydropyridazin-3-yl)-5-(1-(4-(2,2,2-trifluoroethyl)piperazin-1-yl)ethyl)indolizine-7-carboxylate: yield of three steps was 55%. MS (ESI) m/z 508 [M+H]+.

Step 5: Preparation of 6-methyl-1-(6-methylpyridazin-3-yl)-5-(1-(4-(2,2,2-trifluoroethyl)piperazin-1-yl)ethyl)indolizine-7-carboxylic acid: yield 68%. MS (ESI) m/z 462 [M+H]+.

Step 6: Preparation of N-((4-methoxy-6-methyl-2-oxo-1,2-dihydropyridin-3-yl)methyl)-6-methyl-1-(6-methylpyridazin-3-yl)-5-(1-(4-(2,2,2-trifluoroethyl)piperazin-1-yl)ethyl)indolizine-7-carboxamide: yield 52%. $^1$H-NMR (CDCl$_3$, 400 MHz) δ ppm 8.65 (s, 1H), 8.48 (brs, 1H), 7.62-7.58 (m, 2H), 7.25 (d, J=8.8 Hz, 1H), 7.11 (d, J=2.8 Hz, 1H), 5.83 (s, 1H), 4.57 (d, J=5.6 Hz, 2H), 4.09 (q, J=6.8 Hz, 1H), 3.88 (s, 3H), 2.96 (q, J=9.6 Hz, 2H), 2.68-2.63 (m, 9H), 2.39 (s, 3H), 2.32-2.29 (m, 2H), 2.16 (s, 3H), 1.50 (d, J=6.8 Hz, 3H); MS (ESI) m/z 612 [M+H]+.

391

Example 190: Preparation of (S)—N-((4-methoxy-6-methyl-2-oxo-1,2-dihydropyridin-3-yl)methyl)-6-methyl-1-(6-methylpyridazin-3-yl)-5-(1-(4-(2,2,2-trifluoroethyl)piperazin-1-yl)ethyl)indolizine-7-formamide or (R)—N-((4-methoxy-6-methyl-2-oxo-1,2-dihydropyridin-3-yl)methyl)-6-methyl-1-(6-methylpyridazin-3-yl)-5-(1-(4-(2,2,2-trifluoroethyl)piperazin-1-yl)ethyl)indolizine-7-formamide:

Compound 199 was separated by chiral preparative liquid chromatography to provide compound 200 and compound 201

The separation conditions were: column type: AD-H; column size: 0.46 cm ID×15 cm L; injection volume: 2 μL; mobile phase: Hep/EtOH (0.1% DEA)=60/40 (v/v); flow rate: 0.5 ml/min; detection conditions: UVλ=254 nm; column temperature: 25° C.

Compound 200: $^1$H-NMR (CDCl$_3$, 400 MHz) δ ppm 8.65 (s, 1H), 8.48 (brs, 1H), 7.62-7.58 (m, 2H), 7.25 (d, J=8.8 Hz, 1H), 7.11 (d, J=2.8 Hz, 1H), 5.83 (s, 1H), 4.57 (d, J=5.6 Hz, 2H), 4.09 (q, J=6.8 Hz, 1H), 3.88 (s, 3H), 2.96 (q, J=9.6 Hz, 2H), 2.68-2.63 (m, 9H), 2.39 (s, 3H), 2.32-2.29 (m, 2H), 2.16 (s, 3H), 1.50 (d, J=6.8 Hz, 3H); MS (ESI) m/z 612 [M+H]$^+$; $t_R$=5.077 min.

Compound 201: $^1$H-NMR (CDCl$_3$, 400 MHz) δ ppm 8.65 (s, 1H), 8.48 (brs, 1H), 7.62-7.58 (m, 2H), 7.25 (d, J=8.8 Hz, 1H), 7.11 (d, J=2.8 Hz, 1H), 5.83 (s, 1H), 4.57 (d, J=5.6 Hz, 2H), 4.09 (q, J=6.8 Hz, 1H), 3.88 (s, 3H), 2.96 (q, J=9.6 Hz, 2H), 2.68-2.63 (m, 9H), 2.39 (s, 3H), 2.32-2.29 (m, 2H), 2.16 (s, 3H), 1.50 (d, J=6.8 Hz, 3H); MS (ESI) m/z 612 [M+H]$^+$; $t_R$=8.617 min.

Example 191: Preparation of N-((4-methoxy-6-methyl-2-oxo-1,2-dihydropyridin-3-yl)methyl)-6-methyl-5-(methyl(1-(2,2,2-trifluoroethyl)piperidin-4-yl)amino)-1-(1H-pyrazol-5-yl)indolizine-7-carboxamide

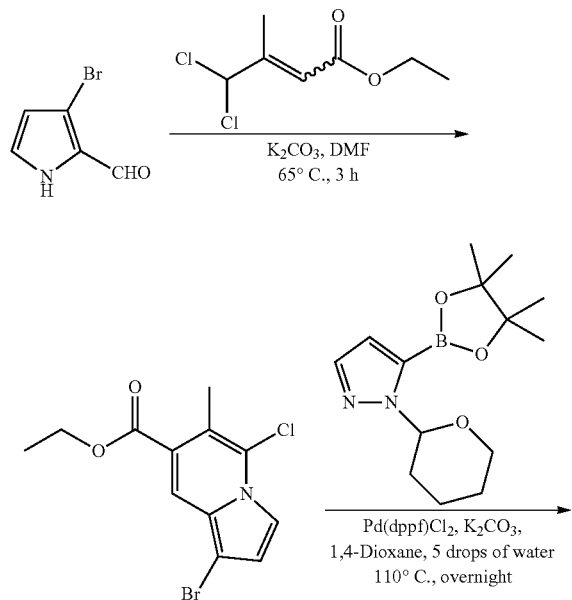

392

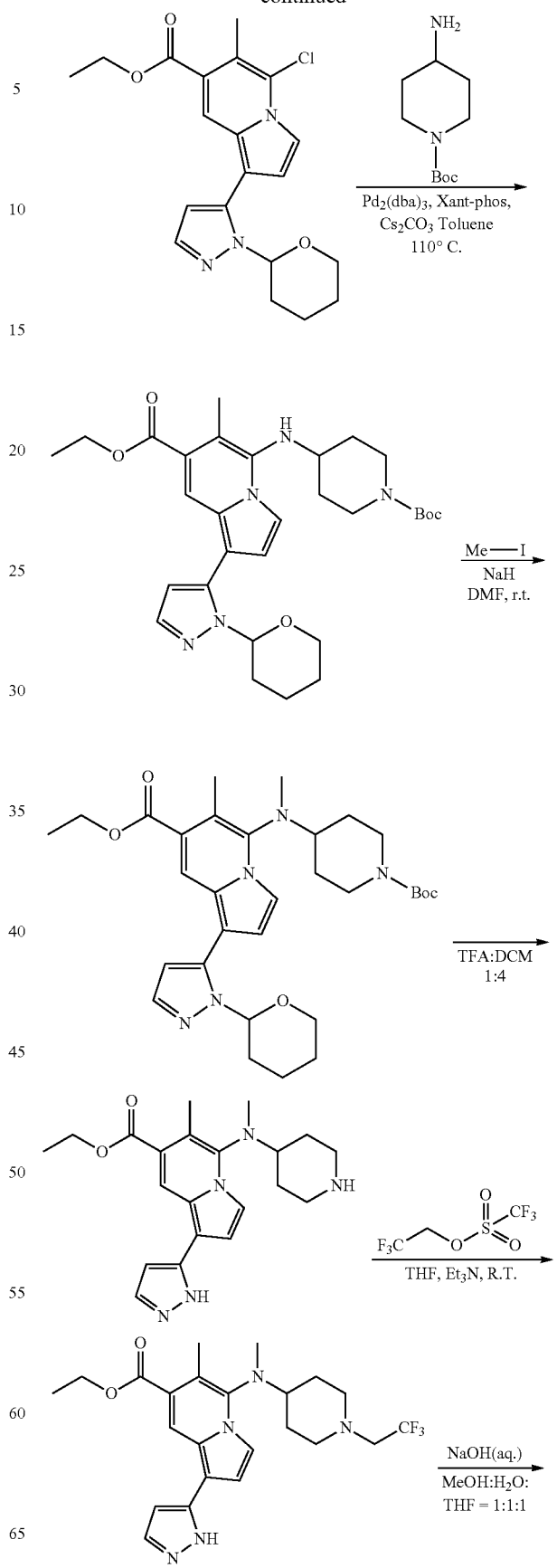

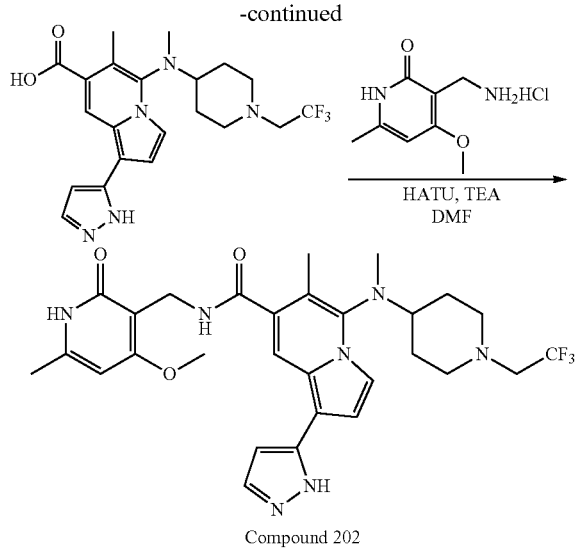

Compound 202

Step 1: Preparation of ethyl 1-bromo-5-chloro-6-methyl-indolizine-7-carboxylate: compound ethyl 4,4-dichloro-3-methyl-2-butenoate (2.0 g, 10.2 mmol) (prepared according to: Owusu-Ansah, E.; Durow, A C; Harding, J R; Jordan, A C; O'Connell, S J, and Willis, C L, Synthesis of dysideaproline E Using organocatalysis. Org. Biomol. Chem., 2011, 9, 265-272), 3-bromo-1H-pyrrole-2-carbaldehyde (1.5 g, 8.5 mmol) (prepared according to: WO2012029942), potassium carbonate (2.5 g, 17.9 mmol) and 10 mL DMF were added into a 100 mL single-necked flask, and stirred overnight in 65° C. oil bath. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=100:1), white solids (1.6 g, yield: 61%) were obtained. $^1$H NMR (400 MHz, CDCl$_3$) δ ppm 8.09 (s, 1H), 7.60 (d, J=2.9 Hz, 1H), 6.94 (d, J=2.9 Hz, 1H), 4.37 (q, J=7.1 Hz, 2H), 2.62 (s, 3H), 1.42 (t, J=7.1 Hz, 3H); MS (ESI) m/z 316 [M+H]$^+$.

Step 2: Preparation of ethyl 5-chloro-6-methyl-1-(1-(tetrahydro-2H-pyran-2-yl)-1H-pyrazol-5-yl)indolizine-7-carboxylate: In a dry nitrogen-protected 50 mL one-neck bottle, ethyl 1-bromo-5-chloro-6-methylpyridazin-7-carboxylate (1.53 g, 4.85 mmol), 1-(tetrahydro-2H-pyran-2-yl)-5-(4,4,5,5-tetramethyl-1,3,2-dioxoborolan-2-yl)-1H-pyrazole (2.70 g, 9.71 mmol), Pd(dppf)Cl$_2$ (666 mg, 0.83 mmol), K$_2$CO$_3$ (1.34 g, 9.71 mmol) were added into 6 mL of 1,4-dioxane and 5 drops of water. The bottle was exchanged for three times with nitrogen and the mixture was stirred in an oil bath at 110° C. overnight. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=100:1), white solids (634 mg, yield: 34%) were obtained. MS (ESI) m/z 304 [M-THP+H]$^+$.

Step 3: Preparation of ethyl 5-((1-tert-butoxycarbonylpiperidin-4-yl)amino)-6-methyl-1-(1-(tetrahydro-2H-pyran-2-yl)-1H-pyrazol-5-yl)indolizine-7-carboxylate: In a dry nitrogen-protected 100 mL single-necked flask, compound ethyl 5-chloro-6-methyl-1-(1-(tetrahydro-2H-pyran-2-yl)-1H-pyrazol-5-yl)indolizine-7-carboxylate (634 mg, 1.64 mmol), 1-tert-butoxycarbonyl-4-aminopiperidine (1.64 g, 8.19 mmol), Pd$_2$(dba)3 (150 mg, 0.164 mmol), Xant-phos (95 mg, 0.164 mmol) and Cs$_2$CO$_3$ (1069 mg, 3.28 mmol) were added into 10 mL of toluene. The flask was exchanged for three times with nitrogen and stirred in an oil bath at 110° C. overnight. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=5:1), yellow solids (443 mg, yield: 49%) were obtained. MS (ESI) m/z 552 [M+H]$^+$.

Step 4: Preparation of ethyl 5-((1-(tert-butoxycarbonyl)piperidin-4-yl)(methyl)amino)-6-methyl-1-(1-(tetrahydro-2H-pyran-2-yl)-1H-pyrazol-5-yl)indolizine-7-carboxylate: In the microwave tube, the compound ethyl 5-((1-tert-butoxycarbonylpiperidin-4-yl)amino)-6-methyl-1-(1-(tetrahydro-2H-pyran-2-yl)-1H-pyrazol-5-yl)indolizine-7-carboxylate (400 mg, 0.73 mmol), sodium hydride (58 mg, 1.45 mmol) were added successively to 2 mL of DMF, stirred for 30 min in ice bath, and then methyl iodide (515 mg, 3.63 mmol) was added and transferred to room temperature and stirred overnight, the reaction was quenched with water, extracted with ethyl acetate (50 mL), washed with water (50 mL×2) and saturated brine (50 mL). The organic phase was dried over anhydrous sodium sulfate, filtered and concentrated to provide a crude product. After purified by column chromatography (petroleum ether:EtOAc=5:1), yellow solids (154 mg, yield: 37%) were obtained. MS (ESI) m/z 566 [M+H]$^+$.

Step 5: Preparation of ethyl 6-methyl-5-(methyl(piperidin-4-yl)amino)-1-(1H-pyrazol-5-yl)indolizine-7-carboxylate: compound ethyl 5-((1-(tert-butoxycarbonyl)piperidin-4-yl)(methyl)amino)-6-methyl-1-(1-(tetrahydro-2H-pyran-2-yl)-1H-pyrazol-5-yl)indolizine-7-carboxylate (154 mg, 0.272 mmol), 2 mL dichloromethane and 0.5 mL of trifluoroacetic acid were added successively to a 50 mL one-neck bottle, and stirred at room temperature for 1 hour. Saturated aqueous solution of sodium hydrogencarbonate was added, and extracted with dichloromethane (50 mL), washed with water (25 mL×2) and brine (25 mL). The organic phase was dried over anhydrous sodium sulfate. The organic phase was dried over anhydrous sodium sulfate, filtered and concentrated to provide a crude product, yellow solid (121 mg, yield 99%). MS (ESI) m/z 382 [M+H]$^+$.

Step 6: Preparation of ethyl 6-methyl-5-(methyl(1-(2,2,2-trifluoroethyl)piperidin-4-yl)amino)-1-(1H-pyrazole-5-yl)indolizine-7-carboxylate: in a dry 50 mL single-necked flask, compound ethyl 6-methyl-5-(methyl(piperidin-4-yl)amino)-1-(1H-pyrazol-5-yl)indolizine-7-carboxylate (121 mg, 0.317 mmol), 2,2,2-trifluoroethyl trifluoromethanesulfonate (110 mg, 0.476 mmol) and triethylamine (48 mg, 0.476 mmol) were added and dissolved in 2 mL of tetrahydrofuran and stirred at room temperature overnight. The reaction was quenched with water and extracted with dichloromethane (50 mL), washed with water (50 mL×2) and saturated brine (50 mL), and organic phase was dried over anhydrous sodium sulfate. The organic phase was dried over anhydrous sodium sulfate, filtered and concentrated to provide a crude product, yellow solids (103 mg, yield 70%). MS (ESI) m/z 464 [M+H]$^+$.

Step 7: Preparation of 6-Methyl-5-(methyl(1-(2,2,2-trifluoroethyl)piperidin-4-yl)amino)-1-(1H-pyrazol-5-yl)indolizine-7-formic acid: The compound ethyl 6-methyl-5-(methyl(1-(2,2,2-trifluoroethyl)piperidin-4-yl)amino)-1-(1H-pyrazol-5-yl)indolizine-7-carboxylic acid (103 mg, 0.222 mmol), 2.5 mL of tetrahydrofuran and 2.5 mL of methanol were successively added into a 25 mL nitrogen-protected one-necked bottle. 50 mg of sodium hydroxide dissolved in 2.5 mL of water was added to the reaction system, and the mixture was heated to 60° C. and stirred under reflux for 5 hours. The reaction solution was neutralized with dilute hydrochloric acid to pH 5, concentrated by filtration and then purified by reverse phase chromatography to give yellow solids (25 mg, yield: 23%). MS (ESI) m/z 436 [M+H]$^+$.

Step 8: Preparation of N-((4-methoxy-6-methyl-2-oxo-1,2-dihydropyridin-3-yl)methyl)-6-methyl-5-(methyl(1-(2,2,2-trifluoroethyl)piperidin-4-yl)amino)-1-(1H-pyrazol-5-yl)indolizine-7-carboxamide: in a microwave tube, 6-methyl-5-(methyl(1-(2,2,2-trifluoroethyl)piperidin-4-yl)amino)-1-(1H-pyrazol-5-yl)indolizine-7-carboxylic acid (25 mg, 0.058 mmol), 3-(aminomethyl)-4-methoxy-6-methylpyridine-2(1H)-one hydrochloride (15 mg, 0.069 mmol), HATU (33 mg, 0.086 mmol), TEA (18 mg, 0.172 mmol) and DMF 2 mL were added, and stirred at room temperature overnight. Yellow solids (10 mg, yield: 29%) were obtained through preparative purification. $^1$H NMR (400 MHz, CDCl$_3$) δ ppm 8.07 (s, 1H), 7.45 (s, 1H), 6.93 (s, 1H), 6.37 (s, 1H), 5.84 (s, 1H), 4.65-4.44 (m, 2H), 3.85 (s, 3H), 3.21-3.07 (m, 2H), 3.00-2.85 (m, 7H), 2.37 (s, 3H), 2.29-2.18 (m, 2H), 2.16 (s, 3H), 2.07-1.95 (m, 4H); MS (ESI) m/z 586 [M+H]$^+$.

Example 192: Preparation of 1-(2-(dimethylamino)pyridin-4-yl)-5-(ethyl(1-(2,2,2-trifluoroethyl)piperidin-4-yl)amino)-N-((4-methoxy-6-methyl-2-oxo-1,2-dihydropyridin-3-yl)methyl)-6-methylindolizine-7-carboxamide: Similar to Example 191

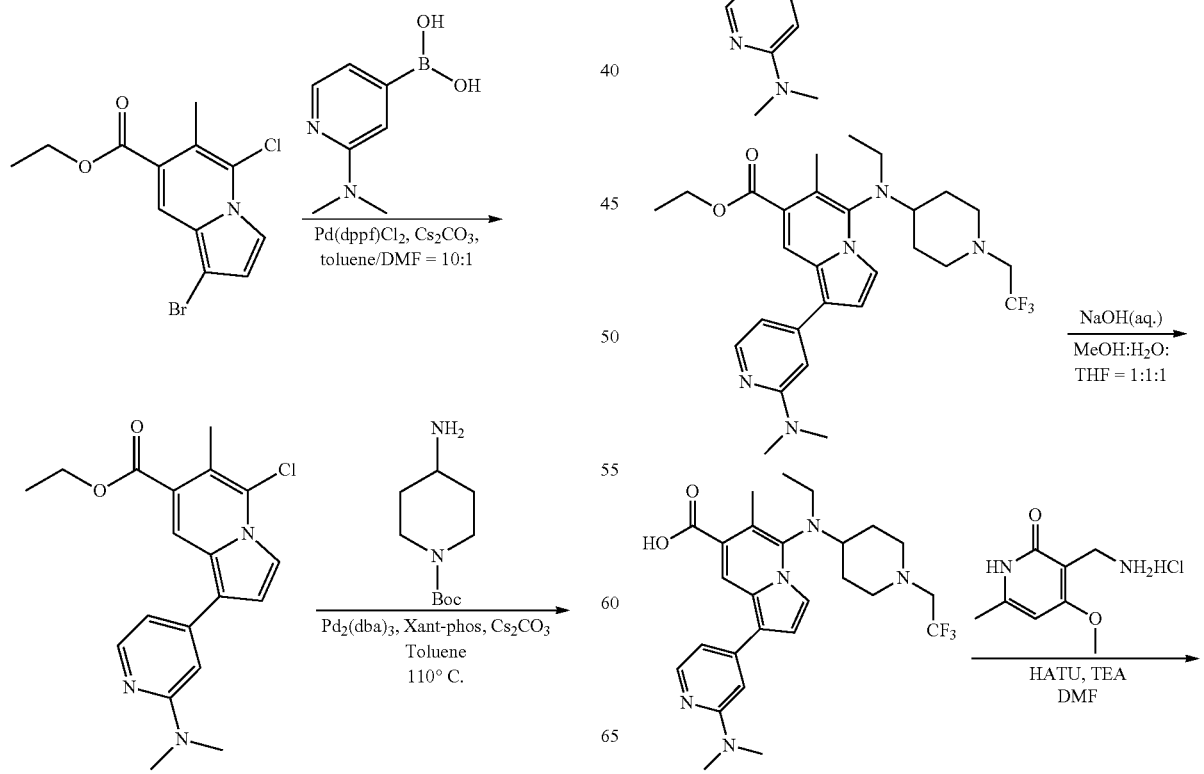

397
-continued

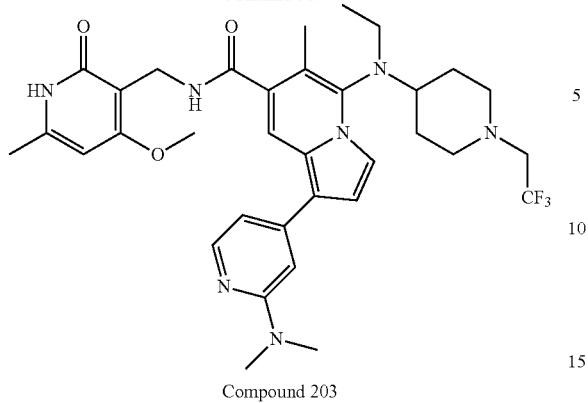

Compound 203

Step 1: Preparation of ethyl 5-chloro-1-(2-(dimethylamino)pyridin-4-yl)-6-methylindolizine-7-carboxylate: yield 44%. MS (ESI) m/z 358 [M+H]⁺.

Step 2: Preparation of ethyl 5-((1-(tert-butoxy)piperidin-4-yl)amino)-1-(2-(dimethylamino)pyridin-4-yl)-6-methylindolizine-7-carboxylate: yield 41%. MS (ESI) m/z 522 [M+H]⁺.

Step 3: Preparation of ethyl 1-(2-(dimethylamino)pyridin-4-yl)-6-methyl-5-(piperidin-4-ylamino)indolizine-7-carboxylate: yield 97%. MS (ESI) m/z 422 [M+H]⁺.

Step 4: Preparation of 1-(2-(dimethylamino)pyridin-4-yl)-6-methyl-5-((1-(2,2,2-trifluoroethyl)piperidin-4-yl)amino) indolizine-7-carboxylate: yield 59%. MS (ESI) m/z 504 [M+H]⁺.

Step 5: Preparation of ethyl 1-(2-(dimethylamino)pyridin-4-yl)-5-(ethyl(1-(2,2,2-trifluoroethyl)piperidin-4-yl)amino)-6-methylindolizine-7-carboxylate: Yield 22%. MS (ESI) m/z 532 [M+H]⁺.

Step 6: Preparation of 1-(2-(dimethylamino)pyridin-4-yl)-5-(ethyl(1-(2,2,2-trifluoroethyl)piperidin-4-yl)amino)-6-methylindolizine-7-carboxylic acid: Yield 79%. MS (ESI) m/z 504 [M+H]⁺.

Step 7: Preparation of 1-(2-(dimethylamino)pyridin-4-yl)-5-(ethyl(1-(2,2,2-trifluoroethyl)piperidin-4-yl)amino)-N-((4-methoxy-6-methyl-2-oxo-1,2-dihydropyridin-3-yl)methyl)-6-methylindolizine-7-carboxamide: yield 26%. ¹H NMR (400 MHz, CDCl₃) δ ppm 8.02 (s, 1H), 7.81 (s, 1H), 7.76 (s, 1H), 7.75 (s, 1H), 6.94 (s, 1H), 6.70 (s, 1H), 6.59 (s, 1H), 5.83 (s, 1H), 4.56 (s, 2H), 3.86 (s, 3H), 3.29-3.10 (m, 3H), 3.09-2.82 (m, 12H), 2.35 (s, 3H), 2.12 (s, 3H), 0.98 (brs, 3H); MS (ESI) m/z 654 [M+H]⁺.

Example 193: Preparation of 1-(2-(dimethylamino)pyridin-4-yl)-5-(ethyl(1-(2,2,2-trifluoroethyl)piperidin-4-yl)amino)-N-((4-methoxy-6-methyl-2-oxo-1,2-dihydropyridin-3-yl)methyl)-6-methylimidazo[1,5-a]pyridine-7-carboxamide

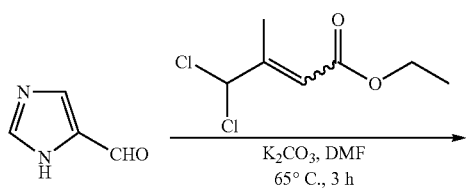

398
-continued

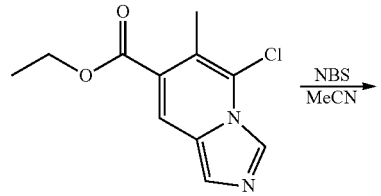

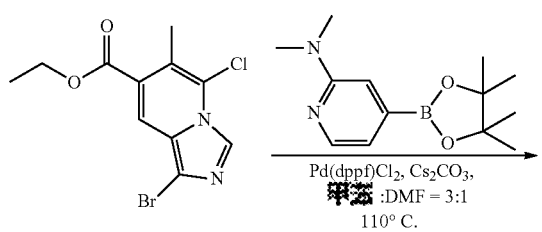

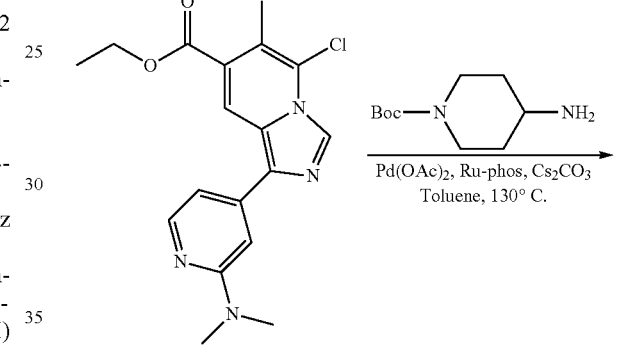

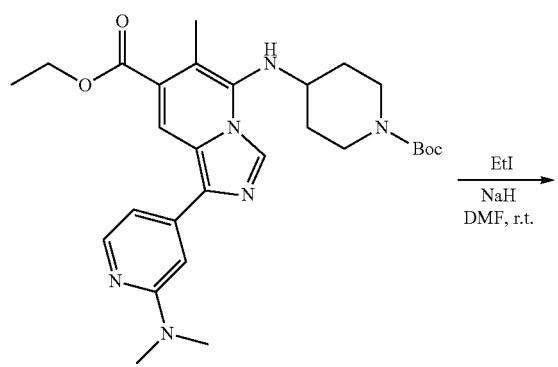

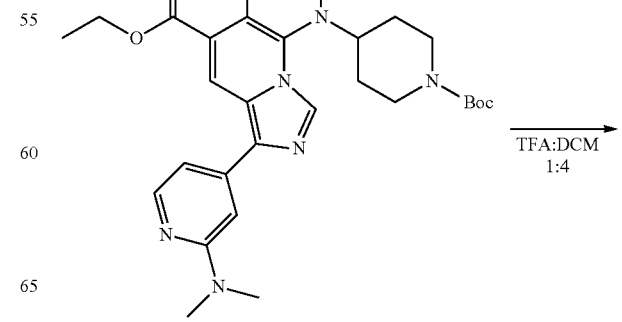

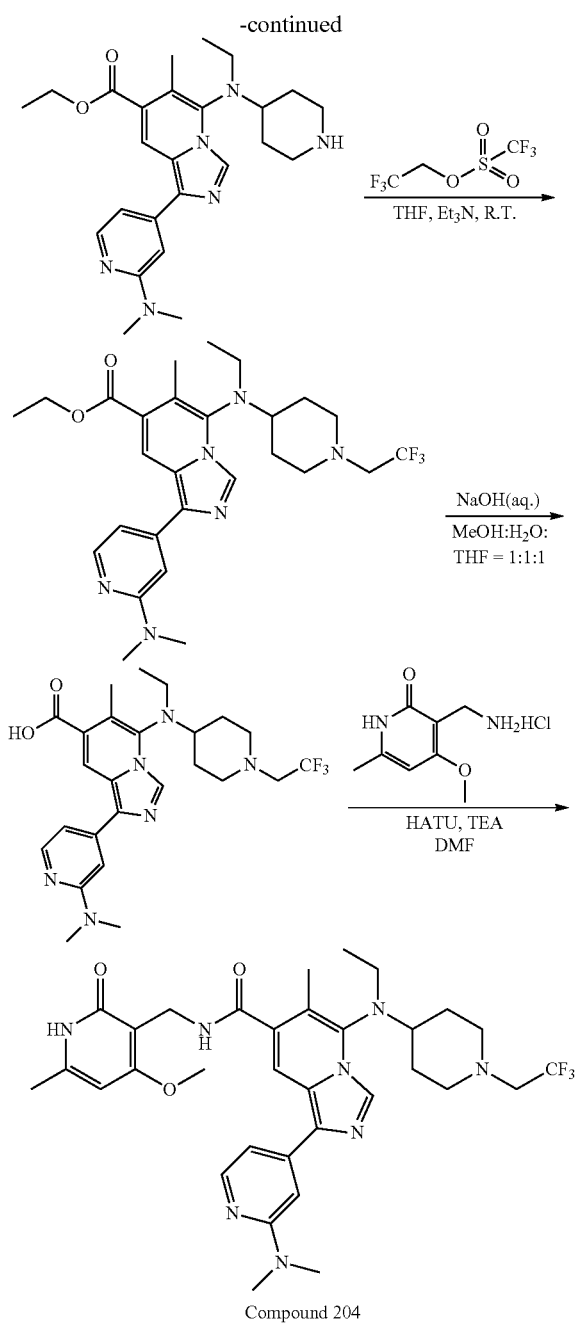

Compound 204

Step 1: Preparation of ethyl 5-chloro-6-methylimidazo[1,5-a]pyridine-7-carboxylate: compound ethyl 4,4-dichloro-3-methyl-2-butenoate (1.53 g, 7.82 mmol), 1H-imidazole-5-carbaldehyde (500 mg, 5.21 mmol), potassium carbonate (2.16 g, 15.62 mmol) and 15 mL DMF were added in a 100 mL single-necked flask, and stirred in a 60° C. oil bath overnight. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=4:1), yellow solids (648 mg, yield: 52%) were obtained. MS (ESI) m/z 239 [M+H]$^+$.

Step 2: Preparation of ethyl 1-bromo-5-chloro-6-methyl-imidazo[1,5-a]pyridine-7-carboxylate: In a 50 mL single-necked flask, ethyl 5-chloro-6-methylimidazo[1,5-a]pyridine-7-carboxylate (442 mg, 1.86 mmol) was dissolved in 25 mL of acetonitrile, transferred to an ice-bath and stirred for 10 min, and NBS (330 mg, 1.86 mmol) was added at three times, and stirred for 1 hour in an ice bath. The acetonitrile was dried by rotary evaporator, and the residue was extracted with methylene chloride (30 mL), washed with water (30 mL×2) and brine (50 mL). The organic phase was dried over anhydrous sodium sulfate, filtered and concentrated to provide a crude product. After purified by column chromatography (petroleum ether:EtOAc=20:1), yellow solids (552 mg, yield: 90%) were obtained. MS (ESI) m/z 317 [M+H]$^+$.

Step 3: Preparation of ethyl 5-chloro-1-(2-(dimethyl-amino)pyridin-4-yl)-6-methylimidazo[1,5-a]pyridine-7-carboxylate: in a nitrogen-protected 50 mL single-necked flask, ethyl 1-bromo-5-chloro-6-methylimidazo[1,5-a]pyridine-7-carboxylate (504 mg, 1.59 mmol), N,N-dimethyl-4-(4,4,5,5-tetramethyl-1,3,2-dioxoborolan-2-yl)pyridin-2-amine (396 mg, 1.59 mmol), Pd(dppf)Cl$_2$ (58 mg, 0.08 mmol), Cs$_2$CO$_3$ (1.04 g, 3.19 mmol) were added into 6 mL of toluene:DMF=3:1. The flask was exchanged for three times with nitrogen and the mixture was stirred in an oil bath at 100° C. overnight. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=5:1), white solids (217 mg, yield: 38%) were obtained. MS (ESI) m/z 359 [M+H]$^+$.

Step 4: preparation of ethyl 5-((1-(tert-butoxycarbonyl)piperidin-4-yl)amino)-1-(2-(dimethylamino)pyridin-4-yl)-6-methylimidazo[1,5-a]pyridine-7-carboxylate: in a microwave tube, ethyl 5-chloro-1-(2-(dimethylamino)pyridin-4-yl)-6-methylimidazo[1,5-a]pyridine-7-carboxylate (217 mg, 0.606 mmol), 1-tert-butoxycarbonyl-4-aminopiperidine (364 mg, 1.82 mmol), Pd(OAc)$_2$ (21 mg, 0.091 mmol), Ru-phos (43 mg, 0.091 mmol), Cs$_2$CO$_3$ (395 mg, 1.21 mmol) were added into 4 mL of toluene. The tube was exchanged for three times with nitrogen and stirred in an oil bath at 130° C. for 2 days. The mixture was extracted with ethyl acetate (100 mL) and washed with water (50 mL×2) and saturated brine (50 mL). The organic phase was dried over anhydrous sodium sulfate, filtered and concentrated to provide a crude product. After purified by column chromatography (petroleum ether:EtOAc=1:1), yellow solids (251 mg, yield: 79%) were obtained. MS (ESI) m/z 523 [M+H]$^+$.

Step 5: Preparation of ethyl 5-((1-(tert-butoxycarbonyl)piperidin-4-yl)(ethyl)amino)-1-(2-(dimethylamino)pyridin-4-yl)-6-methylimidazo[1,5-a]pyridine-7-carboxylate: ethyl 5-((1-(tert-butoxycarbonyl)piperidin-4-yl)amino)-1-(2-(dimethylamino)pyridin-4-yl)-6-methylimidazo[1,5-a]pyridine-7-carboxylate (251 mg, 0.481 mmol), sodium hydride (39 mg, 0.962 mmol) were dissolved in 2 mL of DMF, stirred for 30 min in ice-bath, then ethyl iodide (3.75 g, 24.04 mmol) was added, stirred for 3 hours in an ice bath, then transferred to room temperature and stirred overnight. The reaction was quenched with water and extracted with ethyl acetate (50 mL), washed with water (50 mL×2) and saturated brine (50 mL), and organic phase was dried over anhydrous sodium sulfate. The organic phase was dried over anhydrous sodium sulfate, filtered and concentrated to provide a crude product. After purified by column chromatography (petroleum ether:EtOAc=5:1), yellow solids (169 mg, yield: 64%) were obtained. MS (ESI) m/z 551 [M+H]$^+$.

Step 6: Preparation of 1-(2-(dimethylamino)pyridin-4-yl)-5-(ethyl(piperidin-4-yl)amino)-6-methylimidazo[1,5-a]pyridine-7-formate: In a dry 50 mL single-necked flask, ethyl 5-((1-(tert-butoxycarbonyl)piperidin-4-yl)(ethyl)amino)-1-(2-(dimethylamino)pyridin-4-yl)-6-methylimidazo[1,5-a]pyridine-7-carboxylate (169 mg, 0.307 mmol), 2 mL dichloromethane and 0.5 mL fluoroacetic acid were added successively and stirred at room temperature for 1 hour. Saturated aqueous solution of sodium hydrogencarbonate was added, and extracted with dichloromethane (50 mL), washed with water (25 mL×2) and brine (25 mL). The organic phase was dried over anhydrous sodium sulfate. The organic phase was dried over anhydrous sodium sulfate, filtered and concentrated to provide a crude product, yellow solid (148 mg, yield 91%). MS (ESI) m/z 451 [M+H]+.

Step 7: Preparation of ethyl 1-(2-(dimethylamino)pyridin-4-yl)-5-(ethyl(1-(2,2,2-trifluoroethyl)piperidin-4-yl)amino)-6-methylimidazo[1,5-a]pyridine-7-carboxylate: in dry 50 mL single-necked flask, ethyl 1-(2-(dimethylamino)pyridin-4-yl)-5-(ethyl(piperidin-4-yl)amino)-6-methylimidazo[1,5-a]pyridine-7-carboxylate (169 mg, 0.375 mmol), 2,2,2-trifluoroethyl trifluoromethanesulfonate (131 mg, 0.563 mmol) and triethylamine (57 mg, 0.563 mmol) were added and dissolved in 2 mL THF, and stirred overnight at room temperature. The reaction was quenched with water and extracted with dichloromethane (50 mL), washed with water (50 mL×2) and saturated brine (50 mL), and organic phase was dried over anhydrous sodium sulfate. The organic phase was dried over anhydrous sodium sulfate, filtered and concentrated to provide a crude product, yellow solid (148 mg, yield 74%). MS (ESI) m/z 533 [M+H]+.

Step 8: Preparation of 1-(2-(dimethylamino)pyridin-4-yl)-5-(ethyl(1-(2,2,2-trifluoroethyl)piperidin-4-yl)amino)-6-methylimidazo[1,5-a]pyridine-7-carboxylic acid: The compound ethyl 1-(2-(dimethylamino)pyridin-4-yl)-5-(ethyl(1-(2,2,2-trifluoroethyl)piperidin-4-yl)amino)-6-methylimidazo[1,5-a]pyridine-7-carboxylate (148 mg, 0.278 mmol), 2.5 mL of tetrahydrofuran and 2.5 mL of methanol were successively added into a 25 mL nitrogen-protected one-necked bottle. 50 mg of sodium hydroxide dissolved in 2.5 ml of water was added to the reaction system, and the mixture was heated to 60° C. and stirred under reflux for 5 hours. The reaction solution was neutralized with dilute hydrochloric acid to pH 5, filtered and concentrated and then purified by reverse phase chromatography to give yellow solids (66 mg, yield: 47%). MS (ESI) m/z 505 [M+H]+.

Step 9: Preparation of 1-(2-(dimethylamino)pyridin-4-yl)-5-(ethyl(1-(2,2,2-trifluoroethyl)piperidin-4-yl)amino)-N-((4-methoxy-6-methyl-2-oxo-1,2-dihydropyridin-3-yl)methyl)-6-methylimidazo[1,5-a]pyridine-7-formamide:
1-(2-(dimethylamino)pyridin-4-yl)-5-(ethyl(1-(2,2,2-trifluoroethyl)piperidin-4-yl)amino)-6-methylimidazo[1,5-a]pyridine-7-carboxylic acid (66 mg, 0.131 mmol), 3-(aminomethyl)-4-methoxy-6-methylpyridine-2(1H)-one hydrochloride (32 mg, 0.157 mmol), HATU (75 mg, 0.196 mmol), TEA (40 mg, 0.393 mmol) and DMF 1.5 mL were successively added into a microwave tube, and stirred at room temperature overnight. Yellow solids (25 mg, yield: 29%) were obtained by preparative purification. 1H NMR (400 MHz, CDCl3) δ ppm 12.70 (s, 1H), 8.26 (s, 1H), 8.05 (s, 1H), 8.03 (s, 1H), 7.82 (s, 1H), 7.04 (s, 1H), 6.89 (d, J=5.2 Hz, 1H), 5.83 (s, 1H), 4.64-4.51 (m, 2H), 3.86 (s, 3H), 3.34-3.18 (m, 2H), 3.17-3.09 (m, 2H), 3.07 (s, 6H), 2.90 (q, J=9.4 Hz, 2H), 2.40-2.26 (m, 5H), 2.17 (s, 3H), 0.99 (t, J=7.1 Hz, 3H); MS (ESI) m/z 655 [M+H]+.

Example 194: Preparation of 1-(2-ethylpyridin-4-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: Same as Example 159

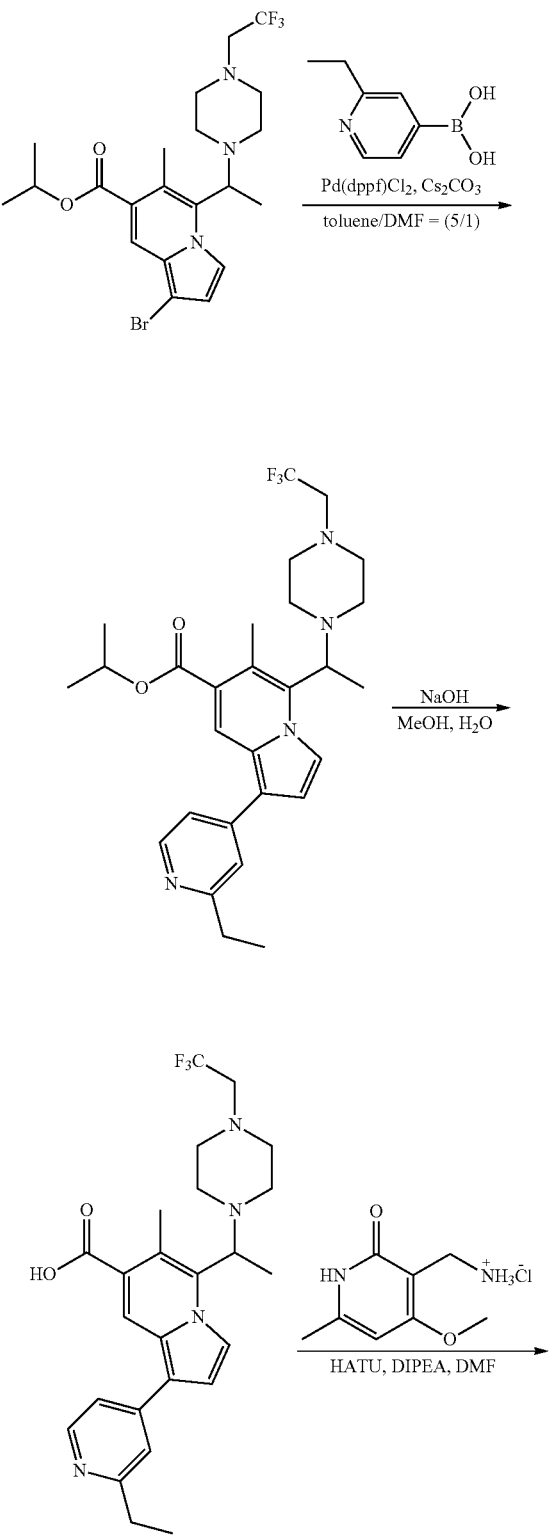

403

-continued

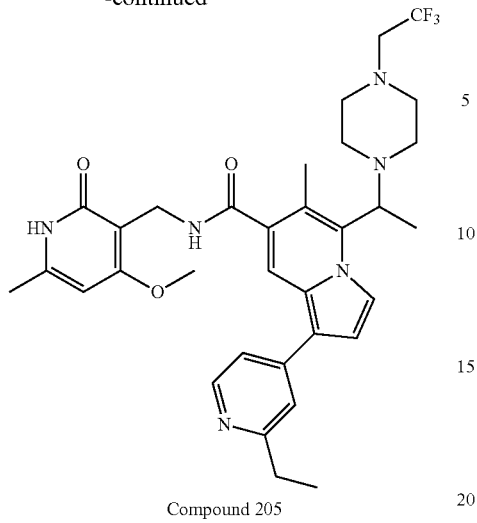

Compound 205

Step 1: Preparation of isopropyl 1-(2-ethylpyridin-4-yl)-6-methyl-5-(1-(4-(2,2,2-trifluoroethyl)piperazin-1-yl)ethyl)indolizine-7-carboxylate: yield of two steps was 31%. MS (ESI) m/z 517 [M+H]⁺.

Step 2: Preparation of 1-(2-ethylpyridin-4-yl)-6-methyl-5-(1-(4-(2,2,2-trifluoroethyl)piperazin-1-yl)ethyl)indolizine-7-carboxylic acid: yield 93%. MS (ESI) m/z 475 [M+H]⁺.

Step 3: Preparation of 1-(2-ethylpyridin-4-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: yield 44%. $^1$H-NMR (CDCl$_3$, 400 MHz) δ ppm 8.46 (s, 1H), 8.34 (d, J=5.2 Hz, 1H), 7.92 (t, J=4.8 Hz, 1H), 7.76 (s, 1H), 7.23-7.20 (m, 2H), 6.93 (d, J=2.8 Hz, 1H), 5.83 (s, 1H), 4.57 (d, J=5.6 Hz, 2H), 4.07 (q, J=6.8 Hz, 1H), 3.87 (s, 3H), 2.95 (q, J=6.8 Hz, 3H), 2.78-2.05 (m, 8H), 2.41 (s, 3H), 2.31-2.19 (m, 2H), 2.11 (s, 3H), 1.48 (d, J=6.8 Hz, 3H), 1.18 (t, J=7.6 Hz, 3H); MS (ESI) m/z 625 [M+H]⁺.

Example 195: Preparation of 1-(2-isopropylpyridin-3-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: Similar to Example 50

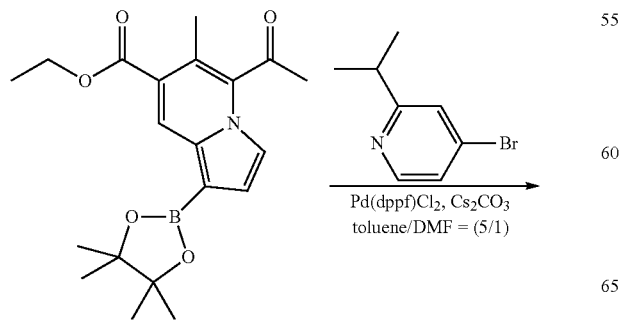

404

-continued

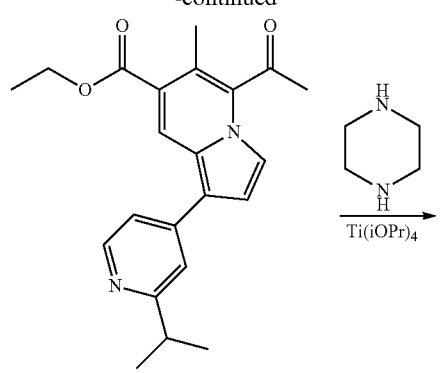

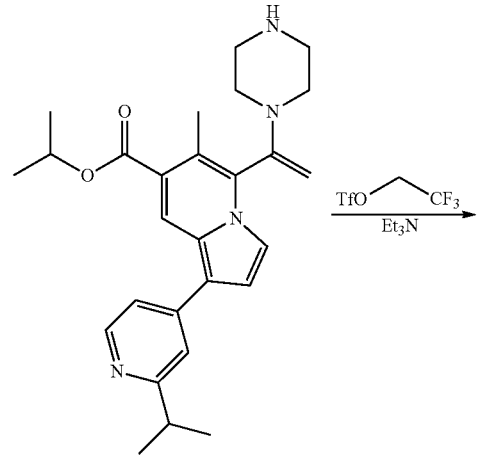

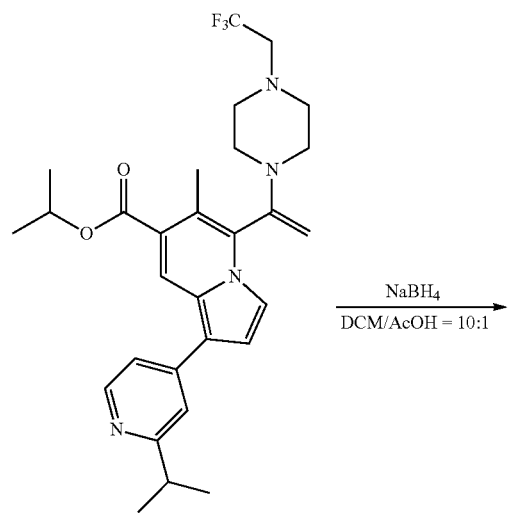

-continued

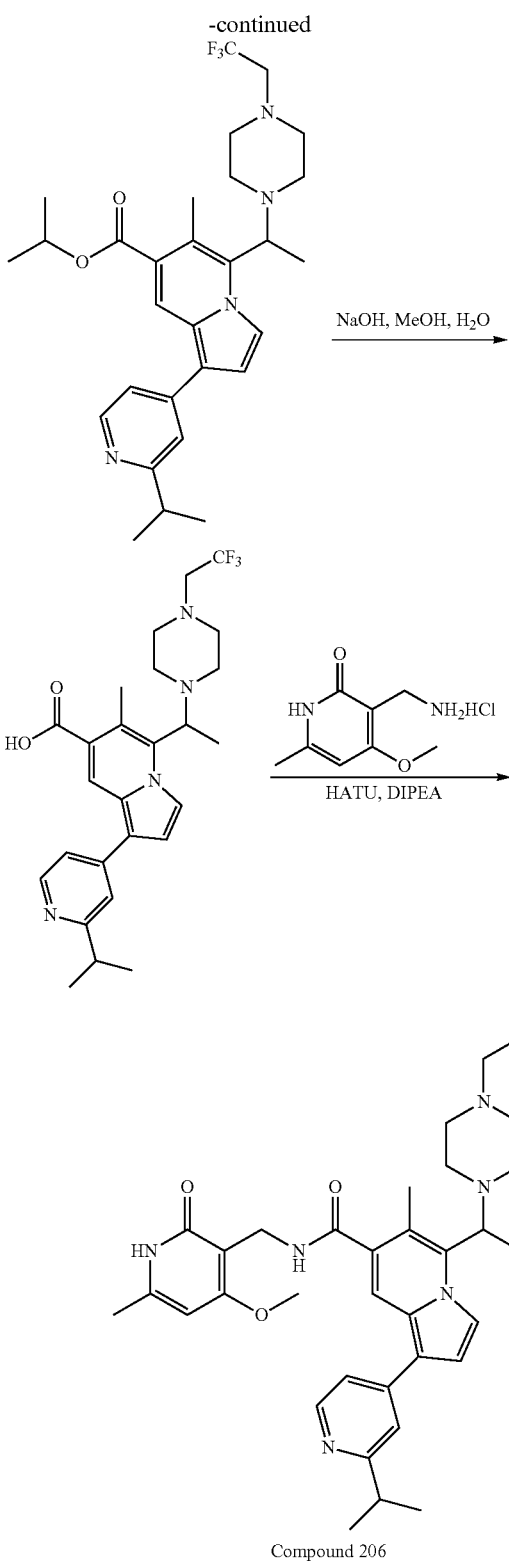

Compound 206

Step 1: Preparation of ethyl 5-acetyl-1-(2-isopropylpyridin-4-yl)-6-methylindolizine-7-carboxylate: yield 54%. MS (ESI) m/z 365 [M+H]+.

Step 2: Preparation of isopropyl 1-(2-isopropylpyridin-4-yl)-6-methyl-5-(1-(piperazin-1-yl)vinyl)indolizine-7-carboxylate: MS (ESI) m/z 447 [M+H]+.

Step 3: Preparation of isopropyl 1-(2-isopropylpyridin-4-yl)-6-methyl-5-(1-(4-(2,2,2-trifluoroethyl)piperazin-1-yl)vinyl)indolizine-7-carboxylate: yield of two steps was 39%. MS (ESI) m/z 529 [M+H]+.

Step 4: Preparation of isopropyl 1-(2-isopropylpyridin-4-yl)-6-methyl-5-(1-(4-(2,2,2-trifluoroethyl)piperazine-1-yl)ethyl)indolizine-7-carboxylate: MS (ESI) m/z 531 [M+H]+.

Step 5: Preparation of 1-(2-isopropylpyridin-4-yl)-6-methyl-5-(1-(4-(2,2,2-trifluoroethyl)piperazine-1-yl)ethyl)indolizine-7-carboxylic acid: MS (ESI) m/z 489 [M+H]+.

Step 6: Preparation of 1-(2-isopropylpyridin-4-yl)-N-((4-methoxy-6-methyl-2-oxo-1,2-dihydropyridin-3-yl)methyl)-6-methyl-5-(1-(4-(2,2,2-trifluoroethyl)piperazin-1-yl)ethyl)indolizine-7-carboxamide: yield of three steps was 34%. $^1$H-NMR (CDCl$_3$, 400 MHz) δ ppm 8.47 (s, 1H), 8.39 (d, J=6.0 Hz, 1H), 7.83 (t, J=4.2 Hz, 1H), 7.75 (s, 1H), 7.24 (d, J=4.4 Hz, 1H), 6.95 (d, J=3.2 Hz, 1H), 5.84 (s, 1H), 4.56 (d, J=5.6 Hz, 2H), 4.07 (q, J=6.8 Hz, 1H), 3.86 (s, 3H), 3.01-2.90 (m, 3H), 2.70-2.61 (m, 6H), 2.41 (s, 3H), 2.28-2.10 (m, 2H), 2.12 (s, 3H), 1.48 (d, J=6.8 Hz, 3H), 1.21 (d, J=7.2 Hz, 6H); MS (ESI) m/z 639 [M+H]+.

Example 196: Preparation of 1-(2,3-dihydro-1H-pyrrolo[2,3-b]pyridin-4-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: Similar to Example 50

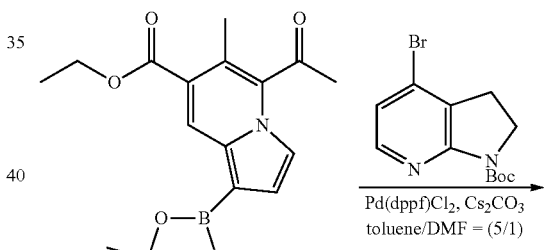

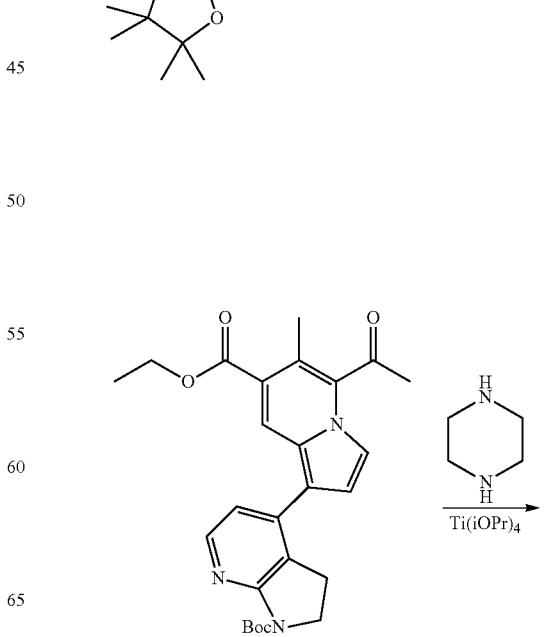

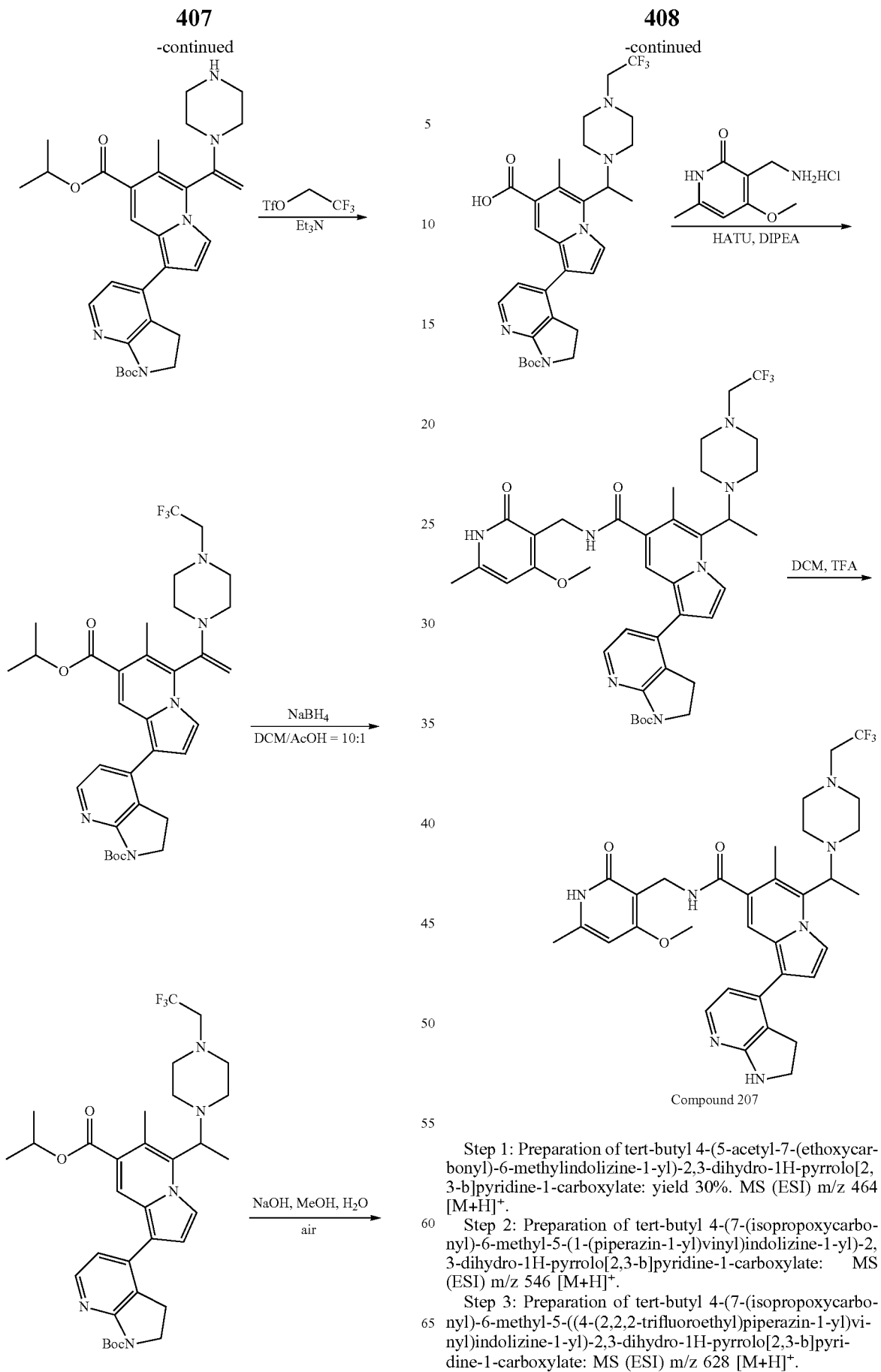

Step 1: Preparation of tert-butyl 4-(5-acetyl-7-(ethoxycarbonyl)-6-methylindolizine-1-yl)-2,3-dihydro-1H-pyrrolo[2,3-b]pyridine-1-carboxylate: yield 30%. MS (ESI) m/z 464 [M+H]⁺.

Step 2: Preparation of tert-butyl 4-(7-(isopropoxycarbonyl)-6-methyl-5-(1-(piperazin-1-yl)vinyl)indolizine-1-yl)-2,3-dihydro-1H-pyrrolo[2,3-b]pyridine-1-carboxylate: MS (ESI) m/z 546 [M+H]⁺.

Step 3: Preparation of tert-butyl 4-(7-(isopropoxycarbonyl)-6-methyl-5-((4-(2,2,2-trifluoroethyl)piperazin-1-yl)vinyl)indolizine-1-yl)-2,3-dihydro-1H-pyrrolo[2,3-b]pyridine-1-carboxylate: MS (ESI) m/z 628 [M+H]⁺.

Step 4: Preparation of tert-butyl 4-(7-(isopropoxycarbonyl)-6-methyl-5-((4-(2,2,2-trifluoroethyl)piperazin-1-yl)ethyl)indolizine-1-yl)-2,3-dihydro-1H-pyrrolo[2,3-b]pyridine-1-carboxylate: yield of three steps was 27%. MS (ESI) m/z 630 [M+H]⁺.

Step 5: Preparation of 1-(1-(tert-butoxycarbonyl)-2,3-dihydro-1H-pyrrolo[2,3-b]pyridin-4-yl)-6-methyl-5-(1-(4-(2,2,2-trifluoroethyl)piperazin-1-yl)ethyl)indolizine-7-carboxylic acid: Yield 68%. MS (ESI) m/z 588 [M+H]⁺.

Step 6: Preparation of tert-butyl 4-(7-((4-methoxy-6-methyl-2-oxo-1,2-dihydropyridin-3-yl)methyl)carbamoyl)-6-methyl-5-(1-(4-(2,2,2-trifluoroethyl)piperazin-1-yl)ethyl)indolizine-1-yl)-2,3-dihydro-1H-pyrrole[2,3-b]pyridine-1-carboxylate: Yield 26%. MS (ESI) m/z 738 [M+H]⁺.

Step 7: Preparation of 1-(2,3-dihydro-1H-pyrrolo[2,3-b]pyridin-4-yl)-N-((4-methoxy-6-methyl-2-oxo)-1,2-dihydropyridin-3-yl)methyl)-6-methyl-5-(1-(4-(2,2,2-trifluoroethyl)piperazin-1-yl)ethyl)indolizine-7-carboxamide: yield 95%. ¹H-NMR (CDCl₃, 400 MHz) δ ppm 8.45 (s, 1H), 7.83 (t, J=4.8 Hz, 1H), 7.68 (d, J=5.6 Hz, 1H), 7.54 (s, 1H), 6.82 (d, J=2.8 Hz, 1H), 6.64 (d, J=5.6 Hz, 1H), 5.90 (s, 1H), 5.55-5.30 (m, 2H), 4.55 (ddd, J=18.0, 13.6, 6.8 Hz, 2H), 4.08 (q, J=6.8 Hz, 1H), 3.88 (s, 3H), 3.50 (t, J=8.4 Hz, 2H), 3.08 (t, J=8.0 Hz, 2H), 2.94 (q, J=8.4 Hz, 2H), 2.80-2.60 (m, 6H), 2.40 (s, 3H), 2.38-2.36 (m, 2H), 2.28 (s, 3H), 1.49 (d, J=6.8 Hz, 3H); MS (ESI) m/z 638 [M+H]⁺.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A compound of formula I, or a pharmaceutically acceptable salt, an enantiomer, a diastereomer, a tautomer, a solvate, or a polymorph thereof,

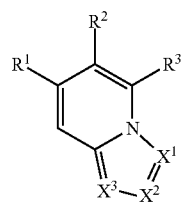

I wherein X¹ is CR⁴ or N;
X² is CR⁵;
X³ is CR⁶ or N; and at most one of X¹, X³ is N;
R⁴ is selected from H, a halogen, substituted or unsubstituted C1-C6 alkyl;
R⁵ or R⁶ is selected from H, a halogen, —COOH, —CN, substituted or unsubstituted 5-8 membered aryl, substituted or unsubstituted 5-8 membered heteroaryl, substituted or unsubstituted 5-8 membered aryl fused to substituted or unsubstituted 5-8 membered heterocyclic group, substituted or unsubstituted 5-8 membered heteroaryl fused to substituted or unsubstituted 5-8 membered heterocyclic group, substituted or unsubstituted 5-8 membered aryl fused to substituted or unsubstituted 5-8 membered carbocyclic group, substituted or unsubstituted 5-8 membered heteroaryl fused to substituted or unsubstituted 5-8 membered carbocyclic group, substituted or unsubstituted 4-8 membered saturated or unsaturated carbocyclic group, substituted or unsubstituted 4-8 membered saturated or unsaturated heterocyclic group, substituted or unsubstituted C1-C6 alkylcarbonyl, —C(O)O-(substituted or unsubstituted C1-C6 alkyl), —C(O)(NRᵃRᵇ), substituted or unsubstituted —(CH₂)ₘNRᵃRᵇ, substituted or unsubstituted C1-C6 alkyl, boronic acid group, substituted or unsubstituted C2-C8 alkenyl, substituted or unsubstituted C2-C8 alkynyl; wherein the heteroaryl or heterocyclic group contains 1-3 hetero atoms selected from N, O, S, P; m is an integer from 0 to 5; and said "substituted" means having one or more substituents selected from group A;

Wherein Rᵃ, Rᵇ are each independently selected from H, a halogen, substituted or unsubstituted C1-C6 alkyl, substituted or unsubstituted 5-8 membered carbocyclic ring, substituted or unsubstituted 5-8 membered heterocyclic ring, or Rᵃ and Rᵇ are bonded to N to form a substituted or unsubstituted 4-8 membered heterocyclic ring; wherein said heterocyclic ring contains 1-3 hetero atoms selected from N, O, S, or P;

R¹ is

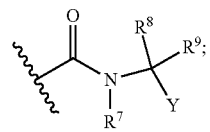

R² is selected from halogen, substituted or unsubstituted C1-C6 alkyl, substituted or unsubstituted aryl;
R³ is

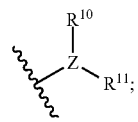

wherein, R⁷ is selected from H, substituted or unsubstituted C1-C6 alkyl;
R⁸ and R⁹ are each independently selected from H, a substituted or unsubstituted C1-C6 alkyl;
Y is selected from

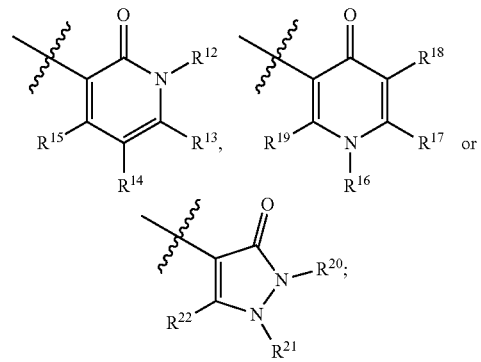

wherein, R¹² and R¹³ are each independently selected from H, substituted or unsubstituted C1-C4 alkyl;
R¹⁴ and R¹⁵ are each independently selected from H, a halogen, —NH₂, —NO₂, —CF₃, substituted or unsubstituted C1-C4 alkyl, substituted or unsubstituted C1-C4 alkoxy, substituted or unsubstituted (CH$_2$)$_n$NR-$^c$R$^d$, or R$^{14}$ and R$^{15}$ are joined to form a substituted or unsubstituted 5-6 membered saturated heterocyclic ring, or R$^{14}$ and R$^{15}$ are linked to form a substituted or unsubstituted 5-6 membered aromatic ring; n is an integer of 0-4;

R$^{16}$ is H, a substituted or unsubstituted C1-C4 alkyl;

R$^{17}$ and R$^{19}$ are each independently selected from H, a substituted or substituted C1-C4 alkyl, substituted or unsubstituted C1-C4 alkoxy, —(CH$_2$)$_n$NR$^c$R$^d$; n is an integer from 0-4;

R$^{18}$ is selected from H, a halogen, —NH$_2$, —NO$_2$, substituted or substituted C1-C4 alkyl, substituted or unsubstituted C1-C4 alkoxy, substituted or unsubstituted (CH$_2$)$_n$NR$^c$R$^d$; where n is an integer from 0-4;

R$^{20}$ and R$^{21}$ are each independently selected from H, a substituted or substituted C1-C4 alkyl;

R$^{22}$ is selected from H, a substituted or unsubstituted C1-C4 alkyl;

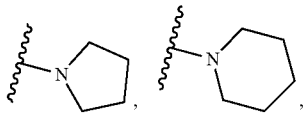

or substituted or unsubstituted C1-C4 alkoxy;

wherein R$^c$, R$^d$ are each independently selected from H, a substituted or unsubstituted C1-C4 alkyl;

Z is selected from N or CH;

R$^{10}$ and R$^{11}$ are each independently selected from: H, —OH, a substituted or unsubstituted C1-C6 alkyl, —OR$^e$, substituted or unsubstituted 4-8 membered heterocyclic group, substituted or unsubstituted 4-8 membered carbocyclic group, substituted or unsubstituted 5-8 membered aryl, —NR$^f$R$^g$; wherein said heterocyclic ring contains 1-3 hetero atoms selected from N, O, S, or P; and said "substituted" means having one or more substituents selected from group B;

wherein R$^e$ is selected from H, a substituted or unsubstituted C1-C6 alkyl, substituted or unsubstituted C2-C6 alkenyl, substituted or unsubstituted C2-C6 alkynyl, substituted or unsubstituted saturated or unsaturated 4-8 membered carbocyclic ring, substituted or unsubstituted saturated or unsaturated 4-8 membered heterocyclic ring, substituted or unsubstituted 5-8 membered aryl, substituted or unsubstituted 5-8 membered heteroaryl, —(CH$_2$)$_p$(substituted or unsubstituted 5-8 membered aryl), —(CH$_2$)$_p$(substituted or unsubstituted 5-8 membered heteroaryl); wherein the heterocyclic or heteroaryl group comprises 1-3 heteroatoms selected from N, O, S, or P; p is an integer from 0 to 3; and said "substituted" refers to one or more of the following substituent: halogen, C1-C4 alkyl, C1-C4 alkoxy, —NO$_2$, —NR$^s$R$^t$;

wherein R$^f$ and R$^g$ are each independently selected from: H, a substituted or unsubstituted C1-C6 alkyl, wherein the substituent is —OH, C1-C4 alkoxy, or —NR$^s$R$^t$;

group A substituents are selected from the group consisting of H, =O, —CN, —COOH, —NR$^s$R$^t$, a halogen, substituted or unsubstituted C1-C6 alkoxycarbonyl, unsubstituted or substituted C1-C6 alkyl, substituted or unsubstituted 4-8 membered heterocyclic group, substituted or unsubstituted C1-C4 alkoxy; wherein the heterocyclic group contains 1-3 hetero atoms selected from N, O, S or P;

group B substituents are selected from the group consisting of H, —OH, a halogen, unsubstituted or substituted C1-C6 alkyl, —NR$^s$R$^t$, —NO$_2$, substituted or unsubstituted C1-C6 alkoxycarbonyl, substituted or unsubstituted C1-C6 alkylsulfonyl, substituted or unsubstituted C1-C6 alkylcarbonyl, substituted or unsubstituted C1-C6 alkoxy, substituted or unsubstituted 4-6 membered heterocyclic ring, substituted or unsubstituted C5-C8 heteroaryl, Boc, benzyl; wherein said heteroaryl comprises 1-3 heteroatoms selected from N, O, S or P;

also, in the group A and group B substituents and R$^a$, R$^b$, the substitution means having one or more substitutions selected from group C: H, a halogen, —OH, —CN, C1-C4 alkyl, C1-C4 alkoxy, —NR$^s$R$^t$, 5-8 membered aryl, 4-8 membered heterocyclic group, Boc, C1-C4 acyl; and said substitution is one or more substituents;

and, in the R$^7$, R$^8$, R$^9$, R$^{12}$, R$^{13}$, R$^{14}$, R$^{15}$, R$^{16}$, R$^{17}$, R$^{18}$, R$^{19}$, R$^{20}$, R$^{21}$, R$^{22}$, R$^c$, R$^d$, the "substituted" means having one or more substituents selected from the group D:H, a halogen, C1-C4 alkyl, C1-C4 haloalkyl, nitro, —OH, amino;

R$^s$ and R$^t$ are each independently selected from the group consisting of: H, a C1-C4 alkyl, C1-C4 haloalkyl.

2. The compound of claim 1, or a pharmaceutically acceptable salt, enantiomer, diastereomer, tautomer, solvate, or polymorph thereof, wherein R$^{10}$ is a substituted or unsubstituted C1-C4 alkoxy, substituted or unsubstituted C1-C4 alkyl.

3. The compound of claim 1, or a pharmaceutically acceptable salt, enantiomer, diastereomer, tautomer, solvate, or polymorph thereof, wherein R$^{11}$ is selected from the group consisting of —OH,

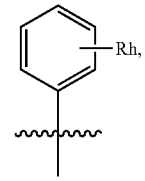

—OR$^c$, —NR$^f$R$^g$,

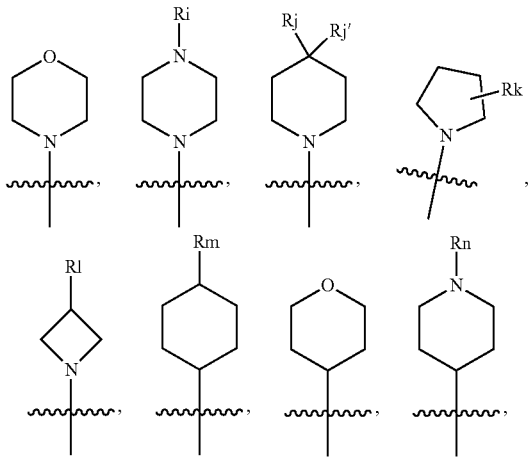

-continued

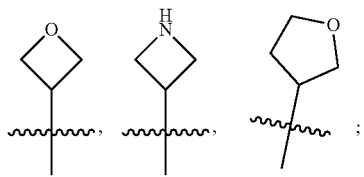

wherein R$^e$ is selected from the group consisting of substituted or unsubstituted C1-C4 alkyl, allyl, isobutenyl, propargyl, cyclohexane group, cyclohexenyl,

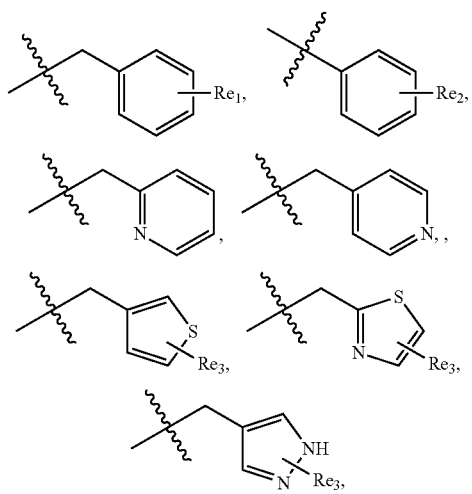

wherein, R$^{e1}$ is selected from the group consisting of H, a halogen, C1-C4 alkoxy; and the number of R$^{e1}$ is 1-3; R$^{e2}$ is selected from —NO$_2$, —NH$_2$, —N(CH$_3$)$_2$; R$^{e3}$ is selected from H, a halogen, —NR$^s$R$^t$, substituted or unsubstituted C1-C4 alkyl (preferably methyl);

R$^f$ is H, a substituted or unsubstituted C1-C4 alkyl;

R$^g$ is a C1-C4 alkoxy or —NR$^s$R$^t$, substituted C1-C4 alkyl;

R$^h$ is selected from H, a halogen;

R$^i$ is selected from H, an unsubstituted or substituted C1-C4 alkyl, substituted or unsubstituted C1-C4 alkylcarbonyl, substituted or unsubstituted C1-C4 alkoxycarbonyl, substituted or unsubstituted C1-C4 alkylsulfonyl, trifluoromethyl C1-C2 alkyl, difluoromethyl C1-C2 alkyl, —NR$^s$R$^t$, and

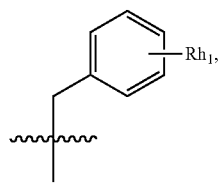

wherein R$^{h1}$ is selected from —OH, —CN, a C1-C4 alkyl;

R$^j$ is selected from the group consisting of: —OH, a halogen, C1-C4 alkoxy, —NR$^s$R$^t$,

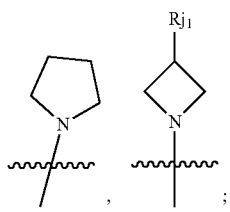

wherein R$^{j1}$ is selected from a C1-C4 alkoxy (preferably a methoxy);

R$^{j'}$ is selected from H or a halogen;

and when R$^j$ is a halogen, then R$^{j'}$ is a halogen;

R$^k$ is selected from the group consisting of H, —OH, a C1-C4 alkoxy,

R$^l$ is selected from the group consisting of H, —NR$^s$R$^t$, preferably H or dimethylamino;

R$^m$ is selected from the group consisting of: H, —NR$^s$R$^t$, preferably H or dimethylamino;

R$^n$ is selected from the group consisting of a trifluoromethyl C1-C4 alkyl, preferably CF$_3$CH$_2$—.

4. The compound of claim 1, or a pharmaceutically acceptable salt, enantiomer, diastereomer, tautomer, solvate, or polymorph thereof, wherein R$^5$ or R$^6$ are each independently selected from the group consisting of H, a substituted or unsubstituted C1-C4 alkyl, —CN, halogen, C1-C4 alkylcarbonyl, R$^{51}$(C1-C4 alkoxy)carbonyl, R$^{52}$C(O)—, —COOH, —C(O)(NR$^a$R$^b$),

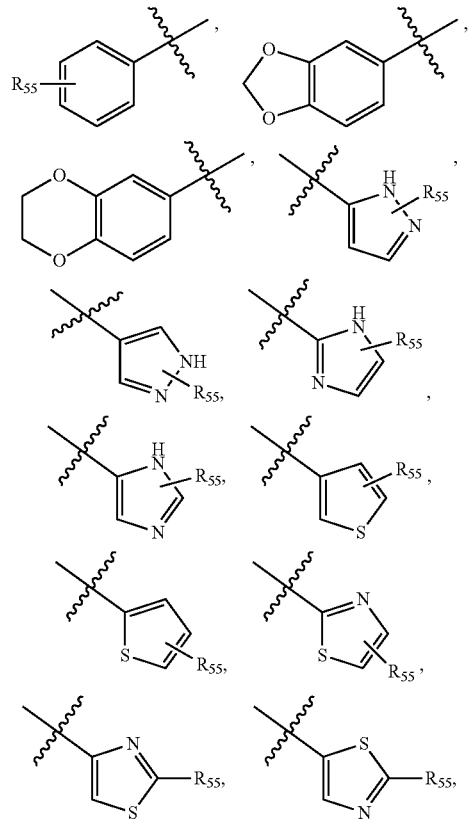

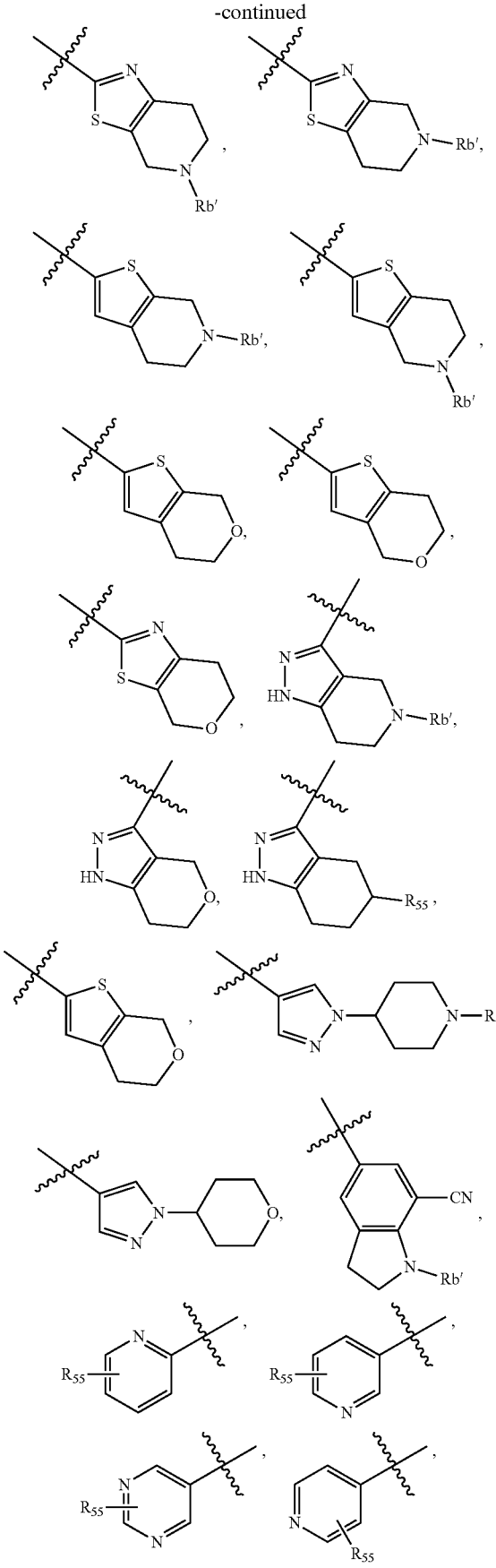

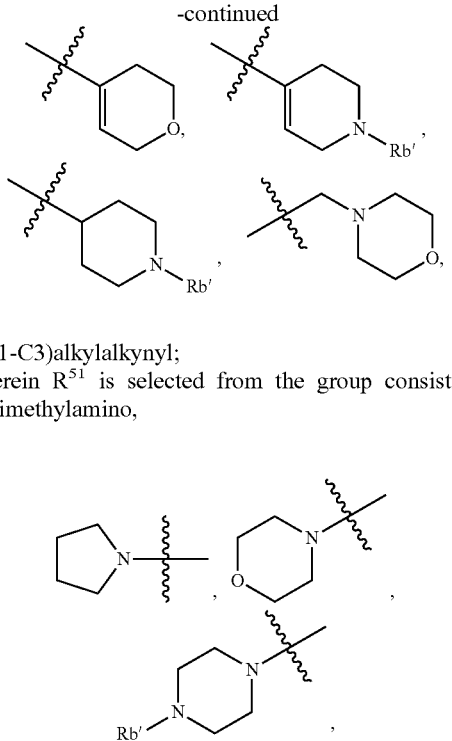

R⁵⁷(C1-C3)alkylalkynyl;
wherein $R^{51}$ is selected from the group consisting of dimethylamino,

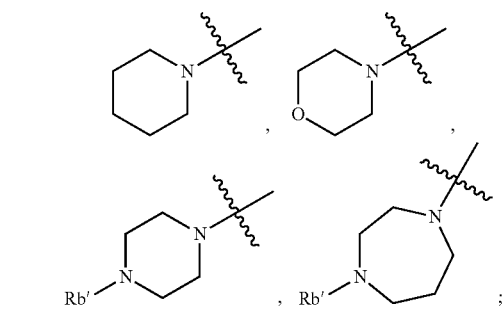

and wherein $R^b$ is selected from the group consisting of H, a C1-C4 alkyl, Boc, C1-C4 acyl;
$R^{52}$ is selected from

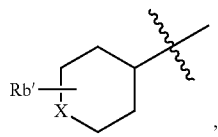

$R^a$ is selected from H, a substituted or unsubstituted C1-C4 alkyl;
$R^b$ is selected from H, a substituted or unsubstituted C1-C4 alkyl, cyclopentyl,
$R^{b''}$(C1-C4)alkyl; wherein X is hetero atom selected from N, O or S;
$R^{55}$ is 1-3 substituents selected from the group consisting of H, $R^{551}$C1-C4 alkyl, halogen, —CN, —NH₂, (C1-C4 alkyl)NH-, ($R^{551}$C1-C4 alkyl)O—, dimethylamino, —CH₂(Me)₂,

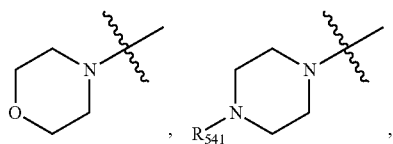

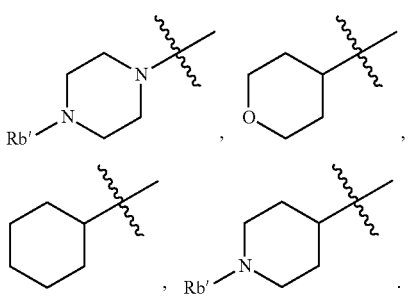

$R^{551}$(C1-C6)alkyl OC(O)—, —COOH, —C(O)(NR$^a$R$^b$); wherein $R^{551}$ is H, —OH, a C1-C4 alkoxy, amino, dimethylamino, methylamino, diethylamino, methylethylamino, ethylamino,

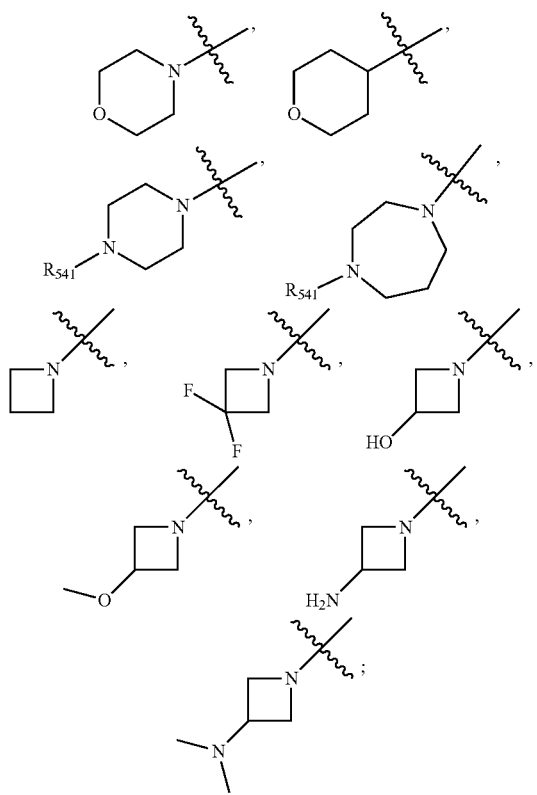

wherein $R^{541}$ is selected from H, a C1-C4 alkyl;
$R^{57}$ is selected from a (C1-C4)alkyl,

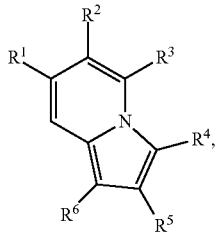

dimethylamino;
$R^b$ is selected from the group consisting of —OH, a C1-C3 alkoxy, dimethylamino,

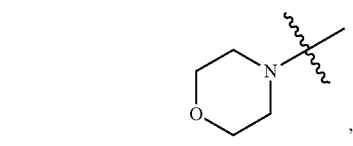 [SMILES: *N1CCOCC1]

5. The compound of claim 1, or a pharmaceutically acceptable salt, enantiomer, diastereomer, tautomer, solvate, or polymorph thereof, wherein the compound of formula I has the structure of formula Ia below:

Ia

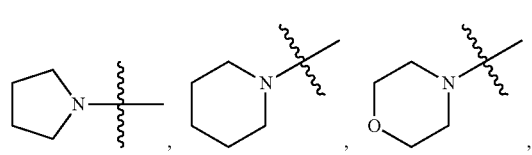

where the said $R^1$, $R^2$, $R^3$, $R^4$, $R^5$, $R^6$ are as described above.

6. A compound, or a pharmaceutically acceptable salt, enantiomer, diastereomer, tautomer, solvate, or polymorph thereof, wherein the compound is selected from the group consisting of

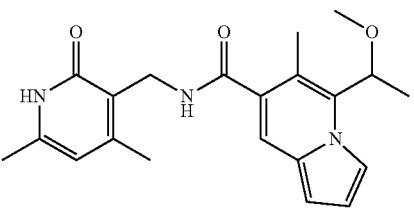

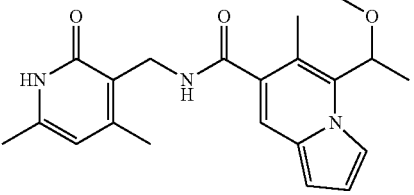

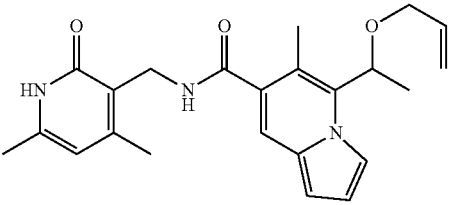

419
-continued
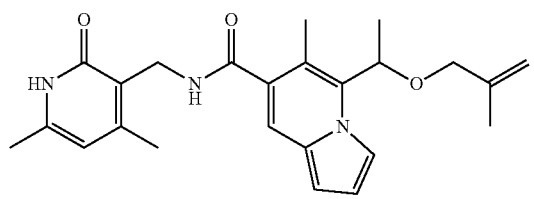
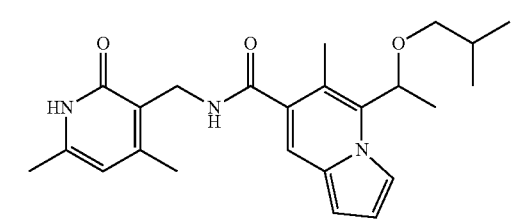
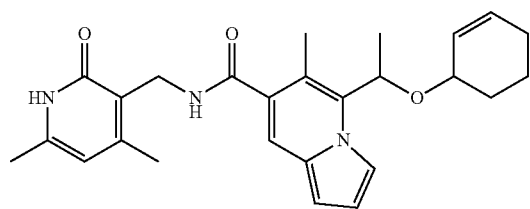
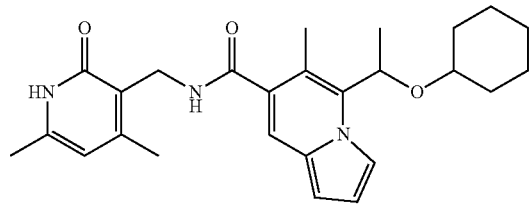
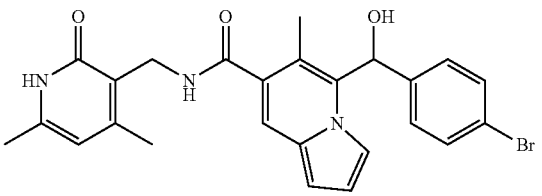
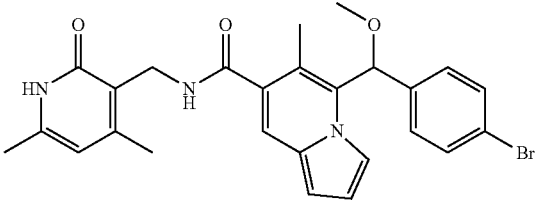
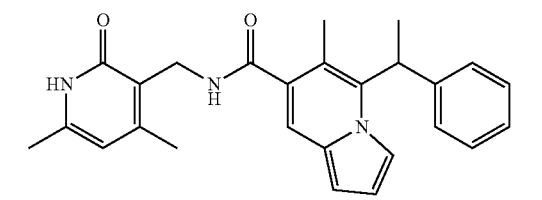
420
-continued
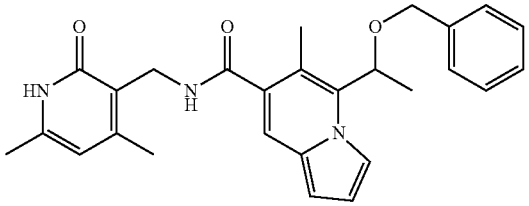
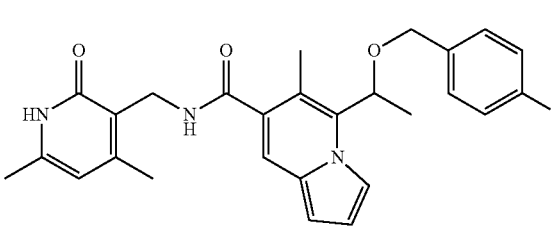
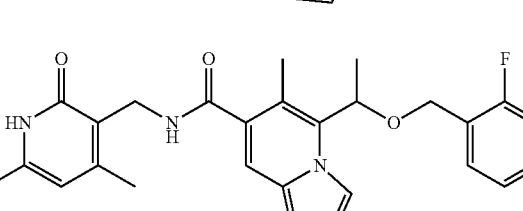
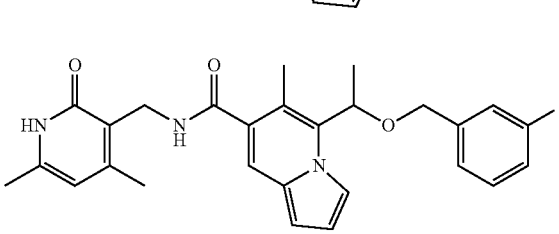
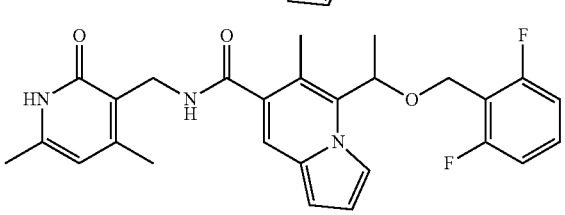
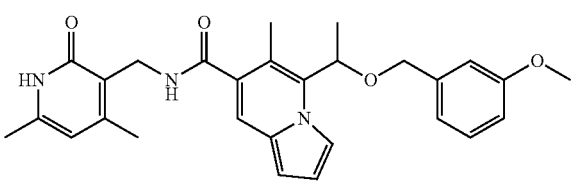
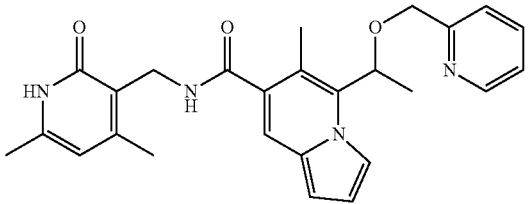
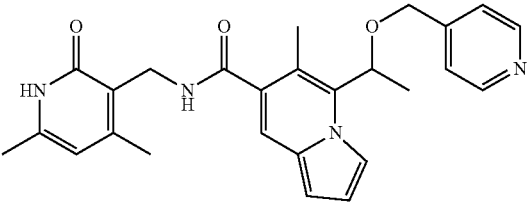

421
-continued
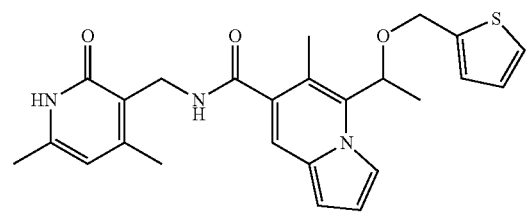
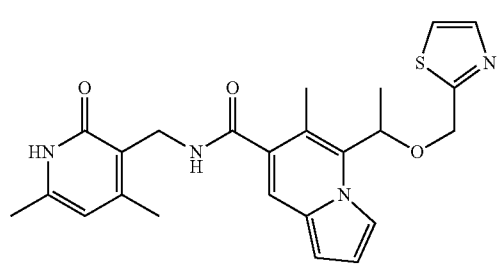
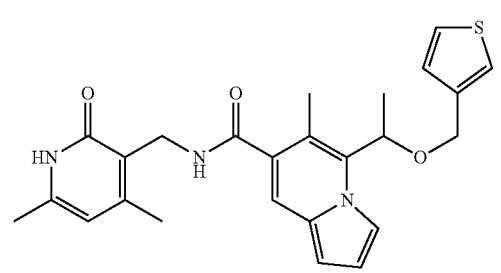
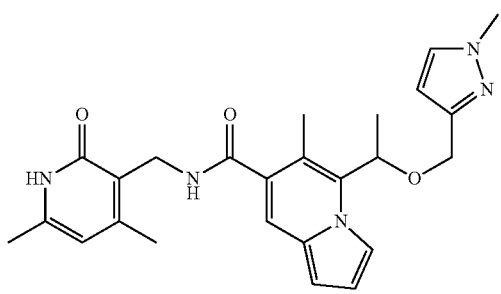
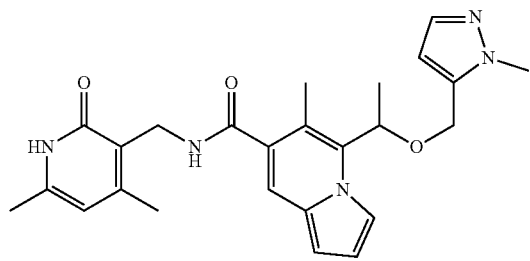
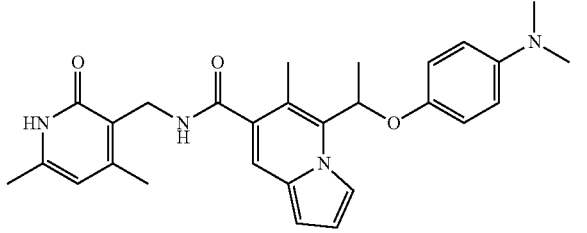
422
-continued
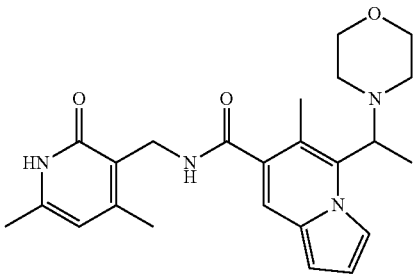
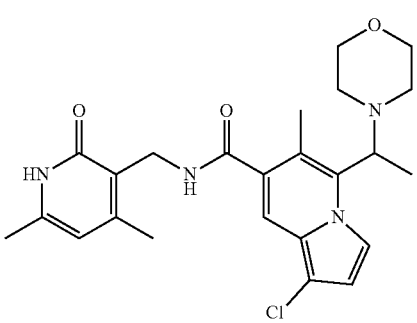
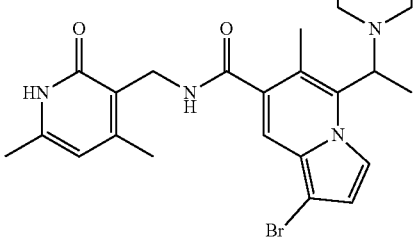
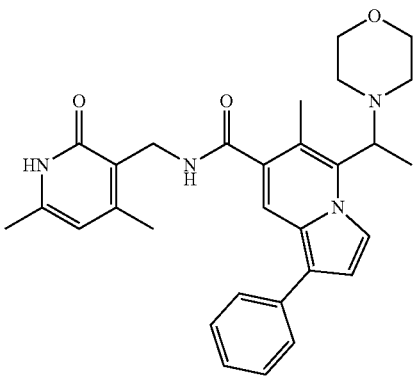
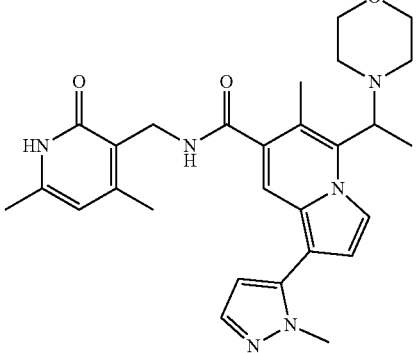

423
-continued
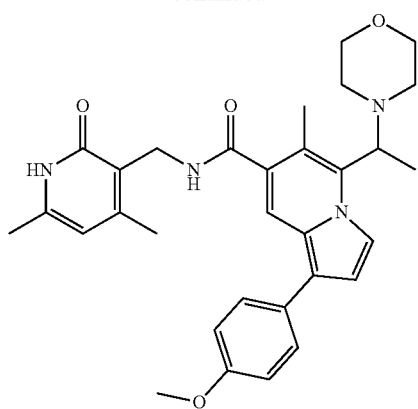
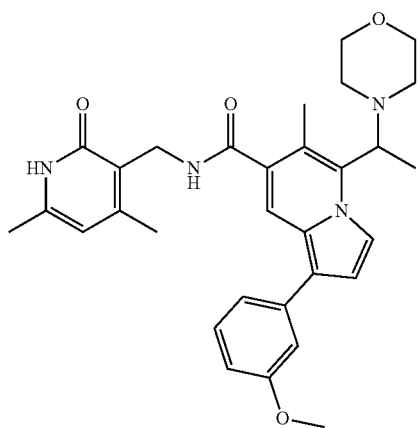
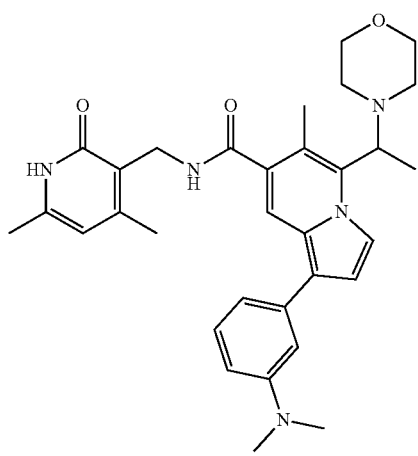
424
-continued
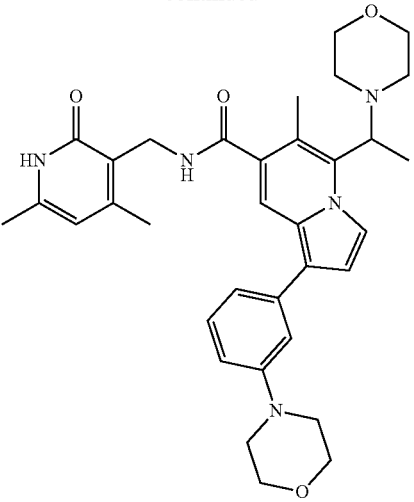
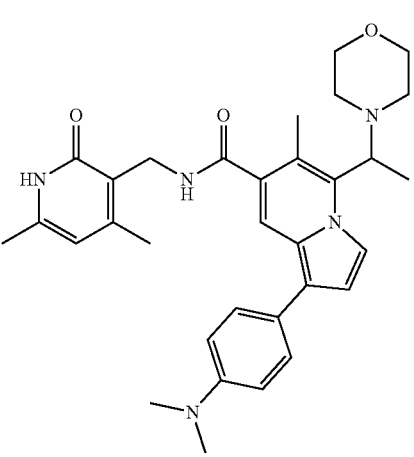
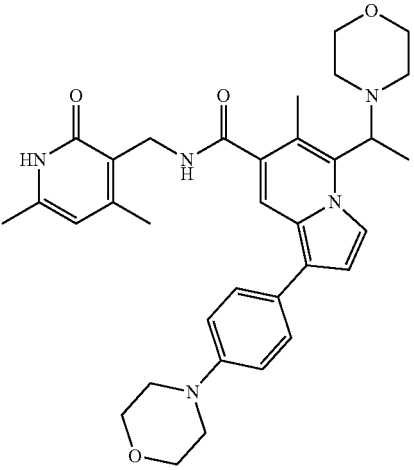

425
-continued
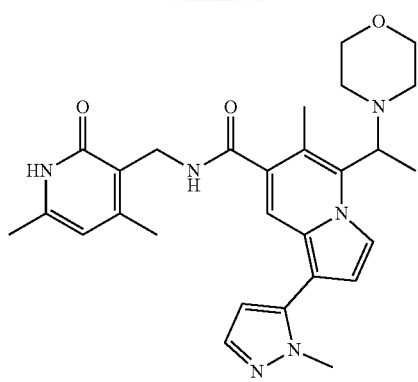
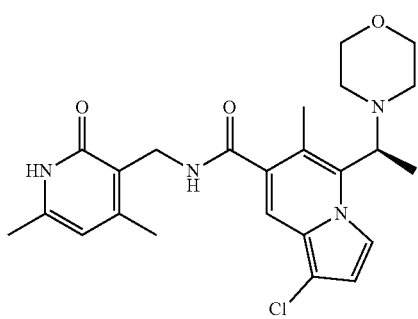
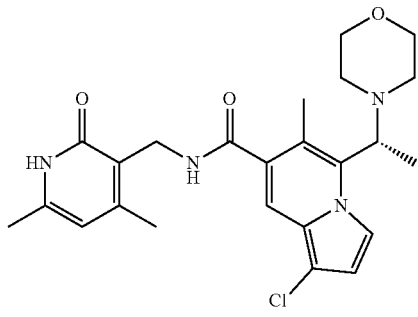
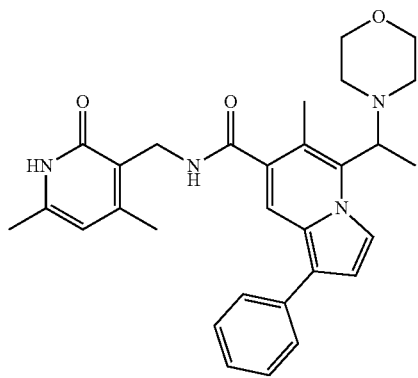
426
-continued
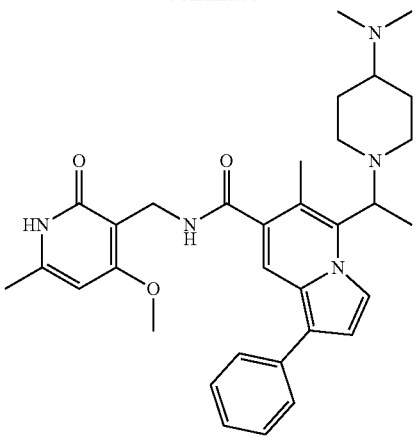
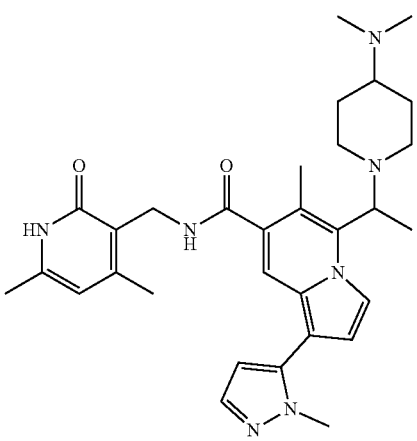
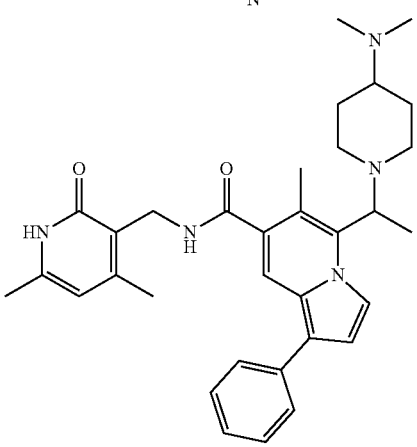
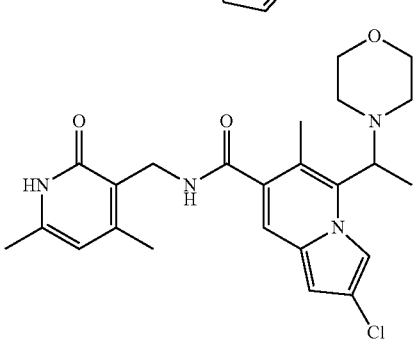

427
-continued
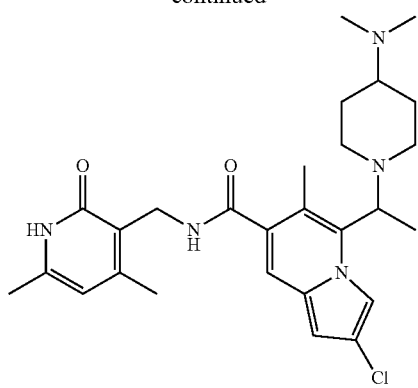
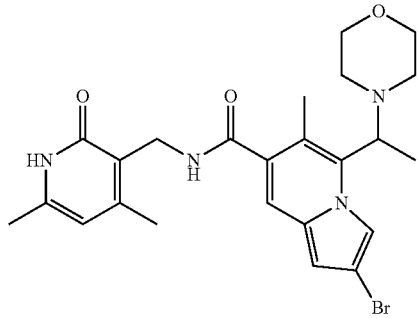
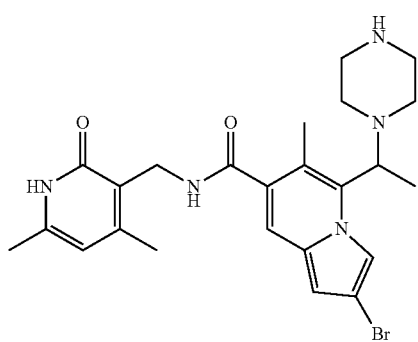
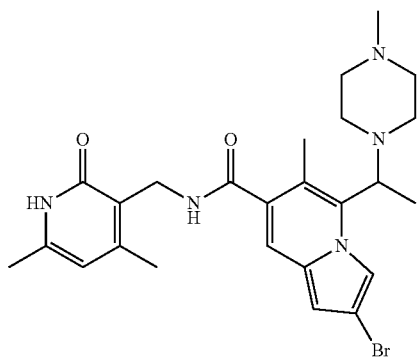
428
-continued
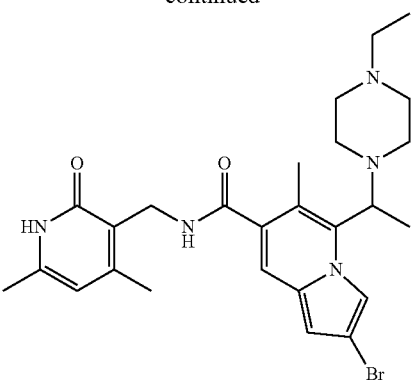
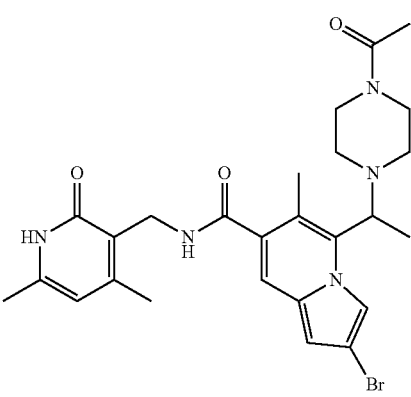
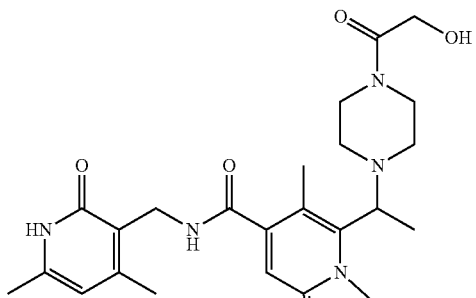
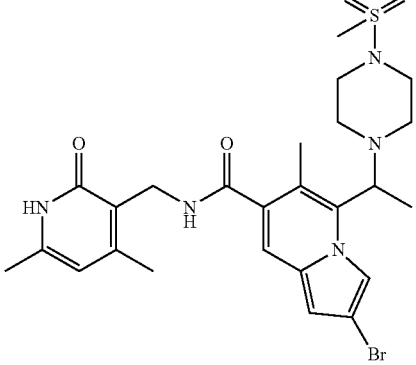

429
-continued
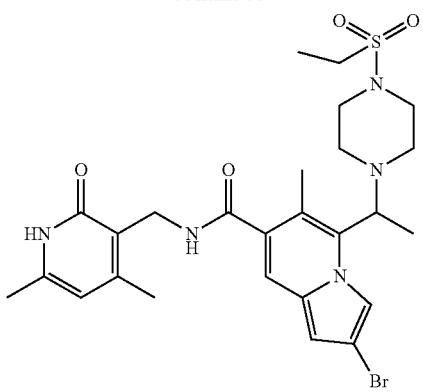
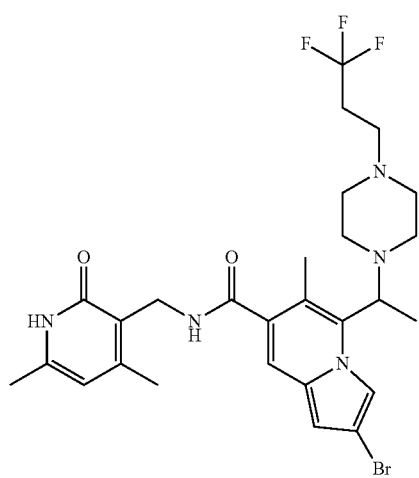
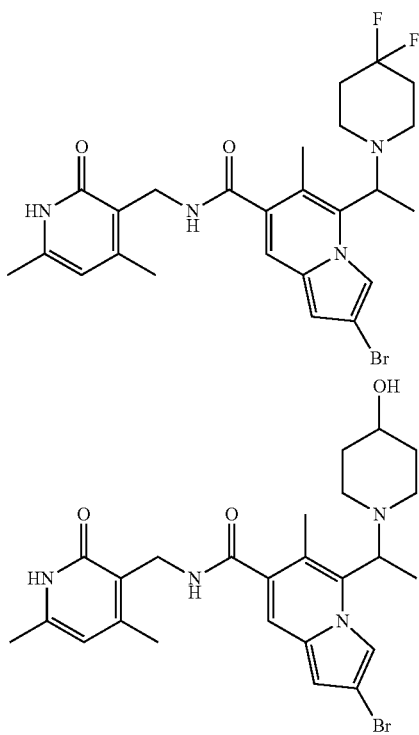
430
-continued
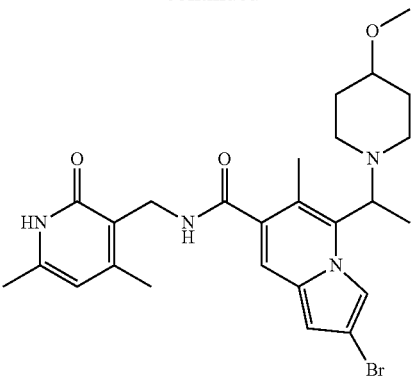
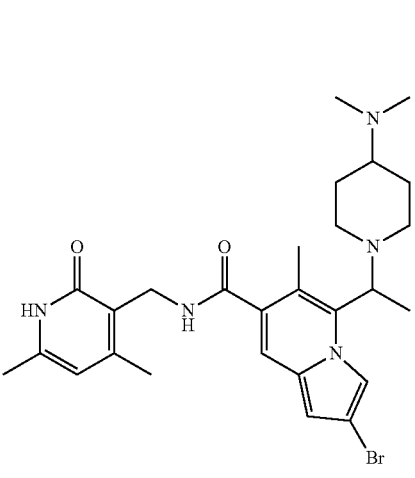
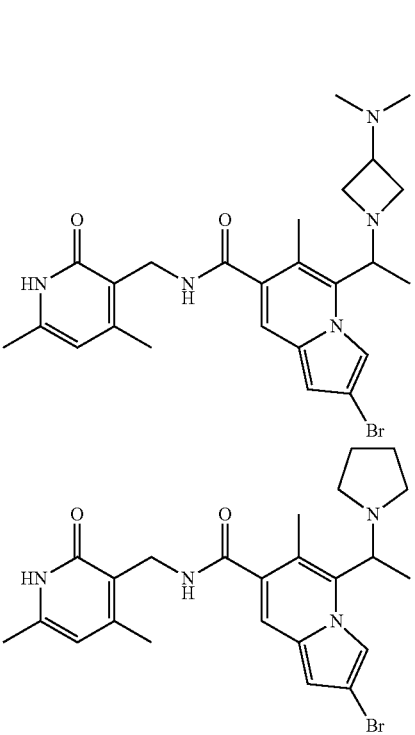

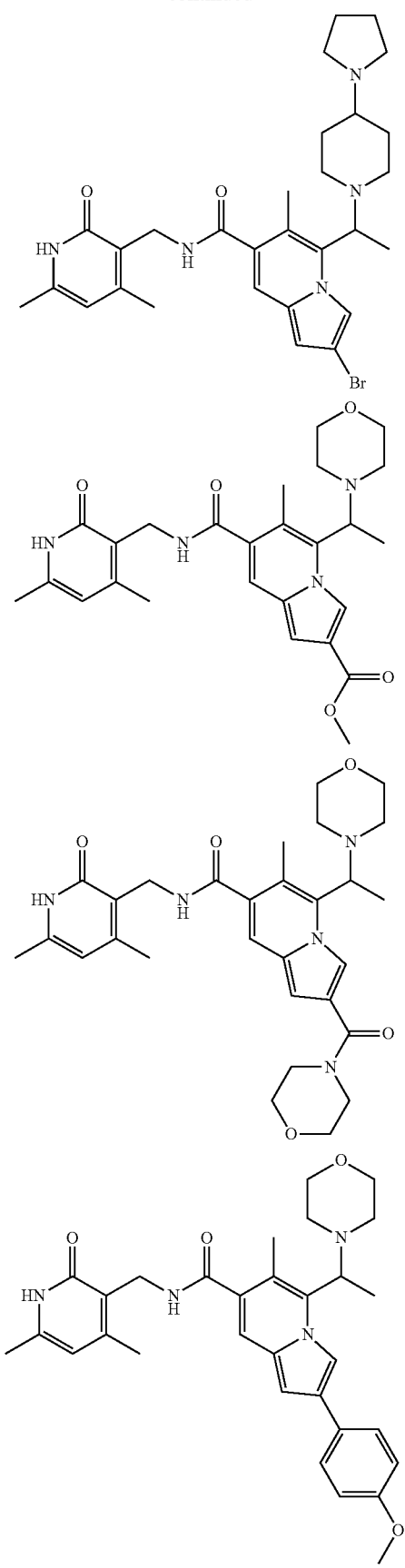
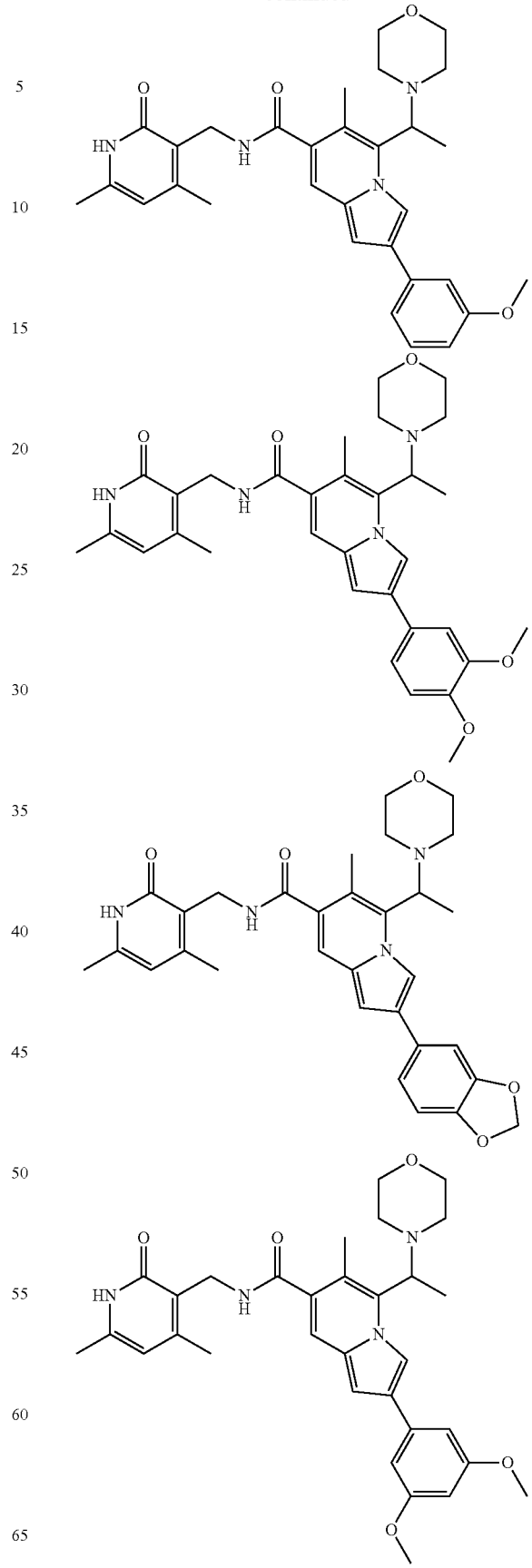

433
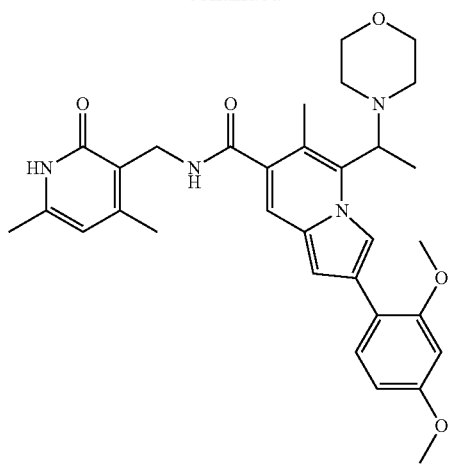
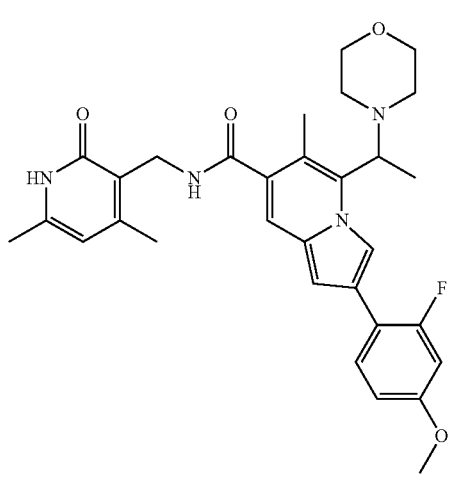
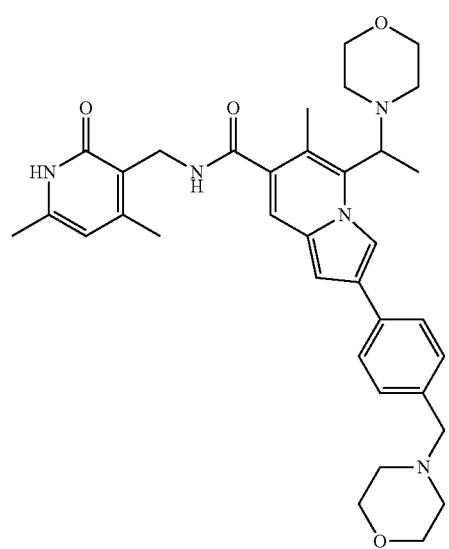
434
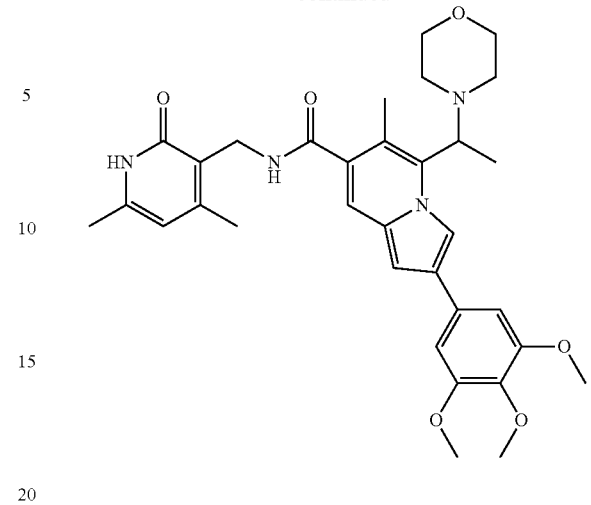
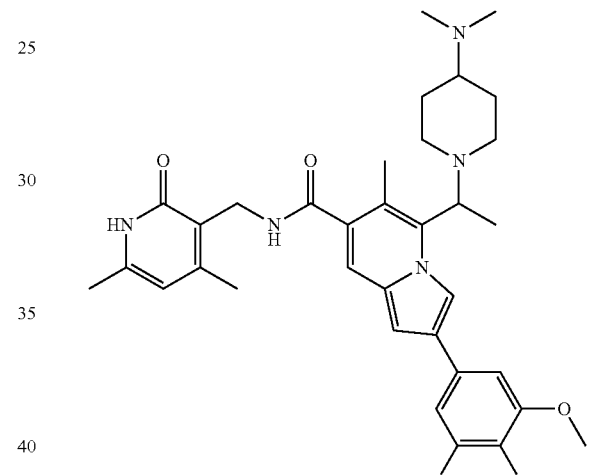
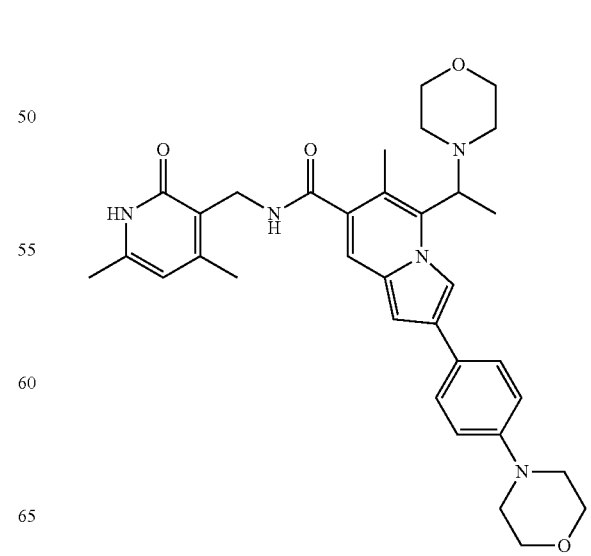

435
-continued
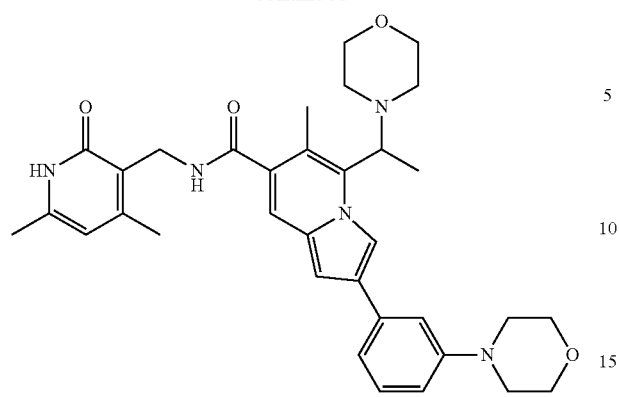
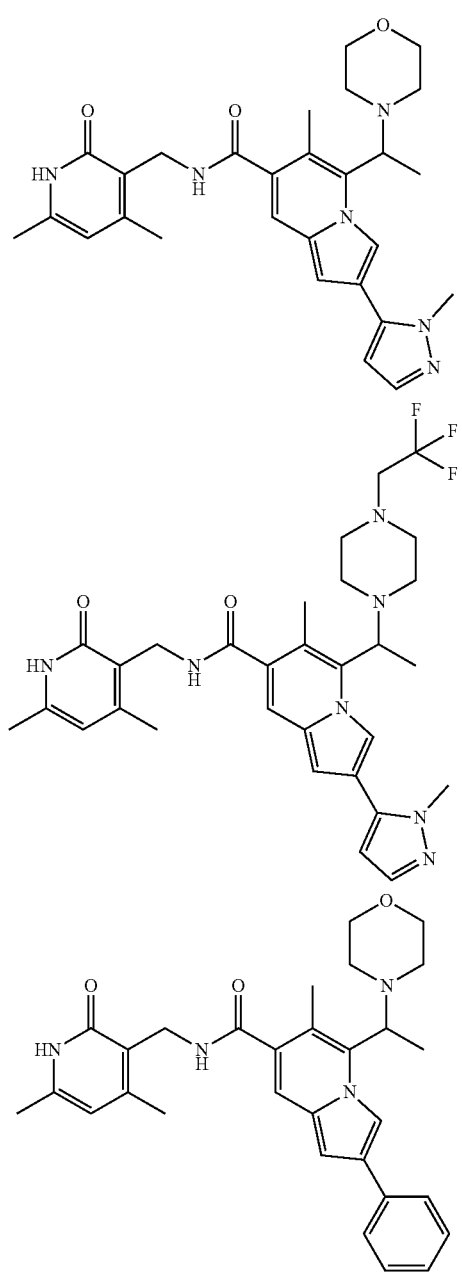
436
-continued
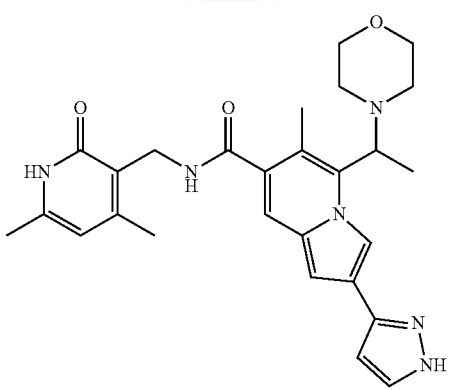
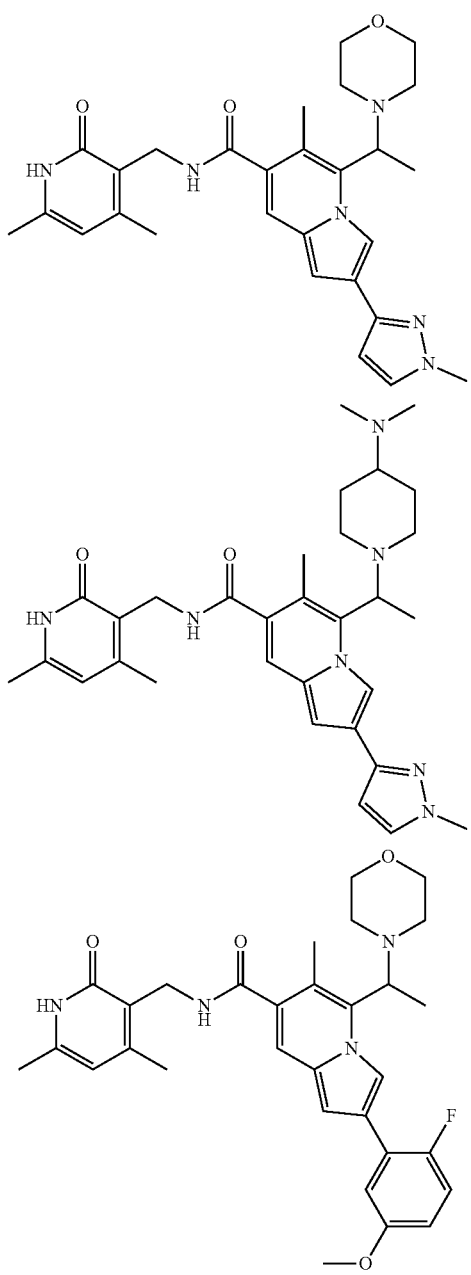

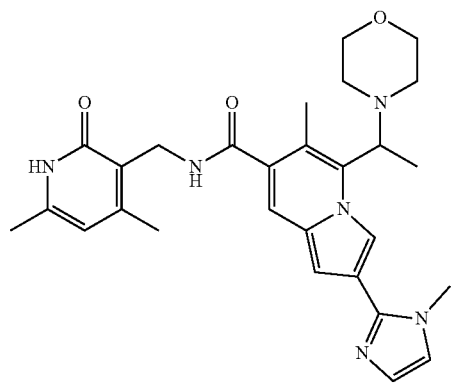
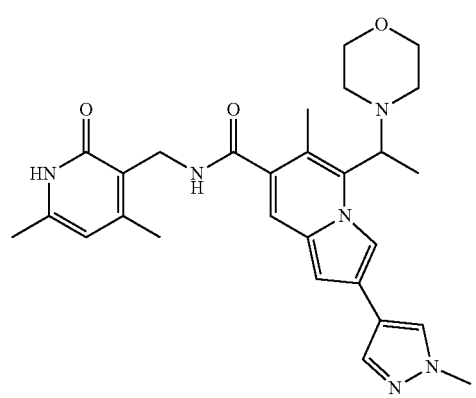
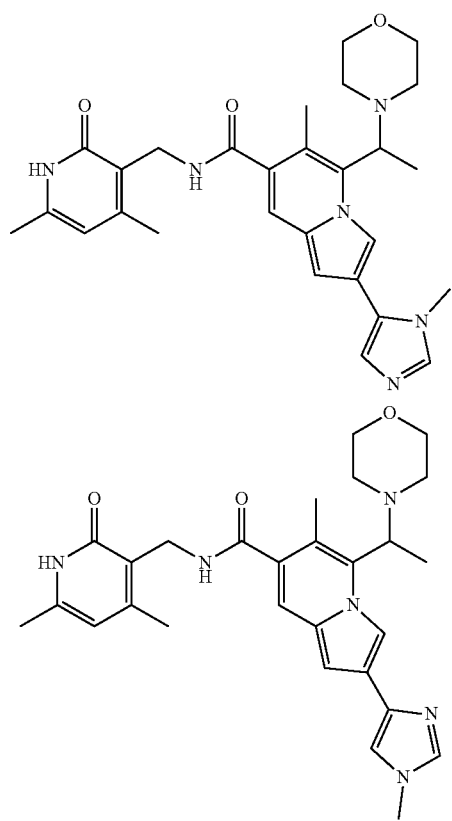
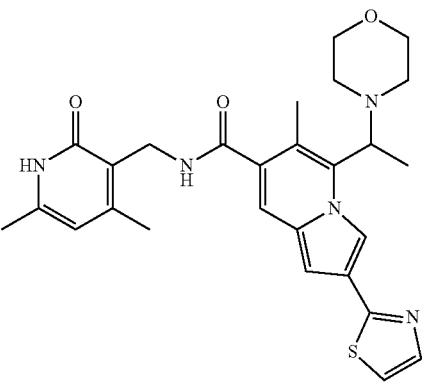
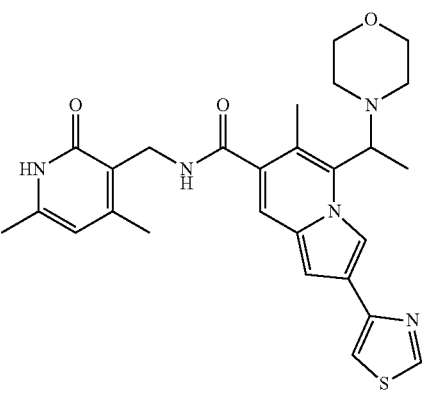
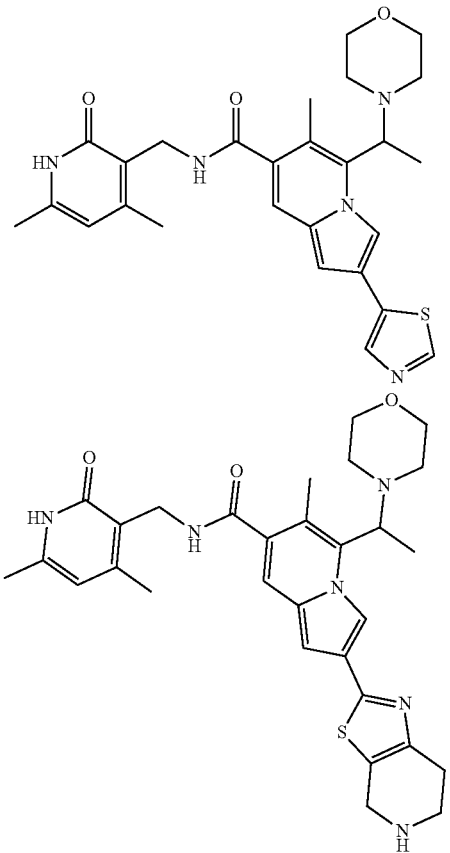

439
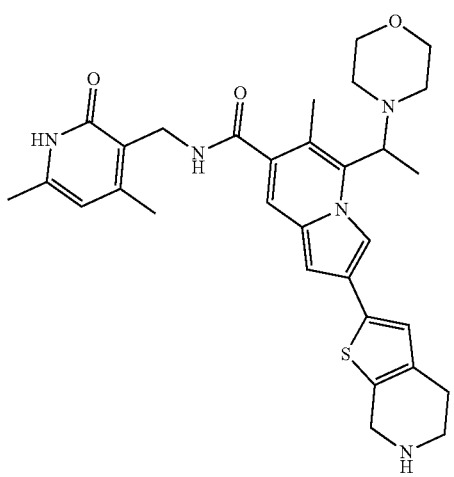
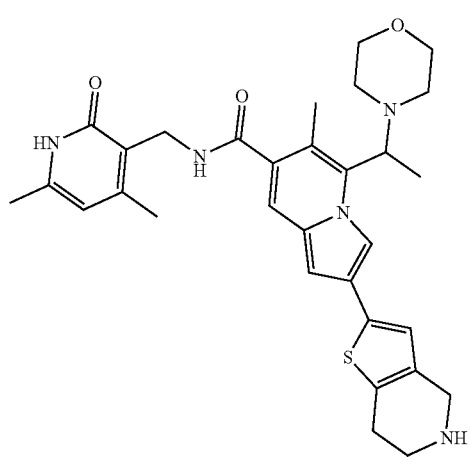
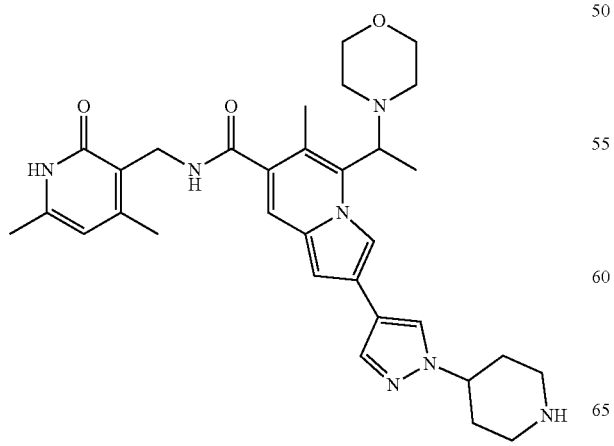
440
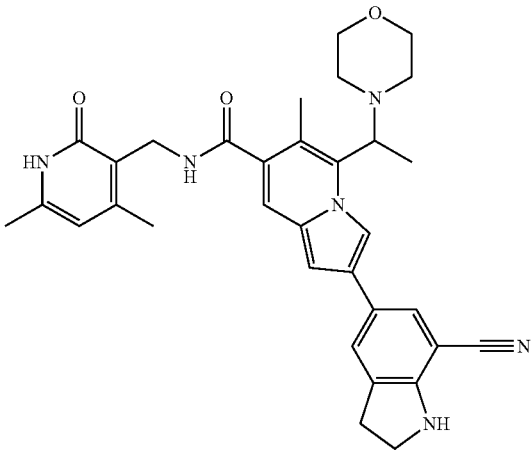
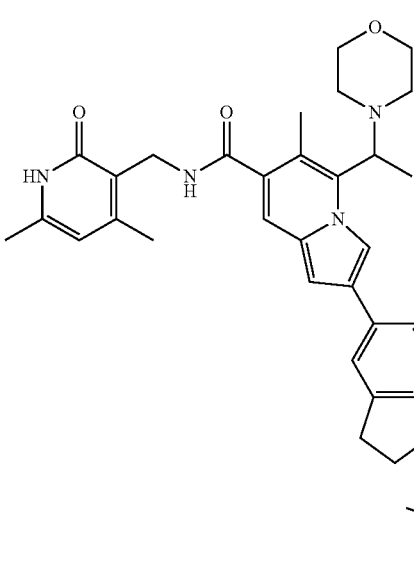
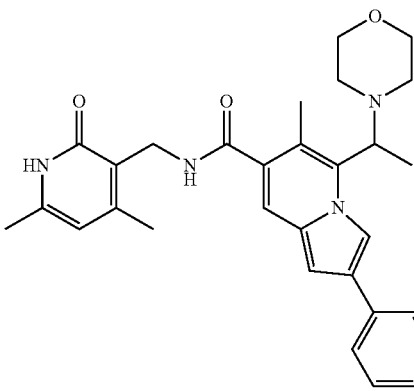

441
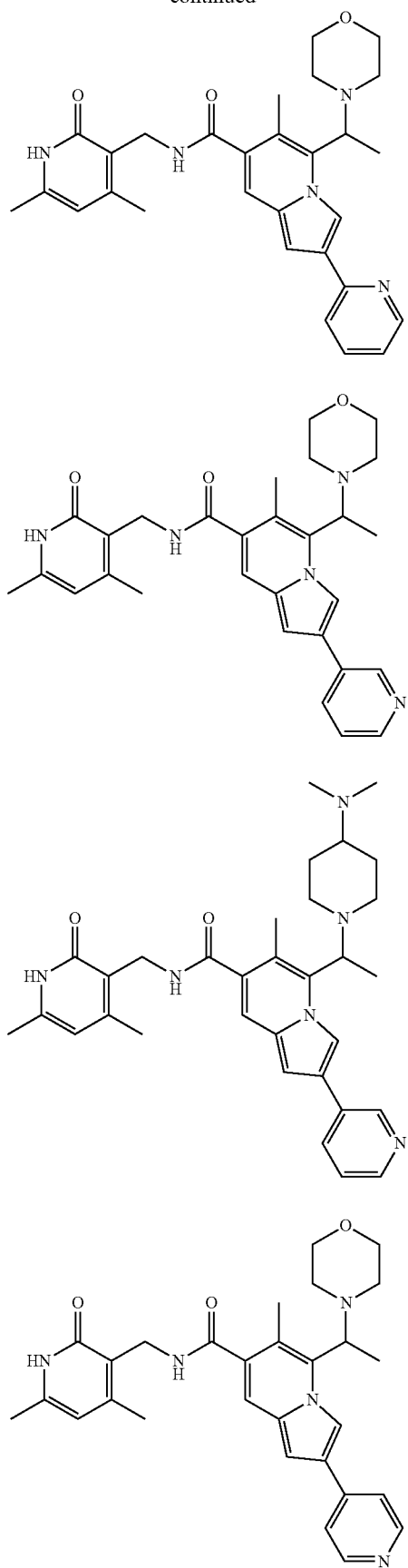
442
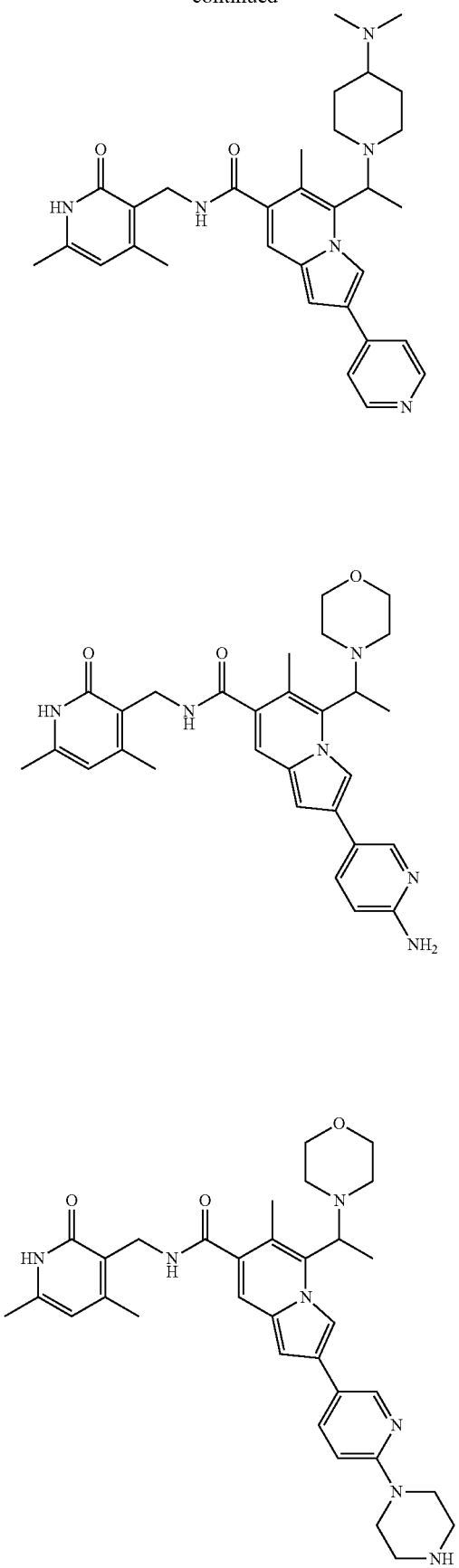

443
-continued
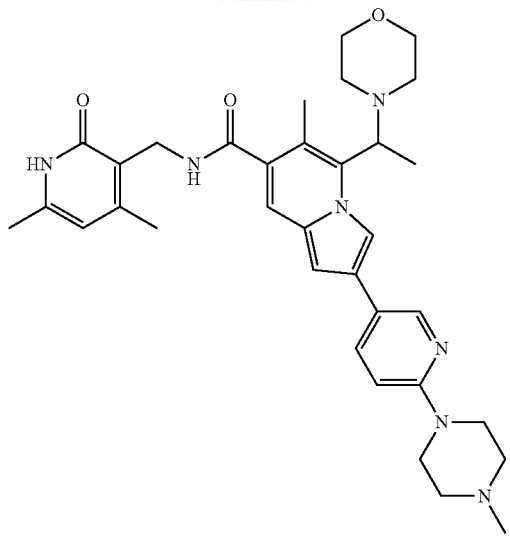
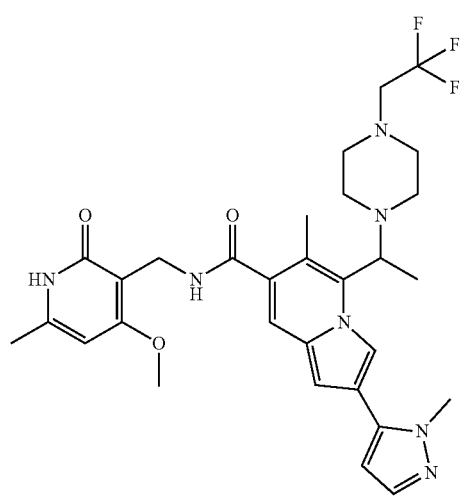
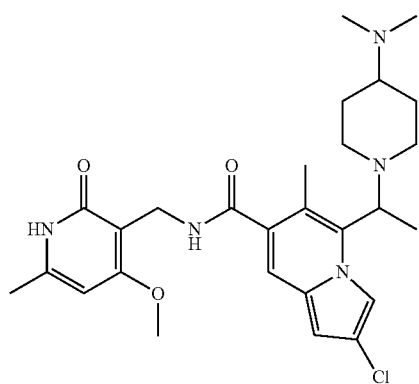
444
-continued
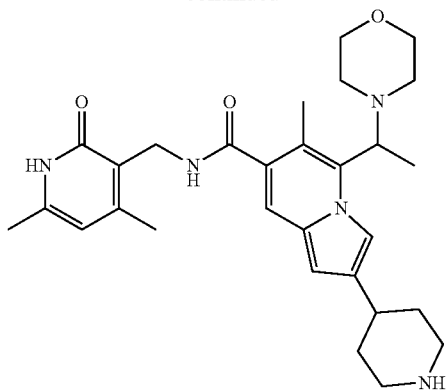
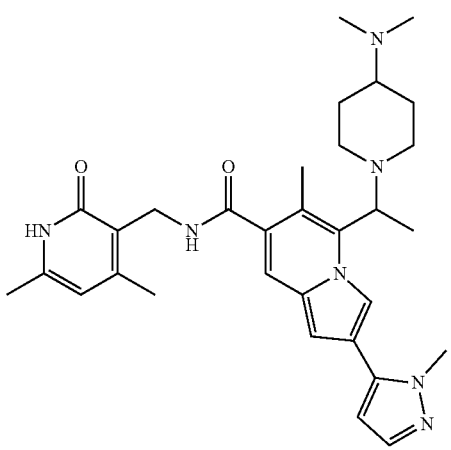
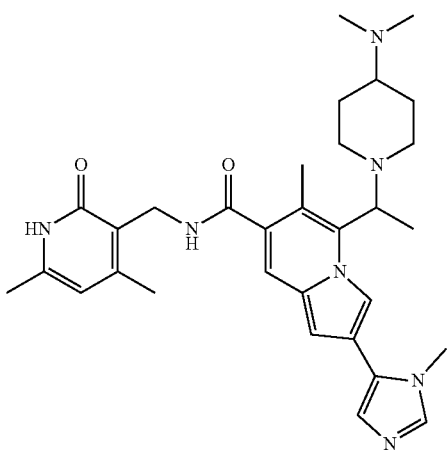

445
-continued
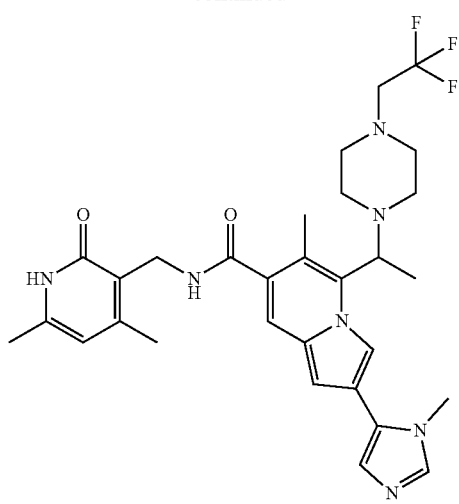
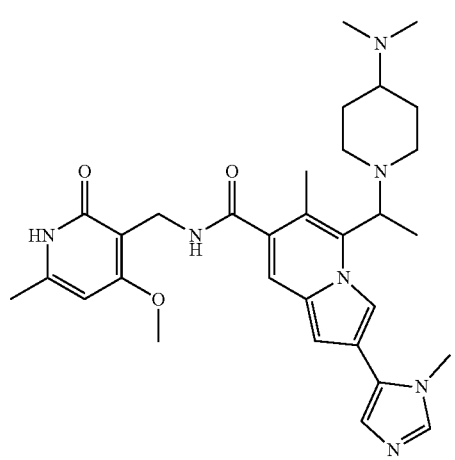
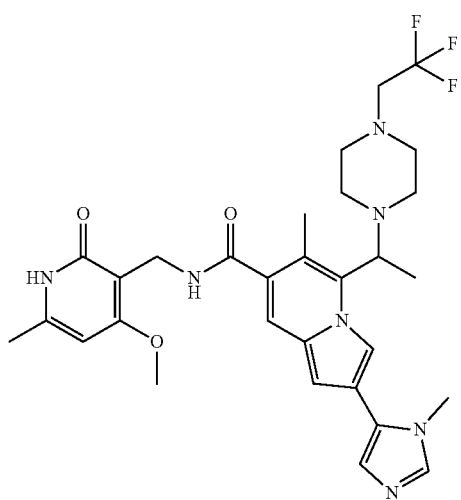
446
-continued
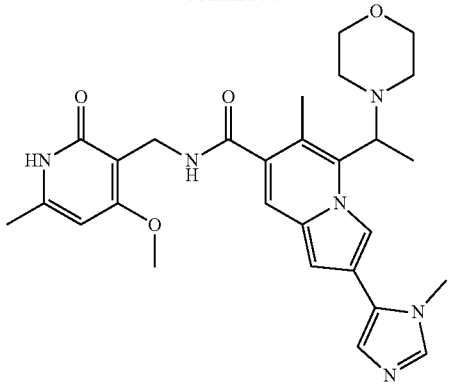
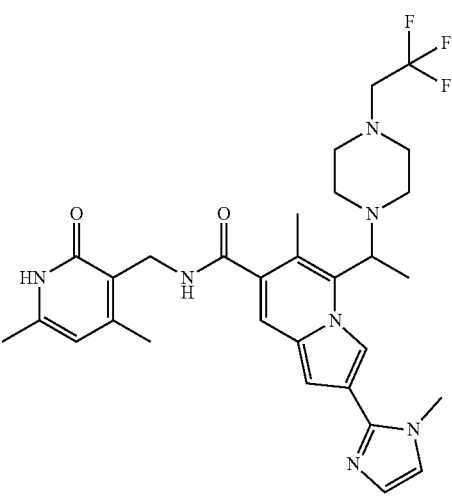
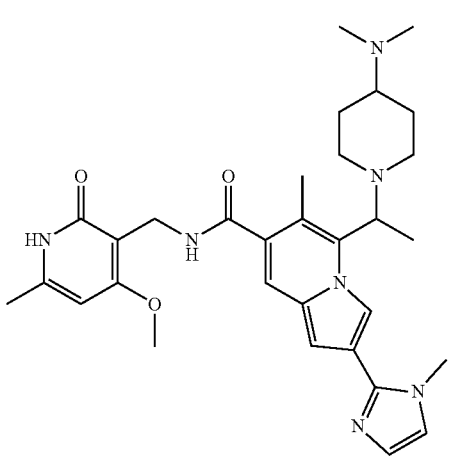

447
-continued
448
-continued
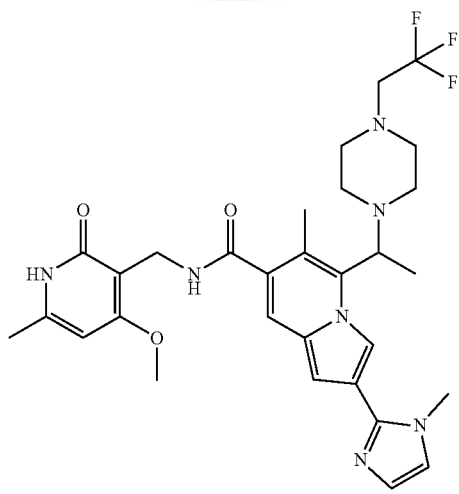
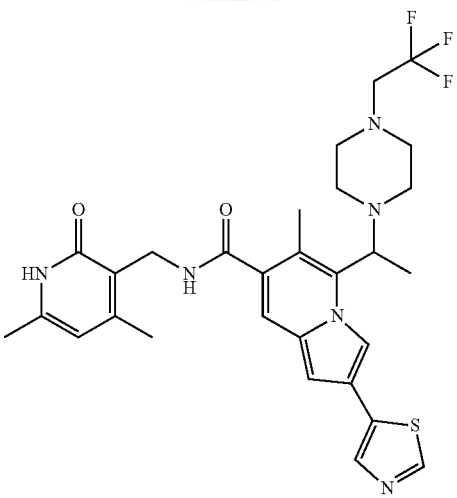
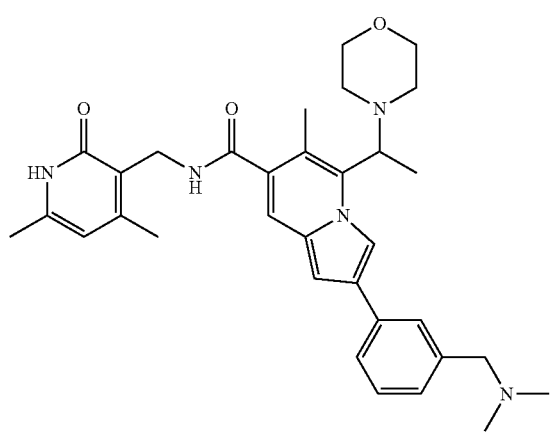
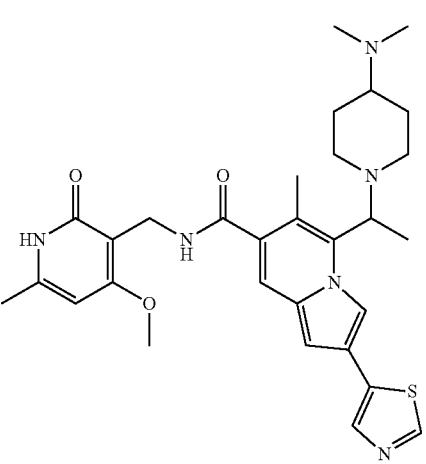
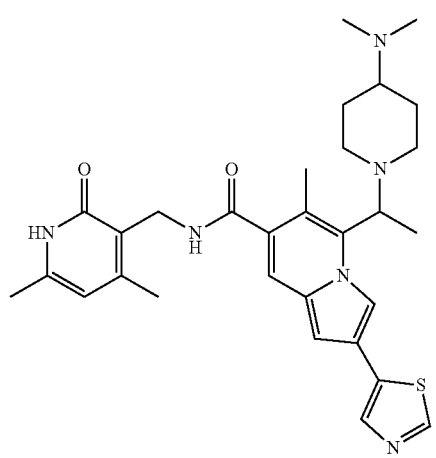
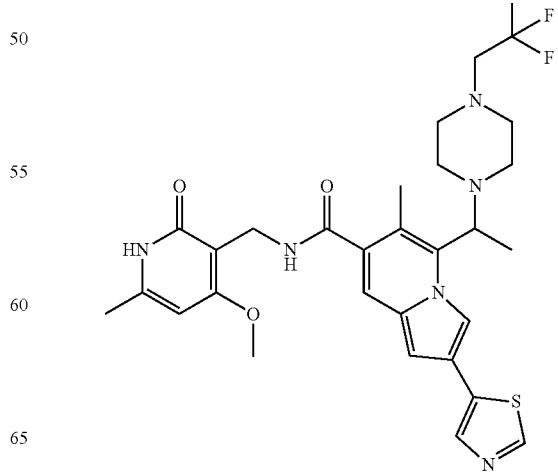

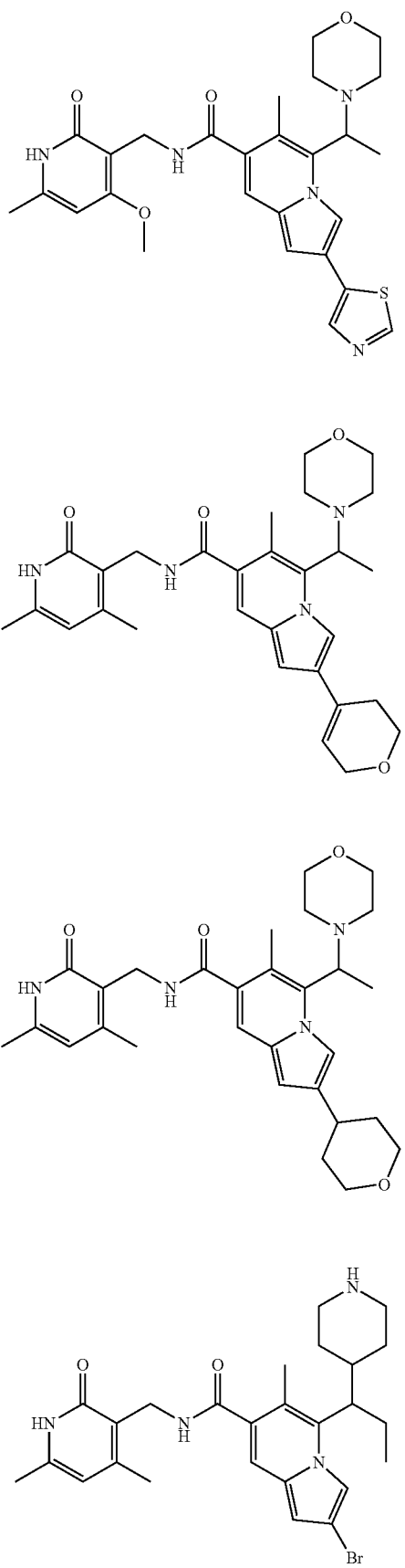
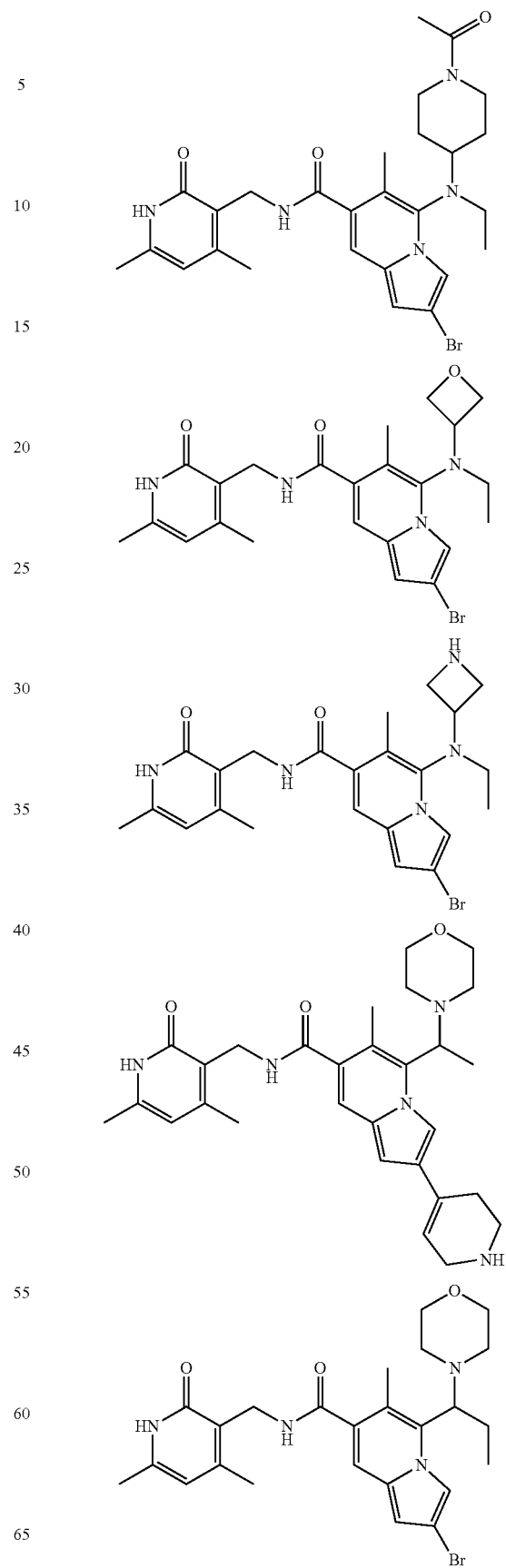

451
-continued
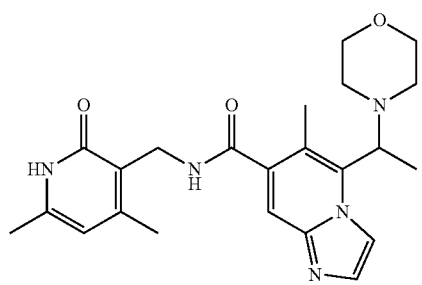
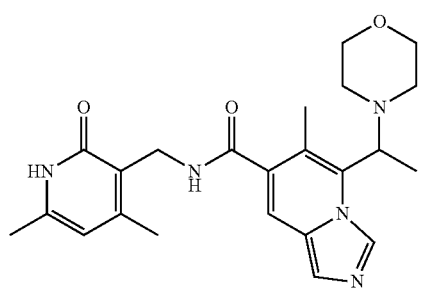
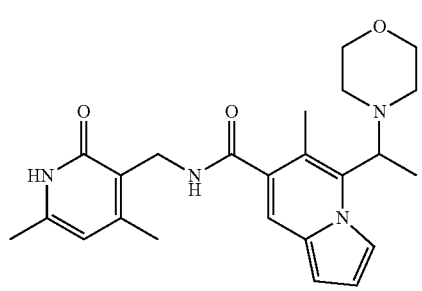
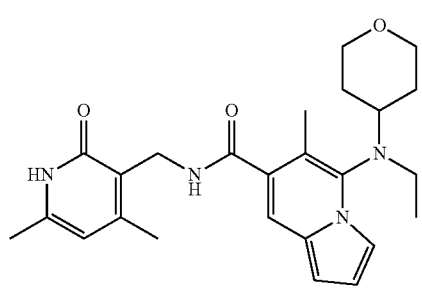
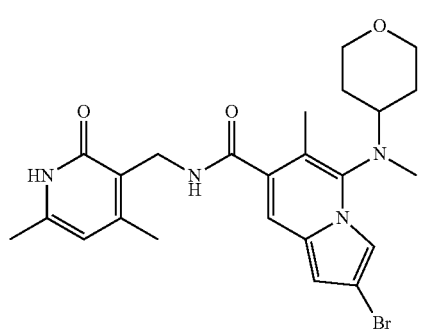
452
-continued
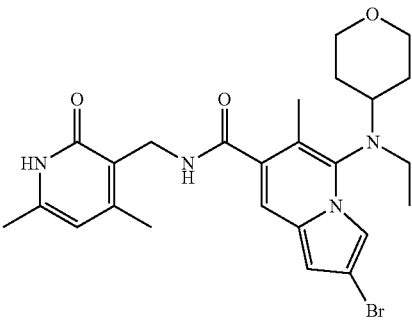
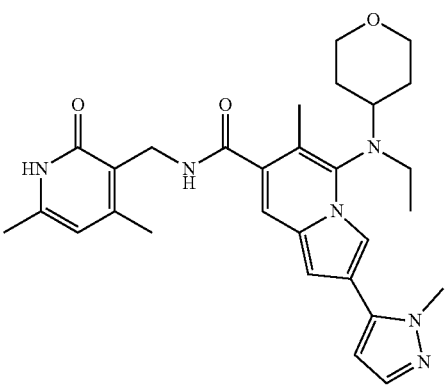
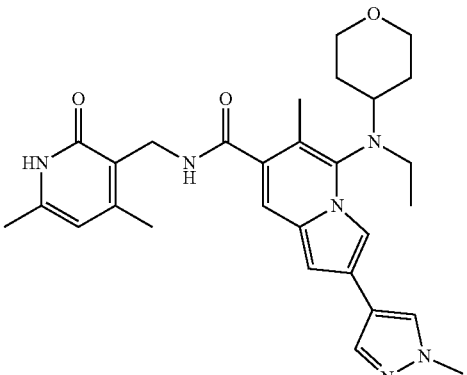
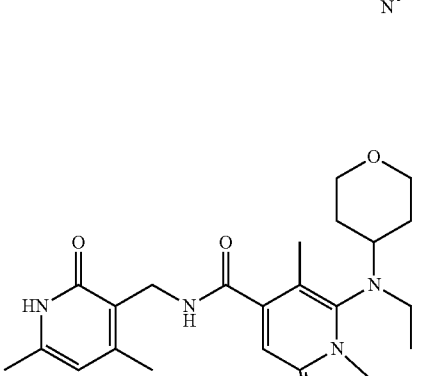

453
-continued
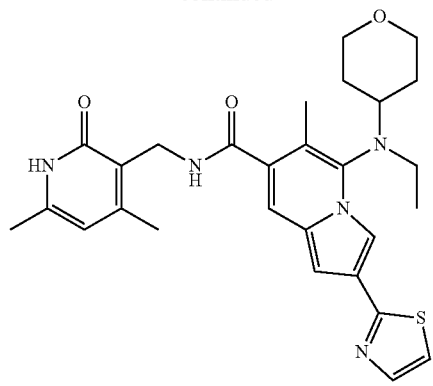
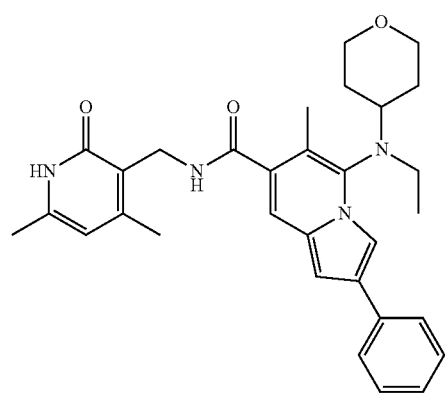
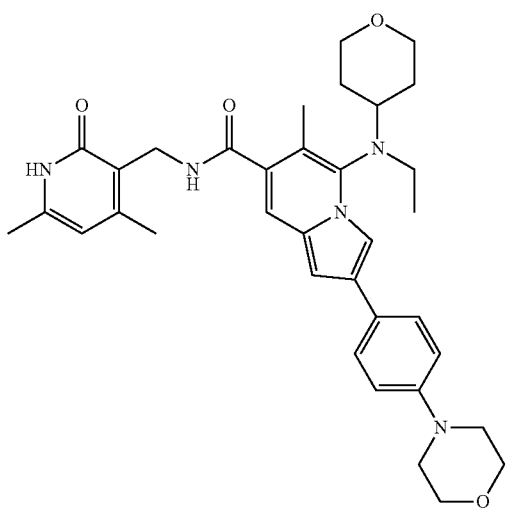
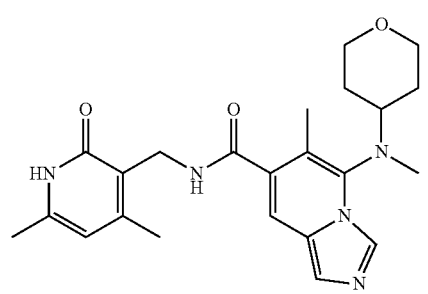
454
-continued
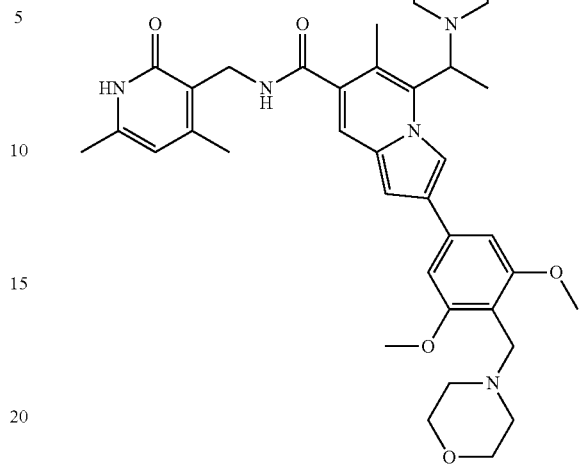
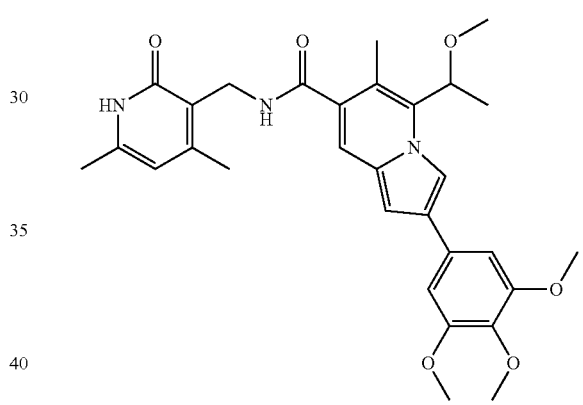
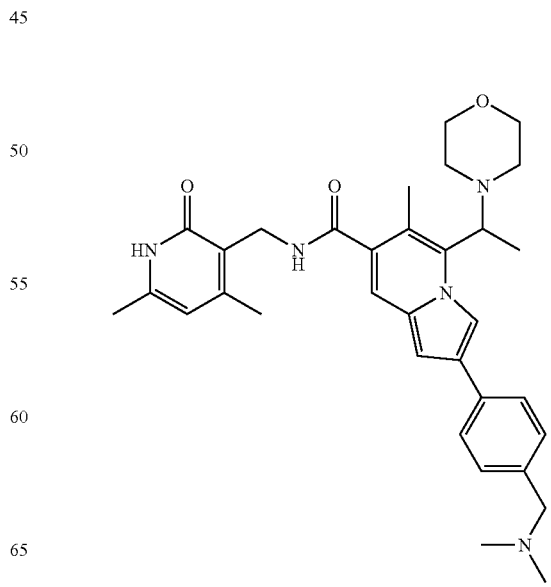

455
-continued
456
-continued
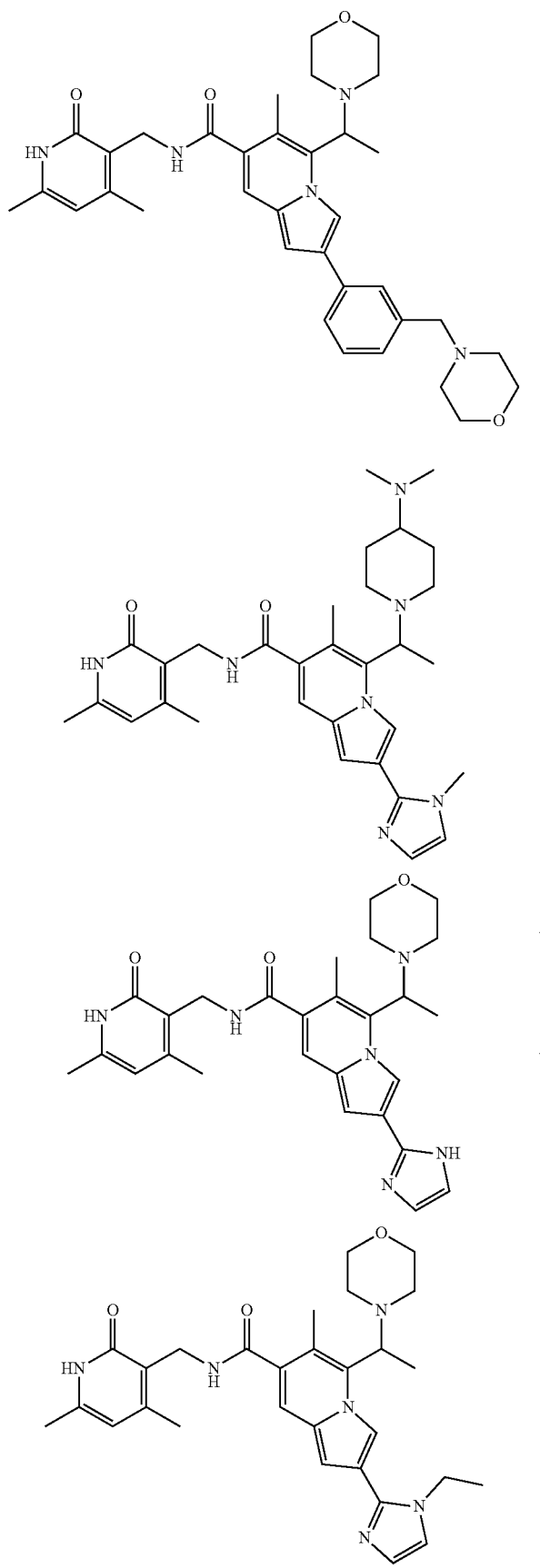
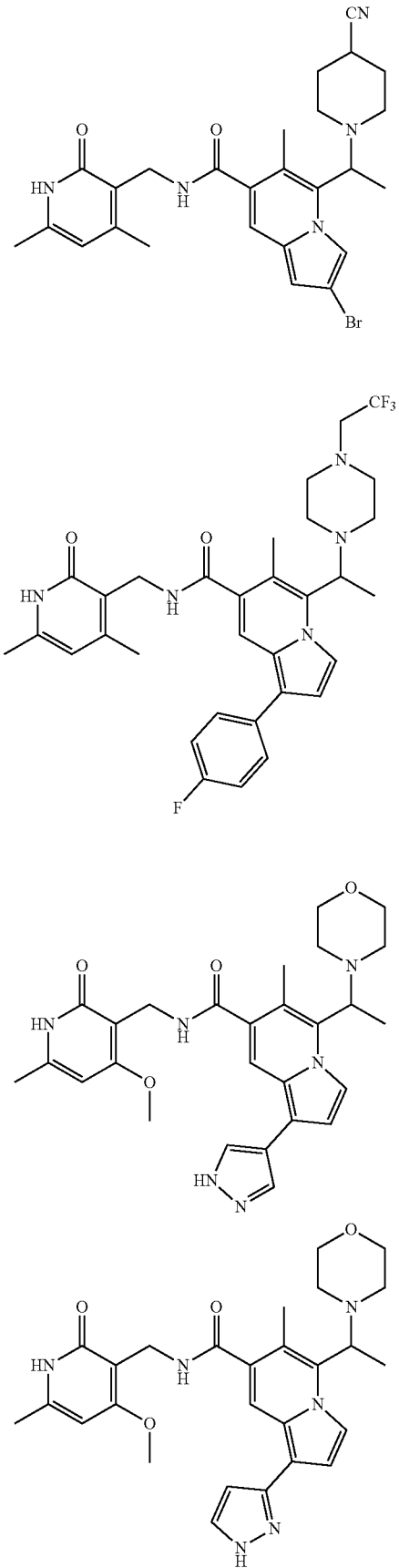

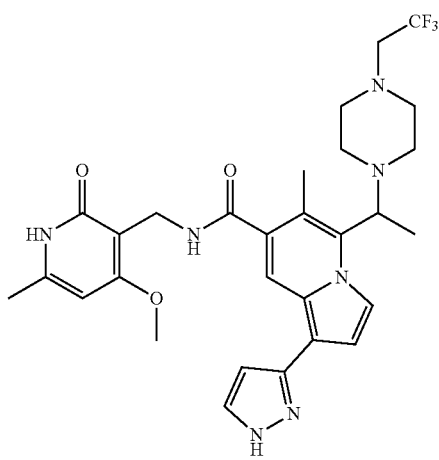
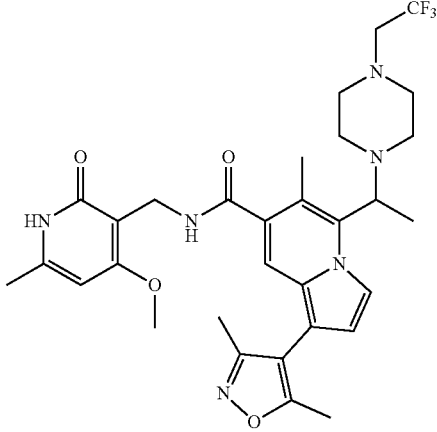
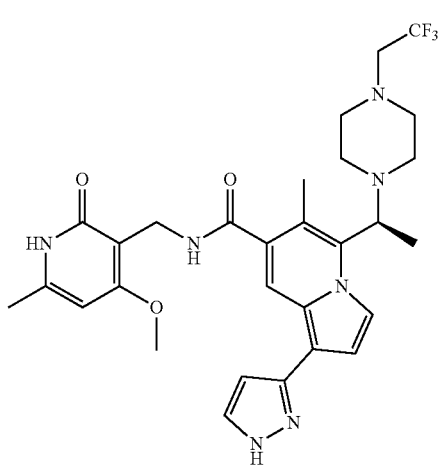
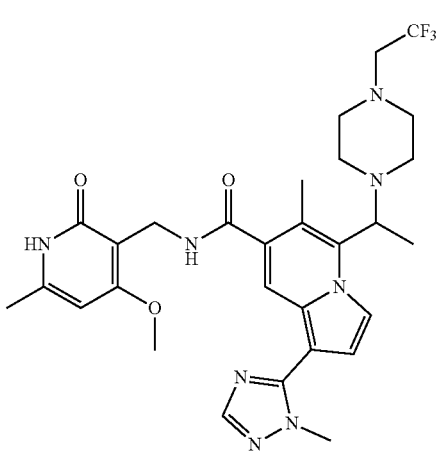
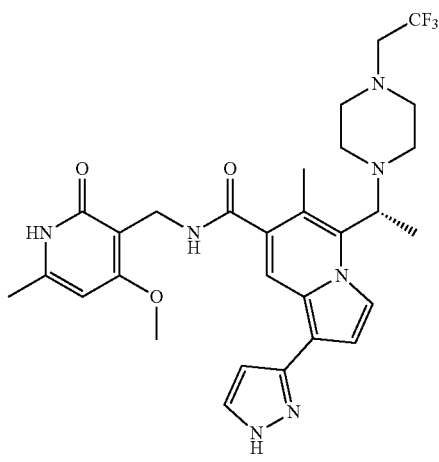
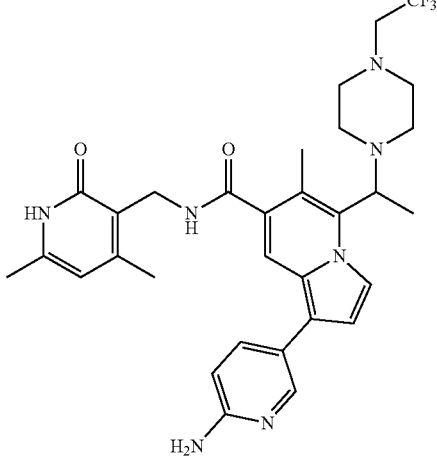

459
-continued
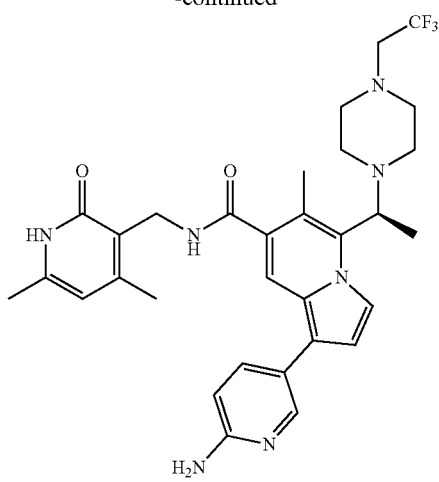
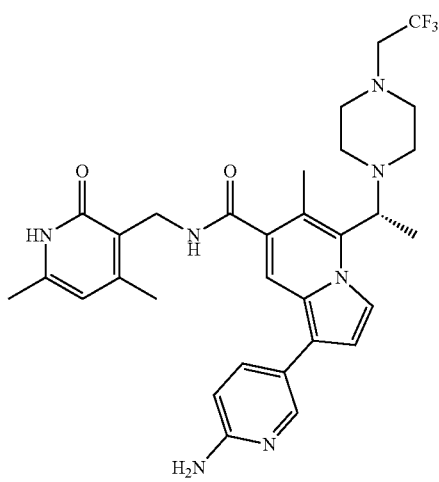
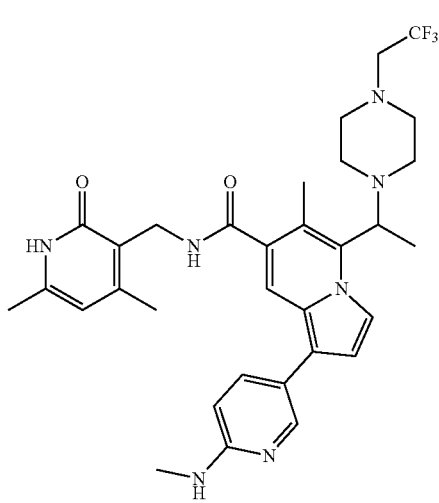
460
-continued
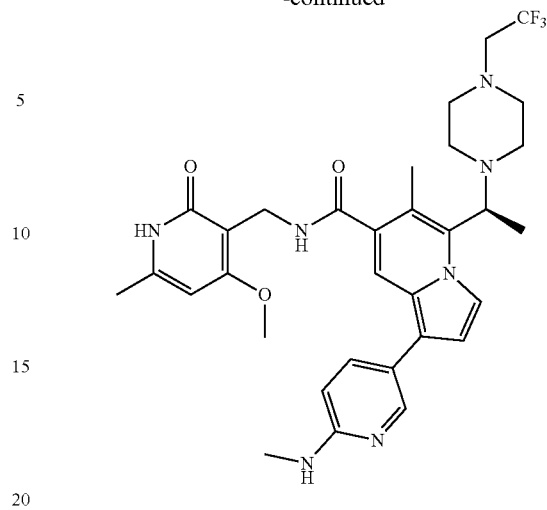
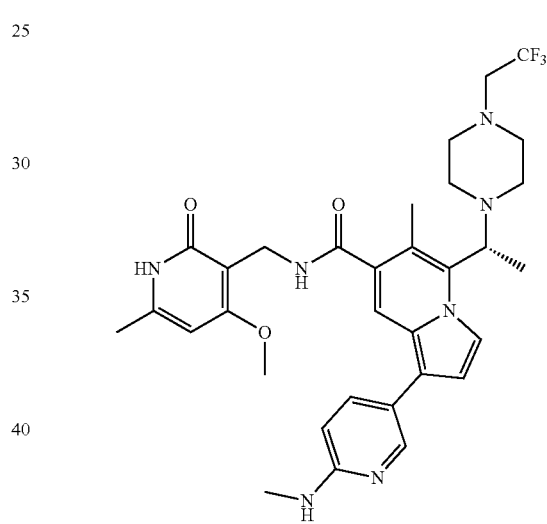
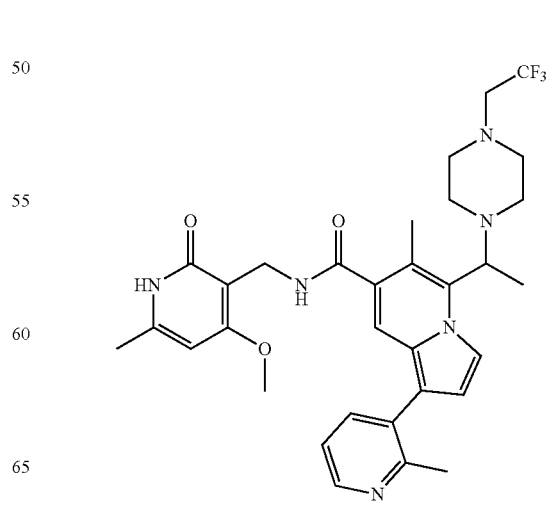

-continued
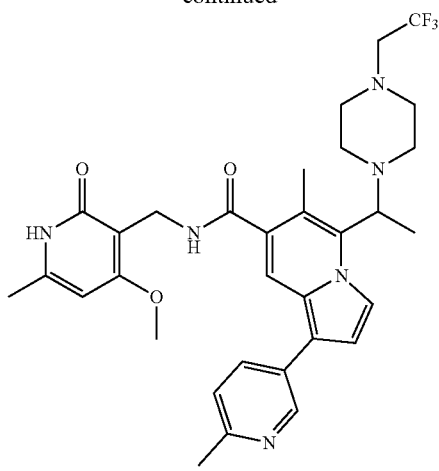
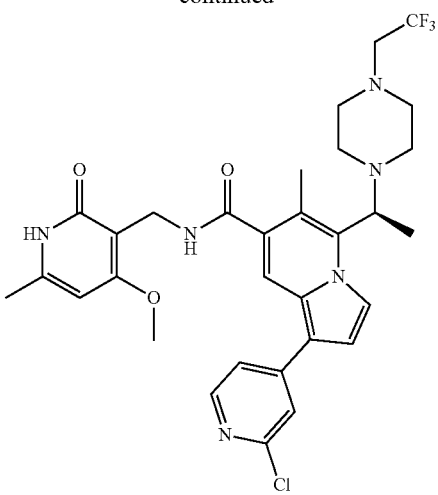
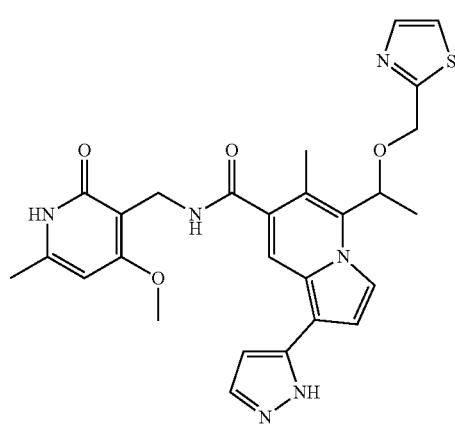
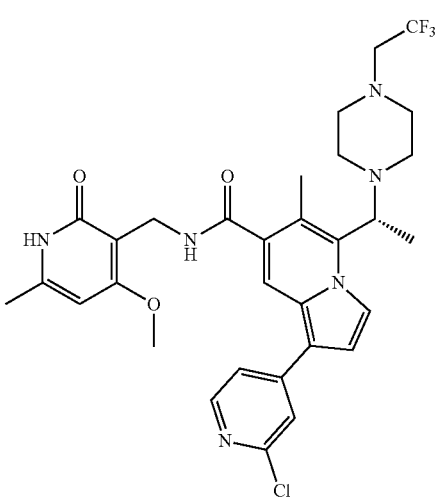
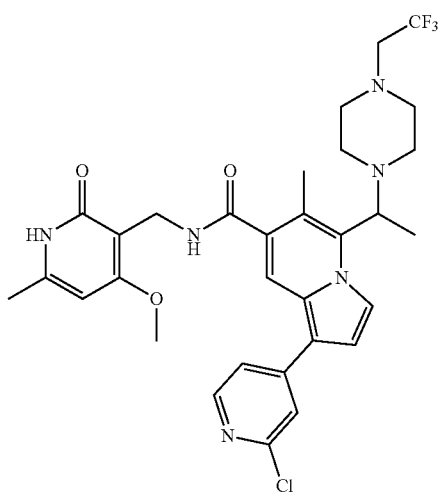
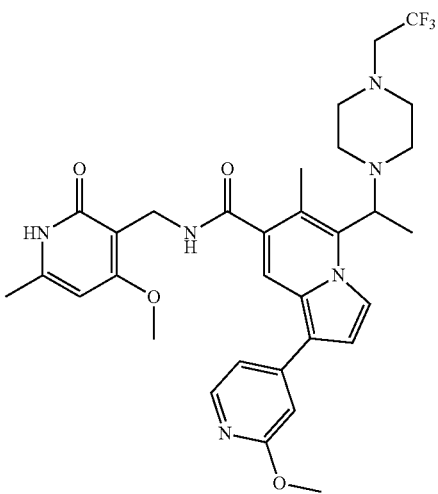

463
-continued
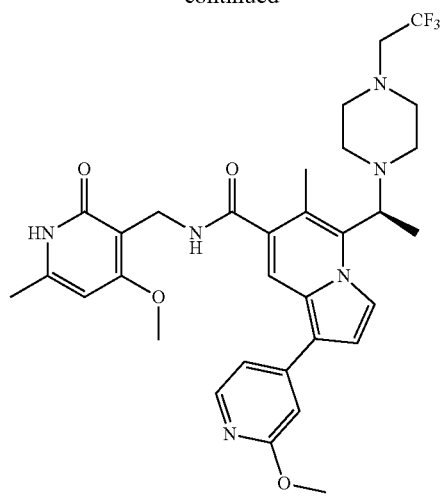
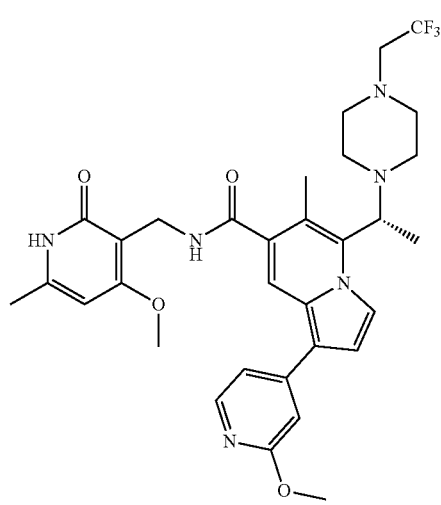
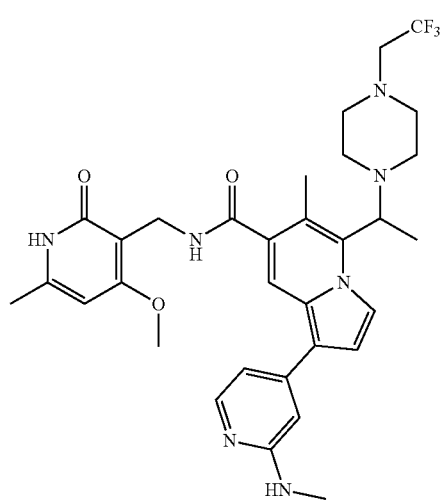
464
-continued
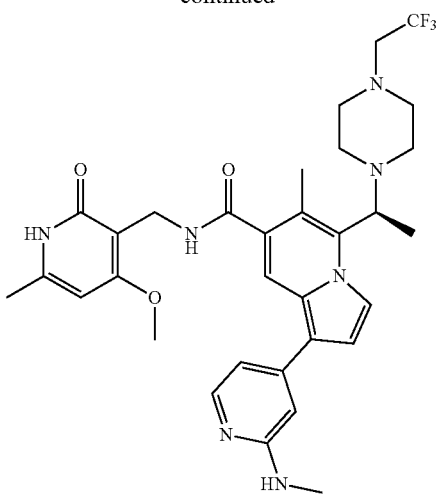
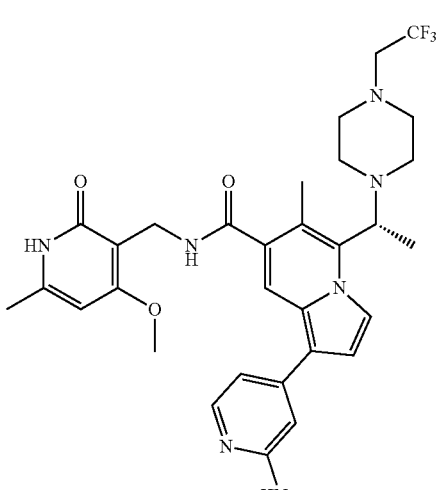
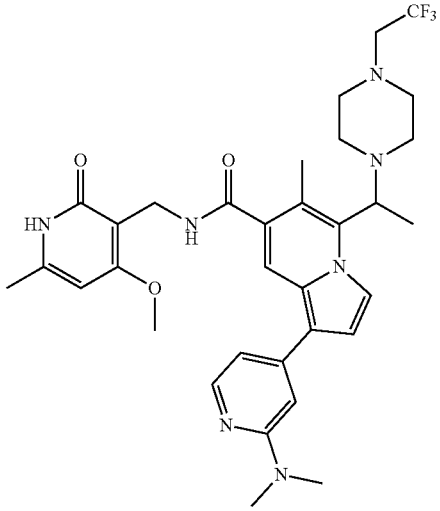

465
-continued
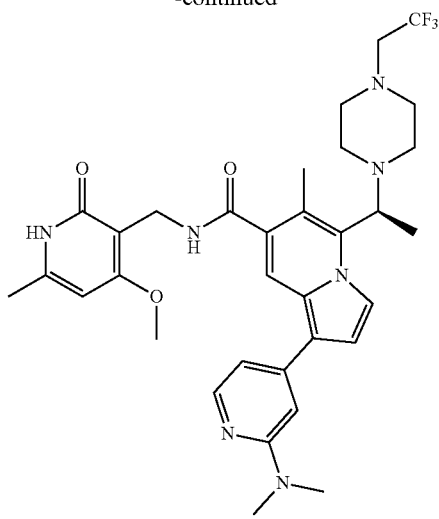
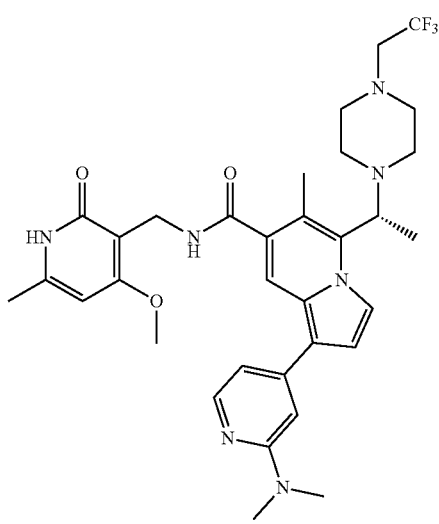
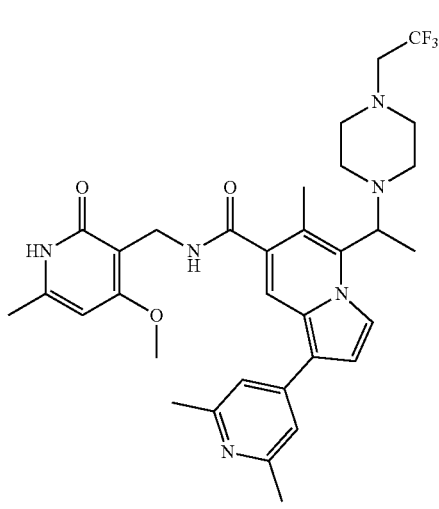
466
-continued
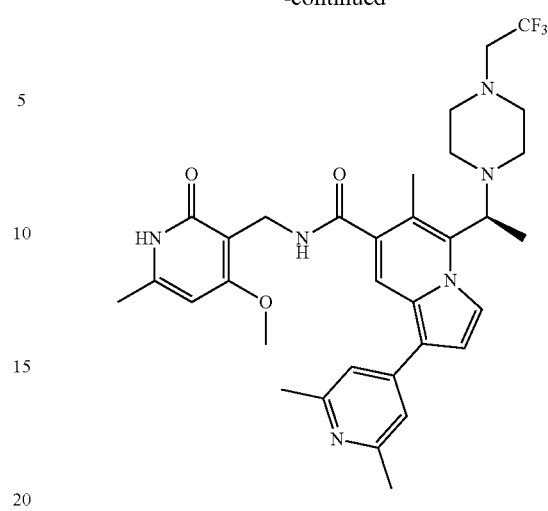
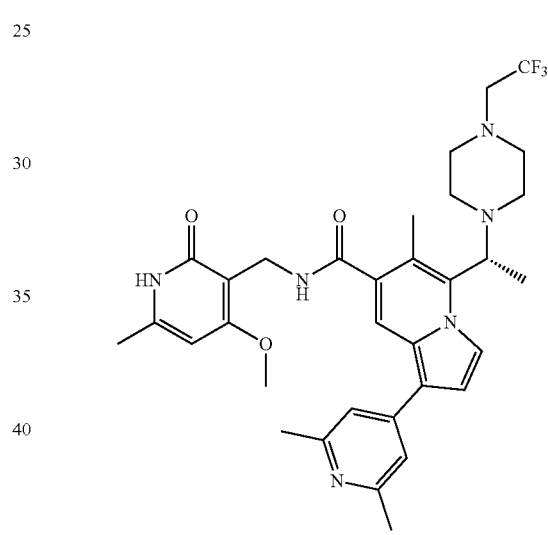
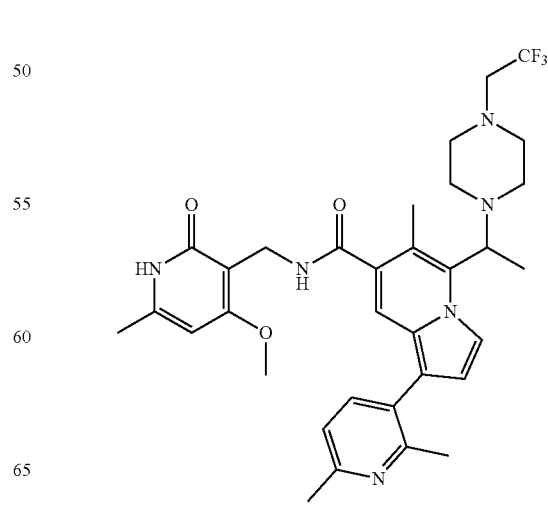

467
-continued
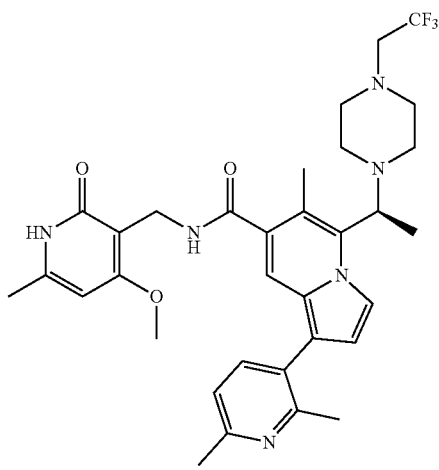
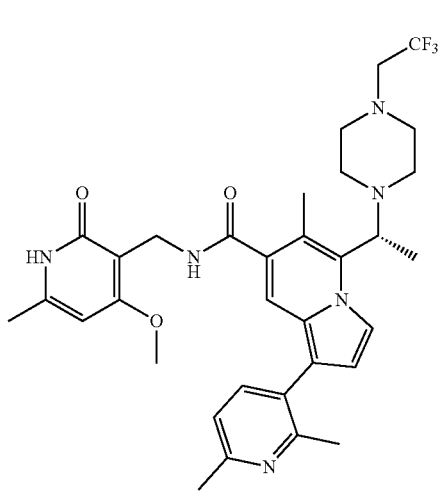
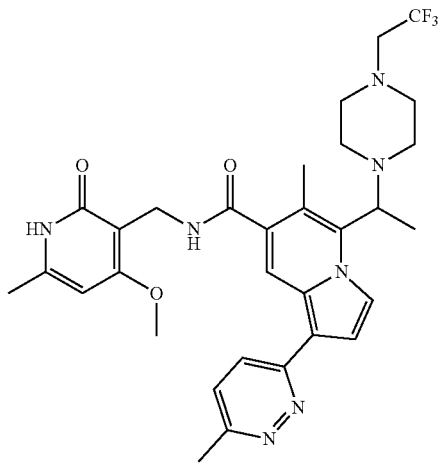
468
-continued
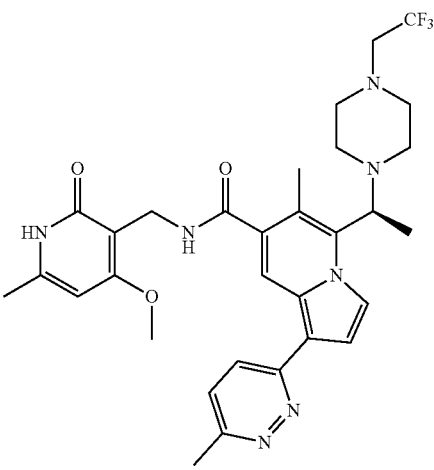
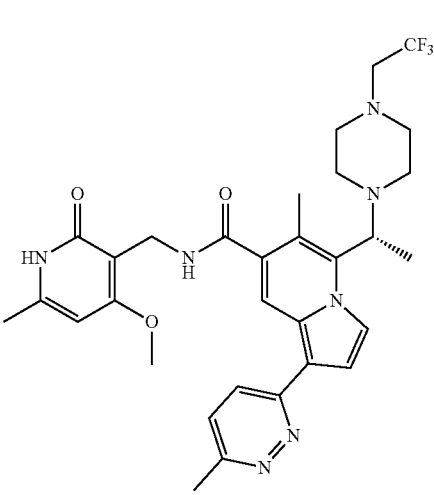
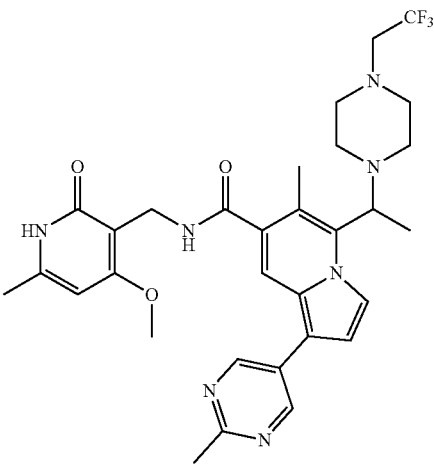

469
-continued
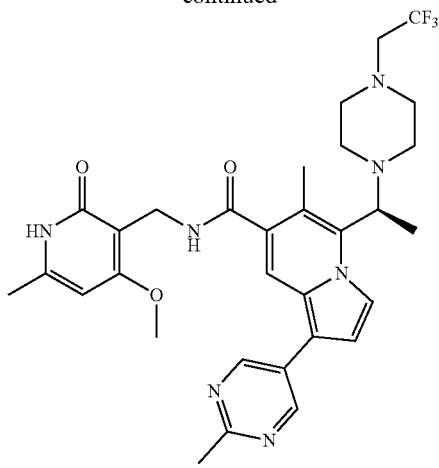
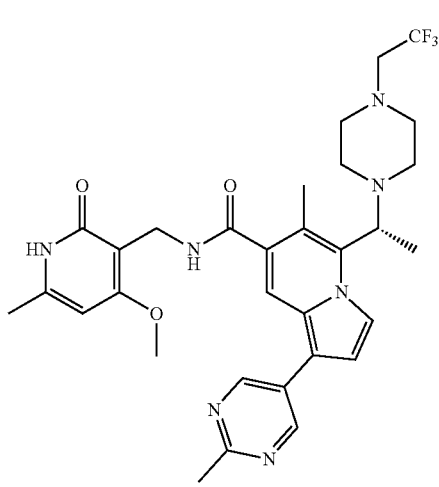
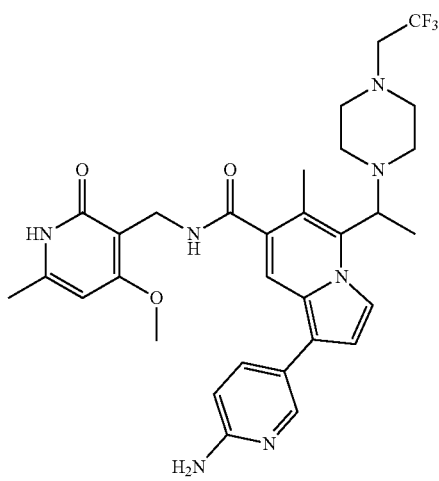
470
-continued
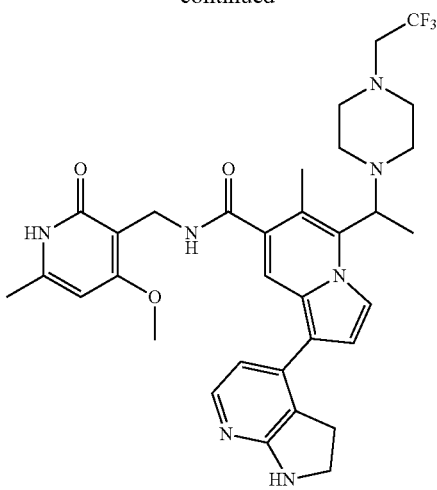
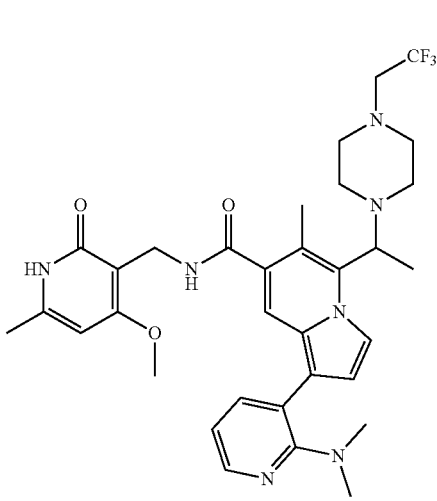
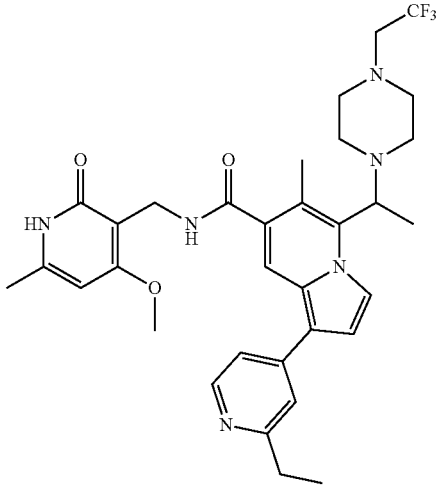

471
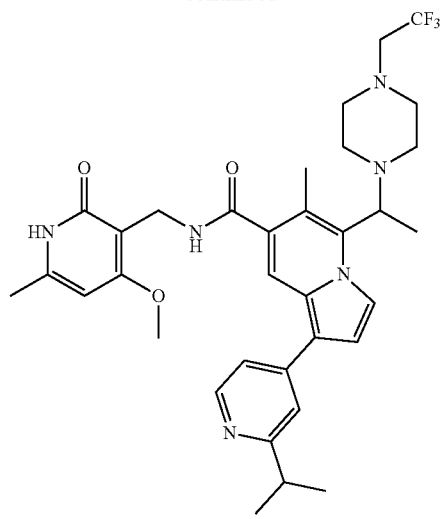
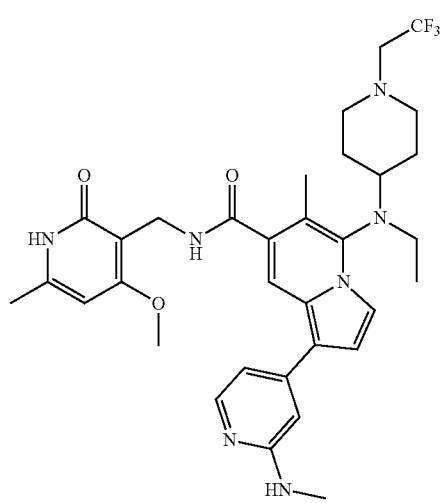
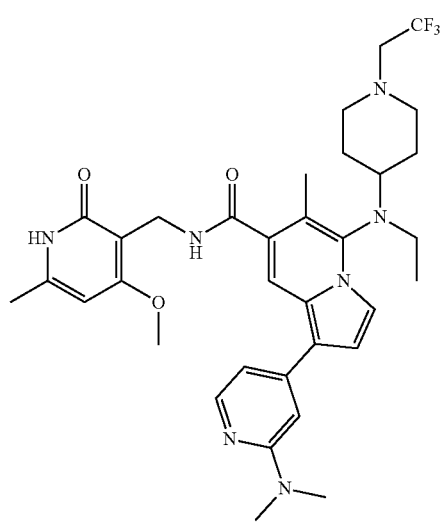
472
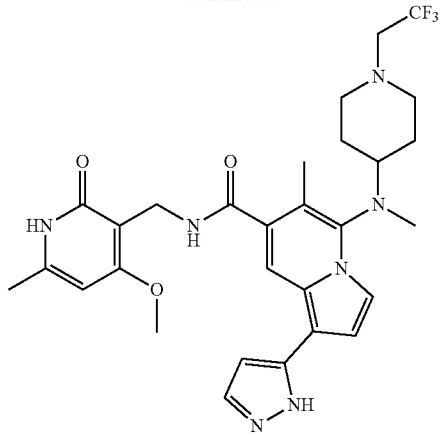
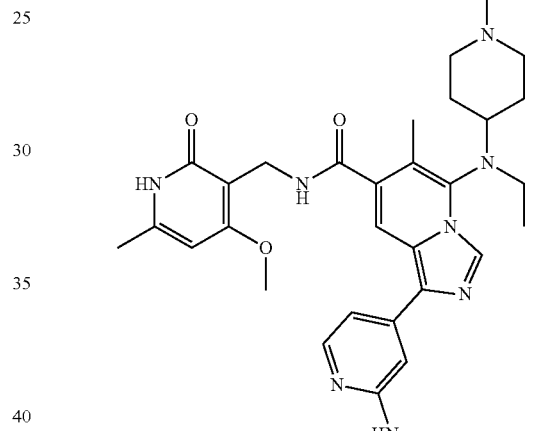
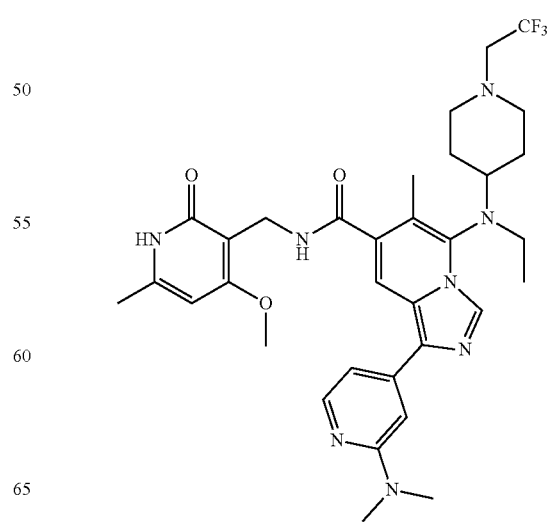

473
-continued
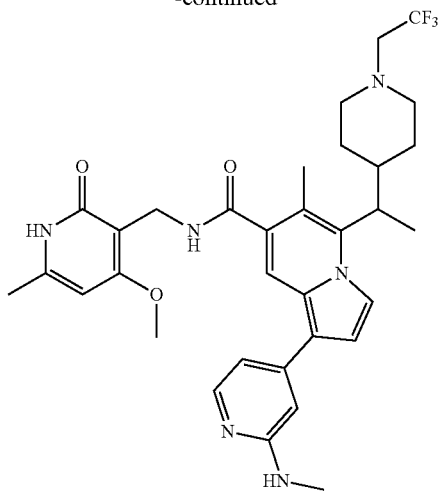
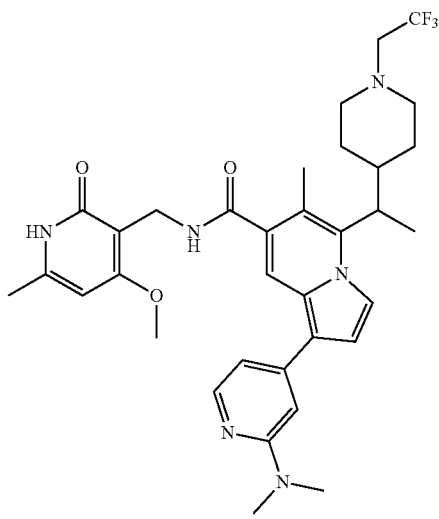
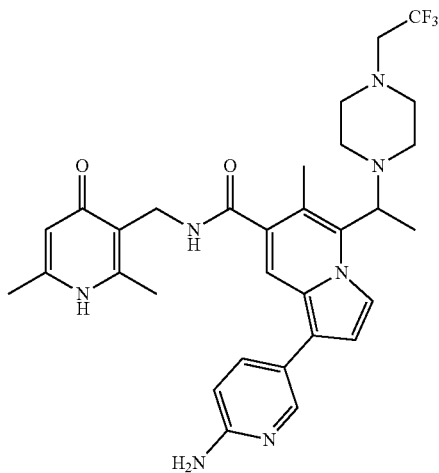
474
-continued
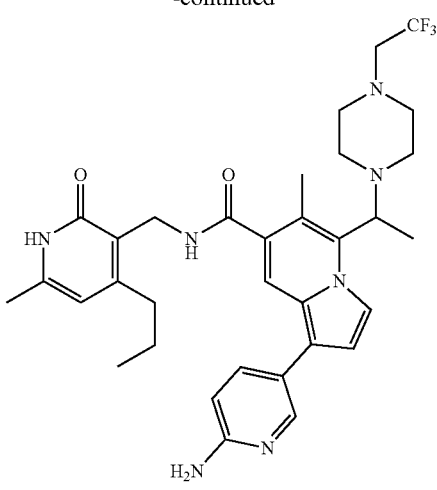
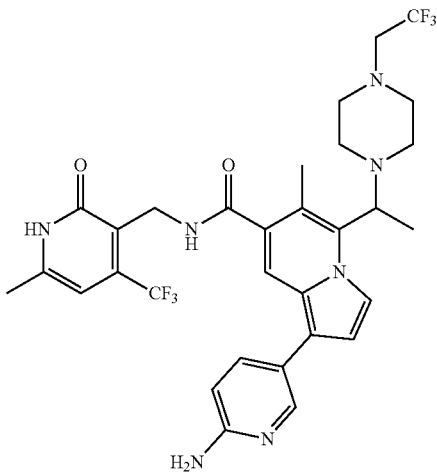
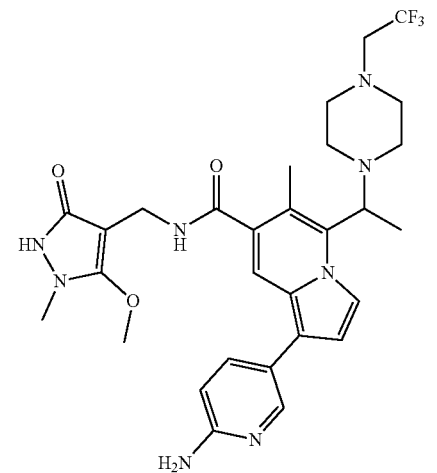

-continued

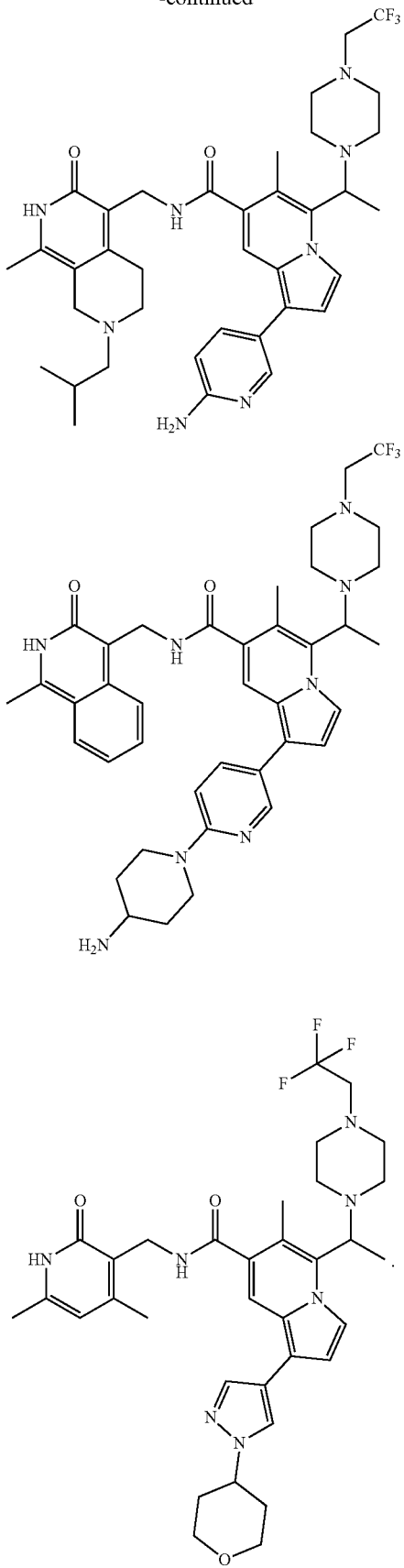

7. A preparation method for the compound of formula I of claim 1, wherein the compound of formula I has the structure shown in formula I-1 and the method comprises the steps:

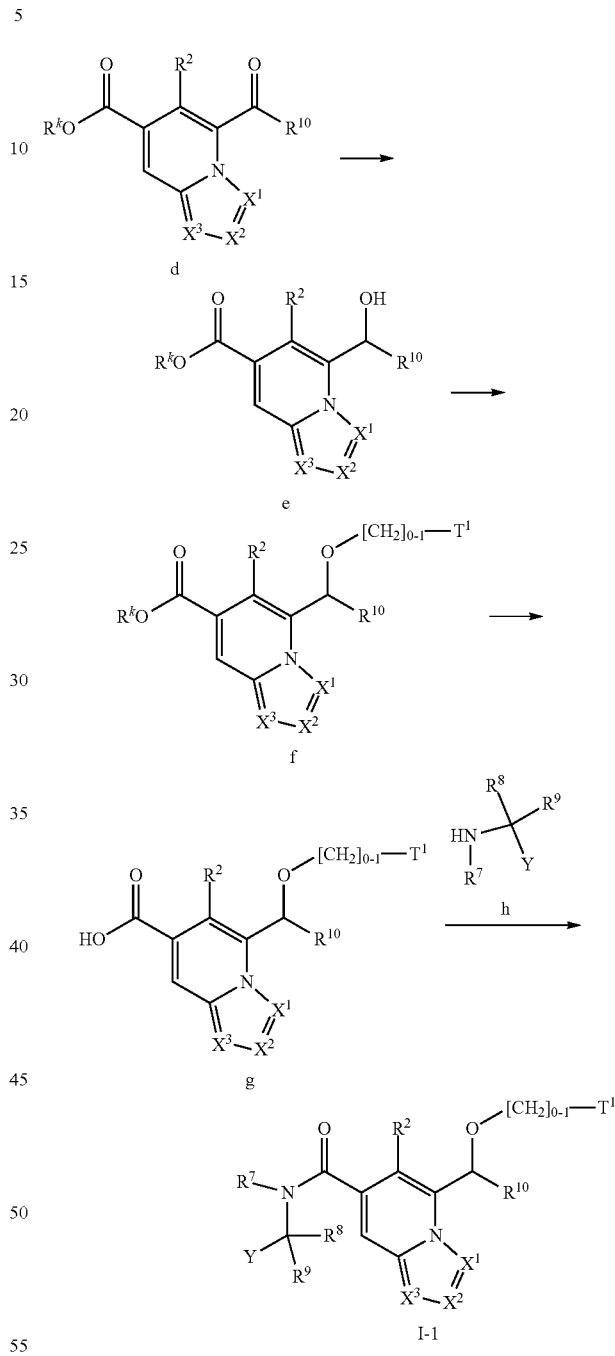

(1) in the presence of a reducing agent, reducing compound d to form compound e, while the reducing agent is selected from the group consisting of sodium borohydride, lithium borohydride, potassium borohydride, or combinations thereof;

(2) in the presence of a base, reacting compound e with a corresponding hydrocarbylation reagent to form compound f, the base is selected from the group consisting of sodium hydride, potassium t-butoxide, sodium hydroxide, potassium hydroxide, n-butyl lithium, lithium diisopropylamide, lithium hexamethyldisilazide, sodium hexamethyldisilazide, potassium hexamethyldisilazide, potassium carbonate, cesium carbonate, sodium carbonate, or combinations thereof; and the alkylating agent is selected from the group consisting of halogenated hydrocarbons, methanesulfonate, p-toluenesulfonate, trifluoroacetate, triflate, or combinations thereof;

(3) hydrolyzing compound f to form compound g;
(4) condensing compound g with an amine compound to form compound I-1, wherein $R^2, R^3, R^7, R^8, R^9, R^{10}, T^1, R^e, R^f, X^1, X^2, X^3$ and Y are as defined above and $R^k$ is, a C1-C4 linear or branched alkyl;

and/or a preparation method for the compound of formula I of claim 1, wherein the compound of formula I has the structure shown in formula I-2 and the method comprises the steps:

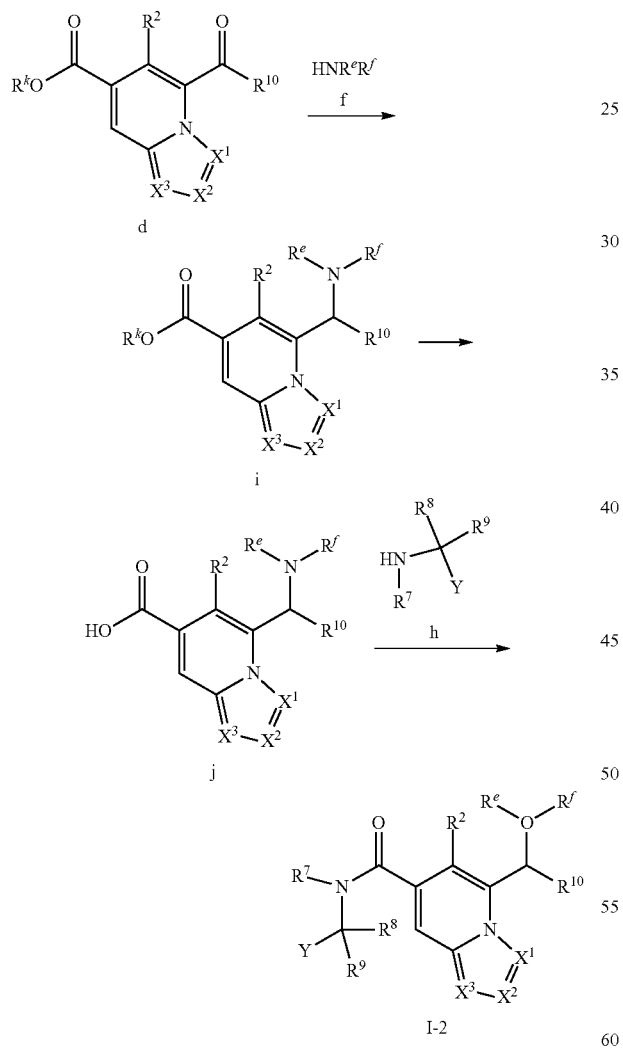

(i) in an inert solvent, in the presence of reducing agent, reacting compound d with compound f to form compound i;
(ii) hydrolyzing compound i to form compound j;
(iii) condensing compound g with amine compound to form compound I-2;

wherein the $R^2, R^3, R^7, R^8, R^9, R^{10}, R^e, R^f, R^k, X^1, X^2, X^3$ and Y are as described above;

and/or a preparation method for the compound of formula I of claim 1, wherein the compound of formula I has the structure shown in formula I-3 and the method comprises the steps:

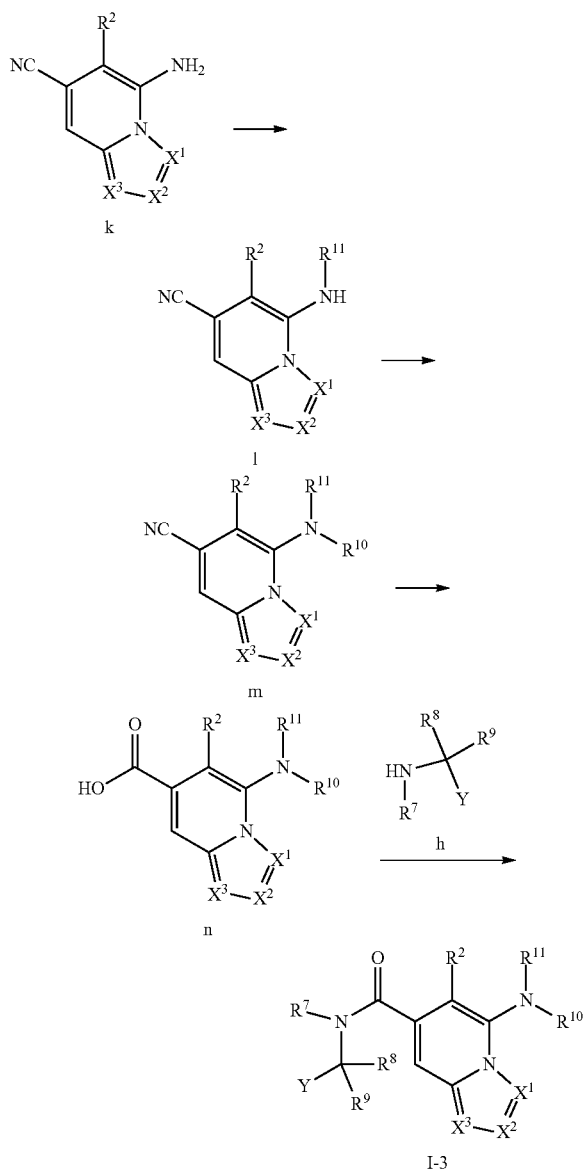

(a) in an inert solvent, in the presence of reducing agent, reducing compound k to form compound l;
(b) in the presence of alkylating agent, reacting compound 1 to form compound m, and said alkylating agent is selected from the group consisting of X—$R^{10'}$, $HSO_4$—$R^{10'}$, HO—$R^{10'}$, $R^{10'}$—O—$R^{10'}$, or combinations thereof;

wherein X is halogen; $R^{10'}$ is a substituted or unsubstituted C1-C6 alkyl, substituted or unsubstituted C2-C6 alkenyl, substituted or unsubstituted C2-C6 alkynyl, substituted or unsubstituted saturated or unsaturated 4-8 membered heterocyclic group, substituted or unsubstituted saturated or unsaturated 4-8 membered carbocyclic group, substituted or unsubstituted 5-8 membered aryl, saturated or unsaturated; wherein said heterocyclic ring comprises 1-3 heteroatoms selected from N, O, S, P; and said "substituted" means having one or more (e.g., 1, 2, 3 or 4) substituents selected from group B as set forth in claim 1;

(c) hydrolyzing compound m to form compound n;

(d) condensing compound n with amine compound to form compound I-3;

wherein the $R^2$, $R^3$, $R^7$, $R^8$, $R^9$, $R^{10}$, $R^e$, $R^f$, $R^k$, $X^1$, $X^2$, $X^3$ and Y are as described above.

8. A pharmaceutical composition, comprising:

(1) a compound of claim 1, or a pharmaceutically acceptable salt, enantiomer, diastereomer, tautomer, solvate, or polymorph thereof;

(2) pharmaceutically acceptable carriers.

9. A method for treating a disease associated with EZH2 mutation, activity or expression, wherein the method comprises the step: administrating the compound of formula I according to claim 1, or a pharmaceutically acceptable salt, enantiomer, diastereomer, tautomer, solvate, or polymorph thereof to a subject in need thereof, wherein the disease associated with EZH2 mutation, activity or expression is tumor; and the tumor is selected from the group consisting of: B cell lymphoma, malignant rhabdomyomas, synovial sarcoma, breast cancer, colorectal cancer, endometrioma, gastric cancer, liver cancer, kidney cancer, lung cancer, melanoma, ovarian cancer, pancreatic cancer, prostate cancer, and bladder cancer.

* * * * *